(12) United States Patent
Lee et al.

(10) Patent No.: US 7,541,434 B2
(45) Date of Patent: Jun. 2, 2009

(54) POLYPEPTIDE FOR A TRP CHANNEL FAMILY MEMBER, TRP-PLIK2, AND SPLICE VARIANTS

(75) Inventors: Ning Lee, Belle Mead, NJ (US); Jian Chen, Princeton, NJ (US); Shujian Wu, Langhorne, PA (US); Han Chang, Princeton Junction, NJ (US); Michael A. Blanar, Malvern, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 93 days.

(21) Appl. No.: 11/726,234

(22) Filed: Mar. 21, 2007

(65) Prior Publication Data
US 2007/0172880 A1    Jul. 26, 2007

Related U.S. Application Data

(62) Division of application No. 10/153,244, filed on May 22, 2002, now Pat. No. 7,223,557.

(60) Provisional application No. 60/292,599, filed on May 22, 2001, provisional application No. 60/362,944, filed on Mar. 8, 2002.

(51) Int. Cl.
  C07K 14/47     (2006.01)
  C12N 15/07     (2006.01)
  C12N 15/64     (2006.01)
  C12P 21/02     (2006.01)

(52) U.S. Cl. .................. 530/350; 435/69.1; 435/320.1; 435/325; 435/471

(58) Field of Classification Search .................. None
See application file for complete search history.

(56) References Cited

U.S. PATENT DOCUMENTS

| 5,849,902 A | 12/1998 | Arrow et al. |
| 2002/0177205 A1 | 11/2002 | Ryazanov |

FOREIGN PATENT DOCUMENTS

| WO | WO0040614 | 7/2000 |
| WO | WO 02/072824 A2 | 9/2002 |
| WO | WO 02/083712 A2 | 10/2002 |
| WO | WO 02/094999 A2 | 11/2002 |

OTHER PUBLICATIONS

NCBI Entrez Accession No. gi|10439092, Watanabe, K. et al., Sep. 29, 2000.
NCBI Entrez Accession No. gi|13569705, Ryazanov, A.G. et al., Apr. 10, 2001.
NCBI Entrez Accession No. gi|18249945, Ryazanov, A.G. et al., Jan. 16, 2002.
NCBI Entrez Accession No. gi|18860924, Ryazanov, A.G. et al., Mar. 4, 2002.
NCBI Entrez Accession No. gi|18921093, Ryazanov, A.G. et al., Nov. 5, 2002.
NCBI Entrez Accession No. gi|20386048, Schlingmann, K.P. et al., Jun. 14, 2002.
Swiss-PROT Accession No. Q9BX94, Jun. 17, 2001.
Riazanova, L.V. et al., "Novel type of signaling molecules: protein kinases covalently linked to ion channels", Mol. Biol. (Mosk), vol. 35(2), pp. 321-332 (2001).
Ryazanov, A.G. et al., "Alpha-kinases: a new class of protein kinases with a novel catalytic domain", Curr. Biol., vol. 9(2), pp. R43-R45 (1999).
Schlingmann, K.P. et al., "Hypomagnesemia with secondary hypocalcemia is caused by mutations in *TRPM6*, a new member of the TRPM gene family", Nature Genetics, vol. 31(2), pp. 166-170 (2002).
Aggarwal,B., "Apoptosis and Nuclear Factor-kB: A Tale of Association and Dissociation", Biochemical Pharmacology, vol. 60, pp. 1033-1039 (2000).
Baldwin, A., "Control of oncogenesis and cancer therapy resistance by the transcription factor NF-kB", The Journal of Clinical Investigation, vol. 107, No. 3, pp. 241-246 (2001).
Baldwin Jr., A., "The transcription factor NF-kB and human disease", The Journal of Clinical Investigation, vol. 107, No. 1, pp. 3-6 (2001).
Basu, et al., "The DNA-Dependent Protein Kinase Participates in the Activation of NFκB Following DNA Damage", Biochemical and Biophysical Research Communications, vol. 247, pp. 79-83, (1998).
Bateman, et al., "The Pfam Protein Families Database", Nucleic Acids Research, vol. 28, No. 1, pp. 263-266, (2000).
Baud, et al., "Signal transduction by tumor necrosis factor and its relatives", Trends in Cell Biology, vol. 11, No. 9, pp. 372-377 (2001).
Blackshear, et al., "The NIEHS *Xenopus* maternal EST project: interim analysis of the first 13,879 ESTs from unfertilized eggs", Gene, vol. 267, pp. 71-87 (2001).
Boulay, et al., "Cloning and Expression of a Novel Mammalian Homolog of Drosophila Transient Receptor Potential(Trp) Involved in Calcium Entry Secondary to Activation of Receptors Coupled by the $G_q$ Class of G Protein", The Journal of Biol Chemistry, vol. 272 pp. 29672-29680 (1997).
Broadway, et al., "The liver isoform of carnitine palmitoyltransferase 1 is not targeted to the endoplasmic reticulum", Biochem, J., vol. 370, pp. 223-231 (2003).

(Continued)

Primary Examiner—Robert Landsman
Assistant Examiner—Ian Dang
(74) Attorney, Agent, or Firm—Stephen C. D'Amico

(57) ABSTRACT

The present invention provides novel polynucleotides encoding TRP-PLIK2 polypeptides, fragments and homologues thereof. The present invention also provides polynucleotides encoding variants and splice variants of TRP-PLIK2 polypeptides, TRP-PLIK2b, TRP-PLIK2c, and TRP-PLIK2d, respectively. Also provided are vectors, host cells, antibodies, and recombinant and synthetic methods for producing said polypeptides. The invention further relates to diagnostic and therapeutic methods for applying these novel TRP-PLIK2, TRP-PLIK2b, TRP-PLIK2c, and TRP-PLIK2d polypeptides to the diagnosis, treatment, and/or prevention of various diseases and/or disorders related to these polypeptides. The invention further relates to screening methods for identifying agonists and antagonists of the polynucleotides and polypeptides of the present invention.

13 Claims, 51 Drawing Sheets

OTHER PUBLICATIONS

Figure 7:
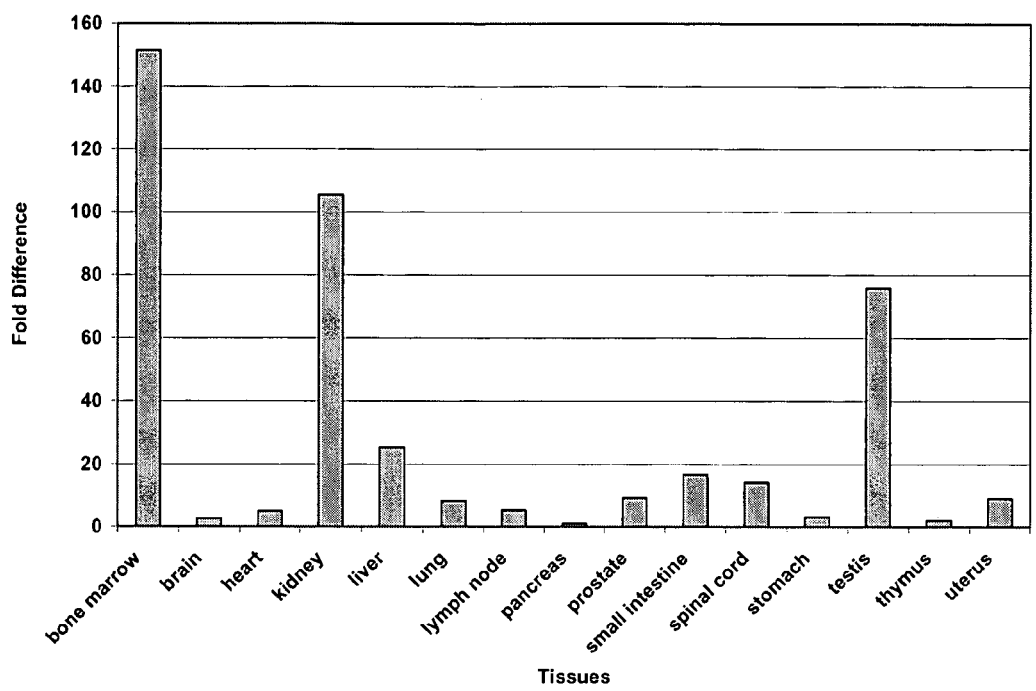

Carninci, et al., "Normalization and Subtraction of Cap-Trapper-Selected cDNAs to Prepare Full-Length cDNA Libraries for Rapid Discovery of New Genes", Genome Research, vol. 10, pp. 1617-1630 (2000).

Carninci, et al., "[2]High-Efficiency Full-Length cDNA Cloning", Methods in Enzymology, vol. 303, pp. 19-44 (1990).

Caterina, et al., "A capsaicin-receptor homologue with a high threshold for noxious heat", Nature, vol. 398, pp. 436-440 (1999).

Caterina, et al., "Impaired Nociception and Pain Sensation in Mice Lacking the Capsaicin Receptor", Science, vol. 288, pp. 306-313, (2000).

C. elegans Sequencing Consortium, "Genome Sequence of the Nematode C. elegans: A Platform for Investigating Biology", Science, vol. 282, pp. 2012-2018 (1998).

Chubanov, et al., "Disruption of TRPM6/TRPM7 complex formation by a mutation in the TRPM6 gene causes hypomagnesemia with secondary hypocalcemia", PNAS, vol. 101, No. 9, pp. 2894-2899 (2004).

Chubanov, et al., "Emerging roles of TRPM6/TRPM7 channel kinase signal transduction complexes", Naunyn-Schmiedeberg's Arch Pharmacol, vol. 371, pp. 334-341 (2005).

Chubanov, et al., "Essential role for TRPM6 in epithelial magnesium transport and body magnesium homeostasis", European Journal of Physiology, pp. 1-13 (2005).

Cohen, et al., "The N-terminal Domain of Rat Liver Carnitine Palmitoyltransferase 1 Contains an Internal Mitochondrial Import Signal and Residues Essential for Folding of its C-terminal Catalytic Domain*", The Journal of Biological Chemistry, vol. 276, No. 7, pp. 5403-5411 (2001).

deVries, et al., "Functional Characterization of Mitochondrial Carnitine Palmitoyltransferases l and ll Expressed in the Yeast *Pichia pastoris*", Biochemistry, vol. 36, pp. 5285-5292 (1997).

Duncan, et al., "Down-Regulation of the Novel Gene *Melastatin* Correlates with Potential for Melanoma Metastasis", Cancer Research, vol. 58, pp. 1515-1520 (1998).

Esser, et al., "Cloning Sequencing and Expression of a cDNA Encoding Rat Liver Carnitine Palmitoyltransferase I", The Journal of Biological Chemistry, vol. 268, No. 8, pp. 5817-5822 (1993).

Freichel, et al., "Lack of an endothelial store-operated $Ca^{2+}$ current impairs agonist-dependent vasorelaxation in $TRP4^{-/-}$ mice", Nature Cell Biology, vol. 3, pp. 121-127 (2001).

Ghosh, et al., "NF-κB and REL Proteins: Evolutionarily Conserved Mediators of Immune Responses", Annu. Rev. Immunol., vol. 16, pp. 225-260 (1998).

Guijarro, et al., "Transcription factor-κB (NF-κB) and renal disease", Kidney International, vol. 59, pp. 415-424 (2001).

Guo, et al., "Identification and Characterization of a Novel Polycystin Family Member, Polycystin-L2, in Mouse and Human: Sequence, Expression, Alternative Splicing, and Chromosomal Localization", Genomics, vol. 64, pp. 241-251 (2000).

Gwanyanya, et al., "Magnesium-inhibited, TRPM6/7-like channel in cardiac myocytes: permeation of divalent cations and pH-mediated regulation", J Physiol, vol. 559, No. 3, pp-761-776 (2004).

Harteneck, Christian, "Function and pharmacology of TRPM cation channels", Naunyn-Schmiedeberg's Arch Pharmacol, vol. 371, pp. 307-314 (2005).

Harteneck, Christian, "From worm to man: three subfamilies of TRP channels", Tins, vol. 23, No. 4, pp. 159-166 (2000).

Henikoff, et al., "Amino acid substitution matrices from protein blocks", Proc. Natl. Acad. Sci. USA, vol. 89 pp. 10915-10919 (1992).

Hoenderop et al., "Epithelial $Ca^{2+}$ and $Mg^{2+}$ Channels in Health and Disease" J Am Soc Nephrol, vol. 16, pp. 15-26 (2005).

Hoenderop et al., "Molecular Identification of the Apical $Ca^{2+}$ Channel in 1,25-Dihydroxyvitamin $D_3$-responsive Epithelia*", The Journal of Biological Chemistry, vol. 274, No. 13, pp. 8375-8378 (1999).

Hunter, et al., "Chromosomal Localization and Genomic Characterization of the Mouse Melastatin Gene (Mlsn1)", Genomics, vol. 54, pp. 116-123 (1998).

Inoue, et al., "The Transient Receptor Potential Protein Homologue TRP6 is the Essential Component of Vascular $α_1$-Adrenoceptor-Activated $Ca^{2+}$-Permeable Cation Channel", Circ. Res., vol. 88, pp. 325-332 (2001).

Itagaki, et al., "Cytoskeletal Reorganization Internalizes Multiple Transient Receptor Potential Channels and Block Calcium Entry into Human Neutrophils[1] ", The Journal of Immunology, vol. 172, pp. 601-607 (2004).

Kerner, et al., "Phosphorylation of Rat Liver Mitochondrial Carnitine Palmitoyltransferase-l", The Journal of Biological Chemistry, vol. 279, No. 39, pp. 41104-41113 (2004).

Konrad, et al., "Insights into the molecular nature of magnesium homeostasis", Am J Physiol Renal Physiol, vol. 286, pp. F599-F605 (2004).

Kraft, et al., "The mammalian melastatin-related transient receptor potential cation channels: an overview", European Journal of Physiology, pp. 1-17 (2005).

Liman, et al., "TRP2: A candidate transduction channel for mammalian pheromone sensory signaling" Proc. Natl. Acad. Sci. USA, vol. 96, pp. 5791-5796 (1999).

Louet, et al., "The Coactivator PGC-1 is Involved in the Regulation of the Liver Carnitine Palmitoyltransferase l Gene Expression by cAMP in Combination with HNF4α and cAMP-response Element-binding Protein(CREB)* ", J of Biol. Chemistry, vol. 277, No. 41, pp. 37991-38000 (2002).

Louet, et al., "Long-chain fatty acids regulate liver carnitine palmitoyltransferase 1 gene (L-CPT 1) expression through a peroxisome-proliferator-activated receptor α (PPARα)-independent pathway", Biochem. J., vol. 354 pp. 189-197 (2001).

Missiaen, et al., "Abnormal intracellular Ca2+ homeostasis and disease", Cell Calcium, vol. 28, No. 1, pp. 1-21 (2000).

Montell, C., "$Mg^{2+}$nificent Dispatch TRPM Chanzmes", Current Biology, vol. 13, pp. R799-R801 (2003).

Moral, et al., "Influence of DMBA-induced mammary cancer on the liver CPT 1, *mit HMG-CoA* synthase and *PPARα* mRNA expression in rats fed a low or high corn oil diet", International Journal of Molecular Medicine, vol. 14, pp. 283-287 (2004).

Mori et al., "Differential distribution of TRP $Ca^{2+}$ channel isoforms in mouse brain", Neuroreport, vol. 9, No. 3, pp. 507-515 (1998).

Morillas, et al., "Structural model of carnitine palmitoyltransferase 1 based on the carnitine acetyltransferase crystal", Biochem, J., vol. 379, pp. 777-784 (2004).

Morillas, et al., "Identification of Conserved Amino Acid Residues in Rat Liver Carnitine Palmitoyltransferase l Critical for Malonyl-CoA Inhibition", The Journal of Biological Chemistry, vol. 278, No. 11, pp. 9058-9063 (2003).

Nagamine, et al., "Molecular Cloning of a Novel Putative $Ca^{2+}$ Channel Protein (TRPC7) Highly Expressed in Brain", Genomics, vol. 54, pp. 124-131 (1998).

Napal, et al., "A Single Amino Acid Change (Substitution of the Conserved Glu-590 with Alanine) in the C-terminal Domain of Rat Liver Carnitine Palmitoyltransferase 1 Increases its Malonyl-CoA Sensitivity Close to that Observed with the Muscle Isoform of the Enzyme*", J. Biol. Chem. vol. 278, No. 36, pp. 34084-34089 (2003).

Nicot, et al., "Pig Liver Carnitine Palmitoyltransferase", The Journal of Biological Chemistry, vol. 277, No. 12, pp. 10044-10049 (2002).

Nijenhuis, et al., "Downregulation of $Ca^{2+}$ and $Mg^{2+}$ Transport Proteins in the Kidney Explains Tacrolimus (FK506)-Induced Hypercalciuria and Hypomagnesemia", J Am Soc Nephrol, vol. 15, pp. 549-557 (2004).

Nijenhuis, et al., "Enhanced passive $Ca^{2+}$ reabsorption and reduced $Mg^{2+}$ channel abundance explains thiazide-induced hypocalciuria and hypomagnesemia", The Journal of Clinical Investigation, vol. 115, No. 6, pp. 1651-1658 (2005).

Obici, et al., "Inhibition of hypothalamic carnitine palmitoyltransferase-1 decreases food intake and glucose production", Nature Medicine, vol. 9, No. 6, pp. 756-761 (2003).

Okada, et al., "Molecular and Functional Characterization of a Novel Mouse Transient Receptor Potential Protein Homologue TRP7", The Journal of Biological Chemistry, vol. 274, No. 39, pp. 27359-27370 (1999).

Pan, et al., "The Extreme C Terminus of Rat Liver Carnitine Palmitoyltransferase l is not Involved in Malonyl-CoA Sensitivity but in Initial Protein Folding*", The Journal of Biological Chemistry, vol. 277, No. 49, pp. 47184-47189 (2002).

Park, et al., "Cloning and characterization of the promoter for the liver isoform of the rat carnitine palmitoyltransferase 1 (L-CPT 1) gene", Biochem. J., vol. 998, vol. 217-224 (1998).

Peng, et al., "Molecular Cloning and Characterization of a Channel-like Transporter Mediating Intestinal Calcium Absorption*", The Journal of Biological Chemistry, vol. 274, No. 32, pp. 22739-22746 (1999).

Perraud, et al., "Novel aspects of signaling and ion-homeostasis regulation in immunocytes The TRPM ion channels and their potential role in modulating the immune response", Molecular Immunology, vol. 41, pp. 657-673 (2004).

Prawitt, et al., "Identification and characterization of MTR1, a novel gene with homology to melastatin(MLSN1) and the trp gene family located in the BWS-WT2 critical region on chromosome 11p15.5 and showing allele-specific expression", Human Molecular Genetics, vol. 9., No. 2, pp. 203-216 (2000).

Rubi, et al., "Advenovirus-mediated overexpression of liver carnitine palmitoyltransferase 1 in INS1E cells: effects on cell metabolism and insulin secretion", Biochem. J., vol. 364, pp. 219-226 (2002).

Runnels, et al., "TRP-PLIK, a Bifunctional Protein with Kinase and Ion Channel Activites", Science, vol. 291, pp. 1043-1047 (2001).

Ryazanov, et al., "Alpha-kinases: a new class of protein kinases with a novel catalytic domain", Current Biology, vol. 9, No. 2, pp. R43-R45 (1998).

Ryazanov, et al., "Identification of a new class of protein kinases represented by eukaryotic elongation factor-2 kinase", Proc. Natl. Acad. Sci. USA, vol. 94, pp. 4884-4889 (1997).

Ryazanova, et al., "Characterization of the Protein Kinase Activity of TRPM7/ChaK1, a Protein Kinase Fused to the Transient Receptor Potential Ion Channel*", The Journal of Biological Chemistry, vol. 279, No. 5, pp. 3708-3716 (2004).

Schlingmann, et al., "Novel TRPM6 Mutations in 21 Families with Primary Hypomagnesemia and Secondary Hypocalcemia", J Am Soc Nephrol, vol. 16, (2005).

Schlingmann, et al., "A critical role of TRPM channel-kinase for human magnesium transport", J Physiol., vol. 566, No. 2, pp. 301-308 (2005).

Schlingmann, et al., "Hypomagnesemia with secondary hypocalcemia is caused by mutations in TRPM6, a new member of the TRPM gene family", Nature Genetics, vol. 31, pp. 166-170 (2002).

Schmitz, et al., "Dual-Function Ion Channel/Protein Kinases: Novel Components of Vertebrate Magnesium Regulatory Mechanisms", Pediatric Research, vol. 55, No. 5, pp. 734-737 (2004).

Shibata, et al., "RIKEN Integrated Sequence Analysis (RISA) System-384-Format Sequencing Pipeline with 384 Multicapillary Sequencer", Genome Research, vol. 10, pp-1757-1771 (2000).

Silverman, et al., "NF-κB signaling pathways in mammalian and insect innate immunity", Genes & Development, vol. 15, pp. 2321-2342 (2001).

Strotmann, et al., "OTRPC4, a nonselective cation channel that confers sensitivity to extracellular osmolarity", Nature Cell Biology, vol. 2, pp. 695-702 (2000).

Thornberry, et al., "Caspases: Enemies Within", Science, vol. 281, pp. 1312-1316 (1998).

Touyz, et al., "Differentail Regulation of Transient Receptor Potential Melastatin 6 and 7 (TRPM6/7) Cation Channels by Angiotensin ll in Vascular Smooth Muscle Cells from Spontaneously Hypertensive Rats.", Am J Physiol Regul Interg Comp Physiol pp. 1-27 (2005).

Treber, et al., "Identification by Mutagenesis of Conserved Arginine and Glutamate Residues in the C-terminal Domain of Rat Liver Carnintine Palmitoyltransferase 1 That Are Important for Catalytic Activity and Malony-CoA Sensitivity", The Journal of Biological Chemistry, vol. 278, No. 13, pp. 11145-11149 (2003).

Tsavaler, et al., "Trp-p8, a Novel Prostate-specific Gene, Is Up-Regulated in Prostate Cancer and Other Malignancies and Shares High Homology with Transient Receptor Potential Calcium Channel Proteins", Cancer Research, vol. 61, pp. 3760-3769 (2001).

Valen, MD, PhD et al., "Nuclear Factor Kappa-B and the Heart", Journal of the American College of Cardiology, vol. 38, No. 2, pp. 307-314 (2001).

Vannier, et al., "Mouse trp2, the homologue of the human trpc2 pseudogene, encodes mTrp2, a store depletion-activated capacitative $Ca^{2+}$ entry channel", Proc. Natl. Acad. Sci. USA, vol. 96, pp. 2060-2064 (1999).

Voets, et al., "TRPM6 Forms the $Mg^{2+}$ Influx Channel Involved in Intestinal and Renal $Mg^{2+}$ Absorption*", The Journal of Biological Chemistry, vol. 279, No. 1, pp. 19-25 (2004).

Walder, et al., "Mutation of TRPM6 causes familial hypomagnesemia with secondary hypocalcemia", Nature Genetics, vol. 31, pp. 171-174 (2002).

Walker, et al., "A Drosophila Mechanosensory Transduction Channel", Science, vol. 287, pp. 2229-2234 (2000).

Wes, et al., "TRPC1, a human homolog of a Drosophila store-operated channel", Proc. Natl. Acad. Sci. USA, vol. 92, pp. 9652-9656 (1995).

Wissenbach, et al., "Trp12, a novel Trp related protein from kidney", FEBS Letters, vol. 485, pp. 127-134 (2000).

Wissenbach, et al., "Structure and mRNA expression of a bovine trp homologue related to mammalian trp2 transcripts", FEBS Letters, vol. 429, pp. 61-66 (1998).

Xu, et al. "TrpC1 is a Membrane-Spanning Subunit of Store-Operated Ca2+ Channels in Native Vascular Smooth Muscle Cells", Circ Res., vol. 88, pp-84-87 (2001).

Yue, et al., "CaT1 manifests the pore properties of the calcium-release-activated calcium channel", Nature, vol. 410, pp. 705-709 (2001).

Zhang, et al., "Peroxisomal Proliferator-activated Receptor-γ Coactivator-1α (PGC-1α) Enhances the Thyroid Hormone Induction of Carnitine Palmitoyltransferase 1 (CPT-Iα)*", The Journal of Biological Chemistry, vol. 279, No. 52, pp. 53963-53971 (2004.

Zhu, et al., "Molecular cloning of a widely expressed human homologue for the Drosophila trp gene", FEBS Letters, vol. 373 pp. 193-198 (1995).

Zygmunt, et al., "Vanilloid receptors on sensory nerves mediate the vasodilator action of anandamide", Nature, vol. 400, pp. 452-457 (1999).

NCBI Entrez Accession No. AF071787 (gi:3243074) Hunter, J. J. et al., Nov. 26, 1998.

NCBI Entrez Accession No. AF346629 (gi:13562152) Ryazanov, A. G. et al., Jan. 26, 2004.

NCBI Entrez Accession No. AF350881 (gi:18860923) Ryazanov, A. G. et al., Mar. 4, 2002.

NCBI Entrez Accession No. AI390333 (gi:4216340) Marra, M. et al., Mar. 15, 2000.

NCBI Entrez Accession No. AK080899 (gi:26099542) Carninci, P. et al., Apr. 3, 2004.

NCBI Entrez Accession No. AL354795 (gi:4272270) Hammond, S. May 18, 2005.

NCBI Entrez Accession No. AW645658 (gi:7403115) Blackshear, P. J. et al., Apr. 26, 2001.

NCBI Entrez Accession No. AW916907 (gi:8082551) Lee, N.H. et al., May 25, 2000.

NCBI Entrez Accession No. BB593693 (gi:16450090) Arakawa, T. et al., Oct. 26, 2001.

NCBI Entrez Accession No. BB650718 (gi:16484973) Arakawa, T. et al., Oct. 26, 2001.

NCBI Entrez Accession No. BE465471 (gi:9511246) NCI-CGAP, Jul. 27, 2000.

NCBI Entrez Accession No. BI754451 (gi:15746029) NIH-MGC, Sep. 25, 2001.

NCBI Entrez Accession No. BJ028793 (gi:17398507) Kitayama, A. et al., Sep. 26, 2003.

NCBI Entrez Accession No. BM472126 (gi:18521168) NIH-MGC, Feb. 5, 2002.

NCBI Entrez Accession No. NP_060132 (gi:18921093) Chubanov, V. et al., Jun. 11, 2005.

NCBI Entrez Accession No. NP_113747 (gi:13928756) Zhang, Y. et al., Aug. 17, 2005.

NCBI Entrez Accession No. Q9BX84 (gi:56404951) Riazanova, L.V. et al., Sep. 13, 2005.

NCBI Entrez Accession No. XP_028830 (gi:18573769) NCBI Annotation Project May 8, 2002.

NCBI Entrez Accession No. XP_528327 (gi:55631831) NCBI Annotation Project, Nov. 9, 2004.

NCBI Entrez Accession No. XP_541279 (gi:57036816) NCBI Annotation Project, Jan. 4, 2005.

NCBI Entrez Accession No. AAB50622 (gi:1911245) Sakura, H. et al., Mar. 27, 1997.

NCBI Entrez Accession No. AAC06146 (gi:2979524) Boulay, G. et al., Mar. 20, 1998.

NCBI Entrez Accession No. AAC80000 (gi:3243075) Hunter, J. J. et al., Nov. 25, 1998.

NCBI Entrez Accession No. AAD10167 (gi:4200415) Zhu, X. et al., Jan. 28, 1999.

NCBI Entrez Accession No. AAD17195 (gi:4324938) Vannier, B. et al., Mar. 15, 1999.

NCBI Entrez Accession No. AAD42069 (gi:5326854) Okada, T. et al., Sep. 21, 1999.

NCBI Entrez Accession No. AAF01468 (gi:6014703) Mori, Y. et al., Oct. 7, 1999.

NCBI Entrez Accession No. AAF02200 (gi:6048344) Zhu, X. et al., Oct. 16, 1999.

NCBI Entrez Accession No. AAF59842 (gi:7328583) Walker, R. G. et al., Mar. 25, 2000.

NCBI Entrez Accession No. AAF73131 (gi:8131903) Matsushita, M., Jun. 1, 2000.

NCBI Entrez Accession No. AAK31202 (gi:18860924) Ryazanov, A. G. et al., Mar. 4, 2002.

NCBI Entrez Accession No. AAM21562 (gi:20386048) Schlingmann, K. P. et al., Jun. 14, 2002.

NCBI Entrez Accession No. AAR03487 (gi:37790762) Chubanov, V. et al., Mar. 3, 2004.

NCBI Entrez Accession No. AAR03488 (gi:37790764) Chubanov, V. et al., Mar. 3, 2004.

NCBI Entrez Accession No. AAR03489 (gi:37790766) Chubanov, V. et al. Mar. 3, 2004.

NCBI Entrez Accession No. AAR03490 (gi:37790768) Chubanov, V. et al., Mar. 3, 2004.

NCBI Entrez Accession No. CAC14420 (gi:11065673) C. elegans Sequencing Consortium, Aug. 25, 2005.

NCBI Entrez Accession No. CAH70894 (gi:5663182) Hammond, S. May 18, 2005.

NCBI Entrez Accession No. AF350881 (gi:13569704), Ryazanov, et al., Apr. 10, 2001.

Figure 1A

```
  1  atgattatcctatctaagtcccagaaatcctggattaaaggagtatttgacaagagagaa   60
  1  M  I  I  L  S  K  S  Q  K  S  W  I  K  G  V  F  D  K  R  E    20

61  tgtagcacaatcatacccagctcaaaaaatcctcacagatgtactccagtatgccaagtc  120
 21  C  S  T  I  I  P  S  S  K  N  P  H  R  C  T  P  V  C  Q  V    40

121  tgccagaatttaatcaggtgttactgtggccgactgattggagaccatgctgggatagat  180
 41  C  Q  N  L  I  R  C  Y  C  G  R  L  I  G  D  H  A  G  I  D    60

181  tattcctggaccatctcagctgccaagggtaaagaaagtgaacaatggtctgttgaaaag  240
 61  Y  S  W  T  I  S  A  A  K  G  K  E  S  E  Q  W  S  V  E  K    80

241  cacacaacgaaaagcccaacagatactttggcacgattaatttccaagatggagagcac  300
 81  H  T  T  K  S  P  T  D  T  F  G  T  I  N  F  Q  D  G  E  H   100

301  acccatcatgccaagtatattagaacttcttatgatacaaaactggatcatctgttacat  360
101  T  H  H  A  K  Y  I  R  T  S  Y  D  T  K  L  D  H  L  L  H   120

361  ttaatgttgaaagagtggaaaatggaactgcccaagcttgtgatctcagtccatggggc  420
121  L  M  L  K  E  W  K  M  E  L  P  K  L  V  I  S  V  H  G  G   140

421  atccagaactttactatgccctctaaattaaagagattttcagccaaggtttggttaaa  480
141  I  Q  N  F  T  M  P  S  K  F  K  E  I  F  S  Q  G  L  V  K   160

481  gctgcagagacaacaggagcgtggataataactgaaggcatcaatacaggagtgtccaag  540
161  A  A  E  T  T  G  A  W  I  I  T  E  G  I  N  T  G  V  S  K   180

541  catgttggggatgccttgaaatcccattcctctcattccttgagaaaaatctggacagtt  600
181  H  V  G  D  A  L  K  S  H  S  S  H  S  L  R  K  I  W  T  V   200

601  ggaatccctccttggggtgtcattgagaaccagagagaccttattggaaagatgtggtg  660
201  G  I  P  P  W  G  V  I  E  N  Q  R  D  L  I  G  K  D  V  V   220

661  tgcctgtaccagactctggataacccctcagcaagctcacaacactcaacagcatgcac  720
221  C  L  Y  Q  T  L  D  N  P  L  S  K  L  T  T  L  N  S  M  H   240

721  tcgcacttcatcctgtctgatgatgggaccgtgggcaagtatggaaatgaaatgaagctc  780
241  S  H  F  I  L  S  D  D  G  T  V  G  K  Y  G  N  E  M  K  L   260

781  agaaggaacctggagaagtacctctctctgcagaaaatacactgccgctcaagacaaggc  840
261  R  R  N  L  E  K  Y  L  S  L  Q  K  I  H  C  R  S  R  Q  G   280

841  gtgccggtcgtggggctggtggtggaaggcggtcccaacgtcatcctgtcagtgtgggag  900
281  V  P  V  V  G  L  V  V  E  G  G  P  N  V  I  L  S  V  W  E   300
```

Figure 1B

```
 901  actgtcaaggacaaggacccagtggtggtgtgtgagggcacaggtagggcggctgacctc   960
 301   T   V   K   D   K   D   P   V   V   V   C   E   G   T   G   R   A   A   D   L    320

961  ctggccttcacacacaaacacctggcagatgaagggatgctgcgacctcaggtgaaagag  1020
 321   L   A   F   T   H   K   H   L   A   D   E   G   M   L   R   P   Q   V   K   E    340

1021  gagatcatctgcatgattcagaacactttcaactttagtcttaaacagtccaagcacctt  1080
 341   E   I   I   C   M   I   Q   N   T   F   N   F   S   L   K   Q   S   K   H   L    360

1081  ttccaaattctaatggagtgtatggttcacagggattgtattaccatatttgatgctgac  1140
 361   F   Q   I   L   M   E   C   M   V   H   R   D   C   I   T   I   F   D   A   D    380

1141  tctgaagagcagcaagacctggacttagcaatcctaacagctttgctgaagggcacaaat  1200
 381   S   E   E   Q   Q   D   L   D   L   A   I   L   T   A   L   L   K   G   T   N    400

1201  ttatcagcgtcagagcaattaaatctggcaatggcttgggacagggtggacattgccaag  1260
 401   L   S   A   S   E   Q   L   N   L   A   M   A   W   D   R   V   D   I   A   K    420

1261  aaacatatcctaatttatgaacaacactggaagcctgatgccctggaacaagcaatgtca  1320
 421   K   H   I   L   I   Y   E   Q   H   W   K   P   D   A   L   E   Q   A   M   S    440

1321  gatgctttagtgatggatcgggtggattttgtgaagctcttaatagaatatggagtgaac  1380
 441   D   A   L   V   M   D   R   V   D   F   V   K   L   L   I   E   Y   G   V   N    460

1381  ctccatcgctttcttaccatccctcgactggaagagctctacaatacaaaacaaggacct  1440
 461   L   H   R   F   L   T   I   P   R   L   E   E   L   Y   N   T   K   Q   G   P    480

1441  actaatacactcttgcatcatctcgtccaagatgtgaaacagcatacccttctttcaggc  1500
 481   T   N   T   L   L   H   H   L   V   Q   D   V   K   Q   H   T   L   L   S   G    500

1501  taccgaataaccttgattgacattggattagtagtagaatacctcattggtagagcatat  1560
 501   Y   R   I   T   L   I   D   I   G   L   V   V   E   Y   L   I   G   R   A   Y    520

1561  cgcagcaactacactagaaaacatttcagagccctctacaacaacctctacagaaaatac  1620
 521   R   S   N   Y   T   R   K   H   F   R   A   L   Y   N   N   L   Y   R   K   Y    540

1621  aagcaccagagacactcctcaggaaatagaaatgagtctgcagaaagtacgctgcactcc  1680
 541   K   H   Q   R   H   S   S   G   N   R   N   E   S   A   E   S   T   L   H   S    560

1681  cagttcattagaactgcacagccatacaaattcaaggaaaagtctatagtccttcataaa  1740
 561   Q   F   I   R   T   A   Q   P   Y   K   F   K   E   K   S   I   V   L   H   K    580

1741  tcaaggaagaagtcaaaagaacaaaatgtatcagatgaccctgagtctactggctttctt  1800
 581   S   R   K   K   S   K   E   Q   N   V   S   D   D   P   E   S   T   G   F   L    600
```

Figure 1C

```
1801 taccct tacaatgacctgctggtttgggctgtgctgatgaaaaggcagaagatggctatg 1860
 601   Y  P  Y  N  D  L  L  V  W  A  V  L  M  K  R  Q  K  M  A  M   620

1861 ttcttctggcagcatggagaggaggccacggttaaagccgtgattgcgtgtatcctctac 1920
 621   F  F  W  Q  H  G  E  E  A  T  V  K  A  V  I  A  C  I  L  Y   640

1921 cgggcaatggcccatgaagctaaggagagtcacatggtggatgatgcctcagaagagttg 1980
 641   R  A  M  A  H  E  A  K  E  S  H  M  V  D  D  A  S  E  E  L   660

1981 aagaattactcaaaacagtttggccagctggctctggacttgttggagaaggcattcaag 2040
 661   K  N  Y  S  K  Q  F  G  Q  L  A  L  D  L  L  E  K  A  F  K   680

2041 cagaatgagcgcatggccatgacgctgttgacgtatgaactcaggaactggagcaattcg 2100
 681   Q  N  E  R  M  A  M  T  L  L  T  Y  E  L  R  N  W  S  N  S   700

2101 acctgcctgaaactggccgtgtcgggaggattacgacccttt gtttcacatacttgtacc 2160
 701   T  C  L  K  L  A  V  S  G  G  L  R  P  F  V  S  H  T  C  T   720

2161 cagatgctactgacagacatgtggatggggaggctgaaaatgaggaaaaactcttggtta 2220
 721   Q  M  L  L  T  D  M  W  M  G  R  L  K  M  R  K  N  S  W  L̲   740

2221 aagattattataagcattattttaccacccaccatt ttgacactggaattt aaaagcaaa 2280
 741   K̲  I̲  I̲  I̲  S̲  I̲  I̲  L̲  P̲  P̲  T̲  I̲  L̲  T̲  L̲  E̲  F̲  K  S  K   760

2281 gctgagatgtcacatgttccccagtcccaggacttccaatttatgtggtattacagtgac 2340
 761   A  E  M  S  H  V  P  Q  S  Q  D  F  Q  F  M  W  Y  Y  S  D   780

2341 cagaacgccagcagttccaaagaaagtgcttctgtgaaagagtatgatttggaaggggc 2400
 781   Q  N  A  S  S  S  K  E  S  A  S  V  K  E  Y  D  L  E  R  G   800

2401 catgatgagaaactggatgaaaatcagcattttggtttggaaagtgggcaccaacacctt 2460
 801   H  D  E  K  L  D  E  N  Q  H  F  G  L  E  S  G  H  Q  H  L   820

2461 ccgtggaccaggaaagtctatgagttctacagtgctccaattgtcaagttttggttttat 2520
 821   P  W  T  R  K  V  Y  E  F  Y  S  A  P  I̲  V̲  K̲  F̲  W̲  F̲  Y̲   840

2521 acgatggcgtatttggcattcctcatgctgttcacttacaccgtgttggtggagatgcag 2580
 841   T̲  M̲  A̲  Y̲  L̲  A̲  F̲  L̲  M̲  L̲  F̲  T  Y  T  V  L  V  E  M  Q   860

2581 ccccagcccagcgtgcaggagtggcttgttagcatttacatcttcaccaatgctattgag 2640
 861   P  Q  P  S  V  Q  E  W  L  V  S  I  Y  I  F  T  N  A  I  E   880

2641 gtggtcagggagatctgtatttcagaacctgggaagtttacccaaaaggtgaaggtatgg 2700
 881   V  V  R  E  I  C  I  S  E  P  G  K  F  T  Q  K  V  K  V  W   900
```

Figure 1D

```
2701  attagtgagtactggaacttaacagaaactgtggccattggcctgttttcagctggcttc  2760
 901  I   S   E   Y   W   N   L   T   E   T   V   A   I   G   L   F   S   A   G   F    920

2761  gtccttcgatggggtgaccctccttttcacacagcgggaagactgatctactgcatagac  2820
 921  V   L   R   W   G   D   P   P   F   H   T   A   G   R   L   I   Y   C   I   D    940

2821  atcatattctggttctcacggctcctggacttctttgctgtgaatcaacatgcaggtcca  2880
 941  I   I   F   W   F   S   R   L   L   D   F   A   V   N   Q   H   A   G   P        960

2881  tatgtgaccatgattgcaaaaatgacagcaaacatgttctatattgtgatcatcatggcc  2940
 961  Y   V   T   M   I   A   K   M   T   A   N   M   F   Y   I   V   I   I   M   A    980

2941  atagtcctgctgagctttggagtggcacgcaaggccatcctttcgccaaaagagccacca  3000
 981  I   V   L   L   S   F   G   V   A   R   K   A   I   L   S   P   K   E   P   P   1000

3001  tcttggagtctagctcgagatattgtatttgagccatactggatgatatacggagaagtc  3060
1001  S   W   S   L   A   R   D   I   V   F   E   P   Y   W   M   I   Y   G   E   V   1020

3061  tatgctggagaaatagatgtttgttcaagccagccatcctgccctcctggttcttttctt  3120
1021  Y   A   G   E   I   D   V   C   S   S   Q   P   S   C   P   P   G   S   F   L   1040

3121  actccattcttgcaagctgtctacctcttcgtgcaatatatcatcatggtgaacctgttg  3180
1041  T   P   F   L   Q   A   V   Y   L   F   V   Q   Y   I   I   M   V   N   L   L   1060

3181  attgctttcttcaacaacgtttacttagatatggaatccatttcaaataacctgtggaaa  3240
1061  I   A   F   F   N   N   V   Y   L   D   M   E   S   I   S   N   N   L   W   K   1080

3241  tacaaccgctatcgctacatcatgacctaccacgagaagccctggctgccccccacctctc  3300
1081  Y   N   R   Y   R   Y   I   M   T   Y   H   E   K   P   W   L   P   P   P   L   1100

3301  atcctgctgagccacgtgggccttctcctccgccgcctgtgctgtcatcgagctcctcac  3360
1101  I   L   L   S   H   V   G   L   L   L   R   R   L   C   C   H   R   A   P   H   1120

3361  gaccaagaagagggtgacgttggattaaaaactctacctcagtaaggaggatctgaaaaaa  3420
1121  D   Q   E   E   G   D   V   G   L   K   L   Y   L   S   K   E   D   L   K   K   1140

3421  cttcatgattttgaggagcagtgcgtggaaaaatacttccatgagaagatggaagatgtg  3480
1141  L   H   D   F   E   E   Q   C   V   E   K   Y   F   H   E   K   M   E   D   V   1160

3481  aattgtagttgtgaggaacgaatccgagtgacatcagaaagggttacagagatgtacttc  3540
1161  N   C   S   C   E   E   R   I   R   V   T   S   E   R   V   T   E   M   Y   F   1180

3541  cagctgaaagaaatgaatgaaaaggtgtctttttataaaggactccttactgtctttggac  3600
1181  Q   L   K   E   M   N   E   K   V   S   F   I   K   D   S   L   L   S   L   D   1200
```

Figure 1E

```
3601  agccaggtgggacacctgcaggatctctctgccctgactgtggatacccctgaaagtcctt  3660
1201  S  Q  V  G  H  L  Q  D  L  S  A  L  T  V  D  T  L  K  V  L     1220

3661  tctgctgttgacactttgcaagaggatgaggctctcctggccaagagaaagcattctact  3720
1221  S  A  V  D  T  L  Q  E  D  E  A  L  L  A  K  R  K  H  S  T     1240

3721  tgcaaaaaacttccccacagctggagcaatgtcatctgtgcagaggttctaggcagcatg  3780
1241  C  K  K  L  P  H  S  W  S  N  V  I  C  A  E  V  L  G  S  M     1260

3781  gagatcgctggagagaagaaataccagtattatagcatgccctcttctttgctgaggagc  3840
1261  E  I  A  G  E  K  K  Y  Q  Y  Y  S  M  P  S  S  L  L  R  S     1280

3841  ctggctggaggccggcatcccccaagagtgcagaggggggcacttcttgagattacaaac  3900
1281  L  A  G  G  R  H  P  P  R  V  Q  R  G  A  L  L  E  I  T  N     1300

3901  agtaaaagagaggctacaaatgtaagaaatgaccaggaaaggcaagaaacacaaagtagt  3960
1301  S  K  R  E  A  T  N  V  R  N  D  Q  E  R  Q  E  T  Q  S  S     1320

3961  atagtggtttctggggtgtctcctaacaggcaagcacactcaaagtatggccagtttctt  4020
1321  I  V  V  S  G  V  S  P  N  R  Q  A  H  S  K  Y  G  Q  F  L     1340

4021  ctggtcccctctaatctaaagcgagttccttttcagcagaaactgtcttgcctctgtcc  4080
1341  L  V  P  S  N  L  K  R  V  P  F  S  A  E  T  V  L  P  L  S     1360

4081  agaccctctgtgccagatgtgctggcaactgaacaggacatccagactgaggttcttgtt  4140
1361  R  P  S  V  P  D  V  L  A  T  E  Q  D  I  Q  T  E  V  L  V     1380

4141  catctgactgggcagaccccagttgtctctgactgggcatcagtggatgaacccaaggaa  4200
1381  H  L  T  G  Q  T  P  V  V  S  D  W  A  S  V  D  E  P  K  E     1400

4201  aagcacgagcctattgctcacttactggatggacaagacaaggcagagcaagtgctaccc  4260
1401  K  H  E  P  I  A  H  L  L  D  G  Q  D  K  A  E  Q  V  L  P     1420

4261  actttgagttgcacacctgaacccatgacaatgagctcccctctttcccaagccaagatc  4320
1421  T  L  S  C  T  P  E  P  M  T  M  S  S  P  L  S  Q  A  K  I     1440

4321  atgcaaactggaggtggatatgtaaactgggcattttcagaaggtgatgaaactggtgtg  4380
1441  M  Q  T  G  G  G  Y  V  N  W  A  F  S  E  G  D  E  T  G  V     1460

4381  tttagcatcaagaaaaagtggcaaacctgcttgccctccacttgtgacagtgattcctct  4440
1461  F  S  I  K  K  K  W  Q  T  C  L  P  S  T  C  D  S  D  S  S     1480

4441  cggagtgaacagcaccagaagcaggcccaggacagctccctatctgataactcaacaaga  4500
1481  R  S  E  Q  H  Q  K  Q  A  Q  D  S  S  L  S  D  N  S  T  R     1500
```

Figure 1F

```
4501  tcggcccagagtagtgaatgctcagaggtgggaccatggcttcagccaaacacatcctttt  4560
1501   S   A   Q   S   S   E   C   S   E   V   G   P   W   L   Q   P   N   T   S   F    1520

4561  tggatcaatcctctccgcagatacaggcccttcgctaggagtcatagttttagattccat  4620
1521   W   I   N   P   L   R   R   Y   R   P   F   A   R   S   H   S   F   R   F   H    1540

4621  aaggaggagaaattgatgaagatctgtaagattaaaaatctttcaggctcttcagaaata  4680
1541   K   E   E   K   L   M   K   I   C   K   I   K   N   L   S   G   S   S   E   I    1560

4681  gggcagggagcatgggtcaaagcgaaaatgctaaccaaagacaggagactgtcaaagaaa  4740
1561   G   Q   G   A   W   V   K   A   K   M   L   T   K   D   R   R   L   S   K   K    1580

4741  aagaagaatactcaaggactccaggtgccaatcataacagtcaatgcctgctctcagagt  4800
1581   K   K   N   T   Q   G   L   Q   V   P   I   I   T   V   N   A   C   S   Q   S    1600

4801  gaccagttgaatccagagccaggagaaaacagcatctctgaagaggagtacagcaagaac  4860
1601   D   Q   L   N   P   E   P   G   E   N   S   I   S   E   E   E   Y   S   K   N    1620

4861  tggttcacagtgtccaaatttagtcacacaggtgtagaaccttacatacatcagaaaatg  4920
1621   W   F   T   V   S   K   F   S   H   T   G   V   E   P   Y   I   H   Q   K   M    1640

4921  aaaactaaagaaattggacaatgtgctatacaaatcagtgattacctaaagcagtctcaa  4980
1641   K   T   K   E   I   G   Q   C   A   I   Q   I   S   D   Y   L   K   Q   S   Q    1660

4981  gaggatctcagcaaaaaactctttgtggaattccaggagcaccaacctcaataggaactcc  5040
1661   E   D   L   S   K   N   S   L   W   N   S   R   S   T   N   L   N   R   N   S    1680

5041  ctgctgaaaagttcaattggagttgacaagatctcagcctccttaaaaagccctcaagag  5100
1681   L   L   K   S   S   I   G   V   D   K   I   S   A   S   L   K   S   P   Q   E    1700

5101  cctcaccatcattattcagccattgaaaggaataatttaatgaggctttctcagaccata  5160
1701   P   H   H   H   Y   S   A   I   E   R   N   N   L   M   R   L   S   Q   T   I    1720

5161  ccatttacaccagtccaactgtttgcaggagaagaaataactgtctacaggttggaggag  5220
1721   P   F   T   P   V   Q   L   F   A   G   E   E   I   T   V   Y   R   L   E   E    1740

5221  agttcccctttaaaccttgataaaagcatgtcctcttggtctcagcgtgggagagcggca  5280
1741   S   S   P   L   N   L   D   K   S   M   S   S   W   S   Q   R   G   R   A   A    1760

5281  atgatccaggtattgtcccgagaggagatggatggggcctccgtaaagctatgagagtc  5340
1761   M   I   Q   V   L   S   R   E   E   M   D   G   G   L   R   K   A   M   R   V    1780

5341  gtcagcacttggtctgaggatgacattctcaagccgggacaagttttcattgtcaagtcc  5400
1781   V   S   T   W   S   E   D   D   I   L   K   P   G   Q   V   F   I   V   K   S    1800
```

Figure 1G

```
5401  tttcttcctgaggttgtgcggacatggcataaaatcttccaggagagcactgtgcttcat  5460
1801   F   L   P   E   V   V   R   T   W   H   K   I   F   Q   E   S   T   V   L   H   1820

5461  ctttgcctcagggaaattcaacaacaaagagctgctcaaaaattgatctatacctt caac  5520
1821   L   C   L   R   E   I   Q   Q   Q   R   A   A   Q   K   L   I   Y   T   F   N   1840

5521  caagtgaaaccacaaaccatacccta cacaccaaggttcctggaagttttcttaatctac  5580
1841   Q   V   K   P   Q   T   I   P   Y   T   P   R   F   L   E   V   F   L   I   Y   1860

5581  tgccattcagccaaccagtggttgaccattgagaagtatatgacaggggagttccggaag  5640
1861   C   H   S   A   N   Q   W   L   T   I   E   K   Y   M   T   G   E   F   R   K   1880

5641  tataacaacaacaatggtgatgaaatcacccccaccaacaccctggaggagctgatgttg  5700
1881   Y   N   N   N   N   G   D   E   I   T   P   T   N   T   L   E   E   L   M   L   1900

5701  gctttctctcactggacctatgagtacactcggggagagctgctggttttagatttgcaa  5760
1901   A   F   S   H   W   T   Y   E   Y   T   R   G   E   L   L   V   L   D   L   Q   1920

5761  ggtgttggagaaaatttgacagatccatctgttataaaacctgaagtcaaacaatcaaga  5820
1921   G   V   G   E   N   L   T   D   P   S   V   I   K   P   E   V   K   Q   S   R   1940

5821  ggaatggtgtttggaccggccaatttgggggaagatgcaattagaaacttcattgcaaaa  5880
1941   G   M   V   F   G   P   A   N   L   G   E   D   A   I   R   N   F   I   A   K   1960

5881  catcattgtaactcctgctgccggaagctcaaactcccggatttaaaaagaaatgactat  5940
1961   H   H   C   N   S   C   C   R   K   L   K   L   P   D   L   K   R   N   D   Y   1980

5941  tcccctgaaaggataaattccacctttggacttgagataaaaatagaatcagctgaggag  6000
1981   S   P   E   R   I   N   S   T   F   G   L   E   I   K   I   E   S   A   E   E   2000

6001  cctccagcaagggagacgggtagaaattccccagaagatgatatgcaactataa  6054
2001   P   P   A   R   E   T   G   R   N   S   P   E   D   D   M   Q   L       2017
```

Figure 2A

```
  1 ATGATTATCCTATCTAAGTCCCAGAAATCCTGGATTAAAGGAGTATTTGACAAGAGAGAA  60
  1  M  I  I  L  S  K  S  Q  K  S  W  I  K  G  V  F  D  K  R  E   20

61 TGTAGCACAATCATACCCAGCTCAAAAAATCCTCACAGATGTACTCCAGTATGCCAAGTC 120
 21  C  S  T  I  I  P  S  S  K  N  P  H  R  C  T  P  V  C  Q  V   40

121 TGCCAGAATTTAATCAGGTGTTACTGTGGCCGACTGATTGGAGACCATGCTGGGATAGAT 180
 41  C  Q  N  L  I  R  C  Y  C  G  R  L  I  G  D  H  A  G  I  D   60

181 TATTCCTGGACCATCTCAGCTGCCAAGGGTAAAGAAAGTGAACAATGGTCTGTTGAAAAG 240
 61  Y  S  W  T  I  S  A  A  K  G  K  E  S  E  Q  W  S  V  E  K   80

241 CACACAACGAAAAGCCCAACAGATACTTTTGGCACGATTAATTTCCAAGATGGAGAGCAC 300
 81  H  T  T  K  S  P  T  D  T  F  G  T  I  N  F  Q  D  G  E  H  100

301 ACCCATCATGCCAAGTATATTAGAACTTCTTATGATACAAAACTGGATCATCTGTTACAT 360
101  T  H  H  A  K  Y  I  R  T  S  Y  D  T  K  L  D  H  L  L  H  120

361 TTAATGTTGAAAGAGTGGAAAATGGAACTGCCCAAGCTTGTGATCTCAGTCCATGGGGGC 420
121  L  M  L  K  E  W  K  M  E  L  P  K  L  V  I  S  V  H  G  G  140

421 ATCCAGAACTTTACTATGCCCTCTAAATTTAAAGAGATTTTCAGCCAAGGTTTGGTTAAA 480
141  I  Q  N  F  T  M  P  S  K  F  K  E  I  F  S  Q  G  L  V  K  160

481 GCTGCAGAGACAACAGGAGCGTGGATAATAACTGAAGGCATCAATACAGGAGTGTCCAAG 540
161  A  A  E  T  T  G  A  W  I  I  T  E  G  I  N  T  G  V  S  K  180

541 CATGTTGGGGATGCCTTGAAATCCCATTCCTCTCATTCCTTGAGAAAAATCTGGACAGTT 600
181  H  V  G  D  A  L  K  S  H  S  S  H  S  L  R  K  I  W  T  V  200

601 GGAATCCCTCCTTGGGGTGTCATTGAGAACCAGAGAGACCTTATTGGAAAAGATGTGGTG 660
201  G  I  P  P  W  G  V  I  E  N  Q  R  D  L  I  G  K  D  V  V  220

661 TGCCTGTACCAGACTCTGGATAACCCCCTCAGCAAGCTCACAACACTCAACAGCATGCAC 720
221  C  L  Y  Q  T  L  D  N  P  L  S  K  L  T  T  L  N  S  M  H  240

721 TCGCACTTCATCCTGTCTGATGATGGGACCGTGGGCAAGTATGGAAATGAAATGAAGCTC 780
241  S  H  F  I  L  S  D  D  G  T  V  G  K  Y  G  N  E  M  K  L  260

781 AGAAGGAACCTGGAGAAGTACCTCTCTCTGCAGAAAATACACTGCCGCTCAAGACAAGGC 840
261  R  R  N  L  E  K  Y  L  S  L  Q  K  I  H  C  R  S  R  Q  G  280

841 GTGCCGGTCGTGGGGCTGGTGGTGGAAGGCGGTCCCAACGTCATCCTGTCAGTGTGGGAG 900
281  V  P  V  V  G  L  V  V  E  G  G  P  N  V  I  L  S  V  W  E  300
```

Figure 2B

```
 901  ACTGTCAAGGACAAGGACCCAGTGGTGGTGTGTGAGGGCACAGGTAGGGCGGCTGACCTC   960
 301   T   V   K   D   K   D   P   V   V   V   C   E   G   T   G   R   A   A   D   L    320

961  CTGGCCTTCACACACAAACACCTGGCAGATGAAGGGATGCTGCGACCTCAGGTGAAAGAG  1020
 321   L   A   F   T   H   K   H   L   A   D   E   G   M   L   R   P   Q   V   K   E    340

1021  GAGATCATCTGCATGATTCAGAACACTTTCAACTTTAGTCTTAAACAGTCCAAGCACCTT  1080
 341   E   I   I   C   M   I   Q   N   T   F   N   F   S   L   K   Q   S   K   H   L    360

1081  TTCCAAATTCTAATGGAGTGTATGGTTCACAGGGATTGTATTACCATATTTGATGCTGAC  1140
 361   F   Q   I   L   M   E   C   M   V   H   R   D   C   I   T   I   F   D   A   D    380

1141  TCTGAAGAGCAGCAAGACCTGGACTTAGCAATCCTAACAGCTTTGCTGAAGGGCACAAAT  1200
 381   S   E   E   Q   Q   D   L   D   L   A   I   L   T   A   L   L   K   G   T   N    400

1201  TTATCAGCGTCAGAGCAATTAAATCTGGCAATGGCTTGGGACAGGGTGGACATTGCCAAG  1260
 401   L   S   A   S   E   Q   L   N   L   A   M   A   W   D   R   V   D   I   A   K    420

1261  AAACATATCCTAATTTATGAACAACACTGGAAGCCTGATGCCCTGGAACAAGCAATGTCA  1320
 421   K   H   I   L   I   Y   E   Q   H   W   K   P   D   A   L   E   Q   A   M   S    440

1321  GATGCTTTAGTGATGGATCGGGTGGATTTTGTGAAGCTCTTAATAGAATATGGAGTGAAC  1380
 441   D   A   L   V   M   D   R   V   D   F   V   K   L   L   I   E   Y   G   V   N    460

1381  CTCCATCGCTTTCTTACCATCCCTCGACTGGAAGAGCTCTACAATACAAAACAAGGACCT  1440
 461   L   H   R   F   L   T   I   P   R   L   E   E   L   Y   N   T   K   Q   G   P    480

1441  ACTAATACACTCTTGCATCATCTCGTCCAAGATGTGAAACAGCACCAGAGACACTCCTCA  1500
 481   T   N   T   L   L   H   H   L   V   Q   D   V   K   Q   H   Q   R   H   S   S    500

1501  GGAAATAGAAATGAGTCTGCAGAAAAGTACGCTGCACTCCCAGTTCATTAGAACTGCACAG  1560
 501   G   N   R   N   E   S   A   E   S   T   L   H   S   Q   F   I   R   T   A   Q    520

1561  CCATACAAATTCAAGGAAAAGTCTATAGTCCTTCATAAATCAAGGAAGAAGTCAAAAGAA  1620
 521   P   Y   K   F   K   E   K   S   I   V   L   H   K   S   R   K   K   S   K   E    540

1621  CAAAATGTATCAGATGACCCTGAGTCTACTGGCTTTCTTTACCCTTACAATGACCTGCTG  1680
 541   Q   N   V   S   D   D   P   E   S   T   G   F   L   Y   P   Y   N   D   L   L    560

1681  GTTTGGGCTGTGCTGATGAAAAGGCAGAAGATGGCTATGTTCTTCTGGCAGCATGGAGAG  1740
 561   V   W   A   V   L   M   K   R   Q   K   M   A   M   F   F   W   Q   H   G   E    580

1741  GAGGCCACGGTTAAAGCCGTGATTGCGTGTATCCTCTACCGGGCAATGGCCCATGAAGCT  1800
 581   E   A   T   V   K   A   V   I   A   C   I   L   Y   R   A   M   A   H   E   A    600
```

Figure 2C

```
1801 AAGGAGAGTCACATGGTGGATGATGCCTCAGAAGAGTTGAAGAATTACTCAAAACAGTTT 1860
 601  K   E   S   H   M   V   D   D   A   S   E   E   L   K   N   Y   S   K   Q   F    620

1861 GGCCAGCTGGCTCTGGACTTGTTGGAGAAGGCATTCAAGCAGAATGAGCGCATGGCCATG 1920
 621  G   Q   L   A   L   D   L   L   E   K   A   F   K   Q   N   E   R   M   A   M    640

1921 ACGCTGTTGACGTATGAACTCAGGAACTGGAGCAATTCGACCTGCCTGAAACTGGCCGTG 1980
 641  T   L   L   T   Y   E   L   R   N   W   S   N   S   T   C   L   K   L   A   V    660

1981 TCGGGAGGATTACGACCCTTTGTTTCACATACTTGTACCCAGATGCTACTGACAGACATG 2040
 661  S   G   G   L   R   P   F   V   S   H   T   C   T   Q   M   L   L   T   D   M    680

2041 TGGATGGGGAGGCTGAAAATGAGGAAAAACTCTTGGTTAAAGATTATTATAAGCATTATT 2100
 681  W   M   G   R   L   K   M   R   K   N   S   W   L   K   I   I   I   S   I   I    700

2101 TTACCACCCACCATTTTGACACTGGAATTTAAAAGCAAAGCTGAGATGTCACATGTTCCC 2160
 701  L   P   P   T   I   L   T   L   E   F   K   S   K   A   E   M   S   H   V   P    720

2161 CAGTCCCAGGACTTCCAATTTATGTGGTATTACAGTGACCAGAACGCCAGCAGTTCCAAA 2220
 721  Q   S   Q   D   F   Q   F   M   W   Y   Y   S   D   Q   N   A   S   S   S   K    740

2221 GAAAGTGCTTCTGTGAAAGAGTATGATTTGGAAAGGGGCCATGATGAGAAACTGGATGAA 2280
 741  E   S   A   S   V   K   E   Y   D   L   E   R   G   H   D   E   K   L   D   E    760

2281 AATCAGCATTTTGGTTTGGAAAGTGGGCACCAACACCTTCCGTGGACCAGGAAAGTCTAT 2340
 761  N   Q   H   F   G   L   E   S   G   H   Q   H   L   P   W   T   R   K   V   Y    780

2341 GAGTTCTACAGTGCTCCAATTGTCAAGTTTTGGTTTTATACGATGGCGTATTTGGCATTC 2400
 781  E   F   Y   S   A   P   I   V   K   F   W   F   Y   T   M   A   Y   L   A   F    800

2401 CTCATGCTGTTCACTTACACCGTGTTGGTGGAGATGCAGCCCCAGCCCAGCGTGCAGGAG 2460
 801  L   M   L   F   T   Y   T   V   L   V   E   M   Q   P   Q   P   S   V   Q   E    820

2461 TGGCTTGTTAGCATTTACATCTTCACCAATGCTATTGAGGTGGTCAGGGAGATCTGTATT 2520
 821  W   L   V   S   I   Y   I   F   T   N   A   I   E   V   V   R   E   I   C   I    840

2521 TCAGAACCTGGGAAGTTTACCCAAAAGGTGAAGGTATGGATTAGTGAGTACTGGAACTTA 2580
 841  S   E   P   G   K   F   T   Q   K   V   K   V   W   I   S   E   Y   W   N   L    860

2581 ACAGAAACTGTGGCCATTGGCCTGTTTTCAGCTGGCTTCGTCCTTCGATGGGGTGACCCT 2640
 861  T   E   T   V   A   I   G   L   F   S   A   G   F   V   L   R   W   G   D   P    880

2641 CCTTTTCACACAGCGGGAAGACTGATCTACTGCATAGACATCATATTCTGGTTCTCACGG 2700
 881  P   F   H   T   A   G   R   L   I   Y   C   I   D   I   I   F   W   F   S   R    900
```

Figure 2D

```
2701  CTCCTGGACTTCTTTGCTGTGAATCAACATGCAGGTCCATATGTGACCATGATTGCAAAA  2760
 901  L  L  D  F  F  A  V  N  Q  H  A  G  P  Y  V  T  M  I  A  K   920

2761  ATGACAGCAAACATGTTCTATATTGTGATCATCATGGCCATAGTCCTGCTGAGCTTTGGA  2820
 921  M  T  A  N  M  F  Y  I  V  I  I  M  A  I  V  L  L  S  F  G   940

2821  GTGGCACGCAAGGCCATCCTTTCGCCAAAAGAGCCACCATCTTGGAGTCTAGCTCGAGAT  2880
 941  V  A  R  K  A  I  L  S  P  K  E  P  P  S  W  S  L  A  R  D   960

2881  ATTGTATTTGAGCCATACTGGATGATATACGGAGAAGTCTATGCTGGAGAAATAGATGTT  2940
 961  I  V  F  E  P  Y  W  M  I  Y  G  E  V  Y  A  G  E  I  D  V   980

2941  TGTTCAAGCCAGCCATCCTGCCCTCCTGGTTCTTTTCTTACTCCATTCTTGCAAGCTGTC  3000
 981  C  S  S  Q  P  S  C  P  P  G  S  F  L  T  P  F  L  Q  A  V  1000

3001  TACCTCTTCGTGCAATATATCATCATGGTGAACCTGTTGATTGCTTTCTTCAACAACGTT  3060
1001  Y  L  F  V  Q  Y  I  I  M  V  N  L  L  I  A  F  F  N  N  V  1020

3061  TACTTAGATATGGAATCCATTTCAAATAACCTGTGGAAATACAACCGCTATCGCTACATC  3120
1021  Y  L  D  M  E  S  I  S  N  N  L  W  K  Y  N  R  Y  R  Y  I  1040

3121  ATGACCTACCACGAGAAGCCCTGGCTGCCCCCACCTCTCATCCTGCTGAGCCACGTGGGC  3180
1041  M  T  Y  H  E  K  P  W  L  P  P  P  L  I  L  L  S  H  V  G  1060

3181  CTTCTCCTCCGCCGCCTGTGCTGTCATCGAGCTCCTCACGACCAAGAAGAGGGTGACGTT  3240
1061  L  L  L  R  R  L  C  C  H  R  A  P  H  D  Q  E  E  G  D  V  1080

3241  GGATTAAAACTCTACCTCAGTAAGGAGGATCTGAAAAAACTTCATGATTTTGAGGAGCAG  3300
1081  G  L  K  L  Y  L  S  K  E  D  L  K  K  L  H  D  F  E  E  Q  1100

3301  TGCGTGGAAAAATACTTCCATGAGAAGATGGAAGATGTGAATTGTAGTTGTGAGGAACGA  3360
1101  C  V  E  K  Y  F  H  E  K  M  E  D  V  N  C  S  C  E  E  R  1120

3361  ATCCGAGTGACATCAGAAAGGGTTACAGAGATGTACTTCCAGCTGAAAGAAATGAATGAA  3420
1121  I  R  V  T  S  E  R  V  T  E  M  Y  F  Q  L  K  E  M  N  E  1140

3421  AAGGTGTCTTTTATAAAGGACTCCTTACTGTCTTTGGACAGCCAGGTGGGACACCTGCAG  3480
1141  K  V  S  F  I  K  D  S  L  L  S  L  D  S  Q  V  G  H  L  Q  1160

3481  GATCTCTCTGCCCTGACTGTGGATACCCTGAAAGTCCTTTCTGCTGTTGACACTTTGCAA  3540
1161  D  L  S  A  L  T  V  D  T  L  K  V  L  S  A  V  D  T  L  Q  1180

3541  GAGGATGAGGCTCTCCTGGCCAAGAGAAAGCATTCTACTTGCAAAAAACTTCCCCACAGC  3600
1181  E  D  E  A  L  L  A  K  R  K  H  S  T  C  K  K  L  P  H  S  1200
```

Figure 2E

```
3601  TGGAGCAATGTCATCTGTGCAGAGGTTCTAGGCAGCATGGAGATCGCTGGAGAGAAGAAA  3660
1201   W  S  N  V  I  C  A  E  V  L  G  S  M  E  I  A  G  E  K  K   1220

3661  TACCAGTATTATAGCATGCCCTCTTCTTTGCTGAGGAGCCTGGCTGGAGGCCGGCATCCC  3720
1221   Y  Q  Y  Y  S  M  P  S  S  L  L  R  S  L  A  G  G  R  H  P   1240

3721  CCAAGAGTGCAGAGGGGGGCACTTCTTGAGATTACAAACAGTAAAAGAGAGGCTACAAAT  3780
1241   P  R  V  Q  R  G  A  L  L  E  I  T  N  S  K  R  E  A  T  N   1260

3781  GTAAGAAATGACCAGGAAAGGCAAGAAACACAAAGTAGTATAGTGGTTTCTGGGGTGTCT  3840
1261   V  R  N  D  Q  E  R  Q  E  T  Q  S  S  I  V  V  S  G  V  S   1280

3841  CCTAACAGGCAAGCACACTCAAAGTATGGCCAGTTTCTTCTGGTCCCCTCTAATCTAAAG  3900
1281   P  N  R  Q  A  H  S  K  Y  G  Q  F  L  L  V  P  S  N  L  K   1300

3901  CGAGTTCCTTTTTCAGCAGAAACTGTCTTGCCTCTGTCCAGACCCTCTGTGCCAGATGTG  3960
1301   R  V  P  F  S  A  E  T  V  L  P  L  S  R  P  S  V  P  D  V   1320

3961  CTGGCAACTGAACAGGACATCCAGACTGAGGTTCTTGTTCATCTGACTGGGCAGACCCCA  4020
1321   L  A  T  E  Q  D  I  Q  T  E  V  L  V  H  L  T  G  Q  T  P   1340

4021  GTTGTCTCTGACTGGGCATCAGTGGATGAACCCAAGGAAAAGCACGAGCCTATTGCTCAC  4080
1341   V  V  S  D  W  A  S  V  D  E  P  K  E  K  H  E  P  I  A  H   1360

4081  TTACTGGATGGACAAGACAAGGCAGAGCAAGTGCTACCCACTTTGAGTTGCACACCTGAA  4140
1361   L  L  D  G  Q  D  K  A  E  Q  V  L  P  T  L  S  C  T  P  E   1380

4141  CCCATGACAATGAGCTCCCCTCTTTCCCAAGCCAAGATCATGCAAACTGGAGGTGGATAT  4200
1381   P  M  T  M  S  S  P  L  S  Q  A  K  I  M  Q  T  G  G  G  Y   1400

4201  GTAAACTGGGCATTTTCAGAAGGTGATGAAACTGGTGTGTTTAGCATCAAGAAAAAGTGG  4260
1401   V  N  W  A  F  S  E  G  D  E  T  G  V  F  S  I  K  K  K  W   1420

4261  CAAACCTGCTTGCCCTCCACTTGTGACAGTGATTCCTCTCGGAGTGAACAGCACCAGAAG  4320
1421   Q  T  C  L  P  S  T  C  D  S  D  S  S  R  S  E  Q  H  Q  K   1440

4321  CAGGCCCAGGACAGCTCCCTATCTGATAACTCAACAAGATCGGCCCAGAGTAGTGAATGC  4380
1441   Q  A  Q  D  S  S  L  S  D  N  S  T  R  S  A  Q  S  S  E  C   1460

4381  TCAGAGGTGGGACCATGGCTTCAGCCAAACACATCCTTTTGGATCAATCCTCTCCGCAGA  4440
1461   S  E  V  G  P  W  L  Q  P  N  T  S  F  W  I  N  P  L  R  R   1480

4441  TACAGGCCCTTCGCTAGGAGTCATAGTTTTAGATTCCATAAGGAGGAGAAATTGATGAAG  4500
1481   Y  R  P  F  A  R  S  H  S  F  R  F  H  K  E  E  K  L  M  K   1500
```

Figure 2F

```
4501 ATCTGTAAGATTAAAAATCTTTCAGGCTCTTCAGAAATAGGGCAGGGAGCATGGGTCAAA 4560
1501  I   C   K   I   K   N   L   S   G   S   S   E   I   G   Q   G   A   W   V   K   1520

4561 GCGAAAATGCTAACCAAAGACAGGAGACTGTCAAAGAAAAAGAAGAATACTCAAGGACTC 4620
1521  A   K   M   L   T   K   D   R   R   L   S   K   K   K   K   N   T   Q   G   L   1540

4621 CAGGTGCCAATCATAACAGTCAATGCCTGCTCTCAGAGTGACCAGTTGAATCCAGAGCCA 4680
1541  Q   V   P   I   I   T   V   N   A   C   S   Q   S   D   Q   L   N   P   E   P   1560

4681 GGAGAAAACAGCATCTCTGAAGAGGAGTACAGCAAGAACTGGTTCACAGTGTCCAAATTT 4740
1561  G   E   N   S   I   S   E   E   E   Y   S   K   N   W   F   T   V   S   K   F   1580

4741 AGTCACACAGGTGTAGAACCTTACATACATCAGAAAATGAAAACTAAAGAAATTGGACAA 4800
1581  S   H   T   G   V   E   P   Y   I   H   Q   K   M   K   T   K   E   I   G   Q   1600

4801 TGTGCTATACAAATCAGTGATTACCTAAAGCAGTCTCAAGAGGATCTCAGCAAAAACTCT 4860
1601  C   A   I   Q   I   S   D   Y   L   K   Q   S   Q   E   D   L   S   K   N   S   1620

4861 TTGTGGAATTCCAGGAGCACCAACCTCAATAGGAACTCCCTGCTGAAAAGTTCAATTGGA 4920
1621  L   W   N   S   R   S   T   N   L   N   R   N   S   L   L   K   S   S   I   G   1640

4921 GTTGACAAGATCTCAGCCTCCTTAAAAAGCCCTCAAGAGCCTCACCATCATTATTCAGCC 4980
1641  V   D   K   I   S   A   S   L   K   S   P   Q   E   P   H   H   H   Y   S   A   1660

4981 ATTGAAAGGAATAATTTAATGAGGCTTTCTCAGACCATACCATTTACACCAGTCCAACTG 5040
1661  I   E   R   N   N   L   M   R   L   S   Q   T   I   P   F   T   P   V   Q   L   1680

5041 TTTGCAGGAGAAGAAATAACTGTCTACAGGTTGGAGGAGAGTTCCCCTTTAAACCTTGAT 5100
1681  F   A   G   E   E   I   T   V   Y   R   L   E   E   S   S   P   L   N   L   D   1700

5101 AAAAGCATGTCCTCTTGGTCTCAGCGTGGGAGAGCGGCAATGATCCAGGTATTGTCCCGA 5160
1701  K   S   M   S   S   W   S   Q   R   G   R   A   A   M   I   Q   V   L   S   R   1720

5161 GAGGAGATGGATGGGGGCCTCCGTAAAGCTATGAGAGTCGTCAGCACTTGGTCTGAGGAT 5220
1721  E   E   M   D   G   G   L   R   K   A   M   R   V   V   S   T   W   S   E   D   1740

5221 GACATTCTCAAGCCGGGACAAGTTTTCATTGTCAAGTCCTTTCTTCCTGAGGTTGTGCGG 5280
1741  D   I   L   K   P   G   Q   V   F   I   V   K   S   F   L   P   E   V   V   R   1760

5281 ACATGGCATAAAATCTTCCAGGAGAGCACTGTGCTTCATCTTTGCCTCAGGGAAATTCAA 5340
1761  T   W   H   K   I   F   Q   E   S   T   V   L   H   L   C   L   R   E   I   Q   1780

5341 CAACAAAGAGCTGCTCAAAAATTGATCTATACCTTCAACCAAGTGAAACCACAAACCATA 5400
1781  Q   Q   R   A   A   Q   K   L   I   Y   T   F   N   Q   V   K   P   Q   T   I   1800
```

Figure 2G

```
5401  CCCTACACACCAAGGTTCCTGGAAGTTTTCTTAATCTACTGCCATTCAGCCAACCAGTGG  5460
1801  P   Y   T   P   R   F   L   E   V   F   L   I   Y   C   H   S   A   N   Q   W   1820

5461  TTGACCATTGAGAAGTATATGACAGGGGAGTTCCGGAAGTATAACAACAACAATGGTGAT  5520
1821  L   T   I   E   K   Y   M   T   G   E   F   R   K   Y   N   N   N   G   D   1840

5521  GAAATCACCCCCACCAACACCCTGGAGGAGCTGATGTTGGCTTTCTCTCACTGGACCTAT  5580
1841  E   I   T   P   T   N   T   L   E   E   L   M   L   A   F   S   H   W   T   Y   1860

5581  GAGTACACTCGGGGAGAGCTGCTGGTTTTAGATTTGCAAGGTGTTGGAGAAAATTTGACA  5640
1861  E   Y   T   R   G   E   L   L   V   L   D   L   Q   G   V   G   E   N   L   T   1880

5641  GATCCATCTGTTATAAAACCTGAAGTCAAACAATCAAGAGGAATGGTGTTTGGACCGGCC  5700
1881  D   P   S   V   I   K   P   E   V   K   Q   S   R   G   M   V   F   G   P   A   1900

5701  AATTTGGGGGAAGATGCAATTAGAAACTTCATTGCAAAACATCATTGTAACTCCTGCTGC  5760
1901  N   L   G   E   D   A   I   R   N   F   I   A   K   H   H   C   N   S   C   C   1920

5761  CGGAAGCTCAAACTCCCGGATTTAAAAAGAAATGACTATTCCCCTGAAAGGATAAATTCC  5820
1921  R   K   L   K   L   P   D   L   K   R   N   D   Y   S   P   E   R   I   N   S   1940

5821  ACCTTTGGACTTGAGATAAAAATAGAATCAGCTGAGGAGCCTCCAGCAAGGGAGACGGGT  5880
1941  T   F   G   L   E   I   K   I   E   S   A   E   E   P   P   A   R   E   T   G   1960

5881  AGAAATTCCCCAGAAGATGATATGCAACTATAA   5913
1961  R   N   S   P   E   D   D   M   Q   L       1970
```

Figure 3A

```
  1  atgattatcctatctaagtcccagaaatcctggattaaaggagtatttgacaagagagaa   60
  1   M  I  I  L  S  K  S  Q  K  S  W  I  K  G  V  F  D  K  R  E    20

61  tgtagcacaatcatacccagctcaaaaaatcctcacagatgtactccagtatgccaagtc  120
 21   C  S  T  I  I  P  S  S  K  N  P  H  R  C  T  P  V  C  Q  V    40

121  tgccagaatttaatcaggtgttactgtggccgactgattggagaccatgctgggatagat  180
 41   C  Q  N  L  I  R  C  Y  C  G  R  L  I  G  D  H  A  G  I  D    60

181  tattcctggaccatctcagctgccaagggtaaagaaagtgaacaatggtctgttgaaaag  240
 61   Y  S  W  T  I  S  A  A  K  G  K  E  S  E  Q  W  S  V  E  K    80

241  cacacaacgaaaagcccaacagatactttggcacgattaatttccaagatggagagcac   300
 81   H  T  T  K  S  P  T  D  T  F  G  T  I  N  F  Q  D  G  E  H   100

301  acccatcatgccaagtatattagaacttcttatgatacaaaactggatcatctgttacat  360
101   T  H  H  A  K  Y  I  R  T  S  Y  D  T  K  L  D  H  L  L  H   120

361  ttaatgttgaaagagtggaaaatggaactgcccaagcttgtgatctcagtccatgggggc  420
121   L  M  L  K  E  W  K  M  E  L  P  K  L  V  I  S  V  H  G  G   140

421  atccagaactttactatgccctctaaatttaaagagatttcagccaaggtttggttaaa   480
141   I  Q  N  F  T  M  P  S  K  F  K  E  I  F  S  Q  G  L  V  K   160

481  gctgcagagacaacaggagcgtggataataactgaaggcatcaatacaggagtgtccaag  540
161   A  A  E  T  T  G  A  W  I  I  T  E  G  I  N  T  G  V  S  K   180

541  catgttggggatgccttgaaatcccattcctctcattccttgagaaaaatctggacagtt  600
181   H  V  G  D  A  L  K  S  H  S  S  H  S  L  R  K  I  W  T  V   200

601  ggaatccctccttggggtgtcattgagaaccagagagaccttattggaaaagatgtggtg  660
201   G  I  P  P  W  G  V  I  E  N  Q  R  D  L  I  G  K  D  V  V   220

661  tgcctgtaccagactctggataacccctcagcaagctcacaacactcaacagcatgcac  720
221   C  L  Y  Q  T  L  D  N  P  L  S  K  L  T  T  L  N  S  M  H   240

721  tcgcacttcatcctgtctgatgatgggaccgtgggcaagtatggaaatgaaatgaagctc  780
241   S  H  F  I  L  S  D  D  G  T  V  G  K  Y  G  N  E  M  K  L   260

781  agaaggaacctggagaagtacctctctctgcagaaaatacactgccgctcaagacaaggc  840
261   R  R  N  L  E  K  Y  L  S  L  Q  K  I  H  C  R  S  R  Q  G   280

841  gtgccggtcgtggggctggtggtggaaggcggtcccaacgtcatcctgtcagtgtgggag  900
281   V  P  V  V  G  L  V  V  E  G  G  P  N  V  I  L  S  V  W  E   300
```

Figure 3B

```
 901   actgtcaaggacaaggacccagtggtggtgtgtgagggcacaggtagggcggctgacctc   960
 301    T  V  K  D  K  D  P  V  V  V  C  E  G  T  G  R  A  A  D  L    320

961   ctggccttcacacacaaacacctggcagatgaagggatgctgcgacctcaggtgaaagag  1020
 321    L  A  F  T  H  K  H  L  A  D  E  G  M  L  R  P  Q  V  K  E    340

1021   gagatcatctgcatgattcagaacacttttcaactttagtcttaaacagtccaagcacctt  1080
 341    E  I  I  C  M  I  Q  N  T  F  N  F  S  L  K  Q  S  K  H  L    360

1081   ttccaaattctaatggagtgtatggttcacagggattgtattaccatatttgatgctgac  1140
 361    F  Q  I  L  M  E  C  M  V  H  R  D  C  I  T  I  F  D  A  D    380

1141   tctgaagagcagcaagacctggacttagcaatcctaacagctttgctgaagggcacaaat  1200
 381    S  E  E  Q  Q  D  L  D  L  A  I  L  T  A  L  L  K  G  T  N    400

1201   ttatcagcgtcagagcaattaaatctggcaatggcttgggacagggtggacattgccaag  1260
 401    L  S  A  S  E  Q  L  N  L  A  M  A  W  D  R  V  D  I  A  K    420

1261   aaacatatcctaatttatgaacaacactggaagcctgatgccctggaacaagcaatgtca  1320
 421    K  H  I  L  I  Y  E  Q  H  W  K  P  D  A  L  E  Q  A  M  S    440

1321   gatgctttagtgatggatcgggtggattttgtgaagctcttaatagaatatggagtgaac  1380
 441    D  A  L  V  M  D  R  V  D  F  V  K  L  L  I  E  Y  G  V  N    460

1381   ctccatcgctttcttaccatccctcgactggaagagctctacaatacaaaacaaggacct  1440
 461    L  H  R  F  L  T  I  P  R  L  E  E  L  Y  N  T  K  Q  G  P    480

1441   actaatacactcttgcatcatctcgtccaagatgtgaaacaggaaaagtctatagtcctt  1500
 481    T  N  T  L  L  H  H  L  V  Q  D  V  K  Q  E  K  S  I  V  L    500

1501   cataaatcaaggaagaagtcaaaagaacaaaatgtatcagatgaccctgagtctactggc  1560
 501    H  K  S  R  K  K  S  K  E  Q  N  V  S  D  D  P  E  S  T  G    520

1561   tttcttttaccccttacaatgacctgctggtttgggctgtgctgatgaaaaggcagaagatg  1620
 521    F  L  Y  P  Y  N  D  L  L  V  W  A  V  L  M  K  R  Q  K  M    540

1621   gctatgttcttctggcagcatggagaggaggccacggttaaagccgtgattgcgtgtatc  1680
 541    A  M  F  F  W  Q  H  G  E  E  A  T  V  K  A  V  I  A  C  I    560

1681   ctctaccgggcaatggcccatgaagctaaggagagtcacatggtggatgatgcctcagaa  1740
 561    L  Y  R  A  M  A  H  E  A  K  E  S  H  M  V  D  D  A  S  E    580

1741   gagttgaagaattactcaaaacagtttggccagctggctctggacttgttggagaaggca  1800
 581    E  L  K  N  Y  S  K  Q  F  G  Q  L  A  L  D  L  L  E  K  A    600
```

Figure 3C

```
1801  ttcaagcagaatgagcgcatggccatgacgctgttgacgtatgaactcaggaactggagc  1860
 601  F   K   Q   N   E   R   M   A   M   T   L   L   T   Y   E   L   R   N   W   S    620

1861  aattcgacctgcctgaaactggccgtgtcgggaggattacgacccttttgtttcacatact  1920
 621  N   S   T   C   L   K   L   A   V   S   G   G   L   R   P   F   V   S   H   T    640

1921  tgtacccagatgctactgacagacatgtggatggggaggctgaaaatgaggaaaaactct  1980
 641  C   T   Q   M   L   L   T   D   M   W   M   G   R   L   K   M   R   K   N   S    660

1981  tggttaaagattattataagcattattttaccacccaccatttttgacactggaatttaaa  2040
 661  W   L   K   I   I   I   S   I   I   L   P   P   T   I   L   T   L   E   F   K    680

2041  agcaaagctgagatgtcacatgttccccagtcccaggacttccaatttatgtggtattac  2100
 681  S   K   A   E   M   S   H   V   P   Q   S   Q   D   F   Q   F   M   W   Y   Y    700

2101  agtgaccagaacgccagcagttccaaagaaagtgcttctgtgaaagagtatgatttggaa  2160
 701  S   D   Q   N   A   S   S   S   K   E   S   A   S   V   K   E   Y   D   L   E    720

2161  aggggccatgatgagaaactggatgaaaatcagcattttggtttggaaagtgggcaccaa  2220
 721  R   G   H   D   E   K   L   D   E   N   Q   H   F   G   L   E   S   G   H   Q    740

2221  caccttccgtggaccaggaaagtctatgagttctacagtgctccaattgtcaagttttgg  2280
 741  H   L   P   W   T   R   K   V   Y   E   F   Y   S   A   P   I   V   K   F   W    760

2281  ttttatacgatggcgtatttggcattcctcatgctgttcacttacaccgtgttggtggag  2340
 761  F   Y   T   M   A   Y   L   A   F   L   M   L   F   T   Y   T   V   L   V   E    780

2341  atgcagccccagcccagcgtgcaggagtggcttgttagcatttacatcttcaccaatgct  2400
 781  M   Q   P   Q   P   S   V   Q   E   W   L   V   S   I   Y   I   F   T   N   A    800

2401  attgaggtggtcagggagatctgtatttcagaacctgggaagtttacccaaaaggtgaag  2460
 801  I   E   V   V   R   E   I   C   I   S   E   P   G   K   F   T   Q   K   V   K    820

2461  gtatggattagtgagtactggaacttaacagaaactgtggccattggcctgttttcagct  2520
 821  V   W   I   S   E   Y   W   N   L   T   E   T   V   A   I   G   L   F   S   A    840

2521  ggcttcgtccttcgatggggtgaccctccttttcacacagcgggaagactgatctactgc  2580
 841  G   F   V   L   R   W   G   D   P   P   F   H   T   A   G   R   L   I   Y   C    860

2581  atagacatcatattctggttctcacggctcctggacttctttgctgtgaatcaacatgca  2640
 861  I   D   I   I   F   W   F   S   R   L   L   D   F   F   A   V   N   Q   H   A    880

2641  ggtccatatgtgaccatgattgcaaaaatgacagcaaacatgttctatattgtgatcatc  2700
 881  G   P   Y   V   T   M   I   A   K   M   T   A   N   M   F   Y   I   V   I   I    900
```

Figure 3D

```
2701  atggccatagtcctgctgagctttggagtggcacgcaaggccatcctttcgccaaaagag  2760
 901   M  A  I  V  L  L  S  F  G  V  A  R  K  A  I  L  S  P  K  E   920

2761  ccaccatcttggagtctagctcgagatattgtatttgagccatactggatgatatacgga  2820
 921   P  P  S  W  S  L  A  R  D  I  V  F  E  P  Y  W  M  I  Y  G   940

2821  gaagtctatgctggagaaatagatgtttgttcaagccagccatcctgccctcctggttct  2880
 941   E  V  Y  A  G  E  I  D  V  C  S  S  Q  P  S  C  P  P  G  S   960

2881  tttcttactccattcttgcaagctgtctacctcttcgtgcaatatatcatcatggtgaac  2940
 961   F  L  T  P  F  L  Q  A  V  Y  L  F  V  Q  Y  I  I  M  V  N   980

2941  ctgttgattgctttcttcaacaacgtttacttagatatggaatccatttcaaataacctg  3000
 981   L  L  I  A  F  F  N  N  V  Y  L  D  M  E  S  I  S  N  N  W  1000

3001  tggaaatacaaccgctatcgctacatcatgacctaccacgagaagccctggctgccccca  3060
1001   W  K  Y  N  R  Y  R  Y  I  M  T  Y  H  E  K  P  W  L  P  P  1020

3061  cctctcatcctgctgagccacgtgggccttctcctccgccgcctgtgctgtcatcgagct  3120
1021   P  L  I  L  L  S  H  V  G  L  L  L  R  R  L  C  C  H  R  A  1040

3121  cctcacgaccaagaagagggtgacgttggattaaaaactctacctcagtaaggaggatctg  3180
1041   P  H  D  Q  E  E  G  D  V  G  L  K  L  Y  L  S  K  E  D  L  1060

3181  aaaaaacttcatgattttgaggagcagtgcgtggaaaaatacttccatgagaagatggaa  3240
1061   K  K  L  H  D  F  E  E  Q  C  V  E  K  Y  F  H  E  K  M  E  1080

3241  gatgtgaattgtagttgtgaggaacgaatccgagtgacatcagaaagggttacagagatg  3300
1081   D  V  N  C  S  C  E  E  R  I  R  V  T  S  E  R  V  T  E  M  1100

3301  tacttccagctgaaagaaatgaatgaaaaggtgtcttttataaaggactccttactgtct  3360
1101   Y  F  Q  L  K  E  M  N  E  K  V  S  F  I  K  D  S  L  L  S  1120

3361  ttggacagccaggtgggacacctgcaggatctctctgccctgactgtggataccctgaaa  3420
1121   L  D  S  Q  V  G  H  L  Q  D  L  S  A  L  T  V  D  T  L  K  1140

3421  gtcctttctgctgttgacactttgcaagaggatgaggctctcctggccaagagaaagcat  3480
1141   V  L  S  A  V  D  T  L  Q  E  D  E  A  L  L  A  K  R  K  H  1160

3481  tctacttgcaaaaaacttccccacagctggagcaatgtcatctgtgcagaggttctaggc  3540
1161   S  T  C  K  K  L  P  H  S  W  S  N  V  I  C  A  E  V  L  G  1180

3541  agcatggagatcgctggagagaagaaataccagtattatagcatgccctcttctttgctg  3600
1181   S  M  E  I  A  G  E  K  K  Y  Q  Y  Y  S  M  P  S  S  L  L  1200
```

Figure 3E

```
3601  aggagcctggctggaggccggcatcccccaagagtgcagaggggggcacttcttgagatt  3660
1201   R   S   L   A   G   G   R   H   P   P   R   V   Q   R   G   A   L   L   E   I   1220

3661  acaaacagtaaaagagaggctacaaatgtaagaaatgaccaggaaaggcaagaaacacaa  3720
1221   T   N   S   K   R   E   A   T   N   V   R   N   D   Q   E   R   Q   E   T   Q   1240

3721  agtagtatagtggtttctggggtgtctcctaacaggcaagcacactcaaagtatggccag  3780
1241   S   S   I   V   V   S   G   V   S   P   N   R   Q   A   H   S   K   Y   G   Q   1260

3781  tttcttctggtccctctaatctaaagcgagttccttttcagcagaaactgtcttgcct  3840
1261   F   L   L   V   P   S   N   L   K   R   V   P   F   S   A   E   T   V   L   P   1280

3841  ctgtccagaccctctgtgccagatgtgctggcaactgaacaggacatccagactgaggtt  3900
1281   L   S   R   P   S   V   P   D   V   L   A   T   E   Q   D   I   Q   T   E   V   1300

3901  cttgttcatctgactgggcagaccccagttgtctctgactgggcatcagtggatgaaccc  3960
1301   L   V   H   L   T   G   Q   T   P   V   V   S   D   W   A   S   V   D   E   P   1320

3961  aaggaaaagcacgagcctattgctcacttactggatggacaagacaaggcagagcaagtg  4020
1321   K   E   K   H   E   P   I   A   H   L   L   D   G   Q   D   K   A   E   Q   V   1340

4021  ctacccactttgagttgcacacctgaacccatgacaatgagctcccctctttcccaagcc  4080
1341   L   P   T   L   S   C   T   P   E   P   M   T   M   S   S   P   L   S   Q   A   1360

4081  aagatcatgcaaactggaggtggatatgtaaactgggcattttcagaaggtgatgaaact  4140
1361   K   I   M   Q   T   G   G   G   Y   V   N   W   A   F   S   E   G   D   E   T   1380

4141  ggtgtgtttagcatcaagaaaaagtggcaaacctgcttgccctccacttgtgacagtgat  4200
1381   G   V   F   S   I   K   K   K   W   Q   T   C   L   P   S   T   C   D   S   D   1400

4201  tcctctcggagtgaacagcaccagaagcaggcccaggacagctccctatctgataactca  4260
1401   S   S   R   S   E   Q   H   Q   K   Q   A   Q   D   S   S   L   S   D   N   S   1420

4261  acaagatcggcccagagtagtgaatgctcagaggtgggaccatggcttcagccaaacaca  4320
1421   T   R   S   A   Q   S   S   E   C   S   E   V   G   P   W   L   Q   P   N   T   1440

4321  tccttttggatcaatcctctccgcagatacaggcccttcgctaggagtcatagttttaga  4380
1441   S   F   W   I   N   P   L   R   R   Y   R   P   F   A   R   S   H   S   F   R   1460

4381  ttccataaggaggagaaattgatgaagatctgtaagattaaaaatctttcaggctcttca  4440
1461   F   H   K   E   E   K   L   M   K   I   C   K   I   K   N   L   S   G   S   S   1480

4441  gaaatagggcagggagcatgggtcaaagcgaaaatgctaaccaaagacaggagactgtca  4500
1481   E   I   G   Q   G   A   W   V   K   A   K   M   L   T   K   D   R   R   L   S   1500
```

Figure 3F

```
4501  aagaaaaagaagaatactcaaggactccaggtgccaatcataacagtcaatgcctgctct  4560
1501  K   K   K   N   T   Q   G   L   Q   V   P   I   I   T   V   N   A   C   S    1520

4561  cagagtgaccagttgaatccagagccaggagaaaacagcatctctgaagaggagtacagc  4620
1521  Q   S   D   Q   L   N   P   E   P   G   E   N   S   I   S   E   E   E   Y   S   1540

4621  aagaactggttcacagtgtccaaatttagtcacacaggtgtagaaccttacatacatcag  4680
1541  K   N   W   F   T   V   S   K   F   S   H   T   G   V   E   P   Y   I   H   Q   1560

4681  aaaatgaaaactaaagaaattggacaatgtgctatacaaatcagtgattacctaaagcag  4740
1561  K   M   K   T   K   E   I   G   Q   C   A   I   Q   I   S   D   Y   L   K   Q   1580

4741  tctcaagaggatctcagcaaaaactctttgtggaattccaggagcaccaacctcaatagg  4800
1581  S   Q   E   D   L   S   K   N   S   L   W   N   S   R   T   N   L   N   R   1600

4801  aactccctgctgaaaagttcaattggagttgacaagatctcagcctccttaaaaagccct  4860
1601  N   S   L   L   K   S   S   I   G   V   D   K   I   S   A   S   L   K   S   P   1620

4861  caagagcctcaccatcattattcagccattgaaaggaataatttaatgaggctttctcag  4920
1621  Q   E   P   H   H   H   Y   S   A   I   E   R   N   N   L   M   R   L   S   Q   1640

4921  accataccatttacaccagtccaactgtttgcaggagaagaaataactgtctacaggttg  4980
1641  T   I   P   F   T   P   V   Q   L   F   A   G   E   E   I   T   V   Y   R   L   1660

4981  gaggagagttccccttta aaccttgataaaagcatgtcctcttggtctcagcgtgggaga  5040
1661  E   E   S   S   P   L   N   L   D   K   S   M   S   S   W   S   Q   R   G   R   1680

5041  gcggcaatgatccaggtattgtcccgagaggagatggatggggcctccgtaaagctatg  5100
1681  A   A   M   I   Q   V   L   S   R   E   E   M   D   G   G   L   R   K   A   M   1700

5101  agagtcgtcagcacttggtctgaggatgacattctcaagccgggacaagttttcattgtc  5160
1701  R   V   V   S   T   W   S   E   D   D   I   L   K   P   G   Q   V   F   I   V   1720

5161  aagtcctttcttcctgaggttgtgcggacatggcataaaatcttccaggagagcactgtg  5220
1721  K   S   F   L   P   E   V   V   R   T   W   H   K   I   F   Q   E   S   T   V   1740

5221  cttcatctttgcctcagggaaattcaacaacaaagagctgctcaaaaattgatctatacc  5280
1741  L   H   L   C   L   R   E   I   Q   Q   Q   R   A   A   Q   K   L   I   Y   T   1760

5281  ttcaaccaagtgaaaccacaaaccatacccta cacaccaaggttcctggaagttttctta  5340
1761  F   N   Q   V   K   P   Q   T   I   P   Y   T   P   R   F   L   E   V   F   L   1780

5341  atctactgccattcagccaaccagtggttgaccattgagaagtatatgacaggggagttc  5400
1781  I   Y   C   H   S   A   N   Q   W   L   T   I   E   K   Y   M   T   G   E   F   1800
```

Figure 3G

```
5401 cggaagtataacaacaacaatggtgatgaaatcacccccaccaacaccctggaggagctg 5460
1801  R   K   Y   N   N   N   G   D   E   I   T   P   T   N   T   L   E   E   L   1820

5461 atgttggctttctctcactggacctatgagtacactcggggagagctgctggtttagat 5520
1821  M   L   A   F   S   H   W   T   Y   E   Y   T   R   G   E   L   L   V   L   D   1840

5521 ttgcaaggtgttggagaaaatttgacagatccatctgttataaaacctgaagtcaaacaa 5580
1841  L   Q   G   V   G   E   N   L   T   D   P   S   V   I   K   P   E   V   K   Q   1860

5581 tcaagaggaatggtgtttggaccggccaatttgggggaagatgcaattagaaacttcatt 5640
1861  S   R   G   M   V   F   G   P   A   N   L   G   E   D   A   I   R   N   F   I   1880

5641 gcaaaacatcattgtaactcctgctgccggaagctcaaactcccggatttaaaaagaaat 5700
1881  A   K   H   H   C   N   S   C   C   R   L   K   L   P   D   L   K   R   N   1900

5701 gactattcccctgaaaggataaaattccacctttggacttgagataaaaatagaatcagct 5760
1901  D   Y   S   P   E   R   I   N   S   T   F   G   L   E   I   K   I   E   S   A   1920

5761 gaggagcctccagcaagggagacgggtagaaattccccagaagatgatatgcaactataa 5820
1921  E   E   P   P   A   R   E   T   G   R   N   S   P   E   D   D   M   Q   L   1939
```

Figure 4A

```
  1 ATGATTATCCTATCTAAGTCCCAGAAATCCTGGATTAAAGGAGTATTTGACAAGAGAGAA   60
  1 M  I  I  L  S  K  S  Q  K  S  W  I  K  G  V  F  D  K  R  E   20

61 TGTAGCACAATCATACCCAGCTCAAAAAATCCTCACAGATGTACTCCAGTATGCCAAGTC  120
 21 C  S  T  I  I  P  S  S  K  N  P  H  R  C  T  P  V  C  Q  V   40

121 TGCCAGAATTTAATCAGGTGTTACTGTGGCCGACTGATTGGAGACCATGCTGGGATAGAT  180
 41 C  Q  N  L  I  R  C  Y  C  G  R  L  I  G  D  H  A  G  I  D   60

181 TATTCCTGGACCATCTCAGCTGCCAAGGGTAAAGAAAGTGAACAATGGTCTGTTGAAAAG  240
 61 Y  S  W  T  I  S  A  A  K  G  K  E  S  E  Q  W  S  V  E  K   80

241 CACACAACGAAAAGCCCAACAGATACTTTTGGCACGATTAATTTCCAAGATGGAGAGCAC  300
 81 H  T  T  K  S  P  T  D  T  F  G  T  I  N  F  Q  D  G  E  H  100

301 ACCCATCATGCCAAGTATATTAGAACTTCTTATGATACAAAACTGGATCATCTGTTACAT  360
101 T  H  H  A  K  Y  I  R  T  S  Y  D  T  K  L  D  H  L  L  H  120

361 TTAATGTTGAAAGAGTGGAAAATGGAACTGCCCAAGCTTGTGATCTCAGTCCATGGGGGC  420
121 L  M  L  K  E  W  K  M  E  L  P  K  L  V  I  S  V  H  G  G  140

421 ATCCAGAACTTTACTATGCCCTCTAAATTTAAAGAGATTTTCAGCCAAGGTTTGGTTAAA  480
141 I  Q  N  F  T  M  P  S  K  F  K  E  I  F  S  Q  G  L  V  K  160

481 GCTGCAGAGACAACAGGAGCGTGGATAATAACTGAAGGCATCAATACAGGAGTGTCCAAG  540
161 A  A  E  T  T  G  A  W  I  I  T  E  G  I  N  T  G  V  S  K  180

541 CATGTTGGGGATGCCTTGAAATCCCATTCCTCTCATTCCTTGAGAAAAATCTGGACAGTT  600
181 H  V  G  D  A  L  K  S  H  S  S  H  S  L  R  K  I  W  T  V  200

601 GGAATCCCTCCTTGGGGTGTCATTGAGAACCAGAGAGACCTTATTGGAAAAGATGTGGTG  660
201 G  I  P  P  W  G  V  I  E  N  Q  R  D  L  I  G  K  D  V  V  220

661 TGCCTGTACCAGACTCTGGATAACCCCCTCAGCAAGCTCACAACACTCAACAGCATGCAC  720
221 C  L  Y  Q  T  L  D  N  P  L  S  K  L  T  T  L  N  S  M  H  240

721 TCGCACTTCATCCTGTCTGATGATGGGACCGTGGGCAAGTATGGAAATGAAATGAAGCTC  780
241 S  H  F  I  L  S  D  D  G  T  V  G  K  Y  G  N  E  M  K  L  260

781 AGAAGGAACCTGGAGAAGTACCTCTCTCTGCAGAAAATACACTGCCGCTCAAGACAAGGC  840
261 R  R  N  L  E  K  Y  L  S  L  Q  K  I  H  C  R  S  R  Q  G  280

841 GTGCCGGTCGTGGGGCTGGTGGTGGAAGGCGGTCCCAACGTCATCCTGTCAGTGTGGGAG  900
281 V  P  V  V  G  L  V  V  E  G  G  P  N  V  I  L  S  V  W  E  300
```

Figure 4B

```
 901  ACTGTCAAGGACAAGGACCCAGTGGTGGTGTGTGAGGGCACAGGTAGGGCGGCTGACCTC   960
 301   T  V  K  D  K  D  P  V  V  V  C  E  G  T  G  R  A  A  D  L    320

961  CTGGCCTTCACACACAAACACCTGGCAGATGAAGGGATGCTGCGACCTCAGGTGAAAGAG  1020
 321   L  A  F  T  H  K  H  L  A  D  E  G  M  L  R  P  Q  V  K  E    340

1021  GAGATCATCTGCATGATTCAGAACACTTTCAACTTTAGTCTTAAACAGTCCAAGCACCTT  1080
 341   E  I  I  C  M  I  Q  N  T  F  N  F  S  L  K  Q  S  K  H  L    360

1081  TTCCAAATTCTAATGGAGTGTATGGTTCACAGGGATTGTATTACCATATTTGATGCTGAC  1140
 361   F  Q  I  L  M  E  C  M  V  H  R  D  C  I  T  I  F  D  A  D    380

1141  TCTGAAGAGCAGCAAGACCTGGACTTAGCAATCCTAACAGCTTTGCTGAAGGGCACAAAT  1200
 381   S  E  E  Q  Q  D  L  D  L  A  I  L  T  A  L  L  K  G  T  N    400

1201  TTATCAGCGTCAGAGCAATTAAATCTGGCAATGGCTTGGGACAGGGTGGACATTGCCAAG  1260
 401   L  S  A  S  E  Q  L  N  L  A  M  A  W  D  R  V  D  I  A  K    420

1261  AAACATATCCTAATTTATGAACAACACTGGAAGCCTGATGCCCTGGAACAAGCAATGTCA  1320
 421   K  H  I  L  I  Y  E  Q  H  W  K  P  D  A  L  E  Q  A  M  S    440

1321  GATGCTTTAGTGATGGATCGGGTGGATTTTGTGAAGCTCTTAATAGAATATGGAGTGAAC  1380
 441   D  A  L  V  M  D  R  V  D  F  V  K  L  L  I  E  Y  G  V  N    460

1381  CTCCATCGCTTTCTTACCATCCCTCGACTGGAAGAGCTCTACAATACAAAACAAGGACCT  1440
 461   L  H  R  F  L  T  I  P  R  L  E  E  L  Y  N  T  K  Q  G  P    480

1441  ACTAATACACTCTTGCATCATCTCGTCCAAGATGTGAAACAGCATACCCTTCTTTCAGGC  1500
 481   T  N  T  L  L  H  H  L  V  Q  D  V  K  Q  H  T  L  L  S  G    500

1501  TACCGAATAACCTTGATTGACATTGGATTAGTAGTAGAATACCTCATTGGTAGAGCATAT  1560
 501   Y  R  I  T  L  I  D  I  G  L  V  V  E  Y  L  I  G  R  A  Y    520

1561  CGCAGCAACTACACTAGAAAACATTTCAGAGCCCTCTACAACAACCTCTACAGAAAATAC  1620
 521   R  S  N  Y  T  R  K  H  F  R  A  L  Y  N  N  L  Y  R  K  Y    540

1621  AAGCACCAGAGACACTCCTCAGGAAATAGAAATGAGTCTGCAGAAAGTACGCTGCACTCC  1680
 541   K  H  Q  R  H  S  S  G  N  R  N  E  S  A  E  S  T  L  H  S    560

1681  CAGTTCATTAGAACTGCACAGCCATACAAATTCAAGGAAAAGTCTATAGTCCTTCATAAA  1740
 561   Q  F  I  R  T  A  Q  P  Y  K  F  K  E  K  S  I  V  L  H  K    580

1741  TCAAGGAAGAAGTCAAAAGAACAAAATGTATCAGATGACCCTGAGTCTACTGGCTTTCTT  1800
 581   S  R  K  K  S  K  E  Q  N  V  S  D  D  P  E  S  T  G  F  L    600
```

Figure 4C

```
1801  TACCCTTACAATGACCTGCTGGTTTGGGCTGTGCTGATGAAAAGGCAGAAGATGGCTATG  1860
 601   Y   P   Y   N   D   L   L   V   W   A   V   L   M   K   R   Q   K   M   A   M    620

1861  TTCTTCTGGCAGCATGGAGAGGAGGCCACGGTTAAAGCCGTGATTGCGTGTATCCTCTAC  1920
 621   F   F   W   Q   H   G   E   E   A   T   V   K   A   V   I   A   C   I   L   Y    640

1921  CGGGCAATGGCCCATGAAGCTAAGGAGAGTCACATGGTGGATGATGCCTCAGAAGAGTTG  1980
 641   R   A   M   A   H   E   A   K   E   S   H   M   V   D   D   A   S   E   E   L    660

1981  AAGAATTACTCAAAACAGTTTGGCCAGCTGGCTCTGGACTTGTTGGAGAAGGCATTCAAG  2040
 661   K   N   Y   S   K   Q   F   G   Q   L   A   L   D   L   L   E   K   A   F   K    680

2041  CAGAATGAGCGCATGGCCATGACGCTGTTGACGTATGAACTCAGGAACTGGAGCAATTCG  2100
 681   Q   N   E   R   M   A   M   T   L   L   T   Y   E   L   R   N   W   S   N   S    700

2101  ACCTGCCTGAAACTGGCCGTGTCGGGAGGATTACGACCCTTTGTTTCACATACTTGTACC  2160
 701   T   C   L   K   L   A   V   S   G   G   L   R   P   F   V   S   H   T   C   T    720

2161  CAGATGCTACTGACAGACATGTGGATGGGGAGGCTGAAAATGAGGAAAAACTCTTGGTTA  2220
 721   Q   M   L   L   T   D   M   W   M   G   R   L   K   M   R   K   N   S   W   L    740

2221  AAGATTATTATAAGCATTATTTTACCACCCACCATTTTGACACTGGAATTTAAAAGCAAA  2280
 741   K   I   I   I   S   I   I   L   P   P   T   I   L   T   L   E   F   K   S   K    760

2281  GCTGAGATGTCACATGTTCCCCAGTCCCAGGACTTCCAATTTATGTGGTATTACAGTGAC  2340
 761   A   E   M   S   H   V   P   Q   S   Q   D   F   Q   F   M   W   Y   Y   S   D    780

2341  CAGAACGCCAGCAGTTCCAAAGAAAGTGCTTCTGTGAAAGAGTATGATTTGGAAGGGGC  2400
 781   Q   N   A   S   S   S   K   E   S   A   S   V   K   E   Y   D   L   E   R   G    800

2401  CATGATGAGAAACTGGATGAAAATCAGCATTTTGGTTTGGAAAGTGGGCACCAACACCTT  2460
 801   H   D   E   K   L   D   E   N   Q   H   F   G   L   E   S   G   H   Q   H   L    820

2461  CCGTGGACCAGGAAAGTCTATGAGTTCTACAGTGCTCCAATTGTCAAGTTTTGGTTTTAT  2520
 821   P   W   T   R   K   V   Y   E   F   Y   S   A   P   I   V   K   F   W   F   Y    840

2521  ACGATCTGTATTTCAGAACCTGGGAAGTTTACCCAAAAGGTGAAGGTATGGATTAGTGAG  2580
 841   T   I   C   I   S   E   P   G   K   F   T   Q   K   V   K   V   W   I   S   E    860

2581  TACTGGAACTTAACAGAAACTGTGGCCATTGGCCTGTTTTCAGCTGGCTTCGTCCTTCGA  2640
 861   Y   W   N   L   T   E   T   V   A   I   G   L   F   S   A   G   F   V   L   R    880

2641  TGGGGTGACCCTCCTTTTCACACAGCGGGAAGACTGATCTACTGCATAGACATCATATTC  2700
 881   W   G   D   P   P   F   H   T   A   G   R   L   I   Y   C   I   D   I   I   F    900
```

Figure 4D

```
2701  TGGTTCTCACGGCTCCTGGACTTCTTTGCTGTGAATCAACATGCAGGTCCATATGTGACC  2760
 901   W  F  S  R  L  L  D  F  F  A  V  N  Q  H  A  G  P  Y  V  T   920

2761  ATGATTGCAAAAATGACAGCAAACATGTTCTATATTGTGATCATCATGGCCATAGTCCTG  2820
 921   M  I  A  K  M  T  A  N  M  F  Y  I  V  I  I  M  A  I  V  L   940

2821  CTGAGCTTTGGAGTGGCACGCAAGGCCATCCTTTCGCCAAAAGAGCCACCATCTTGGAGT  2880
 941   L  S  F  G  V  A  R  K  A  I  L  S  P  K  E  P  P  S  W  S   960

2881  CTAGCTCGAGATATTGTATTTGAGCCATACTGGATGATATACGGAGAAGTCTATGCTGGA  2940
 961   L  A  R  D  I  V  F  E  P  Y  W  M  I  Y  G  E  V  Y  A  G   980

2941  GAAATAGATGTTTGTTCAAGCCAGCCATCCTGCCCTCCTGGTTCTTTTCTTACTCCATTC  3000
 981   E  I  D  V  C  S  S  Q  P  S  C  P  P  G  S  F  L  T  P  F  1000

3001  TTGCAAGCTGTCTACCTCTTCGTGCAATATATCATCATGGTGAACCTGTTGATTGCTTTC  3060
1001   L  Q  A  V  Y  L  F  V  Q  Y  I  I  M  V  N  L  L  I  A  F  1020

3061  TTCAACAACGTTTACTTAGATATGGAATCCATTTCAAATAACCTGTGGAAATACAACCGC  3120
1021   F  N  N  V  Y  L  D  M  E  S  I  S  N  N  L  W  K  Y  N  R  1040

3121  TATCGCTACATCATGACCTACCACGAGAAGCCCTGGCTGCCCCCACCTCTCATCCTGCTG  3180
1041   Y  R  Y  I  M  T  Y  H  E  K  P  W  L  P  P  P  L  I  L  L  1060

3181  AGCCACGTGGGCCTTCTCCTCCGCCGCCTGTGCTGTCATCGAGCTCCTCACGACCAAGAA  3240
1061   S  H  V  G  L  L  L  R  R  L  C  C  H  R  A  P  H  D  Q  E  1080

3241  GAGGGTGACGTTGGATTAAAACTCTACCTCAGTAAGGAGGATCTGAAAAAACTTCATGAT  3300
1081   E  G  D  V  G  L  K  L  Y  L  S  K  E  D  L  K  K  L  H  D  1100

3301  TTTGAGGAGCAGTGCGTGGAAAAATACTTCCATGAGAAGATGGAAGATGTGAATTGTAGT  3360
1101   F  E  E  Q  C  V  E  K  Y  F  H  E  K  M  E  D  V  N  C  S  1120

3361  TGTGAGGAACGAATCCGAGTGACATCAGAAAGGGTTACAGAGATGTACTTCCAGCTGAAA  3420
1121   C  E  E  R  I  R  V  T  S  E  R  V  T  E  M  Y  F  Q  L  K  1140

3421  GAAATGAATGAAAAGGTGTCTTTTATAAAGGACTCCTTACTGTCTTTGGACAGCCAGGTG  3480
1141   E  M  N  E  K  V  S  F  I  K  D  S  L  L  S  L  D  S  Q  V  1160

3481  GGACACCTGCAGGATCTCTCTGCCCTGACTGTGGATACCCTGAAAGTCCTTTCTGCTGTT  3540
1161   G  H  L  Q  D  L  S  A  L  T  V  D  T  L  K  V  L  S  A  V  1180

3541  GACACTTTGCAAGAGGATGAGGCTCTCCTGGCCAAGAGAAAGCATTCTACTTGCAAAAAA  3600
1181   D  T  L  Q  E  D  E  A  L  L  A  K  R  K  H  S  T  C  K  K  1200
```

Figure 4E

```
3601  CTTCCCCACAGCTGGAGCAATGTCATCTGTGCAGAGGTTCTAGGCAGCATGGAGATCGCT  3660
1201  L   P   H   S   W   S   N   V   I   C   A   E   V   L   G   S   M   E   I   A    1220

3661  GGAGAGAAGAAATACCAGTATTATAGCATGCCCTCTTCTTTGCTGAGGAGCCTGGCTGGA  3720
1221  G   E   K   K   Y   Q   Y   Y   S   M   P   S   S   L   L   R   S   L   A   G    1240

3721  GGCCGGCATCCCCCAAGAGTGCAGAGGGGGCACTTCTTGAGATTACAAACAGTAAAAGA   3780
1241  G   R   H   P   P   R   V   Q   R   G   A   L   L   E   I   T   N   S   K   R    1260

3781  GAGGCTACAAATGTAAGAAATGACCAGGAAAGGCAAGAAACACAAAGTAGTATAGTGGTT  3840
1261  E   A   T   N   V   R   N   D   Q   E   R   Q   E   T   Q   S   S   I   V   V    1280

3841  TCTGGGGTGTCTCCTAACAGGCAAGCACACTCAAAGTATGGCCAGTTTCTTCTGGTCCCC  3900
1281  S   G   V   S   P   N   R   Q   A   H   S   K   Y   G   Q   F   L   L   V   P    1300

3901  TCTAATCTAAAGCGAGTTCCTTTTTCAGCAGAAACTGTCTTGCCTCTGTCCAGACCCTCT  3960
1301  S   N   L   K   R   V   P   F   S   A   E   T   V   L   P   L   S   R   P   S    1320

3961  GTGCCAGATGTGCTGGCAACTGAACAGGACATCCAGACTGAGGTTCTTGTTCATCTGACT  4020
1321  V   P   D   V   L   A   T   E   Q   D   I   Q   T   E   V   L   V   H   L   T    1340

4021  GGGCAGACCCCAGTTGTCTCTGACTGGGCATCAGTGGATGAACCCAAGGAAAAGCACGAG  4080
1341  G   Q   T   P   V   V   S   D   W   A   S   V   D   E   P   K   E   K   H   E    1360

4081  CCTATTGCTCACTTACTGGATGGACAAGACAAGGCAGAGCAAGTGCTACCCACTTTGAGT  4140
1361  P   I   A   H   L   L   D   G   Q   D   K   A   E   Q   V   L   P   T   L   S    1380

4141  TGCACACCTGAACCCATGACAATGAGCTCCCCTCTTTCCCAAGCCAAGATCATGCAAACT  4200
1381  C   T   P   E   P   M   T   M   S   S   P   L   S   Q   A   K   I   M   Q   T    1400

4201  GGAGGTGGATATGTAAACTGGGCATTTTCAGAAGGTGATGAAACTGGTGTGTTTAGCATC  4260
1401  G   G   G   Y   V   N   W   A   F   S   E   G   D   E   T   G   V   F   S   I    1420

4261  AAGAAAAAGTGGCAAACCTGCTTGCCCTCCACTTGTGACAGTGATTCCTCTCGGAGTGAA  4320
1421  K   K   K   W   Q   T   C   L   P   S   T   C   D   S   D   S   S   R   S   E    1440

4321  CAGCACCAGAAGCAGGCCCAGGACAGCTCCCTATCTGATAACTCAACAAGATCGGCCCAG  4380
1441  Q   H   Q   K   Q   A   Q   D   S   S   L   S   D   N   S   T   R   S   A   Q    1460

4381  AGTAGTGAATGCTCAGAGGTGGGACCATGGCTTCAGCCAAACACATCCTTTTGGATCAAT  4440
1461  S   S   E   C   S   E   V   G   P   W   L   Q   P   N   T   S   F   W   I   N    1480

4441  CCTCTCCGCAGATACAGGCCCTTCGCTAGGAGTCATAGTTTTAGATTCCATAAGGAGGAG  4500
1481  P   L   R   R   Y   R   P   F   A   R   S   H   S   F   R   F   H   K   E   E    1500
```

Figure 4F

```
4501  AAATTGATGAAGATCTGTAAGATTAAAAATCTTTCAGGCTCTTCAGAAATAGGGCAGGGA  4560
1501   K  L  M  K  I  C  K  I  K  N  L  S  G  S  S  E  I  G  Q  G   1520

4561  GCATGGGTCAAAGCGAAAATGCTAACCAAAGACAGGAGACTGTCAAAGAAAAAGAAGAAT  4620
1521   A  W  V  K  A  K  M  L  T  K  D  R  R  L  S  K  K  K  K  N   1540

4621  ACTCAAGGACTCCAGGTGCCAATCATAACAGTCAATGCCTGCTCTCAGAGTGACCAGTTG  4680
1541   T  Q  G  L  Q  V  P  I  I  T  V  N  A  C  S  Q  S  D  Q  L   1560

4681  AATCCAGAGCCAGGAGAAAACAGCATCTCTGAAGAGGAGTACAGCAAGAACTGGTTCACA  4740
1561   N  P  E  P  G  E  N  S  I  S  E  E  E  Y  S  K  N  W  F  T   1580

4741  GTGTCCAAATTTAGTCACACAGGTGTAGAACCTTACATACATCAGAAAATGAAAACTAAA  4800
1581   V  S  K  F  S  H  T  G  V  E  P  Y  I  H  Q  K  M  K  T  K   1600

4801  GAAATTGGACAATGTGCTATACAAATCAGTGATTACCTAAAGCAGTCTCAAGAGGATCTC  4860
1601   E  I  G  Q  C  A  I  Q  I  S  D  Y  L  K  Q  S  Q  E  D  L   1620

4861  AGCAAAAACTCTTTGTGGAATTCCAGGAGCACCAACCTCAATAGGAACTCCCTGCTGAAA  4920
1621   S  K  N  S  L  W  N  S  R  S  T  N  L  N  R  N  S  L  L  K   1640

4921  AGTTCAATTGGAGTTGACAAGATCTCAGCCTCCTTAAAAAGCCCTCAAGAGCCTCACCAT  4980
1641   S  S  I  G  V  D  K  I  S  A  S  L  K  S  P  Q  E  P  H  H   1660

4981  CATTATTCAGCCATTGAAAGGAATAATTTAATGAGGCTTTCTCAGACCATACCATTTACA  5040
1661   H  Y  S  A  I  E  R  N  N  L  M  R  L  S  Q  T  I  P  F  T   1680

5041  CCAGTCCAACTGTTTGCAGGAGAAGAAATAACTGTCTACAGGTTGGAGGAGAGTTCCCCT  5100
1681   P  V  Q  L  F  A  G  E  E  I  T  V  Y  R  L  E  E  S  S  P   1700

5101  TTAAACCTTGATAAAAGCATGTCCTCTTGGTCTCAGCGTGGGAGAGCGGCAATGATCCAG  5160
1701   L  N  L  D  K  S  M  S  S  W  S  Q  R  G  R  A  A  M  I  Q   1720

5161  GTATTGTCCCGAGAGGAGATGGATGGGGGCCTCCGTAAAGCTATGAGAGTCGTCAGCACT  5220
1721   V  L  S  R  E  E  M  D  G  G  L  R  K  A  M  R  V  V  S  T   1740

5221  TGGTCTGAGGATGACATTCTCAAGCCGGGACAAGTTTTCATTGTCAAGTCCTTTCTTCCT  5280
1741   W  S  E  D  D  I  L  K  P  G  Q  V  F  I  V  K  S  F  L  P   1760

5281  GAGGTTGTGCGGACATGGCATAAAATCTTCCAGGAGAGCACTGTGCTTCATCTTTGCCTC  5340
1761   E  V  V  R  T  W  H  K  I  F  Q  E  S  T  V  L  H  L  C  L   1780

5341  AGGGAAATTCAACAACAAAGAGCTGCTCAAAAATTGATCTATACCTTCAACCAAGTGAAA  5400
1781   R  E  I  Q  Q  Q  R  A  A  Q  K  L  I  Y  T  F  N  Q  V  K   1800
```

Figure 4G

```
5401  CCACAAACCATACCCTACACACCAAGGTTCCTGGAAGTTTTCTTAATCTACTGCCATTCA  5460
1801   P   Q   T   I   P   Y   T   P   R   F   L   E   V   F   L   I   Y   C   H   S    1820

5461  GCCAACCAGTGGTTGACCATTGAGAAGTATATGACAGGGGAGTTCCGGAAGTATAACAAC  5520
1821   A   N   Q   W   L   T   I   E   K   Y   M   T   G   E   F   R   K   Y   N   N    1840

5521  AACAATGGTGATGAAATCACCCCCACCAACACCCTGGAGGAGCTGATGTTGGCTTTCTCT  5580
1841   N   N   G   D   E   I   T   P   T   N   T   L   E   E   L   M   L   A   F   S    1860

5581  CACTGGACCTATGAGTACACTCGGGGAGAGCTGCTGGTTTTAGATTTGCAAGGTGTTGGA  5640
1861   H   W   T   Y   E   Y   T   R   G   E   L   L   V   L   D   L   Q   G   V   G    1880

5641  GAAAATTTGACAGATCCATCTGTTATAAAACCTGAAGTCAAACAATCAAGAGGAATGGTG  5700
1881   E   N   L   T   D   P   S   V   I   K   P   E   V   K   Q   S   R   G   M   V    1900

5701  TTTGGACCGGCCAATTTGGGGGAAGATGCAATTAGAAACTTCATTGCAAAACATCATTGT  5760
1901   F   G   P   A   N   L   G   E   D   A   I   R   N   F   I   A   K   H   H   C    1920

5761  AACTCCTGCTGCCGGAAGCTCAAACTCCCGGATTTAAAAAGAAATGACTATTCCCCTGAA  5820
1921   N   S   C   C   R   K   L   K   L   P   D   L   K   R   N   D   Y   S   P   E    1940

5821  AGGATAAAATTCCACCTTTGGACTTGAGATAAAAATAGAATCAGCTGAGGAGCCTCCAGCA  5880
1941   R   I   N   S   T   F   G   L   E   I   K   I   E   S   A   E   E   P   P   A    1960

5881  AGGGAGACGGGTAGAAATTCCCCAGAAGATGATATGCAACTATAA   5925
1961   R   E   T   G   R   N   S   P   E   D   D   M   Q   L        1974
```

Figure 5A

```
                    1                                                50
TRP-PLIK2    (1)    MIILSKSQKSWIKGVFDKRECSTIIPSSKNPHRCTPVCQVCQNLIRCYCG
TRP-PLIK2b   (1)    MIILSKSQKSWIKGVFDKRECSTIIPSSKNPHRCTPVCQVCQNLIRCYCG
TRP-PLIK2c   (1)    MIILSKSQKSWIKGVFDKRECSTIIPSSKNPHRCTPVCQVCQNLIRCYCG
TRP-PLIK2d   (1)    MIILSKSQKSWIKGVFDKRECSTIIPSSKNPHRCTPVCQVCQNLIRCYCG
CHAK1        (1)    -----MSQKSWIESTLTKRECVYIIPSSKDPHRCLPGCQICQQLVRCFCG
Melastatin1  (1)    --------------------------------------------------

51                                               100
TRP-PLIK2    (51)   RLIGDHAGIDYSWTISAAKGKE------SEQWSVEKHTTKSPTDTFGTI
TRP-PLIK2b   (51)   RLIGDHAGIDYSWTISAAKGKE------SEQWSVEKHTTKSPTDTFGTI
TRP-PLIK2c   (51)   RLIGDHAGIDYSWTISAAKGKE------SEQWSVEKHTTKSPTDTFGTI
TRP-PLIK2d   (51)   RLIGDHAGIDYSWTISAAKGKE------SEQWSVEKHTTKSPTDTFGTI
CHAK1        (46)   RLVKQHACFTASLAMKYSDVKLGDHFNQAIEEWSVEKHTEQSPTDAYGVI
Melastatin1  (1)    --------------------------------------------------

101                                              150
TRP-PLIK2    (94)   NFQDGEHTHHAKYIRTSYDTKLDHLLHLMLKEWKMELPKLVISVHGGIQN
TRP-PLIK2b   (94)   NFQDGEHTHHAKYIRTSYDTKLDHLLHLMLKEWKMELPKLVISVHGGIQN
TRP-PLIK2c   (94)   NFQDGEHTHHAKYIRTSYDTKLDHLLHLMLKEWKMELPKLVISVHGGIQN
TRP-PLIK2d   (94)   NFQDGEHTHHAKYIRTSYDTKLDHLLHLMLKEWKMELPKLVISVHGGIQN
CHAK1        (96)   NFQGGSHSYRAKYVRLSYDTKPEVILQLLLKEWQMELPKLVISVHGGMQK
Melastatin1  (1)    -----------MYIRVSYDTKPDSLLHLMVKDWQLELPKLLISVHGGLQN 151                                              200
TRP-PLIK2    (144)  FTMPSKFKEIFSQGLVKAAETTGAWIITEGINTGVSKHVGDALKSHSSHS
TRP-PLIK2b   (144)  FTMPSKFKEIFSQGLVKAAETTGAWIITEGINTGVSKHVGDALKSHSSHS
TRP-PLIK2c   (144)  FTMPSKFKEIFSQGLVKAAETTGAWIITEGINTGVSKHVGDALKSHSSHS
TRP-PLIK2d   (144)  FTMPSKFKEIFSQGLVKAAETTGAWIITEGINTGVSKHVGDALKSHSSHS
CHAK1        (146)  FELHPRIKQLLGKGLIKAAVTTGAWILTCGVNTGVAKHVGDALKEHASRS
Melastatin1  (40)   FEMQPKLKQVFGKGLIKAAMTTGAWIFTGGVSTGVISHVGDALKDHSSKS 201                                              250
TRP-PLIK2    (194)  LRKIWTVGIPPWGVIENQRDLIGKDVVCLYQTLDNPLSKLTTLNSMHSHF
TRP-PLIK2b   (194)  LRKIWTVGIPPWGVIENQRDLIGKDVVCLYQTLDNPLSKLTTLNSMHSHF
TRP-PLIK2c   (194)  LRKIWTVGIPPWGVIENQRDLIGKDVVCLYQTLDNPLSKLTTLNSMHSHF
TRP-PLIK2d   (194)  LRKIWTVGIPPWGVIENQRDLIGKDVVCLYQTLDNPLSKLTTLNSMHSHF
CHAK1        (196)  SRKICTIGIAPWGVIENRNDLVGRDVVAPYQTLLNPLSKLNVLNNLHSHF
Melastatin1  (90)   RGRVCAIGIAPWGIVENKEDLVGKDVTRVYQTMSNPLSKLSVLNNSHTHF 251                                              300
TRP-PLIK2    (244)  ILSDDGTVGKYGNEMKLRRNLEKYLSLQKIHCRSRQGVPVVGLVVEGGPN
TRP-PLIK2b   (244)  ILSDDGTVGKYGNEMKLRRNLEKYLSLQKIHCRSRQGVPVVGLVVEGGPN
TRP-PLIK2c   (244)  ILSDDGTVGKYGNEMKLRRNLEKYLSLQKIHCRSRQGVPVVGLVVEGGPN
TRP-PLIK2d   (244)  ILSDDGTVGKYGNEMKLRRNLEKYLSLQKIHCRSRQGVPVVGLVVEGGPN
CHAK1        (246)  ILVDDGTVGKYGAEVRLRRELEKTINQQRIHARIGQGVPVVALIFEGGPN
Melastatin1  (140) ILADNGTLGKYGAEVKLRRLLEKHISLQKINTRLGQGVPLVGLVVEGGPN 301                                              350
TRP-PLIK2    (294)  VILSVWETVKDKD--PVVVCEGTGRAADLLAFTHKHLADEGMLRPQVKEE
TRP-PLIK2b   (294)  VILSVWETVKDKD--PVVVCEGTGRAADLLAFTHKHLADEGMLRPQVKEE
TRP-PLIK2c   (294)  VILSVWETVKDKD--PVVVCEGTGRAADLLAFTHKHLADEGMLRPQVKEE
TRP-PLIK2d   (294)  VILSVWETVKDKD--PVVVCEGTGRAADLLAFTHKHLADEGMLRPQVKEE
CHAK1        (296)  VILTVLEYLQESPPVPVVVCEGTGRAADLLAYIHKQTEEGGNLPDAAEPD
Melastatin1  (190) VVSIVLEYLQEEPPIPVVICDGSGRASDILSFAHKYCEEGGIINESLREQ 351                                              400
TRP-PLIK2    (342)  IICMIQNTFNFSLKQSKHLFQILMECMVHRDCITIFDADSEEQQDLDLAI
TRP-PLIK2b   (342)  IICMIQNTFNFSLKQSKHLFQILMECMVHRDCITIFDADSEEQQDLDLAI
TRP-PLIK2c   (342)  IICMIQNTFNFSLKQSKHLFQILMECMVHRDCITIFDADSEEQQDLDLAI
TRP-PLIK2d   (342)  IICMIQNTFNFSLKQSKHLFQILMECMVHRDCITIFDADSEEQQDLDLAI
CHAK1        (346)  IISTIKKTFNFGQNEALHLFQTLMECMKRKELITVFHIGSEEHQDIDVAI
Melastatin1  (240) LLVTIQKTFNYNKAQSHQLFAIIMECMKKELVTVFRMGSEGQQDIEMAI
```

Figure 5B

```
                401                                              450
TRP-PLIK2  (392) LTALLKGTNLSASEQLNLAMAWDRVDIAKKHILIYEQHWKPD--------
TRP-PLIK2b (392) LTALLKGTNLSASEQLNLAMAWDRVDIAKKHILIYEQHWKPD--------
TRP-PLIK2c (392) LTALLKGTNLSASEQLNLAMAWDRVDIAKKHILIYEQHWKPD--------
TRP-PLIK2d (392) LTALLKGTNLSASEQLNLAMAWDRVDIAKKHILIYEQHWKPD--------
CHAK1      (396) LTALLKGTNASAPDQLILTLAWDRVDIAKNHVFVYGQQWLVG--------
Melastatin1(290) LTALLKGTNVSAPDQLSLALAWNRVDIARSQIFVEGPHWTPLGSLAPPTD 451                                              500
TRP-PLIK2  (434) --------------------------------------------------
TRP-PLIK2b (434) --------------------------------------------------
TRP-PLIK2c (434) --------------------------------------------------
TRP-PLIK2d (434) --------------------------------------------------
CHAK1      (438) --------------------------------------------------
Melastatin1(340) SKATEKEKKPPMATTKGGRGKGKGKKKGKVKEEVEEETDPRKIELLNWVN 501                                              550
TRP-PLIK2  (434) ALEQAMSDALVMDRVDFVKLLIEYGVNLHRFLTIPRLEELYNTKQGPTNT
TRP-PLIK2b (434) ALEQAMSDALVMDRVDFVKLLIEYGVNLHRFLTIPRLEELYNTKQGPTNT
TRP-PLIK2c (434) ALEQAMSDALVMDRVDFVKLLIEYGVNLHRFLTIPRLEELYNTKQGPTNT
TRP-PLIK2d (434) ALEQAMSDALVMDRVDFVKLLIEYGVNLHRFLTIPRLEELYNTKQGPTNT
CHAK1      (438) SLEQAMLDALVMDRVAFVKLLIENGVSMHKFLTIPRLEELYNTKQGPTNP
Melastatin1(390) ALEQAMLDALVLDRVDFVKLLIENGVNMQHFLTIPRLEELYNTRLGPPN- 551                                              600
TRP-PLIK2  (484) LLHHLVQDVKQHTLLSGYRITLIDIGLVVEYLIGRAYRSNYTRKHFRALY
TRP-PLIK2b (484) LLHHLVQDVKQHQRHS----------------------------------
TRP-PLIK2c (484) LLHHLVQDVKQ---------------------------------------
TRP-PLIK2d (484) LLHHLVQDVKQHTLLSGYRITLIDIGLVVEYLIGRAYRSNYTRKHFRALY
CHAK1      (488) MLFHLVRDVKQGNLPPGYKITLIDIGLVIEYLMGGTYRCTYTRKRFRLTY
Melastatin1(439) TLHLLVRDVKKSNLPPDYHISLIDIGLVLEYLMGCAYRCNYTRKNFRTLY 601                                              650
TRP-PLIK2  (534) NNL-------------YRKYKHQRHSSGNRNESAESTLHSQFIRTAQPY
TRP-PLIK2b (500) -------------------------SGNRNESAESTLHSQFIRTAQPY
TRP-PLIK2c (495) ------------------------------------------------
TRP-PLIK2d (534) NNL-------------YRKYKHQRHSSGNRNESAESTLHSQFIRTAQPY
CHAK1      (538) NSLGGNNRRSGRNTSSSTPQLRKSHESFGNRADKKEKMRHNHFIKTAQPY
Melastatin1(489) NNLFG-----------------------PKRPKALKLLGMEDD 651                                              700
TRP-PLIK2  (570) KFKEKSIVLHKSRK-KSKEQNVSDDPESTGFLYPYNDLLVWAVLMKRQKM
TRP-PLIK2b (523) KFKEKSIVLHKSRK-KSKEQNVSDDPESTGFLYPYNDLLVWAVLMKRQKM
TRP-PLIK2c (495) ---EKSIVLHKSRK-KSKEQNVSDDPESTGFLYPYNDLLVWAVLMKRQKM
TRP-PLIK2d (570) KFKEKSIVLHKSRK-KSKEQNVSDDPESTGFLYPYNDLLVWAVLMKRQKM
CHAK1      (588) RPKIDTVMEEGKKKRTKDEIVDIDDPETKRFPYPLNELLIWACLMKRQVM
Melastatin1(509) EPPAKGKKKKKKKK-EEEIDIDVDDPAVSRFQYPFHELMVWAVLMKRQKM 701                                              750
TRP-PLIK2  (619) AMFFWQHGEEATVKAVIACILYRAMAHEAKESHMVDDASEELKNYSKQFG
TRP-PLIK2b (572) AMFFWQHGEEATVKAVIACILYRAMAHEAKESHMVDDASEELKNYSKQFG
TRP-PLIK2c (541) AMFFWQHGEEATVKAVIACILYRAMAHEAKESHMVDDASEELKNYSKQFG
TRP-PLIK2d (619) AMFFWQHGEEATVKAVIACILYRAMAHEAKESHMVDDASEELKNYSKQFG
CHAK1      (638) ARFLWQHGEESMAKALVACKIYRSMAYEAKQSDLVDDTSEELKQYSNDFG
Melastatin1(558) AVFLWQRGEESMAKALVACKLYKAMAHESSESDLVDDISQDLDNNSKDFG 751                                              800
TRP-PLIK2  (669) QLALDLLEKAFKQNERMAMTLLTYELRNWSNSTCLKLAVSGGLRPFVSHT
TRP-PLIK2b (622) QLALDLLEKAFKQNERMAMTLLTYELRNWSNSTCLKLAVSGGLRPFVSHT
TRP-PLIK2c (591) QLALDLLEKAFKQNERMAMTLLTYELRNWSNSTCLKLAVSGGLRPFVSHT
TRP-PLIK2d (669) QLALDLLEKAFKQNERMAMTLLTYELRNWSNSTCLKLAVSGGLRPFVSHT
CHAK1      (688) QLAVELLEQSFRQDETMAMKLLTYELKNWSNSTCLKLAVSSRLRPFVAHT
Melastatin1(608) QLALELLDQSYKHDEQIAMKLLTYELKNWSNSTCLKLAVAAKHRDFIAHT
```

Figure 5C

```
                    801                                                850
TRP-PLIK2   (719)   CTQMLLTDMWMGRLKMRKNSWLKIIISIILPPTILTLEFKSKAEMSHVPQ
TRP-PLIK2b  (672)   CTQMLLTDMWMGRLKMRKNSWLKIIISIILPPTILTLEFKSKAEMSHVPQ
TRP-PLIK2c  (641)   CTQMLLTDMWMGRLKMRKNSWLKIIISIILPPTILTLEFKSKAEMSHVPQ
TRP-PLIK2d  (719)   CTQMLLTDMWMGRLKMRKNSWLKIIISIILPPTILTLEFKSKAEMSHVPQ
CHAK1       (738)   CTQMLLSDMWMGRLNMRKNSWYKVILSILVPPAILLEYKTKAEMSHIPQ
Melastatin1 (658)   CSQMLLTDMWMGRLRMRKNPGLKVIMGILLPPTILFLEFRTYDDFSYQTS 851                                                900
TRP-PLIK2   (769)   SQDFQFMWYYSDQNASSSKESASVKEYDLERGHDEKLDENQHFGLESGHQ
TRP-PLIK2b  (722)   SQDFQFMWYYSDQNASSSKESASVKEYDLERGHDEKLDENQHFGLESGHQ
TRP-PLIK2c  (691)   SQDFQFMWYYSDQNASSSKESASVKEYDLERGHDEKLDENQHFGLESGHQ
TRP-PLIK2d  (769)   SQDFQFMWYYSDQNASSSKESASVKEYDLERGHDEKLDENQHFGLESGHQ
CHAK1       (788)   SQDAHQMTMDDSENNFQNITEEIPMEVFKEVRILDSNEGKNEMEIQMKSK
Melastatin1 (708)   K--------ENEDGKE--KEEENTDANADAGSRKGDEENE--HKKQRS- 901                                                950
TRP-PLIK2   (819)   HLPWTRKVYEFYSAPIVKFWFYTMAYLAFLMLFTYTVLVEMQPQPSVQEW
TRP-PLIK2b  (772)   HLPWTRKVYEFYSAPIVKFWFYTMAYLAFLMLFTYTVLVEMQPQPSVQEW
TRP-PLIK2c  (741)   HLPWTRKVYEFYSAPIVKFWFYTMAYLAFLMLFTYTVLVEMQPQPSVQEW
TRP-PLIK2d  (819)   HLPWTRKVYEFYSAPIVKFWFY---------------------------
CHAK1       (838)   KLPITRKFYAFYHAPIVKFWFNTLAYLGFLMLYTFVVLVQMEQLPSVQEW
Melastatin1 (744)   -IPIGTKTCEFYNAPIVKFWFYTTSYLGYLLLFNYVILVRMDGWPSLQEW 951                                               1000
TRP-PLIK2   (869)   LVSIYIFTNAIEVVREICISEPGKFTQKVKVWISEYWNLTETVAIGLFSA
TRP-PLIK2b  (822)   LVSIYIFTNAIEVVREICISEPGKFTQKVKVWISEYWNLTETVAIGLFSA
TRP-PLIK2c  (791)   LVSIYIFTNAIEVVREICISEPGKFTQKVKVWISEYWNLTETVAIGLFSA
TRP-PLIK2d  (841)   ---------------TICISEPGKFTQKVKVWISEYWNLTETVAIGLFSA
CHAK1       (888)   IVIAYIFTYAIEKVREIFMSEAGKVNQKIKVWFSDYFNISDTIAIISFFI
Melastatin1 (793)   IVISYIVSLALEKIREILMSEPGKLSQKIKVWLQEYWNITDLVAISTFMI 1001                                              1050
TRP-PLIK2   (919)   GFVLRWG---------DPPFHTAGRLIYCIDIIFWFSRLLDFFAVNQHAG
TRP-PLIK2b  (872)   GFVLRWG---------DPPFHTAGRLIYCIDIIFWFSRLLDFFAVNQHAG
TRP-PLIK2c  (841)   GFVLRWG---------DPPFHTAGRLIYCIDIIFWFSRLLDFFAVNQHAG
TRP-PLIK2d  (876)   GFVLRWG---------DPPFHTAGRLIYCIDIIFWFSRLLDFFAVNQHAG
CHAK1       (938)   GFGLRFGAKWNFANAYDNHVFVAGRLIYCLNIIFWYVRLLDFLAVNQQAG
Melastatin1 (843)   GAILRLQ---------NQPYMGYCRVIYCVDIIFWYIRVLDIFGVNKYLG 1051                                              1100
TRP-PLIK2   (960)   PYVTMIAKMTANMFYIVIIMAIVLLSFGVARKAILSPKEPPSWSLARDIV
TRP-PLIK2b  (913)   PYVTMIAKMTANMFYIVIIMAIVLLSFGVARKAILSPKEPPSWSLARDIV
TRP-PLIK2c  (882)   PYVTMIAKMTANMFYIVIIMAIVLLSFGVARKAILSPKEPPSWSLARDIV
TRP-PLIK2d  (917)   PYVTMIAKMTANMFYIVIIMAIVLLSFGVARKAILSPKEPPSWSLARDIV
CHAK1       (988)   PYVMMIGKMVANMFYIVVIMALVLLSFGVPRKAILYPHEAPSWTLAKDIV
Melastatin1 (884)   PYVMMIGKMMIDMLYFVVIMLVVLMSFGVARQAILHPEEKPSWKLARNIF 1101                                              1150
TRP-PLIK2   (1010)  FEPYWMIYGEVYAGEIDVCSSQ----------------PSCPPGSFLTP
TRP-PLIK2b  (963)   FEPYWMIYGEVYAGEIDVCSSQ----------------PSCPPGSFLTP
TRP-PLIK2c  (932)   FEPYWMIYGEVYAGEIDVCSSQ----------------PSCPPGSFLTP
TRP-PLIK2d  (967)   FEPYWMIYGEVYAGEIDVCSSQ----------------PSCPPGSFLTP
CHAK1       (1038)  FHPYWMIEGEVYAYEIDVCANDS------------VIPQICGPGTWLTP
Melastatin1 (934)   YMPYWMIYGEVFADQIDLYAMEINPPCGENLYDEEGKRLPECIPGAWLTP 1151                                              1200
TRP-PLIK2   (1043)  FLQAVYLFVQYIIMVNLLIAFFNNVYLDMESISNNLWKYNRYRYIMTYHE
TRP-PLIK2b  (996)   FLQAVYLFVQYIIMVNLLIAFFNNVYLDMESISNNLWKYNRYRYIMTYHE
TRP-PLIK2c  (965)   FLQAVYLFVQYIIMVNLLIAFFNNVYLDMESISNNLWKYNRYRYIMTYHE
TRP-PLIK2d  (1000)  FLQAVYLFVQYIIMVNLLIAFFNNVYLDMESISNNLWKYNRYRYIMTYHE
CHAK1       (1075)  FLQAVYLFVQYIIMVNLLIAFFNNVYLQVKAISNIVWKYQRYHFIMAYHE
Melastatin1 (984)   ALMACYLLVANILLVNLLIAVFNNTFFEVKSISNQVWKEQRYQLIMTFHD
```

Figure 5D

```
                      1201                                                1250
   TRP-PLIK2  (1093)  KPWLPPPLILLSHVGLLLRRLCCHRAPH---DQEEGDVGLKLYLSKEDLK
   TRP-PLIK2b (1046)  KPWLPPPLILLSHVGLLLRRLCCHRAPH---DQEEGDVGLKLYLSKEDLK
   TRP-PLIK2c (1015)  KPWLPPPLILLSHVGLLLRRLCCHRAPH---DQEEGDVGLKLYLSKEDLK
   TRP-PLIK2d (1050)  KPWLPPPLILLSHVGLLLRRLCCHRAPH---DQEEGDVGLKLYLSKEDLK
        CHAK1 (1125)  KPVLPPPLITLSHIVSLECCICKRRK------KDKTSDGPKLFLTEEDQK
   Melastatin1 (1034) RPVLPPEMIILSHIYTIIMRLSGRCRKKREGDQEERDRGLKLELSDEELK 1251                                                1300
   TRP-PLIK2  (1140)  KLHDFEEQCVEKYFHEKMEDVNCSCEERIRVTSERVTEMYFQLKEMNEKV
   TRP-PLIK2b (1093)  KLHDFEEQCVEKYFHEKMEDVNCSCEERIRVTSERVTEMYFQLKEMNEKV
   TRP-PLIK2c (1062)  KLHDFEEQCVEKYFHEKMEDVNCSCEERIRVTSERVTEMYFQLKEMNEKV
   TRP-PLIK2d (1097)  KLHDFEEQCVEKYFHEKMEDVNCSCEERIRVTSERVTEMYFQLKEMNEKV
        CHAK1 (1169)  KLHDFEEQCVEMYFNEKDDKFHSGSEERIRVTFERVEQMCIQIKEVGDRV
   Melastatin1 (1084) RLHEFEEQCVQEHFREKEDEQQSSSDERIRVTSERVENMSMRLEEINERE 1301                                                1350
   TRP-PLIK2  (1190)  SFIKDSLLSLDSQVGHLQDLSALTVDTLKVLSAVDTLQEDEALLAKRKHS
   TRP-PLIK2b (1143)  SFIKDSLLSLDSQVGHLQDLSALTVDTLKVLSAVDTLQEDEALLAKRKHS
   TRP-PLIK2c (1112)  SFIKDSLLSLDSQVGHLQDLSALTVDTLKVLSAVDTLQEDEALLAKRKHS
   TRP-PLIK2d (1147)  SFIKDSLLSLDSQVGHLQDLSALTVDTLKVLSAVDTLQEDEALLAKRKHS
        CHAK1 (1219)  NYIKRSLQSLDSQIGHLQDLEELSNRMVNALENLAGIDR-----------
   Melastatin1 (1134) TFMKTSLQTVDLRLAQLEELSNRMVNALENLAGIDR-----------S 1351                                                1400
   TRP-PLIK2  (1240)  TCKKLPHSWSNVICAEVLGSMEIAGEKKYQYYSMPSSLLRSLAGGRHPPR
   TRP-PLIK2b (1193)  TCKKLPHSWSNVICAEVLGSMEIAGEKKYQYYSMPSSLLRSLAGGRHPPR
   TRP-PLIK2c (1162)  TCKKLPHSWSNVICAEVLGSMEIAGEKKYQYYSMPSSLLRSLAGGRHPPR
   TRP-PLIK2d (1197)  TCKKLPHSWSNVICAEVLGSMEIAGEKKYQYYSMPSSLLRSLAGGRHPPR
        CHAK1 (1254)  --------------------ASEASKVHNEITRELSISKHLAQNLIDDG
   Melastatin1 (1171) DLIQAR--------------SRASSECEATYLLRQSSINSADGYSLYRYH 1401                                                1450
   TRP-PLIK2  (1290)  VQRGALLEITNSKREATNVRNDQERQETQSSIVVSGVSPNRQAHSKYGQF
   TRP-PLIK2b (1243)  VQRGALLEITNSKREATNVRNDQERQETQSSIVVSGVSPNRQAHSKYGQF
   TRP-PLIK2c (1212)  VQRGALLEITNSKREATNVRNDQERQETQSSIVVSGVSPNRQAHSKYGQF
   TRP-PLIK2d (1247)  VQRGALLEITNSKREATNVRNDQERQETQSSIVVSGVSPNRQAHSKYGQF
        CHAK1 (1283)  PVRPSVWKKHGVVNTLSSSLPQGDLE------------------------
   Melastatin1 (1207) FNGEELLFEDTSLSTSPGTGVRKKTCSFRIK-------------------

1451                                                1500
   TRP-PLIK2  (1340)  LLVPSNLKRVPFSAETVLPLSRPSVPDVLATEQDIQTEVLVHLTGQTPVV
   TRP-PLIK2b (1293)  LLVPSNLKRVPFSAETVLPLSRPSVPDVLATEQDIQTEVLVHLTGQTPVV
   TRP-PLIK2c (1262)  LLVPSNLKRVPFSAETVLPLSRPSVPDVLATEQDIQTEVLVHLTGQTPVV
   TRP-PLIK2d (1297)  LLVPSNLKRVPFSAETVLPLSRPSVPDVLATEQDIQTEVLVHLTGQTPVV
        CHAK1 (1309)  ------------------------SNNPFHCNELMKDDKDPQ
   Melastatin1 (1238) ------------------------E-EKDVKTHLVPECQNSLHLS 1501                                                1550
   TRP-PLIK2  (1390)  SDWASVDEPKEKHEPIAHLLDGQDKAEQVLPTLSCTPEPMTMSSPLSQAK
   TRP-PLIK2b (1343)  SDWASVDEPKEKHEPIAHLLDGQDKAEQVLPTLSCTPEPMTMSSPLSQAK
   TRP-PLIK2c (1312)  SDWASVDEPKEKHEPIAHLLDGQDKAEQVLPTLSCTPEPMTMSSPLSQAK
   TRP-PLIK2d (1347)  SDWASVDEPKEKHEPIAHLLDGQDKAEQVLPTLSCTPEPMTMSSPLSQAK
        CHAK1 (1327)  CNIFGQDLPAVPQRKEFNEPEAGSSSGALFPSAVSPPE---LRQRLHGVE
   Melastatin1 (1258) LGTSTSATPDGSHLAVDDLKNAEES--KLGPDIGISKEDDERQTDSKKEE 1551                                                1600
   TRP-PLIK2  (1440)  IMQTGGGYVNWAFSEGDETGVFSIKKKWQTCLPSTCDSDSSRSEQHQKQA
   TRP-PLIK2b (1393)  IMQTGGGYVNWAFSEGDETGVFSIKKKWQTCLPSTCDSDSSRSEQHQKQA
   TRP-PLIK2c (1362)  IMQTGGGYVNWAFSEGDETGVFSIKKKWQTCLPSTCDSDSSRSEQHQKQA
   TRP-PLIK2d (1397)  IMQTGGGYVNWAFSEGDETGVFSIKKKWQTCLPSTCDSDSSRSEQHQKQA
        CHAK1 (1374)  LLKIFNKN--QKEGS-SSTSTPHLSSPPTKFEVSTPSQPSCKSHLETGTK
   Melastatin1 (1306) TISPSLNKTDVIHGQDKSDVQNTQLIVETTNIEGTISYPLEETKITRYFP
```

Figure 5E

```
                          1601                                               1650
    TRP-PLIK2  (1490)    QDSSLSDNSTRSAQSSECSEVGPWLQPNTSFWINPLRRYRPFARSHSFRF
    TRP-PLIK2b (1443)    QDSSLSDNSTRSAQSSECSEVGPWLQPNTSFWINPLRRYRPFARSHSFRF
    TRP-PLIK2c (1412)    QDSSLSDNSTRSAQSSECSEVGPWLQPNTSFWINPLRRYRPFARSHSFRF
    TRP-PLIK2d (1447)    QDSSLSDNSTRSAQSSECSEVGPWLQPNTSFWINPLRRYRPFARSHSFRF
        CHAK1  (1421)    DQETVCSKATEGDNTEFGAFVG--HRDSMDLQRFKETSN----------
    Melastatin1 (1356)   DETINACKTMKSRS------------------------------------

1651                                               1700
    TRP-PLIK2  (1540)    HKEEKLMKICKIKNLSGSSEIGQGAWVKAKMLTKDRRLSKKKKNTQGLQV
    TRP-PLIK2b (1493)    HKEEKLMKICKIKNLSGSSEIGQGAWVKAKMLTKDRRLSKKKKNTQGLQV
    TRP-PLIK2c (1462)    HKEEKLMKICKIKNLSGSSEIGQGAWVKAKMLTKDRRLSKKKKNTQGLQV
    TRP-PLIK2d (1497)    HKEEKLMKICKIKNLSGSSEIGQGAWVKAKMLTKDRRLSKKKKNTQGLQV
        CHAK1  (1458)    ------KIKILSNNN----------------TSENTLKRVSSLAGFTDC
    Melastatin1 (1370)   --------EVYSRGRK---------------LVGGVNQDVEYSSITDQ 1701                                               1750
    TRP-PLIK2  (1590)    PIITVNACSQSDQLNPEPGENSISEEEYSKNWFTVSKFSHTGVEPYIHQK
    TRP-PLIK2b (1543)    PIITVNACSQSDQLNPEPGENSISEEEYSKNWFTVSKFSHTGVEPYIHQK
    TRP-PLIK2c (1512)    PIITVNACSQSDQLNPEPGENSISEEEYSKNWFTVSKFSHTGVEPYIHQK
    TRP-PLIK2d (1547)    PIITVNACSQSDQLNPEPGENSISEEEYSKNWFTVSKFSHTGVEPYIHQK
        CHAK1  (1485)    HRTSTPVHSKQEKISRRP--------------S----------------T
    Melastatin1 (1395)   QETTEWQCQVQKITRSHS-------------------------------

1751                                               1800
    TRP-PLIK2  (1640)    MKTKEIGQCAIQISDYLKQSQEDLSKNSLWNSRSTNLNRNSLLKSSIGVD
    TRP-PLIK2b (1593)    MKTKEIGQCAIQISDYLKQSQEDLSKNSLWNSRSTNLNRNSLLKSSIGVD
    TRP-PLIK2c (1562)    MKTKEIGQCAIQISDYLKQSQEDLSKNSLWNSRSTNLNRNSLLKSSIGVD
    TRP-PLIK2d (1597)    MKTKEIGQCAIQISDYLKQSQEDLSKNSLWNSRSTNLNRNSLLKSSIGVD
        CHAK1  (1505)    EDTHEVDSKAALIPVWLQDRP----------------SNREMPSEEGTEN
    Melastatin1 (1413)   -T--DIPYIVSEAAVQAEQKE---------------QFADMQDEHHVA 1801                                               1850
    TRP-PLIK2  (1690)    KISASLKSPQEPHHHYSAIERNNLMRLSQTIPFTPVQLFAGEEITVYRLE
    TRP-PLIK2b (1643)    KISASLKSPQEPHHHYSAIERNNLMRLSQTIPFTPVQLFAGEEITVYRLE
    TRP-PLIK2c (1612)    KISASLKSPQEPHHHYSAIERNNLMRLSQTIPFTPVQLFAGEEITVYRLE
    TRP-PLIK2d (1647)    KISASLKSPQEPHHHYSAIERNNLMRLSQTIPFTPVQLFAGEEITVYRLE
        CHAK1  (1539)    GETSPFKPAMDTNYYYSAVERNNLMRLSQSIPFTPVPPRG-EPVTVYRLE
    Melastatin1 (1443)   EAIPRLPRLSLTITDRNGMENLLSVKPDQTLGFPSLRSKS--------LH 1851                                               1900
    TRP-PLIK2  (1740)    ESSPLNLDKSMSSWSQRGRAAMIQVLSREEMDGGLRKAMRVVSTWSEDDI
    TRP-PLIK2b (1693)    ESSPLNLDKSMSSWSQRGRAAMIQVLSREEMDGGLRKAMRVVSTWSEDDI
    TRP-PLIK2c (1662)    ESSPLNLDKSMSSWSQRGRAAMIQVLSREEMDGGLRKAMRVVSTWSEDDI
    TRP-PLIK2d (1697)    ESSPLNLDKSMSSWSQRGRAAMIQVLSREEMDGGLRKAMRVVSTWSEDDI
        CHAK1  (1588)    ESSPNILNNSMSSWSQLGLCAKIEFLSKEEMGGLRRAVKVQCTWSEHDI
    Melastatin1 (1485)   -GHPRNVKSIQGKLDRSGHASSVSSLVIVSGMTAEEKKVKKEKASTETEC 1901                                               1950
    TRP-PLIK2  (1790)    LKPGQVFIVKSFLPEVVRTWHKIFQESTVLHLCLREIQQQRAAQKLIYTF
    TRP-PLIK2b (1743)    LKPGQVFIVKSFLPEVVRTWHKIFQESTVLHLCLREIQQQRAAQKLIYTF
    TRP-PLIK2c (1712)    LKPGQVFIVKSFLPEVVRTWHKIFQESTVLHLCLREIQQQRAAQKLIYTF
    TRP-PLIK2d (1747)    LKPGQVFIVKSFLPEVVRTWHKIFQESTVLHLCLREIQQQRAAQKLIYTF
        CHAK1  (1638)    LKSGHLYIIKSFLPEVVNTWSSIYKEDTVLHLCLREIQQQRAAQKLTEAF
    Melastatin1 (1534)   -------------------------------------------------

1951                                               2000
    TRP-PLIK2  (1840)    NQVKPQTIPYTPRFLEVFLIYCHSANQWLTIEKYMTGEFRKYNNNNGDEI
    TRP-PLIK2b (1793)    NQVKPQTIPYTPRFLEVFLIYCHSANQWLTIEKYMTGEFRKYNNNNGDEI
    TRP-PLIK2c (1762)    NQVKPQTIPYTPRFLEVFLIYCHSANQWLTIEKYMTGEFRKYNNNNGDEI
    TRP-PLIK2d (1797)    NQVKPQTIPYTPRFLEVFLIYCHSANQWLTIEKYMTGEFRKYNNNNGDEI
        CHAK1  (1688)    NQMKPKSIPYSPRFLEVFLLYCHSAGQWFAVEECMTGEFRKYNNNNGDEI
    Melastatin1 (1534)   -------------------------------------------------
```

Figure 5F

```
                    2001                                              2050
TRP-PLIK2  (1890)   TPTNTLEELMLAFSHWTYEYTRGELLVLDLQGVGENLTDPSVIKPEVKQS
TRP-PLIK2b (1843)   TPTNTLEELMLAFSHWTYEYTRGELLVLDLQGVGENLTDPSVIKPEVKQS
TRP-PLIK2c (1812)   TPTNTLEELMLAFSHWTYEYTRGELLVLDLQGVGENLTDPSVIKPEVKQS
TRP-PLIK2d (1847)   TPTNTLEELMLAFSHWTYEYTRGELLVLDLQGVGENLTDPSVIKPEVKQS
     CHAK1 (1738)   IPTNTLEEIMLAFSHWTYEYTRGELLVLDLQGVGENLTDPSVIKAEEKRS
Melastatin1 (1534)  --------------------------------------------------

2051                                              2100
TRP-PLIK2  (1940)   RGMVFGPANLGEDAIRNFIAKHHCNSCCRKLKLPDLKRNDYSPERINSTF
TRP-PLIK2b (1893)   RGMVFGPANLGEDAIRNFIAKHHCNSCCRKLKLPDLKRNDYSPERINSTF
TRP-PLIK2c (1862)   RGMVFGPANLGEDAIRNFIAKHHCNSCCRKLKLPDLKRNDYSPERINSTF
TRP-PLIK2d (1897)   RGMVFGPANLGEDAIRNFIAKHHCNSCCRKLKLPDLKRNDYSPERINSTF
     CHAK1 (1788)   CDMVFGPANLGEDAIKNFRAKHHCNSCCRKLKLPDLKRNDYTPDKIIFPQ
Melastatin1 (1534)  --------------------------------------------------

2101                   2128
TRP-PLIK2  (1990)   GLEIKIESAEEPPARETGRNSPEDDMQL
TRP-PLIK2b (1943)   GLEIKIESAEEPPARETGRNSPEDDMQL
TRP-PLIK2c (1912)   GLEIKIESAEEPPARETGRNSPEDDMQL
TRP-PLIK2d (1947)   GLEIKIESAEEPPARETGRNSPEDDMQL
     CHAK1 (1838)   DEPSDLNLQPGNSTKESESTNSVRLML-
Melastatin1 (1534)  ----------------------------
```

Figure 6A

```
                        1                                                    50
TRP-PLIK     (1)   MIILSKSQKSWIKGVFDKRECSTIIPSSKNPHRCTPVCQVCQNLIRCYCG
TRP-PLIKb    (1)   MIILSKSQKSWIKGVFDKRECSTIIPSSKNPHRCTPVCQVCQNLIRCYCG
TRP-PLIKc    (1)   MIILSKSQKSWIKGVFDKRECSTIIPSSKNPHRCTPVCQVCQNLIRCYCG
TRP-PLIK2d   (1)   MIILSKSQKSWIKGVFDKRECSTIIPSSKNPHRCTPVCQVCQNLIRCYCG 51                                                   100
TRP-PLIK     (51)  RLIGDHAGIDYSWTISAAKGKESEQWSVEKHTTKSPTDTFGTINFQDGEH
TRP-PLIKb    (51)  RLIGDHAGIDYSWTISAAKGKESEQWSVEKHTTKSPTDTFGTINFQDGEH
TRP-PLIKc    (51)  RLIGDHAGIDYSWTISAAKGKESEQWSVEKHTTKSPTDTFGTINFQDGEH
TRP-PLIK2d   (51)  RLIGDHAGIDYSWTISAAKGKESEQWSVEKHTTKSPTDTFGTINFQDGEH 101                                                  150
TRP-PLIK     (101) THHAKYIRTSYDTKLDHLLHLMLKEWKMELPKLVISVHGGIQNFTMPSKF
TRP-PLIKb    (101) THHAKYIRTSYDTKLDHLLHLMLKEWKMELPKLVISVHGGIQNFTMPSKF
TRP-PLIKc    (101) THHAKYIRTSYDTKLDHLLHLMLKEWKMELPKLVISVHGGIQNFTMPSKF
TRP-PLIK2d   (101) THHAKYIRTSYDTKLDHLLHLMLKEWKMELPKLVISVHGGIQNFTMPSKF 151                                                  200
TRP-PLIK     (151) KEIFSQGLVKAAETTGAWIITEGINTGVSKHVGDALKSHSSHSLRKIWTV
TRP-PLIKb    (151) KEIFSQGLVKAAETTGAWIITEGINTGVSKHVGDALKSHSSHSLRKIWTV
TRP-PLIKc    (151) KEIFSQGLVKAAETTGAWIITEGINTGVSKHVGDALKSHSSHSLRKIWTV
TRP-PLIK2d   (151) KEIFSQGLVKAAETTGAWIITEGINTGVSKHVGDALKSHSSHSLRKIWTV 201                                                  250
TRP-PLIK     (201) GIPPWGVIENQRDLIGKDVVCLYQTLDNPLSKLTTLNSMHSHFILSDDGT
TRP-PLIKb    (201) GIPPWGVIENQRDLIGKDVVCLYQTLDNPLSKLTTLNSMHSHFILSDDGT
TRP-PLIKc    (201) GIPPWGVIENQRDLIGKDVVCLYQTLDNPLSKLTTLNSMHSHFILSDDGT
TRP-PLIK2d   (201) GIPPWGVIENQRDLIGKDVVCLYQTLDNPLSKLTTLNSMHSHFILSDDGT 251                                                  300
TRP-PLIK     (251) VGKYGNEMKLRRNLEKYLSLQKIHCRSRQGVPVVGLVVEGGPNVILSVWE
TRP-PLIKb    (251) VGKYGNEMKLRRNLEKYLSLQKIHCRSRQGVPVVGLVVEGGPNVILSVWE
TRP-PLIKc    (251) VGKYGNEMKLRRNLEKYLSLQKIHCRSRQGVPVVGLVVEGGPNVILSVWE
TRP-PLIK2d   (251) VGKYGNEMKLRRNLEKYLSLQKIHCRSRQGVPVVGLVVEGGPNVILSVWE 301                                                  350
TRP-PLIK     (301) TVKDKDPVVVCEGTGRAADLLAFTHKHLADEGMLRPQVKEEIICMIQNTF
TRP-PLIKb    (301) TVKDKDPVVVCEGTGRAADLLAFTHKHLADEGMLRPQVKEEIICMIQNTF
TRP-PLIKc    (301) TVKDKDPVVVCEGTGRAADLLAFTHKHLADEGMLRPQVKEEIICMIQNTF
TRP-PLIK2d   (301) TVKDKDPVVVCEGTGRAADLLAFTHKHLADEGMLRPQVKEEIICMIQNTF 351                                                  400
TRP-PLIK     (351) NFSLKQSKHLFQILMECMVHRDCITIFDADSEEQQDLDLAILTALLKGTN
TRP-PLIKb    (351) NFSLKQSKHLFQILMECMVHRDCITIFDADSEEQQDLDLAILTALLKGTN
TRP-PLIKc    (351) NFSLKQSKHLFQILMECMVHRDCITIFDADSEEQQDLDLAILTALLKGTN
TRP-PLIK2d   (351) NFSLKQSKHLFQILMECMVHRDCITIFDADSEEQQDLDLAILTALLKGTN 401                                                  450
TRP-PLIK     (401) LSASEQLNLAMAWDRVDIAKKHILIYEQHWKPDALEQAMSDALVMDRVDF
TRP-PLIKb    (401) LSASEQLNLAMAWDRVDIAKKHILIYEQHWKPDALEQAMSDALVMDRVDF
TRP-PLIKc    (401) LSASEQLNLAMAWDRVDIAKKHILIYEQHWKPDALEQAMSDALVMDRVDF
TRP-PLIK2d   (401) LSASEQLNLAMAWDRVDIAKKHILIYEQHWKPDALEQAMSDALVMDRVDF 451                                                  500
TRP-PLIK     (451) VKLLIEYGVNLHRFLTIPRLEELYNTKQGPTNTLLHHLVQDVKQHTLLSG
TRP-PLIKb    (451) VKLLIEYGVNLHRFLTIPRLEELYNTKQGPTNTLLHHLVQDVKQH-----
TRP-PLIKc    (451) VKLLIEYGVNLHRFLTIPRLEELYNTKQGPTNTLLHHLVQDVKQ------
TRP-PLIK2d   (451) VKLLIEYGVNLHRFLTIPRLEELYNTKQGPTNTLLHHLVQDVKQHTLLSG
```

Figure 6B

```
                 501                                                550
TRP-PLIK   (501) YRITLIDIGLVVEYLIGRAYRSNYTRKHFRALYNNLYRKYKHQRHSSGNR
TRP-PLIKb  (496) -----Q--------------------------------------RHSSGNR
TRP-PLIKc  (495) --------------------------------------------------
TRP-PLIK2d (501) YRITLIDIGLVVEYLIGRAYRSNYTRKHFRALYNNLYRKYKHQRHSSGNR 551                                                600
TRP-PLIK   (551) NESAESTLHSQFIRTAQPYKFKEKSIVLHKSRKKSKEQNVSDDPESTGFL
TRP-PLIKb  (504) NESAESTLHSQFIRTAQPYKFKEKSIVLHKSRKKSKEQNVSDDPESTGFL
TRP-PLIKc  (495) --------------------EKSIVLHKSRKKSKEQNVSDDPESTGFL
TRP-PLIK2d (551) NESAESTLHSQFIRTAQPYKFKEKSIVLHKSRKKSKEQNVSDDPESTGFL 601                                                650
TRP-PLIK   (601) YPYNDLLVWAVLMKRQKMAMFFWQHGEEATVKAVIACILYRAMAHEAKES
TRP-PLIKb  (554) YPYNDLLVWAVLMKRQKMAMFFWQHGEEATVKAVIACILYRAMAHEAKES
TRP-PLIKc  (523) YPYNDLLVWAVLMKRQKMAMFFWQHGEEATVKAVIACILYRAMAHEAKES
TRP-PLIK2d (601) YPYNDLLVWAVLMKRQKMAMFFWQHGEEATVKAVIACILYRAMAHEAKES 651                                                700
TRP-PLIK   (651) HMVDDASEELKNYSKQFGQLALDLLEKAFKQNERMAMTLLTYELRNWSNS
TRP-PLIKb  (604) HMVDDASEELKNYSKQFGQLALDLLEKAFKQNERMAMTLLTYELRNWSNS
TRP-PLIKc  (573) HMVDDASEELKNYSKQFGQLALDLLEKAFKQNERMAMTLLTYELRNWSNS
TRP-PLIK2d (651) HMVDDASEELKNYSKQFGQLALDLLEKAFKQNERMAMTLLTYELRNWSNS 701                                                750
TRP-PLIK   (701) TCLKLAVSGGLRPFVSHTCTQMLLTDMWMGRLKMRKNSWLKIIISIILPP
TRP-PLIKb  (654) TCLKLAVSGGLRPFVSHTCTQMLLTDMWMGRLKMRKNSWLKIIISIILPP
TRP-PLIKc  (623) TCLKLAVSGGLRPFVSHTCTQMLLTDMWMGRLKMRKNSWLKIIISIILPP
TRP-PLIK2d (701) TCLKLAVSGGLRPFVSHTCTQMLLTDMWMGRLKMRKNSWLKIIISIILPP 751                                                800
TRP-PLIK   (751) TILTLEFKSKAEMSHVPQSQDFQFMWYYSDQNASSSKESASVKEYDLERG
TRP-PLIKb  (704) TILTLEFKSKAEMSHVPQSQDFQFMWYYSDQNASSSKESASVKEYDLERG
TRP-PLIKc  (673) TILTLEFKSKAEMSHVPQSQDFQFMWYYSDQNASSSKESASVKEYDLERG
TRP-PLIK2d (751) TILTLEFKSKAEMSHVPQSQDFQFMWYYSDQNASSSKESASVKEYDLERG 801                                                850
TRP-PLIK   (801) HDEKLDENQHFGLESGHQHLPWTRKVYEFYSAPIVKFWFYTMAYLAFLML
TRP-PLIKb  (754) HDEKLDENQHFGLESGHQHLPWTRKVYEFYSAPIVKFWFYTMAYLAFLML
TRP-PLIKc  (723) HDEKLDENQHFGLESGHQHLPWTRKVYEFYSAPIVKFWFYTMAYLAFLML
TRP-PLIK2d (801) HDEKLDENQHFGLESGHQHLPWTRKVYEFYSAPIVKFWFY----------

851                                                900
TRP-PLIK   (851) FTYTVLVEMQPQPSVQEWLVSIYIFTNAIEVVREICISEPGKFTQKVKVW
TRP-PLIKb  (804) FTYTVLVEMQPQPSVQEWLVSIYIFTNAIEVVREICISEPGKFTQKVKVW
TRP-PLIKc  (773) FTYTVLVEMQPQPSVQEWLVSIYIFTNAIEVVREICISEPGKFTQKVKVW
TRP-PLIK2d (841) -------------------------------TICISEPGKFTQKVKVW 901                                                950
TRP-PLIK   (901) ISEYWNLTETVAIGLFSAGFVLRWGDPPFHTAGRLIYCIDIIFWFSRLLD
TRP-PLIKb  (854) ISEYWNLTETVAIGLFSAGFVLRWGDPPFHTAGRLIYCIDIIFWFSRLLD
TRP-PLIKc  (823) ISEYWNLTETVAIGLFSAGFVLRWGDPPFHTAGRLIYCIDIIFWFSRLLD
TRP-PLIK2d (858) ISEYWNLTETVAIGLFSAGFVLRWGDPPFHTAGRLIYCIDIIFWFSRLLD 951                                               1000
TRP-PLIK   (951) FFAVNQHAGPYVTMIAKMTANMFYIVIIMAIVLLSFGVARKAILSPKEPP
TRP-PLIKb  (904) FFAVNQHAGPYVTMIAKMTANMFYIVIIMAIVLLSFGVARKAILSPKEPP
TRP-PLIKc  (873) FFAVNQHAGPYVTMIAKMTANMFYIVIIMAIVLLSFGVARKAILSPKEPP
TRP-PLIK2d (908) FFAVNQHAGPYVTMIAKMTANMFYIVIIMAIVLLSFGVARKAILSPKEPP
```

Figure 6C

```
                      1001                                              1050
TRP-PLIK   (1001)  SWSLARDIVFEPYWMIYGEVYAGEIDVCSSQPSCPPGSFLTPFLQAVYLF
TRP-PLIKb  ( 954)  SWSLARDIVFEPYWMIYGEVYAGEIDVCSSQPSCPPGSFLTPFLQAVYLF
TRP-PLIKc  ( 923)  SWSLARDIVFEPYWMIYGEVYAGEIDVCSSQPSCPPGSFLTPFLQAVYLF
TRP-PLIK2d ( 958)  SWSLARDIVFEPYWMIYGEVYAGEIDVCSSQPSCPPGSFLTPFLQAVYLF 1051                                              1100
TRP-PLIK   (1051)  VQYIIMVNLLIAFFNNVYLDMESISNNLWKYNRYRYIMTYHEKPWLPPPL
TRP-PLIKb  (1004)  VQYIIMVNLLIAFFNNVYLDMESISNNLWKYNRYRYIMTYHEKPWLPPPL
TRP-PLIKc  ( 973)  VQYIIMVNLLIAFFNNVYLDMESISNNLWKYNRYRYIMTYHEKPWLPPPL
TRP-PLIK2d (1008)  VQYIIMVNLLIAFFNNVYLDMESISNNLWKYNRYRYIMTYHEKPWLPPPL 1101                                              1150
TRP-PLIK   (1101)  ILLSHVGLLLRRLCCHRAPHDQEEGDVGLKLYLSKEDLKKLHDFEEQCVE
TRP-PLIKb  (1054)  ILLSHVGLLLRRLCCHRAPHDQEEGDVGLKLYLSKEDLKKLHDFEEQCVE
TRP-PLIKc  (1023)  ILLSHVGLLLRRLCCHRAPHDQEEGDVGLKLYLSKEDLKKLHDFEEQCVE
TRP-PLIK2d (1058)  ILLSHVGLLLRRLCCHRAPHDQEEGDVGLKLYLSKEDLKKLHDFEEQCVE 1151                                              1200
TRP-PLIK   (1151)  KYFHEKMEDVNCSCEERIRVTSERVTEMYFQLKEMNEKVSFIKDSLLSLD
TRP-PLIKb  (1104)  KYFHEKMEDVNCSCEERIRVTSERVTEMYFQLKEMNEKVSFIKDSLLSLD
TRP-PLIKc  (1073)  KYFHEKMEDVNCSCEERIRVTSERVTEMYFQLKEMNEKVSFIKDSLLSLD
TRP-PLIK2d (1108)  KYFHEKMEDVNCSCEERIRVTSERVTEMYFQLKEMNEKVSFIKDSLLSLD 1201                                              1250
TRP-PLIK   (1201)  SQVGHLQDLSALTVDTLKVLSAVDTLQEDEALLAKRKHSTCKKLPHSWSN
TRP-PLIKb  (1154)  SQVGHLQDLSALTVDTLKVLSAVDTLQEDEALLAKRKHSTCKKLPHSWSN
TRP-PLIKc  (1123)  SQVGHLQDLSALTVDTLKVLSAVDTLQEDEALLAKRKHSTCKKLPHSWSN
TRP-PLIK2d (1158)  SQVGHLQDLSALTVDTLKVLSAVDTLQEDEALLAKRKHSTCKKLPHSWSN 1251                                              1300
TRP-PLIK   (1251)  VICAEVLGSMEIAGEKKYQYYSMPSSLLRSLAGGRHPPRVQRGALLEITN
TRP-PLIKb  (1204)  VICAEVLGSMEIAGEKKYQYYSMPSSLLRSLAGGRHPPRVQRGALLEITN
TRP-PLIKc  (1173)  VICAEVLGSMEIAGEKKYQYYSMPSSLLRSLAGGRHPPRVQRGALLEITN
TRP-PLIK2d (1208)  VICAEVLGSMEIAGEKKYQYYSMPSSLLRSLAGGRHPPRVQRGALLEITN 1301                                              1350
TRP-PLIK   (1301)  SKREATNVRNDQERQETQSSIVVSGVSPNRQAHSKYGQFLLVPSNLKRVP
TRP-PLIKb  (1254)  SKREATNVRNDQERQETQSSIVVSGVSPNRQAHSKYGQFLLVPSNLKRVP
TRP-PLIKc  (1223)  SKREATNVRNDQERQETQSSIVVSGVSPNRQAHSKYGQFLLVPSNLKRVP
TRP-PLIK2d (1258)  SKREATNVRNDQERQETQSSIVVSGVSPNRQAHSKYGQFLLVPSNLKRVP 1351                                              1400
TRP-PLIK   (1351)  FSAETVLPLSRPSVPDVLATEQDIQTEVLVHLTGQTPVVSDWASVDEPKE
TRP-PLIKb  (1304)  FSAETVLPLSRPSVPDVLATEQDIQTEVLVHLTGQTPVVSDWASVDEPKE
TRP-PLIKc  (1273)  FSAETVLPLSRPSVPDVLATEQDIQTEVLVHLTGQTPVVSDWASVDEPKE
TRP-PLIK2d (1308)  FSAETVLPLSRPSVPDVLATEQDIQTEVLVHLTGQTPVVSDWASVDEPKE 1401                                              1450
TRP-PLIK   (1401)  KHEPIAHLLDGQDKAEQVLPTLSCTPEPMTMSSPLSQAKIMQTGGGYVNW
TRP-PLIKb  (1354)  KHEPIAHLLDGQDKAEQVLPTLSCTPEPMTMSSPLSQAKIMQTGGGYVNW
TRP-PLIKc  (1323)  KHEPIAHLLDGQDKAEQVLPTLSCTPEPMTMSSPLSQAKIMQTGGGYVNW
TRP-PLIK2d (1358)  KHEPIAHLLDGQDKAEQVLPTLSCTPEPMTMSSPLSQAKIMQTGGGYVNW 1451                                              1500
TRP-PLIK   (1451)  AFSEGDETGVFSIKKKWQTCLPSTCDSDSSRSEQHQKQAQDSSLSDNSTR
TRP-PLIKb  (1404)  AFSEGDETGVFSIKKKWQTCLPSTCDSDSSRSEQHQKQAQDSSLSDNSTR
TRP-PLIKc  (1373)  AFSEGDETGVFSIKKKWQTCLPSTCDSDSSRSEQHQKQAQDSSLSDNSTR
TRP-PLIK2d (1408)  AFSEGDETGVFSIKKKWQTCLPSTCDSDSSRSEQHQKQAQDSSLSDNSTR
```

Figure 6D

```
                  1501                                              1550
TRP-PLIK   (1501) SAQSSECSEVGPWLQPNTSFWINPLRRYRPFARSHSFRFHKEEKLMKICK
TRP-PLIKb  (1454) SAQSSECSEVGPWLQPNTSFWINPLRRYRPFARSHSFRFHKEEKLMKICK
TRP-PLIKc  (1423) SAQSSECSEVGPWLQPNTSFWINPLRRYRPFARSHSFRFHKEEKLMKICK
TRP-PLIK2d (1458) SAQSSECSEVGPWLQPNTSFWINPLRRYRPFARSHSFRFHKEEKLMKICK 1551                                              1600
TRP-PLIK   (1551) IKNLSGSSEIGQGAWVKAKMLTKDRRLSKKKKNTQGLQVPIITVNACSQS
TRP-PLIKb  (1504) IKNLSGSSEIGQGAWVKAKMLTKDRRLSKKKKNTQGLQVPIITVNACSQS
TRP-PLIKc  (1473) IKNLSGSSEIGQGAWVKAKMLTKDRRLSKKKKNTQGLQVPIITVNACSQS
TRP-PLIK2d (1508) IKNLSGSSEIGQGAWVKAKMLTKDRRLSKKKKNTQGLQVPIITVNACSQS 1601                                              1650
TRP-PLIK   (1601) DQLNPEPGENSISEEEYSKNWFTVSKFSHTGVEPYIHQKMKTKEIGQCAI
TRP-PLIKb  (1554) DQLNPEPGENSISEEEYSKNWFTVSKFSHTGVEPYIHQKMKTKEIGQCAI
TRP-PLIKc  (1523) DQLNPEPGENSISEEEYSKNWFTVSKFSHTGVEPYIHQKMKTKEIGQCAI
TRP-PLIK2d (1558) DQLNPEPGENSISEEEYSKNWFTVSKFSHTGVEPYIHQKMKTKEIGQCAI 1651                                              1700
TRP-PLIK   (1651) QISDYLKQSQEDLSKNSLWNSRSTNLNRNSLLKSSIGVDKISASLKSPQE
TRP-PLIKb  (1604) QISDYLKQSQEDLSKNSLWNSRSTNLNRNSLLKSSIGVDKISASLKSPQE
TRP-PLIKc  (1573) QISDYLKQSQEDLSKNSLWNSRSTNLNRNSLLKSSIGVDKISASLKSPQE
TRP-PLIK2d (1608) QISDYLKQSQEDLSKNSLWNSRSTNLNRNSLLKSSIGVDKISASLKSPQE 1701                                              1750
TRP-PLIK   (1701) PHHHYSAIERNNLMRLSQTIPFTPVQLFAGEEITVYRLEESSPLNLDKSM
TRP-PLIKb  (1654) PHHHYSAIERNNLMRLSQTIPFTPVQLFAGEEITVYRLEESSPLNLDKSM
TRP-PLIKc  (1623) PHHHYSAIERNNLMRLSQTIPFTPVQLFAGEEITVYRLEESSPLNLDKSM
TRP-PLIK2d (1658) PHHHYSAIERNNLMRLSQTIPFTPVQLFAGEEITVYRLEESSPLNLDKSM 1751                                              1800
TRP-PLIK   (1751) SSWSQRGRAAMIQVLSREEMDGGLRKAMRVVSTWSEDDILKPGQVFIVKS
TRP-PLIKb  (1704) SSWSQRGRAAMIQVLSREEMDGGLRKAMRVVSTWSEDDILKPGQVFIVKS
TRP-PLIKc  (1673) SSWSQRGRAAMIQVLSREEMDGGLRKAMRVVSTWSEDDILKPGQVFIVKS
TRP-PLIK2d (1708) SSWSQRGRAAMIQVLSREEMDGGLRKAMRVVSTWSEDDILKPGQVFIVKS 1801                                              1850
TRP-PLIK   (1801) FLPEVVRTWHKIFQESTVLHLCLREIQQQRAAQKLIYTFNQVKPQTIPYT
TRP-PLIKb  (1754) FLPEVVRTWHKIFQESTVLHLCLREIQQQRAAQKLIYTFNQVKPQTIPYT
TRP-PLIKc  (1723) FLPEVVRTWHKIFQESTVLHLCLREIQQQRAAQKLIYTFNQVKPQTIPYT
TRP-PLIK2d (1758) FLPEVVRTWHKIFQESTVLHLCLREIQQQRAAQKLIYTFNQVKPQTIPYT 1851                                              1900
TRP-PLIK   (1851) PRFLEVFLIYCHSANQWLTIEKYMTGEFRKYNNNNGDEITPTNTLEELML
TRP-PLIKb  (1804) PRFLEVFLIYCHSANQWLTIEKYMTGEFRKYNNNNGDEITPTNTLEELML
TRP-PLIKc  (1773) PRFLEVFLIYCHSANQWLTIEKYMTGEFRKYNNNNGDEITPTNTLEELML
TRP-PLIK2d (1808) PRFLEVFLIYCHSANQWLTIEKYMTGEFRKYNNNNGDEITPTNTLEELML 1901                                              1950
TRP-PLIK   (1901) AFSHWTYEYTRGELLVLDLQGVGENLTDPSVIKPEVKQSRGMVFGPANLG
TRP-PLIKb  (1854) AFSHWTYEYTRGELLVLDLQGVGENLTDPSVIKPEVKQSRGMVFGPANLG
TRP-PLIKc  (1823) AFSHWTYEYTRGELLVLDLQGVGENLTDPSVIKPEVKQSRGMVFGPANLG
TRP-PLIK2d (1858) AFSHWTYEYTRGELLVLDLQGVGENLTDPSVIKPEVKQSRGMVFGPANLG 1951                                              2000
TRP-PLIK   (1951) EDAIRNFIAKHHCNSCCRKLKLPDLKRNDYSPERINSTFGLEIKIESAEE
TRP-PLIKb  (1904) EDAIRNFIAKHHCNSCCRKLKLPDLKRNDYSPERINSTFGLEIKIESAEE
TRP-PLIKc  (1873) EDAIRNFIAKHHCNSCCRKLKLPDLKRNDYSPERINSTFGLEIKIESAEE
TRP-PLIK2d (1908) EDAIRNFIAKHHCNSCCRKLKLPDLKRNDYSPERINSTFGLEIKIESAEE
```

Figure 6E

```
                      2001            2017
TRP-PLIK   (2001)  PPARETGRNSPEDDMQL
TRP-PLIKb  (1954)  PPARETGRNSPEDDMQL
TRP-PLIKc  (1923)  PPARETGRNSPEDDMQL
TRP-PLIK2d (1958)  PPARETGRNSPEDDMQL
```

Figure 9.

TRP-PLIK2

| Protein | Genbank ID | Identities | Similarities |
|---|---|---|---|
| human channel-kinase 1 | gi|AF346629 | 58.0% | 66.0% |
| human melastatin 1 | gi|3243075 | 48.1% | 58.6% |

TRP-PLIK2b

| Protein | Genbank ID | Identities | Similarities |
|---|---|---|---|
| human channel-kinase 1 | gi|AF346629 | 58.1% | 66.1% |
| human melastatin 1 | gi|3243075 | 47.2% | 57.9% |

TRP-PLIK2c

| Protein | Genbank ID | Identities | Similarities |
|---|---|---|---|
| human channel-kinase 1 | gi|AF346629 | 58.5% | 66.5% |
| human melastatin 1 | gi|3243075 | 47.8% | 58.7% |

TRP-PLIK2d

| Protein | Genbank ID | Identities | Similarities |
|---|---|---|---|
| human channel-kinase 1 | gi|AF346629 | 57.9% | 65.7% |
| human melastatin 1 | gi|3243075 | 48.0% | 58.4% |

Figure 10A

>AL354795_15.[2992:2751].sp
CATGGCAGACAGTTTGGCCAGCTGGCTCTGGACTTGTTGGAGAAGGCATT
CAAGCAGAATGAGCGCATGGCCATGACGCTGTTGACGTATGAACTCAGGA
ACTGGAGCAATTCGACCTGCCTTAAACTGGCCGTGTCGGGAGGATTACGA
CCCTTTGTTTCACATACTTGTACCCAGATGCTACTGACAGACATGTGGATG
GGGAGGCTGAAAATGAGGAAAAACTCTTGGTTAAAGGTA (SEQ ID NO:10)
//
>AL354795_13.[4328:4585].sp
AAATCAAGGAAGAAGTCAAAAGAACAAAATGTATCAGATGACCCTGAGT
CTACTGGCTTTCTTTACCCTTACAATGACCTGCTGGTTTGGGCTGTGCTGAT
GAAAAGGCAGAAGATGGCTATGTTCTTCTGGCAGCATGGAGAGGAGGCC
ACGGTTAAAGCCGTGATTGCGTGTATCCTCTACCGGGCAATGGCCCATGA
AGCTAAGGAGAGTCACATGGTGGATGATGCCTCAGAAGAGTTGAAGAATT
ACTCAAAG (SEQ ID NO:11)
//
>AL354795_17.[787:1270].sp
AACATGTTCTATATTGTGATCATCATGGCCATAGTCCTGCTGAGCTTTGGA
GTGGCACGCAAGGCCATCCTTTCGCCAAAAGAGCCACCATCTTGGAGTCT
AGCTCGAGATATTGTATTTGAGCCATACTGGATGATATACGGAGAAGTCT
ATGCTGGAGAAATAGATGGTGTGTATGGGATTTTACCGTCATGCAGAAAT
TGTGCCTTCATAGTTAACAAGATTTGTTCAAGCCAGCCATCCTGCCCTCCT
GGTTCTTTTCTTACTCCATTCTTGCAAGCTGTCTACCTCTTCGTGCAATATA
TCATCATGGTGAACCTGTTGATTGCTTTCTTC (SEQ ID NO:12)
//
>AL354795_2.[2422:2247].sp
GTGGTGTGCCTGTACCAGACTCTGGATAACCCCCTCAGCAAGCTCACAAC
ACTCAACAGCATGCACTCGCACTTCATCCTGTCTGATGATGGGACCGTGG
GCAAGTATGGAAATGAAATGAAGCTCAGAAGGAACCTGGAGAAGTACCT
CTCTCTGCAGAAAATACACTGCCGT (SEQ ID NO:13)
//
>AL354795_25.[1778:1540].sp
CTTACTTCATCTTACAGCAACGTTTACTTAGATATGGAATCCATTTCAAAT
AACCTGTGGAAATACAACCGCTATCGCTACATCATGACCTACCACGAGAA
GCCCTGGCTGCCCCCACCTCTCATCCTGCTGAGCCACGTGGGCCTTCTCCT
CCGCCGCCTGTGCTGTCATCGAGCTCCTCACGACCAAGAAGAGGGTGACG
TTGGATTAAGTAAGTTGTTCTATGTGAGGCAGGAG (SEQ ID NO:14)
//
>AL354795_19.[912:1204].sp
ATTACCATATTTGATGCTGACTCTGAAGAGCAGCAAGACCTGGACTTAGC
AATCCTAACAGCTTTGCTGAAGGGCACAAATTTATCAGCGTCAGAGCAAT
TAAATCTGGCAATGGCTTGGGACAGGGTGGACATTGCCAAGAAACATATC
CTAATTTATGAACAACACTGG (SEQ ID NO:15)

Figure 10B

>AL354795_23.[865:702].sp
CAAGGCGTGCCGGTCGTGGGGCTGGTGGTGGAAGGCGGTCCCAACGTCAT
CCTGTCAGTGTGGGAGACTGTCAAGGACAAGGACCCAGTGGTGGTGTGTG
AGGGCACAGGTAGGGCGGTTGACCTCCTGGCCTTCACACACAAACACCTG
GCAGATGAAGGG (SEQ ID NO:16)

>AL354795_12.[3748:3858].sp
TACCGAATAACCTTGATTGACATTGGATTAGTAGTAGAATACCTCATTGGT
AGAGCATATCGCAGCAACTACACTAGAAAACATTTCAGAGCCCTCTACAA
CAACCTCTAC (SEQ ID NO:17)
//
>AL354795_3.[5350:5214].sp
GGAGTGTCCAAGCATGTTGGGGATGCCTTGAAATCCCATTCCTCTCATTCC
TTGAGAAAAATCTGGACAGTTGGAATCCCTCCTTGGGGTGTCATTGAGAA
CCAGAGAGACCTTATTGGAAAGATGTAAGTAGA (SEQ ID NO:18)
//
>AL354795_11.[2359:2220].sp
ATAGAACTCTACCTCAGTAAGGAGGATCTGAAAAAACTTCATGATTTTGA
GGAGCAGTGCGTGGAAAAATACTTCCATGAGAAGATGGAAGATGTGAATT
GTAGTTGTGAGGAACGAATCCGAGTGACATCAGGAAGG (SEQ ID NO:19)
//
>AL354795_16.[2585:2452].sp
ATGGCGTATTTGGCATTCCTCATGCTGTTCACTTACACCGTGTTGGTGGAG
ATGCAGCCCCAGCCCAGCGTGCAGGAGTGGCTTGTTAGCATTTACATCTTC
ACCAATGCTATTGAGGTGGTCAGGGAGGTG (SEQ ID NO:20)
//
>AL354795_24.[1814:1681].sp
ATGCTGCGACCTCAGGTGAAAGAGGAGATCATCTGCATGATTCAGAACAC
TTTCAACTTTAGTTTTAAACAGTACAAGCACCTTACCCAAATACTAATGGA
GTGTATGGTTCACAGGGATTGTGTGAGTATG (SEQ ID NO:21)
//
>AL354795_14.[4053:3974].sp
TTACAGATTATTATAAGCATTATTTTACCACCCACCATTTTGACACTGGAA
TTTAAAAGCAAAGCTGAGATGTCACAT (SEQ ID NO:22)
//
>AL354795_18.[1407:1550].sp
TCCATTTTAAGGCTGAATAATATTCCCTTGGGTATATATGCCATATTTTGTT
TATCCATCCAGAAATCTATTTCTATGTCAGTGGTATTGTTCTGTTGGTCTG
GTGGCACAACAGGTATTTAGCTCAATTTTTAATGATTGTG (SEQ ID NO:23)

>AL354795_17.[2079:1979].sp
AAGAAAAAGAAAGAAAGGAAAGAAAAGAAAAGGAAACGAAAGAGAGG
AAAGGAGAGGAGAGGAAAGGAGAGGAAGAAAGAGAGAGAGAAAGA
GAGA (SEQ ID NO:24)

Figure 11A

```
  1  CAAGTTCTCTGGTCTCCACCCAAAGATGATTATCCTATCTAAGTCCCAGAAATCCTGGAT   60
  1                           M  I  I  L  S  K  S  Q  K  S  W  I   12

61  TAAAGGAGTATTTGACAAGAGAGAATGTAGCACAATCATACCCAGCTCAAAAAATCCTCA  120
 13   K  G  V  F  D  K  R  E  C  S  T  I  I  P  S  S  K  N  P  H   32

121  CAGATGTACTCCAGTATGCCAAGTCTGCCAGAATTTAATCAGGTGTTACTGTGGCCGACT  180
 33   R  C  T  P  V  C  Q  V  C  Q  N  L  I  R  C  Y  C  G  R  L   52

181  GATTGGAGACCATGCTGGGATAGATTATTCCTGGACCATCTCAGCTGCCAAGGGTAAAGA  240
 53   I  G  D  H  A  G  I  D  Y  S  W  T  I  S  A  A  K  G  K  E   72

241  AAGTGAACAATGGTCTGTTGAAAAGCACACAACGAAAAGCCCAACAGATACTTTTGGCAC  300
 73   S  E  Q  W  S  V  E  K  H  T  T  K  S  P  T  D  T  F  G  T   92

301  GATTAATTTCCAAGATGGAGAGCACACCCATCATGCCAAGTATATTAGAACTTCTTATGA  360
 93   I  N  F  Q  D  G  E  H  T  H  H  A  K  Y  I  R  T  S  Y  D  112

361  TACAAAACTGGATCATCTGTTACATTTAATGTTGAAAGAGTGGAAAATGGAACTGCCCAA  420
113   T  K  L  D  H  L  L  H  L  M  L  K  E  W  K  M  E  L  P  K  132

421  GCTTGTGATCTCAGTCCATGGGGGCATCCAGAACTTTACTATGCCCTCTAAATTTAAAGA  480
133   L  V  I  S  V  H  G  G  I  Q  N  F  T  M  P  S  K  F  K  E  152

481  GATTTTCAGCCAAGGTTTGGTTAAAGCTGCAGAGACAACAGGAGCGTGGATAATAACTGA  540
153   I  F  S  Q  G  L  V  K  A  A  E  T  T  G  A  W  I  I  T  E  172

541  AGGCATCAATACAGGAGTGTCCAAGCATGTTGGGGATGCCTTGAAATCCCATTCCTCTCA  600
173   G  I  N  T  G  V  S  K  H  V  G  D  A  L  K  S  H  S  S  H  192

601  TTCCTTGAGAAAAATCTGGACAGTTGGAATCCCTCCTTGGGGTGTCATTGAGAACCAGAG  660
193   S  L  R  K  I  W  T  V  G  I  P  P  W  G  V  I  E  N  Q  R  212

661  AGACCTTATTGGAAAAGATGTGGTGTGCCTGTACCAGACTCTGGATAACCCCCTCAGCAA  720
213   D  L  I  G  K  D  V  V  C  L  Y  Q  T  L  D  N  P  L  S  K  232

721  GCTCACAACACTCAACAGCATGCACTCGCACTTCATCCTGTCTGATGATGGGACCGTGGG  780
233   L  T  T  L  N  S  M  H  S  H  F  I  L  S  D  D  G  T  V  G  252

781  CAAGTATGGAAATGAAATGAAGCTCAGAAGGAACCTGGAGAAGTACCTCTCTCTGCAGAA  840
253   K  Y  G  N  E  M  K  L  R  R  N  L  E  K  Y  L  S  L  Q  K  272
```

Figure 11B

```
 841  AATACACTGCCGCTCAAGACAAGGCGTGCCGGTCGTGGGGCTGGTGGTGGAAGGCGGTCC   900
 273   I  H  C  R  S  R  Q  G  V  P  V  V  G  L  V  V  E  G  G  P   292

901  CAACGTCATCCTGTCAGTGTGGGAGACTGTCAAGGACAAGGACCCAGTGGTGGTGTGTGA   960
 293   N  V  I  L  S  V  W  E  T  V  K  D  K  D  P  V  V  V  C  E   312

961  GGGCACAGGTAGGGCGGCTGACCTCCTGGCCTTCACACACAAACACCTGGCAGATGAAGG  1020
 313   G  T  G  R  A  A  D  L  L  A  F  T  H  K  H  L  A  D  E  G   332

1021  GATGCTGCGACCTCAGGTGAAAGAGGAGATCATCTGCATGATTCAGAACACTTTCAACTT  1080
 333   M  L  R  P  Q  V  K  E  E  I  I  C  M  I  Q  N  T  F  N  F   352

1081  TAGTCTTAAACAGTCCAAGCACCTTTTCCAAATTCTAATGGAGTGTATGGTTCACAGGGA  1140
 353   S  L  K  Q  S  K  H  L  F  Q  I  L  M  E  C  M  V  H  R  D   372

1141  TTGTATTACCATATTTGATGCTGACTCTGAAGAGCAGCAAGACCTGGACTTAGCAATCCT  1200
 373   C  I  T  I  F  D  A  D  S  E  E  Q  Q  D  L  D  L  A  I  L   392

1201  AACAGCTTTGCTGAAGGGCACAAATTTATCAGCGTCAGAGCAATTAAATCTGGCAATGGC  1260
 393   T  A  L  L  K  G  T  N  L  S  A  S  E  Q  L  N  L  A  M  A   412

1261  TTGGGACAGGGTGGACATTGCCAAGAAACATATCCTAATTTATGAACAACACTGGAAGCC  1320
 413   W  D  R  V  D  I  A  K  K  H  I  L  I  Y  E  Q  H  W  K  P   432

1321  TGATGCCCTGGAACAAGCAATGTCAGATGCTTTAGTGATGGATCGGGTGGATTTTGTGAA  1380
 433   D  A  L  E  Q  A  M  S  D  A  L  V  M  D  R  V  D  F  V  K   452

1381  GCTCTTAATAGAATATGGAGTGAACCTCCATCGCTTTCTTACCATCCCTCGACTGGAAGA  1440
 453   L  L  I  E  Y  G  V  N  L  H  R  F  L  T  I  P  R  L  E  E   472

1441  GCTCTACAATACAAAACAAGGACCTACTAATACACTCTTGCATCATCTCGTCCAAGATGT  1500
 473   L  Y  N  T  K  Q  G  P  T  N  T  L  L  H  H  L  V  Q  D  V   492

1501  GAAACAGGTAACCTAATTAAGAAGGCGTGAACATGTCTTTGTGTATTGCCTTAGCTTTGT  1560
 493   K  Q  V  T                                                   496

1561  GTTGGAGGAGTCACTGAATTTTGCTTTGTAAAATGCAGATTTGGATTGTTTTGTTAATTA  1620

1621  CCTATCTTCTTTACCTTGATTTGAACAAGTTCATCAACAAACCACATTCGTACACTTTTT  1680

1681  TCCTTAATTTACTTTATGTTTTAAAAGACTTGATCCATCAGTTAGGTGATATTTGCTAAT  1740

1741  AAAAAGCCATGAATCAGAGACATGCAATGCTTCTAATCAGAACTTCAGCTTACCCCGATA  1800
```

Figure 11C

1801  CCGTGGTGGTGCCTATGATGATGATACCAGCTGGAAATAAATAACTTTGTGGTTGTGTTA  1860

1861  TCCTTAAAAAAAAAAAAAAAAAAAAAAAAAAAAAAAAAAAAAAAAAAAAAAAAAAAAAAA  1920

1921  AAAAAAAAAAAAA  1933

SEQUENCE LISTING

<160> NUMBER OF SEQ ID NOS: 335

<210> SEQ ID NO 1
<211> LENGTH: 6054
<212> TYPE: DNA
<213> ORGANISM: Homo sapiens
<220> FEATURE:
<221> NAME/KEY: CDS
<222> LOCATION: (1)..(6051)

<400> SEQUENCE: 1

```
atg att atc cta tct aag tcc cag aaa tcc tgg att aaa gga gta ttt        48
Met Ile Ile Leu Ser Lys Ser Gln Lys Ser Trp Ile Lys Gly Val Phe
1               5                   10                  15 gac aag aga gaa tgt agc aca atc ata ccc agc tca aaa aat cct cac        96
Asp Lys Arg Glu Cys Ser Thr Ile Ile Pro Ser Ser Lys Asn Pro His
                20                  25                  30 aga tgt act cca gta tgc caa gtc tgc cag aat tta atc agg tgt tac       144
Arg Cys Thr Pro Val Cys Gln Val Cys Gln Asn Leu Ile Arg Cys Tyr
            35                  40                  45 tgt ggc cga ctg att gga gac cat gct ggg ata gat tat tcc tgg acc       192
Cys Gly Arg Leu Ile Gly Asp His Ala Gly Ile Asp Tyr Ser Trp Thr
        50                  55                  60 atc tca gct gcc aag ggt aaa gaa agt gaa caa tgg tct gtt gaa aag       240
Ile Ser Ala Ala Lys Gly Lys Glu Ser Glu Gln Trp Ser Val Glu Lys
65                  70                  75                  80 cac aca acg aaa agc cca aca gat act ttt ggc acg att aat ttc caa       288
His Thr Thr Lys Ser Pro Thr Asp Thr Phe Gly Thr Ile Asn Phe Gln
                85                  90                  95 gat gga gag cac acc cat cat gcc aag tat att aga act tct tat gat       336
Asp Gly Glu His Thr His His Ala Lys Tyr Ile Arg Thr Ser Tyr Asp
                100                 105                 110 aca aaa ctg gat cat ctg tta cat tta atg ttg aaa gag tgg aaa atg       384
Thr Lys Leu Asp His Leu Leu His Leu Met Leu Lys Glu Trp Lys Met
            115                 120                 125 gaa ctg ccc aag ctt gtg atc tca gtc cat ggg ggc atc cag aac ttt       432
Glu Leu Pro Lys Leu Val Ile Ser Val His Gly Gly Ile Gln Asn Phe
        130                 135                 140 act atg ccc tct aaa ttt aaa gag att ttc agc caa ggt ttg gtt aaa       480
Thr Met Pro Ser Lys Phe Lys Glu Ile Phe Ser Gln Gly Leu Val Lys
145                 150                 155                 160 gct gca gag aca aca gga gcg tgg ata ata act gaa ggc atc aat aca       528
Ala Ala Glu Thr Thr Gly Ala Trp Ile Ile Thr Glu Gly Ile Asn Thr
                165                 170                 175 gga gtg tcc aag cat gtt ggg gat gcc ttg aaa tcc cat tcc tct cat       576
Gly Val Ser Lys His Val Gly Asp Ala Leu Lys Ser His Ser Ser His
                180                 185                 190 tcc ttg aga aaa atc tgg aca gtt gga atc cct cct tgg ggt gtc att       624
Ser Leu Arg Lys Ile Trp Thr Val Gly Ile Pro Pro Trp Gly Val Ile
            195                 200                 205 gag aac cag aga gac ctt att gga aaa gat gtg gtg tgc ctg tac cag       672
Glu Asn Gln Arg Asp Leu Ile Gly Lys Asp Val Val Cys Leu Tyr Gln
        210                 215                 220 act ctg gat aac ccc ctc agc aag ctc aca aca ctc aac agc atg cac       720
Thr Leu Asp Asn Pro Leu Ser Lys Leu Thr Thr Leu Asn Ser Met His
225                 230                 235                 240 tcg cac ttc atc ctg tct gat gat ggg acc gtg ggc aag tat gga aat       768
Ser His Phe Ile Leu Ser Asp Asp Gly Thr Val Gly Lys Tyr Gly Asn
                245                 250                 255
```

-continued

| | | |
|---|---|---|
| gaa atg aag ctc aga agg aac ctg gag aag tac ctc tct ctg cag aaa<br>Glu Met Lys Leu Arg Arg Asn Leu Glu Lys Tyr Leu Ser Leu Gln Lys<br>260                                    265                        270 | 816 |
| ata cac tgc cgc tca aga caa ggc gtg ccg gtc gtg ggg ctg gtg gtg<br>Ile His Cys Arg Ser Arg Gln Gly Val Pro Val Val Gly Leu Val Val<br>275                               280                        285 | 864 |
| gaa ggc ggt ccc aac gtc atc ctg tca gtg tgg gag act gtc aag gac<br>Glu Gly Gly Pro Asn Val Ile Leu Ser Val Trp Glu Thr Val Lys Asp<br>290                             295                        300 | 912 |
| aag gac cca gtg gtg gtg tgt gag ggc aca ggt agg gcg gct gac ctc<br>Lys Asp Pro Val Val Val Cys Glu Gly Thr Gly Arg Ala Ala Asp Leu<br>305                            310                        315                        320 | 960 |
| ctg gcc ttc aca cac aaa cac ctg gca gat gaa ggg atg ctg cga cct<br>Leu Ala Phe Thr His Lys His Leu Ala Asp Glu Gly Met Leu Arg Pro<br>                        325                        330                        335 | 1008 |
| cag gtg aaa gag gag atc atc tgc atg att cag aac act ttc aac ttt<br>Gln Val Lys Glu Glu Ile Ile Cys Met Ile Gln Asn Thr Phe Asn Phe<br>                        340                        345                        350 | 1056 |
| agt ctt aaa cag tcc aag cac ctt ttc caa att cta atg gag tgt atg<br>Ser Leu Lys Gln Ser Lys His Leu Phe Gln Ile Leu Met Glu Cys Met<br>                        355                        360                        365 | 1104 |
| gtt cac agg gat tgt att acc ata ttt gat gct gac tct gaa gag cag<br>Val His Arg Asp Cys Ile Thr Ile Phe Asp Ala Asp Ser Glu Glu Gln<br>370                              375                        380 | 1152 |
| caa gac ctg gac tta gca atc cta aca gct ttg ctg aag ggc aca aat<br>Gln Asp Leu Asp Leu Ala Ile Leu Thr Ala Leu Leu Lys Gly Thr Asn<br>385                            390                        395                        400 | 1200 |
| tta tca gcg tca gag caa tta aat ctg gca atg gct tgg gac agg gtg<br>Leu Ser Ala Ser Glu Gln Leu Asn Leu Ala Met Ala Trp Asp Arg Val<br>                        405                        410                        415 | 1248 |
| gac att gcc aag aaa cat atc cta att tat gaa caa cac tgg aag cct<br>Asp Ile Ala Lys Lys His Ile Leu Ile Tyr Glu Gln His Trp Lys Pro<br>                        420                        425                        430 | 1296 |
| gat gcc ctg gaa caa gca atg tca gat gct tta gtg atg gat cgg gtg<br>Asp Ala Leu Glu Gln Ala Met Ser Asp Ala Leu Val Met Asp Arg Val<br>435                            440                        445 | 1344 |
| gat ttt gtg aag ctc tta ata gaa tat gga gtg aac ctc cat cgc ttt<br>Asp Phe Val Lys Leu Leu Ile Glu Tyr Gly Val Asn Leu His Arg Phe<br>450                            455                        460 | 1392 |
| ctt acc atc cct cga ctg gaa gag ctc tac aat aca aaa caa gga cct<br>Leu Thr Ile Pro Arg Leu Glu Glu Leu Tyr Asn Thr Lys Gln Gly Pro<br>465                            470                        475                        480 | 1440 |
| act aat aca ctc ttg cat cat ctc gtc caa gat gtg aaa cag cat acc<br>Thr Asn Thr Leu Leu His His Leu Val Gln Asp Val Lys Gln His Thr<br>                        485                        490                        495 | 1488 |
| ctt ctt tca ggc tac cga ata acc ttg att gac att gga tta gta gta<br>Leu Leu Ser Gly Tyr Arg Ile Thr Leu Ile Asp Ile Gly Leu Val Val<br>                        500                        505                        510 | 1536 |
| gaa tac ctc att ggt aga gca tat cgc agc aac tac act aga aaa cat<br>Glu Tyr Leu Ile Gly Arg Ala Tyr Arg Ser Asn Tyr Thr Arg Lys His<br>                        515                        520                        525 | 1584 |
| ttc aga gcc ctc tac aac aac ctc tac aga aaa tac aag cac cag aga<br>Phe Arg Ala Leu Tyr Asn Asn Leu Tyr Arg Lys Tyr Lys His Gln Arg<br>530                            535                        540 | 1632 |
| cac tcc tca gga aat aga aat gag tct gca gaa agt acg ctg cac tcc<br>His Ser Ser Gly Asn Arg Asn Glu Ser Ala Glu Ser Thr Leu His Ser<br>545                            550                        555                        560 | 1680 |
| cag ttc att aga act gca cag cca tac aaa ttc aag gaa aag tct ata<br>Gln Phe Ile Arg Thr Ala Gln Pro Tyr Lys Phe Lys Glu Lys Ser Ile<br>                        565                        570                        575 | 1728 |

```
gtc ctt cat aaa tca agg aag aag tca aaa gaa caa aat gta tca gat      1776
Val Leu His Lys Ser Arg Lys Lys Ser Lys Glu Gln Asn Val Ser Asp
            580                 585                 590 gac cct gag tct act ggc ttt ctt tac cct tac aat gac ctg ctg gtt      1824
Asp Pro Glu Ser Thr Gly Phe Leu Tyr Pro Tyr Asn Asp Leu Leu Val
        595                 600                 605 tgg gct gtg ctg atg aaa agg cag aag atg gct atg ttc ttc tgg cag      1872
Trp Ala Val Leu Met Lys Arg Gln Lys Met Ala Met Phe Phe Trp Gln
610                 615                 620 cat gga gag gag gcc acg gtt aaa gcc gtg att gcg tgt atc ctc tac      1920
His Gly Glu Glu Ala Thr Val Lys Ala Val Ile Ala Cys Ile Leu Tyr
625                 630                 635                 640 cgg gca atg gcc cat gaa gct aag gag agt cac atg gtg gat gat gcc      1968
Arg Ala Met Ala His Glu Ala Lys Glu Ser His Met Val Asp Asp Ala
                645                 650                 655 tca gaa gag ttg aag aat tac tca aaa cag ttt ggc cag ctg gct ctg      2016
Ser Glu Glu Leu Lys Asn Tyr Ser Lys Gln Phe Gly Gln Leu Ala Leu
            660                 665                 670 gac ttg ttg gag aag gca ttc aag cag aat gag cgc atg gcc atg acg      2064
Asp Leu Leu Glu Lys Ala Phe Lys Gln Asn Glu Arg Met Ala Met Thr
        675                 680                 685 ctg ttg acg tat gaa ctc agg aac tgg agc aat tcg acc tgc ctg aaa      2112
Leu Leu Thr Tyr Glu Leu Arg Asn Trp Ser Asn Ser Thr Cys Leu Lys
690                 695                 700 ctg gcc gtg tcg gga gga tta cga ccc ttt gtt tca cat act tgt acc      2160
Leu Ala Val Ser Gly Gly Leu Arg Pro Phe Val Ser His Thr Cys Thr
705                 710                 715                 720 cag atg cta ctg aca gac atg tgg atg ggg agg ctg aaa atg agg aaa      2208
Gln Met Leu Leu Thr Asp Met Trp Met Gly Arg Leu Lys Met Arg Lys
                725                 730                 735 aac tct tgg tta aag att att ata agc att att tta cca ccc acc att      2256
Asn Ser Trp Leu Lys Ile Ile Ile Ser Ile Ile Leu Pro Pro Thr Ile
            740                 745                 750 ttg aca ctg gaa ttt aaa agc aaa gct gag atg tca cat gtt ccc cag      2304
Leu Thr Leu Glu Phe Lys Ser Lys Ala Glu Met Ser His Val Pro Gln
        755                 760                 765 tcc cag gac ttc caa ttt atg tgg tat tac agt gac cag aac gcc agc      2352
Ser Gln Asp Phe Gln Phe Met Trp Tyr Tyr Ser Asp Gln Asn Ala Ser
770                 775                 780 agt tcc aaa gaa agt gct tct gtg aaa gag tat gat ttg gaa agg ggc      2400
Ser Ser Lys Glu Ser Ala Ser Val Lys Glu Tyr Asp Leu Glu Arg Gly
785                 790                 795                 800 cat gat gag aaa ctg gat gaa aat cag cat ttt ggt ttg gaa agt ggg      2448
His Asp Glu Lys Leu Asp Glu Asn Gln His Phe Gly Leu Glu Ser Gly
                805                 810                 815 cac caa cac ctt ccg tgg acc agg aaa gtc tat gag ttc tac agt gct      2496
His Gln His Leu Pro Trp Thr Arg Lys Val Tyr Glu Phe Tyr Ser Ala
            820                 825                 830 cca att gtc aag ttt tgg ttt tat acg atg gcg tat ttg gca ttc ctc      2544
Pro Ile Val Lys Phe Trp Phe Tyr Thr Met Ala Tyr Leu Ala Phe Leu
        835                 840                 845 atg ctg ttc act tac acc gtg ttg gtg gag atg cag ccc cag ccc agc      2592
Met Leu Phe Thr Tyr Thr Val Leu Val Glu Met Gln Pro Gln Pro Ser
850                 855                 860 gtg cag gag tgg ctt gtt agc att tac atc ttc acc aat gct att gag      2640
Val Gln Glu Trp Leu Val Ser Ile Tyr Ile Phe Thr Asn Ala Ile Glu
865                 870                 875                 880 gtg gtc agg gag atc tgt att tca gaa cct ggg aag ttt acc caa aag      2688
Val Val Arg Glu Ile Cys Ile Ser Glu Pro Gly Lys Phe Thr Gln Lys
                885                 890                 895
```

```
gtg aag gta tgg att agt gag tac tgg aac tta aca gaa act gtg gcc    2736
Val Lys Val Trp Ile Ser Glu Tyr Trp Asn Leu Thr Glu Thr Val Ala
            900                 905                 910 att ggc ctg ttt tca gct ggc ttc gtc ctt cga tgg ggt gac cct cct    2784
Ile Gly Leu Phe Ser Ala Gly Phe Val Leu Arg Trp Gly Asp Pro Pro
        915                 920                 925 ttt cac aca gcg gga aga ctg atc tac tgc ata gac atc ata ttc tgg    2832
Phe His Thr Ala Gly Arg Leu Ile Tyr Cys Ile Asp Ile Ile Phe Trp
        930                 935                 940 ttc tca cgg ctc ctg gac ttc ttt gct gtg aat caa cat gca ggt cca    2880
Phe Ser Arg Leu Leu Asp Phe Phe Ala Val Asn Gln His Ala Gly Pro
945                 950                 955                 960 tat gtg acc atg att gca aaa atg aca gca aac atg ttc tat att gtg    2928
Tyr Val Thr Met Ile Ala Lys Met Thr Ala Asn Met Phe Tyr Ile Val
            965                 970                 975 atc atc atg gcc ata gtc ctg ctg agc ttt gga gtg gca cgc aag gcc    2976
Ile Ile Met Ala Ile Val Leu Leu Ser Phe Gly Val Ala Arg Lys Ala
        980                 985                 990 atc ctt tcg cca aaa gag cca cca tct tgg agt cta gct cga gat att    3024
Ile Leu Ser Pro Lys Glu Pro Pro Ser Trp Ser Leu Ala Arg Asp Ile
        995                 1000                1005 gta ttt gag cca tac tgg atg ata tac gga gaa gtc tat gct gga        3069
Val Phe Glu Pro Tyr Trp Met Ile Tyr Gly Glu Val Tyr Ala Gly
        1010                1015                1020 gaa ata gat gtt tgt tca agc cag cca tcc tgc cct cct ggt tct        3114
Glu Ile Asp Val Cys Ser Ser Gln Pro Ser Cys Pro Pro Gly Ser
    1025                1030                1035 ttt ctt act cca ttc ttg caa gct gtc tac ctc ttc gtg caa tat        3159
Phe Leu Thr Pro Phe Leu Gln Ala Val Tyr Leu Phe Val Gln Tyr
    1040                1045                1050 atc atc atg gtg aac ctg ttg att gct ttc ttc aac aac gtt tac        3204
Ile Ile Met Val Asn Leu Leu Ile Ala Phe Phe Asn Asn Val Tyr
    1055                1060                1065 tta gat atg gaa tcc att tca aat aac ctg tgg aaa tac aac cgc        3249
Leu Asp Met Glu Ser Ile Ser Asn Asn Leu Trp Lys Tyr Asn Arg
    1070                1075                1080 tat cgc tac atc atg acc tac cac gag aag ccc tgg ctg ccc cca        3294
Tyr Arg Tyr Ile Met Thr Tyr His Glu Lys Pro Trp Leu Pro Pro
    1085                1090                1095 cct ctc atc ctg ctg agc cac gtg ggc ctt ctc ctc cgc cgc ctg        3339
Pro Leu Ile Leu Leu Ser His Val Gly Leu Leu Leu Arg Arg Leu
    1100                1105                1110 tgc tgt cat cga gct cct cac gac caa gaa gag ggt gac gtt gga        3384
Cys Cys His Arg Ala Pro His Asp Gln Glu Glu Gly Asp Val Gly
    1115                1120                1125 tta aaa ctc tac ctc agt aag gag gat ctg aaa aaa ctt cat gat        3429
Leu Lys Leu Tyr Leu Ser Lys Glu Asp Leu Lys Lys Leu His Asp
    1130                1135                1140 ttt gag gag cag tgc gtg gaa aaa tac ttc cat gag aag atg gaa        3474
Phe Glu Glu Gln Cys Val Glu Lys Tyr Phe His Glu Lys Met Glu
    1145                1150                1155 gat gtg aat tgt agt tgt gag gaa cga atc cga gtg aca tca gaa        3519
Asp Val Asn Cys Ser Cys Glu Glu Arg Ile Arg Val Thr Ser Glu
    1160                1165                1170 agg gtt aca gag atg tac ttc cag ctg aaa gaa atg aat gaa aag        3564
Arg Val Thr Glu Met Tyr Phe Gln Leu Lys Glu Met Asn Glu Lys
    1175                1180                1185 gtg tct ttt ata aag gac tcc tta ctg tct ttg gac agc cag gtg        3609
Val Ser Phe Ile Lys Asp Ser Leu Leu Ser Leu Asp Ser Gln Val
    1190                1195                1200
```

```
                                        -continued
gga cac ctg cag gat ctc tct gcc ctg act gtg gat acc ctg aaa         3654
Gly His Leu Gln Asp Leu Ser Ala Leu Thr Val Asp Thr Leu Lys
    1205            1210                1215 gtc ctt tct gct gtt gac act ttg caa gag gat gag gct ctc ctg         3699
Val Leu Ser Ala Val Asp Thr Leu Gln Glu Asp Glu Ala Leu Leu
    1220            1225                1230 gcc aag aga aag cat tct act tgc aaa aaa ctt ccc cac agc tgg         3744
Ala Lys Arg Lys His Ser Thr Cys Lys Lys Leu Pro His Ser Trp
1235            1240                1245 agc aat gtc atc tgt gca gag gtt cta ggc agc atg gag atc gct         3789
Ser Asn Val Ile Cys Ala Glu Val Leu Gly Ser Met Glu Ile Ala
    1250            1255                1260 gga gag aag aaa tac cag tat tat agc atg ccc tct tct ttg ctg         3834
Gly Glu Lys Lys Tyr Gln Tyr Tyr Ser Met Pro Ser Ser Leu Leu
    1265            1270                1275 agg agc ctg gct gga ggc cgg cat ccc cca aga gtg cag agg ggg         3879
Arg Ser Leu Ala Gly Gly Arg His Pro Pro Arg Val Gln Arg Gly
    1280            1285                1290 gca ctt ctt gag att aca aac agt aaa aga gag gct aca aat gta         3924
Ala Leu Leu Glu Ile Thr Asn Ser Lys Arg Glu Ala Thr Asn Val
    1295            1300                1305 aga aat gac cag gaa agg caa gaa aca caa agt agt ata gtg gtt         3969
Arg Asn Asp Gln Glu Arg Gln Glu Thr Gln Ser Ser Ile Val Val
    1310            1315                1320 tct ggg gtg tct cct aac agg caa gca cac tca aag tat ggc cag         4014
Ser Gly Val Ser Pro Asn Arg Gln Ala His Ser Lys Tyr Gly Gln
1325            1330                1335 ttt ctt ctg gtc ccc tct aat cta aag cga gtt cct ttt tca gca         4059
Phe Leu Leu Val Pro Ser Asn Leu Lys Arg Val Pro Phe Ser Ala
    1340            1345                1350 gaa act gtc ttg cct ctg tcc aga ccc tct gtg cca gat gtg ctg         4104
Glu Thr Val Leu Pro Leu Ser Arg Pro Ser Val Pro Asp Val Leu
    1355            1360                1365 gca act gaa cag gac atc cag act gag gtt ctt gtt cat ctg act         4149
Ala Thr Glu Gln Asp Ile Gln Thr Glu Val Leu Val His Leu Thr
    1370            1375                1380 ggg cag acc cca gtt gtc tct gac tgg gca tca gtg gat gaa ccc         4194
Gly Gln Thr Pro Val Val Ser Asp Trp Ala Ser Val Asp Glu Pro
    1385            1390                1395 aag gaa aag cac gag cct att gct cac tta ctg gat gga caa gac         4239
Lys Glu Lys His Glu Pro Ile Ala His Leu Leu Asp Gly Gln Asp
1400            1405                1410 aag gca gag caa gtg cta ccc act ttg agt tgc aca cct gaa ccc         4284
Lys Ala Glu Gln Val Leu Pro Thr Leu Ser Cys Thr Pro Glu Pro
    1415            1420                1425 atg aca atg agc tcc cct ctt tcc caa gcc aag atc atg caa act         4329
Met Thr Met Ser Ser Pro Leu Ser Gln Ala Lys Ile Met Gln Thr
    1430            1435                1440 gga ggt gga tat gta aac tgg gca ttt tca gaa ggt gat gaa act         4374
Gly Gly Gly Tyr Val Asn Trp Ala Phe Ser Glu Gly Asp Glu Thr
    1445            1450                1455 ggt gtg ttt agc atc aag aaa aag tgg caa acc tgc ttg ccc tcc         4419
Gly Val Phe Ser Ile Lys Lys Lys Trp Gln Thr Cys Leu Pro Ser
1460            1465                1470 act tgt gac agt gat tcc tct cgg agt gaa cag cac cag aag cag         4464
Thr Cys Asp Ser Asp Ser Ser Arg Ser Glu Gln His Gln Lys Gln
    1475            1480                1485 gcc cag gac agc tcc cta tct gat aac tca aca aga tcg gcc cag         4509
Ala Gln Asp Ser Ser Leu Ser Asp Asn Ser Thr Arg Ser Ala Gln
    1490            1495                1500
```

```
agt agt gaa tgc tca gag gtg gga cca tgg ctt cag cca aac aca       4554
Ser Ser Glu Cys Ser Glu Val Gly Pro Trp Leu Gln Pro Asn Thr
1505            1510                1515 tcc ttt tgg atc aat cct ctc cgc aga tac agg ccc ttc gct agg       4599
Ser Phe Trp Ile Asn Pro Leu Arg Arg Tyr Arg Pro Phe Ala Arg
    1520            1525                1530 agt cat agt ttt aga ttc cat aag gag gag aaa ttg atg aag atc       4644
Ser His Ser Phe Arg Phe His Lys Glu Glu Lys Leu Met Lys Ile
1535            1540                1545 tgt aag att aaa aat ctt tca ggc tct tca gaa ata ggg cag gga       4689
Cys Lys Ile Lys Asn Leu Ser Gly Ser Ser Glu Ile Gly Gln Gly
    1550            1555                1560 gca tgg gtc aaa gcg aaa atg cta acc aaa gac agg aga ctg tca       4734
Ala Trp Val Lys Ala Lys Met Leu Thr Lys Asp Arg Arg Leu Ser
1565            1570                1575 aag aaa aag aag aat act caa gga ctc cag gtg cca atc ata aca       4779
Lys Lys Lys Lys Asn Thr Gln Gly Leu Gln Val Pro Ile Ile Thr
    1580            1585                1590 gtc aat gcc tgc tct cag agt gac cag ttg aat cca gag cca gga       4824
Val Asn Ala Cys Ser Gln Ser Asp Gln Leu Asn Pro Glu Pro Gly
1595            1600                1605 gaa aac agc atc tct gaa gag gag tac agc aag aac tgg ttc aca       4869
Glu Asn Ser Ile Ser Glu Glu Glu Tyr Ser Lys Asn Trp Phe Thr
    1610            1615                1620 gtg tcc aaa ttt agt cac aca ggt gta gaa cct tac ata cat cag       4914
Val Ser Lys Phe Ser His Thr Gly Val Glu Pro Tyr Ile His Gln
1625            1630                1635 aaa atg aaa act aaa gaa att gga caa tgt gct ata caa atc agt       4959
Lys Met Lys Thr Lys Glu Ile Gly Gln Cys Ala Ile Gln Ile Ser
    1640            1645                1650 gat tac cta aag cag tct caa gag gat ctc agc aaa aac tct ttg       5004
Asp Tyr Leu Lys Gln Ser Gln Glu Asp Leu Ser Lys Asn Ser Leu
1655            1660                1665 tgg aat tcc agg agc acc aac ctc aat agg aac tcc ctg ctg aaa       5049
Trp Asn Ser Arg Ser Thr Asn Leu Asn Arg Asn Ser Leu Leu Lys
    1670            1675                1680 agt tca att gga gtt gac aag atc tca gcc tcc tta aaa agc cct       5094
Ser Ser Ile Gly Val Asp Lys Ile Ser Ala Ser Leu Lys Ser Pro
1685            1690                1695 caa gag cct cac cat cat tat tca gcc att gaa agg aat aat tta       5139
Gln Glu Pro His His His Tyr Ser Ala Ile Glu Arg Asn Asn Leu
    1700            1705                1710 atg agg ctt tct cag acc ata cca ttt aca cca gtc caa ctg ttt       5184
Met Arg Leu Ser Gln Thr Ile Pro Phe Thr Pro Val Gln Leu Phe
1715            1720                1725 gca gga gaa gaa ata act gtc tac agg ttg gag gag agt tcc cct       5229
Ala Gly Glu Glu Ile Thr Val Tyr Arg Leu Glu Glu Ser Ser Pro
    1730            1735                1740 tta aac ctt gat aaa agc atg tcc tct tgg tct cag cgt ggg aga       5274
Leu Asn Leu Asp Lys Ser Met Ser Ser Trp Ser Gln Arg Gly Arg
1745            1750                1755 gcg gca atg atc cag gta ttg tcc cga gag gag atg gat ggg ggc       5319
Ala Ala Met Ile Gln Val Leu Ser Arg Glu Glu Met Asp Gly Gly
    1760            1765                1770 ctc cgt aaa gct atg aga gtc gtc agc act tgg tct gag gat gac       5364
Leu Arg Lys Ala Met Arg Val Val Ser Thr Trp Ser Glu Asp Asp
1775            1780                1785 att ctc aag ccg gga caa gtt ttc att gtc aag tcc ttt ctt cct       5409
Ile Leu Lys Pro Gly Gln Val Phe Ile Val Lys Ser Phe Leu Pro
    1790            1795                1800
```

```
gag gtt gtg cgg aca tgg cat aaa atc ttc cag gag agc act gtg      5454
Glu Val Val Arg Thr Trp His Lys Ile Phe Gln Glu Ser Thr Val
    1805                1810                1815 ctt cat ctt tgc ctc agg gaa att caa caa aga gct gct caa          5499
Leu His Leu Cys Leu Arg Glu Ile Gln Gln Gln Arg Ala Ala Gln
    1820                1825                1830 aaa ttg atc tat acc ttc aac caa gtg aaa cca caa acc ata ccc      5544
Lys Leu Ile Tyr Thr Phe Asn Gln Val Lys Pro Gln Thr Ile Pro
    1835                1840                1845 tac aca cca agg ttc ctg gaa gtt ttc tta atc tac tgc cat tca      5589
Tyr Thr Pro Arg Phe Leu Glu Val Phe Leu Ile Tyr Cys His Ser
    1850                1855                1860 gcc aac cag tgg ttg acc att gag aag tat atg aca ggg gag ttc      5634
Ala Asn Gln Trp Leu Thr Ile Glu Lys Tyr Met Thr Gly Glu Phe
    1865                1870                1875 cgg aag tat aac aac aac aat ggt gat gaa atc acc ccc acc aac      5679
Arg Lys Tyr Asn Asn Asn Asn Gly Asp Glu Ile Thr Pro Thr Asn
    1880                1885                1890 acc ctg gag gag ctg atg ttg gct ttc tct cac tgg acc tat gag      5724
Thr Leu Glu Glu Leu Met Leu Ala Phe Ser His Trp Thr Tyr Glu
    1895                1900                1905 tac act cgg gga gag ctg ctg gtt tta gat ttg caa ggt gtt gga      5769
Tyr Thr Arg Gly Glu Leu Leu Val Leu Asp Leu Gln Gly Val Gly
    1910                1915                1920 gaa aat ttg aca gat cca tct gtt ata aaa cct gaa gtc aaa caa      5814
Glu Asn Leu Thr Asp Pro Ser Val Ile Lys Pro Glu Val Lys Gln
    1925                1930                1935 tca aga gga atg gtg ttt gga ccg gcc aat ttg ggg gaa gat gca      5859
Ser Arg Gly Met Val Phe Gly Pro Ala Asn Leu Gly Glu Asp Ala
    1940                1945                1950 att aga aac ttc att gca aaa cat cat tgt aac tcc tgc tgc cgg      5904
Ile Arg Asn Phe Ile Ala Lys His His Cys Asn Ser Cys Cys Arg
    1955                1960                1965 aag ctc aaa ctc ccg gat tta aaa aga aat gac tat tcc cct gaa      5949
Lys Leu Lys Leu Pro Asp Leu Lys Arg Asn Asp Tyr Ser Pro Glu
    1970                1975                1980 agg ata aat tcc acc ttt gga ctt gag ata aaa ata gaa tca gct      5994
Arg Ile Asn Ser Thr Phe Gly Leu Glu Ile Lys Ile Glu Ser Ala
    1985                1990                1995 gag gag cct cca gca agg gag acg ggt aga aat tcc cca gaa gat      6039
Glu Glu Pro Pro Ala Arg Glu Thr Gly Arg Asn Ser Pro Glu Asp
    2000                2005                2010 gat atg caa cta taa                                              6054
Asp Met Gln Leu
    2015
```

<210> SEQ ID NO 2
<211> LENGTH: 2017
<212> TYPE: PRT
<213> ORGANISM: Homo sapiens

<400> SEQUENCE: 2

```
Met Ile Ile Leu Ser Lys Ser Gln Lys Ser Trp Ile Lys Gly Val Phe
1               5                   10                  15

Asp Lys Arg Glu Cys Ser Thr Ile Pro Ser Ser Lys Asn Pro His
            20                  25                  30

Arg Cys Thr Pro Val Cys Gln Val Cys Gln Asn Leu Ile Arg Cys Tyr
        35                  40                  45

Cys Gly Arg Leu Ile Gly Asp His Ala Gly Ile Asp Tyr Ser Trp Thr
    50                  55                  60
```

-continued

```
Ile Ser Ala Ala Lys Gly Lys Glu Ser Glu Gln Trp Ser Val Glu Lys
65                  70                  75                  80

His Thr Thr Lys Ser Pro Thr Asp Thr Phe Gly Thr Ile Asn Phe Gln
                85                  90                  95

Asp Gly Glu His Thr His His Ala Lys Tyr Ile Arg Thr Ser Tyr Asp
            100                 105                 110

Thr Lys Leu Asp His Leu Leu His Leu Met Leu Lys Glu Trp Lys Met
            115                 120                 125

Glu Leu Pro Lys Leu Val Ile Ser Val His Gly Gly Ile Gln Asn Phe
        130                 135                 140

Thr Met Pro Ser Lys Phe Lys Glu Ile Phe Ser Gln Gly Leu Val Lys
145                 150                 155                 160

Ala Ala Glu Thr Thr Gly Ala Trp Ile Ile Thr Glu Gly Ile Asn Thr
                165                 170                 175

Gly Val Ser Lys His Val Gly Asp Ala Leu Lys Ser His Ser Ser His
            180                 185                 190

Ser Leu Arg Lys Ile Trp Thr Val Gly Ile Pro Pro Trp Gly Val Ile
            195                 200                 205

Glu Asn Gln Arg Asp Leu Ile Gly Lys Asp Val Val Cys Leu Tyr Gln
        210                 215                 220

Thr Leu Asp Asn Pro Leu Ser Lys Leu Thr Thr Leu Asn Ser Met His
225                 230                 235                 240

Ser His Phe Ile Leu Ser Asp Asp Gly Thr Val Gly Lys Tyr Gly Asn
                245                 250                 255

Glu Met Lys Leu Arg Arg Asn Leu Glu Lys Tyr Leu Ser Leu Gln Lys
            260                 265                 270

Ile His Cys Arg Ser Arg Gln Gly Val Pro Val Gly Leu Val Val
            275                 280                 285

Glu Gly Gly Pro Asn Val Ile Leu Ser Val Trp Glu Thr Val Lys Asp
        290                 295                 300

Lys Asp Pro Val Val Val Cys Glu Gly Thr Gly Arg Ala Ala Asp Leu
305                 310                 315                 320

Leu Ala Phe Thr His Lys His Leu Ala Asp Glu Gly Met Leu Arg Pro
                325                 330                 335

Gln Val Lys Glu Glu Ile Ile Cys Met Ile Gln Asn Thr Phe Asn Phe
            340                 345                 350

Ser Leu Lys Gln Ser Lys His Leu Phe Gln Ile Leu Met Glu Cys Met
            355                 360                 365

Val His Arg Asp Cys Ile Thr Ile Phe Asp Ala Asp Ser Glu Glu Gln
        370                 375                 380

Gln Asp Leu Asp Leu Ala Ile Leu Thr Ala Leu Leu Lys Gly Thr Asn
385                 390                 395                 400

Leu Ser Ala Ser Glu Gln Leu Asn Leu Ala Met Ala Trp Asp Arg Val
                405                 410                 415

Asp Ile Ala Lys Lys His Ile Leu Ile Tyr Glu Gln His Trp Lys Pro
            420                 425                 430

Asp Ala Leu Glu Gln Ala Met Ser Asp Ala Leu Val Met Asp Arg Val
            435                 440                 445

Asp Phe Val Lys Leu Leu Ile Glu Tyr Gly Val Asn Leu His Arg Phe
        450                 455                 460

Leu Thr Ile Pro Arg Leu Glu Glu Leu Tyr Asn Thr Lys Gln Gly Pro
465                 470                 475                 480
```

```
Thr Asn Thr Leu Leu His His Leu Val Gln Asp Val Lys Gln His Thr
            485                 490                 495

Leu Leu Ser Gly Tyr Arg Ile Thr Leu Ile Asp Ile Gly Leu Val Val
            500                 505                 510

Glu Tyr Leu Ile Gly Arg Ala Tyr Arg Ser Asn Tyr Thr Arg Lys His
            515                 520                 525

Phe Arg Ala Leu Tyr Asn Asn Leu Tyr Arg Lys Tyr Lys His Gln Arg
530                 535                 540

His Ser Ser Gly Asn Arg Asn Glu Ser Ala Glu Ser Thr Leu His Ser
545                 550                 555                 560

Gln Phe Ile Arg Thr Ala Gln Pro Tyr Lys Phe Lys Glu Lys Ser Ile
                565                 570                 575

Val Leu His Lys Ser Arg Lys Ser Lys Glu Gln Asn Val Ser Asp
            580                 585                 590

Asp Pro Glu Ser Thr Gly Phe Leu Tyr Pro Tyr Asn Asp Leu Leu Val
            595                 600                 605

Trp Ala Val Leu Met Lys Arg Gln Lys Met Ala Met Phe Phe Trp Gln
610                 615                 620

His Gly Glu Glu Ala Thr Val Lys Ala Val Ile Ala Cys Ile Leu Tyr
625                 630                 635                 640

Arg Ala Met Ala His Glu Ala Lys Glu Ser His Met Val Asp Asp Ala
                645                 650                 655

Ser Glu Glu Leu Lys Asn Tyr Ser Lys Gln Phe Gly Gln Leu Ala Leu
            660                 665                 670

Asp Leu Leu Glu Lys Ala Phe Lys Gln Asn Glu Arg Met Ala Met Thr
            675                 680                 685

Leu Leu Thr Tyr Glu Leu Arg Asn Trp Ser Asn Ser Thr Cys Leu Lys
            690                 695                 700

Leu Ala Val Ser Gly Gly Leu Arg Pro Phe Val Ser His Thr Cys Thr
705                 710                 715                 720

Gln Met Leu Leu Thr Asp Met Trp Met Gly Arg Leu Lys Met Arg Lys
                725                 730                 735

Asn Ser Trp Leu Lys Ile Ile Ile Ser Ile Ile Leu Pro Pro Thr Ile
            740                 745                 750

Leu Thr Leu Glu Phe Lys Ser Lys Ala Glu Met Ser His Val Pro Gln
            755                 760                 765

Ser Gln Asp Phe Gln Phe Met Trp Tyr Tyr Ser Asp Gln Asn Ala Ser
            770                 775                 780

Ser Ser Lys Glu Ser Ala Ser Val Lys Glu Tyr Asp Leu Glu Arg Gly
785                 790                 795                 800

His Asp Glu Lys Leu Asp Glu Asn Gln His Phe Gly Leu Glu Ser Gly
                805                 810                 815

His Gln His Leu Pro Trp Thr Arg Lys Val Tyr Glu Phe Tyr Ser Ala
                820                 825                 830

Pro Ile Val Lys Phe Trp Phe Tyr Thr Met Ala Tyr Leu Ala Phe Leu
            835                 840                 845

Met Leu Phe Thr Tyr Thr Val Leu Val Glu Met Gln Pro Gln Pro Ser
            850                 855                 860

Val Gln Glu Trp Leu Val Ser Ile Tyr Ile Phe Thr Asn Ala Ile Glu
865                 870                 875                 880

Val Val Arg Glu Ile Cys Ile Ser Glu Pro Gly Lys Phe Thr Gln Lys
                885                 890                 895
```

-continued

```
Val Lys Val Trp Ile Ser Glu Tyr Trp Asn Leu Thr Glu Thr Val Ala
            900                 905                 910
Ile Gly Leu Phe Ser Ala Gly Phe Val Leu Arg Trp Gly Asp Pro Pro
            915                 920                 925
Phe His Thr Ala Gly Arg Leu Ile Tyr Cys Ile Asp Ile Ile Phe Trp
            930                 935                 940
Phe Ser Arg Leu Leu Asp Phe Phe Ala Val Asn Gln His Ala Gly Pro
945                 950                 955                 960
Tyr Val Thr Met Ile Ala Lys Met Thr Ala Asn Met Phe Tyr Ile Val
                965                 970                 975
Ile Ile Met Ala Ile Val Leu Ser Phe Gly Val Ala Arg Lys Ala
                980                 985                 990
Ile Leu Ser Pro Lys Glu Pro Pro  Ser Trp Ser Leu Ala  Arg Asp Ile
            995                 1000                1005
Val Phe Glu Pro Tyr Trp Met  Ile Tyr Gly Glu Val  Tyr Ala Gly
    1010                1015                1020
Glu Ile Asp Val Cys Ser Ser  Gln Pro Ser Cys Pro  Pro Gly Ser
    1025                1030                1035
Phe Leu Thr Pro Phe Leu Gln  Ala Val Tyr Leu Phe  Val Gln Tyr
    1040                1045                1050
Ile Ile Met Val Asn Leu Leu  Ile Ala Phe Phe Asn  Asn Val Tyr
    1055                1060                1065
Leu Asp Met Glu Ser Ile Ser  Asn Asn Leu Trp Lys  Tyr Asn Arg
    1070                1075                1080
Tyr Arg Tyr Ile Met Thr Tyr  His Glu Lys Pro Trp  Leu Pro Pro
    1085                1090                1095
Pro Leu Ile Leu Leu Ser His  Val Gly Leu Leu Leu  Arg Arg Leu
    1100                1105                1110
Cys Cys His Arg Ala Pro His  Asp Gln Glu Glu Gly  Asp Val Gly
    1115                1120                1125
Leu Lys Leu Tyr Leu Ser Lys  Glu Asp Leu Lys Lys  Leu His Asp
    1130                1135                1140
Phe Glu Glu Gln Cys Val Glu  Lys Tyr Phe His Glu  Lys Met Glu
    1145                1150                1155
Asp Val Asn Cys Ser Cys Glu  Glu Arg Ile Arg Val  Thr Ser Glu
    1160                1165                1170
Arg Val Thr Glu Met Tyr Phe  Gln Leu Lys Glu Met  Asn Glu Lys
    1175                1180                1185
Val Ser Phe Ile Lys Asp Ser  Leu Leu Ser Leu Asp  Ser Gln Val
    1190                1195                1200
Gly His Leu Gln Asp Leu Ser  Ala Leu Thr Val Asp  Thr Leu Lys
    1205                1210                1215
Val Leu Ser Ala Val Asp Thr  Leu Gln Glu Asp Glu  Ala Leu Leu
    1220                1225                1230
Ala Lys Arg Lys His Ser Thr  Cys Lys Lys Leu Pro  His Ser Trp
    1235                1240                1245
Ser Asn Val Ile Cys Ala Glu  Val Leu Gly Ser Met  Glu Ile Ala
    1250                1255                1260
Gly Glu Lys Lys Tyr Gln Tyr  Tyr Ser Met Pro Ser  Ser Leu Leu
    1265                1270                1275
Arg Ser Leu Ala Gly Gly Arg  His Pro Pro Arg Val  Gln Arg Gly
    1280                1285                1290
```

-continued

```
Ala Leu Leu Glu Ile Thr Asn Ser Lys Arg Glu Ala Thr Asn Val
    1295                1300                1305

Arg Asn Asp Gln Glu Arg Gln Glu Thr Gln Ser Ser Ile Val Val
    1310                1315                1320

Ser Gly Val Ser Pro Asn Arg Gln Ala His Ser Lys Tyr Gly Gln
    1325                1330                1335

Phe Leu Leu Val Pro Ser Asn Leu Lys Arg Val Pro Phe Ser Ala
    1340                1345                1350

Glu Thr Val Leu Pro Leu Ser Arg Pro Ser Val Pro Asp Val Leu
    1355                1360                1365

Ala Thr Glu Gln Asp Ile Gln Thr Glu Val Leu Val His Leu Thr
    1370                1375                1380

Gly Gln Thr Pro Val Val Ser Asp Trp Ala Ser Val Asp Glu Pro
    1385                1390                1395

Lys Glu Lys His Glu Pro Ile Ala His Leu Leu Asp Gly Gln Asp
    1400                1405                1410

Lys Ala Glu Gln Val Leu Pro Thr Leu Ser Cys Thr Pro Glu Pro
    1415                1420                1425

Met Thr Met Ser Ser Pro Leu Ser Gln Ala Lys Ile Met Gln Thr
    1430                1435                1440

Gly Gly Gly Tyr Val Asn Trp Ala Phe Ser Glu Gly Asp Glu Thr
    1445                1450                1455

Gly Val Phe Ser Ile Lys Lys Lys Trp Gln Thr Cys Leu Pro Ser
    1460                1465                1470

Thr Cys Asp Ser Asp Ser Ser Arg Ser Glu Gln His Gln Lys Gln
    1475                1480                1485

Ala Gln Asp Ser Ser Leu Ser Asp Asn Ser Thr Arg Ser Ala Gln
    1490                1495                1500

Ser Ser Glu Cys Ser Glu Val Gly Pro Trp Leu Gln Pro Asn Thr
    1505                1510                1515

Ser Phe Trp Ile Asn Pro Leu Arg Arg Tyr Arg Pro Phe Ala Arg
    1520                1525                1530

Ser His Ser Phe Arg Phe His Lys Glu Glu Lys Leu Met Lys Ile
    1535                1540                1545

Cys Lys Ile Lys Asn Leu Ser Gly Ser Ser Glu Ile Gly Gln Gly
    1550                1555                1560

Ala Trp Val Lys Ala Lys Met Leu Thr Lys Asp Arg Arg Leu Ser
    1565                1570                1575

Lys Lys Lys Lys Asn Thr Gln Gly Leu Gln Val Pro Ile Ile Thr
    1580                1585                1590

Val Asn Ala Cys Ser Gln Ser Asp Gln Leu Asn Pro Glu Pro Gly
    1595                1600                1605

Glu Asn Ser Ile Ser Glu Glu Glu Tyr Ser Lys Asn Trp Phe Thr
    1610                1615                1620

Val Ser Lys Phe Ser His Thr Gly Val Glu Pro Tyr Ile His Gln
    1625                1630                1635

Lys Met Lys Thr Lys Glu Ile Gly Gln Cys Ala Ile Gln Ile Ser
    1640                1645                1650

Asp Tyr Leu Lys Gln Ser Gln Glu Asp Leu Ser Lys Asn Ser Leu
    1655                1660                1665

Trp Asn Ser Arg Ser Thr Asn Leu Asn Arg Asn Ser Leu Leu Lys
    1670                1675                1680
```

```
Ser Ser Ile Gly Val Asp Lys Ile Ser Ala Ser Leu Lys Ser Pro
1685                1690                1695

Gln Glu Pro His His His Tyr Ser Ala Ile Glu Arg Asn Asn Leu
1700                1705                1710

Met Arg Leu Ser Gln Thr Ile Pro Phe Thr Pro Val Gln Leu Phe
1715                1720                1725

Ala Gly Glu Glu Ile Thr Val Tyr Arg Leu Glu Ser Ser Pro
1730                1735                1740

Leu Asn Leu Asp Lys Ser Met Ser Ser Trp Ser Gln Arg Gly Arg
1745                1750                1755

Ala Ala Met Ile Gln Val Leu Ser Arg Glu Glu Met Asp Gly Gly
1760                1765                1770

Leu Arg Lys Ala Met Arg Val Val Ser Thr Trp Ser Glu Asp Asp
1775                1780                1785

Ile Leu Lys Pro Gly Gln Val Phe Ile Val Lys Ser Phe Leu Pro
1790                1795                1800

Glu Val Val Arg Thr Trp His Lys Ile Phe Gln Glu Ser Thr Val
1805                1810                1815

Leu His Leu Cys Leu Arg Glu Ile Gln Gln Gln Arg Ala Ala Gln
1820                1825                1830

Lys Leu Ile Tyr Thr Phe Asn Gln Val Lys Pro Gln Thr Ile Pro
1835                1840                1845

Tyr Thr Pro Arg Phe Leu Glu Val Phe Leu Ile Tyr Cys His Ser
1850                1855                1860

Ala Asn Gln Trp Leu Thr Ile Glu Lys Tyr Met Thr Gly Glu Phe
1865                1870                1875

Arg Lys Tyr Asn Asn Asn Gly Asp Glu Ile Thr Pro Thr Asn
1880                1885                1890

Thr Leu Glu Glu Leu Met Leu Ala Phe Ser His Trp Thr Tyr Glu
1895                1900                1905

Tyr Thr Arg Gly Glu Leu Leu Val Leu Asp Leu Gln Gly Val Gly
1910                1915                1920

Glu Asn Leu Thr Asp Pro Ser Val Ile Lys Pro Glu Val Lys Gln
1925                1930                1935

Ser Arg Gly Met Val Phe Gly Pro Ala Asn Leu Gly Glu Asp Ala
1940                1945                1950

Ile Arg Asn Phe Ile Ala Lys His His Cys Asn Ser Cys Cys Arg
1955                1960                1965

Lys Leu Lys Leu Pro Asp Leu Lys Arg Asn Asp Tyr Ser Pro Glu
1970                1975                1980

Arg Ile Asn Ser Thr Phe Gly Leu Glu Ile Lys Ile Glu Ser Ala
1985                1990                1995

Glu Glu Pro Pro Ala Arg Glu Thr Gly Arg Asn Ser Pro Glu Asp
2000                2005                2010

Asp Met Gln Leu
     2015
```

<210> SEQ ID NO 3
<211> LENGTH: 5913
<212> TYPE: DNA
<213> ORGANISM: Homo sapiens
<220> FEATURE:
<221> NAME/KEY: CDS
<222> LOCATION: (1)..(5910)

```
<400> SEQUENCE: 3 atg att atc cta tct aag tcc cag aaa tcc tgg att aaa gga gta ttt      48
Met Ile Ile Leu Ser Lys Ser Gln Lys Ser Trp Ile Lys Gly Val Phe
1               5                   10                  15 gac aag aga gaa tgt agc aca atc ata ccc agc tca aaa aat cct cac      96
Asp Lys Arg Glu Cys Ser Thr Ile Ile Pro Ser Ser Lys Asn Pro His
            20                  25                  30 aga tgt act cca gta tgc caa gtc tgc cag aat tta atc agg tgt tac     144
Arg Cys Thr Pro Val Cys Gln Val Cys Gln Asn Leu Ile Arg Cys Tyr
        35                  40                  45 tgt ggc cga ctg att gga gac cat gct ggg ata gat tat tcc tgg acc     192
Cys Gly Arg Leu Ile Gly Asp His Ala Gly Ile Asp Tyr Ser Trp Thr
50                  55                  60 atc tca gct gcc aag ggt aaa gaa agt gaa caa tgg tct gtt gaa aag     240
Ile Ser Ala Ala Lys Gly Lys Glu Ser Glu Gln Trp Ser Val Glu Lys
65                  70                  75                  80 cac aca acg aaa agc cca aca gat act ttt ggc acg att aat ttc caa     288
His Thr Thr Lys Ser Pro Thr Asp Thr Phe Gly Thr Ile Asn Phe Gln
                85                  90                  95 gat gga gag cac acc cat cat gcc aag tat att aga act tct tat gat     336
Asp Gly Glu His Thr His His Ala Lys Tyr Ile Arg Thr Ser Tyr Asp
            100                 105                 110 aca aaa ctg gat cat ctg tta cat tta atg ttg aaa gag tgg aaa atg     384
Thr Lys Leu Asp His Leu Leu His Leu Met Leu Lys Glu Trp Lys Met
        115                 120                 125 gaa ctg ccc aag ctt gtg atc tca gtc cat ggg ggc atc cag aac ttt     432
Glu Leu Pro Lys Leu Val Ile Ser Val His Gly Gly Ile Gln Asn Phe
130                 135                 140 act atg ccc tct aaa ttt aaa gag att ttc agc caa ggt ttg gtt aaa     480
Thr Met Pro Ser Lys Phe Lys Glu Ile Phe Ser Gln Gly Leu Val Lys
145                 150                 155                 160 gct gca gag aca aca gga gcg tgg ata ata act gaa ggc atc aat aca     528
Ala Ala Glu Thr Thr Gly Ala Trp Ile Ile Thr Glu Gly Ile Asn Thr
                165                 170                 175 gga gtg tcc aag cat gtt ggg gat gcc ttg aaa tcc cat tcc tct cat     576
Gly Val Ser Lys His Val Gly Asp Ala Leu Lys Ser His Ser Ser His
            180                 185                 190 tcc ttg aga aaa atc tgg aca gtt gga atc cct cct tgg ggt gtc att     624
Ser Leu Arg Lys Ile Trp Thr Val Gly Ile Pro Pro Trp Gly Val Ile
        195                 200                 205 gag aac cag aga gac ctt att gga aaa gat gtg gtg tgc ctg tac cag     672
Glu Asn Gln Arg Asp Leu Ile Gly Lys Asp Val Val Cys Leu Tyr Gln
210                 215                 220 act ctg gat aac ccc ctc agc aag ctc aca aca ctc aac agc atg cac     720
Thr Leu Asp Asn Pro Leu Ser Lys Leu Thr Thr Leu Asn Ser Met His
225                 230                 235                 240 tcg cac ttc atc ctg tct gat gat ggg acc gtg ggc aag tat gga aat     768
Ser His Phe Ile Leu Ser Asp Asp Gly Thr Val Gly Lys Tyr Gly Asn
                245                 250                 255 gaa atg aag ctc aga agg aac ctg gag aag tac ctc tct ctg cag aaa     816
Glu Met Lys Leu Arg Arg Asn Leu Glu Lys Tyr Leu Ser Leu Gln Lys
            260                 265                 270 ata cac tgc cgc tca aga caa ggc gtg ccg gtc gtg ggg ctg gtg gtg     864
Ile His Cys Arg Ser Arg Gln Gly Val Pro Val Val Gly Leu Val Val
        275                 280                 285 gaa ggc ggt ccc aac gtc atc ctg tca gtg tgg gag act gtc aag gac     912
Glu Gly Gly Pro Asn Val Ile Leu Ser Val Trp Glu Thr Val Lys Asp
290                 295                 300
```

```
aag gac cca gtg gtg gtg tgt gag ggc aca ggt agg gcg gct gac ctc      960
Lys Asp Pro Val Val Val Cys Glu Gly Thr Gly Arg Ala Ala Asp Leu
305             310                 315                 320 ctg gcc ttc aca cac aaa cac ctg gca gat gaa ggg atg ctg cga cct     1008
Leu Ala Phe Thr His Lys His Leu Ala Asp Glu Gly Met Leu Arg Pro
                325                 330                 335 cag gtg aaa gag gag atc atc tgc atg att cag aac act ttc aac ttt     1056
Gln Val Lys Glu Glu Ile Ile Cys Met Ile Gln Asn Thr Phe Asn Phe
            340                 345                 350 agt ctt aaa cag tcc aag cac ctt ttc caa att cta atg gag tgt atg     1104
Ser Leu Lys Gln Ser Lys His Leu Phe Gln Ile Leu Met Glu Cys Met
        355                 360                 365 gtt cac agg gat tgt att acc ata ttt gat gct gac tct gaa gag cag     1152
Val His Arg Asp Cys Ile Thr Ile Phe Asp Ala Asp Ser Glu Glu Gln
    370                 375                 380 caa gac ctg gac tta gca atc cta aca gct ttg ctg aag ggc aca aat     1200
Gln Asp Leu Asp Leu Ala Ile Leu Thr Ala Leu Leu Lys Gly Thr Asn
385                 390                 395                 400 tta tca gcg tca gag caa tta aat ctg gca atg gct tgg gac agg gtg     1248
Leu Ser Ala Ser Glu Gln Leu Asn Leu Ala Met Ala Trp Asp Arg Val
                405                 410                 415 gac att gcc aag aaa cat atc cta att tat gaa caa cac tgg aag cct     1296
Asp Ile Ala Lys Lys His Ile Leu Ile Tyr Glu Gln His Trp Lys Pro
                420                 425                 430 gat gcc ctg gaa caa gca atg tca gat gct tta gtg atg gat cgg gtg     1344
Asp Ala Leu Glu Gln Ala Met Ser Asp Ala Leu Val Met Asp Arg Val
            435                 440                 445 gat ttt gtg aag ctc tta ata gaa tat gga gtg aac ctc cat cgc ttt     1392
Asp Phe Val Lys Leu Leu Ile Glu Tyr Gly Val Asn Leu His Arg Phe
        450                 455                 460 ctt acc atc cct cga ctg gaa gag ctc tac aat aca aaa caa gga cct     1440
Leu Thr Ile Pro Arg Leu Glu Glu Leu Tyr Asn Thr Lys Gln Gly Pro
465                 470                 475                 480 act aat aca ctc ttg cat cat ctc gtc caa gat gtg aaa cag cac cag     1488
Thr Asn Thr Leu Leu His His Leu Val Gln Asp Val Lys Gln His Gln
                485                 490                 495 aga cac tcc tca gga aat aga aat gag tct gca gaa agt acg ctg cac     1536
Arg His Ser Ser Gly Asn Arg Asn Glu Ser Ala Glu Ser Thr Leu His
                500                 505                 510 tcc cag ttc att aga act gca cag cca tac aaa ttc aag gaa aag tct     1584
Ser Gln Phe Ile Arg Thr Ala Gln Pro Tyr Lys Phe Lys Glu Lys Ser
            515                 520                 525 ata gtc ctt cat aaa tca agg aag aag tca aaa gaa caa aat gta tca     1632
Ile Val Leu His Lys Ser Arg Lys Lys Ser Lys Glu Gln Asn Val Ser
530                 535                 540 gat gac cct gag tct act ggc ttt ctt tac cct tac aat gac ctg ctg     1680
Asp Asp Pro Glu Ser Thr Gly Phe Leu Tyr Pro Tyr Asn Asp Leu Leu
545                 550                 555                 560 gtt tgg gct gtg ctg atg aaa agg cag aag atg gct atg ttc ttc tgg     1728
Val Trp Ala Val Leu Met Lys Arg Gln Lys Met Ala Met Phe Phe Trp
                565                 570                 575 cag cat gga gag gag gcc acg gtt aaa gcc gtg att gcg tgt atc ctc     1776
Gln His Gly Glu Glu Ala Thr Val Lys Ala Val Ile Ala Cys Ile Leu
            580                 585                 590 tac cgg gca atg gcc cat gaa gct aag gag agt cac atg gtg gat gat     1824
Tyr Arg Ala Met Ala His Glu Ala Lys Glu Ser His Met Val Asp Asp
        595                 600                 605 gcc tca gaa gag ttg aag aat tac tca aaa cag ttt ggc cag ctg gct     1872
Ala Ser Glu Glu Leu Lys Asn Tyr Ser Lys Gln Phe Gly Gln Leu Ala
    610                 615                 620
```

```
ctg gac ttg ttg gag aag gca ttc aag cag aat gag cgc atg gcc atg    1920
Leu Asp Leu Leu Glu Lys Ala Phe Lys Gln Asn Glu Arg Met Ala Met
625                 630                 635                 640 acg ctg ttg acg tat gaa ctc agg aac tgg agc aat tcg acc tgc ctg    1968
Thr Leu Leu Thr Tyr Glu Leu Arg Asn Trp Ser Asn Ser Thr Cys Leu
                645                 650                 655 aaa ctg gcc gtg tcg gga gga tta cga ccc ttt gtt tca cat act tgt    2016
Lys Leu Ala Val Ser Gly Gly Leu Arg Pro Phe Val Ser His Thr Cys
            660                 665                 670 acc cag atg cta ctg aca gac atg tgg atg ggg agg ctg aaa atg agg    2064
Thr Gln Met Leu Leu Thr Asp Met Trp Met Gly Arg Leu Lys Met Arg
        675                 680                 685 aaa aac tct tgg tta aag att att ata agc att att tta cca ccc acc    2112
Lys Asn Ser Trp Leu Lys Ile Ile Ile Ser Ile Ile Leu Pro Pro Thr
    690                 695                 700 att ttg aca ctg gaa ttt aaa agc aaa gct gag atg tca cat gtt ccc    2160
Ile Leu Thr Leu Glu Phe Lys Ser Lys Ala Glu Met Ser His Val Pro
705                 710                 715                 720 cag tcc cag gac ttc caa ttt atg tgg tat tac agt gac cag aac gcc    2208
Gln Ser Gln Asp Phe Gln Phe Met Trp Tyr Tyr Ser Asp Gln Asn Ala
                725                 730                 735 agc agt tcc aaa gaa agt gct tct gtg aaa gag tat gat ttg gaa agg    2256
Ser Ser Ser Lys Glu Ser Ala Ser Val Lys Glu Tyr Asp Leu Glu Arg
            740                 745                 750 ggc cat gat gag aaa ctg gat gaa aat cag cat ttt ggt ttg gaa agt    2304
Gly His Asp Glu Lys Leu Asp Glu Asn Gln His Phe Gly Leu Glu Ser
        755                 760                 765 ggg cac caa cac ctt ccg tgg acc agg aaa gtc tat gag ttc tac agt    2352
Gly His Gln His Leu Pro Trp Thr Arg Lys Val Tyr Glu Phe Tyr Ser
    770                 775                 780 gct cca att gtc aag ttt tgg ttt tat acg atg gcg tat ttg gca ttc    2400
Ala Pro Ile Val Lys Phe Trp Phe Tyr Thr Met Ala Tyr Leu Ala Phe
785                 790                 795                 800 ctc atg ctg ttc act tac acc gtg ttg gtg gag atg cag ccc cag ccc    2448
Leu Met Leu Phe Thr Tyr Thr Val Leu Val Glu Met Gln Pro Gln Pro
                805                 810                 815 agc gtg cag gag tgg ctt gtt agc att tac atc ttc acc aat gct att    2496
Ser Val Gln Glu Trp Leu Val Ser Ile Tyr Ile Phe Thr Asn Ala Ile
            820                 825                 830 gag gtg gtc agg gag atc tgt att tca gaa cct ggg aag ttt acc caa    2544
Glu Val Val Arg Glu Ile Cys Ile Ser Glu Pro Gly Lys Phe Thr Gln
        835                 840                 845 aag gtg aag gta tgg att agt gag tac tgg aac tta aca gaa act gtg    2592
Lys Val Lys Val Trp Ile Ser Glu Tyr Trp Asn Leu Thr Glu Thr Val
    850                 855                 860 gcc att ggc ctg ttt tca gct ggc ttc gtc ctt cga tgg ggt gac cct    2640
Ala Ile Gly Leu Phe Ser Ala Gly Phe Val Leu Arg Trp Gly Asp Pro
865                 870                 875                 880 cct ttt cac aca gcg gga aga ctg atc tac tgc ata gac atc ata ttc    2688
Pro Phe His Thr Ala Gly Arg Leu Ile Tyr Cys Ile Asp Ile Ile Phe
                885                 890                 895 tgg ttc tca cgg ctc ctg gac ttc ttt gct gtg aat caa cat gca ggt    2736
Trp Phe Ser Arg Leu Leu Asp Phe Phe Ala Val Asn Gln His Ala Gly
            900                 905                 910 cca tat gtg acc atg att gca aaa atg aca gca aac atg ttc tat att    2784
Pro Tyr Val Thr Met Ile Ala Lys Met Thr Ala Asn Met Phe Tyr Ile
        915                 920                 925 gtg atc atc atg gcc ata gtc ctg ctg agc ttt gga gtg gca cgc aag    2832
Val Ile Ile Met Ala Ile Val Leu Leu Ser Phe Gly Val Ala Arg Lys
    930                 935                 940
```

```
                                                          -continued gcc atc ctt tcg cca aaa gag cca cca tct tgg agt cta gct cga gat    2880
Ala Ile Leu Ser Pro Lys Glu Pro Pro Ser Trp Ser Leu Ala Arg Asp
945                 950                 955                 960 att gta ttt gag cca tac tgg atg ata tac gga gaa gtc tat gct gga    2928
Ile Val Phe Glu Pro Tyr Trp Met Ile Tyr Gly Glu Val Tyr Ala Gly
                965                 970                 975 gaa ata gat gtt tgt tca agc cag cca tcc tgc cct cct ggt tct ttt    2976
Glu Ile Asp Val Cys Ser Ser Gln Pro Ser Cys Pro Pro Gly Ser Phe
            980                 985                 990 ctt act cca ttc ttg caa gct gtc tac ctc ttc gtg caa tat atc atc    3024
Leu Thr Pro Phe Leu Gln Ala Val Tyr Leu Phe Val Gln Tyr Ile Ile
        995                 1000                1005 atg gtg aac ctg ttg att gct ttc ttc aac aac gtt tac tta gat        3069
Met Val Asn Leu Leu Ile Ala Phe Phe Asn Asn Val Tyr Leu Asp
1010                1015                1020 atg gaa tcc att tca aat aac ctg tgg aaa tac aac cgc tat cgc        3114
Met Glu Ser Ile Ser Asn Asn Leu Trp Lys Tyr Asn Arg Tyr Arg
1025                1030                1035 tac atc atg acc tac cac gag aag ccc tgg ctg cca cca cct ctc        3159
Tyr Ile Met Thr Tyr His Glu Lys Pro Trp Leu Pro Pro Pro Leu
1040                1045                1050 atc ctg ctg agc cac gtg ggc ctt ctc ctc cgc cgc ctg tgc tgt        3204
Ile Leu Leu Ser His Val Gly Leu Leu Leu Arg Arg Leu Cys Cys
1055                1060                1065 cat cga gct cct cac gac caa gaa gag ggt gac gtt gga tta aaa        3249
His Arg Ala Pro His Asp Gln Glu Glu Gly Asp Val Gly Leu Lys
1070                1075                1080 ctc tac ctc agt aag gag gat ctg aaa aaa ctt cat gat ttt gag        3294
Leu Tyr Leu Ser Lys Glu Asp Leu Lys Lys Leu His Asp Phe Glu
1085                1090                1095 gag cag tgc gtg gaa aaa tac ttc cat gag aag atg gaa gat gtg        3339
Glu Gln Cys Val Glu Lys Tyr Phe His Glu Lys Met Glu Asp Val
1100                1105                1110 aat tgt agt tgt gag gaa cga atc cga gtg aca tca gaa agg gtt        3384
Asn Cys Ser Cys Glu Glu Arg Ile Arg Val Thr Ser Glu Arg Val
1115                1120                1125 aca gag atg tac ttc cag ctg aaa gaa atg aat gaa aag gtg tct        3429
Thr Glu Met Tyr Phe Gln Leu Lys Glu Met Asn Glu Lys Val Ser
1130                1135                1140 ttt ata aag gac tcc tta ctg tct ttg gac agc cag gtg gga cac        3474
Phe Ile Lys Asp Ser Leu Leu Ser Leu Asp Ser Gln Val Gly His
1145                1150                1155 ctg cag gat ctc tct gcc ctg act gtg gat acc ctg aaa gtc ctt        3519
Leu Gln Asp Leu Ser Ala Leu Thr Val Asp Thr Leu Lys Val Leu
1160                1165                1170 tct gct gtt gac act ttg caa gag gat gag gct ctc ctg gcc aag        3564
Ser Ala Val Asp Thr Leu Gln Glu Asp Glu Ala Leu Leu Ala Lys
1175                1180                1185 aga aag cat tct act tgc aaa aaa ctt ccc cac agc tgg agc aat        3609
Arg Lys His Ser Thr Cys Lys Lys Leu Pro His Ser Trp Ser Asn
1190                1195                1200 gtc atc tgt gca gag gtt cta ggc agc atg gag atc gct gga gag        3654
Val Ile Cys Ala Glu Val Leu Gly Ser Met Glu Ile Ala Gly Glu
1205                1210                1215 aag aaa tac cag tat tat agc atg ccc tct tct ttg ctg agg agc        3699
Lys Lys Tyr Gln Tyr Tyr Ser Met Pro Ser Ser Leu Leu Arg Ser
1220                1225                1230 ctg gct gga ggc cgg cat ccc cca aga gtg cag agg ggg gca ctt        3744
Leu Ala Gly Gly Arg His Pro Pro Arg Val Gln Arg Gly Ala Leu
1235                1240                1245
```

```
                                                      -continued ctt gag att aca aac agt aaa aga gag gct aca aat gta aga aat          3789
Leu Glu Ile Thr Asn Ser Lys Arg Glu Ala Thr Asn Val Arg Asn
    1250            1255                1260 gac cag gaa agg caa gaa aca caa agt agt ata gtg gtt tct ggg          3834
Asp Gln Glu Arg Gln Glu Thr Gln Ser Ser Ile Val Val Ser Gly
    1265            1270                1275 gtg tct cct aac agg caa gca cac tca aag tat ggc cag ttt ctt          3879
Val Ser Pro Asn Arg Gln Ala His Ser Lys Tyr Gly Gln Phe Leu
    1280            1285                1290 ctg gtc ccc tct aat cta aag cga gtt cct ttt tca gca gaa act          3924
Leu Val Pro Ser Asn Leu Lys Arg Val Pro Phe Ser Ala Glu Thr
    1295            1300                1305 gtc ttg cct ctg tcc aga ccc tct gtg cca gat gtg ctg gca act          3969
Val Leu Pro Leu Ser Arg Pro Ser Val Pro Asp Val Leu Ala Thr
    1310            1315                1320 gaa cag gac atc cag act gag gtt ctt gtt cat ctg act ggg cag          4014
Glu Gln Asp Ile Gln Thr Glu Val Leu Val His Leu Thr Gly Gln
    1325            1330                1335 acc cca gtt gtc tct gac tgg gca tca gtg gat gaa ccc aag gaa          4059
Thr Pro Val Val Ser Asp Trp Ala Ser Val Asp Glu Pro Lys Glu
    1340            1345                1350 aag cac gag cct att gct cac tta ctg gat gga caa gac aag gca          4104
Lys His Glu Pro Ile Ala His Leu Leu Asp Gly Gln Asp Lys Ala
    1355            1360                1365 gag caa gtg cta ccc act ttg agt tgc aca cct gaa ccc atg aca          4149
Glu Gln Val Leu Pro Thr Leu Ser Cys Thr Pro Glu Pro Met Thr
    1370            1375                1380 atg agc tcc cct ctt tcc caa gcc aag atc atg caa act gga ggt          4194
Met Ser Ser Pro Leu Ser Gln Ala Lys Ile Met Gln Thr Gly Gly
    1385            1390                1395 gga tat gta aac tgg gca ttt tca gaa ggt gat gaa act ggt gtg          4239
Gly Tyr Val Asn Trp Ala Phe Ser Glu Gly Asp Glu Thr Gly Val
    1400            1405                1410 ttt agc atc aag aaa aag tgg caa acc tgc ttg ccc tcc act tgt          4284
Phe Ser Ile Lys Lys Lys Trp Gln Thr Cys Leu Pro Ser Thr Cys
    1415            1420                1425 gac agt gat tcc tct cgg agt gaa cag cac cag aag cag gcc cag          4329
Asp Ser Asp Ser Ser Arg Ser Glu Gln His Gln Lys Gln Ala Gln
    1430            1435                1440 gac agc tcc cta tct gat aac tca aca aga tcg gcc cag agt agt          4374
Asp Ser Ser Leu Ser Asp Asn Ser Thr Arg Ser Ala Gln Ser Ser
    1445            1450                1455 gaa tgc tca gag gtg gga cca tgg ctt cag cca aac aca tcc ttt          4419
Glu Cys Ser Glu Val Gly Pro Trp Leu Gln Pro Asn Thr Ser Phe
    1460            1465                1470 tgg atc aat cct ctc cgc aga tac agg ccc ttc gct agg agt cat          4464
Trp Ile Asn Pro Leu Arg Arg Tyr Arg Pro Phe Ala Arg Ser His
    1475            1480                1485 agt ttt aga ttc cat aag gag gag aaa ttg atg aag atc tgt aag          4509
Ser Phe Arg Phe His Lys Glu Glu Lys Leu Met Lys Ile Cys Lys
    1490            1495                1500 att aaa aat ctt tca ggc tct tca gaa ata ggg cag gga gca tgg          4554
Ile Lys Asn Leu Ser Gly Ser Ser Glu Ile Gly Gln Gly Ala Trp
    1505            1510                1515 gtc aaa gcg aaa atg cta acc aaa gac agg aga ctg tca aag aaa          4599
Val Lys Ala Lys Met Leu Thr Lys Asp Arg Arg Leu Ser Lys Lys
    1520            1525                1530 aag aag aat act caa gga ctc cag gtg cca atc ata aca gtc aat          4644
Lys Lys Asn Thr Gln Gly Leu Gln Val Pro Ile Ile Thr Val Asn
    1535            1540                1545
```

```
                                            -continued
gcc  tgc  tct  cag  agt  gac  cag  ttg  aat  cca  gag  cca  gga  gaa  aac    4689
Ala  Cys  Ser  Gln  Ser  Asp  Gln  Leu  Asn  Pro  Glu  Pro  Gly  Glu  Asn
     1550               1555                    1560 agc  atc  tct  gaa  gag  gag  tac  agc  aag  aac  tgg  ttc  aca  gtg  tcc    4734
Ser  Ile  Ser  Glu  Glu  Glu  Tyr  Ser  Lys  Asn  Trp  Phe  Thr  Val  Ser
1565                    1570                    1575 aaa  ttt  agt  cac  aca  ggt  gta  gaa  cct  tac  ata  cat  cag  aaa  atg    4779
Lys  Phe  Ser  His  Thr  Gly  Val  Glu  Pro  Tyr  Ile  His  Gln  Lys  Met
          1580                    1585                    1590 aaa  act  aaa  gaa  att  gga  caa  tgt  gct  ata  caa  atc  agt  gat  tac    4824
Lys  Thr  Lys  Glu  Ile  Gly  Gln  Cys  Ala  Ile  Gln  Ile  Ser  Asp  Tyr
1595                    1600                    1605 cta  aag  cag  tct  caa  gag  gat  ctc  agc  aaa  aac  tct  ttg  tgg  aat    4869
Leu  Lys  Gln  Ser  Gln  Glu  Asp  Leu  Ser  Lys  Asn  Ser  Leu  Trp  Asn
     1610               1615                    1620 tcc  agg  agc  acc  aac  ctc  aat  agg  aac  tcc  ctg  ctg  aaa  agt  tca    4914
Ser  Arg  Ser  Thr  Asn  Leu  Asn  Arg  Asn  Ser  Leu  Leu  Lys  Ser  Ser
1625                    1630                    1635 att  gga  gtt  gac  aag  atc  tca  gcc  tcc  tta  aaa  agc  cct  caa  gag    4959
Ile  Gly  Val  Asp  Lys  Ile  Ser  Ala  Ser  Leu  Lys  Ser  Pro  Gln  Glu
          1640                    1645                    1650 cct  cac  cat  cat  tat  tca  gcc  att  gaa  agg  aat  aat  tta  atg  agg    5004
Pro  His  His  His  Tyr  Ser  Ala  Ile  Glu  Arg  Asn  Asn  Leu  Met  Arg
1655                    1660                    1665 ctt  tct  cag  acc  ata  cca  ttt  aca  cca  gtc  caa  ctg  ttt  gca  gga    5049
Leu  Ser  Gln  Thr  Ile  Pro  Phe  Thr  Pro  Val  Gln  Leu  Phe  Ala  Gly
     1670               1675                    1680 gaa  gaa  ata  act  gtc  tac  agg  ttg  gag  gag  agt  tcc  cct  tta  aac    5094
Glu  Glu  Ile  Thr  Val  Tyr  Arg  Leu  Glu  Glu  Ser  Ser  Pro  Leu  Asn
1685                    1690                    1695 ctt  gat  aaa  agc  atg  tcc  tct  tgg  tct  cag  cgt  ggg  aga  gcg  gca    5139
Leu  Asp  Lys  Ser  Met  Ser  Ser  Trp  Ser  Gln  Arg  Gly  Arg  Ala  Ala
          1700                    1705                    1710 atg  atc  cag  gta  ttg  tcc  cga  gag  gag  atg  gat  ggg  ggc  ctc  cgt    5184
Met  Ile  Gln  Val  Leu  Ser  Arg  Glu  Glu  Met  Asp  Gly  Gly  Leu  Arg
1715                    1720                    1725 aaa  gct  atg  aga  gtc  gtc  agc  act  tgg  tct  gag  gat  gac  att  ctc    5229
Lys  Ala  Met  Arg  Val  Val  Ser  Thr  Trp  Ser  Glu  Asp  Asp  Ile  Leu
     1730               1735                    1740 aag  ccg  gga  caa  gtt  ttc  att  gtc  aag  tcc  ttt  ctt  cct  gag  gtt    5274
Lys  Pro  Gly  Gln  Val  Phe  Ile  Val  Lys  Ser  Phe  Leu  Pro  Glu  Val
1745                    1750                    1755 gtg  cgg  aca  tgg  cat  aaa  atc  ttc  cag  gag  agc  act  gtg  ctt  cat    5319
Val  Arg  Thr  Trp  His  Lys  Ile  Phe  Gln  Glu  Ser  Thr  Val  Leu  His
          1760                    1765                    1770 ctt  tgc  ctc  agg  gaa  att  caa  caa  caa  aga  gct  gct  caa  aaa  ttg    5364
Leu  Cys  Leu  Arg  Glu  Ile  Gln  Gln  Gln  Arg  Ala  Ala  Gln  Lys  Leu
1775                    1780                    1785 atc  tat  acc  ttc  aac  caa  gtg  aaa  cca  caa  acc  ata  ccc  tac  aca    5409
Ile  Tyr  Thr  Phe  Asn  Gln  Val  Lys  Pro  Gln  Thr  Ile  Pro  Tyr  Thr
     1790               1795                    1800 cca  agg  ttc  ctg  gaa  gtt  ttc  tta  atc  tac  tgc  cat  tca  gcc  aac    5454
Pro  Arg  Phe  Leu  Glu  Val  Phe  Leu  Ile  Tyr  Cys  His  Ser  Ala  Asn
1805                    1810                    1815 cag  tgg  ttg  acc  att  gag  aag  tat  atg  aca  ggg  gag  ttc  cgg  aag    5499
Gln  Trp  Leu  Thr  Ile  Glu  Lys  Tyr  Met  Thr  Gly  Glu  Phe  Arg  Lys
          1820                    1825                    1830 tat  aac  aac  aac  aat  ggt  gat  gaa  atc  acc  ccc  acc  aac  acc  ctg    5544
Tyr  Asn  Asn  Asn  Asn  Gly  Asp  Glu  Ile  Thr  Pro  Thr  Asn  Thr  Leu
1835                    1840                    1845
```

-continued

```
gag gag ctg atg ttg gct ttc tct cac tgg acc tat gag tac act      5589
Glu Glu Leu Met Leu Ala Phe Ser His Trp Thr Tyr Glu Tyr Thr
1850                1855                1860 cgg gga gag ctg ctg gtt tta gat ttg caa ggt gtt gga gaa aat      5634
Arg Gly Glu Leu Leu Val Leu Asp Leu Gln Gly Val Gly Glu Asn
    1865                1870                1875 ttg aca gat cca tct gtt ata aaa cct gaa gtc aaa caa tca aga      5679
Leu Thr Asp Pro Ser Val Ile Lys Pro Glu Val Lys Gln Ser Arg
1880                1885                1890 gga atg gtg ttt gga ccg gcc aat ttg ggg gaa gat gca att aga      5724
Gly Met Val Phe Gly Pro Ala Asn Leu Gly Glu Asp Ala Ile Arg
    1895                1900                1905 aac ttc att gca aaa cat cat tgt aac tcc tgc tgc cgg aag ctc      5769
Asn Phe Ile Ala Lys His His Cys Asn Ser Cys Cys Arg Lys Leu
1910                1915                1920 aaa ctc ccg gat tta aaa aga aat gac tat tcc cct gaa agg ata      5814
Lys Leu Pro Asp Leu Lys Arg Asn Asp Tyr Ser Pro Glu Arg Ile
    1925                1930                1935 aat tcc acc ttt gga ctt gag ata aaa ata gaa tca gct gag gag      5859
Asn Ser Thr Phe Gly Leu Glu Ile Lys Ile Glu Ser Ala Glu Glu
1940                1945                1950 cct cca gca agg gag acg ggt aga aat tcc cca gaa gat gat atg      5904
Pro Pro Ala Arg Glu Thr Gly Arg Asn Ser Pro Glu Asp Asp Met
    1955                1960                1965 caa cta taa                                                       5913
Gln Leu
1970

<210> SEQ ID NO 4
<211> LENGTH: 1970
<212> TYPE: PRT
<213> ORGANISM: Homo sapiens

<400> SEQUENCE: 4

Met Ile Ile Leu Ser Lys Ser Gln Lys Ser Trp Ile Lys Gly Val Phe
1               5                   10                  15

Asp Lys Arg Glu Cys Ser Thr Ile Ile Pro Ser Ser Lys Asn Pro His
            20                  25                  30

Arg Cys Thr Pro Val Cys Gln Val Cys Gln Asn Leu Ile Arg Cys Tyr
        35                  40                  45

Cys Gly Arg Leu Ile Gly Asp His Ala Gly Ile Asp Tyr Ser Trp Thr
    50                  55                  60

Ile Ser Ala Ala Lys Gly Lys Glu Ser Glu Gln Trp Ser Val Glu Lys
65                  70                  75                  80

His Thr Thr Lys Ser Pro Thr Asp Thr Phe Gly Thr Ile Asn Phe Gln
                85                  90                  95

Asp Gly Glu His Thr His His Ala Lys Tyr Ile Arg Thr Ser Tyr Asp
            100                 105                 110

Thr Lys Leu Asp His Leu Leu His Leu Met Leu Lys Glu Trp Lys Met
        115                 120                 125

Glu Leu Pro Lys Leu Val Ile Ser Val His Gly Gly Ile Gln Asn Phe
    130                 135                 140

Thr Met Pro Ser Lys Phe Lys Glu Ile Phe Ser Gln Gly Leu Val Lys
145                 150                 155                 160

Ala Ala Glu Thr Thr Gly Ala Trp Ile Ile Thr Glu Gly Ile Asn Thr
                165                 170                 175

Gly Val Ser Lys His Val Gly Asp Ala Leu Lys Ser His Ser Ser His
            180                 185                 190
```

-continued

```
Ser Leu Arg Lys Ile Trp Thr Val Gly Ile Pro Pro Trp Gly Val Ile
    195                 200                 205

Glu Asn Gln Arg Asp Leu Ile Gly Lys Asp Val Val Cys Leu Tyr Gln
    210                 215                 220

Thr Leu Asp Asn Pro Leu Ser Lys Leu Thr Thr Leu Asn Ser Met His
225                 230                 235                 240

Ser His Phe Ile Leu Ser Asp Asp Gly Thr Val Gly Lys Tyr Gly Asn
                245                 250                 255

Glu Met Lys Leu Arg Arg Asn Leu Glu Lys Tyr Leu Ser Leu Gln Lys
                260                 265                 270

Ile His Cys Arg Ser Arg Gln Gly Val Pro Val Val Gly Leu Val Val
                275                 280                 285

Glu Gly Gly Pro Asn Val Ile Leu Ser Val Trp Glu Thr Val Lys Asp
    290                 295                 300

Lys Asp Pro Val Val Val Cys Glu Gly Thr Gly Arg Ala Ala Asp Leu
305                 310                 315                 320

Leu Ala Phe Thr His Lys His Leu Ala Asp Glu Gly Met Leu Arg Pro
                325                 330                 335

Gln Val Lys Glu Glu Ile Ile Cys Met Ile Gln Asn Thr Phe Asn Phe
                340                 345                 350

Ser Leu Lys Gln Ser Lys His Leu Phe Gln Ile Leu Met Glu Cys Met
                355                 360                 365

Val His Arg Asp Cys Ile Thr Ile Phe Asp Ala Asp Ser Glu Glu Gln
    370                 375                 380

Gln Asp Leu Asp Leu Ala Ile Leu Thr Ala Leu Leu Lys Gly Thr Asn
385                 390                 395                 400

Leu Ser Ala Ser Glu Gln Leu Asn Leu Ala Met Ala Trp Asp Arg Val
                405                 410                 415

Asp Ile Ala Lys Lys His Ile Leu Ile Tyr Glu Gln His Trp Lys Pro
                420                 425                 430

Asp Ala Leu Glu Gln Ala Met Ser Asp Ala Leu Val Met Asp Arg Val
                435                 440                 445

Asp Phe Val Lys Leu Leu Ile Glu Tyr Gly Val Asn Leu His Arg Phe
    450                 455                 460

Leu Thr Ile Pro Arg Leu Glu Glu Leu Tyr Asn Thr Lys Gln Gly Pro
465                 470                 475                 480

Thr Asn Thr Leu Leu His His Leu Val Gln Asp Val Lys Gln His Gln
                485                 490                 495

Arg His Ser Ser Gly Asn Arg Asn Glu Ser Ala Glu Ser Thr Leu His
                500                 505                 510

Ser Gln Phe Ile Arg Thr Ala Gln Pro Tyr Lys Phe Lys Glu Lys Ser
                515                 520                 525

Ile Val Leu His Lys Ser Arg Lys Ser Lys Glu Gln Asn Val Ser
                530                 535                 540

Asp Asp Pro Glu Ser Thr Gly Phe Leu Tyr Pro Tyr Asn Asp Leu Leu
545                 550                 555                 560

Val Trp Ala Val Leu Met Lys Arg Gln Lys Met Ala Met Phe Phe Trp
                565                 570                 575

Gln His Gly Glu Glu Ala Thr Val Lys Ala Val Ile Ala Cys Ile Leu
                580                 585                 590

Tyr Arg Ala Met Ala His Glu Ala Lys Glu Ser His Met Val Asp Asp
                595                 600                 605
```

-continued

Ala Ser Glu Glu Leu Lys Asn Tyr Ser Lys Gln Phe Gly Gln Leu Ala
    610                 615                 620

Leu Asp Leu Leu Glu Lys Ala Phe Lys Gln Asn Glu Arg Met Ala Met
625                 630                 635                 640

Thr Leu Leu Thr Tyr Glu Leu Arg Asn Trp Ser Asn Ser Thr Cys Leu
            645                 650                 655

Lys Leu Ala Val Ser Gly Leu Arg Pro Phe Val Ser His Thr Cys
            660                 665                 670

Thr Gln Met Leu Leu Thr Asp Met Trp Met Gly Arg Leu Lys Met Arg
        675                 680                 685

Lys Asn Ser Trp Leu Lys Ile Ile Ser Ile Ile Leu Pro Pro Thr
    690                 695                 700

Ile Leu Thr Leu Glu Phe Lys Ser Lys Ala Glu Met Ser His Val Pro
705                 710                 715                 720

Gln Ser Gln Asp Phe Gln Phe Met Trp Tyr Tyr Ser Asp Gln Asn Ala
                725                 730                 735

Ser Ser Ser Lys Glu Ser Ala Ser Val Lys Glu Tyr Asp Leu Glu Arg
            740                 745                 750

Gly His Asp Glu Lys Leu Asp Glu Asn Gln His Phe Gly Leu Glu Ser
        755                 760                 765

Gly His Gln His Leu Pro Trp Thr Arg Lys Val Tyr Glu Phe Tyr Ser
770                 775                 780

Ala Pro Ile Val Lys Phe Trp Phe Tyr Thr Met Ala Tyr Leu Ala Phe
785                 790                 795                 800

Leu Met Leu Phe Thr Tyr Thr Val Leu Val Glu Met Gln Pro Gln Pro
                805                 810                 815

Ser Val Gln Glu Trp Leu Val Ser Ile Tyr Ile Phe Thr Asn Ala Ile
            820                 825                 830

Glu Val Val Arg Glu Ile Cys Ile Ser Glu Pro Gly Lys Phe Thr Gln
        835                 840                 845

Lys Val Lys Val Trp Ile Ser Glu Tyr Trp Asn Leu Thr Glu Thr Val
    850                 855                 860

Ala Ile Gly Leu Phe Ser Ala Gly Phe Val Leu Arg Trp Gly Asp Pro
865                 870                 875                 880

Pro Phe His Thr Ala Gly Arg Leu Ile Tyr Cys Ile Asp Ile Ile Phe
                885                 890                 895

Trp Phe Ser Arg Leu Leu Asp Phe Phe Ala Val Asn Gln His Ala Gly
            900                 905                 910

Pro Tyr Val Thr Met Ile Ala Lys Met Thr Ala Asn Met Phe Tyr Ile
        915                 920                 925

Val Ile Ile Met Ala Ile Val Leu Leu Ser Phe Gly Val Ala Arg Lys
    930                 935                 940

Ala Ile Leu Ser Pro Lys Glu Pro Ser Trp Ser Leu Ala Arg Asp
945                 950                 955                 960

Ile Val Phe Glu Pro Tyr Trp Met Ile Tyr Gly Glu Val Tyr Ala Gly
                965                 970                 975

Glu Ile Asp Val Cys Ser Ser Gln Pro Ser Cys Pro Pro Gly Ser Phe
            980                 985                 990

Leu Thr Pro Phe Leu Gln Ala Val Tyr Leu Phe Val Gln Tyr Ile Ile
        995                 1000                1005

Met Val Asn Leu Leu Ile Ala Phe Phe Asn Asn Val Tyr Leu Asp
    1010                1015                1020

-continued

```
Met Glu Ser Ile Ser Asn Asn Leu Trp Lys Tyr Asn Arg Tyr Arg
1025                1030                1035

Tyr Ile Met Thr Tyr His Glu Lys Pro Trp Leu Pro Pro Pro Leu
1040                1045                1050

Ile Leu Leu Ser His Val Gly Leu Leu Leu Arg Arg Leu Cys Cys
1055                1060                1065

His Arg Ala Pro His Asp Gln Glu Glu Gly Asp Val Gly Leu Lys
1070                1075                1080

Leu Tyr Leu Ser Lys Glu Asp Leu Lys Lys Leu His Asp Phe Glu
1085                1090                1095

Glu Gln Cys Val Glu Lys Tyr Phe His Glu Lys Met Glu Asp Val
1100                1105                1110

Asn Cys Ser Cys Glu Glu Arg Ile Arg Val Thr Ser Glu Arg Val
1115                1120                1125

Thr Glu Met Tyr Phe Gln Leu Lys Glu Met Asn Glu Lys Val Ser
1130                1135                1140

Phe Ile Lys Asp Ser Leu Leu Ser Leu Asp Ser Gln Val Gly His
1145                1150                1155

Leu Gln Asp Leu Ser Ala Leu Thr Val Asp Thr Leu Lys Val Leu
1160                1165                1170

Ser Ala Val Asp Thr Leu Gln Glu Asp Glu Ala Leu Leu Ala Lys
1175                1180                1185

Arg Lys His Ser Thr Cys Lys Lys Leu Pro His Ser Trp Ser Asn
1190                1195                1200

Val Ile Cys Ala Glu Val Leu Gly Ser Met Glu Ile Ala Gly Glu
1205                1210                1215

Lys Lys Tyr Gln Tyr Tyr Ser Met Pro Ser Ser Leu Leu Arg Ser
1220                1225                1230

Leu Ala Gly Gly Arg His Pro Pro Arg Val Gln Arg Gly Ala Leu
1235                1240                1245

Leu Glu Ile Thr Asn Ser Lys Arg Glu Ala Thr Asn Val Arg Asn
1250                1255                1260

Asp Gln Glu Arg Gln Glu Thr Gln Ser Ser Ile Val Val Ser Gly
1265                1270                1275

Val Ser Pro Asn Arg Gln Ala His Ser Lys Tyr Gly Gln Phe Leu
1280                1285                1290

Leu Val Pro Ser Asn Leu Lys Arg Val Pro Phe Ser Ala Glu Thr
1295                1300                1305

Val Leu Pro Leu Ser Arg Pro Ser Val Pro Asp Val Leu Ala Thr
1310                1315                1320

Glu Gln Asp Ile Gln Thr Glu Val Leu Val His Leu Thr Gly Gln
1325                1330                1335

Thr Pro Val Val Ser Asp Trp Ala Ser Val Asp Glu Pro Lys Glu
1340                1345                1350

Lys His Glu Pro Ile Ala His Leu Leu Asp Gly Gln Asp Lys Ala
1355                1360                1365

Glu Gln Val Leu Pro Thr Leu Ser Cys Thr Pro Glu Pro Met Thr
1370                1375                1380

Met Ser Ser Pro Leu Ser Gln Ala Lys Ile Met Gln Thr Gly Gly
1385                1390                1395

Gly Tyr Val Asn Trp Ala Phe Ser Glu Gly Asp Glu Thr Gly Val
1400                1405                1410
```

-continued

```
Phe Ser Ile Lys Lys Lys Trp Gln Thr Cys Leu Pro Ser Thr Cys
    1415                1420                1425

Asp Ser Asp Ser Ser Arg Ser Glu Gln His Gln Lys Gln Ala Gln
    1430                1435                1440

Asp Ser Ser Leu Ser Asp Asn Ser Thr Arg Ser Ala Gln Ser Ser
    1445                1450                1455

Glu Cys Ser Glu Val Gly Pro Trp Leu Gln Pro Asn Thr Ser Phe
    1460                1465                1470

Trp Ile Asn Pro Leu Arg Arg Tyr Arg Pro Phe Ala Arg Ser His
    1475                1480                1485

Ser Phe Arg Phe His Lys Glu Lys Leu Met Lys Ile Cys Lys
    1490                1495                1500

Ile Lys Asn Leu Ser Gly Ser Ser Glu Ile Gly Gln Gly Ala Trp
    1505                1510                1515

Val Lys Ala Lys Met Leu Thr Lys Asp Arg Arg Leu Ser Lys Lys
    1520                1525                1530

Lys Lys Asn Thr Gln Gly Leu Gln Val Pro Ile Ile Thr Val Asn
    1535                1540                1545

Ala Cys Ser Gln Ser Asp Gln Leu Asn Pro Glu Pro Gly Glu Asn
    1550                1555                1560

Ser Ile Ser Glu Glu Glu Tyr Ser Lys Asn Trp Phe Thr Val Ser
    1565                1570                1575

Lys Phe Ser His Thr Gly Val Glu Pro Tyr Ile His Gln Lys Met
    1580                1585                1590

Lys Thr Lys Glu Ile Gly Gln Cys Ala Ile Gln Ile Ser Asp Tyr
    1595                1600                1605

Leu Lys Gln Ser Gln Glu Asp Leu Ser Lys Asn Ser Leu Trp Asn
    1610                1615                1620

Ser Arg Ser Thr Asn Leu Asn Arg Asn Ser Leu Leu Lys Ser Ser
    1625                1630                1635

Ile Gly Val Asp Lys Ile Ser Ala Ser Leu Lys Ser Pro Gln Glu
    1640                1645                1650

Pro His His His Tyr Ser Ala Ile Glu Arg Asn Asn Leu Met Arg
    1655                1660                1665

Leu Ser Gln Thr Ile Pro Phe Thr Pro Val Gln Leu Phe Ala Gly
    1670                1675                1680

Glu Glu Ile Thr Val Tyr Arg Leu Glu Glu Ser Ser Pro Leu Asn
    1685                1690                1695

Leu Asp Lys Ser Met Ser Ser Trp Ser Gln Arg Gly Arg Ala Ala
    1700                1705                1710

Met Ile Gln Val Leu Ser Arg Glu Glu Met Asp Gly Gly Leu Arg
    1715                1720                1725

Lys Ala Met Arg Val Val Ser Thr Trp Ser Glu Asp Asp Ile Leu
    1730                1735                1740

Lys Pro Gly Gln Val Phe Ile Val Lys Ser Phe Leu Pro Glu Val
    1745                1750                1755

Val Arg Thr Trp His Lys Ile Phe Gln Glu Ser Thr Val Leu His
    1760                1765                1770

Leu Cys Leu Arg Glu Ile Gln Gln Gln Arg Ala Ala Gln Lys Leu
    1775                1780                1785

Ile Tyr Thr Phe Asn Gln Val Lys Pro Gln Thr Ile Pro Tyr Thr
    1790                1795                1800
```

-continued

Pro Arg Phe Leu Glu Val Phe Leu Ile Tyr Cys His Ser Ala Asn
1805                1810                1815

Gln Trp Leu Thr Ile Glu Lys Tyr Met Thr Gly Glu Phe Arg Lys
1820                1825                1830

Tyr Asn Asn Asn Asn Gly Asp Glu Ile Thr Pro Thr Asn Thr Leu
1835                1840                1845

Glu Glu Leu Met Leu Ala Phe Ser His Trp Thr Tyr Glu Tyr Thr
1850                1855                1860

Arg Gly Glu Leu Leu Val Leu Asp Leu Gln Val Gly Glu Asn
1865                1870                1875

Leu Thr Asp Pro Ser Val Ile Lys Pro Glu Val Lys Gln Ser Arg
1880                1885                1890

Gly Met Val Phe Gly Pro Ala Asn Leu Gly Glu Asp Ala Ile Arg
1895                1900                1905

Asn Phe Ile Ala Lys His His Cys Asn Ser Cys Cys Arg Lys Leu
1910                1915                1920

Lys Leu Pro Asp Leu Lys Arg Asn Asp Tyr Ser Pro Glu Arg Ile
1925                1930                1935

Asn Ser Thr Phe Gly Leu Glu Ile Lys Ile Glu Ser Ala Glu Glu
1940                1945                1950

Pro Pro Ala Arg Glu Thr Gly Arg Asn Ser Pro Glu Asp Asp Met
1955                1960                1965

Gln Leu
1970

<210> SEQ ID NO 5
<211> LENGTH: 5820
<212> TYPE: DNA
<213> ORGANISM: Homo sapiens
<220> FEATURE:
<221> NAME/KEY: CDS
<222> LOCATION: (1)..(5817)

<400> SEQUENCE: 5

```
atg att atc cta tct aag tcc cag aaa tcc tgg att aaa gga gta ttt      48
Met Ile Ile Leu Ser Lys Ser Gln Lys Ser Trp Ile Lys Gly Val Phe
1               5                   10                  15 gac aag aga gaa tgt agc aca atc ata ccc agc tca aaa aat cct cac      96
Asp Lys Arg Glu Cys Ser Thr Ile Ile Pro Ser Ser Lys Asn Pro His
            20                  25                  30 aga tgt act cca gta tgc caa gtc tgc cag aat tta atc agg tgt tac     144
Arg Cys Thr Pro Val Cys Gln Val Cys Gln Asn Leu Ile Arg Cys Tyr
        35                  40                  45 tgt ggc cga ctg att gga gac cat gct ggg ata gat tat tcc tgg acc     192
Cys Gly Arg Leu Ile Gly Asp His Ala Gly Ile Asp Tyr Ser Trp Thr
    50                  55                  60 atc tca gct gcc aag ggt aaa gaa agt gaa caa tgg tct gtt gaa aag     240
Ile Ser Ala Ala Lys Gly Lys Glu Ser Glu Gln Trp Ser Val Glu Lys
65                  70                  75                  80 cac aca acg aaa agc cca aca gat act ttt ggc acg att aat ttc caa     288
His Thr Thr Lys Ser Pro Thr Asp Thr Phe Gly Thr Ile Asn Phe Gln
                85                  90                  95 gat gga gag cac acc cat cat gcc aag tat att aga act tct tat gat     336
Asp Gly Glu His Thr His His Ala Lys Tyr Ile Arg Thr Ser Tyr Asp
            100                 105                 110 aca aaa ctg gat cat ctg tta cat tta atg ttg aaa gag tgg aaa atg     384
Thr Lys Leu Asp His Leu Leu His Leu Met Leu Lys Glu Trp Lys Met
        115                 120                 125
```

```
                                                         -continued
gaa ctg ccc aag ctt gtg atc tca gtc cat ggg ggc atc cag aac ttt      432
Glu Leu Pro Lys Leu Val Ile Ser Val His Gly Gly Ile Gln Asn Phe
    130                 135                 140 act atg ccc tct aaa ttt aaa gag att ttc agc caa ggt ttg gtt aaa      480
Thr Met Pro Ser Lys Phe Lys Glu Ile Phe Ser Gln Gly Leu Val Lys
145                 150                 155                 160 gct gca gag aca aca gga gcg tgg ata ata act gaa ggc atc aat aca      528
Ala Ala Glu Thr Thr Gly Ala Trp Ile Ile Thr Glu Gly Ile Asn Thr
                165                 170                 175 gga gtg tcc aag cat gtt ggg gat gcc ttg aaa tcc cat tcc tct cat      576
Gly Val Ser Lys His Val Gly Asp Ala Leu Lys Ser His Ser Ser His
            180                 185                 190 tcc ttg aga aaa atc tgg aca gtt gga atc cct cct tgg ggt gtc att      624
Ser Leu Arg Lys Ile Trp Thr Val Gly Ile Pro Pro Trp Gly Val Ile
        195                 200                 205 gag aac cag aga gac ctt att gga aaa gat gtg gtg tgc ctg tac cag      672
Glu Asn Gln Arg Asp Leu Ile Gly Lys Asp Val Val Cys Leu Tyr Gln
    210                 215                 220 act ctg gat aac ccc ctc agc aag ctc aca aca ctc aac agc atg cac      720
Thr Leu Asp Asn Pro Leu Ser Lys Leu Thr Thr Leu Asn Ser Met His
225                 230                 235                 240 tcg cac ttc atc ctg tct gat gat ggg acc gtg ggc aag tat gga aat      768
Ser His Phe Ile Leu Ser Asp Asp Gly Thr Val Gly Lys Tyr Gly Asn
                245                 250                 255 gaa atg aag ctc aga agg aac ctg gag aag tac ctc tct ctg cag aaa      816
Glu Met Lys Leu Arg Arg Asn Leu Glu Lys Tyr Leu Ser Leu Gln Lys
            260                 265                 270 ata cac tgc cgc tca aga caa ggc gtg ccg gtc gtg ggg ctg gtg gtg      864
Ile His Cys Arg Ser Arg Gln Gly Val Pro Val Val Gly Leu Val Val
        275                 280                 285 gaa ggc ggt ccc aac gtc atc ctg tca gtg tgg gag act gtc aag gac      912
Glu Gly Gly Pro Asn Val Ile Leu Ser Val Trp Glu Thr Val Lys Asp
    290                 295                 300 aag gac cca gtg gtg gtg tgt gag ggc aca ggt agg gcg gct gac ctc      960
Lys Asp Pro Val Val Val Cys Glu Gly Thr Gly Arg Ala Ala Asp Leu
305                 310                 315                 320 ctg gcc ttc aca cac aaa cac ctg gca gat gaa ggg atg ctg cga cct     1008
Leu Ala Phe Thr His Lys His Leu Ala Asp Glu Gly Met Leu Arg Pro
                325                 330                 335 cag gtg aaa gag gag atc atc tgc atg att cag aac act ttc aac ttt     1056
Gln Val Lys Glu Glu Ile Ile Cys Met Ile Gln Asn Thr Phe Asn Phe
            340                 345                 350 agt ctt aaa cag tcc aag cac ctt ttc caa att cta atg gag tgt atg     1104
Ser Leu Lys Gln Ser Lys His Leu Phe Gln Ile Leu Met Glu Cys Met
        355                 360                 365 gtt cac agg gat tgt att acc ata ttt gat gct gac tct gaa gag cag     1152
Val His Arg Asp Cys Ile Thr Ile Phe Asp Ala Asp Ser Glu Glu Gln
    370                 375                 380 caa gac ctg gac tta gca atc cta aca gct ttg ctg aag ggc aca aat     1200
Gln Asp Leu Asp Leu Ala Ile Leu Thr Ala Leu Leu Lys Gly Thr Asn
385                 390                 395                 400 tta tca gcg tca gag caa tta aat ctg gca atg gct tgg gac agg gtg     1248
Leu Ser Ala Ser Glu Gln Leu Asn Leu Ala Met Ala Trp Asp Arg Val
                405                 410                 415 gac att gcc aag aaa cat atc cta att tat gaa caa cac tgg aag cct     1296
Asp Ile Ala Lys Lys His Ile Leu Ile Tyr Glu Gln His Trp Lys Pro
            420                 425                 430 gat gcc ctg gaa caa gca atg tca gat gct tta gtg atg gat cgg gtg     1344
Asp Ala Leu Glu Gln Ala Met Ser Asp Ala Leu Val Met Asp Arg Val
        435                 440                 445
```

-continued

```
gat ttt gtg aag ctc tta ata gaa tat gga gtg aac ctc cat cgc ttt      1392
Asp Phe Val Lys Leu Leu Ile Glu Tyr Gly Val Asn Leu His Arg Phe
    450                 455                 460 ctt acc atc cct cga ctg gaa gag ctc tac aat aca aaa caa gga cct      1440
Leu Thr Ile Pro Arg Leu Glu Glu Leu Tyr Asn Thr Lys Gln Gly Pro
465                 470                 475                 480 act aat aca ctc ttg cat cat ctc gtc caa gat gtg aaa cag gaa aag      1488
Thr Asn Thr Leu Leu His His Leu Val Gln Asp Val Lys Gln Glu Lys
                485                 490                 495 tct ata gtc ctt cat aaa tca agg aag aag tca aaa gaa caa aat gta      1536
Ser Ile Val Leu His Lys Ser Arg Lys Lys Ser Lys Glu Gln Asn Val
            500                 505                 510 tca gat gac cct gag tct act ggc ttt ctt tac cct tac aat gac ctg      1584
Ser Asp Asp Pro Glu Ser Thr Gly Phe Leu Tyr Pro Tyr Asn Asp Leu
        515                 520                 525 ctg gtt tgg gct gtg ctg atg aaa agg cag aag atg gct atg ttc ttc      1632
Leu Val Trp Ala Val Leu Met Lys Arg Gln Lys Met Ala Met Phe Phe
530                 535                 540 tgg cag cat gga gag gag gcc acg gtt aaa gcc gtg att gcg tgt atc      1680
Trp Gln His Gly Glu Glu Ala Thr Val Lys Ala Val Ile Ala Cys Ile
545                 550                 555                 560 ctc tac cgg gca atg gcc cat gaa gct aag gag agt cac atg gtg gat      1728
Leu Tyr Arg Ala Met Ala His Glu Ala Lys Glu Ser His Met Val Asp
                565                 570                 575 gat gcc tca gaa gag ttg aag aat tac tca aaa cag ttt ggc cag ctg      1776
Asp Ala Ser Glu Glu Leu Lys Asn Tyr Ser Lys Gln Phe Gly Gln Leu
            580                 585                 590 gct ctg gac ttg ttg gag aag gca ttc aag cag aat gag cgc atg gcc      1824
Ala Leu Asp Leu Leu Glu Lys Ala Phe Lys Gln Asn Glu Arg Met Ala
        595                 600                 605 atg acg ctg ttg acg tat gaa ctc agg aac tgg agc aat tcg acc tgc      1872
Met Thr Leu Leu Thr Tyr Glu Leu Arg Asn Trp Ser Asn Ser Thr Cys
610                 615                 620 ctg aaa ctg gcc gtg tcg gga gga tta cga ccc ttt gtt tca cat act      1920
Leu Lys Leu Ala Val Ser Gly Gly Leu Arg Pro Phe Val Ser His Thr
625                 630                 635                 640 tgt acc cag atg cta ctg aca gac atg tgg atg ggg agg ctg aaa atg      1968
Cys Thr Gln Met Leu Leu Thr Asp Met Trp Met Gly Arg Leu Lys Met
                645                 650                 655 agg aaa aac tct tgg tta aag att att ata agc att att tta cca ccc      2016
Arg Lys Asn Ser Trp Leu Lys Ile Ile Ile Ser Ile Ile Leu Pro Pro
            660                 665                 670 acc att ttg aca ctg gaa ttt aaa agc aaa gct gag atg tca cat gtt      2064
Thr Ile Leu Thr Leu Glu Phe Lys Ser Lys Ala Glu Met Ser His Val
        675                 680                 685 ccc cag tcc cag gac ttc caa ttt atg tgg tat tac agt gac cag aac      2112
Pro Gln Ser Gln Asp Phe Gln Phe Met Trp Tyr Tyr Ser Asp Gln Asn
690                 695                 700 gcc agc agt tcc aaa gaa agt gct tct gtg aaa gag tat gat ttg gaa      2160
Ala Ser Ser Ser Lys Glu Ser Ala Ser Val Lys Glu Tyr Asp Leu Glu
705                 710                 715                 720 agg ggc cat gat gag aaa ctg gat gaa aat cag cat ttt ggt ttg gaa      2208
Arg Gly His Asp Glu Lys Leu Asp Glu Asn Gln His Phe Gly Leu Glu
                725                 730                 735 agt ggg cac caa cac ctt ccg tgg acc agg aaa gtc tat gag ttc tac      2256
Ser Gly His Gln His Leu Pro Trp Thr Arg Lys Val Tyr Glu Phe Tyr
            740                 745                 750 agt gct cca att gtc aag ttt tgg ttt tat acg atg gcg tat ttg gca      2304
Ser Ala Pro Ile Val Lys Phe Trp Phe Tyr Thr Met Ala Tyr Leu Ala
        755                 760                 765
```

```
ttc ctc atg ctg ttc act tac acc gtg ttg gtg gag atg cag ccc cag      2352
Phe Leu Met Leu Phe Thr Tyr Thr Val Leu Val Glu Met Gln Pro Gln
    770                 775                 780 ccc agc gtg cag gag tgg ctt gtt agc att tac atc ttc acc aat gct      2400
Pro Ser Val Gln Glu Trp Leu Val Ser Ile Tyr Ile Phe Thr Asn Ala
785                 790                 795                 800 att gag gtg gtc agg gag atc tgt att tca gaa cct ggg aag ttt acc      2448
Ile Glu Val Val Arg Glu Ile Cys Ile Ser Glu Pro Gly Lys Phe Thr
            805                 810                 815 caa aag gtg aag gta tgg att agt gag tac tgg aac tta aca gaa act      2496
Gln Lys Val Lys Val Trp Ile Ser Glu Tyr Trp Asn Leu Thr Glu Thr
        820                 825                 830 gtg gcc att ggc ctg ttt tca gct ggc ttc gtc ctt cga tgg ggt gac      2544
Val Ala Ile Gly Leu Phe Ser Ala Gly Phe Val Leu Arg Trp Gly Asp
    835                 840                 845 cct cct ttt cac aca gcg gga aga ctg atc tac tgc ata gac atc ata      2592
Pro Pro Phe His Thr Ala Gly Arg Leu Ile Tyr Cys Ile Asp Ile Ile
850                 855                 860 ttc tgg ttc tca cgg ctc ctg gac ttc ttt gct gtg aat caa cat gca      2640
Phe Trp Phe Ser Arg Leu Leu Asp Phe Phe Ala Val Asn Gln His Ala
865                 870                 875                 880 ggt cca tat gtg acc atg att gca aaa atg aca gca aac atg ttc tat      2688
Gly Pro Tyr Val Thr Met Ile Ala Lys Met Thr Ala Asn Met Phe Tyr
            885                 890                 895 att gtg atc atc atg gcc ata gtc ctg ctg agc ttt gga gtg gca cgc      2736
Ile Val Ile Ile Met Ala Ile Val Leu Leu Ser Phe Gly Val Ala Arg
        900                 905                 910 aag gcc atc ctt tcg cca aaa gag cca cca tct tgg agt cta gct cga      2784
Lys Ala Ile Leu Ser Pro Lys Glu Pro Pro Ser Trp Ser Leu Ala Arg
    915                 920                 925 gat att gta ttt gag cca tac tgg atg ata tac gga gaa gtc tat gct      2832
Asp Ile Val Phe Glu Pro Tyr Trp Met Ile Tyr Gly Glu Val Tyr Ala
930                 935                 940 gga gaa ata gat gtt tgt tca agc cag cca tcc tgc cct cct ggt tct      2880
Gly Glu Ile Asp Val Cys Ser Ser Gln Pro Ser Cys Pro Pro Gly Ser
945                 950                 955                 960 ttt ctt act cca ttc ttg caa gct gtc tac ctc ttc gtg caa tat atc      2928
Phe Leu Thr Pro Phe Leu Gln Ala Val Tyr Leu Phe Val Gln Tyr Ile
            965                 970                 975 atc atg gtg aac ctg ttg att gct ttc ttc aac aac gtt tac tta gat      2976
Ile Met Val Asn Leu Leu Ile Ala Phe Phe Asn Asn Val Tyr Leu Asp
        980                 985                 990 atg gaa tcc att tca aat aac ctg tgg aaa tac aac cgc tat cgc tac      3024
Met Glu Ser Ile Ser Asn Asn Leu Trp Lys Tyr Asn Arg Tyr Arg Tyr
    995                 1000                1005 atc atg acc tac cac gag aag ccc tgg ctg ccc cca cct ctc atc        3069
Ile Met Thr Tyr His Glu Lys Pro Trp Leu Pro Pro Pro Leu Ile
    1010                1015                1020 ctg ctg agc cac gtg ggc ctt ctc ctc cgc cgc ctg tgc tgt cat        3114
Leu Leu Ser His Val Gly Leu Leu Leu Arg Arg Leu Cys Cys His
    1025                1030                1035 cga gct cct cac gac caa gaa gag ggt gac gtt gga tta aaa ctc        3159
Arg Ala Pro His Asp Gln Glu Glu Gly Asp Val Gly Leu Lys Leu
    1040                1045                1050 tac ctc agt aag gag gat ctg aaa aaa ctt cat gat ttt gag gag        3204
Tyr Leu Ser Lys Glu Asp Leu Lys Lys Leu His Asp Phe Glu Glu
    1055                1060                1065 cag tgc gtg gaa aaa tac ttc cat gag aag atg gaa gat gtg aat        3249
Gln Cys Val Glu Lys Tyr Phe His Glu Lys Met Glu Asp Val Asn
    1070                1075                1080
```

```
                                          -continued tgt agt tgt gag gaa cga atc cga gtc aca tca gaa agg gtt aca      3294
Cys Ser Cys Glu Glu Arg Ile Arg Val Thr Ser Glu Arg Val Thr
1085             1090                1095 gag atg tac ttc cag ctg aaa gaa atg aat gaa aag gtg tct ttt      3339
Glu Met Tyr Phe Gln Leu Lys Glu Met Asn Glu Lys Val Ser Phe
    1100                1105                1110 ata aag gac tcc tta ctg tct ttg gac agc cag gtg gga cac ctg      3384
Ile Lys Asp Ser Leu Leu Ser Leu Asp Ser Gln Val Gly His Leu
1115                 1120                1125 cag gat ctc tct gcc ctg act gtg gat acc ctg aaa gtc ctt tct      3429
Gln Asp Leu Ser Ala Leu Thr Val Asp Thr Leu Lys Val Leu Ser
    1130                1135                1140 gct gtt gac act ttg caa gag gat gag gct ctc ctg gcc aag aga      3474
Ala Val Asp Thr Leu Gln Glu Asp Glu Ala Leu Leu Ala Lys Arg
1145                 1150                1155 aag cat tct act tgc aaa aaa ctt ccc cac agc tgg agc aat gtc      3519
Lys His Ser Thr Cys Lys Lys Leu Pro His Ser Trp Ser Asn Val
    1160                1165                1170 atc tgt gca gag gtt cta ggc agc atg gag atc gct gga gag aag      3564
Ile Cys Ala Glu Val Leu Gly Ser Met Glu Ile Ala Gly Glu Lys
1175                 1180                1185 aaa tac cag tat tat agc atg ccc tct tct ttg ctg agg agc ctg      3609
Lys Tyr Gln Tyr Tyr Ser Met Pro Ser Ser Leu Leu Arg Ser Leu
    1190                1195                1200 gct gga ggc cgg cat ccc cca aga gtg cag agg ggg gca ctt ctt      3654
Ala Gly Gly Arg His Pro Pro Arg Val Gln Arg Gly Ala Leu Leu
1205                 1210                1215 gag att aca aac agt aaa aga gag gct aca aat gta aga aat gac      3699
Glu Ile Thr Asn Ser Lys Arg Glu Ala Thr Asn Val Arg Asn Asp
    1220                1225                1230 cag gaa agg caa gaa aca caa agt agt ata gtg gtt tct ggg gtg      3744
Gln Glu Arg Gln Glu Thr Gln Ser Ser Ile Val Val Ser Gly Val
1235                 1240                1245 tct cct aac agg caa gca cac tca aag tat ggc cag ttt ctt ctg      3789
Ser Pro Asn Arg Gln Ala His Ser Lys Tyr Gly Gln Phe Leu Leu
    1250                1255                1260 gtc ccc tct aat cta aag cga gtt cct ttt tca gca gaa act gtc      3834
Val Pro Ser Asn Leu Lys Arg Val Pro Phe Ser Ala Glu Thr Val
1265                 1270                1275 ttg cct ctg tcc aga ccc tct gtg cca gat gtg ctg gca act gaa      3879
Leu Pro Leu Ser Arg Pro Ser Val Pro Asp Val Leu Ala Thr Glu
    1280                1285                1290 cag gac atc cag act gag gtt ctt gtt cat ctg act ggg cag acc      3924
Gln Asp Ile Gln Thr Glu Val Leu Val His Leu Thr Gly Gln Thr
1295                 1300                1305 cca gtt gtc tct gac tgg gca tca gtg gat gaa ccc aag gaa aag      3969
Pro Val Val Ser Asp Trp Ala Ser Val Asp Glu Pro Lys Glu Lys
    1310                1315                1320 cac gag cct att gct cac tta ctg gat gga caa gac aag gca gag      4014
His Glu Pro Ile Ala His Leu Leu Asp Gly Gln Asp Lys Ala Glu
1325                 1330                1335 caa gtg cta ccc act ttg agt tgc aca cct gaa ccc atg aca atg      4059
Gln Val Leu Pro Thr Leu Ser Cys Thr Pro Glu Pro Met Thr Met
    1340                1345                1350 agc tcc cct ctt tcc caa gcc aag atc atg caa act gga ggt gga      4104
Ser Ser Pro Leu Ser Gln Ala Lys Ile Met Gln Thr Gly Gly Gly
1355                 1360                1365 tat gta aac tgg gca ttt tca gaa ggt gat gaa act ggt gtg ttt      4149
Tyr Val Asn Trp Ala Phe Ser Glu Gly Asp Glu Thr Gly Val Phe
1370                 1375                1380
```

```
                                                    -continued
agc atc aag aaa aag tgg caa acc tgc ttg ccc tcc act tgt gac      4194
Ser Ile Lys Lys Lys Trp Gln Thr Cys Leu Pro Ser Thr Cys Asp
    1385                1390                1395 agt gat tcc tct cgg agt gaa cag cac cag aag cag gcc cag gac      4239
Ser Asp Ser Ser Arg Ser Glu Gln His Gln Lys Gln Ala Gln Asp
1400                1405                1410 agc tcc cta tct gat aac tca aca aga tcg gcc cag agt agt gaa      4284
Ser Ser Leu Ser Asp Asn Ser Thr Arg Ser Ala Gln Ser Ser Glu
    1415                1420                1425 tgc tca gag gtg gga cca tgg ctt cag cca aac aca tcc ttt tgg      4329
Cys Ser Glu Val Gly Pro Trp Leu Gln Pro Asn Thr Ser Phe Trp
1430                1435                1440 atc aat cct ctc cgc aga tac agg ccc ttc gct agg agt cat agt      4374
Ile Asn Pro Leu Arg Arg Tyr Arg Pro Phe Ala Arg Ser His Ser
    1445                1450                1455 ttt aga ttc cat aag gag gag aaa ttg atg aag atc tgt aag att      4419
Phe Arg Phe His Lys Glu Glu Lys Leu Met Lys Ile Cys Lys Ile
1460                1465                1470 aaa aat ctt tca ggc tct tca gaa ata ggg cag gga gca tgg gtc      4464
Lys Asn Leu Ser Gly Ser Ser Glu Ile Gly Gln Gly Ala Trp Val
    1475                1480                1485 aaa gcg aaa atg cta acc aaa gac agg aga ctg tca aag aaa aag      4509
Lys Ala Lys Met Leu Thr Lys Asp Arg Arg Leu Ser Lys Lys Lys
1490                1495                1500 aag aat act caa gga ctc cag gtg cca atc ata aca gtc aat gcc      4554
Lys Asn Thr Gln Gly Leu Gln Val Pro Ile Ile Thr Val Asn Ala
    1505                1510                1515 tgc tct cag agt gac cag ttg aat cca gag cca gga gaa aac agc      4599
Cys Ser Gln Ser Asp Gln Leu Asn Pro Glu Pro Gly Glu Asn Ser
1520                1525                1530 atc tct gaa gag gag tac agc aag aac tgg ttc aca gtg tcc aaa      4644
Ile Ser Glu Glu Glu Tyr Ser Lys Asn Trp Phe Thr Val Ser Lys
    1535                1540                1545 ttt agt cac aca ggt gta gaa cct tac ata cat cag aaa atg aaa      4689
Phe Ser His Thr Gly Val Glu Pro Tyr Ile His Gln Lys Met Lys
1550                1555                1560 act aaa gaa att gga caa tgt gct ata caa atc agt gat tac cta      4734
Thr Lys Glu Ile Gly Gln Cys Ala Ile Gln Ile Ser Asp Tyr Leu
    1565                1570                1575 aag cag tct caa gag gat ctc agc aaa aac tct ttg tgg aat tcc      4779
Lys Gln Ser Gln Glu Asp Leu Ser Lys Asn Ser Leu Trp Asn Ser
1580                1585                1590 agg agc acc aac ctc aat agg aac tcc ctg ctg aaa agt tca att      4824
Arg Ser Thr Asn Leu Asn Arg Asn Ser Leu Leu Lys Ser Ser Ile
    1595                1600                1605 gga gtt gac aag atc tca gcc tcc tta aaa agc cct caa gag cct      4869
Gly Val Asp Lys Ile Ser Ala Ser Leu Lys Ser Pro Gln Glu Pro
1610                1615                1620 cac cat cat tat tca gcc att gaa agg aat aat tta atg agg ctt      4914
His His His Tyr Ser Ala Ile Glu Arg Asn Asn Leu Met Arg Leu
    1625                1630                1635 tct cag acc ata cca ttt aca cca gtc caa ctg ttt gca gga gaa      4959
Ser Gln Thr Ile Pro Phe Thr Pro Val Gln Leu Phe Ala Gly Glu
1640                1645                1650 gaa ata act gtc tac agg ttg gag gag agt tcc cct tta aac ctt      5004
Glu Ile Thr Val Tyr Arg Leu Glu Glu Ser Ser Pro Leu Asn Leu
    1655                1660                1665 gat aaa agc atg tcc tct tgg tct cag cgt ggg aga gcg gca atg      5049
Asp Lys Ser Met Ser Ser Trp Ser Gln Arg Gly Arg Ala Ala Met
1670                1675                1680
```

```
atc cag gta ttg tcc cga gag gag atg gat ggg ggc ctc cgt aaa        5094
Ile Gln Val Leu Ser Arg Glu Glu Met Asp Gly Gly Leu Arg Lys
    1685                1690                1695 gct atg aga gtc gtc agc act tgg tct gag gat gac att ctc aag        5139
Ala Met Arg Val Val Ser Thr Trp Ser Glu Asp Asp Ile Leu Lys
1700                1705                1710 ccg gga caa gtt ttc att gtc aag tcc ttt ctt cct gag gtt gtg        5184
Pro Gly Gln Val Phe Ile Val Lys Ser Phe Leu Pro Glu Val Val
    1715                1720                1725 cgg aca tgg cat aaa atc ttc cag gag agc act gtg ctt cat ctt        5229
Arg Thr Trp His Lys Ile Phe Gln Glu Ser Thr Val Leu His Leu
1730                1735                1740 tgc ctc agg gaa att caa caa caa aga gct gct caa aaa ttg atc        5274
Cys Leu Arg Glu Ile Gln Gln Gln Arg Ala Ala Gln Lys Leu Ile
    1745                1750                1755 tat acc ttc aac caa gtg aaa cca caa acc ata ccc tac aca cca        5319
Tyr Thr Phe Asn Gln Val Lys Pro Gln Thr Ile Pro Tyr Thr Pro
1760                1765                1770 agg ttc ctg gaa gtt ttc tta atc tac tgc cat tca gcc aac cag        5364
Arg Phe Leu Glu Val Phe Leu Ile Tyr Cys His Ser Ala Asn Gln
    1775                1780                1785 tgg ttg acc att gag aag tat atg aca ggg gag ttc cgg aag tat        5409
Trp Leu Thr Ile Glu Lys Tyr Met Thr Gly Glu Phe Arg Lys Tyr
1790                1795                1800 aac aac aac aat ggt gat gaa atc acc ccc acc aac acc ctg gag        5454
Asn Asn Asn Asn Gly Asp Glu Ile Thr Pro Thr Asn Thr Leu Glu
    1805                1810                1815 gag ctg atg ttg gct ttc tct cac tgg acc tat gag tac act cgg        5499
Glu Leu Met Leu Ala Phe Ser His Trp Thr Tyr Glu Tyr Thr Arg
1820                1825                1830 gga gag ctg ctg gtt tta gat ttg caa ggt gtt gga gaa aat ttg        5544
Gly Glu Leu Leu Val Leu Asp Leu Gln Gly Val Gly Glu Asn Leu
    1835                1840                1845 aca gat cca tct gtt ata aaa cct gaa gtc aaa caa tca aga gga        5589
Thr Asp Pro Ser Val Ile Lys Pro Glu Val Lys Gln Ser Arg Gly
1850                1855                1860 atg gtg ttt gga ccg gcc aat ttg ggg gaa gat gca att aga aac        5634
Met Val Phe Gly Pro Ala Asn Leu Gly Glu Asp Ala Ile Arg Asn
    1865                1870                1875 ttc att gca aaa cat cat tgt aac tcc tgc tgc cgg aag ctc aaa        5679
Phe Ile Ala Lys His His Cys Asn Ser Cys Cys Arg Lys Leu Lys
1880                1885                1890 ctc ccg gat tta aaa aga aat gac tat tcc cct gaa agg ata aat        5724
Leu Pro Asp Leu Lys Arg Asn Asp Tyr Ser Pro Glu Arg Ile Asn
    1895                1900                1905 tcc acc ttt gga ctt gag ata aaa ata gaa tca gct gag gag cct        5769
Ser Thr Phe Gly Leu Glu Ile Lys Ile Glu Ser Ala Glu Glu Pro
1910                1915                1920 cca gca agg gag acg ggt aga aat tcc cca gaa gat gat atg caa        5814
Pro Ala Arg Glu Thr Gly Arg Asn Ser Pro Glu Asp Asp Met Gln
    1925                1930                1935 cta taa                                                             5820
Leu

<210> SEQ ID NO 6
<211> LENGTH: 1939
<212> TYPE: PRT
<213> ORGANISM: Homo sapiens
```

-continued

```
<400> SEQUENCE: 6

Met Ile Ile Leu Ser Lys Ser Gln Lys Ser Trp Ile Lys Gly Val Phe
1               5                   10                  15

Asp Lys Arg Glu Cys Ser Thr Ile Ile Pro Ser Ser Lys Asn Pro His
            20                  25                  30

Arg Cys Thr Pro Val Cys Gln Val Cys Gln Asn Leu Ile Arg Cys Tyr
        35                  40                  45

Cys Gly Arg Leu Ile Gly Asp His Ala Gly Ile Asp Tyr Ser Trp Thr
    50                  55                  60

Ile Ser Ala Ala Lys Gly Lys Glu Ser Glu Gln Trp Ser Val Glu Lys
65                  70                  75                  80

His Thr Thr Lys Ser Pro Thr Asp Thr Phe Gly Thr Ile Asn Phe Gln
                85                  90                  95

Asp Gly Glu His Thr His His Ala Lys Tyr Ile Arg Thr Ser Tyr Asp
            100                 105                 110

Thr Lys Leu Asp His Leu Leu His Leu Met Leu Lys Glu Trp Lys Met
        115                 120                 125

Glu Leu Pro Lys Leu Val Ile Ser Val His Gly Gly Ile Gln Asn Phe
    130                 135                 140

Thr Met Pro Ser Lys Phe Lys Glu Ile Phe Ser Gln Gly Leu Val Lys
145                 150                 155                 160

Ala Ala Glu Thr Thr Gly Ala Trp Ile Ile Thr Glu Gly Ile Asn Thr
                165                 170                 175

Gly Val Ser Lys His Val Gly Asp Ala Leu Lys Ser His Ser Ser His
            180                 185                 190

Ser Leu Arg Lys Ile Trp Thr Val Gly Ile Pro Pro Trp Gly Val Ile
        195                 200                 205

Glu Asn Gln Arg Asp Leu Ile Gly Lys Asp Val Val Cys Leu Tyr Gln
    210                 215                 220

Thr Leu Asp Asn Pro Leu Ser Lys Leu Thr Thr Leu Asn Ser Met His
225                 230                 235                 240

Ser His Phe Ile Leu Ser Asp Asp Gly Thr Val Gly Lys Tyr Gly Asn
                245                 250                 255

Glu Met Lys Leu Arg Arg Asn Leu Glu Lys Tyr Leu Ser Leu Gln Lys
            260                 265                 270

Ile His Cys Arg Ser Arg Gln Gly Val Pro Val Val Gly Leu Val Val
        275                 280                 285

Glu Gly Gly Pro Asn Val Ile Leu Ser Val Trp Glu Thr Val Lys Asp
    290                 295                 300

Lys Asp Pro Val Val Cys Glu Gly Thr Gly Arg Ala Ala Asp Leu
305                 310                 315                 320

Leu Ala Phe Thr His Lys His Leu Ala Asp Glu Gly Met Leu Arg Pro
                325                 330                 335

Gln Val Lys Glu Glu Ile Ile Cys Met Ile Gln Asn Thr Phe Asn Phe
            340                 345                 350

Ser Leu Lys Gln Ser Lys His Leu Phe Gln Ile Leu Met Glu Cys Met
        355                 360                 365

Val His Arg Asp Cys Ile Thr Ile Phe Asp Ala Asp Ser Glu Glu Gln
    370                 375                 380

Gln Asp Leu Asp Leu Ala Ile Leu Thr Ala Leu Leu Lys Gly Thr Asn
385                 390                 395                 400

Leu Ser Ala Ser Glu Gln Leu Asn Leu Ala Met Ala Trp Asp Arg Val
                405                 410                 415
```

-continued

```
Asp Ile Ala Lys Lys His Ile Leu Ile Tyr Glu Gln His Trp Lys Pro
            420                 425                 430

Asp Ala Leu Glu Gln Ala Met Ser Asp Ala Leu Val Met Asp Arg Val
            435                 440                 445

Asp Phe Val Lys Leu Leu Ile Glu Tyr Gly Val Asn Leu His Arg Phe
            450                 455                 460

Leu Thr Ile Pro Arg Leu Glu Glu Leu Tyr Asn Thr Lys Gln Gly Pro
465                 470                 475                 480

Thr Asn Thr Leu Leu His His Leu Val Gln Asp Val Lys Gln Glu Lys
            485                 490                 495

Ser Ile Val Leu His Lys Ser Arg Lys Ser Lys Glu Gln Asn Val
            500                 505                 510

Ser Asp Asp Pro Glu Ser Thr Gly Phe Leu Tyr Pro Tyr Asn Asp Leu
            515                 520                 525

Leu Val Trp Ala Val Leu Met Lys Arg Gln Lys Met Ala Met Phe Phe
            530                 535                 540

Trp Gln His Gly Glu Glu Ala Thr Val Lys Ala Val Ile Ala Cys Ile
545                 550                 555                 560

Leu Tyr Arg Ala Met Ala His Glu Ala Lys Glu Ser His Met Val Asp
            565                 570                 575

Asp Ala Ser Glu Glu Leu Lys Asn Tyr Ser Lys Gln Phe Gly Gln Leu
            580                 585                 590

Ala Leu Asp Leu Leu Glu Lys Ala Phe Lys Gln Asn Glu Arg Met Ala
            595                 600                 605

Met Thr Leu Leu Thr Tyr Glu Leu Arg Asn Trp Ser Asn Ser Thr Cys
            610                 615                 620

Leu Lys Leu Ala Val Ser Gly Gly Leu Arg Pro Phe Val Ser His Thr
625                 630                 635                 640

Cys Thr Gln Met Leu Leu Thr Asp Met Trp Met Gly Arg Leu Lys Met
            645                 650                 655

Arg Lys Asn Ser Trp Leu Lys Ile Ile Ile Ser Ile Ile Leu Pro Pro
            660                 665                 670

Thr Ile Leu Thr Leu Glu Phe Lys Ser Lys Ala Glu Met Ser His Val
            675                 680                 685

Pro Gln Ser Gln Asp Phe Gln Phe Met Trp Tyr Tyr Ser Asp Gln Asn
            690                 695                 700

Ala Ser Ser Ser Lys Glu Ser Ala Ser Val Lys Glu Tyr Asp Leu Glu
705                 710                 715                 720

Arg Gly His Asp Glu Lys Leu Asp Glu Asn Gln His Phe Gly Leu Glu
            725                 730                 735

Ser Gly His Gln His Leu Pro Trp Thr Arg Lys Val Tyr Glu Phe Tyr
            740                 745                 750

Ser Ala Pro Ile Val Lys Phe Trp Phe Tyr Thr Met Ala Tyr Leu Ala
            755                 760                 765

Phe Leu Met Leu Phe Thr Tyr Thr Val Leu Val Glu Met Gln Pro Gln
            770                 775                 780

Pro Ser Val Gln Glu Trp Leu Val Ser Ile Tyr Ile Phe Thr Asn Ala
785                 790                 795                 800

Ile Glu Val Val Arg Glu Ile Cys Ile Ser Glu Pro Gly Lys Phe Thr
            805                 810                 815

Gln Lys Val Lys Val Trp Ile Ser Glu Tyr Trp Asn Leu Thr Glu Thr
            820                 825                 830
```

-continued

```
Val Ala Ile Gly Leu Phe Ser Ala Gly Phe Val Leu Arg Trp Gly Asp
        835                 840                 845

Pro Pro Phe His Thr Ala Gly Arg Leu Ile Tyr Cys Ile Asp Ile Ile
850                 855                 860

Phe Trp Phe Ser Arg Leu Leu Asp Phe Ala Val Asn Gln His Ala
865                 870                 875                 880

Gly Pro Tyr Val Thr Met Ile Ala Lys Met Thr Ala Asn Met Phe Tyr
                    885                 890                 895

Ile Val Ile Ile Met Ala Ile Val Leu Leu Ser Phe Gly Val Ala Arg
                900                 905                 910

Lys Ala Ile Leu Ser Pro Lys Glu Pro Ser Trp Ser Leu Ala Arg
        915                 920                 925

Asp Ile Val Phe Glu Pro Tyr Trp Met Ile Tyr Gly Glu Val Tyr Ala
        930                 935                 940

Gly Glu Ile Asp Val Cys Ser Ser Gln Pro Ser Cys Pro Pro Gly Ser
945                 950                 955                 960

Phe Leu Thr Pro Phe Leu Gln Ala Val Tyr Leu Phe Val Gln Tyr Ile
                    965                 970                 975

Ile Met Val Asn Leu Leu Ile Ala Phe Phe Asn Asn Val Tyr Leu Asp
                980                 985                 990

Met Glu Ser Ile Ser Asn Asn Leu Trp Lys Tyr Asn Arg Tyr Arg Tyr
                995                1000                1005

Ile Met Thr Tyr His Glu Lys Pro Trp Leu Pro Pro Pro Leu Ile
        1010                1015                1020

Leu Leu Ser His Val Gly Leu Leu Leu Arg Arg Leu Cys Cys His
        1025                1030                1035

Arg Ala Pro His Asp Gln Glu Glu Gly Asp Val Gly Leu Lys Leu
        1040                1045                1050

Tyr Leu Ser Lys Glu Asp Leu Lys Lys Leu His Asp Phe Glu Glu
        1055                1060                1065

Gln Cys Val Glu Lys Tyr Phe His Glu Lys Met Glu Asp Val Asn
        1070                1075                1080

Cys Ser Cys Glu Glu Arg Ile Arg Val Thr Ser Glu Arg Val Thr
        1085                1090                1095

Glu Met Tyr Phe Gln Leu Lys Glu Met Asn Glu Lys Val Ser Phe
        1100                1105                1110

Ile Lys Asp Ser Leu Leu Ser Leu Asp Ser Gln Val Gly His Leu
        1115                1120                1125

Gln Asp Leu Ser Ala Leu Thr Val Asp Thr Leu Lys Val Leu Ser
        1130                1135                1140

Ala Val Asp Thr Leu Gln Glu Asp Glu Ala Leu Leu Ala Lys Arg
        1145                1150                1155

Lys His Ser Thr Cys Lys Lys Leu Pro His Ser Trp Ser Asn Val
        1160                1165                1170

Ile Cys Ala Glu Val Leu Gly Ser Met Glu Ile Ala Gly Glu Lys
        1175                1180                1185

Lys Tyr Gln Tyr Tyr Ser Met Pro Ser Ser Leu Leu Arg Ser Leu
        1190                1195                1200

Ala Gly Gly Arg His Pro Pro Arg Val Gln Arg Gly Ala Leu Leu
        1205                1210                1215

Glu Ile Thr Asn Ser Lys Arg Glu Ala Thr Asn Val Arg Asn Asp
        1220                1225                1230
```

-continued

```
Gln Glu Arg Gln Glu Thr Gln Ser Ser Ile Val Val Ser Gly Val
    1235                1240                1245

Ser Pro Asn Arg Gln Ala His Ser Lys Tyr Gly Gln Phe Leu Leu
    1250                1255                1260

Val Pro Ser Asn Leu Lys Arg Val Pro Phe Ser Ala Glu Thr Val
    1265                1270                1275

Leu Pro Leu Ser Arg Pro Ser Val Pro Asp Val Leu Ala Thr Glu
    1280                1285                1290

Gln Asp Ile Gln Thr Glu Val Leu Val His Leu Thr Gly Gln Thr
    1295                1300                1305

Pro Val Val Ser Asp Trp Ala Ser Val Asp Glu Pro Lys Glu Lys
    1310                1315                1320

His Glu Pro Ile Ala His Leu Leu Asp Gly Gln Asp Lys Ala Glu
    1325                1330                1335

Gln Val Leu Pro Thr Leu Ser Cys Thr Pro Glu Pro Met Thr Met
    1340                1345                1350

Ser Ser Pro Leu Ser Gln Ala Lys Ile Met Gln Thr Gly Gly Gly
    1355                1360                1365

Tyr Val Asn Trp Ala Phe Ser Glu Gly Asp Glu Thr Gly Val Phe
    1370                1375                1380

Ser Ile Lys Lys Lys Trp Gln Thr Cys Leu Pro Ser Thr Cys Asp
    1385                1390                1395

Ser Asp Ser Ser Arg Ser Glu Gln His Gln Lys Gln Ala Gln Asp
    1400                1405                1410

Ser Ser Leu Ser Asp Asn Ser Thr Arg Ser Ala Gln Ser Ser Glu
    1415                1420                1425

Cys Ser Glu Val Gly Pro Trp Leu Gln Pro Asn Thr Ser Phe Trp
    1430                1435                1440

Ile Asn Pro Leu Arg Arg Tyr Arg Pro Phe Ala Arg Ser His Ser
    1445                1450                1455

Phe Arg Phe His Lys Glu Glu Lys Leu Met Lys Ile Cys Lys Ile
    1460                1465                1470

Lys Asn Leu Ser Gly Ser Ser Glu Ile Gly Gln Gly Ala Trp Val
    1475                1480                1485

Lys Ala Lys Met Leu Thr Lys Asp Arg Arg Leu Ser Lys Lys Lys
    1490                1495                1500

Lys Asn Thr Gln Gly Leu Gln Val Pro Ile Ile Thr Val Asn Ala
    1505                1510                1515

Cys Ser Gln Ser Asp Gln Leu Asn Pro Glu Pro Gly Glu Asn Ser
    1520                1525                1530

Ile Ser Glu Glu Glu Tyr Ser Lys Asn Trp Phe Thr Val Ser Lys
    1535                1540                1545

Phe Ser His Thr Gly Val Glu Pro Tyr Ile His Gln Lys Met Lys
    1550                1555                1560

Thr Lys Glu Ile Gly Gln Cys Ala Ile Gln Ile Ser Asp Tyr Leu
    1565                1570                1575

Lys Gln Ser Gln Glu Asp Leu Ser Lys Asn Ser Leu Trp Asn Ser
    1580                1585                1590

Arg Ser Thr Asn Leu Asn Arg Asn Ser Leu Leu Lys Ser Ser Ile
    1595                1600                1605

Gly Val Asp Lys Ile Ser Ala Ser Leu Lys Ser Pro Gln Glu Pro
    1610                1615                1620
```

```
His His His Tyr Ser Ala Ile Glu Arg Asn Asn Leu Met Arg Leu
    1625                1630                1635

Ser Gln Thr Ile Pro Phe Thr Pro Val Gln Leu Phe Ala Gly Glu
    1640                1645                1650

Glu Ile Thr Val Tyr Arg Leu Glu Glu Ser Ser Pro Leu Asn Leu
    1655                1660                1665

Asp Lys Ser Met Ser Ser Trp Ser Gln Arg Gly Arg Ala Ala Met
    1670                1675                1680

Ile Gln Val Leu Ser Arg Glu Glu Met Asp Gly Gly Leu Arg Lys
    1685                1690                1695

Ala Met Arg Val Val Ser Thr Trp Ser Glu Asp Asp Ile Leu Lys
    1700                1705                1710

Pro Gly Gln Val Phe Ile Val Lys Ser Phe Leu Pro Glu Val Val
    1715                1720                1725

Arg Thr Trp His Lys Ile Phe Gln Glu Ser Thr Val Leu His Leu
    1730                1735                1740

Cys Leu Arg Glu Ile Gln Gln Gln Arg Ala Ala Gln Lys Leu Ile
    1745                1750                1755

Tyr Thr Phe Asn Gln Val Lys Pro Gln Thr Ile Pro Tyr Thr Pro
    1760                1765                1770

Arg Phe Leu Glu Val Phe Leu Ile Tyr Cys His Ser Ala Asn Gln
    1775                1780                1785

Trp Leu Thr Ile Glu Lys Tyr Met Thr Gly Glu Phe Arg Lys Tyr
    1790                1795                1800

Asn Asn Asn Asn Gly Asp Glu Ile Thr Pro Thr Asn Thr Leu Glu
    1805                1810                1815

Glu Leu Met Leu Ala Phe Ser His Trp Thr Tyr Glu Tyr Thr Arg
    1820                1825                1830

Gly Glu Leu Leu Val Leu Asp Leu Gln Gly Val Gly Glu Asn Leu
    1835                1840                1845

Thr Asp Pro Ser Val Ile Lys Pro Glu Val Lys Gln Ser Arg Gly
    1850                1855                1860

Met Val Phe Gly Pro Ala Asn Leu Gly Glu Asp Ala Ile Arg Asn
    1865                1870                1875

Phe Ile Ala Lys His His Cys Asn Ser Cys Cys Arg Lys Leu Lys
    1880                1885                1890

Leu Pro Asp Leu Lys Arg Asn Asp Tyr Ser Pro Glu Arg Ile Asn
    1895                1900                1905

Ser Thr Phe Gly Leu Glu Ile Lys Ile Glu Ser Ala Glu Glu Pro
    1910                1915                1920

Pro Ala Arg Glu Thr Gly Arg Asn Ser Pro Glu Asp Asp Met Gln
    1925                1930                1935

Leu

<210> SEQ ID NO 7
<211> LENGTH: 5925
<212> TYPE: DNA
<213> ORGANISM: Homo sapiens
<220> FEATURE:
<221> NAME/KEY: CDS
<222> LOCATION: (1)..(5922)

<400> SEQUENCE: 7 atg att atc cta tct aag tcc cag aaa tcc tgg att aaa gga gta ttt       48
Met Ile Ile Leu Ser Lys Ser Gln Lys Ser Trp Ile Lys Gly Val Phe
1               5                   10                  15
```

```
gac aag aga gaa tgt agc aca atc ata ccc agc tca aaa aat cct cac      96
Asp Lys Arg Glu Cys Ser Thr Ile Ile Pro Ser Ser Lys Asn Pro His
         20                  25                  30 aga tgt act cca gta tgc caa gtc tgc cag aat tta atc agg tgt tac     144
Arg Cys Thr Pro Val Cys Gln Val Cys Gln Asn Leu Ile Arg Cys Tyr
     35                  40                  45 tgt ggc cga ctg att gga gac cat gct ggg ata gat tat tcc tgg acc     192
Cys Gly Arg Leu Ile Gly Asp His Ala Gly Ile Asp Tyr Ser Trp Thr
 50                  55                  60 atc tca gct gcc aag ggt aaa gaa agt gaa caa tgg tct gtt gaa aag     240
Ile Ser Ala Ala Lys Gly Lys Glu Ser Glu Gln Trp Ser Val Glu Lys
 65                  70                  75                  80 cac acg aaa agc cca aca gat act ttt ggc acg att aat ttc caa         288
His Thr Thr Lys Ser Pro Thr Asp Thr Phe Gly Thr Ile Asn Phe Gln
                 85                  90                  95 gat gga gag cac acc cat cat gcc aag tat att aga act tct tat gat     336
Asp Gly Glu His Thr His His Ala Lys Tyr Ile Arg Thr Ser Tyr Asp
                100                 105                 110 aca aaa ctg gat cat ctg tta cat tta atg ttg aaa gag tgg aaa atg     384
Thr Lys Leu Asp His Leu Leu His Leu Met Leu Lys Glu Trp Lys Met
         115                 120                 125 gaa ctg ccc aag ctt gtg atc tca gtc cat ggg ggc atc cag aac ttt     432
Glu Leu Pro Lys Leu Val Ile Ser Val His Gly Gly Ile Gln Asn Phe
    130                 135                 140 act atg ccc tct aaa ttt aaa gag att ttc agc caa ggt ttg gtt aaa     480
Thr Met Pro Ser Lys Phe Lys Glu Ile Phe Ser Gln Gly Leu Val Lys
145                 150                 155                 160 gct gca gag aca aca gga gcg tgg ata ata act gaa ggc atc aat aca     528
Ala Ala Glu Thr Thr Gly Ala Trp Ile Ile Thr Glu Gly Ile Asn Thr
                165                 170                 175 gga gtg tcc aag cat gtt ggg gat gcc ttg aaa tcc cat tcc tct cat     576
Gly Val Ser Lys His Val Gly Asp Ala Leu Lys Ser His Ser Ser His
            180                 185                 190 tcc ttg aga aaa atc tgg aca gtt gga atc cct cct tgg ggt gtc att     624
Ser Leu Arg Lys Ile Trp Thr Val Gly Ile Pro Pro Trp Gly Val Ile
        195                 200                 205 gag aac cag aga gac ctt att gga aaa gat gtg gtg tgc ctg tac cag     672
Glu Asn Gln Arg Asp Leu Ile Gly Lys Asp Val Val Cys Leu Tyr Gln
    210                 215                 220 act ctg gat aac ccc ctc agc aag ctc aca aca ctc aac agc atg cac     720
Thr Leu Asp Asn Pro Leu Ser Lys Leu Thr Thr Leu Asn Ser Met His
225                 230                 235                 240 tcg cac ttc atc ctg tct gat gat ggg acc gtg ggc aag tat gga aat     768
Ser His Phe Ile Leu Ser Asp Asp Gly Thr Val Gly Lys Tyr Gly Asn
                245                 250                 255 gaa atg aag ctc aga agg aac ctg gag aag tac ctc tct ctg cag aaa     816
Glu Met Lys Leu Arg Arg Asn Leu Glu Lys Tyr Leu Ser Leu Gln Lys
            260                 265                 270 ata cac tgc cgc tca aga caa ggc gtg ccg gtc gtg ggg ctg gtg gtg     864
Ile His Cys Arg Ser Arg Gln Gly Val Pro Val Val Gly Leu Val Val
        275                 280                 285 gaa ggc ggt ccc aac gtc atc ctg tca gtg tgg gag act gtc aag gac     912
Glu Gly Gly Pro Asn Val Ile Leu Ser Val Trp Glu Thr Val Lys Asp
    290                 295                 300 aag gac cca gtg gtg gtg tgt gag ggc aca ggt agg gcg gct gac ctc     960
Lys Asp Pro Val Val Val Cys Glu Gly Thr Gly Arg Ala Ala Asp Leu
305                 310                 315                 320 ctg gcc ttc aca cac aaa cac ctg gca gat gaa ggg atg ctg cga cct    1008
Leu Ala Phe Thr His Lys His Leu Ala Asp Glu Gly Met Leu Arg Pro
                325                 330                 335
```

```
cag gtg aaa gag gag atc atc tgc atg att cag aac act ttc aac ttt    1056
Gln Val Lys Glu Glu Ile Ile Cys Met Ile Gln Asn Thr Phe Asn Phe
        340                 345                 350 agt ctt aaa cag tcc aag cac ctt ttc caa att cta atg gag tgt atg    1104
Ser Leu Lys Gln Ser Lys His Leu Phe Gln Ile Leu Met Glu Cys Met
    355                 360                 365 gtt cac agg gat tgt att acc ata ttt gat gct gac tct gaa gag cag    1152
Val His Arg Asp Cys Ile Thr Ile Phe Asp Ala Asp Ser Glu Glu Gln
370                 375                 380 caa gac ctg gac tta gca atc cta aca gct ttg ctg aag ggc aca aat    1200
Gln Asp Leu Asp Leu Ala Ile Leu Thr Ala Leu Leu Lys Gly Thr Asn
385                 390                 395                 400 tta tca gcg tca gag caa tta aat ctg gca atg gct tgg gac agg gtg    1248
Leu Ser Ala Ser Glu Gln Leu Asn Leu Ala Met Ala Trp Asp Arg Val
            405                 410                 415 gac att gcc aag aaa cat atc cta att tat gaa caa cac tgg aag cct    1296
Asp Ile Ala Lys Lys His Ile Leu Ile Tyr Glu Gln His Trp Lys Pro
        420                 425                 430 gat gcc ctg gaa caa gca atg tca gat gct tta gtg atg gat cgg gtg    1344
Asp Ala Leu Glu Gln Ala Met Ser Asp Ala Leu Val Met Asp Arg Val
    435                 440                 445 gat ttt gtg aag ctc tta ata gaa tat gga gtg aac ctc cat cgc ttt    1392
Asp Phe Val Lys Leu Leu Ile Glu Tyr Gly Val Asn Leu His Arg Phe
450                 455                 460 ctt acc atc cct cga ctg gaa gag ctc tac aat aca aaa caa gga cct    1440
Leu Thr Ile Pro Arg Leu Glu Glu Leu Tyr Asn Thr Lys Gln Gly Pro
465                 470                 475                 480 act aat aca ctc ttg cat cat ctc gtc caa gat gtg aaa cag cat acc    1488
Thr Asn Thr Leu Leu His His Leu Val Gln Asp Val Lys Gln His Thr
            485                 490                 495 ctt ctt tca ggc tac cga ata acc ttg att gac att gga tta gta gta    1536
Leu Leu Ser Gly Tyr Arg Ile Thr Leu Ile Asp Ile Gly Leu Val Val
        500                 505                 510 gaa tac ctc att ggt aga gca tat cgc agc aac tac act aga aaa cat    1584
Glu Tyr Leu Ile Gly Arg Ala Tyr Arg Ser Asn Tyr Thr Arg Lys His
    515                 520                 525 ttc aga gcc ctc tac aac aac ctc tac aga aaa tac aag cac cag aga    1632
Phe Arg Ala Leu Tyr Asn Asn Leu Tyr Arg Lys Tyr Lys His Gln Arg
530                 535                 540 cac tcc tca gga aat aga aat gag tct gca gaa agt acg ctg cac tcc    1680
His Ser Ser Gly Asn Arg Asn Glu Ser Ala Glu Ser Thr Leu His Ser
545                 550                 555                 560 cag ttc att aga act gca cag cca tac aaa ttc aag gaa aag tct ata    1728
Gln Phe Ile Arg Thr Ala Gln Pro Tyr Lys Phe Lys Glu Lys Ser Ile
            565                 570                 575 gtc ctt cat aaa tca agg aag aag tca aaa gaa caa aat gta tca gat    1776
Val Leu His Lys Ser Arg Lys Lys Ser Lys Glu Gln Asn Val Ser Asp
        580                 585                 590 gac cct gag tct act ggc ttt ctt tac cct tac aat gac ctg ctg gtt    1824
Asp Pro Glu Ser Thr Gly Phe Leu Tyr Pro Tyr Asn Asp Leu Leu Val
    595                 600                 605 tgg gct gtg ctg atg aaa agg cag aag atg gct atg ttc ttc tgg cag    1872
Trp Ala Val Leu Met Lys Arg Gln Lys Met Ala Met Phe Phe Trp Gln
610                 615                 620 cat gga gag gag gcc acg gtt aaa gcc gtg att gcg tgt atc ctc tac    1920
His Gly Glu Glu Ala Thr Val Lys Ala Val Ile Ala Cys Ile Leu Tyr
625                 630                 635                 640 cgg gca atg gcc cat gaa gct aag gag agt cac atg gtg gat gat gcc    1968
Arg Ala Met Ala His Glu Ala Lys Glu Ser His Met Val Asp Asp Ala
            645                 650                 655
```

```
                                              -continued tca gaa gag ttg aag aat tac tca aaa cag ttt ggc cag ctg gct ctg    2016
Ser Glu Glu Leu Lys Asn Tyr Ser Lys Gln Phe Gly Gln Leu Ala Leu
            660                 665                 670 gac ttg ttg gag aag gca ttc aag cag aat gag cgc atg gcc atg acg    2064
Asp Leu Leu Glu Lys Ala Phe Lys Gln Asn Glu Arg Met Ala Met Thr
        675                 680                 685 ctg ttg acg tat gaa ctc agg aac tgg agc aat tcg acc tgc ctg aaa    2112
Leu Leu Thr Tyr Glu Leu Arg Asn Trp Ser Asn Ser Thr Cys Leu Lys
    690                 695                 700 ctg gcc gtg tcg gga gga tta cga ccc ttt gtt tca cat act tgt acc    2160
Leu Ala Val Ser Gly Gly Leu Arg Pro Phe Val Ser His Thr Cys Thr
705                 710                 715                 720 cag atg cta ctg aca gac atg tgg atg ggg agg ctg aaa atg agg aaa    2208
Gln Met Leu Leu Thr Asp Met Trp Met Gly Arg Leu Lys Met Arg Lys
                725                 730                 735 aac tct tgg tta aag att att ata agc att att tta cca ccc acc att    2256
Asn Ser Trp Leu Lys Ile Ile Ile Ser Ile Ile Leu Pro Pro Thr Ile
            740                 745                 750 ttg aca ctg gaa ttt aaa agc aaa gct gag atg tca cat gtt ccc cag    2304
Leu Thr Leu Glu Phe Lys Ser Lys Ala Glu Met Ser His Val Pro Gln
        755                 760                 765 tcc cag gac ttc caa ttt atg tgg tat tac agt gac cag aac gcc agc    2352
Ser Gln Asp Phe Gln Phe Met Trp Tyr Tyr Ser Asp Gln Asn Ala Ser
    770                 775                 780 agt tcc aaa gaa agt gct tct gtg aaa gag tat gat ttg gaa agg ggc    2400
Ser Ser Lys Glu Ser Ala Ser Val Lys Glu Tyr Asp Leu Glu Arg Gly
785                 790                 795                 800 cat gat gag aaa ctg gat gaa aat cag cat ttt ggt ttg gaa agt ggg    2448
His Asp Glu Lys Leu Asp Glu Asn Gln His Phe Gly Leu Glu Ser Gly
                805                 810                 815 cac caa cac ctt ccg tgg acc agg aaa gtc tat gag ttc tac agt gct    2496
His Gln His Leu Pro Trp Thr Arg Lys Val Tyr Glu Phe Tyr Ser Ala
            820                 825                 830 cca att gtc aag ttt tgg ttt tat acg atc tgt att tca gaa cct ggg    2544
Pro Ile Val Lys Phe Trp Phe Tyr Thr Ile Cys Ile Ser Glu Pro Gly
        835                 840                 845 aag ttt acc caa aag gtg aag gta tgg att agt gag tac tgg aac tta    2592
Lys Phe Thr Gln Lys Val Lys Val Trp Ile Ser Glu Tyr Trp Asn Leu
    850                 855                 860 aca gaa act gtg gcc att ggc ctg ttt tca gct ggc ttc gtc ctt cga    2640
Thr Glu Thr Val Ala Ile Gly Leu Phe Ser Ala Gly Phe Val Leu Arg
865                 870                 875                 880 tgg ggt gac cct cct ttt cac aca gcg gga aga ctg atc tac tgc ata    2688
Trp Gly Asp Pro Pro Phe His Thr Ala Gly Arg Leu Ile Tyr Cys Ile
                885                 890                 895 gac atc ata ttc tgg ttc tca cgg ctc ctg gac ttc ttt gct gtg aat    2736
Asp Ile Ile Phe Trp Phe Ser Arg Leu Leu Asp Phe Phe Ala Val Asn
            900                 905                 910 caa cat gca ggt cca tat gtg acc atg att gca aaa atg aca gca aac    2784
Gln His Ala Gly Pro Tyr Val Thr Met Ile Ala Lys Met Thr Ala Asn
        915                 920                 925 atg ttc tat att gtg atc atc atg gcc ata gtc ctg ctg agc ttt gga    2832
Met Phe Tyr Ile Val Ile Ile Met Ala Ile Val Leu Leu Ser Phe Gly
    930                 935                 940 gtg gca cgc aag gcc atc ctt tcg cca aaa gag cca cca tct tgg agt    2880
Val Ala Arg Lys Ala Ile Leu Ser Pro Lys Glu Pro Pro Ser Trp Ser
945                 950                 955                 960 cta gct cga gat att gta ttt gag cca tac tgg atg ata tac gga gaa    2928
Leu Ala Arg Asp Ile Val Phe Glu Pro Tyr Trp Met Ile Tyr Gly Glu
                965                 970                 975
```

```
gtc tat gct gga gaa ata gat gtt tgt tca agc cag cca tcc tgc cct    2976
Val Tyr Ala Gly Glu Ile Asp Val Cys Ser Ser Gln Pro Ser Cys Pro
            980                 985                 990 cct ggt tct ttt ctt act cca ttc ttg caa gct gtc tac ctc ttc gtg    3024
Pro Gly Ser Phe Leu Thr Pro Phe Leu Gln Ala Val Tyr Leu Phe Val
            995                 1000                1005 caa tat atc atc atg gtg aac ctg ttg att gct ttc ttc aac aac        3069
Gln Tyr Ile Ile Met Val Asn Leu Leu Ile Ala Phe Phe Asn Asn
        1010                1015                1020 gtt tac tta gat atg gaa tcc att tca aat aac ctg tgg aaa tac        3114
Val Tyr Leu Asp Met Glu Ser Ile Ser Asn Asn Leu Trp Lys Tyr
        1025                1030                1035 aac cgc tat cgc tac atc atg acc tac cac gag aag ccc tgg ctg        3159
Asn Arg Tyr Arg Tyr Ile Met Thr Tyr His Glu Lys Pro Trp Leu
        1040                1045                1050 ccc cca cct ctc atc ctg ctg agc cac gtg ggc ctt ctc ctc cgc        3204
Pro Pro Pro Leu Ile Leu Leu Ser His Val Gly Leu Leu Leu Arg
        1055                1060                1065 cgc ctg tgc tgt cat cga gct cct cac gac caa gaa gag ggt gac        3249
Arg Leu Cys Cys His Arg Ala Pro His Asp Gln Glu Glu Gly Asp
        1070                1075                1080 gtt gga tta aaa ctc tac ctc agt aag gag gat ctg aaa aaa ctt        3294
Val Gly Leu Lys Leu Tyr Leu Ser Lys Glu Asp Leu Lys Lys Leu
        1085                1090                1095 cat gat ttt gag gag cag tgc gtg gaa aaa tac ttc cat gag aag        3339
His Asp Phe Glu Glu Gln Cys Val Glu Lys Tyr Phe His Glu Lys
        1100                1105                1110 atg gaa gat gtg aat tgt agt tgt gag gaa cga atc cga gtg aca        3384
Met Glu Asp Val Asn Cys Ser Cys Glu Glu Arg Ile Arg Val Thr
        1115                1120                1125 tca gaa agg gtt aca gag atg tac ttc cag ctg aaa gaa atg aat        3429
Ser Glu Arg Val Thr Glu Met Tyr Phe Gln Leu Lys Glu Met Asn
        1130                1135                1140 gaa aag gtg tct ttt ata aag gac tcc tta ctg tct ttg gac agc        3474
Glu Lys Val Ser Phe Ile Lys Asp Ser Leu Leu Ser Leu Asp Ser
        1145                1150                1155 cag gtg gga cac ctg cag gat ctc tct gcc ctg act gtg gat acc        3519
Gln Val Gly His Leu Gln Asp Leu Ser Ala Leu Thr Val Asp Thr
        1160                1165                1170 ctg aaa gtc ctt tct gct gtt gac act ttg caa gag gat gag gct        3564
Leu Lys Val Leu Ser Ala Val Asp Thr Leu Gln Glu Asp Glu Ala
        1175                1180                1185 ctc ctg gcc aag aga aag cat tct act tgc aaa aaa ctt ccc cac        3609
Leu Leu Ala Lys Arg Lys His Ser Thr Cys Lys Lys Leu Pro His
        1190                1195                1200 agc tgg agc aat gtc atc tgt gca gag gtt cta ggc agc atg gag        3654
Ser Trp Ser Asn Val Ile Cys Ala Glu Val Leu Gly Ser Met Glu
        1205                1210                1215 atc gct gga gag aag aaa tac cag tat tat agc atg ccc tct tct        3699
Ile Ala Gly Glu Lys Lys Tyr Gln Tyr Tyr Ser Met Pro Ser Ser
        1220                1225                1230 ttg ctg agg agc ctg gct gga ggc cgg cat ccc cca aga gtg cag        3744
Leu Leu Arg Ser Leu Ala Gly Gly Arg His Pro Pro Arg Val Gln
        1235                1240                1245 agg ggg gca ctt ctt gag att aca aac agt aaa aga gag gct aca        3789
Arg Gly Ala Leu Leu Glu Ile Thr Asn Ser Lys Arg Glu Ala Thr
        1250                1255                1260 aat gta aga aat gac cag gaa agg caa gaa aca caa agt agt ata        3834
Asn Val Arg Asn Asp Gln Glu Arg Gln Glu Thr Gln Ser Ser Ile
        1265                1270                1275
```

```
gtg gtt tct ggg gtg tct cct aac agg caa gca cac tca aag tat       3879
Val Val Ser Gly Val Ser Pro Asn Arg Gln Ala His Ser Lys Tyr
    1280             1285             1290 ggc cag ttt ctt ctg gtc ccc tct aat cta aag cga gtt cct ttt       3924
Gly Gln Phe Leu Leu Val Pro Ser Asn Leu Lys Arg Val Pro Phe
1295             1300             1305 tca gca gaa act gtc ttg cct ctg tcc aga ccc tct gtg cca gat       3969
Ser Ala Glu Thr Val Leu Pro Leu Ser Arg Pro Ser Val Pro Asp
    1310             1315             1320 gtg ctg gca act gaa cag gac atc cag act gag gtt ctt gtt cat       4014
Val Leu Ala Thr Glu Gln Asp Ile Gln Thr Glu Val Leu Val His
1325             1330             1335 ctg act ggg cag acc cca gtt gtc tct gac tgg gca tca gtg gat       4059
Leu Thr Gly Gln Thr Pro Val Val Ser Asp Trp Ala Ser Val Asp
    1340             1345             1350 gaa ccc aag gaa aag cac gag cct att gct cac tta ctg gat gga       4104
Glu Pro Lys Glu Lys His Glu Pro Ile Ala His Leu Leu Asp Gly
1355             1360             1365 caa gac aag gca gag caa gtg cta ccc act ttg agt tgc aca cct       4149
Gln Asp Lys Ala Glu Gln Val Leu Pro Thr Leu Ser Cys Thr Pro
    1370             1375             1380 gaa ccc atg aca atg agc tcc cct ctt tcc caa gcc aag atc atg       4194
Glu Pro Met Thr Met Ser Ser Pro Leu Ser Gln Ala Lys Ile Met
1385             1390             1395 caa act gga ggt gga tat gta aac tgg gca ttt tca gaa ggt gat       4239
Gln Thr Gly Gly Gly Tyr Val Asn Trp Ala Phe Ser Glu Gly Asp
    1400             1405             1410 gaa act ggt gtg ttt agc atc aag aaa aag tgg caa acc tgc ttg       4284
Glu Thr Gly Val Phe Ser Ile Lys Lys Lys Trp Gln Thr Cys Leu
1415             1420             1425 ccc tcc act tgt gac agt gat tcc tct cgg agt gaa cag cac cag       4329
Pro Ser Thr Cys Asp Ser Asp Ser Ser Arg Ser Glu Gln His Gln
    1430             1435             1440 aag cag gcc cag gac agc tcc cta tct gat aac tca aca aga tcg       4374
Lys Gln Ala Gln Asp Ser Ser Leu Ser Asp Asn Ser Thr Arg Ser
1445             1450             1455 gcc cag agt agt gaa tgc tca gag gtg gga cca tgg ctt cag cca       4419
Ala Gln Ser Ser Glu Cys Ser Glu Val Gly Pro Trp Leu Gln Pro
    1460             1465             1470 aac aca tcc ttt tgg atc aat cct ctc cgc aga tac agg ccc ttc       4464
Asn Thr Ser Phe Trp Ile Asn Pro Leu Arg Arg Tyr Arg Pro Phe
1475             1480             1485 gct agg agt cat agt ttt aga ttc cat aag gag gag aaa ttg atg       4509
Ala Arg Ser His Ser Phe Arg Phe His Lys Glu Glu Lys Leu Met
    1490             1495             1500 aag atc tgt aag att aaa aat ctt tca ggc tct tca gaa ata ggg       4554
Lys Ile Cys Lys Ile Lys Asn Leu Ser Gly Ser Ser Glu Ile Gly
1505             1510             1515 cag gga gca tgg gtc aaa gcg aaa atg cta acc aaa gac agg aga       4599
Gln Gly Ala Trp Val Lys Ala Lys Met Leu Thr Lys Asp Arg Arg
    1520             1525             1530 ctg tca aag aaa aag aag aat act caa gga ctc cag gtg cca atc       4644
Leu Ser Lys Lys Lys Lys Asn Thr Gln Gly Leu Gln Val Pro Ile
1535             1540             1545 ata aca gtc aat gcc tgc tct cag agt gac cag ttg aat cca gag       4689
Ile Thr Val Asn Ala Cys Ser Gln Ser Asp Gln Leu Asn Pro Glu
    1550             1555             1560 cca gga gaa aac agc atc tct gaa gag gag tac agc aag aac tgg       4734
Pro Gly Glu Asn Ser Ile Ser Glu Glu Glu Tyr Ser Lys Asn Trp
1565             1570             1575
```

| | | |
|---|---|---|
| ttc aca gtg tcc aaa ttt agt cac aca ggt gta gaa cct tac ata<br>Phe Thr Val Ser Lys Phe Ser His Thr Gly Val Glu Pro Tyr Ile<br>1580                     1585                     1590 | 4779 |
| cat cag aaa atg aaa act aaa gaa att gga caa tgt gct ata caa<br>His Gln Lys Met Lys Thr Lys Glu Ile Gly Gln Cys Ala Ile Gln<br>1595                     1600                     1605 | 4824 |
| atc agt gat tac cta aag cag tct caa gag gat ctc agc aaa aac<br>Ile Ser Asp Tyr Leu Lys Gln Ser Gln Glu Asp Leu Ser Lys Asn<br>1610                     1615                     1620 | 4869 |
| tct ttg tgg aat tcc agg agc acc aac ctc aat agg aac tcc ctg<br>Ser Leu Trp Asn Ser Arg Ser Thr Asn Leu Asn Arg Asn Ser Leu<br>1625                     1630                     1635 | 4914 |
| ctg aaa agt tca att gga gtt gac aag atc tca gcc tcc tta aaa<br>Leu Lys Ser Ser Ile Gly Val Asp Lys Ile Ser Ala Ser Leu Lys<br>1640                     1645                     1650 | 4959 |
| agc cct caa gag cct cac cat cat tat tca gcc att gaa agg aat<br>Ser Pro Gln Glu Pro His His His Tyr Ser Ala Ile Glu Arg Asn<br>1655                     1660                     1665 | 5004 |
| aat tta atg agg ctt tct cag acc ata cca ttt aca cca gtc caa<br>Asn Leu Met Arg Leu Ser Gln Thr Ile Pro Phe Thr Pro Val Gln<br>1670                     1675                     1680 | 5049 |
| ctg ttt gca gga gaa gaa ata act gtc tac agg ttg gag gag agt<br>Leu Phe Ala Gly Glu Glu Ile Thr Val Tyr Arg Leu Glu Glu Ser<br>1685                     1690                     1695 | 5094 |
| tcc cct tta aac ctt gat aaa agc atg tcc tct tgg tct cag cgt<br>Ser Pro Leu Asn Leu Asp Lys Ser Met Ser Ser Trp Ser Gln Arg<br>1700                     1705                     1710 | 5139 |
| ggg aga gcg gca atg atc cag gta ttg tcc cga gag gag atg gat<br>Gly Arg Ala Ala Met Ile Gln Val Leu Ser Arg Glu Glu Met Asp<br>1715                     1720                     1725 | 5184 |
| ggg ggc ctc cgt aaa gct atg aga gtc gtc agc act tgg tct gag<br>Gly Gly Leu Arg Lys Ala Met Arg Val Val Ser Thr Trp Ser Glu<br>1730                     1735                     1740 | 5229 |
| gat gac att ctc aag ccg gga caa gtt ttc att gtc aag tcc ttt<br>Asp Asp Ile Leu Lys Pro Gly Gln Val Phe Ile Val Lys Ser Phe<br>1745                     1750                     1755 | 5274 |
| ctt cct gag gtt gtg cgg aca tgg cat aaa atc ttc cag gag agc<br>Leu Pro Glu Val Val Arg Thr Trp His Lys Ile Phe Gln Glu Ser<br>1760                     1765                     1770 | 5319 |
| act gtg ctt cat ctt tgc ctc agg gaa att caa caa caa aga gct<br>Thr Val Leu His Leu Cys Leu Arg Glu Ile Gln Gln Gln Arg Ala<br>1775                     1780                     1785 | 5364 |
| gct caa aaa ttg atc tat acc ttc aac caa gtg aaa cca caa acc<br>Ala Gln Lys Leu Ile Tyr Thr Phe Asn Gln Val Lys Pro Gln Thr<br>1790                     1795                     1800 | 5409 |
| ata ccc tac aca cca agg ttc ctg gaa gtt ttc tta atc tac tgc<br>Ile Pro Tyr Thr Pro Arg Phe Leu Glu Val Phe Leu Ile Tyr Cys<br>1805                     1810                     1815 | 5454 |
| cat tca gcc aac cag tgg ttg acc att gag aag tat atg aca ggg<br>His Ser Ala Asn Gln Trp Leu Thr Ile Glu Lys Tyr Met Thr Gly<br>1820                     1825                     1830 | 5499 |
| gag ttc cgg aag tat aac aac aac aat ggt gat gaa atc acc ccc<br>Glu Phe Arg Lys Tyr Asn Asn Asn Asn Gly Asp Glu Ile Thr Pro<br>1835                     1840                     1845 | 5544 |
| acc aac acc ctg gag gag ctg atg ttg gct ttc tct cac tgg acc<br>Thr Asn Thr Leu Glu Glu Leu Met Leu Ala Phe Ser His Trp Thr<br>1850                     1855                     1860 | 5589 |
| tat gag tac act cgg gga gag ctg ctg gtt tta gat ttg caa ggt<br>Tyr Glu Tyr Thr Arg Gly Glu Leu Leu Val Leu Asp Leu Gln Gly<br>1865                     1870                     1875 | 5634 |

```
gtt gga gaa aat ttg aca gat cca tct gtt ata aaa cct gaa gtc      5679
Val Gly Glu Asn Leu Thr Asp Pro Ser Val Ile Lys Pro Glu Val
    1880                1885                1890 aaa caa tca aga gga atg gtg ttt gga ccg gcc aat ttg ggg gaa      5724
Lys Gln Ser Arg Gly Met Val Phe Gly Pro Ala Asn Leu Gly Glu
1895                1900                1905 gat gca att aga aac ttc att gca aaa cat cat tgt aac tcc tgc      5769
Asp Ala Ile Arg Asn Phe Ile Ala Lys His His Cys Asn Ser Cys
    1910                1915                1920 tgc cgg aag ctc aaa ctc ccg gat tta aaa aga aat gac tat tcc      5814
Cys Arg Lys Leu Lys Leu Pro Asp Leu Lys Arg Asn Asp Tyr Ser
1925                1930                1935 cct gaa agg ata aat tcc acc ttt gga ctt gag ata aaa ata gaa      5859
Pro Glu Arg Ile Asn Ser Thr Phe Gly Leu Glu Ile Lys Ile Glu
    1940                1945                1950 tca gct gag gag cct cca gca agg gag acg ggt aga aat tcc cca      5904
Ser Ala Glu Glu Pro Pro Ala Arg Glu Thr Gly Arg Asn Ser Pro
1955                1960                1965 gaa gat gat atg caa cta taa                                      5925
Glu Asp Asp Met Gln Leu
    1970

<210> SEQ ID NO 8
<211> LENGTH: 1974
<212> TYPE: PRT
<213> ORGANISM: Homo sapiens

<400> SEQUENCE: 8

Met Ile Ile Leu Ser Lys Ser Gln Lys Ser Trp Ile Lys Gly Val Phe
1               5                   10                  15

Asp Lys Arg Glu Cys Ser Thr Ile Ile Pro Ser Ser Lys Asn Pro His
            20                  25                  30

Arg Cys Thr Pro Val Cys Gln Val Cys Gln Asn Leu Ile Arg Cys Tyr
        35                  40                  45

Cys Gly Arg Leu Ile Gly Asp His Ala Gly Ile Asp Tyr Ser Trp Thr
    50                  55                  60

Ile Ser Ala Ala Lys Gly Lys Glu Ser Glu Gln Trp Ser Val Glu Lys
65                  70                  75                  80

His Thr Thr Lys Ser Pro Thr Asp Thr Phe Gly Thr Ile Asn Phe Gln
                85                  90                  95

Asp Gly Glu His Thr His Ala Lys Tyr Ile Arg Thr Ser Tyr Asp
            100                 105                 110

Thr Lys Leu Asp His Leu Leu His Leu Met Leu Lys Glu Trp Lys Met
        115                 120                 125

Glu Leu Pro Lys Leu Val Ile Ser Val His Gly Gly Ile Gln Asn Phe
    130                 135                 140

Thr Met Pro Ser Lys Phe Lys Glu Ile Phe Ser Gln Gly Leu Val Lys
145                 150                 155                 160

Ala Ala Glu Thr Thr Gly Ala Trp Ile Ile Thr Glu Gly Ile Asn Thr
                165                 170                 175

Gly Val Ser Lys His Val Gly Asp Ala Leu Lys Ser Ser Ser His
            180                 185                 190

Ser Leu Arg Lys Ile Trp Thr Val Gly Ile Pro Pro Trp Gly Val Ile
        195                 200                 205

Glu Asn Gln Arg Asp Leu Ile Gly Lys Asp Val Val Cys Leu Tyr Gln
    210                 215                 220
```

-continued

```
Thr Leu Asp Asn Pro Leu Ser Lys Leu Thr Thr Leu Asn Ser Met His
225                 230                 235                 240

Ser His Phe Ile Leu Ser Asp Asp Gly Thr Val Gly Lys Tyr Gly Asn
            245                 250                 255

Glu Met Lys Leu Arg Arg Asn Leu Glu Lys Tyr Leu Ser Leu Gln Lys
        260                 265                 270

Ile His Cys Arg Ser Arg Gln Gly Val Pro Val Val Gly Leu Val Val
    275                 280                 285

Glu Gly Gly Pro Asn Val Ile Leu Ser Val Trp Glu Thr Val Lys Asp
    290                 295                 300

Lys Asp Pro Val Val Val Cys Glu Gly Thr Gly Arg Ala Ala Asp Leu
305                 310                 315                 320

Leu Ala Phe Thr His Lys His Leu Ala Asp Glu Gly Met Leu Arg Pro
            325                 330                 335

Gln Val Lys Glu Glu Ile Ile Cys Met Ile Gln Asn Thr Phe Asn Phe
        340                 345                 350

Ser Leu Lys Gln Ser Lys His Leu Phe Gln Ile Leu Met Glu Cys Met
    355                 360                 365

Val His Arg Asp Cys Ile Thr Ile Phe Asp Ala Asp Ser Glu Glu Gln
    370                 375                 380

Gln Asp Leu Asp Leu Ala Ile Leu Thr Ala Leu Leu Lys Gly Thr Asn
385                 390                 395                 400

Leu Ser Ala Ser Glu Gln Leu Asn Leu Ala Met Ala Trp Asp Arg Val
            405                 410                 415

Asp Ile Ala Lys Lys His Ile Leu Ile Tyr Glu Gln His Trp Lys Pro
        420                 425                 430

Asp Ala Leu Glu Gln Ala Met Ser Asp Ala Leu Val Met Asp Arg Val
    435                 440                 445

Asp Phe Val Lys Leu Leu Ile Glu Tyr Gly Val Asn Leu His Arg Phe
    450                 455                 460

Leu Thr Ile Pro Arg Leu Glu Glu Leu Tyr Asn Thr Lys Gln Gly Pro
465                 470                 475                 480

Thr Asn Thr Leu Leu His His Leu Val Gln Asp Val Lys Gln His Thr
            485                 490                 495

Leu Leu Ser Gly Tyr Arg Ile Thr Leu Ile Asp Ile Gly Leu Val Val
        500                 505                 510

Glu Tyr Leu Ile Gly Arg Ala Tyr Arg Ser Asn Tyr Thr Arg Lys His
    515                 520                 525

Phe Arg Ala Leu Tyr Asn Asn Leu Tyr Arg Lys Tyr Lys His Gln Arg
    530                 535                 540

His Ser Ser Gly Asn Arg Asn Glu Ser Ala Glu Ser Thr Leu His Ser
545                 550                 555                 560

Gln Phe Ile Arg Thr Ala Gln Pro Tyr Lys Phe Lys Glu Lys Ser Ile
            565                 570                 575

Val Leu His Lys Ser Arg Lys Lys Ser Lys Glu Gln Asn Val Ser Asp
        580                 585                 590

Asp Pro Glu Ser Thr Gly Phe Leu Tyr Pro Tyr Asn Asp Leu Leu Val
    595                 600                 605

Trp Ala Val Leu Met Lys Arg Gln Lys Met Ala Met Phe Phe Trp Gln
    610                 615                 620

His Gly Glu Glu Ala Thr Val Lys Ala Val Ile Ala Cys Ile Leu Tyr
625                 630                 635                 640
```

```
Arg Ala Met Ala His Glu Ala Lys Glu Ser His Met Val Asp Asp Ala
            645                 650                 655

Ser Glu Glu Leu Lys Asn Tyr Ser Lys Gln Phe Gly Gln Leu Ala Leu
            660                 665                 670

Asp Leu Leu Glu Lys Ala Phe Lys Gln Asn Glu Arg Met Ala Met Thr
            675                 680                 685

Leu Leu Thr Tyr Glu Leu Arg Asn Trp Ser Asn Ser Thr Cys Leu Lys
            690                 695                 700

Leu Ala Val Ser Gly Gly Leu Arg Pro Phe Val Ser His Thr Cys Thr
705                 710                 715                 720

Gln Met Leu Leu Thr Asp Met Trp Met Gly Arg Leu Lys Met Arg Lys
                725                 730                 735

Asn Ser Trp Leu Lys Ile Ile Ile Ser Ile Ile Leu Pro Pro Thr Ile
                740                 745                 750

Leu Thr Leu Glu Phe Lys Ser Lys Ala Glu Met Ser His Val Pro Gln
            755                 760                 765

Ser Gln Asp Phe Gln Phe Met Trp Tyr Tyr Ser Asp Gln Asn Ala Ser
770                 775                 780

Ser Ser Lys Glu Ser Ala Ser Val Lys Glu Tyr Asp Leu Glu Arg Gly
785                 790                 795                 800

His Asp Glu Lys Leu Asp Glu Asn Gln His Phe Gly Leu Glu Ser Gly
                805                 810                 815

His Gln His Leu Pro Trp Thr Arg Lys Val Tyr Glu Phe Tyr Ser Ala
                820                 825                 830

Pro Ile Val Lys Phe Trp Phe Tyr Thr Ile Cys Ile Ser Glu Pro Gly
            835                 840                 845

Lys Phe Thr Gln Lys Val Lys Val Trp Ile Ser Glu Tyr Trp Asn Leu
            850                 855                 860

Thr Glu Thr Val Ala Ile Gly Leu Phe Ser Ala Gly Phe Val Leu Arg
865                 870                 875                 880

Trp Gly Asp Pro Pro Phe His Thr Ala Gly Arg Leu Ile Tyr Cys Ile
                885                 890                 895

Asp Ile Ile Phe Trp Phe Ser Arg Leu Leu Asp Phe Phe Ala Val Asn
                900                 905                 910

Gln His Ala Gly Pro Tyr Val Thr Met Ile Ala Lys Met Thr Ala Asn
            915                 920                 925

Met Phe Tyr Ile Val Ile Met Ala Ile Val Leu Leu Ser Phe Gly
            930                 935                 940

Val Ala Arg Lys Ala Ile Leu Ser Pro Lys Glu Pro Pro Ser Trp Ser
945                 950                 955                 960

Leu Ala Arg Asp Ile Val Phe Glu Pro Tyr Trp Met Ile Tyr Gly Glu
                965                 970                 975

Val Tyr Ala Gly Glu Ile Asp Val Cys Ser Ser Gln Pro Ser Cys Pro
            980                 985                 990

Pro Gly Ser Phe Leu Thr Pro Phe Leu Gln Ala Val Tyr Leu Phe Val
            995                 1000                1005

Gln Tyr Ile Ile Met Val Asn Leu Leu Ile Ala Phe Phe Asn Asn
            1010                1015                1020

Val Tyr Leu Asp Met Glu Ser Ile Ser Asn Asn Leu Trp Lys Tyr
            1025                1030                1035

Asn Arg Tyr Arg Tyr Ile Met Thr Tyr His Glu Lys Pro Trp Leu
            1040                1045                1050
```

-continued

```
Pro Pro Pro Leu Ile Leu Leu Ser His Val Gly Leu Leu Leu Arg
    1055                1060                1065

Arg Leu Cys Cys His Arg Ala Pro His Asp Gln Glu Glu Gly Asp
    1070                1075                1080

Val Gly Leu Lys Leu Tyr Leu Ser Lys Glu Asp Leu Lys Lys Leu
    1085                1090                1095

His Asp Phe Glu Glu Gln Cys Val Glu Lys Tyr Phe His Glu Lys
    1100                1105                1110

Met Glu Asp Val Asn Cys Ser Cys Glu Glu Arg Ile Arg Val Thr
    1115                1120                1125

Ser Glu Arg Val Thr Glu Met Tyr Phe Gln Leu Lys Glu Met Asn
    1130                1135                1140

Glu Lys Val Ser Phe Ile Lys Asp Ser Leu Leu Ser Leu Asp Ser
    1145                1150                1155

Gln Val Gly His Leu Gln Asp Leu Ser Ala Leu Thr Val Asp Thr
    1160                1165                1170

Leu Lys Val Leu Ser Ala Val Asp Thr Leu Gln Glu Asp Glu Ala
    1175                1180                1185

Leu Leu Ala Lys Arg Lys His Ser Thr Cys Lys Lys Leu Pro His
    1190                1195                1200

Ser Trp Ser Asn Val Ile Cys Ala Glu Val Leu Gly Ser Met Glu
    1205                1210                1215

Ile Ala Gly Glu Lys Lys Tyr Gln Tyr Tyr Ser Met Pro Ser Ser
    1220                1225                1230

Leu Leu Arg Ser Leu Ala Gly Gly Arg His Pro Pro Arg Val Gln
    1235                1240                1245

Arg Gly Ala Leu Leu Glu Ile Thr Asn Ser Lys Arg Glu Ala Thr
    1250                1255                1260

Asn Val Arg Asn Asp Gln Glu Arg Gln Glu Thr Gln Ser Ser Ile
    1265                1270                1275

Val Val Ser Gly Val Ser Pro Asn Arg Gln Ala His Ser Lys Tyr
    1280                1285                1290

Gly Gln Phe Leu Leu Val Pro Ser Asn Leu Lys Arg Val Pro Phe
    1295                1300                1305

Ser Ala Glu Thr Val Leu Pro Leu Ser Arg Pro Ser Val Pro Asp
    1310                1315                1320

Val Leu Ala Thr Glu Gln Asp Ile Gln Thr Glu Val Leu Val His
    1325                1330                1335

Leu Thr Gly Gln Thr Pro Val Val Ser Asp Trp Ala Ser Val Asp
    1340                1345                1350

Glu Pro Lys Glu Lys His Glu Pro Ile Ala His Leu Leu Asp Gly
    1355                1360                1365

Gln Asp Lys Ala Glu Gln Val Leu Pro Thr Leu Ser Cys Thr Pro
    1370                1375                1380

Glu Pro Met Thr Met Ser Ser Pro Leu Ser Gln Ala Lys Ile Met
    1385                1390                1395

Gln Thr Gly Gly Gly Tyr Val Asn Trp Ala Phe Ser Glu Gly Asp
    1400                1405                1410

Glu Thr Gly Val Phe Ser Ile Lys Lys Lys Trp Gln Thr Cys Leu
    1415                1420                1425

Pro Ser Thr Cys Asp Ser Asp Ser Ser Arg Ser Glu Gln His Gln
    1430                1435                1440
```

-continued

| | | | | | | | | | | | |
|---|---|---|---|---|---|---|---|---|---|---|---|
|Lys|Gln|Ala|Gln|Asp|Ser|Ser|Leu|Ser|Asp|Asn|Ser|Thr|Arg|Ser|
| |1445| | | |1450| | | |1455| | | | | |
|Ala|Gln|Ser|Ser|Glu|Cys|Ser|Glu|Val|Gly|Pro|Trp|Leu|Gln|Pro|
| |1460| | | |1465| | | |1470| | | | | |
|Asn|Thr|Ser|Phe|Trp|Ile|Asn|Pro|Leu|Arg|Arg|Tyr|Arg|Pro|Phe|
| |1475| | | |1480| | | |1485| | | | | |
|Ala|Arg|Ser|His|Ser|Phe|Arg|Phe|His|Lys|Glu|Glu|Lys|Leu|Met|
| |1490| | | |1495| | | |1500| | | | | |
|Lys|Ile|Cys|Lys|Ile|Lys|Asn|Leu|Ser|Gly|Ser|Ser|Glu|Ile|Gly|
| |1505| | | |1510| | | |1515| | | | | |
|Gln|Gly|Ala|Trp|Val|Lys|Ala|Lys|Met|Leu|Thr|Lys|Asp|Arg|Arg|
| |1520| | | |1525| | | |1530| | | | | |
|Leu|Ser|Lys|Lys|Lys|Lys|Asn|Thr|Gln|Gly|Leu|Gln|Val|Pro|Ile|
| |1535| | | |1540| | | |1545| | | | | |
|Ile|Thr|Val|Asn|Ala|Cys|Ser|Gln|Ser|Asp|Gln|Leu|Asn|Pro|Glu|
| |1550| | | |1555| | | |1560| | | | | |
|Pro|Gly|Glu|Asn|Ser|Ile|Ser|Glu|Glu|Tyr|Ser|Lys|Asn|Trp|
| |1565| | | |1570| | | |1575| | | | |
|Phe|Thr|Val|Ser|Lys|Phe|Ser|His|Thr|Gly|Val|Glu|Pro|Tyr|Ile|
| |1580| | | |1585| | | |1590| | | | | |
|His|Gln|Lys|Met|Lys|Thr|Lys|Glu|Ile|Gly|Gln|Cys|Ala|Ile|Gln|
| |1595| | | |1600| | | |1605| | | | | |
|Ile|Ser|Asp|Tyr|Leu|Lys|Gln|Ser|Gln|Glu|Asp|Leu|Ser|Lys|Asn|
| |1610| | | |1615| | | |1620| | | | | |
|Ser|Leu|Trp|Asn|Ser|Arg|Ser|Thr|Asn|Leu|Asn|Arg|Asn|Ser|Leu|
| |1625| | | |1630| | | |1635| | | | | |
|Leu|Lys|Ser|Ser|Ile|Gly|Val|Asp|Lys|Ile|Ser|Ala|Ser|Leu|Lys|
| |1640| | | |1645| | | |1650| | | | | |
|Ser|Pro|Gln|Glu|Pro|His|His|His|Tyr|Ser|Ala|Ile|Glu|Arg|Asn|
| |1655| | | |1660| | | |1665| | | | | |
|Asn|Leu|Met|Arg|Leu|Ser|Gln|Thr|Ile|Pro|Phe|Thr|Pro|Val|Gln|
| |1670| | | |1675| | | |1680| | | | | |
|Leu|Phe|Ala|Gly|Glu|Glu|Ile|Thr|Val|Tyr|Arg|Leu|Glu|Glu|Ser|
| |1685| | | |1690| | | |1695| | | | | |
|Ser|Pro|Leu|Asn|Leu|Asp|Lys|Ser|Met|Ser|Ser|Trp|Ser|Gln|Arg|
| |1700| | | |1705| | | |1710| | | | | |
|Gly|Arg|Ala|Ala|Met|Ile|Gln|Val|Leu|Ser|Arg|Glu|Glu|Met|Asp|
| |1715| | | |1720| | | |1725| | | | | |
|Gly|Gly|Leu|Arg|Lys|Ala|Met|Arg|Val|Val|Ser|Thr|Trp|Ser|Glu|
| |1730| | | |1735| | | |1740| | | | | |
|Asp|Asp|Ile|Leu|Lys|Pro|Gly|Gln|Val|Phe|Ile|Val|Lys|Ser|Phe|
| |1745| | | |1750| | | |1755| | | | | |
|Leu|Pro|Glu|Val|Val|Arg|Thr|Trp|His|Lys|Ile|Phe|Gln|Glu|Ser|
| |1760| | | |1765| | | |1770| | | | | |
|Thr|Val|Leu|His|Leu|Cys|Leu|Arg|Glu|Ile|Gln|Gln|Gln|Arg|Ala|
| |1775| | | |1780| | | |1785| | | | | |
|Ala|Gln|Lys|Leu|Ile|Tyr|Thr|Phe|Asn|Gln|Val|Lys|Pro|Gln|Thr|
| |1790| | | |1795| | | |1800| | | | | |
|Ile|Pro|Tyr|Thr|Pro|Arg|Phe|Leu|Glu|Val|Phe|Leu|Ile|Tyr|Cys|
| |1805| | | |1810| | | |1815| | | | | |
|His|Ser|Ala|Asn|Gln|Trp|Leu|Thr|Ile|Glu|Lys|Tyr|Met|Thr|Gly|
| |1820| | | |1825| | | |1830| | | | | |

-continued

```
Glu Phe Arg Lys Tyr Asn Asn Asn Gly Asp Glu Ile Thr Pro
    1835                1840                1845

Thr Asn Thr Leu Glu Glu Leu Met Leu Ala Phe Ser His Trp Thr
    1850                1855                1860

Tyr Glu Tyr Thr Arg Gly Leu Leu Val Leu Asp Leu Gln Gly
    1865                1870                1875

Val Gly Glu Asn Leu Thr Asp Pro Ser Val Ile Lys Pro Glu Val
    1880                1885                1890

Lys Gln Ser Arg Gly Met Val Phe Gly Pro Ala Asn Leu Gly Glu
    1895                1900                1905

Asp Ala Ile Arg Asn Phe Ile Ala Lys His His Cys Asn Ser Cys
    1910                1915                1920

Cys Arg Lys Leu Lys Leu Pro Asp Leu Lys Arg Asn Asp Tyr Ser
    1925                1930                1935

Pro Glu Arg Ile Asn Ser Thr Phe Gly Leu Glu Ile Lys Ile Glu
    1940                1945                1950

Ser Ala Glu Glu Pro Pro Ala Arg Glu Thr Gly Arg Asn Ser Pro
    1955                1960                1965

Glu Asp Asp Met Gln Leu
    1970

<210> SEQ ID NO 9
<211> LENGTH: 1864
<212> TYPE: PRT
<213> ORGANISM: Homo sapiens

<400> SEQUENCE: 9

Met Ser Gln Lys Ser Trp Ile Glu Ser Thr Leu Thr Lys Arg Glu Cys
1               5                   10                  15

Val Tyr Ile Ile Pro Ser Ser Lys Asp Pro His Arg Cys Leu Pro Gly
                20                  25                  30

Cys Gln Ile Cys Gln Gln Leu Val Arg Cys Phe Cys Gly Arg Leu Val
            35                  40                  45

Lys Gln His Ala Cys Phe Thr Ala Ser Leu Ala Met Lys Tyr Ser Asp
        50                  55                  60

Val Lys Leu Gly Asp His Phe Asn Gln Ala Ile Glu Glu Trp Ser Val
65                  70                  75                  80

Glu Lys His Thr Glu Gln Ser Pro Thr Asp Ala Tyr Gly Val Ile Asn
                85                  90                  95

Phe Gln Gly Gly Ser His Ser Tyr Arg Ala Lys Tyr Val Arg Leu Ser
            100                 105                 110

Tyr Asp Thr Lys Pro Glu Val Ile Leu Gln Leu Leu Leu Lys Glu Trp
        115                 120                 125

Gln Met Glu Leu Pro Lys Leu Val Ile Ser Val His Gly Gly Met Gln
    130                 135                 140

Lys Phe Glu Leu His Pro Arg Ile Lys Gln Leu Leu Gly Lys Gly Leu
145                 150                 155                 160

Ile Lys Ala Ala Val Thr Thr Gly Ala Trp Ile Leu Thr Gly Gly Val
                165                 170                 175

Asn Thr Gly Val Ala Lys His Val Gly Asp Ala Leu Lys Glu His Ala
            180                 185                 190

Ser Arg Ser Ser Arg Lys Ile Cys Thr Ile Gly Ile Ala Pro Trp Gly
        195                 200                 205

Val Ile Glu Asn Arg Asn Asp Leu Val Gly Arg Asp Val Val Ala Pro
    210                 215                 220
```

```
Tyr Gln Thr Leu Leu Asn Pro Leu Ser Lys Leu Asn Val Leu Asn Asn
225                 230                 235                 240

Leu His Ser His Phe Ile Leu Val Asp Asp Gly Thr Val Gly Lys Tyr
                245                 250                 255

Gly Ala Glu Val Arg Leu Arg Arg Glu Leu Glu Lys Thr Ile Asn Gln
            260                 265                 270

Gln Arg Ile His Ala Arg Ile Gly Gln Gly Val Pro Val Ala Leu
        275                 280                 285

Ile Phe Glu Gly Gly Pro Asn Val Ile Leu Thr Val Leu Glu Tyr Leu
    290                 295                 300

Gln Glu Ser Pro Pro Val Pro Val Val Cys Glu Gly Thr Gly Arg
305                 310                 315                 320

Ala Ala Asp Leu Leu Ala Tyr Ile His Lys Gln Thr Glu Glu Gly Gly
                325                 330                 335

Asn Leu Pro Asp Ala Ala Glu Pro Asp Ile Ile Ser Thr Ile Lys Lys
            340                 345                 350

Thr Phe Asn Phe Gly Gln Asn Glu Ala Leu His Leu Phe Gln Thr Leu
        355                 360                 365

Met Glu Cys Met Lys Arg Lys Glu Leu Ile Thr Val Phe His Ile Gly
370                 375                 380

Ser Asp Glu His Gln Asp Ile Asp Val Ala Ile Leu Thr Ala Leu Leu
385                 390                 395                 400

Lys Gly Thr Asn Ala Ser Ala Phe Asp Gln Leu Ile Leu Thr Leu Ala
            405                 410                 415

Trp Asp Arg Val Asp Ile Ala Lys Asn His Val Phe Val Tyr Gly Gln
        420                 425                 430

Gln Trp Leu Val Gly Ser Leu Glu Gln Ala Met Leu Asp Ala Leu Val
    435                 440                 445

Met Asp Arg Val Ala Phe Val Lys Leu Leu Ile Glu Asn Gly Val Ser
450                 455                 460

Met His Lys Phe Leu Thr Ile Pro Arg Leu Glu Glu Leu Tyr Asn Thr
465                 470                 475                 480

Lys Gln Gly Pro Thr Asn Pro Met Leu Phe His Leu Val Arg Asp Val
            485                 490                 495

Lys Gln Gly Asn Leu Pro Pro Gly Tyr Lys Ile Thr Leu Ile Asp Ile
        500                 505                 510

Gly Leu Val Ile Glu Tyr Leu Met Gly Gly Thr Tyr Arg Cys Thr Tyr
    515                 520                 525

Thr Arg Lys Arg Phe Arg Leu Ile Tyr Asn Ser Leu Gly Gly Asn Asn
530                 535                 540

Arg Arg Ser Gly Arg Asn Thr Ser Ser Ser Thr Pro Gln Leu Arg Lys
545                 550                 555                 560

Ser His Glu Ser Phe Gly Asn Arg Ala Asp Lys Lys Glu Lys Met Arg
            565                 570                 575

His Asn His Phe Ile Lys Thr Ala Gln Pro Tyr Arg Pro Lys Ile Asp
        580                 585                 590

Thr Val Met Glu Glu Gly Lys Lys Lys Arg Thr Lys Asp Glu Ile Val
    595                 600                 605

Asp Ile Asp Asp Pro Glu Thr Lys Arg Phe Pro Tyr Pro Leu Asn Glu
610                 615                 620

Leu Leu Ile Trp Ala Cys Leu Met Lys Arg Gln Val Met Ala Arg Phe
625                 630                 635                 640
```

-continued

```
Leu Trp Gln His Gly Glu Ser Met Ala Lys Ala Leu Val Ala Cys
            645                 650                 655

Lys Ile Tyr Arg Ser Met Ala Tyr Glu Ala Lys Gln Ser Asp Leu Val
            660                 665                 670

Asp Asp Thr Ser Glu Glu Leu Lys Gln Tyr Ser Asn Asp Phe Gly Gln
            675                 680                 685

Leu Ala Val Glu Leu Leu Glu Gln Ser Phe Arg Gln Asp Glu Thr Met
        690                 695                 700

Ala Met Lys Leu Leu Thr Tyr Glu Leu Lys Asn Trp Ser Asn Ser Thr
705                 710                 715                 720

Cys Leu Lys Leu Ala Val Ser Ser Arg Leu Arg Pro Phe Val Ala His
                725                 730                 735

Thr Cys Thr Gln Met Leu Leu Ser Asp Met Trp Met Gly Arg Leu Asn
            740                 745                 750

Met Arg Lys Asn Ser Trp Tyr Lys Val Ile Leu Ser Ile Leu Val Pro
            755                 760                 765

Pro Ala Ile Leu Leu Leu Glu Tyr Lys Thr Lys Ala Glu Met Ser His
        770                 775                 780

Ile Pro Gln Ser Gln Asp Ala His Gln Met Thr Met Asp Asp Ser Glu
785                 790                 795                 800

Asn Asn Phe Gln Asn Ile Thr Glu Glu Ile Pro Met Glu Val Phe Lys
                805                 810                 815

Glu Val Arg Ile Leu Asp Ser Asn Glu Gly Lys Asn Glu Met Glu Ile
            820                 825                 830

Gln Met Lys Ser Lys Lys Leu Pro Ile Thr Arg Lys Phe Tyr Ala Phe
        835                 840                 845

Tyr His Ala Pro Ile Val Lys Phe Trp Phe Asn Thr Leu Ala Tyr Leu
        850                 855                 860

Gly Phe Leu Met Leu Tyr Thr Phe Val Val Leu Val Gln Met Glu Gln
865                 870                 875                 880

Leu Pro Ser Val Gln Glu Trp Ile Val Ile Ala Tyr Ile Phe Thr Tyr
                885                 890                 895

Ala Ile Glu Lys Val Arg Glu Ile Phe Met Ser Glu Ala Gly Lys Val
            900                 905                 910

Asn Gln Lys Ile Lys Val Trp Phe Ser Asp Tyr Phe Asn Ile Ser Asp
        915                 920                 925

Thr Ile Ala Ile Ile Ser Phe Phe Ile Gly Phe Gly Leu Arg Phe Gly
        930                 935                 940

Ala Lys Trp Asn Phe Ala Asn Ala Tyr Asp Asn His Val Phe Val Ala
945                 950                 955                 960

Gly Arg Leu Ile Tyr Cys Leu Asn Ile Ile Phe Trp Tyr Val Arg Leu
                965                 970                 975

Leu Asp Phe Leu Ala Val Asn Gln Gln Ala Gly Pro Tyr Val Met Met
            980                 985                 990

Ile Gly Lys Met Val Ala Asn Met Phe Tyr Ile Val Val Ile Met Ala
        995                 1000                1005

Leu Val Leu Leu Ser Phe Gly Val Pro Arg Lys Ala Ile Leu Tyr
    1010                1015                1020

Pro His Glu Ala Pro Ser Trp Thr Leu Ala Lys Asp Ile Val Phe
    1025                1030                1035

His Pro Tyr Trp Met Ile Phe Gly Glu Val Tyr Ala Tyr Glu Ile
    1040                1045                1050
```

-continued

Asp Val Cys Ala Asn Asp Ser Val Ile Pro Gln Ile Cys Gly Pro
1055                    1060                1065

Gly Thr Trp Leu Thr Pro Phe Leu Gln Ala Val Tyr Leu Phe Val
1070                    1075                1080

Gln Tyr Ile Ile Met Val Asn Leu Leu Ile Ala Phe Phe Asn Asn
1085                    1090                1095

Val Tyr Leu Gln Val Lys Ala Ile Ser Asn Ile Val Trp Lys Tyr
1100                    1105                1110

Gln Arg Tyr His Phe Ile Met Ala Tyr His Glu Lys Pro Val Leu
1115                    1120                1125

Pro Pro Pro Leu Ile Ile Leu Ser His Ile Val Ser Leu Phe Cys
1130                    1135                1140

Cys Ile Cys Lys Arg Arg Lys Lys Asp Lys Thr Ser Asp Gly Pro
1145                    1150                1155

Lys Leu Phe Leu Thr Glu Glu Asp Gln Lys Lys Leu His Asp Phe
1160                    1165                1170

Glu Glu Gln Cys Val Glu Met Tyr Phe Asn Glu Lys Asp Asp Lys
1175                    1180                1185

Phe His Ser Gly Ser Glu Glu Arg Ile Arg Val Thr Phe Glu Arg
1190                    1195                1200

Val Glu Gln Met Cys Ile Gln Ile Lys Glu Val Gly Asp Arg Val
1205                    1210                1215

Asn Tyr Ile Lys Arg Ser Leu Gln Ser Leu Asp Ser Gln Ile Gly
1220                    1225                1230

His Leu Gln Asp Leu Ser Ala Leu Thr Val Asp Thr Leu Lys Thr
1235                    1240                1245

Leu Thr Ala Gln Lys Ala Ser Glu Ala Ser Lys Val His Asn Glu
1250                    1255                1260

Ile Thr Arg Glu Leu Ser Ile Ser Lys His Leu Ala Gln Asn Leu
1265                    1270                1275

Ile Asp Asp Gly Pro Val Arg Pro Ser Val Trp Lys Lys His Gly
1280                    1285                1290

Val Val Asn Thr Leu Ser Ser Leu Pro Gln Gly Asp Leu Glu
1295                    1300                1305

Ser Asn Asn Pro Phe His Cys Asn Ile Leu Met Lys Asp Asp Lys
1310                    1315                1320

Asp Pro Gln Cys Asn Ile Phe Gly Gln Asp Leu Pro Ala Val Pro
1325                    1330                1335

Gln Arg Lys Glu Phe Asn Phe Pro Glu Ala Gly Ser Ser Ser Gly
1340                    1345                1350

Ala Leu Phe Pro Ser Ala Val Ser Pro Pro Glu Leu Arg Gln Arg
1355                    1360                1365

Leu His Gly Val Glu Leu Leu Lys Ile Phe Asn Lys Asn Gln Lys
1370                    1375                1380

Leu Gly Ser Ser Ser Thr Ser Ile Pro His Leu Ser Ser Pro Pro
1385                    1390                1395

Thr Lys Phe Phe Val Ser Thr Pro Ser Gln Pro Ser Cys Lys Ser
1400                    1405                1410

His Leu Glu Thr Gly Thr Lys Asp Gln Glu Thr Val Cys Ser Lys
1415                    1420                1425

Ala Thr Glu Gly Asp Asn Thr Glu Phe Gly Ala Phe Val Gly His
1430                    1435                1440

-continued

```
Arg Asp Ser Met Asp Leu Gln Arg Phe Lys Glu Thr Ser Asn Lys
    1445                1450                1455

Ile Lys Ile Leu Ser Asn Asn Asn Thr Ser Glu Asn Thr Leu Lys
    1460                1465                1470

Arg Val Ser Ser Leu Ala Gly Phe Thr Asp Cys His Arg Thr Ser
    1475                1480                1485

Ile Pro Val His Ser Lys Gln Glu Lys Ile Ser Arg Arg Pro Ser
    1490                1495                1500

Thr Glu Asp Thr His Glu Val Asp Ser Lys Ala Ala Leu Ile Pro
    1505                1510                1515

Val Trp Leu Gln Asp Arg Pro Ser Asn Arg Glu Met Pro Ser Glu
    1520                1525                1530

Glu Gly Thr Leu Asn Gly Leu Thr Ser Pro Phe Lys Pro Ala Met
    1535                1540                1545

Asp Thr Asn Tyr Tyr Ser Ala Val Glu Arg Asn Asn Leu Met
    1550                1555                1560

Arg Leu Ser Gln Ser Ile Pro Phe Thr Pro Val Pro Pro Arg Gly
    1565                1570                1575

Glu Pro Val Thr Val Tyr Arg Leu Glu Glu Ser Ser Pro Asn Ile
    1580                1585                1590

Leu Asn Asn Ser Met Ser Ser Trp Ser Gln Leu Gly Leu Cys Ala
    1595                1600                1605

Lys Ile Glu Phe Leu Ser Lys Glu Glu Met Gly Gly Gly Leu Arg
    1610                1615                1620

Arg Ala Val Lys Val Gln Cys Thr Trp Ser Glu His Asp Ile Leu
    1625                1630                1635

Lys Ser Gly His Leu Tyr Ile Ile Lys Ser Phe Leu Pro Glu Val
    1640                1645                1650

Val Asn Thr Trp Ser Ser Ile Tyr Lys Glu Asp Thr Val Leu His
    1655                1660                1665

Leu Cys Leu Arg Glu Ile Gln Gln Arg Ala Ala Gln Lys Leu
    1670                1675                1680

Thr Phe Ala Phe Asn Gln Met Lys Pro Lys Ser Ile Pro Tyr Ser
    1685                1690                1695

Pro Arg Phe Leu Glu Val Phe Leu Leu Tyr Cys His Ser Ala Gly
    1700                1705                1710

Gln Trp Phe Ala Val Glu Glu Cys Met Thr Gly Glu Phe Arg Lys
    1715                1720                1725

Tyr Asn Asn Asn Asn Gly Asp Glu Ile Ile Pro Thr Asn Thr Leu
    1730                1735                1740

Glu Glu Ile Met Leu Ala Phe Ser His Trp Thr Tyr Glu Tyr Thr
    1745                1750                1755

Arg Gly Glu Leu Leu Val Leu Asp Leu Gln Gly Val Gly Glu Asn
    1760                1765                1770

Leu Thr Asp Pro Ser Val Ile Lys Ala Glu Glu Lys Arg Ser Cys
    1775                1780                1785

Asp Met Val Phe Gly Pro Ala Asn Leu Gly Glu Asp Ala Ile Lys
    1790                1795                1800

Asn Phe Arg Ala Lys His His Cys Asn Ser Cys Cys Arg Lys Leu
    1805                1810                1815

Lys Leu Pro Asp Leu Lys Arg Asn Asp Tyr Thr Pro Asp Lys Ile
    1820                1825                1830
```

```
Ile Phe Pro Gln Asp Glu Pro Ser Asp Leu Asn Leu Gln Pro Gly
1835                1840                1845

Asn Ser Thr Lys Glu Ser Glu Ser Thr Asn Ser Val Arg Leu Met
    1850                1855                1860

Leu

<210> SEQ ID NO 10
<211> LENGTH: 240
<212> TYPE: DNA
<213> ORGANISM: Homo sapiens

<400> SEQUENCE: 10
catggcagac agtttggcca gctggctctg gacttgttgg agaaggcatt caagcagaat      60
gagcgcatgg ccatgacgct gttgacgtat gaactcagga actggagcaa ttcgacctgc     120
cttaaactgg ccgtgtcggg aggattacga cccttttgttt cacatacttg tacccagatg    180
ctactgacag acatgtggat ggggaggctg aaaatgagga aaaactcttg gttaaaggta     240

<210> SEQ ID NO 11
<211> LENGTH: 258
<212> TYPE: DNA
<213> ORGANISM: Homo sapiens

<400> SEQUENCE: 11
aaatcaagga agaagtcaaa agaacaaaat gtatcagatg accctgagtc tactggcttt      60 ctttacccctt acaatgacct gctggtttgg gctgtgctga tgaaaaggca gaagatggct    120
atgttcttct ggcagcatgg agaggaggcc acggttaaag ccgtgattgc gtgtatcctc    180
taccgggcaa tggcccatga agctaaggag agtcacatgg tggatgatgc ctcagaagag    240
ttgaagaatt actcaaag                                                  258

<210> SEQ ID NO 12
<211> LENGTH: 336
<212> TYPE: DNA
<213> ORGANISM: Homo sapiens

<400> SEQUENCE: 12
aacatgttct atattgtgat catcatggcc atagtcctgc tgagctttgg agtggcacgc      60
aaggccatcc tttcgccaaa agagccacca tcttggagtc tagctcgaga tattgtattt    120
gagccatact ggatgatata cggagaagtc tatgctggag aaatagatgg tgtgtatggg    180
attttaccgt catgcagaaa ttgtgccttc atagttaaca gatttgttc aagccagcca    240 tcctgccctc ctggttcttt tcttactcca ttcttgcaag ctgtctacct cttcgtgcaa    300
tatatcatca tggtgaacct gttgattgct ttcttc                              336

<210> SEQ ID NO 13
<211> LENGTH: 174
<212> TYPE: DNA
<213> ORGANISM: Homo sapiens

<400> SEQUENCE: 13
gtggtgtgcc tgtaccagac tctggataac cccctcagca agctcacaac actcaacagc      60
atgcactcgc acttcatcct gtctgatgat gggaccgtgg gcaagtatgg aaatgaaatg    120
aagctcagaa ggaacctgga gaagtacctc tctctgcaga aaatacactg ccgt          174
```

<210> SEQ ID NO 14
<211> LENGTH: 237
<212> TYPE: DNA
<213> ORGANISM: Homo sapiens

<400> SEQUENCE: 14

```
cttacttcat cttacagcaa cgtttactta gatatggaat ccatttcaaa taacctgtgg      60
aaatacaacc gctatcgcta catcatgacc taccacgaga agccctggct gcccccacct     120
ctcatcctgc tgagccacgt gggccttctc ctccgccgcc tgtgctgtca tcgagctcct     180
cacgaccaag aagagggtga cgttggatta agtaagttgt tctatgtgag gcaggag       237
```

<210> SEQ ID NO 15
<211> LENGTH: 171
<212> TYPE: DNA
<213> ORGANISM: Homo sapiens

<400> SEQUENCE: 15

```
attaccatat ttgatgctga ctctgaagag cagcaagacc tggacttagc aatcctaaca      60
gctttgctga agggcacaaa tttatcagcg tcagagcaat taaatctggc aatggcttgg     120
gacagggtgg acattgccaa gaaacatatc ctaatttatg aacaacactg g              171
```

<210> SEQ ID NO 16
<211> LENGTH: 162
<212> TYPE: DNA
<213> ORGANISM: Homo sapiens

<400> SEQUENCE: 16

```
caaggcgtgc cggtcgtggg gctggtggtg gaaggcggtc ccaacgtcat cctgtcagtg      60
tgggagactg tcaaggacaa ggacccagtg gtggtgtgtg agggcacagg tagggcggtt     120
gacctcctgg ccttcacaca caaacacctg gcagatgaag gg                        162
```

<210> SEQ ID NO 17
<211> LENGTH: 111
<212> TYPE: DNA
<213> ORGANISM: Homo sapiens

<400> SEQUENCE: 17

```
taccgaataa ccttgattga cattggatta gtagtagaat acctcattgg tagagcatat      60
cgcagcaact acactagaaa acatttcaga gccctctaca caacctcta c               111
```

<210> SEQ ID NO 18
<211> LENGTH: 135
<212> TYPE: DNA
<213> ORGANISM: Homo sapiens

<400> SEQUENCE: 18

```
ggagtgtcca agcatgttgg ggatgccttg aaatcccatt cctctcattc cttgagaaaa      60
atctggacag ttggaatccc tccttggggt gtcattgaga accagagaga ccttattgga     120
aaagatgtaa gtaga                                                      135
```

<210> SEQ ID NO 19
<211> LENGTH: 138
<212> TYPE: DNA
<213> ORGANISM: Homo sapiens

```
<400> SEQUENCE: 19
atagaactct acctcagtaa ggaggatctg aaaaaacttc atgatttga ggagcagtgc        60 gtggaaaaat acttccatga gaagatggaa gatgtgaatt gtagttgtga ggaacgaatc       120
cgagtgacat caggaagg                                                     138

<210> SEQ ID NO 20
<211> LENGTH: 132
<212> TYPE: DNA
<213> ORGANISM: Homo sapiens

<400> SEQUENCE: 20
atggcgtatt tggcattcct catgctgttc acttacaccg tgttggtgga gatgcagccc        60
cagcccagcg tgcaggagtg gcttgttagc atttacatct tcaccaatgc tattgaggtg      120
gtcagggagg tg                                                           132

<210> SEQ ID NO 21
<211> LENGTH: 132
<212> TYPE: DNA
<213> ORGANISM: Homo sapiens

<400> SEQUENCE: 21
atgctgcgac ctcaggtgaa agaggagatc atctgcatga ttcagaacac tttcaacttt        60
agttttaaac agtacaagca ccttacccaa atactaatgg agtgtatggt tcacagggat       120
tgtgtgagta tg                                                           132

<210> SEQ ID NO 22
<211> LENGTH: 78
<212> TYPE: DNA
<213> ORGANISM: Homo sapiens

<400> SEQUENCE: 22
ttacagatta ttataagcat tatttttacca cccaccattt tgacactgga atttaaaagc       60
aaagctgaga tgtcacat                                                      78

<210> SEQ ID NO 23
<211> LENGTH: 144
<212> TYPE: DNA
<213> ORGANISM: Homo sapiens

<400> SEQUENCE: 23 tccatttta ggctgaataa tattcccttg ggtatatatg ccatattttg tttatccatc         60
cagaaaatct atttctatgt cagtggtatt gttctgttgg tctggtggca caacaggtat      120
ttagctcaat ttttaatgat tgtg                                              144

<210> SEQ ID NO 24
<211> LENGTH: 99
<212> TYPE: DNA
<213> ORGANISM: Homo sapiens

<400> SEQUENCE: 24 aagaaaaga agaaaggaa aagaaaagaa aaggaaacga aagagaggaa aggagaggag          60
aggaaaggag aggaagaaag agagagagag aaagagaga                               99

<210> SEQ ID NO 25
<211> LENGTH: 77
<212> TYPE: DNA
<213> ORGANISM: Homo sapiens
```

-continued

<400> SEQUENCE: 25
ttctcaatga cacccccaagg agggattcca actgtccaga tttttctcaa ggaatgagag    60
gaatgggatt tcaaggc    77

<210> SEQ ID NO 26
<211> LENGTH: 20
<212> TYPE: DNA
<213> ORGANISM: Homo sapiens

<400> SEQUENCE: 26
taatacgact cactataggg    20

<210> SEQ ID NO 27
<211> LENGTH: 19
<212> TYPE: DNA
<213> ORGANISM: Homo sapiens

<400> SEQUENCE: 27
gtccaagcat gttggggat    19

<210> SEQ ID NO 28
<211> LENGTH: 24
<212> TYPE: DNA
<213> ORGANISM: Homo sapiens

<400> SEQUENCE: 28
tcttttccaa taaggtctct ctgg    24

<210> SEQ ID NO 29
<211> LENGTH: 29
<212> TYPE: DNA
<213> ORGANISM: Homo sapiens

<400> SEQUENCE: 29
atgattatcc tatctaagtc ccagaaatc    29

<210> SEQ ID NO 30
<211> LENGTH: 24
<212> TYPE: DNA
<213> ORGANISM: Homo sapiens

<400> SEQUENCE: 30
caaggaatga gaggaatggg attt    24

<210> SEQ ID NO 31
<211> LENGTH: 24
<212> TYPE: DNA
<213> ORGANISM: Homo sapiens

<400> SEQUENCE: 31
aaatcccatt cctctcattc cttg    24

<210> SEQ ID NO 32
<211> LENGTH: 24
<212> TYPE: DNA
<213> ORGANISM: Homo sapiens

<400> SEQUENCE: 32
gtagcctgaa agaagggtat gctg    24

```
<210> SEQ ID NO 33
<211> LENGTH: 24
<212> TYPE: DNA
<213> ORGANISM: Homo sapiens

<400> SEQUENCE: 33
cagcataccc ttctttcagg ctac                                              24

<210> SEQ ID NO 34
<211> LENGTH: 24
<212> TYPE: DNA
<213> ORGANISM: Homo sapiens

<400> SEQUENCE: 34
gaacatgtga catctcagct ttgc                                              24

<210> SEQ ID NO 35
<211> LENGTH: 24
<212> TYPE: DNA
<213> ORGANISM: Homo sapiens

<400> SEQUENCE: 35
gcaaagctga gatgtcacat gttc                                              24

<210> SEQ ID NO 36
<211> LENGTH: 21
<212> TYPE: DNA
<213> ORGANISM: Homo sapiens

<400> SEQUENCE: 36
agggcaggat ggctggcttg a                                                 21

<210> SEQ ID NO 37
<211> LENGTH: 21
<212> TYPE: DNA
<213> ORGANISM: Homo sapiens

<400> SEQUENCE: 37
tcaagccagc catcctgccc t                                                 21

<210> SEQ ID NO 38
<211> LENGTH: 24
<212> TYPE: DNA
<213> ORGANISM: Homo sapiens

<400> SEQUENCE: 38
gcaagtagaa tgctttctct tggc                                              24

<210> SEQ ID NO 39
<211> LENGTH: 24
<212> TYPE: DNA
<213> ORGANISM: Homo sapiens

<400> SEQUENCE: 39
gccaagagaa agcattctac ttgc                                              24

<210> SEQ ID NO 40
<211> LENGTH: 21
<212> TYPE: DNA
<213> ORGANISM: Homo sapiens

<400> SEQUENCE: 40
aggggagctc attgtcatgg g                                                 21
```

```
<210> SEQ ID NO 41
<211> LENGTH: 22
<212> TYPE: DNA
<213> ORGANISM: Homo sapiens

<400> SEQUENCE: 41
cccatgacaa tgagctcccc tc                                              22

<210> SEQ ID NO 42
<211> LENGTH: 28
<212> TYPE: DNA
<213> ORGANISM: Homo sapiens

<400> SEQUENCE: 42
ccaacctgta gacagttatt tcttctcc                                        28

<210> SEQ ID NO 43
<211> LENGTH: 28
<212> TYPE: DNA
<213> ORGANISM: Homo sapiens

<400> SEQUENCE: 43
ggagaagaaa taactgtcta caggttgg                                        28

<210> SEQ ID NO 44
<211> LENGTH: 27
<212> TYPE: DNA
<213> ORGANISM: Homo sapiens

<400> SEQUENCE: 44
ttatagttgc atatcatctt ctgggga                                         27

<210> SEQ ID NO 45
<211> LENGTH: 18
<212> TYPE: PRT
<213> ORGANISM: Homo sapiens

<400> SEQUENCE: 45

Leu Lys Ile Ile Ile Ser Ile Ile Leu Pro Pro Thr Ile Leu Thr Leu
1               5                   10                  15

Glu Phe

<210> SEQ ID NO 46
<211> LENGTH: 18
<212> TYPE: PRT
<213> ORGANISM: Homo sapiens

<400> SEQUENCE: 46

Ile Val Lys Phe Trp Phe Tyr Thr Met Ala Tyr Leu Ala Phe Leu Met
1               5                   10                  15

Leu Phe

<210> SEQ ID NO 47
<211> LENGTH: 13
<212> TYPE: PRT
<213> ORGANISM: Homo sapiens

<400> SEQUENCE: 47

Thr Glu Thr Val Ala Ile Gly Leu Phe Ser Ala Gly Phe
1               5                   10
```

```
<210> SEQ ID NO 48
<211> LENGTH: 18
<212> TYPE: PRT
<213> ORGANISM: Homo sapiens

<400> SEQUENCE: 48

Arg Leu Ile Tyr Cys Ile Asp Ile Ile Phe Trp Phe Ser Arg Leu Leu
1               5                   10                  15

Asp Phe

<210> SEQ ID NO 49
<211> LENGTH: 18
<212> TYPE: PRT
<213> ORGANISM: Homo sapiens

<400> SEQUENCE: 49

Met Thr Ala Asn Met Phe Tyr Ile Val Ile Met Ala Ile Val Leu
1               5                   10                  15

Leu Ser

<210> SEQ ID NO 50
<211> LENGTH: 20
<212> TYPE: PRT
<213> ORGANISM: Homo sapiens

<400> SEQUENCE: 50

Phe Leu Gln Ala Val Tyr Leu Phe Val Gln Tyr Ile Ile Met Val Asn
1               5                   10                  15

Leu Leu Ile Ala
            20

<210> SEQ ID NO 51
<211> LENGTH: 13
<212> TYPE: PRT
<213> ORGANISM: Homo sapiens

<400> SEQUENCE: 51

Ile Ile Leu Ser Lys Ser Gln Lys Ser Trp Ile Lys Gly
1               5                   10

<210> SEQ ID NO 52
<211> LENGTH: 13
<212> TYPE: PRT
<213> ORGANISM: Homo sapiens

<400> SEQUENCE: 52

Ser Thr Ile Ile Pro Ser Ser Lys Asn Pro His Arg Cys
1               5                   10

<210> SEQ ID NO 53
<211> LENGTH: 13
<212> TYPE: PRT
<213> ORGANISM: Homo sapiens

<400> SEQUENCE: 53

Ser Val Glu Lys His Thr Thr Lys Ser Pro Thr Asp Thr
1               5                   10

<210> SEQ ID NO 54
<211> LENGTH: 13
<212> TYPE: PRT
<213> ORGANISM: Homo sapiens
```

-continued

```
<400> SEQUENCE: 54

Ser His Ser Ser His Ser Leu Arg Lys Ile Trp Thr Val
1               5                   10

<210> SEQ ID NO 55
<211> LENGTH: 13
<212> TYPE: PRT
<213> ORGANISM: Homo sapiens

<400> SEQUENCE: 55

Leu Ser Val Trp Glu Thr Val Lys Asp Lys Asp Pro Val
1               5                   10

<210> SEQ ID NO 56
<211> LENGTH: 13
<212> TYPE: PRT
<213> ORGANISM: Homo sapiens

<400> SEQUENCE: 56

Val Val Cys Glu Gly Thr Gly Arg Ala Ala Asp Leu Leu
1               5                   10

<210> SEQ ID NO 57
<211> LENGTH: 13
<212> TYPE: PRT
<213> ORGANISM: Homo sapiens

<400> SEQUENCE: 57

Asp Leu Leu Ala Phe Thr His Lys His Leu Ala Asp Glu
1               5                   10

<210> SEQ ID NO 58
<211> LENGTH: 13
<212> TYPE: PRT
<213> ORGANISM: Homo sapiens

<400> SEQUENCE: 58

Asn Thr Phe Asn Phe Ser Leu Lys Gln Ser Lys His Leu
1               5                   10

<210> SEQ ID NO 59
<211> LENGTH: 13
<212> TYPE: PRT
<213> ORGANISM: Homo sapiens

<400> SEQUENCE: 59

Tyr Arg Ser Asn Tyr Thr Arg Lys His Phe Arg Ala Leu
1               5                   10

<210> SEQ ID NO 60
<211> LENGTH: 13
<212> TYPE: PRT
<213> ORGANISM: Homo sapiens

<400> SEQUENCE: 60

Ile Val Leu His Lys Ser Arg Lys Lys Ser Lys Glu Gln
1               5                   10

<210> SEQ ID NO 61
<211> LENGTH: 13
<212> TYPE: PRT
<213> ORGANISM: Homo sapiens
```

-continued

```
<400> SEQUENCE: 61

His Gly Glu Glu Ala Thr Val Lys Ala Val Ile Ala Cys
1               5                   10

<210> SEQ ID NO 62
<211> LENGTH: 13
<212> TYPE: PRT
<213> ORGANISM: Homo sapiens

<400> SEQUENCE: 62

Asp Gln Asn Ala Ser Ser Ser Lys Glu Ser Ala Ser Val
1               5                   10

<210> SEQ ID NO 63
<211> LENGTH: 13
<212> TYPE: PRT
<213> ORGANISM: Homo sapiens

<400> SEQUENCE: 63

Ser Lys Glu Ser Ala Ser Val Lys Glu Tyr Asp Leu Glu
1               5                   10

<210> SEQ ID NO 64
<211> LENGTH: 13
<212> TYPE: PRT
<213> ORGANISM: Homo sapiens

<400> SEQUENCE: 64

Gln His Leu Pro Trp Thr Arg Lys Val Tyr Glu Phe Tyr
1               5                   10

<210> SEQ ID NO 65
<211> LENGTH: 13
<212> TYPE: PRT
<213> ORGANISM: Homo sapiens

<400> SEQUENCE: 65

Glu Pro Gly Lys Phe Thr Gln Lys Val Lys Val Trp Ile
1               5                   10

<210> SEQ ID NO 66
<211> LENGTH: 13
<212> TYPE: PRT
<213> ORGANISM: Homo sapiens

<400> SEQUENCE: 66

Arg Lys Ala Ile Leu Ser Pro Lys Glu Pro Pro Ser Trp
1               5                   10

<210> SEQ ID NO 67
<211> LENGTH: 13
<212> TYPE: PRT
<213> ORGANISM: Homo sapiens

<400> SEQUENCE: 67

Arg Ile Arg Val Thr Ser Glu Arg Val Thr Glu Met Tyr
1               5                   10

<210> SEQ ID NO 68
<211> LENGTH: 13
<212> TYPE: PRT
<213> ORGANISM: Homo sapiens
```

-continued

<400> SEQUENCE: 68

Ala Leu Thr Val Asp Thr Leu Lys Val Leu Ser Ala Val
1               5                   10

<210> SEQ ID NO 69
<211> LENGTH: 13
<212> TYPE: PRT
<213> ORGANISM: Homo sapiens

<400> SEQUENCE: 69

Lys Arg Lys His Ser Thr Cys Lys Lys Leu Pro His Ser
1               5                   10

<210> SEQ ID NO 70
<211> LENGTH: 13
<212> TYPE: PRT
<213> ORGANISM: Homo sapiens

<400> SEQUENCE: 70

Leu Glu Ile Thr Asn Ser Lys Arg Glu Ala Thr Asn Val
1               5                   10

<210> SEQ ID NO 71
<211> LENGTH: 13
<212> TYPE: PRT
<213> ORGANISM: Homo sapiens

<400> SEQUENCE: 71

Glu Thr Gly Val Phe Ser Ile Lys Lys Trp Gln Thr
1               5                   10

<210> SEQ ID NO 72
<211> LENGTH: 13
<212> TYPE: PRT
<213> ORGANISM: Homo sapiens

<400> SEQUENCE: 72

Thr Cys Asp Ser Asp Ser Ser Arg Ser Glu Gln His Gln
1               5                   10

<210> SEQ ID NO 73
<211> LENGTH: 13
<212> TYPE: PRT
<213> ORGANISM: Homo sapiens

<400> SEQUENCE: 73

Ser Leu Ser Asp Asn Ser Thr Arg Ser Ala Gln Ser Ser
1               5                   10

<210> SEQ ID NO 74
<211> LENGTH: 13
<212> TYPE: PRT
<213> ORGANISM: Homo sapiens

<400> SEQUENCE: 74

Phe Ala Arg Ser His Ser Phe Arg Phe His Lys Glu Glu
1               5                   10

<210> SEQ ID NO 75
<211> LENGTH: 13
<212> TYPE: PRT
<213> ORGANISM: Homo sapiens

```
<400> SEQUENCE: 75

Lys Asp Arg Arg Leu Ser Lys Lys Lys Asn Thr Gln
1               5                   10

<210> SEQ ID NO 76
<211> LENGTH: 13
<212> TYPE: PRT
<213> ORGANISM: Homo sapiens

<400> SEQUENCE: 76

Asp Lys Ile Ser Ala Ser Leu Lys Ser Pro Gln Glu Pro
1               5                   10

<210> SEQ ID NO 77
<211> LENGTH: 13
<212> TYPE: PRT
<213> ORGANISM: Homo sapiens

<400> SEQUENCE: 77

Ser Met Ser Ser Trp Ser Gln Arg Gly Arg Ala Ala Met
1               5                   10

<210> SEQ ID NO 78
<211> LENGTH: 13
<212> TYPE: PRT
<213> ORGANISM: Homo sapiens

<400> SEQUENCE: 78

Gln Thr Ile Pro Tyr Thr Pro Arg Phe Leu Glu Val Phe
1               5                   10

<210> SEQ ID NO 79
<211> LENGTH: 13
<212> TYPE: PRT
<213> ORGANISM: Homo sapiens

<400> SEQUENCE: 79

Pro Pro Ala Arg Glu Thr Gly Arg Asn Ser Pro Glu Asp
1               5                   10

<210> SEQ ID NO 80
<211> LENGTH: 14
<212> TYPE: PRT
<213> ORGANISM: Homo sapiens

<400> SEQUENCE: 80

His Gly Gly Ile Gln Asn Phe Thr Met Pro Ser Lys Phe Lys
1               5                   10

<210> SEQ ID NO 81
<211> LENGTH: 14
<212> TYPE: PRT
<213> ORGANISM: Homo sapiens

<400> SEQUENCE: 81

Ile Gln Asn Thr Phe Asn Phe Ser Leu Lys Gln Ser Lys His
1               5                   10

<210> SEQ ID NO 82
<211> LENGTH: 14
<212> TYPE: PRT
<213> ORGANISM: Homo sapiens
```

```
<400> SEQUENCE: 82

Leu Leu Lys Gly Thr Asn Leu Ser Ala Ser Glu Gln Leu Asn
1               5                   10

<210> SEQ ID NO 83
<211> LENGTH: 14
<212> TYPE: PRT
<213> ORGANISM: Homo sapiens

<400> SEQUENCE: 83

Arg Ala Tyr Arg Ser Asn Tyr Thr Arg Lys His Phe Arg Ala
1               5                   10

<210> SEQ ID NO 84
<211> LENGTH: 14
<212> TYPE: PRT
<213> ORGANISM: Homo sapiens

<400> SEQUENCE: 84

Ser Ser Gly Asn Arg Asn Glu Ser Ala Glu Ser Thr Leu His
1               5                   10

<210> SEQ ID NO 85
<211> LENGTH: 14
<212> TYPE: PRT
<213> ORGANISM: Homo sapiens

<400> SEQUENCE: 85

Lys Ser Lys Glu Gln Asn Val Ser Asp Asp Pro Glu Ser Thr
1               5                   10

<210> SEQ ID NO 86
<211> LENGTH: 14
<212> TYPE: PRT
<213> ORGANISM: Homo sapiens

<400> SEQUENCE: 86

Ser Glu Glu Leu Lys Asn Tyr Ser Lys Gln Phe Gly Gln Leu
1               5                   10

<210> SEQ ID NO 87
<211> LENGTH: 14
<212> TYPE: PRT
<213> ORGANISM: Homo sapiens

<400> SEQUENCE: 87

Thr Tyr Glu Leu Arg Asn Trp Ser Asn Ser Thr Cys Leu Lys
1               5                   10

<210> SEQ ID NO 88
<211> LENGTH: 14
<212> TYPE: PRT
<213> ORGANISM: Homo sapiens

<400> SEQUENCE: 88

Leu Arg Asn Trp Ser Asn Ser Thr Cys Leu Lys Leu Ala Val
1               5                   10

<210> SEQ ID NO 89
<211> LENGTH: 14
<212> TYPE: PRT
<213> ORGANISM: Homo sapiens
```

```
<400> SEQUENCE: 89

Tyr Tyr Ser Asp Gln Asn Ala Ser Ser Ser Lys Glu Ser Ala
1               5                   10

<210> SEQ ID NO 90
<211> LENGTH: 14
<212> TYPE: PRT
<213> ORGANISM: Homo sapiens

<400> SEQUENCE: 90

Ile Ser Glu Tyr Trp Asn Leu Thr Glu Thr Val Ala Ile Gly
1               5                   10

<210> SEQ ID NO 91
<211> LENGTH: 14
<212> TYPE: PRT
<213> ORGANISM: Homo sapiens

<400> SEQUENCE: 91

Lys Met Glu Asp Val Asn Cys Ser Cys Glu Glu Arg Ile Arg
1               5                   10

<210> SEQ ID NO 92
<211> LENGTH: 14
<212> TYPE: PRT
<213> ORGANISM: Homo sapiens

<400> SEQUENCE: 92

Ser Ser Leu Ser Asp Asn Ser Thr Arg Ser Ala Gln Ser Ser
1               5                   10

<210> SEQ ID NO 93
<211> LENGTH: 14
<212> TYPE: PRT
<213> ORGANISM: Homo sapiens

<400> SEQUENCE: 93

Pro Trp Leu Gln Pro Asn Thr Ser Phe Trp Ile Asn Pro Leu
1               5                   10

<210> SEQ ID NO 94
<211> LENGTH: 14
<212> TYPE: PRT
<213> ORGANISM: Homo sapiens

<400> SEQUENCE: 94

Ile Cys Lys Ile Lys Asn Leu Ser Gly Ser Ser Glu Ile Gly
1               5                   10

<210> SEQ ID NO 95
<211> LENGTH: 14
<212> TYPE: PRT
<213> ORGANISM: Homo sapiens

<400> SEQUENCE: 95

Gln Gly Val Gly Glu Asn Leu Thr Asp Pro Ser Val Ile Lys
1               5                   10

<210> SEQ ID NO 96
<211> LENGTH: 14
<212> TYPE: PRT
<213> ORGANISM: Homo sapiens
```

<400> SEQUENCE: 96

Ser Pro Glu Arg Ile Asn Ser Thr Phe Gly Leu Glu Ile Lys
1               5                   10

<210> SEQ ID NO 97
<211> LENGTH: 1933
<212> TYPE: DNA
<213> ORGANISM: Homo sapiens

<400> SEQUENCE: 97

```
caagttctct ggtctccacc caaagatgat tatcctatct aagtcccaga atcctggat      60
taaaggagta tttgacaaga gagaatgtag cacaatcata cccagctcaa aaatcctca    120
cagatgtact ccagtatgcc aagtctgcca gaatttaatc aggtgttact gtggccgact   180
gattggagac catgctggga tagattattc ctggaccatc tcagctgcca agggtaaaga   240
aagtgaacaa tggtctgttg aaaagcacac aacgaaaagc ccaacagata cttttggcac   300
gattaatttc caagatggag agcacaccca tcatgccaag tatattagaa cttcttatga   360
tacaaaactg gatcatctgt tacatttaat gttgaaagag tggaaaatgg aactgcccaa   420
gcttgtgatc tcagtccatg ggggcatcca gaactttact atgccctcta aatttaaaga   480
gattttcagc caaggtttgg ttaaagctgc agagacaaca ggagcgtgga taataactga   540
aggcatcaat acaggagtgt ccaagcatgt tggggatgcc ttgaaatccc attcctctca   600
ttccttgaga aaaatctgga cagttggaat ccctccttgg ggtgtcattg agaaccagag   660
agaccttatt ggaaaagatg tggtgtgcct gtaccagact ctggataacc ccctcagcaa   720
gctcacaaca ctcaacagca tgcactcgca cttcatcctg tctgatgatg ggaccgtggg   780
caagtatgga atgaaatgaa gctcagaaag gaacctggaa aagtacctct ctctgcagaa   840
aatacactgc cgctcaagac aaggcgtgcc ggtcgtgggg ctggtggtgg aaggcggtcc   900
caacgtcatc ctgtcagtgt gggagactgt caaggacaag gacccagtgg tggtgtgtga   960
gggcacaggt agggcggctg acctcctggc cttcacacac aaacacctgg cagatgaagg  1020
gatgctgcga cctcaggtga agaggagat catctgcatg attcagaaca ctttcaactt  1080
tagtcttaaa cagtccaagc accttttcca aattctaatg gagtgtatgg ttcacaggga  1140
ttgtattacc atatttgatg ctgactctga agagcagcaa gacctggact tagcaatcct  1200
aacagctttg ctgaagggca caaatttatc agcgtcagag caattaaatc tggcaatggc  1260
ttgggacagg gtggacattg ccaagaaaca tatcctaatt tatgaacaac actggaagcc  1320
tgatgccctg gaacaagcaa tgtcagatgc tttagtgatg gatcgggtgg attttgtgaa  1380
gctcttaata gaatatggag tgaacctcca tcgctttctt accatccctc gactggaaga  1440
gctctacaat acaaaacaag gacctactaa tacactcttg catcatctcg tccaagatgt  1500
gaaacaggta acctaattaa gaaggcgtga acatgtcttt gtgtattgcc ttagctttgt  1560
gttggaggag tcactgaatt ttgctttgta aaatgcagat ttggattgtt ttgttaatta  1620
cctatcttct ttaccttgat ttgaacaagt tcatcaacaa accacattcg tacactttt  1680
tccttaattt actttatgtt ttaaaagact tgatccatca gttaggtgat atttgctaat  1740
aaaaagccat gaatcagaga catgcaatgc ttctaatcag aacttcagct taccccgata  1800
ccgtggtggt gcctatgatg atgataccag ctggaaataa ataactttgt ggttgtgtta  1860
tccttaaaaa aaaaaaaaaa aaaaaaaaaa aaaaaaaaa aaaaaaaaa aaaaaaaaa    1920
aaaaaaaaaa aaa                                                      1933
```

<210> SEQ ID NO 98
<211> LENGTH: 496
<212> TYPE: PRT
<213> ORGANISM: Homo sapiens

<400> SEQUENCE: 98

Met Ile Ile Leu Ser Lys Ser Gln Lys Ser Trp Ile Lys Gly Val Phe
1               5                   10                  15

Asp Lys Arg Glu Cys Ser Thr Ile Ile Pro Ser Ser Lys Asn Pro His
            20                  25                  30

Arg Cys Thr Pro Val Cys Gln Val Cys Gln Asn Leu Ile Arg Cys Tyr
        35                  40                  45

Cys Gly Arg Leu Ile Gly Asp His Ala Gly Ile Asp Tyr Ser Trp Thr
    50                  55                  60

Ile Ser Ala Ala Lys Gly Lys Glu Ser Glu Gln Trp Ser Val Glu Lys
65                  70                  75                  80

His Thr Thr Lys Ser Pro Thr Asp Thr Phe Gly Thr Ile Asn Phe Gln
                85                  90                  95

Asp Gly Glu His Thr His His Ala Lys Tyr Ile Arg Thr Ser Tyr Asp
            100                 105                 110

Thr Lys Leu Asp His Leu Leu His Leu Met Leu Lys Glu Trp Lys Met
        115                 120                 125

Glu Leu Pro Lys Leu Val Ile Ser Val His Gly Ile Gln Asn Phe
    130                 135                 140

Thr Met Pro Ser Lys Phe Lys Glu Ile Phe Ser Gln Gly Leu Val Lys
145                 150                 155                 160

Ala Ala Glu Thr Thr Gly Ala Trp Ile Ile Thr Glu Gly Ile Asn Thr
                165                 170                 175

Gly Val Ser Lys His Val Gly Asp Ala Leu Lys Ser His Ser Ser His
            180                 185                 190

Ser Leu Arg Lys Ile Trp Thr Val Gly Ile Pro Pro Trp Gly Val Ile
        195                 200                 205

Glu Asn Gln Arg Asp Leu Ile Gly Lys Asp Val Val Cys Leu Tyr Gln
    210                 215                 220

Thr Leu Asp Asn Pro Leu Ser Lys Leu Thr Thr Leu Asn Ser Met His
225                 230                 235                 240

Ser His Phe Ile Leu Ser Asp Asp Gly Thr Val Gly Lys Tyr Gly Asn
                245                 250                 255

Glu Met Lys Leu Arg Arg Asn Leu Glu Lys Tyr Leu Ser Leu Gln Lys
            260                 265                 270

Ile His Cys Arg Ser Arg Gln Gly Val Pro Val Val Gly Leu Val Val
        275                 280                 285

Glu Gly Gly Pro Asn Val Ile Leu Ser Val Trp Glu Thr Val Lys Asp
    290                 295                 300

Lys Asp Pro Val Val Cys Glu Gly Thr Gly Arg Ala Ala Asp Leu
305                 310                 315                 320

Leu Ala Phe Thr His Lys His Leu Ala Asp Glu Gly Met Leu Arg Pro
                325                 330                 335

Gln Val Lys Glu Glu Ile Cys Met Ile Gln Asn Thr Phe Asn Phe
            340                 345                 350

Ser Leu Lys Gln Ser Lys His Leu Phe Gln Ile Leu Met Glu Cys Met
        355                 360                 365

Val His Arg Asp Cys Ile Thr Ile Phe Asp Ala Asp Ser Glu Glu Gln
    370                 375                 380

```
Gln Asp Leu Asp Leu Ala Ile Leu Thr Ala Leu Leu Lys Gly Thr Asn
385                 390                 395                 400

Leu Ser Ala Ser Glu Gln Leu Asn Leu Ala Met Ala Trp Asp Arg Val
            405                 410                 415

Asp Ile Ala Lys Lys His Ile Leu Ile Tyr Glu Gln His Trp Lys Pro
            420                 425                 430

Asp Ala Leu Glu Gln Ala Met Ser Asp Ala Leu Val Met Asp Arg Val
            435                 440                 445

Asp Phe Val Lys Leu Leu Ile Glu Tyr Gly Val Asn Leu His Arg Phe
        450                 455                 460

Leu Thr Ile Pro Arg Leu Glu Glu Leu Tyr Asn Thr Lys Gln Gly Pro
465                 470                 475                 480

Thr Asn Thr Leu Leu His His Leu Val Gln Asp Val Lys Gln Val Thr
                485                 490                 495

<210> SEQ ID NO 99
<211> LENGTH: 461
<212> TYPE: PRT
<213> ORGANISM: Caenorhabditis elegans

<400> SEQUENCE: 99

Lys Phe Ile Phe Asp Leu Met Val Cys Gly Lys Thr Asn Asp Asn Glu
1               5                   10                  15

Pro Leu Gln Glu Phe Ile Leu Gln Ser Pro Ala Pro Ile Glu Thr Ala
            20                  25                  30

Val Lys Leu Ser Ala Leu Tyr Arg Asp Met Ser Glu Lys Glu Lys Glu
        35                  40                  45

Arg Ala Lys Asp Leu Leu Asn Val Ala Val Phe Ser Glu Asn Met Ala
    50                  55                  60

Val Glu Leu Leu Gly Ile Thr Ala Thr Glu Tyr Asn Ala Ala Leu Leu
65                  70                  75                  80

Leu Lys Ala Lys Asp Asn Arg Gly Arg Pro Leu Leu Asp Val Leu Ile
                85                  90                  95

Glu Asn Glu Gln Lys Glu Val Val Ser Tyr Ala Ser Val Gln Arg Tyr
            100                 105                 110

Leu Thr Glu Val Trp Thr Ala Arg Val Asp Trp Ser Phe Gly Lys Phe
        115                 120                 125

Val Ala Phe Ser Leu Phe Val Leu Ile Cys Pro Pro Ala Trp Phe Tyr
    130                 135                 140

Phe Ser Leu Pro Leu Asp Ser Arg Ile Gly Arg Ala Pro Ile Ile Lys
145                 150                 155                 160

Phe Val Cys His Ile Val Ser His Val Tyr Phe Thr Ile Leu Leu Thr
                165                 170                 175

Ile Val Val Leu Asn Ile Thr His Lys Met Tyr Glu Val Thr Ser Val
            180                 185                 190

Val Pro Asn Pro Val Glu Trp Leu Leu Leu Trp Leu Ser Gly Asn
        195                 200                 205

Leu Val Ser Glu Leu Ser Thr Val Gly Gly Ser Gly Leu Gly Ile
    210                 215                 220

Val Lys Val Leu Ile Leu Val Leu Ser Ala Met Ala Ile Ala Val His
225                 230                 235                 240

Val Leu Ala Phe Leu Leu Pro Ala Val Phe Leu Thr His Leu Asp Asn
                245                 250                 255

Asp Glu Lys Leu His Phe Ala Arg Thr Met Leu Tyr Leu Lys Asn Gln
            260                 265                 270
```

```
Leu Phe Ala Phe Ala Leu Leu Phe Ala Phe Val Glu Tyr Leu Asp Phe
            275                 280                 285

Leu Thr Val His His Leu Phe Gly Pro Trp Ala Ile Ile Ile Arg Asp
        290                 295                 300

Leu Met Tyr Asp Leu Ala Arg Phe Leu Val Ile Leu Met Leu Phe Val
305                 310                 315                 320

Ala Gly Phe Thr Leu His Val Thr Ser Ile Phe Gln Pro Ala Tyr Gln
                325                 330                 335

Pro Val Asp Glu Asp Ser Ala Glu Leu Met Arg Leu Ala Ser Pro Ser
                340                 345                 350

Gln Thr Leu Glu Met Leu Phe Phe Ser Leu Phe Gly Leu Val Glu Pro
            355                 360                 365

Asp Ser Met Pro Pro Leu His Leu Val Pro Asp Phe Ala Lys Ile Ile
        370                 375                 380

Leu Lys Leu Leu Phe Gly Ile Tyr Met Met Val Thr Leu Ile Val Leu
385                 390                 395                 400

Ile Asn Leu Leu Ile Ala Met Met Ser Asp Thr Tyr Gln Arg Ile Gln
                405                 410                 415

Ala Gln Ser Asp Lys Glu Trp Lys Phe Gly Arg Ala Ile Leu Ile Arg
                420                 425                 430

Gln Met Asn Lys Lys Ser Ala Thr Pro Ser Pro Ile Asn Met Leu Thr
            435                 440                 445

Lys Leu Ile Ile Val Leu Arg Val Ala Trp Arg Asn Arg
        450                 455                 460

<210> SEQ ID NO 100
<211> LENGTH: 476
<212> TYPE: PRT
<213> ORGANISM: Drosophila melanogaster

<400> SEQUENCE: 100

Arg Phe Val Tyr Asn Leu Met Val Val Ser Lys Asn His Asn Asn Lys
1               5                   10                  15

Pro Ile Gln Glu Phe Val Leu Val Ser Pro Ala Pro Val Asp Thr Ala
            20                  25                  30

Ala Lys Leu Ser Asn Ile Tyr Ile Val Leu Ser Thr Lys Glu Lys Glu
        35                  40                  45

Arg Ala Lys Asp Leu Val Ala Ala Gly Lys Gln Cys Glu Ala Met Ala
    50                  55                  60

Thr Glu Leu Leu Ala Leu Ala Ala Gly Ser Asp Ser Ala Gly Lys Ile
65                  70                  75                  80

Leu Gln Ala Thr Asp Lys Arg Asn Val Glu Phe Leu Asp Val Leu Ile
                85                  90                  95

Glu Asn Glu Gln Lys Glu Val Ile Ala His Thr Val Gln Arg Tyr
            100                 105                 110

Leu Gln Glu Leu Trp His Gly Ser Leu Thr Trp Ala Ser Trp Lys Ile
        115                 120                 125

Leu Leu Leu Leu Val Ala Phe Ile Val Cys Pro Val Trp Ile Gly
    130                 135                 140

Phe Thr Phe Pro Met Gly His Lys Phe Asn Lys Val Pro Ile Ile Lys
145                 150                 155                 160

Phe Met Ser Tyr Leu Thr Ser His Ile Tyr Leu Met Ile His Leu Ser
                165                 170                 175

Ile Val Gly Ile Thr Pro Ile Tyr Pro Val Leu Arg Leu Ser Leu Val
            180                 185                 190
```

```
Pro Tyr Trp Tyr Glu Val Gly Leu Leu Ile Trp Leu Ser Gly Leu Leu
        195                 200                 205

Leu Phe Glu Leu Thr Asn Pro Ser Asp Lys Ser Gly Leu Gly Ser Ile
    210                 215                 220

Lys Val Leu Val Leu Leu Gly Met Ala Gly Val Gly Val His Val
225                 230                 235                 240

Ser Ala Phe Leu Phe Val Ser Lys Glu Tyr Trp Pro Thr Leu Val Tyr
                245                 250                 255

Cys Arg Asn Gln Cys Phe Ala Leu Ala Phe Leu Leu Ala Cys Val Gln
                260                 265                 270

Ile Leu Asp Phe Leu Ser Phe His His Leu Phe Gly Pro Trp Ala Ile
                275                 280                 285

Ile Ile Gly Asp Leu Leu Lys Asp Leu Ala Arg Phe Leu Ala Val Leu
        290                 295                 300

Ala Ile Phe Val Phe Gly Phe Ser Met His Ile Val Ala Leu Asn Gln
305                 310                 315                 320

Ser Phe Ala Asn Phe Ser Pro Glu Asp Leu Arg Ser Phe Glu Lys Lys
                325                 330                 335

Asn Arg Asn Arg Gly Tyr Phe Ser Asp Val Arg Met His Pro Ile Asn
                340                 345                 350

Ser Phe Glu Leu Leu Phe Phe Ala Val Phe Gly Gln Thr Thr Thr Glu
                355                 360                 365

Gln Thr Gln Val Asp Lys Ile Lys Asn Val Ala Thr Pro Thr Gln Pro
        370                 375                 380

Tyr Trp Val Glu Tyr Leu Phe Lys Ile Val Phe Gly Ile Tyr Met Leu
385                 390                 395                 400

Val Ser Val Val Val Leu Ile Asn Leu Leu Ile Ala Met Met Ser Asp
                405                 410                 415

Thr Tyr Gln Arg Ile Gln Val Val Leu Leu Asn Ala Leu Leu Ser Asn
                420                 425                 430

Ser Thr Leu Phe Ile Asn Ser Tyr Phe Asn His Lys Tyr Ile Asn Phe
        435                 440                 445

Ile Leu His Cys Val Leu Ile Ile Leu Tyr Phe Ser Ile Arg Ser Lys
                450                 455                 460

Phe Thr Tyr Glu Asp Asp Leu Tyr Phe Leu Asp Ile
465                 470                 475

<210> SEQ ID NO 101
<211> LENGTH: 862
<212> TYPE: PRT
<213> ORGANISM: Mus musculus

<400> SEQUENCE: 101

Met Leu Gly Ser Asn Thr Phe Lys Asn Met Gln Arg Arg His Thr Thr
1               5                   10                  15

Leu Arg Glu Lys Gly Arg Arg Gln Ala Ile Arg Gly Pro Ala Tyr Met
                20                  25                  30

Phe Asn Glu Lys Gly Thr Ser Leu Thr Pro Glu Glu Arg Phe Leu
            35                  40                  45

Asp Ser Ala Glu Tyr Gly Asn Ile Pro Val Val Arg Lys Met Leu Glu
    50                  55                  60

Glu Ser Lys Thr Leu Asn Phe Asn Cys Val Asp Tyr Met Gly Gln Asn
65              70                  75                  80

Ala Leu Gln Leu Ala Val Gly Asn Glu His Leu Glu Val Thr Glu Leu
                85                  90                  95
```

-continued

```
Leu Leu Lys Lys Glu Asn Leu Ala Arg Val Gly Asp Ala Leu Leu Leu
            100                 105                 110
Ala Ile Ser Lys Gly Tyr Val Arg Ile Val Glu Ala Ile Leu Ser His
        115                 120                 125
Pro Ala Phe Ala Gln Gly Gln Arg Leu Thr Leu Ser Pro Leu Glu Gln
    130                 135                 140
Glu Leu Arg Asp Asp Asp Phe Tyr Ala Tyr Asp Glu Asp Gly Thr Arg
145                 150                 155                 160
Phe Ser His Asp Ile Thr Pro Ile Ile Leu Ala Ala His Cys Gln Glu
                165                 170                 175
Tyr Glu Ile Val His Ile Leu Leu Lys Gly Ala Arg Ile Glu Arg
            180                 185                 190
Pro His Asp Tyr Phe Cys Lys Cys Asn Glu Cys Thr Glu Lys Gln Arg
        195                 200                 205
Lys Asp Ser Phe Ser His Ser Arg Ser Arg Met Asn Ala Tyr Lys Gly
    210                 215                 220
Leu Ala Ser Ala Ala Tyr Leu Ser Leu Ser Ser Glu Asp Pro Val Leu
225                 230                 235                 240
Thr Ala Leu Glu Leu Ser Asn Glu Leu Ala Arg Leu Ala Asn Ile Glu
                245                 250                 255
Thr Glu Phe Lys Asn Asp Tyr Arg Lys Leu Ser Met Gln Cys Lys Asp
            260                 265                 270
Phe Val Val Gly Val Leu Asp Leu Cys Arg Asp Thr Glu Glu Val Glu
        275                 280                 285
Ala Ile Leu Asn Gly Asp Val Asn Leu Gln Val Trp Ser Asp His His
    290                 295                 300
Arg Pro Ser Leu Ser Arg Ile Lys Leu Ala Ile Lys Tyr Glu Val Lys
305                 310                 315                 320
Lys Phe Val Ala His Pro Asn Cys Gln Gln Gln Leu Leu Thr Met Trp
                325                 330                 335
Tyr Glu Asn Leu Ser Gly Leu Arg Gln Gln Ser Ile Ala Val Lys Phe
            340                 345                 350
Leu Ala Val Phe Gly Val Ser Ile Gly Leu Pro Phe Leu Ala Ile Ala
        355                 360                 365
Tyr Trp Ile Ala Pro Cys Ser Lys Leu Gly Gln Thr Leu Arg Ser Pro
    370                 375                 380
Phe Met Lys Phe Val Ala His Ala Val Ser Phe Thr Ile Phe Leu Gly
385                 390                 395                 400
Leu Leu Val Val Asn Ala Ser Asp Arg Phe Glu Gly Val Lys Thr Leu
                405                 410                 415
Pro Asn Glu Thr Phe Thr Asp Tyr Pro Lys Gln Ile Phe Arg Val Lys
            420                 425                 430
Thr Thr Gln Phe Ser Trp Thr Glu Met Leu Ile Met Lys Trp Val Leu
        435                 440                 445
Gly Met Ile Trp Ser Glu Cys Lys Glu Ile Trp Glu Glu Gly Pro Arg
    450                 455                 460
Glu Tyr Val Leu His Leu Trp Asn Leu Leu Asp Phe Gly Met Leu Ser
465                 470                 475                 480
Ile Phe Val Ala Ser Phe Thr Ala Arg Phe Met Ala Phe Leu Lys Ala
                485                 490                 495
Ser Glu Ala Gln Leu Tyr Val Asp Gln Tyr Val Gln Asp Val Thr Leu
            500                 505                 510
```

-continued

```
His Asn Val Ser Leu Pro Pro Glu Val Ala Tyr Phe Thr Tyr Ala Arg
            515                 520                 525

Asp Lys Trp Trp Pro Ser Asp Pro Gln Ile Ile Ser Glu Gly Leu Tyr
        530                 535                 540

Ala Ile Ala Val Val Leu Ser Phe Ser Arg Ile Ala Tyr Ile Leu Pro
545                 550                 555                 560

Ala Asn Glu Ser Phe Gly Pro Leu Gln Ile Ser Leu Gly Arg Thr Val
                565                 570                 575

Lys Asp Ile Phe Lys Phe Met Val Ile Phe Ile Met Val Phe Val Ala
            580                 585                 590

Phe Met Ile Gly Met Phe Asn Leu Tyr Ser Tyr Tyr Arg Gly Ala Lys
        595                 600                 605

Tyr Asn Pro Ala Phe Thr Thr Val Glu Glu Ser Phe Lys Thr Leu Phe
610                 615                 620

Trp Ser Ile Phe Gly Leu Ser Glu Val Ile Ser Val Val Leu Lys Tyr
625                 630                 635                 640

Asp His Lys Phe Ile Glu Asn Ile Gly Tyr Val Leu Tyr Gly Val Tyr
                645                 650                 655

Asn Val Thr Met Val Val Val Leu Leu Asn Met Leu Ile Ala Met Ile
            660                 665                 670

Asn Asn Ser Tyr Gln Glu Ile Glu Glu Asp Ala Asp Val Glu Trp Lys
        675                 680                 685

Phe Ala Arg Ala Lys Leu Trp Leu Ser Tyr Phe Asp Glu Gly Arg Thr
690                 695                 700

Leu Pro Ala Pro Phe Asn Leu Val Pro Ser Pro Lys Ser Phe Tyr Tyr
705                 710                 715                 720

Leu Ile Met Arg Ile Lys Met Cys Leu Ile Glu Leu Cys Gln Ser Lys
                725                 730                 735

Ala Lys Arg Cys Glu Asn Asp Leu Glu Met Gly Met Leu Asn Ser Lys
            740                 745                 750

Phe Arg Lys Thr Arg Tyr Gln Ala Gly Met Arg Asn Ser Glu Asn Leu
        755                 760                 765

Thr Ala Asn Ser Thr Phe Ser Lys Pro Thr Arg Tyr Gln Lys Ile Met
770                 775                 780

Lys Arg Leu Ile Lys Arg Tyr Val Leu Lys Ala Gln Val Asp Arg Glu
785                 790                 795                 800

Asn Asp Glu Val Asn Glu Gly Glu Leu Lys Glu Ile Lys Gln Asp Ile
                805                 810                 815

Ser Ser Leu Arg Tyr Glu Leu Leu Glu Glu Lys Ser Gln Ala Thr Gly
            820                 825                 830

Glu Leu Ala Asp Leu Ile Gln Gln Leu Ser Glu Lys Phe Gly Lys Asn
        835                 840                 845

Leu Asn Lys Asp His Leu Arg Val Asn Gln Gly Lys Asp Ile
850                 855                 860
```

<210> SEQ ID NO 102
<211> LENGTH: 930
<212> TYPE: PRT
<213> ORGANISM: Mus musculus

<400> SEQUENCE: 102

```
Met Ser Gln Ser Pro Arg Phe Val Thr Arg Gly Gly Ser Leu Lys
1               5                   10                  15

Ala Ala Pro Gly Ala Gly Thr Arg Arg Asn Glu Ser Gln Asp Tyr Leu
            20                  25                  30
```

-continued

```
Leu Met Asp Glu Leu Gly Asp Asp Gly Tyr Pro Gln Leu Pro Leu Pro
        35                  40                  45
Pro Tyr Gly Tyr Tyr Pro Ser Phe Arg Gly Asn Glu Asn Arg Leu Thr
        50                  55                  60
His Arg Arg Gln Thr Ile Leu Arg Glu Lys Gly Arg Arg Leu Ala Asn
65                  70                  75                  80
Arg Gly Pro Ala Tyr Met Phe Asn Asp His Ser Thr Ser Leu Ser Ile
                85                  90                  95
Glu Glu Glu Arg Phe Leu Asp Ala Val Glu Tyr Gly Asn Ile Pro Val
                100                 105                 110
Val Trp Lys Met Leu Glu Glu Cys His Ser Leu Asn Val Asn Cys Val
                115                 120                 125
Asp Tyr Met Gly Gln Asn Ala Leu Gln Leu Ala Val Ala Asn Glu His
        130                 135                 140
Leu Glu Ile Thr Glu Leu Leu Leu Lys Lys Glu Asn Leu Ser Arg Val
145                 150                 155                 160
Gly Asp Ala Leu Leu Leu Ala Ile Ser Lys Gly Tyr Val Arg Ile Val
                165                 170                 175
Glu Ala Ile Leu Asn His Pro Ser Phe Ala Glu Gly Lys Arg Leu Ala
                180                 185                 190
Thr Ser Pro Ser Gln Ser Glu Leu Gln Gln Asp Asp Phe Tyr Ala Tyr
        195                 200                 205
Asp Glu Asp Gly Thr Arg Phe Ser His Asp Val Thr Pro Ile Ile Leu
        210                 215                 220
Ala Ala His Cys Gln Glu Tyr Glu Ile Val His Thr Leu Leu Arg Lys
225                 230                 235                 240
Gly Ala Arg Ile Glu Arg Pro His Asp Tyr Phe Cys Lys Cys Thr Glu
                245                 250                 255
Cys Ser Gln Lys Gln Lys His Asp Ser Phe Ser His Ser Arg Ser Arg
        260                 265                 270
Ile Asn Ala Tyr Lys Gly Leu Ala Ser Pro Ala Tyr Leu Ser Leu Ser
        275                 280                 285
Ser Glu Asp Pro Val Met Thr Ala Leu Glu Leu Ser Asn Glu Leu Ala
        290                 295                 300
Val Leu Ala Asn Ile Glu Lys Glu Phe Lys Asn Asp Tyr Arg Lys Leu
305                 310                 315                 320
Ser Met Gln Cys Lys Asp Phe Val Val Gly Leu Leu Asp Leu Cys Arg
                325                 330                 335
Asn Thr Glu Glu Val Glu Ala Ile Leu Asn Gly Asp Ala Glu Thr Arg
                340                 345                 350
Gln Pro Gly Asp Phe Gly Arg Pro Asn Leu Ser Arg Leu Lys Leu Ala
        355                 360                 365
Ile Lys Asp Glu Val Lys Lys Phe Val Ala His Pro Asn Cys Gln Gln
        370                 375                 380
Gln Leu Leu Ser Ile Trp Tyr Glu Asn Leu Ser Gly Leu Arg Gln Gln
385                 390                 395                 400
Thr Met Ala Val Lys Phe Leu Val Val Leu Ala Val Ala Ile Gly Leu
                405                 410                 415
Pro Phe Leu Ala Leu Ile Tyr Trp Cys Ala Pro Cys Ser Lys Met Gly
                420                 425                 430
Lys Ile Leu Pro Arg Pro Phe Met Lys Phe Val Ala His Ala Ala Ser
        435                 440                 445
```

-continued

```
Phe Thr Ile Phe Leu Gly Leu Leu Val Met Asn Ala Ala Asp Arg Phe
    450                 455                 460

Glu Gly Thr Lys Leu Leu Pro Asn Glu Thr Ser Thr Asp Asn Ala Arg
465                 470                 475                 480

Gln Leu Phe Arg Met Lys Thr Ser Cys Phe Ser Trp Met Glu Met Leu
                485                 490                 495

Ile Ile Ser Trp Val Ile Gly Met Ile Trp Ala Glu Cys Lys Glu Ile
            500                 505                 510

Trp Thr Gln Gly Pro Lys Glu Tyr Leu Phe Glu Leu Trp Asn Met Leu
        515                 520                 525

Asp Phe Gly Met Leu Ala Ile Phe Ala Ala Ser Phe Ile Ala Arg Phe
    530                 535                 540

Met Ala Phe Trp His Ala Ser Lys Ala Gln Ser Ile Ile Asp Ala Asn
545                 550                 555                 560

Asp Thr Leu Lys Asp Leu Thr Lys Val Thr Leu Gly Asp Asn Val Lys
                565                 570                 575

Tyr Tyr Asn Leu Ala Arg Ile Lys Trp Asp Pro Thr Asp Pro Gln Ile
                580                 585                 590

Ile Ser Glu Gly Leu Tyr Ala Ile Ala Val Val Leu Ser Phe Ser Arg
            595                 600                 605

Ile Ala Tyr Ile Leu Pro Ala Asn Glu Ser Phe Gly Pro Leu Gln Ile
        610                 615                 620

Ser Leu Gly Arg Thr Val Lys Asp Ile Phe Lys Phe Met Val Ile Phe
625                 630                 635                 640

Ile Met Val Phe Val Ala Phe Met Ile Gly Met Phe Asn Leu Tyr Ser
                645                 650                 655

Tyr Tyr Ile Gly Ala Lys Gln Asn Glu Ala Phe Thr Thr Val Glu Glu
                660                 665                 670

Ser Phe Lys Thr Leu Phe Trp Ala Ile Phe Gly Leu Ser Glu Val Lys
            675                 680                 685

Ser Val Val Ile Asn Tyr Asn His Lys Phe Ile Glu Asn Ile Gly Tyr
        690                 695                 700

Val Leu Tyr Gly Val Tyr Asn Val Thr Met Val Ile Val Leu Leu Asn
705                 710                 715                 720

Met Leu Ile Ala Met Ile Asn Ser Ser Phe Gln Glu Ile Glu Asp Asp
                725                 730                 735

Ala Asp Val Glu Trp Lys Phe Ala Arg Ala Lys Leu Trp Phe Ser Tyr
                740                 745                 750

Phe Glu Glu Gly Arg Thr Leu Pro Val Pro Phe Asn Leu Val Pro Ser
            755                 760                 765

Pro Lys Ser Leu Leu Tyr Leu Leu Lys Phe Lys Lys Trp Met Cys
        770                 775                 780

Glu Leu Ile Gln Gly Gln Lys Gln Gly Phe Gln Glu Asp Ala Glu Met
785                 790                 795                 800

Asn Lys Arg Asn Glu Glu Lys Lys Phe Gly Ile Ser Gly Ser His Glu
                805                 810                 815

Asp Leu Ser Lys Phe Ser Leu Asp Lys Asn Gln Leu Ala His Asn Lys
                820                 825                 830

Gln Ser Ser Thr Arg Ser Ser Glu Asp Tyr His Leu Asn Ser Phe Ser
            835                 840                 845

Asn Pro Pro Arg Gln Tyr Gln Lys Ile Met Lys Arg Leu Ile Lys Arg
        850                 855                 860
```

```
Tyr Val Leu Gln Ala Gln Ile Asp Lys Glu Ser Asp Glu Val Asn Glu
865                 870                 875                 880

Gly Glu Leu Lys Glu Ile Lys Gln Asp Ile Ser Ser Leu Arg Tyr Glu
            885                 890                 895

Leu Leu Glu Glu Lys Ser Gln Asn Ser Glu Asp Leu Ala Glu Leu Ile
                900                 905                 910

Arg Lys Leu Gly Glu Arg Leu Ser Leu Glu Pro Lys Leu Glu Glu Ser
        915                 920                 925

Arg Arg
    930

<210> SEQ ID NO 103
<211> LENGTH: 836
<212> TYPE: PRT
<213> ORGANISM: Mus musculus

<400> SEQUENCE: 103

Met Arg Asp Lys Gly Arg Arg Gln Ala Val Arg Gly Pro Ala Phe Met
1               5                   10                  15

Phe Gly Ala Arg Gly Pro Ser Leu Thr Ala Glu Glu Arg Phe Leu
            20                  25                  30

Asp Ala Ala Glu Tyr Gly Asn Ile Pro Val Val Arg Lys Met Leu Glu
        35                  40                  45

Glu Ser Arg Thr Leu Asn Val Asn Cys Val Asp Tyr Met Gly Gln Asn
    50                  55                  60

Ala Leu Gln Leu Ala Val Gly Asn Glu His Leu Glu Val Thr Glu Leu
65                  70                  75                  80

Leu Leu Lys Lys Glu Asn Leu Ala Arg Ile Gly Asp Ala Leu Leu Leu
                85                  90                  95

Ala Ile Ser Lys Gly Tyr Val Arg Ile Val Glu Ala Ile Leu Gly His
            100                 105                 110

Pro Gly Phe Ala Ala Ser Arg Arg Leu Thr Leu Ser Pro Cys Glu Gln
        115                 120                 125

Glu Leu Arg Asp Asp Asp Phe Tyr Ala Tyr Asp Glu Asp Gly Thr Arg
130                 135                 140

Phe Ser Pro Asp Ile Thr Pro Ile Ile Leu Ala Ala His Cys His Lys
145                 150                 155                 160

Tyr Glu Val Val His Leu Leu Leu Leu Lys Gly Ala Arg Ile Glu Arg
                165                 170                 175

Ala His Asp Tyr Phe Cys Arg Cys Ser Asp Cys Ala Glu Lys Gln Arg
            180                 185                 190

Leu Asp Ala Phe Ser His Ser Arg Ser Arg Ile Asn Ala Tyr Lys Gly
        195                 200                 205

Leu Ala Ser Pro Ala Tyr Leu Ser Leu Ser Ser Glu Asp Pro Val Leu
    210                 215                 220

Thr Ala Leu Glu Leu Ser Asn Glu Leu Ala Lys Leu Ala Asn Ile Glu
225                 230                 235                 240

Lys Glu Phe Lys Asn Asp Tyr Arg Lys Leu Ser Met Gln Cys Lys Asp
                245                 250                 255

Phe Val Val Gly Val Leu Asp Leu Cys Arg Asp Ser Glu Glu Val Glu
            260                 265                 270

Ala Ile Leu Asn Gly Asp Leu Glu Ser Ala Glu Pro Leu Glu Arg His
        275                 280                 285

Gly His Lys Ala Ser Leu Ser Arg Val Lys Leu Ala Ile Lys Tyr Glu
    290                 295                 300
```

-continued

```
Val Lys Lys Phe Val Ala His Pro Asn Cys Gln Gln Leu Leu Thr
305                 310                 315                 320

Ile Trp Tyr Glu Asn Leu Ser Gly Leu Arg Glu Gln Thr Ile Ala Ile
                325                 330                 335

Lys Cys Leu Val Val Leu Val Val Ala Leu Gly Leu Pro Phe Leu Ala
                340                 345                 350

Ile Gly Tyr Trp Ile Ala Pro Cys Ser Arg Leu Gly Lys Ile Leu Arg
            355                 360                 365

Ser Pro Phe Met Lys Phe Val Ala His Ala Ala Ser Phe Ile Ile Phe
    370                 375                 380

Leu Gly Leu Leu Val Phe Asn Ala Ser Asp Arg Phe Glu Gly Ile Thr
385                 390                 395                 400

Thr Leu Pro Asn Ile Thr Val Ile Asp Tyr Pro Lys Gln Ile Phe Arg
                405                 410                 415

Val Lys Thr Thr Gln Phe Thr Trp Thr Glu Met Leu Ile Met Val Trp
                420                 425                 430

Val Leu Gly Met Met Trp Ser Glu Cys Lys Glu Leu Trp Leu Glu Gly
            435                 440                 445

Pro Arg Glu Tyr Ile Val Gln Leu Trp Asn Val Leu Asp Phe Gly Met
    450                 455                 460

Leu Ser Ile Phe Ile Ala Ala Phe Thr Ala Arg Phe Leu Ala Phe Leu
465                 470                 475                 480

Gln Ala Thr Lys Ala Gln Gln Tyr Val Asp Ser His Val Gln Glu Ser
                485                 490                 495

Asp Leu Ser Glu Val Thr Leu Pro Pro Glu Val Gln Tyr Phe Thr Tyr
            500                 505                 510

Ala Arg Asp Lys Trp Leu Pro Ser Asp Pro Gln Ile Ile Ser Glu Gly
            515                 520                 525

Leu Tyr Ala Ile Ala Val Val Leu Ser Phe Ser Arg Ile Ala Tyr Ile
    530                 535                 540

Leu Pro Ala Asn Glu Ser Phe Gly Pro Leu Gln Ile Ser Leu Gly Arg
545                 550                 555                 560

Thr Val Lys Asp Ile Phe Lys Phe Met Val Leu Phe Ile Met Val Phe
                565                 570                 575

Leu Ala Phe Met Ile Gly Met Phe Ile Leu Tyr Ser Tyr Tyr Leu Gly
                580                 585                 590

Ala Lys Val Asn Pro Ala Phe Thr Thr Val Glu Glu Ser Phe Lys Thr
            595                 600                 605

Leu Phe Trp Ser Ile Phe Gly Leu Ser Glu Val Thr Ser Val Val Leu
610                 615                 620

Lys Tyr Asp His Lys Phe Ile Glu Asn Ile Gly Tyr Val Leu Tyr Gly
625                 630                 635                 640

Ile Tyr Asn Val Thr Met Val Val Leu Leu Asn Met Leu Ile Ala
            645                 650                 655

Met Ile Asn Ser Ser Tyr Gln Glu Ile Glu Asp Asp Ser Asp Val Glu
                660                 665                 670

Trp Lys Phe Ala Arg Ser Lys Leu Trp Leu Ser Tyr Phe Asp Asp Gly
                675                 680                 685

Lys Thr Leu Pro Pro Pro Phe Ser Leu Val Pro Ser Pro Lys Ser Phe
            690                 695                 700

Val Tyr Phe Ile Met Arg Ile Thr Asn Phe Ser Lys Cys Arg Arg Arg
705                 710                 715                 720
```

-continued

```
Arg Leu Gln Lys Asp Leu Glu Leu Gly Met Gly Asn Ser Lys Ser Arg
                725                 730                 735

Leu Asn Leu Phe Thr Gln Ser Asn Ser Arg Val Phe Glu Ser His Ser
            740                 745                 750

Phe Asn Ser Ile Leu Asn Gln Pro Thr Arg Tyr Gln Gln Ile Met Lys
        755                 760                 765

Arg Leu Ile Lys Arg Tyr Val Leu Lys Ala Gln Val Asp Lys Glu Asn
    770                 775                 780

Asp Glu Val Asn Glu Gly Leu Lys Glu Ile Lys Gln Asp Ile Ser
785                 790                 795                 800

Ser Leu Arg Tyr Glu Leu Leu Glu Asp Lys Ser Gln Ala Thr Glu Glu
                805                 810                 815

Leu Ala Ile Leu Ile His Lys Leu Ser Glu Lys Leu Asn Pro Ser Val
            820                 825                 830

Leu Arg Cys Glu
        835

<210> SEQ ID NO 104
<211> LENGTH: 1503
<212> TYPE: PRT
<213> ORGANISM: Homo sapiens

<400> SEQUENCE: 104

Met Glu Pro Ser Ala Leu Arg Lys Ala Gly Ser Glu Gln Glu Glu Gly
1               5                   10                  15

Phe Glu Gly Leu Pro Arg Arg Val Thr Asp Leu Gly Met Val Ser Asn
            20                  25                  30

Leu Arg Arg Ser Asn Ser Ser Leu Phe Lys Ser Trp Arg Leu Gln Cys
        35                  40                  45

Pro Phe Gly Asn Asn Asp Lys Gln Glu Ser Leu Ser Ser Trp Ile Pro
    50                  55                  60

Glu Asn Ile Lys Lys Lys Glu Cys Val Tyr Phe Val Glu Ser Ser Lys
65                  70                  75                  80

Leu Ser Asp Ala Gly Lys Val Val Cys Gln Cys Gly Tyr Thr His Glu
                85                  90                  95

Gln His Leu Glu Glu Ala Thr Lys Pro His Thr Phe Gln Gly Thr Gln
            100                 105                 110

Trp Asp Pro Lys Lys His Val Gln Glu Met Pro Thr Asp Ala Phe Gly
        115                 120                 125

Asp Ile Val Phe Thr Gly Leu Ser Gln Lys Val Lys Lys Tyr Val Arg
    130                 135                 140

Val Ser Gln Asp Thr Pro Ser Ser Val Ile Tyr His Leu Met Thr Gln
145                 150                 155                 160

His Trp Gly Leu Asp Val Pro Asn Leu Leu Ile Ser Val Thr Gly Gly
                165                 170                 175

Ala Lys Asn Phe Asn Met Lys Pro Arg Leu Lys Ser Ile Phe Arg Arg
            180                 185                 190

Gly Leu Val Lys Val Ala Gln Thr Thr Gly Ala Trp Ile Ile Thr Gly
        195                 200                 205

Gly Ser His Thr Gly Val Met Lys Gln Val Gly Glu Ala Val Arg Asp
    210                 215                 220

Phe Ser Leu Ser Ser Ser Tyr Lys Glu Gly Glu Leu Ile Thr Ile Gly
225                 230                 235                 240

Val Ala Thr Trp Gly Thr Val His Arg Arg Glu Gly Leu Ile His Pro
                245                 250                 255
```

-continued

```
Thr Gly Ser Phe Pro Ala Glu Tyr Ile Leu Asp Glu Asp Gly Gln Gly
            260                 265                 270

Asn Leu Thr Cys Leu Asp Ser Asn His Ser His Phe Ile Leu Val Asp
            275                 280                 285

Asp Gly Thr His Gly Gln Tyr Gly Val Glu Ile Pro Leu Arg Thr Arg
            290                 295                 300

Leu Glu Lys Phe Ile Ser Glu Gln Thr Lys Glu Arg Gly Gly Val Ala
305                 310                 315                 320

Ile Lys Ile Pro Ile Val Cys Val Leu Glu Gly Pro Gly Thr
                    325                 330                 335

Leu His Thr Ile Asp Asn Ala Thr Thr Asn Gly Thr Pro Cys Val Val
            340                 345                 350

Val Glu Gly Ser Gly Arg Val Ala Asp Val Ile Ala Gln Val Ala Asn
            355                 360                 365

Leu Pro Val Ser Asp Ile Thr Ile Ser Leu Ile Gln Gln Lys Leu Ser
            370                 375                 380

Val Phe Phe Gln Glu Met Phe Glu Thr Phe Thr Glu Ser Arg Ile Val
385                 390                 395                 400

Glu Trp Thr Lys Lys Ile Gln Asp Ile Val Arg Arg Gln Leu Leu
                    405                 410                 415

Thr Val Phe Arg Glu Gly Lys Asp Gly Gln Gln Asp Val Asp Val Ala
            420                 425                 430

Ile Leu Gln Ala Leu Leu Lys Ala Ser Arg Ser Gln Asp His Phe Gly
            435                 440                 445

His Glu Asn Trp Asp His Gln Leu Lys Leu Ala Val Ala Trp Asn Arg
450                 455                 460

Val Asp Ile Ala Arg Ser Glu Ile Phe Met Asp Glu Trp Gln Trp Lys
465                 470                 475                 480

Pro Ser Asp Leu His Pro Thr Met Thr Ala Ala Leu Ile Ser Asn Lys
                    485                 490                 495

Pro Glu Phe Val Lys Leu Phe Leu Glu Asn Gly Val Gln Leu Lys Glu
            500                 505                 510

Phe Val Thr Trp Asp Thr Leu Leu Tyr Leu Tyr Glu Asn Leu Asp Pro
            515                 520                 525

Ser Cys Leu Phe His Ser Lys Leu Gln Lys Val Leu Val Glu Asp Pro
530                 535                 540

Glu Arg Pro Ala Cys Ala Pro Ala Ala Pro Arg Leu Gln Met His His
545                 550                 555                 560

Val Ala Gln Val Leu Arg Glu Leu Leu Gly Asp Phe Thr Gln Pro Leu
                    565                 570                 575

Tyr Pro Arg Pro Arg His Asn Asp Arg Leu Arg Leu Leu Pro Val
            580                 585                 590

Pro His Val Lys Leu Asn Val Gln Gly Val Ser Leu Arg Ser Leu Tyr
            595                 600                 605

Lys Arg Ser Ser Gly His Val Thr Phe Thr Met Asp Pro Ile Arg Asp
610                 615                 620

Leu Leu Ile Trp Ala Ile Val Gln Asn Arg Arg Glu Leu Ala Gly Ile
625                 630                 635                 640

Ile Trp Ala Gln Ser Gln Asp Cys Ile Ala Ala Leu Ala Cys Ser
                    645                 650                 655

Lys Ile Leu Lys Glu Leu Ser Lys Glu Glu Asp Thr Asp Ser Ser
            660                 665                 670
```

```
Glu Glu Met Leu Ala Leu Ala Glu Glu Tyr Glu His Arg Ala Ile Gly
            675                 680                 685

Val Phe Thr Glu Cys Tyr Arg Lys Asp Glu Glu Arg Ala Gln Lys Leu
        690                 695                 700

Leu Thr Arg Val Ser Glu Ala Trp Gly Lys Thr Thr Cys Leu Gln Leu
705                 710                 715                 720

Ala Leu Glu Ala Lys Asp Met Lys Phe Val Ser His Gly Gly Ile Gln
                725                 730                 735

Ala Phe Leu Thr Lys Val Trp Trp Gly Gln Leu Ser Val Asp Asn Gly
                740                 745                 750

Leu Trp Arg Val Thr Leu Cys Met Leu Ala Phe Pro Leu Leu Leu Thr
                755                 760                 765

Gly Leu Ile Ser Phe Arg Glu Lys Arg Leu Gln Asp Val Gly Thr Pro
        770                 775                 780

Ala Ala Arg Ala Arg Ala Phe Phe Thr Ala Pro Val Val Phe His
785                 790                 795                 800

Leu Asn Ile Leu Ser Tyr Phe Ala Phe Leu Cys Leu Phe Ala Tyr Val
                805                 810                 815

Leu Met Val Asp Phe Gln Pro Val Pro Ser Trp Cys Glu Cys Ala Ile
                820                 825                 830

Tyr Leu Trp Leu Phe Ser Leu Val Cys Glu Glu Met Arg Gln Leu Phe
        835                 840                 845

Tyr Asp Pro Asp Glu Cys Gly Leu Met Lys Lys Ala Ala Leu Tyr Phe
        850                 855                 860

Ser Asp Phe Trp Asn Lys Leu Asp Val Gly Ala Ile Leu Leu Phe Val
865                 870                 875                 880

Ala Gly Leu Thr Cys Arg Leu Ile Pro Ala Thr Leu Tyr Pro Gly Arg
                885                 890                 895

Val Ile Leu Ser Leu Asp Phe Ile Leu Phe Cys Leu Arg Leu Met His
                900                 905                 910

Ile Phe Thr Ile Ser Lys Thr Leu Gly Pro Lys Ile Ile Val Lys
                915                 920                 925

Arg Met Met Lys Asp Val Phe Phe Phe Leu Phe Leu Leu Ala Val Trp
930                 935                 940

Val Val Ser Phe Gly Val Ala Lys Gln Ala Ile Leu Ile His Asn Glu
945                 950                 955                 960

Arg Arg Val Asp Trp Leu Phe Arg Gly Ala Val Tyr His Ser Tyr Leu
                965                 970                 975

Thr Ile Phe Gly Gln Ile Pro Gly Tyr Ile Asp Gly Val Asn Phe Asn
                980                 985                 990

Pro Glu His Cys Ser Pro Asn Gly Thr Asp Pro Tyr Lys Pro Lys Cys
                995                 1000                1005

Pro Glu Ser Asp Ala Thr Gln Gln Arg Pro Ala Phe Pro Glu Trp
        1010                1015                1020

Leu Thr Val Leu Leu Leu Cys Leu Tyr Leu Leu Phe Thr Asn Ile
        1025                1030                1035

Leu Leu Leu Asn Leu Leu Ile Ala Met Phe Asn Tyr Thr Phe Gln
        1040                1045                1050

Gln Val Gln Glu His Thr Asp Gln Ile Trp Lys Phe Gln Arg His
        1055                1060                1065

Asp Leu Ile Glu Glu Tyr His Gly Arg Pro Ala Ala Pro Pro Pro
        1070                1075                1080
```

-continued

```
Phe Ile Leu Leu Ser His Leu Gln Leu Phe Ile Lys Arg Val Val
    1085                1090                1095

Leu Lys Thr Pro Ala Lys Arg His Lys Gln Leu Lys Asn Lys Leu
    1100                1105                1110

Glu Lys Asn Glu Glu Ala Ala Leu Leu Ser Trp Glu Ile Tyr Leu
    1115                1120                1125

Lys Glu Asn Tyr Leu Gln Asn Arg Gln Phe Gln Gln Lys Gln Arg
    1130                1135                1140

Pro Glu Gln Lys Ile Glu Asp Ile Ser Asn Lys Val Asp Ala Met
    1145                1150                1155

Val Asp Leu Leu Asp Leu Asp Pro Leu Lys Arg Ser Gly Ser Met
    1160                1165                1170

Glu Gln Arg Leu Ala Ser Leu Glu Glu Gln Val Ala Gln Thr Ala
    1175                1180                1185

Arg Ala Leu His Trp Ile Val Arg Thr Leu Arg Ala Ser Gly Phe
    1190                1195                1200

Ser Ser Glu Ala Asp Val Pro Thr Leu Ala Ser Gln Lys Ala Ala
    1205                1210                1215

Glu Glu Pro Asp Ala Glu Pro Gly Gly Arg Lys Lys Thr Glu Glu
    1220                1225                1230

Pro Gly Asp Ser Tyr His Val Asn Ala Arg His Leu Leu Tyr Pro
    1235                1240                1245

Asn Cys Pro Val Thr Arg Phe Pro Val Pro Asn Glu Lys Val Pro
    1250                1255                1260

Trp Glu Thr Glu Phe Leu Ile Tyr Asp Pro Pro Phe Tyr Thr Ala
    1265                1270                1275

Glu Arg Lys Asp Ala Ala Ala Met Asp Pro Met Gly Asp Thr Leu
    1280                1285                1290

Glu Pro Leu Ser Thr Ile Gln Tyr Asn Val Val Asp Gly Leu Arg
    1295                1300                1305

Asp Arg Arg Ser Phe His Gly Pro Tyr Thr Val Gln Ala Gly Leu
    1310                1315                1320

Pro Leu Asn Pro Met Gly Arg Thr Gly Leu Arg Gly Arg Gly Ser
    1325                1330                1335

Leu Ser Cys Phe Gly Pro Asn His Thr Leu Tyr Pro Met Val Thr
    1340                1345                1350

Arg Trp Arg Arg Asn Glu Asp Gly Ala Ile Cys Arg Lys Ser Ile
    1355                1360                1365

Lys Lys Met Leu Glu Val Leu Val Val Lys Leu Pro Leu Ser Glu
    1370                1375                1380

His Trp Ala Leu Pro Gly Gly Ser Arg Glu Pro Gly Glu Met Leu
    1385                1390                1395

Pro Arg Lys Leu Lys Arg Ile Leu Arg Gln Glu His Trp Pro Ser
    1400                1405                1410

Phe Glu Asn Leu Leu Lys Cys Gly Met Glu Val Tyr Lys Gly Tyr
    1415                1420                1425

Met Asp Asp Pro Arg Asn Thr Asp Asn Ala Trp Ile Glu Thr Val
    1430                1435                1440

Ala Val Ser Val His Phe Gln Asp Gln Asn Asp Val Glu Leu Asn
    1445                1450                1455

Arg Leu Asn Ser Asn Leu His Ala Cys Asp Ser Gly Ala Ser Ile
    1460                1465                1470
```

```
Arg Trp Gln Val Val Asp Arg Ile Pro Leu Tyr Ala Asn His
    1475                1480                1485

Lys Thr Leu Leu Gln Lys Ala Ala Ala Glu Phe Gly Ala His Tyr
    1490                1495                1500

<210> SEQ ID NO 105
<211> LENGTH: 966
<212> TYPE: PRT
<213> ORGANISM: Mus musculus

<400> SEQUENCE: 105

Met Ala Gln Leu Tyr Tyr Lys Lys Val Asn Tyr Ser Pro Tyr Arg Asp
1               5                   10                  15

Arg Ile Pro Leu Gln Ile Val Arg Ala Glu Thr Glu Leu Ser Ala Glu
                20                  25                  30

Glu Lys Ala Phe Leu Ser Ala Val Glu Lys Gly Asp Tyr Ala Thr Val
            35                  40                  45

Lys Gln Ala Leu Gln Glu Ala Glu Ile Tyr Tyr Asn Val Asn Ile Asn
        50                  55                  60

Cys Met Asp Pro Leu Gly Arg Ser Ala Leu Leu Ile Ala Ile Glu Asn
65                  70                  75                  80

Glu Asn Leu Glu Ile Met Glu Leu Leu Leu Asn His Ser Val Tyr Val
                85                  90                  95

Gly Asp Ala Leu Leu Tyr Ala Ile Arg Lys Glu Val Val Gly Ala Val
            100                 105                 110

Glu Leu Leu Leu Ser Tyr Arg Lys Pro Ser Gly Glu Lys Gln Val Pro
        115                 120                 125

Thr Leu Met Met Asp Thr Gln Phe Ser Glu Phe Thr Pro Asp Ile Thr
130                 135                 140

Pro Ile Met Leu Ala Ala His Thr Asn Asn Tyr Glu Ile Ile Lys Leu
145                 150                 155                 160

Leu Val Gln Lys Arg Val Thr Ile Pro Arg Pro His Gln Ile Arg Cys
                165                 170                 175

Asn Cys Val Glu Cys Val Ser Ser Ser Glu Val Asp Ser Leu Arg His
            180                 185                 190

Ser Arg Ser Arg Leu Asn Ile Tyr Lys Ala Leu Ala Ser Pro Ser Leu
        195                 200                 205

Ile Ala Leu Ser Ser Glu Asp Pro Ile Leu Thr Ala Phe Arg Leu Gly
    210                 215                 220

Trp Glu Leu Lys Glu Leu Ser Lys Val Glu Asn Glu Phe Lys Ala Glu
225                 230                 235                 240

Tyr Glu Glu Leu Ser Gln Gln Cys Lys Leu Phe Ala Lys Asp Leu Leu
                245                 250                 255

Asp Gln Ala Arg Ser Ser Arg Glu Leu Glu Ile Ile Leu Asn His Arg
            260                 265                 270

Asp Asp His Ser Glu Glu Leu Asp Pro Gln Lys Tyr His Asp Leu Ala
        275                 280                 285

Lys Leu Lys Val Ala Ile Lys Tyr His Gln Lys Glu Phe Val Ala Gln
    290                 295                 300

Pro Asn Cys Gln Gln Leu Leu Ala Thr Leu Trp Tyr Asp Gly Phe Pro
305                 310                 315                 320

Gly Trp Arg Arg Lys His Trp Val Val Lys Leu Leu Thr Cys Met Thr
                325                 330                 335

Ile Gly Phe Leu Phe Pro Met Leu Ser Ile Ala Tyr Leu Ile Ser Pro
            340                 345                 350
```

-continued

```
Arg Ser Asn Leu Gly Leu Phe Ile Lys Lys Pro Phe Ile Lys Phe Ile
        355                 360                 365

Cys His Thr Ala Ser Tyr Leu Thr Phe Leu Phe Met Leu Leu Leu Ala
        370                 375                 380

Ser Gln His Ile Val Arg Thr Asp Leu His Val Gln Gly Pro Pro Pro
385                 390                 395                 400

Thr Val Val Glu Trp Met Ile Leu Pro Trp Val Leu Gly Phe Ile Trp
                    405                 410                 415

Gly Glu Ile Lys Glu Met Trp Asp Gly Gly Phe Thr Glu Tyr Ile His
                420                 425                 430

Asp Trp Trp Asn Leu Met Asp Phe Ala Met Asn Ser Leu Tyr Leu Ala
            435                 440                 445

Thr Ile Ser Leu Lys Ile Val Ala Tyr Val Lys Tyr Asn Gly Ser Arg
        450                 455                 460

Pro Arg Glu Glu Trp Glu Met Trp His Pro Thr Leu Ile Ala Glu Ala
465                 470                 475                 480

Leu Phe Ala Ile Ser Asn Ile Leu Ser Ser Leu Arg Leu Ile Ser Leu
                    485                 490                 495

Phe Thr Ala Asn Ser His Leu Gly Pro Leu Gln Ile Ser Leu Gly Arg
                500                 505                 510

Met Leu Leu Asp Ile Leu Lys Phe Leu Phe Ile Tyr Cys Leu Val Leu
            515                 520                 525

Leu Ala Phe Ala Asn Gly Leu Asn Gln Leu Tyr Phe Tyr Tyr Glu Thr
        530                 535                 540

Arg Ala Ile Asp Glu Pro Asn Asn Cys Lys Gly Ile Arg Cys Glu Lys
545                 550                 555                 560

Gln Asn Asn Ala Phe Ser Thr Leu Phe Glu Thr Leu Gln Ser Leu Phe
                    565                 570                 575

Trp Ser Val Phe Gly Leu Leu Asn Leu Tyr Val Thr Asn Val Lys Ala
                580                 585                 590

Arg His Glu Phe Thr Glu Phe Val Gly Ala Thr Met Phe Gly Thr Tyr
            595                 600                 605

Asn Val Ile Ser Leu Val Val Leu Leu Asn Met Leu Ile Ala Met Met
        610                 615                 620

Asn Asn Ser Tyr Gln Leu Ile Ala Asp His Ala Asp Ile Glu Trp Lys
625                 630                 635                 640

Phe Ala Arg Thr Lys Leu Trp Met Ser Tyr Phe Asp Glu Gly Gly Thr
                    645                 650                 655

Leu Pro Pro Pro Phe Asn Ile Ile Pro Ser Pro Lys Ser Phe Leu Tyr
                660                 665                 670

Leu Gly Asn Trp Phe Asn Asn Thr Phe Cys Pro Lys Arg Asp Pro Asp
            675                 680                 685

Gly Arg Arg Arg Arg His Asn Leu Arg Ser Phe Thr Glu Arg His Ala
        690                 695                 700

Asp Ser Leu Ile Gln Asn Gln His Tyr Gln Glu Val Ile Arg Asn Leu
705                 710                 715                 720

Val Lys Arg Tyr Val Ala Ala Met Ile Arg Asn Ser Lys Thr Asn Glu
                    725                 730                 735

Gly Leu Thr Glu Glu Asn Phe Lys Glu Leu Lys Gln Asp Ile Ser Ser
                740                 745                 750

Phe Arg Tyr Glu Val Leu Asp Leu Leu Gly Asn Arg Lys His Pro Arg
            755                 760                 765
```

-continued

```
Arg Ser Leu Ser Thr Ser Ser Ala Asp Phe Ser Gln Arg Asp Asp Thr
        770                 775                 780
Asn Asp Gly Ser Gly Gly Ala Arg Ala Lys Ser Lys Ser Val Ser Phe
785                 790                 795                 800
Asn Val Gly Cys Lys Lys Ala Cys His Gly Ala Pro Leu Ile Arg
                805                 810                 815
Thr Val Pro Arg Ala Ser Gly Ala Gln Gly Lys Pro Lys Ser Glu Ser
            820                 825                 830
Ser Ser Lys Arg Ser Phe Met Gly Pro Ser Phe Lys Lys Leu Gly Leu
        835                 840                 845
Phe Phe Ser Lys Phe Asn Gly Gln Thr Ser Glu Pro Thr Ser Glu Pro
    850                 855                 860
Met Tyr Thr Ile Ser Asp Gly Ile Ala Gln Gln His Cys Met Trp Gln
865                 870                 875                 880
Asp Ile Arg Tyr Ser Gln Met Glu Lys Gly Lys Ala Glu Ala Cys Ser
                885                 890                 895
Gln Ser Gln Met Asn Leu Gly Glu Val Glu Leu Gly Glu Ile Arg Gly
            900                 905                 910
Ala Ala Ala Arg Ser Ser Glu Cys Pro Leu Ala Cys Ser Ser Ser Leu
        915                 920                 925
His Cys Ala Ser Gly Ile Cys Ser Ser Asn Ser Lys Leu Leu Asp Ser
    930                 935                 940
Ser Glu Asp Val Phe Glu Thr Trp Gly Glu Ala Cys Asp Leu Leu Met
945                 950                 955                 960
His Lys Trp Gly Asp Gly
                965
```

```
<210> SEQ ID NO 106
<211> LENGTH: 974
<212> TYPE: PRT
<213> ORGANISM: Mus musculus

<400> SEQUENCE: 106
```

```
Met Ala Gln Phe Tyr Tyr Lys Arg Asn Val Asn Ala Pro Tyr Arg Asp
1               5                   10                  15
Arg Ile Pro Leu Arg Ile Val Arg Ala Glu Ser Glu Leu Ser Pro Ser
            20                  25                  30
Glu Lys Ala Tyr Leu Asn Ala Val Glu Lys Gly Asp Tyr Ala Ser Val
        35                  40                  45
Lys Lys Ser Leu Glu Glu Ala Glu Ile Tyr Phe Lys Ile Asn Ile Asn
    50                  55                  60
Cys Ile Asp Pro Leu Gly Arg Thr Ala Leu Leu Ile Ala Ile Glu Asn
65                  70                  75                  80
Glu Asn Leu Glu Leu Ile Glu Leu Leu Leu Ser Phe Asn Val Tyr Val
                85                  90                  95
Gly Asp Ala Leu Leu His Ala Ile Arg Lys Glu Val Val Gly Ala Val
            100                 105                 110
Glu Leu Leu Leu Asn His Lys Lys Pro Ser Gly Glu Lys Gln Val Pro
        115                 120                 125
Pro Ile Leu Leu Asp Lys Gln Phe Ser Glu Phe Thr Pro Asp Ile Thr
    130                 135                 140
Pro Ile Ile Leu Ala Ala His Thr Asn Asn Tyr Glu Ile Ile Lys Leu
145                 150                 155                 160
Leu Val Gln Lys Gly Val Ser Val Pro Arg Pro His Glu Val Arg Cys
                165                 170                 175
```

-continued

```
Asn Cys Val Glu Cys Val Ser Ser Ser Asp Val Asp Ser Leu Arg His
                180                 185                 190

Ser Arg Ser Arg Leu Asn Ile Tyr Lys Ala Leu Ala Ser Pro Ser Leu
            195                 200                 205

Ile Ala Leu Ser Ser Glu Asp Pro Phe Leu Thr Ala Phe Gln Leu Ser
        210                 215                 220

Trp Glu Leu Gln Glu Leu Ser Lys Val Glu Asn Glu Phe Lys Ser Glu
225                 230                 235                 240

Tyr Glu Glu Leu Ser Arg Gln Cys Lys Gln Phe Ala Lys Asp Leu Leu
                245                 250                 255

Asp Gln Thr Arg Ser Ser Arg Glu Leu Glu Ile Ile Leu Asn Tyr Arg
            260                 265                 270

Asp Asp Asn Ser Leu Ile Glu Glu Gln Ser Gly Asn Asp Leu Ala Arg
        275                 280                 285

Leu Lys Leu Ala Ile Lys Tyr Arg Gln Lys Glu Phe Val Ala Gln Pro
290                 295                 300

Asn Cys Gln Gln Leu Leu Ala Ser Arg Trp Tyr Asp Glu Phe Pro Gly
305                 310                 315                 320

Trp Arg Arg Arg His Trp Ala Val Lys Met Val Thr Cys Phe Ile Ile
                325                 330                 335

Gly Leu Leu Phe Pro Val Phe Ser Val Cys Tyr Leu Ile Ala Pro Lys
            340                 345                 350

Ser Pro Leu Gly Leu Phe Ile Arg Lys Pro Phe Ile Lys Phe Ile Cys
        355                 360                 365

His Thr Ala Ser Tyr Leu Thr Phe Leu Phe Leu Leu Leu Leu Ala Ser
    370                 375                 380

Gln His Ile Asp Arg Ser Asp Leu Asn Arg Gln Gly Pro Pro Pro Thr
385                 390                 395                 400

Ile Val Glu Trp Met Ile Leu Pro Trp Val Leu Gly Phe Ile Trp Gly
                405                 410                 415

Glu Ile Lys Gln Met Trp Asp Gly Gly Leu Gln Asp Tyr Ile His Asp
            420                 425                 430

Trp Trp Asn Leu Met Asp Phe Val Met Asn Ser Leu Tyr Leu Ala Thr
        435                 440                 445

Ile Ser Leu Lys Ile Val Ala Phe Val Lys Tyr Ser Ala Leu Asn Pro
450                 455                 460

Arg Glu Ser Trp Asp Met Trp His Pro Thr Leu Val Ala Glu Ala Leu
465                 470                 475                 480

Phe Ala Ile Ala Asn Ile Phe Ser Ser Leu Arg Leu Ile Ser Leu Phe
                485                 490                 495

Thr Ala Asn Ser His Leu Gly Pro Leu Gln Ile Ser Leu Gly Arg Met
            500                 505                 510

Leu Leu Asp Ile Leu Lys Phe Leu Phe Ile Tyr Cys Leu Val Leu Leu
        515                 520                 525

Ala Phe Ala Asn Gly Leu Asn Gln Leu Tyr Phe Tyr Tyr Glu Glu Thr
    530                 535                 540

Lys Gly Leu Ser Cys Lys Gly Ile Arg Cys Glu Lys Gln Asn Asn Ala
545                 550                 555                 560

Phe Ser Thr Leu Phe Glu Thr Leu Gln Ser Leu Phe Trp Ser Ile Phe
                565                 570                 575

Gly Leu Ile Asn Leu Tyr Val Thr Asn Val Lys Ala Gln His Glu Phe
            580                 585                 590
```

-continued

```
Thr Glu Phe Val Gly Ala Thr Met Phe Gly Thr Tyr Asn Val Ile Ser
        595                 600                 605
Leu Val Val Leu Leu Asn Met Leu Ile Ala Met Met Asn Asn Ser Tyr
    610                 615                 620
Gln Leu Ile Ala Asp His Ala Asp Ile Glu Trp Lys Phe Ala Arg Thr
625                 630                 635                 640
Lys Leu Trp Met Ser Tyr Phe Glu Gly Gly Thr Leu Pro Thr Pro
                645                 650                 655
Phe Asn Val Ile Pro Ser Pro Lys Ser Leu Trp Tyr Leu Val Lys Trp
            660                 665                 670
Ile Trp Thr His Leu Cys Lys Lys Met Arg Arg Lys Pro Glu Ser
        675                 680                 685
Phe Gly Thr Ile Gly Arg Arg Ala Ala Asp Asn Leu Arg Arg His His
    690                 695                 700
Gln Tyr Gln Glu Val Met Arg Asn Leu Val Lys Arg Tyr Val Ala Ala
705                 710                 715                 720
Met Ile Arg Glu Ala Lys Thr Glu Glu Gly Leu Thr Glu Glu Asn Val
                725                 730                 735
Lys Glu Leu Lys Gln Asp Ile Ser Ser Phe Arg Phe Glu Val Leu Gly
            740                 745                 750
Leu Leu Arg Gly Ser Lys Leu Ser Thr Ile Gln Ser Ala Asn Ala Ala
        755                 760                 765
Ser Ser Ala Asp Ser Asp Glu Lys Ser Gln Ser Glu Gly Asn Gly Lys
    770                 775                 780
Asp Lys Arg Lys Asn Leu Ser Leu Phe Asp Leu Thr Thr Leu Ile His
785                 790                 795                 800
Pro Arg Ser Ala Ala Ile Ala Ser Glu Arg His Asn Leu Ser Asn Gly
                805                 810                 815
Ser Ala Leu Val Val Gln Glu Pro Pro Arg Glu Lys Gln Arg Lys Val
            820                 825                 830
Asn Phe Val Ala Asp Ile Lys Asn Phe Gly Leu Phe His Arg Arg Ser
        835                 840                 845
Lys Gln Asn Ala Ala Glu Gln Asn Ala Asn Gln Ile Phe Ser Val Ser
    850                 855                 860
Glu Glu Ile Thr Arg Gln Gln Ala Ala Gly Ala Leu Glu Arg Asn Ile
865                 870                 875                 880
Glu Leu Glu Ser Lys Gly Leu Ala Ser Arg Gly Asp Arg Ser Ile Pro
                885                 890                 895
Gly Leu Asn Glu Gln Cys Val Leu Val Asp His Arg Glu Arg Asn Thr
            900                 905                 910
Asp Thr Leu Gly Leu Gln Val Gly Lys Arg Val Cys Ser Thr Phe Lys
        915                 920                 925
Ser Glu Lys Val Val Val Glu Asp Thr Val Pro Ile Ile Pro Lys Glu
    930                 935                 940
Lys His Ala His Glu Glu Asp Ser Ser Ile Asp Tyr Asp Leu Ser Pro
945                 950                 955                 960
Thr Asp Thr Ala Ala His Glu Asp Tyr Val Thr Thr Arg Leu
                965                 970
```

<210> SEQ ID NO 107
<211> LENGTH: 1072
<212> TYPE: PRT
<213> ORGANISM: Mus musculus

<400> SEQUENCE: 107

```
Met Gly Thr Lys Thr His Pro Val Val Pro Trp Ser Thr Lys Glu Ile
1               5                   10                  15

Ser Glu Leu Lys Gly Met Leu Lys Gln Leu Gln Pro Gly Pro Leu Gly
            20                  25                  30

Arg Ala Ala Arg Met Val Leu Ser Ala Arg Lys Ala Pro Pro Ala
        35                  40                  45

Ser Val Val Ser Pro Asn Asn Ser His Gly Glu Pro Gly Pro Ser Arg
            50                  55                  60

Ala Glu Ser Ala Glu Pro Arg Ala Glu Pro Asn Arg Lys Thr Ala
65                  70                  75                  80

Val Gly Arg Arg Lys Arg Arg Lys Val Gln Glu Pro Arg Arg Ser Leu
                85                  90                  95

Ser Asn Ser Ser Ser Gln Pro Asn Arg Arg Thr Gly Arg Thr Arg Gln
            100                 105                 110

Arg Gln His Arg Pro Gln Thr Lys Ser Asp Asp Gly Val Gln Ala
        115                 120                 125

Ala Gly Gln Cys Pro Ile Cys Ala Gly Phe Phe Ser Ile Glu Thr Leu
130                 135                 140

Pro Gln His Ala Ala Thr Cys Gly Glu Ser Pro Pro Gln Pro Ala
145                 150                 155                 160

Ser Pro Ala Ser Leu Ser Ser Ser Glu Ser Val Leu Arg Arg His His
            165                 170                 175

Val Ala Leu Thr Pro Val Pro Leu Val Pro Lys Pro Gln Pro Asn Trp
            180                 185                 190

Thr Glu Ile Val Asn Lys Lys Leu Lys Phe Pro Pro Thr Leu Leu Arg
            195                 200                 205

Ala Ile Gln Glu Gly Gln Leu Gly Leu Val Gln Gln Leu Leu Glu Ser
        210                 215                 220

Ser Ser Asp Ala Ser Gly Ala Gly Pro Gly Gly Pro Leu Arg Asn Val
225                 230                 235                 240

Glu Glu Ser Glu Asp Arg Ser Trp Arg Glu Ala Leu Asn Leu Ala Ile
                245                 250                 255

Arg Leu Gly His Glu Val Ile Thr Asp Val Leu Leu Ala Asn Val Lys
            260                 265                 270

Phe Asp Phe Arg Gln Ile His Glu Ala Leu Leu Val Ala Val Asp Thr
        275                 280                 285

Asn Gln Pro Ala Val Val Arg Leu Leu Ala Arg Leu Glu Arg Glu
        290                 295                 300

Lys Gly Arg Lys Val Asp Thr Lys Ser Phe Ser Leu Ala Phe Phe Asp
305                 310                 315                 320

Ser Ser Ile Asp Gly Ser Arg Phe Ala Pro Gly Val Thr Pro Leu Thr
                325                 330                 335

Leu Ala Cys Gln Lys Asp Leu Tyr Glu Ile Ala Gln Leu Leu Met Asp
            340                 345                 350

Gln Gly His Thr Ile Ala Arg Pro His Pro Val Ser Cys Ala Cys Leu
        355                 360                 365

Glu Cys Ser Asn Ala Arg Arg Tyr Asp Leu Leu Lys Phe Ser Leu Ser
370                 375                 380

Arg Ile Asn Thr Tyr Arg Gly Ile Ala Ser Arg Ala His Leu Ser Leu
385                 390                 395                 400

Ala Ser Glu Asp Ala Met Leu Ala Ala Phe Gln Leu Ser Arg Glu Leu
                405                 410                 415
```

```
Arg Arg Leu Ala Arg Lys Glu Pro Glu Phe Lys Pro Gln Tyr Ile Ala
            420                 425                 430

Leu Glu Ser Leu Cys Gln Asp Tyr Gly Phe Glu Leu Leu Gly Met Cys
            435                 440                 445

Arg Asn Gln Ser Glu Val Thr Ala Val Leu Asn Asp Leu Gly Glu Asp
            450                 455                 460

Ser Glu Thr Glu Pro Glu Ala Glu Gly Leu Gly Gln Ala Phe Glu Glu
465                 470                 475                 480

Gly Ile Pro Asn Leu Ala Arg Leu Arg Leu Ala Val Asn Tyr Asn Gln
                485                 490                 495

Lys Gln Phe Val Ala His Pro Ile Cys Gln Gln Val Leu Ser Ser Ile
            500                 505                 510

Trp Cys Gly Asn Leu Ala Gly Trp Arg Gly Ser Thr Thr Ile Trp Arg
            515                 520                 525

Leu Phe Val Ala Ser Leu Ile Phe Leu Thr Met Pro Phe Leu Cys Ile
            530                 535                 540

Gly Tyr Trp Leu Ala Pro Lys Ser Gln Leu Gly Arg Leu Leu Lys Ile
545                 550                 555                 560

Pro Val Leu Lys Phe Leu Leu His Ser Ala Ser Tyr Leu Trp Phe Leu
                565                 570                 575

Ile Phe Leu Leu Gly Glu Ser Leu Val Met Glu Thr Gln Leu Ser Thr
            580                 585                 590

Phe Lys Gly Arg Ser Gln Ser Val Trp Glu Thr Ser Leu His Met Ile
            595                 600                 605

Trp Val Thr Gly Phe Leu Trp Phe Glu Cys Lys Glu Val Trp Ile Glu
            610                 615                 620

Gly Leu Arg Ser Tyr Leu Leu Asp Trp Trp Asn Phe Leu Asp Val Val
625                 630                 635                 640

Ile Leu Ser Leu Tyr Leu Ala Ser Phe Ala Leu Arg Leu Leu Leu Ala
                645                 650                 655

Gly Leu Ala Tyr Met His Cys Arg Asp Ala Ser Asp Ser Thr Thr Cys
            660                 665                 670

Arg Cys Phe Thr Thr Ala Glu Arg Ser Glu Trp Arg Thr Glu Asp Pro
            675                 680                 685

Gln Phe Leu Ala Glu Val Leu Phe Thr Val Thr Ser Met Leu Ser Phe
            690                 695                 700

Thr Arg Leu Ala Tyr Ile Leu Pro Ala His Glu Ser Leu Gly Thr Leu
705                 710                 715                 720

Gln Ile Ser Ile Gly Lys Met Ile Asp Asp Met Ile Arg Phe Met Phe
                725                 730                 735

Ile Leu Met Ile Ile Leu Thr Ala Phe Leu Cys Gly Leu Asn Asn Ile
            740                 745                 750

Tyr Val Pro Tyr Gln Glu Ser Glu Lys Leu Gly Asn Phe Asn Glu Thr
            755                 760                 765

Phe Gln Phe Leu Phe Trp Thr Met Phe Gly Met Glu Glu His Thr Val
            770                 775                 780

Val Asp Met Pro Gln Phe Leu Val Pro Glu Phe Val Gly Arg Ala Met
785                 790                 795                 800

Tyr Gly Ile Phe Thr Ile Val Met Val Ile Leu Leu Asn Met Leu
                805                 810                 815

Ile Ala Met Ile Thr Asn Ser Phe Gln Lys Ile Glu Asp Asp Ala Asp
            820                 825                 830
```

-continued

Val Glu Trp Lys Phe Ala Arg Ser Lys Leu Tyr Leu Ser Tyr Phe Arg
            835                 840                 845

Glu Gly Leu Thr Leu Pro Val Pro Phe Asn Ile Leu Pro Ser Pro Lys
            850                 855                 860

Ala Ala Phe Tyr Leu Val Arg Arg Ile Phe Arg Phe Leu Cys Cys Gly
865                 870                 875                 880

Ser Ser Cys Cys Lys Ala Lys Lys Ser Asp Tyr Pro Pro Ile Gly Thr
                885                 890                 895

Phe Thr Asn Pro Gly Ala Arg Ala Gly Ser Ala Gly Glu Gly Glu Arg
            900                 905                 910

Val Ser Tyr Arg Leu Arg Val Ile Lys Ala Leu Val Gln Arg Tyr Ile
            915                 920                 925

Glu Thr Ala Arg Arg Glu Phe Glu Glu Thr Arg Arg Lys Asp Leu Gly
            930                 935                 940

Asn Arg Leu Thr Glu Leu Thr Lys Thr Val Ser Arg Leu Gln Ser Glu
945                 950                 955                 960

Val Ala Ser Val Gln Lys Asn Leu Ala Ala Gly Gly Ala Pro Arg Pro
                965                 970                 975

Pro Asp Gly Ala Ser Ile Leu Ser Arg Tyr Ile Thr Arg Val Arg Asn
            980                 985                 990

Ser Phe Gln Asn Leu Gly Pro Pro Thr Ser Asp Thr Pro Ala Glu Leu
            995                 1000                1005

Thr Met Pro Gly Ile Val Glu Thr Glu Val Ser Leu Gly Asp Gly
            1010                1015                1020

Leu Asp Gly Thr Gly Glu Ala Gly Ala Pro Ala Pro Gly Glu Pro
            1025                1030                1035

Gly Ser Ser Ser Ser Ala His Val Leu Val His Arg Glu Gln Glu
            1040                1045                1050

Ala Glu Gly Ser Gly Asp Leu Leu Glu Gly Asp Leu Glu Thr
            1055                1060                1065

Lys Gly Glu Ser
            1070

<210> SEQ ID NO 108
<211> LENGTH: 809
<212> TYPE: PRT
<213> ORGANISM: Mus musculus

<400> SEQUENCE: 108

Met Gly Ala Pro Pro Ser Pro Gly Leu Pro Pro Ser Trp Ala Ala
1               5                   10                  15

Met Met Ala Ala Leu Tyr Pro Ser Thr Asp Leu Ser Gly Val Ser Ser
            20                  25                  30

Ser Ser Leu Pro Ser Pro Ser Ser Ser Pro Asn Glu Val Met
            35                  40                  45

Ala Leu Lys Asp Val Arg Glu Val Lys Glu Glu Asn Thr Leu Asn Glu
            50                  55                  60

Lys Leu Phe Leu Leu Ala Cys Asp Lys Gly Asp Tyr Tyr Met Val Lys
65                  70                  75                  80

Lys Ile Leu Glu Glu Asn Ser Ser Gly Asp Leu Asn Ile Asn Cys Val
                85                  90                  95

Asp Val Leu Gly Arg Asn Ala Val Thr Ile Thr Ile Glu Asn Glu Ser
                100                 105                 110

Leu Asp Ile Leu Gln Leu Leu Leu Asp Tyr Gly Cys Gln Ser Ala Asp
            115                 120                 125

-continued

```
Ala Leu Leu Val Ala Ile Asp Ser Glu Val Val Gly Ala Val Asp Ile
        130                 135                 140

Leu Leu Asn His Arg Pro Lys Arg Ser Ser Arg Pro Thr Ile Val Lys
145                 150                 155                 160

Leu Met Glu Arg Ile Gln Asn Pro Glu Tyr Ser Thr Thr Met Asp Val
                165                 170                 175

Ala Pro Val Ile Leu Ala Ala His Arg Asn Asn Tyr Glu Ile Leu Thr
            180                 185                 190

Met Leu Leu Lys Gln Asp Val Ser Leu Pro Lys Pro His Ala Val Gly
        195                 200                 205

Cys Glu Cys Thr Leu Cys Ser Ala Lys Asn Lys Lys Asp Ser Leu Arg
210                 215                 220

His Ser Arg Phe Arg Leu Asp Ile Tyr Arg Cys Leu Ala Ser Pro Ala
225                 230                 235                 240

Leu Ile Met Leu Thr Glu Glu Asp Pro Ile Leu Arg Ala Phe Glu Leu
                245                 250                 255

Ser Ala Asp Leu Lys Glu Leu Ser Leu Val Glu Val Glu Phe Arg Asn
            260                 265                 270

Asp Tyr Glu Glu Leu Ala Arg Gln Cys Lys Met Phe Ala Lys Asp Leu
        275                 280                 285

Leu Ala Gln Ala Arg Asn Ser Arg Glu Leu Glu Val Ile Leu Asn His
290                 295                 300

Thr Ser Ser Asp Glu Pro Leu Asp Lys Arg Gly Leu Leu Glu Glu Arg
305                 310                 315                 320

Met Asn Leu Ser Arg Leu Lys Leu Ala Ile Lys Tyr Asn Gln Lys Glu
                325                 330                 335

Phe Val Ser Gln Ser Asn Cys Gln Gln Phe Leu Asn Thr Val Trp Phe
            340                 345                 350

Gly Gln Met Ser Gly Tyr Arg Arg Lys Pro Thr Cys Lys Lys Ile Met
        355                 360                 365

Thr Val Leu Thr Val Gly Ile Phe Trp Pro Val Leu Ser Leu Cys Tyr
370                 375                 380

Leu Ile Ala Pro Lys Ser Gln Phe Gly Arg Ile Ile His Thr Pro Phe
385                 390                 395                 400

Met Lys Phe Ile Ile His Gly Ala Ser Tyr Phe Thr Phe Leu Leu Leu
                405                 410                 415

Leu Asn Leu Tyr Ser Leu Val Tyr Asn Glu Asp Lys Lys Asn Thr Met
            420                 425                 430

Gly Pro Ala Leu Glu Arg Ile Asp Tyr Leu Leu Ile Leu Trp Ile Ile
        435                 440                 445

Gly Met Ile Trp Ser Asp Ile Lys Arg Leu Trp Tyr Glu Gly Leu Glu
450                 455                 460

Asp Phe Leu Glu Glu Ser Arg Asn Gln Leu Ser Phe Val Met Asn Ser
465                 470                 475                 480

Leu Tyr Leu Ala Thr Phe Ala Leu Lys Val Val Ala His Asn Lys Phe
                485                 490                 495

His Asp Phe Ala Asp Arg Lys Asp Trp Asp Ala Phe His Pro Thr Leu
            500                 505                 510

Val Ala Glu Gly Leu Phe Ala Phe Ala Asn Val Leu Ser Tyr Leu Arg
        515                 520                 525

Leu Phe Phe Met Tyr Thr Thr Ser Ser Ile Leu Gly Pro Leu Gln Ile
530                 535                 540
```

```
Ser Met Gly Gln Met Leu Gln Asp Phe Gly Lys Phe Leu Gly Met Phe
545                 550                 555                 560

Leu Leu Val Leu Phe Ser Phe Thr Ile Gly Leu Thr Gln Leu Tyr Asp
                565                 570                 575

Lys Gly Tyr Thr Ser Lys Glu Gln Lys Asp Cys Val Gly Ile Phe Cys
            580                 585                 590

Glu Gln Gln Ser Asn Asp Thr Phe His Ser Phe Ile Gly Thr Cys Phe
        595                 600                 605

Ala Leu Phe Trp Tyr Ile Phe Ser Leu Ala His Val Ala Ile Phe Val
    610                 615                 620

Thr Arg Phe Ser Tyr Gly Glu Glu Leu Gln Ser Phe Val Gly Ala Val
625                 630                 635                 640

Ile Val Gly Thr Tyr Asn Val Val Val Ile Val Leu Thr Lys Leu
                645                 650                 655

Leu Val Ala Met Leu His Lys Ser Phe Gln Leu Ile Ala Asn His Glu
                660                 665                 670

Asp Lys Glu Trp Lys Phe Ala Arg Ala Lys Leu Trp Leu Ser Tyr Phe
            675                 680                 685

Asp Asp Lys Cys Thr Leu Pro Pro Pro Phe Asn Ile Ile Pro Ser Pro
        690                 695                 700

Lys Thr Ile Cys Tyr Met Ile Ser Ser Leu Ser Lys Trp Ile Cys Ser
705                 710                 715                 720

His Thr Ser Lys Gly Lys Val Lys Arg Gln Asn Ser Leu Lys Glu Trp
                725                 730                 735

Arg Asn Leu Lys Gln Lys Arg Asp Glu Asn Tyr Gln Lys Val Met Cys
                740                 745                 750

Cys Leu Val His Arg Tyr Leu Thr Ser Met Arg Gln Lys Met Gln Ser
            755                 760                 765

Thr Asp Gln Ala Thr Val Glu Asn Leu Asn Glu Leu Arg Gln Asp Leu
        770                 775                 780

Ser Lys Phe Arg Asn Glu Ile Arg Asp Leu Leu Gly Phe Arg Thr Ser
785                 790                 795                 800

Lys Tyr Ala Met Phe Tyr Pro Arg Asn
                805

<210> SEQ ID NO 109
<211> LENGTH: 18
<212> TYPE: PRT
<213> ORGANISM: Homo sapiens

<400> SEQUENCE: 109

Leu Lys Ile Ile Ile Ser Ile Ile Leu Pro Pro Thr Ile Leu Thr Leu
1               5                   10                  15

Glu Phe

<210> SEQ ID NO 110
<211> LENGTH: 18
<212> TYPE: PRT
<213> ORGANISM: Homo sapiens

<400> SEQUENCE: 110

Ile Val Lys Phe Trp Phe Tyr Thr Met Ala Tyr Leu Ala Phe Leu Met
1               5                   10                  15

Leu Phe
```

-continued

<210> SEQ ID NO 111
<211> LENGTH: 13
<212> TYPE: PRT
<213> ORGANISM: Homo sapiens

<400> SEQUENCE: 111

Thr Glu Thr Val Ala Ile Gly Leu Phe Ser Ala Gly Phe
1               5                   10

<210> SEQ ID NO 112
<211> LENGTH: 18
<212> TYPE: PRT
<213> ORGANISM: Homo sapiens

<400> SEQUENCE: 112

Arg Leu Ile Tyr Cys Ile Asp Ile Ile Phe Trp Phe Ser Arg Leu Leu
1               5                   10                  15

Asp Phe

<210> SEQ ID NO 113
<211> LENGTH: 18
<212> TYPE: PRT
<213> ORGANISM: Homo sapiens

<400> SEQUENCE: 113

Met Thr Ala Asn Met Phe Tyr Ile Val Ile Met Ala Ile Val Leu
1               5                   10                  15

Leu Ser

<210> SEQ ID NO 114
<211> LENGTH: 20
<212> TYPE: PRT
<213> ORGANISM: Homo sapiens

<400> SEQUENCE: 114

Phe Leu Gln Ala Val Tyr Leu Phe Val Gln Tyr Ile Ile Met Val Asn
1               5                   10                  15

Leu Leu Ile Ala
            20

<210> SEQ ID NO 115
<211> LENGTH: 13
<212> TYPE: PRT
<213> ORGANISM: Homo sapiens

<400> SEQUENCE: 115

Ile Ile Leu Ser Lys Ser Gln Lys Ser Trp Ile Lys Gly
1               5                   10

<210> SEQ ID NO 116
<211> LENGTH: 13
<212> TYPE: PRT
<213> ORGANISM: Homo sapiens

<400> SEQUENCE: 116

Ser Thr Ile Ile Pro Ser Ser Lys Asn Pro His Arg Cys
1               5                   10

<210> SEQ ID NO 117
<211> LENGTH: 13
<212> TYPE: PRT
<213> ORGANISM: Homo sapiens

```
<400> SEQUENCE: 117

Ser Val Glu Lys His Thr Thr Lys Ser Pro Thr Asp Thr
1               5                   10

<210> SEQ ID NO 118
<211> LENGTH: 13
<212> TYPE: PRT
<213> ORGANISM: Homo sapiens

<400> SEQUENCE: 118

Ser His Ser Ser His Ser Leu Arg Lys Ile Trp Thr Val
1               5                   10

<210> SEQ ID NO 119
<211> LENGTH: 13
<212> TYPE: PRT
<213> ORGANISM: Homo sapiens

<400> SEQUENCE: 119

Leu Ser Val Trp Glu Thr Val Lys Asp Lys Asp Pro Val
1               5                   10

<210> SEQ ID NO 120
<211> LENGTH: 13
<212> TYPE: PRT
<213> ORGANISM: Homo sapiens

<400> SEQUENCE: 120

Val Val Cys Glu Gly Thr Gly Arg Ala Ala Asp Leu Leu
1               5                   10

<210> SEQ ID NO 121
<211> LENGTH: 13
<212> TYPE: PRT
<213> ORGANISM: Homo sapiens

<400> SEQUENCE: 121

Asp Leu Leu Ala Phe Thr His Lys His Leu Ala Asp Glu
1               5                   10

<210> SEQ ID NO 122
<211> LENGTH: 13
<212> TYPE: PRT
<213> ORGANISM: Homo sapiens

<400> SEQUENCE: 122

Asn Thr Phe Asn Phe Ser Leu Lys Gln Ser Lys His Leu
1               5                   10

<210> SEQ ID NO 123
<211> LENGTH: 13
<212> TYPE: PRT
<213> ORGANISM: Homo sapiens

<400> SEQUENCE: 123

Ile Val Leu His Lys Ser Arg Lys Lys Ser Lys Glu Gln
1               5                   10

<210> SEQ ID NO 124
<211> LENGTH: 13
<212> TYPE: PRT
<213> ORGANISM: Homo sapiens
```

-continued

```
<400> SEQUENCE: 124

His Gly Glu Glu Ala Thr Val Lys Ala Val Ile Ala Cys
1               5                   10

<210> SEQ ID NO 125
<211> LENGTH: 13
<212> TYPE: PRT
<213> ORGANISM: Homo sapiens

<400> SEQUENCE: 125

Asp Gln Asn Ala Ser Ser Lys Glu Ser Ala Ser Val
1               5                   10

<210> SEQ ID NO 126
<211> LENGTH: 13
<212> TYPE: PRT
<213> ORGANISM: Homo sapiens

<400> SEQUENCE: 126

Ser Lys Glu Ser Ala Ser Val Lys Glu Tyr Asp Leu Glu
1               5                   10

<210> SEQ ID NO 127
<211> LENGTH: 13
<212> TYPE: PRT
<213> ORGANISM: Homo sapiens

<400> SEQUENCE: 127

Gln His Leu Pro Trp Thr Arg Lys Val Tyr Glu Phe Tyr
1               5                   10

<210> SEQ ID NO 128
<211> LENGTH: 13
<212> TYPE: PRT
<213> ORGANISM: Homo sapiens

<400> SEQUENCE: 128

Glu Pro Gly Lys Phe Thr Gln Lys Val Lys Val Trp Ile
1               5                   10

<210> SEQ ID NO 129
<211> LENGTH: 13
<212> TYPE: PRT
<213> ORGANISM: Homo sapiens

<400> SEQUENCE: 129

Arg Lys Ala Ile Leu Ser Pro Lys Glu Pro Pro Ser Trp
1               5                   10

<210> SEQ ID NO 130
<211> LENGTH: 13
<212> TYPE: PRT
<213> ORGANISM: Homo sapiens

<400> SEQUENCE: 130

Arg Ile Arg Val Thr Ser Glu Arg Val Thr Glu Met Tyr
1               5                   10

<210> SEQ ID NO 131
<211> LENGTH: 13
<212> TYPE: PRT
<213> ORGANISM: Homo sapiens
```

```
<400> SEQUENCE: 131

Ala Leu Thr Val Asp Thr Leu Lys Val Leu Ser Ala Val
1               5                   10

<210> SEQ ID NO 132
<211> LENGTH: 13
<212> TYPE: PRT
<213> ORGANISM: Homo sapiens

<400> SEQUENCE: 132

Lys Arg Lys His Ser Thr Cys Lys Lys Leu Pro His Ser
1               5                   10

<210> SEQ ID NO 133
<211> LENGTH: 13
<212> TYPE: PRT
<213> ORGANISM: Homo sapiens

<400> SEQUENCE: 133

Leu Glu Ile Thr Asn Ser Lys Arg Glu Ala Thr Asn Val
1               5                   10

<210> SEQ ID NO 134
<211> LENGTH: 13
<212> TYPE: PRT
<213> ORGANISM: Homo sapiens

<400> SEQUENCE: 134

Glu Thr Gly Val Phe Ser Ile Lys Lys Lys Trp Gln Thr
1               5                   10

<210> SEQ ID NO 135
<211> LENGTH: 13
<212> TYPE: PRT
<213> ORGANISM: Homo sapiens

<400> SEQUENCE: 135

Thr Cys Asp Ser Asp Ser Ser Arg Ser Glu Gln His Gln
1               5                   10

<210> SEQ ID NO 136
<211> LENGTH: 13
<212> TYPE: PRT
<213> ORGANISM: Homo sapiens

<400> SEQUENCE: 136

Ser Leu Ser Asp Asn Ser Thr Arg Ser Ala Gln Ser Ser
1               5                   10

<210> SEQ ID NO 137
<211> LENGTH: 13
<212> TYPE: PRT
<213> ORGANISM: Homo sapiens

<400> SEQUENCE: 137

Phe Ala Arg Ser His Ser Phe Arg Phe His Lys Glu Glu
1               5                   10

<210> SEQ ID NO 138
<211> LENGTH: 13
<212> TYPE: PRT
<213> ORGANISM: Homo sapiens
```

```
<400> SEQUENCE: 138

Lys Asp Arg Arg Leu Ser Lys Lys Lys Asn Thr Gln
1               5                   10

<210> SEQ ID NO 139
<211> LENGTH: 13
<212> TYPE: PRT
<213> ORGANISM: Homo sapiens

<400> SEQUENCE: 139

Asp Lys Ile Ser Ala Ser Leu Lys Ser Pro Gln Glu Pro
1               5                   10

<210> SEQ ID NO 140
<211> LENGTH: 13
<212> TYPE: PRT
<213> ORGANISM: Homo sapiens

<400> SEQUENCE: 140

Ser Met Ser Ser Trp Ser Gln Arg Gly Arg Ala Ala Met
1               5                   10

<210> SEQ ID NO 141
<211> LENGTH: 13
<212> TYPE: PRT
<213> ORGANISM: Homo sapiens

<400> SEQUENCE: 141

Gln Thr Ile Pro Tyr Thr Pro Arg Phe Leu Glu Val Phe
1               5                   10

<210> SEQ ID NO 142
<211> LENGTH: 13
<212> TYPE: PRT
<213> ORGANISM: Homo sapiens

<400> SEQUENCE: 142

Pro Pro Ala Arg Glu Thr Gly Arg Asn Ser Pro Glu Asp
1               5                   10

<210> SEQ ID NO 143
<211> LENGTH: 14
<212> TYPE: PRT
<213> ORGANISM: Homo sapiens

<400> SEQUENCE: 143

His Gly Gly Ile Gln Asn Phe Thr Met Pro Ser Lys Phe Lys
1               5                   10

<210> SEQ ID NO 144
<211> LENGTH: 14
<212> TYPE: PRT
<213> ORGANISM: Homo sapiens

<400> SEQUENCE: 144

Ile Gln Asn Thr Phe Asn Phe Ser Leu Lys Gln Ser Lys His
1               5                   10

<210> SEQ ID NO 145
<211> LENGTH: 14
<212> TYPE: PRT
<213> ORGANISM: Homo sapiens
```

-continued

<400> SEQUENCE: 145

Leu Leu Lys Gly Thr Asn Leu Ser Ala Ser Glu Gln Leu Asn
1               5                   10

<210> SEQ ID NO 146
<211> LENGTH: 14
<212> TYPE: PRT
<213> ORGANISM: Homo sapiens

<400> SEQUENCE: 146

Ser Ser Gly Asn Arg Asn Glu Ser Ala Glu Ser Thr Leu His
1               5                   10

<210> SEQ ID NO 147
<211> LENGTH: 14
<212> TYPE: PRT
<213> ORGANISM: Homo sapiens

<400> SEQUENCE: 147

Lys Ser Lys Glu Gln Asn Val Ser Asp Asp Pro Glu Ser Thr
1               5                   10

<210> SEQ ID NO 148
<211> LENGTH: 14
<212> TYPE: PRT
<213> ORGANISM: Homo sapiens

<400> SEQUENCE: 148

Ser Glu Glu Leu Lys Asn Tyr Ser Lys Gln Phe Gly Gln Leu
1               5                   10

<210> SEQ ID NO 149
<211> LENGTH: 14
<212> TYPE: PRT
<213> ORGANISM: Homo sapiens

<400> SEQUENCE: 149

Thr Tyr Glu Leu Arg Asn Trp Ser Asn Ser Thr Cys Leu Lys
1               5                   10

<210> SEQ ID NO 150
<211> LENGTH: 14
<212> TYPE: PRT
<213> ORGANISM: Homo sapiens

<400> SEQUENCE: 150

Leu Arg Asn Trp Ser Asn Ser Thr Cys Leu Lys Leu Ala Val
1               5                   10

<210> SEQ ID NO 151
<211> LENGTH: 14
<212> TYPE: PRT
<213> ORGANISM: Homo sapiens

<400> SEQUENCE: 151

Tyr Tyr Ser Asp Gln Asn Ala Ser Ser Ser Lys Glu Ser Ala
1               5                   10

<210> SEQ ID NO 152
<211> LENGTH: 14
<212> TYPE: PRT
<213> ORGANISM: Homo sapiens -continued

```
<400> SEQUENCE: 152

Ile Ser Glu Tyr Trp Asn Leu Thr Glu Thr Val Ala Ile Gly
1               5                   10

<210> SEQ ID NO 153
<211> LENGTH: 14
<212> TYPE: PRT
<213> ORGANISM: Homo sapiens

<400> SEQUENCE: 153

Lys Met Glu Asp Val Asn Cys Ser Cys Glu Glu Arg Ile Arg
1               5                   10

<210> SEQ ID NO 154
<211> LENGTH: 14
<212> TYPE: PRT
<213> ORGANISM: Homo sapiens

<400> SEQUENCE: 154

Ser Ser Leu Ser Asp Asn Ser Thr Arg Ser Ala Gln Ser Ser
1               5                   10

<210> SEQ ID NO 155
<211> LENGTH: 14
<212> TYPE: PRT
<213> ORGANISM: Homo sapiens

<400> SEQUENCE: 155

Pro Trp Leu Gln Pro Asn Thr Ser Phe Trp Ile Asn Pro Leu
1               5                   10

<210> SEQ ID NO 156
<211> LENGTH: 14
<212> TYPE: PRT
<213> ORGANISM: Homo sapiens

<400> SEQUENCE: 156

Ile Cys Lys Ile Lys Asn Leu Ser Gly Ser Ser Glu Ile Gly
1               5                   10

<210> SEQ ID NO 157
<211> LENGTH: 14
<212> TYPE: PRT
<213> ORGANISM: Homo sapiens

<400> SEQUENCE: 157

Gln Gly Val Gly Glu Asn Leu Thr Asp Pro Ser Val Ile Lys
1               5                   10

<210> SEQ ID NO 158
<211> LENGTH: 14
<212> TYPE: PRT
<213> ORGANISM: Homo sapiens

<400> SEQUENCE: 158

Ser Pro Glu Arg Ile Asn Ser Thr Phe Gly Leu Glu Ile Lys
1               5                   10

<210> SEQ ID NO 159
<211> LENGTH: 18
<212> TYPE: PRT
<213> ORGANISM: Homo sapiens
```

-continued

<400> SEQUENCE: 159

Leu Lys Ile Ile Ile Ser Ile Ile Leu Pro Pro Thr Ile Leu Thr Leu
1               5                   10                  15

Glu Phe

<210> SEQ ID NO 160
<211> LENGTH: 18
<212> TYPE: PRT
<213> ORGANISM: Homo sapiens

<400> SEQUENCE: 160

Ile Val Lys Phe Trp Phe Tyr Thr Met Ala Tyr Leu Ala Phe Leu Met
1               5                   10                  15

Leu Phe

<210> SEQ ID NO 161
<211> LENGTH: 13
<212> TYPE: PRT
<213> ORGANISM: Homo sapiens

<400> SEQUENCE: 161

Thr Glu Thr Val Ala Ile Gly Leu Phe Ser Ala Gly Phe
1               5                   10

<210> SEQ ID NO 162
<211> LENGTH: 18
<212> TYPE: PRT
<213> ORGANISM: Homo sapiens

<400> SEQUENCE: 162

Arg Leu Ile Tyr Cys Ile Asp Ile Ile Phe Trp Phe Ser Arg Leu Leu
1               5                   10                  15

Asp Phe

<210> SEQ ID NO 163
<211> LENGTH: 18
<212> TYPE: PRT
<213> ORGANISM: Homo sapiens

<400> SEQUENCE: 163

Met Thr Ala Asn Met Phe Tyr Ile Val Ile Ile Met Ala Ile Val Leu
1               5                   10                  15

Leu Ser

<210> SEQ ID NO 164
<211> LENGTH: 20
<212> TYPE: PRT
<213> ORGANISM: Homo sapiens

<400> SEQUENCE: 164

Phe Leu Gln Ala Val Tyr Leu Phe Val Gln Tyr Ile Ile Met Val Asn
1               5                   10                  15

Leu Leu Ile Ala
            20

<210> SEQ ID NO 165
<211> LENGTH: 13
<212> TYPE: PRT
<213> ORGANISM: Homo sapiens -continued

<400> SEQUENCE: 165

Ile Ile Leu Ser Lys Ser Gln Lys Ser Trp Ile Lys Gly
1               5                   10

<210> SEQ ID NO 166
<211> LENGTH: 13
<212> TYPE: PRT
<213> ORGANISM: Homo sapiens

<400> SEQUENCE: 166

Ser Thr Ile Ile Pro Ser Ser Lys Asn Pro His Arg Cys
1               5                   10

<210> SEQ ID NO 167
<211> LENGTH: 13
<212> TYPE: PRT
<213> ORGANISM: Homo sapiens

<400> SEQUENCE: 167

Ser Val Glu Lys His Thr Thr Lys Ser Pro Thr Asp Thr
1               5                   10

<210> SEQ ID NO 168
<211> LENGTH: 13
<212> TYPE: PRT
<213> ORGANISM: Homo sapiens

<400> SEQUENCE: 168

Ser His Ser Ser His Ser Leu Arg Lys Ile Trp Thr Val
1               5                   10

<210> SEQ ID NO 169
<211> LENGTH: 13
<212> TYPE: PRT
<213> ORGANISM: Homo sapiens

<400> SEQUENCE: 169

Leu Ser Val Trp Glu Thr Val Lys Asp Lys Asp Pro Val
1               5                   10

<210> SEQ ID NO 170
<211> LENGTH: 13
<212> TYPE: PRT
<213> ORGANISM: Homo sapiens

<400> SEQUENCE: 170

Val Val Cys Glu Gly Thr Gly Arg Ala Ala Asp Leu Leu
1               5                   10

<210> SEQ ID NO 171
<211> LENGTH: 13
<212> TYPE: PRT
<213> ORGANISM: Homo sapiens

<400> SEQUENCE: 171

Asp Leu Leu Ala Phe Thr His Lys His Leu Asp Glu
1               5                   10

<210> SEQ ID NO 172
<211> LENGTH: 13
<212> TYPE: PRT
<213> ORGANISM: Homo sapiens

<400> SEQUENCE: 172

Asn Thr Phe Asn Phe Ser Leu Lys Gln Ser Lys His Leu
1               5                   10

<210> SEQ ID NO 173
<211> LENGTH: 13
<212> TYPE: PRT
<213> ORGANISM: Homo sapiens

<400> SEQUENCE: 173

Ile Val Leu His Lys Ser Arg Lys Lys Ser Lys Glu Gln
1               5                   10

<210> SEQ ID NO 174
<211> LENGTH: 13
<212> TYPE: PRT
<213> ORGANISM: Homo sapiens

<400> SEQUENCE: 174

His Gly Glu Glu Ala Thr Val Lys Ala Val Ile Ala Cys
1               5                   10

<210> SEQ ID NO 175
<211> LENGTH: 13
<212> TYPE: PRT
<213> ORGANISM: Homo sapiens

<400> SEQUENCE: 175

Asp Gln Asn Ala Ser Ser Ser Lys Glu Ser Ala Ser Val
1               5                   10

<210> SEQ ID NO 176
<211> LENGTH: 13
<212> TYPE: PRT
<213> ORGANISM: Homo sapiens

<400> SEQUENCE: 176

Ser Lys Glu Ser Ala Ser Val Lys Glu Tyr Asp Leu Glu
1               5                   10

<210> SEQ ID NO 177
<211> LENGTH: 13
<212> TYPE: PRT
<213> ORGANISM: Homo sapiens

<400> SEQUENCE: 177

Gln His Leu Pro Trp Thr Arg Lys Val Tyr Glu Phe Tyr
1               5                   10

<210> SEQ ID NO 178
<211> LENGTH: 13
<212> TYPE: PRT
<213> ORGANISM: Homo sapiens

<400> SEQUENCE: 178

Glu Pro Gly Lys Phe Thr Gln Lys Val Lys Val Trp Ile
1               5                   10

<210> SEQ ID NO 179
<211> LENGTH: 13
<212> TYPE: PRT
<213> ORGANISM: Homo sapiens

```
<400> SEQUENCE: 179

Arg Lys Ala Ile Leu Ser Pro Lys Glu Pro Pro Ser Trp
1               5                   10

<210> SEQ ID NO 180
<211> LENGTH: 13
<212> TYPE: PRT
<213> ORGANISM: Homo sapiens

<400> SEQUENCE: 180

Arg Ile Arg Val Thr Ser Glu Arg Val Thr Glu Met Tyr
1               5                   10

<210> SEQ ID NO 181
<211> LENGTH: 13
<212> TYPE: PRT
<213> ORGANISM: Homo sapiens

<400> SEQUENCE: 181

Ala Leu Thr Val Asp Thr Leu Lys Val Leu Ser Ala Val
1               5                   10

<210> SEQ ID NO 182
<211> LENGTH: 13
<212> TYPE: PRT
<213> ORGANISM: Homo sapiens

<400> SEQUENCE: 182

Lys Arg Lys His Ser Thr Cys Lys Lys Leu Pro His Ser
1               5                   10

<210> SEQ ID NO 183
<211> LENGTH: 13
<212> TYPE: PRT
<213> ORGANISM: Homo sapiens

<400> SEQUENCE: 183

Leu Glu Ile Thr Asn Ser Lys Arg Glu Ala Thr Asn Val
1               5                   10

<210> SEQ ID NO 184
<211> LENGTH: 13
<212> TYPE: PRT
<213> ORGANISM: Homo sapiens

<400> SEQUENCE: 184

Glu Thr Gly Val Phe Ser Ile Lys Lys Lys Trp Gln Thr
1               5                   10

<210> SEQ ID NO 185
<211> LENGTH: 13
<212> TYPE: PRT
<213> ORGANISM: Homo sapiens

<400> SEQUENCE: 185

Thr Cys Asp Ser Asp Ser Ser Arg Ser Glu Gln His Gln
1               5                   10

<210> SEQ ID NO 186
<211> LENGTH: 13
<212> TYPE: PRT
<213> ORGANISM: Homo sapiens
```

-continued

<400> SEQUENCE: 186

Ser Leu Ser Asp Asn Ser Thr Arg Ser Ala Gln Ser Ser
1               5                   10

<210> SEQ ID NO 187
<211> LENGTH: 13
<212> TYPE: PRT
<213> ORGANISM: Homo sapiens

<400> SEQUENCE: 187

Phe Ala Arg Ser His Ser Phe Arg Phe His Lys Glu Glu
1               5                   10

<210> SEQ ID NO 188
<211> LENGTH: 13
<212> TYPE: PRT
<213> ORGANISM: Homo sapiens

<400> SEQUENCE: 188

Lys Asp Arg Arg Leu Ser Lys Lys Lys Asn Thr Gln
1               5                   10

<210> SEQ ID NO 189
<211> LENGTH: 13
<212> TYPE: PRT
<213> ORGANISM: Homo sapiens

<400> SEQUENCE: 189

Asp Lys Ile Ser Ala Ser Leu Lys Ser Pro Gln Glu Pro
1               5                   10

<210> SEQ ID NO 190
<211> LENGTH: 13
<212> TYPE: PRT
<213> ORGANISM: Homo sapiens

<400> SEQUENCE: 190

Ser Met Ser Ser Trp Ser Gln Arg Gly Arg Ala Ala Met
1               5                   10

<210> SEQ ID NO 191
<211> LENGTH: 13
<212> TYPE: PRT
<213> ORGANISM: Homo sapiens

<400> SEQUENCE: 191

Gln Thr Ile Pro Tyr Thr Pro Arg Phe Leu Glu Val Phe
1               5                   10

<210> SEQ ID NO 192
<211> LENGTH: 13
<212> TYPE: PRT
<213> ORGANISM: Homo sapiens

<400> SEQUENCE: 192

Pro Pro Ala Arg Glu Thr Gly Arg Asn Ser Pro Glu Asp
1               5                   10

<210> SEQ ID NO 193
<211> LENGTH: 14
<212> TYPE: PRT
<213> ORGANISM: Homo sapiens -continued

```
<400> SEQUENCE: 193

His Gly Gly Ile Gln Asn Phe Thr Met Pro Ser Lys Phe Lys
1               5                   10

<210> SEQ ID NO 194
<211> LENGTH: 14
<212> TYPE: PRT
<213> ORGANISM: Homo sapiens

<400> SEQUENCE: 194

Ile Gln Asn Thr Phe Asn Phe Ser Leu Lys Gln Ser Lys His
1               5                   10

<210> SEQ ID NO 195
<211> LENGTH: 14
<212> TYPE: PRT
<213> ORGANISM: Homo sapiens

<400> SEQUENCE: 195

Leu Leu Lys Gly Thr Asn Leu Ser Ala Ser Glu Gln Leu Asn
1               5                   10

<210> SEQ ID NO 196
<211> LENGTH: 14
<212> TYPE: PRT
<213> ORGANISM: Homo sapiens

<400> SEQUENCE: 196

Lys Ser Lys Glu Gln Asn Val Ser Asp Asp Pro Glu Ser Thr
1               5                   10

<210> SEQ ID NO 197
<211> LENGTH: 14
<212> TYPE: PRT
<213> ORGANISM: Homo sapiens

<400> SEQUENCE: 197

Ser Glu Glu Leu Lys Asn Tyr Ser Lys Gln Phe Gly Gln Leu
1               5                   10

<210> SEQ ID NO 198
<211> LENGTH: 14
<212> TYPE: PRT
<213> ORGANISM: Homo sapiens

<400> SEQUENCE: 198

Thr Tyr Glu Leu Arg Asn Trp Ser Asn Ser Thr Cys Leu Lys
1               5                   10

<210> SEQ ID NO 199
<211> LENGTH: 14
<212> TYPE: PRT
<213> ORGANISM: Homo sapiens

<400> SEQUENCE: 199

Leu Arg Asn Trp Ser Asn Ser Thr Cys Leu Lys Leu Ala Val
1               5                   10

<210> SEQ ID NO 200
<211> LENGTH: 14
<212> TYPE: PRT
<213> ORGANISM: Homo sapiens
```

```
<400> SEQUENCE: 200

Tyr Tyr Ser Asp Gln Asn Ala Ser Ser Ser Lys Glu Ser Ala
1               5                   10

<210> SEQ ID NO 201
<211> LENGTH: 14
<212> TYPE: PRT
<213> ORGANISM: Homo sapiens

<400> SEQUENCE: 201

Ile Ser Glu Tyr Trp Asn Leu Thr Glu Thr Val Ala Ile Gly
1               5                   10

<210> SEQ ID NO 202
<211> LENGTH: 14
<212> TYPE: PRT
<213> ORGANISM: Homo sapiens

<400> SEQUENCE: 202

Lys Met Glu Asp Val Asn Cys Ser Cys Glu Glu Arg Ile Arg
1               5                   10

<210> SEQ ID NO 203
<211> LENGTH: 14
<212> TYPE: PRT
<213> ORGANISM: Homo sapiens

<400> SEQUENCE: 203

Ser Ser Leu Ser Asp Asn Ser Thr Arg Ser Ala Gln Ser Ser
1               5                   10

<210> SEQ ID NO 204
<211> LENGTH: 14
<212> TYPE: PRT
<213> ORGANISM: Homo sapiens

<400> SEQUENCE: 204

Pro Trp Leu Gln Pro Asn Thr Ser Phe Trp Ile Asn Pro Leu
1               5                   10

<210> SEQ ID NO 205
<211> LENGTH: 14
<212> TYPE: PRT
<213> ORGANISM: Homo sapiens

<400> SEQUENCE: 205

Ile Cys Lys Ile Lys Asn Leu Ser Gly Ser Ser Glu Ile Gly
1               5                   10

<210> SEQ ID NO 206
<211> LENGTH: 14
<212> TYPE: PRT
<213> ORGANISM: Homo sapiens

<400> SEQUENCE: 206

Gln Gly Val Gly Glu Asn Leu Thr Asp Pro Ser Val Ile Lys
1               5                   10

<210> SEQ ID NO 207
<211> LENGTH: 14
<212> TYPE: PRT
<213> ORGANISM: Homo sapiens
```

-continued

```
<400> SEQUENCE: 207

Ser Pro Glu Arg Ile Asn Ser Thr Phe Gly Leu Glu Ile Lys
1               5                   10

<210> SEQ ID NO 208
<211> LENGTH: 18
<212> TYPE: PRT
<213> ORGANISM: Homo sapiens

<400> SEQUENCE: 208

Leu Lys Ile Ile Ile Ser Ile Ile Leu Pro Pro Thr Ile Leu Thr Leu
1               5                   10                  15

Glu Phe

<210> SEQ ID NO 209
<211> LENGTH: 12
<212> TYPE: PRT
<213> ORGANISM: Homo sapiens

<400> SEQUENCE: 209

Ile Val Lys Phe Trp Phe Tyr Thr Ile Cys Ile Ser
1               5                   10

<210> SEQ ID NO 210
<211> LENGTH: 20
<212> TYPE: PRT
<213> ORGANISM: Homo sapiens

<400> SEQUENCE: 210

Tyr Trp Asn Leu Thr Glu Thr Val Ala Ile Gly Leu Phe Ser Ala Gly
1               5                   10                  15

Phe Val Leu Arg
            20

<210> SEQ ID NO 211
<211> LENGTH: 18
<212> TYPE: PRT
<213> ORGANISM: Homo sapiens

<400> SEQUENCE: 211

Leu Ile Tyr Cys Ile Asp Ile Ile Phe Trp Phe Ser Arg Leu Leu Asp
1               5                   10                  15

Phe Phe

<210> SEQ ID NO 212
<211> LENGTH: 22
<212> TYPE: PRT
<213> ORGANISM: Homo sapiens

<400> SEQUENCE: 212

Met Thr Ala Asn Met Phe Tyr Ile Val Ile Ile Met Ala Ile Val Leu
1               5                   10                  15

Leu Ser Phe Gly Val Ala
            20

<210> SEQ ID NO 213
<211> LENGTH: 31
<212> TYPE: PRT
<213> ORGANISM: Homo sapiens
```

-continued

<400> SEQUENCE: 213

Phe Leu Thr Pro Phe Leu Gln Ala Val Tyr Leu Phe Val Gln Tyr Ile
1               5                   10                  15

Ile Met Val Asn Leu Leu Ile Ala Phe Phe Asn Asn Val Tyr Leu
            20                  25                  30

<210> SEQ ID NO 214
<211> LENGTH: 13
<212> TYPE: PRT
<213> ORGANISM: Homo sapiens

<400> SEQUENCE: 214

Ile Ile Leu Ser Lys Ser Gln Lys Ser Trp Ile Lys Gly
1               5                   10

<210> SEQ ID NO 215
<211> LENGTH: 13
<212> TYPE: PRT
<213> ORGANISM: Homo sapiens

<400> SEQUENCE: 215

Ser Thr Ile Ile Pro Ser Ser Lys Asn Pro His Arg Cys
1               5                   10

<210> SEQ ID NO 216
<211> LENGTH: 13
<212> TYPE: PRT
<213> ORGANISM: Homo sapiens

<400> SEQUENCE: 216

Ser Val Glu Lys His Thr Thr Lys Ser Pro Thr Asp Thr
1               5                   10

<210> SEQ ID NO 217
<211> LENGTH: 13
<212> TYPE: PRT
<213> ORGANISM: Homo sapiens

<400> SEQUENCE: 217

Ser His Ser Ser His Ser Leu Arg Lys Ile Trp Thr Val
1               5                   10

<210> SEQ ID NO 218
<211> LENGTH: 13
<212> TYPE: PRT
<213> ORGANISM: Homo sapiens

<400> SEQUENCE: 218

Leu Ser Val Trp Glu Thr Val Lys Asp Lys Asp Pro Val
1               5                   10

<210> SEQ ID NO 219
<211> LENGTH: 13
<212> TYPE: PRT
<213> ORGANISM: Homo sapiens

<400> SEQUENCE: 219

Val Val Cys Glu Gly Thr Gly Arg Ala Ala Asp Leu Leu
1               5                   10

<210> SEQ ID NO 220
<211> LENGTH: 13
<212> TYPE: PRT
<213> ORGANISM: Homo sapiens -continued

```
<400> SEQUENCE: 220

Asp Leu Leu Ala Phe Thr His Lys His Leu Ala Asp Glu
1               5                   10

<210> SEQ ID NO 221
<211> LENGTH: 13
<212> TYPE: PRT
<213> ORGANISM: Homo sapiens

<400> SEQUENCE: 221

Asn Thr Phe Asn Phe Ser Leu Lys Gln Ser Lys His Leu
1               5                   10

<210> SEQ ID NO 222
<211> LENGTH: 13
<212> TYPE: PRT
<213> ORGANISM: Homo sapiens

<400> SEQUENCE: 222

Tyr Arg Ser Asn Tyr Thr Arg Lys His Phe Arg Ala Leu
1               5                   10

<210> SEQ ID NO 223
<211> LENGTH: 13
<212> TYPE: PRT
<213> ORGANISM: Homo sapiens

<400> SEQUENCE: 223

Ile Val Leu His Lys Ser Arg Lys Lys Ser Lys Glu Gln
1               5                   10

<210> SEQ ID NO 224
<211> LENGTH: 13
<212> TYPE: PRT
<213> ORGANISM: Homo sapiens

<400> SEQUENCE: 224

His Gly Glu Glu Ala Thr Val Lys Ala Val Ile Ala Cys
1               5                   10

<210> SEQ ID NO 225
<211> LENGTH: 13
<212> TYPE: PRT
<213> ORGANISM: Homo sapiens

<400> SEQUENCE: 225

Asp Gln Asn Ala Ser Ser Ser Lys Glu Ser Ala Ser Val
1               5                   10

<210> SEQ ID NO 226
<211> LENGTH: 13
<212> TYPE: PRT
<213> ORGANISM: Homo sapiens

<400> SEQUENCE: 226

Ser Lys Glu Ser Ala Ser Val Lys Glu Tyr Asp Leu Glu
1               5                   10

<210> SEQ ID NO 227
<211> LENGTH: 13
<212> TYPE: PRT
<213> ORGANISM: Homo sapiens
```

-continued

<400> SEQUENCE: 227

Gln His Leu Pro Trp Thr Arg Lys Val Tyr Glu Phe Tyr
1               5                   10

<210> SEQ ID NO 228
<211> LENGTH: 13
<212> TYPE: PRT
<213> ORGANISM: Homo sapiens

<400> SEQUENCE: 228

Glu Pro Gly Lys Phe Thr Gln Lys Val Lys Val Trp Ile
1               5                   10

<210> SEQ ID NO 229
<211> LENGTH: 13
<212> TYPE: PRT
<213> ORGANISM: Homo sapiens

<400> SEQUENCE: 229

Arg Lys Ala Ile Leu Ser Pro Lys Glu Pro Pro Ser Trp
1               5                   10

<210> SEQ ID NO 230
<211> LENGTH: 13
<212> TYPE: PRT
<213> ORGANISM: Homo sapiens

<400> SEQUENCE: 230

Arg Ile Arg Val Thr Ser Glu Arg Val Thr Glu Met Tyr
1               5                   10

<210> SEQ ID NO 231
<211> LENGTH: 13
<212> TYPE: PRT
<213> ORGANISM: Homo sapiens

<400> SEQUENCE: 231

Ala Leu Thr Val Asp Thr Leu Lys Val Leu Ser Ala Val
1               5                   10

<210> SEQ ID NO 232
<211> LENGTH: 13
<212> TYPE: PRT
<213> ORGANISM: Homo sapiens

<400> SEQUENCE: 232

Lys Arg Lys His Ser Thr Cys Lys Lys Leu Pro His Ser
1               5                   10

<210> SEQ ID NO 233
<211> LENGTH: 13
<212> TYPE: PRT
<213> ORGANISM: Homo sapiens

<400> SEQUENCE: 233

Leu Glu Ile Thr Asn Ser Lys Arg Glu Ala Thr Asn Val
1               5                   10

<210> SEQ ID NO 234
<211> LENGTH: 13
<212> TYPE: PRT
<213> ORGANISM: Homo sapiens -continued

```
<400> SEQUENCE: 234

Glu Thr Gly Val Phe Ser Ile Lys Lys Lys Trp Gln Thr
1               5                   10

<210> SEQ ID NO 235
<211> LENGTH: 13
<212> TYPE: PRT
<213> ORGANISM: Homo sapiens

<400> SEQUENCE: 235

Thr Cys Asp Ser Asp Ser Ser Arg Ser Glu Gln His Gln
1               5                   10

<210> SEQ ID NO 236
<211> LENGTH: 13
<212> TYPE: PRT
<213> ORGANISM: Homo sapiens

<400> SEQUENCE: 236

Ser Leu Ser Asp Asn Ser Thr Arg Ser Ala Gln Ser Ser
1               5                   10

<210> SEQ ID NO 237
<211> LENGTH: 13
<212> TYPE: PRT
<213> ORGANISM: Homo sapiens

<400> SEQUENCE: 237

Phe Ala Arg Ser His Ser Phe Arg Phe His Lys Glu Glu
1               5                   10

<210> SEQ ID NO 238
<211> LENGTH: 13
<212> TYPE: PRT
<213> ORGANISM: Homo sapiens

<400> SEQUENCE: 238

Lys Asp Arg Arg Leu Ser Lys Lys Lys Lys Asn Thr Gln
1               5                   10

<210> SEQ ID NO 239
<211> LENGTH: 13
<212> TYPE: PRT
<213> ORGANISM: Homo sapiens

<400> SEQUENCE: 239

Asp Lys Ile Ser Ala Ser Leu Lys Ser Pro Gln Glu Pro
1               5                   10

<210> SEQ ID NO 240
<211> LENGTH: 13
<212> TYPE: PRT
<213> ORGANISM: Homo sapiens

<400> SEQUENCE: 240

Ser Met Ser Ser Trp Ser Gln Arg Gly Arg Ala Ala Met
1               5                   10

<210> SEQ ID NO 241
<211> LENGTH: 13
<212> TYPE: PRT
<213> ORGANISM: Homo sapiens
```

-continued

```
<400> SEQUENCE: 241

Gln Thr Ile Pro Tyr Thr Pro Arg Phe Leu Glu Val Phe
1               5                   10

<210> SEQ ID NO 242
<211> LENGTH: 13
<212> TYPE: PRT
<213> ORGANISM: Homo sapiens

<400> SEQUENCE: 242

Pro Pro Ala Arg Glu Thr Gly Arg Asn Ser Pro Glu Asp
1               5                   10

<210> SEQ ID NO 243
<211> LENGTH: 14
<212> TYPE: PRT
<213> ORGANISM: Homo sapiens

<400> SEQUENCE: 243

His Gly Gly Ile Gln Asn Phe Thr Met Pro Ser Lys Phe Lys
1               5                   10

<210> SEQ ID NO 244
<211> LENGTH: 14
<212> TYPE: PRT
<213> ORGANISM: Homo sapiens

<400> SEQUENCE: 244

Ile Gln Asn Thr Phe Asn Phe Ser Leu Lys Gln Ser Lys His
1               5                   10

<210> SEQ ID NO 245
<211> LENGTH: 14
<212> TYPE: PRT
<213> ORGANISM: Homo sapiens

<400> SEQUENCE: 245

Leu Leu Lys Gly Thr Asn Leu Ser Ala Ser Glu Gln Leu Asn
1               5                   10

<210> SEQ ID NO 246
<211> LENGTH: 14
<212> TYPE: PRT
<213> ORGANISM: Homo sapiens

<400> SEQUENCE: 246

Arg Ala Tyr Arg Ser Asn Tyr Thr Arg Lys His Phe Arg Ala
1               5                   10

<210> SEQ ID NO 247
<211> LENGTH: 14
<212> TYPE: PRT
<213> ORGANISM: Homo sapiens

<400> SEQUENCE: 247

Ser Ser Gly Asn Arg Asn Glu Ser Ala Glu Ser Thr Leu His
1               5                   10

<210> SEQ ID NO 248
<211> LENGTH: 14
<212> TYPE: PRT
<213> ORGANISM: Homo sapiens
```

-continued

```
<400> SEQUENCE: 248

Lys Ser Lys Glu Gln Asn Val Ser Asp Asp Pro Glu Ser Thr
1               5                   10

<210> SEQ ID NO 249
<211> LENGTH: 14
<212> TYPE: PRT
<213> ORGANISM: Homo sapiens

<400> SEQUENCE: 249

Ser Glu Glu Leu Lys Asn Tyr Ser Lys Gln Phe Gly Gln Leu
1               5                   10

<210> SEQ ID NO 250
<211> LENGTH: 14
<212> TYPE: PRT
<213> ORGANISM: Homo sapiens

<400> SEQUENCE: 250

Thr Tyr Glu Leu Arg Asn Trp Ser Asn Ser Thr Cys Leu Lys
1               5                   10

<210> SEQ ID NO 251
<211> LENGTH: 14
<212> TYPE: PRT
<213> ORGANISM: Homo sapiens

<400> SEQUENCE: 251

Leu Arg Asn Trp Ser Asn Ser Thr Cys Leu Lys Leu Ala Val
1               5                   10

<210> SEQ ID NO 252
<211> LENGTH: 14
<212> TYPE: PRT
<213> ORGANISM: Homo sapiens

<400> SEQUENCE: 252

Tyr Tyr Ser Asp Gln Asn Ala Ser Ser Ser Lys Glu Ser Ala
1               5                   10

<210> SEQ ID NO 253
<211> LENGTH: 14
<212> TYPE: PRT
<213> ORGANISM: Homo sapiens

<400> SEQUENCE: 253

Ile Ser Glu Tyr Trp Asn Leu Thr Glu Thr Val Ala Ile Gly
1               5                   10

<210> SEQ ID NO 254
<211> LENGTH: 14
<212> TYPE: PRT
<213> ORGANISM: Homo sapiens

<400> SEQUENCE: 254

Lys Met Glu Asp Val Asn Cys Ser Cys Glu Glu Arg Ile Arg
1               5                   10

<210> SEQ ID NO 255
<211> LENGTH: 14
<212> TYPE: PRT
<213> ORGANISM: Homo sapiens
```

-continued

```
<400> SEQUENCE: 255

Ser Ser Leu Ser Asp Asn Ser Thr Arg Ser Ala Gln Ser Ser
1               5                  10

<210> SEQ ID NO 256
<211> LENGTH: 14
<212> TYPE: PRT
<213> ORGANISM: Homo sapiens

<400> SEQUENCE: 256

Pro Trp Leu Gln Pro Asn Thr Ser Phe Trp Ile Asn Pro Leu
1               5                  10

<210> SEQ ID NO 257
<211> LENGTH: 14
<212> TYPE: PRT
<213> ORGANISM: Homo sapiens

<400> SEQUENCE: 257

Ile Cys Lys Ile Lys Asn Leu Ser Gly Ser Ser Glu Ile Gly
1               5                  10

<210> SEQ ID NO 258
<211> LENGTH: 14
<212> TYPE: PRT
<213> ORGANISM: Homo sapiens

<400> SEQUENCE: 258

Gln Gly Val Gly Glu Asn Leu Thr Asp Pro Ser Val Ile Lys
1               5                  10

<210> SEQ ID NO 259
<211> LENGTH: 14
<212> TYPE: PRT
<213> ORGANISM: Homo sapiens

<400> SEQUENCE: 259

Ser Pro Glu Arg Ile Asn Ser Thr Phe Gly Leu Glu Ile Lys
1               5                  10

<210> SEQ ID NO 260
<211> LENGTH: 1533
<212> TYPE: PRT
<213> ORGANISM: Homo sapiens

<400> SEQUENCE: 260

Met Tyr Ile Arg Val Ser Tyr Asp Thr Lys Pro Asp Ser Leu Leu His
1               5                  10                  15

Leu Met Val Lys Asp Trp Gln Leu Glu Leu Pro Lys Leu Leu Ile Ser
                20                  25                  30

Val His Gly Gly Leu Gln Asn Phe Glu Met Gln Pro Lys Leu Lys Gln
        35                  40                  45

Val Phe Gly Lys Gly Leu Ile Lys Ala Ala Met Thr Thr Gly Ala Trp
    50                  55                  60

Ile Phe Thr Gly Gly Val Ser Thr Gly Val Ile Ser His Val Gly Asp
65                  70                  75                  80

Ala Leu Lys Asp His Ser Ser Lys Ser Arg Gly Arg Val Cys Ala Ile
                85                  90                  95

Gly Ile Ala Pro Trp Gly Ile Val Glu Asn Lys Glu Asp Leu Val Gly
                100                 105                 110
```

-continued

```
Lys Asp Val Thr Arg Val Tyr Gln Thr Met Ser Asn Pro Leu Ser Lys
        115                 120                 125

Leu Ser Val Leu Asn Asn Ser His Thr His Phe Ile Leu Ala Asp Asn
130                 135                 140

Gly Thr Leu Gly Lys Tyr Gly Ala Glu Val Lys Leu Arg Arg Leu Leu
145                 150                 155                 160

Glu Lys His Ile Ser Leu Gln Lys Ile Asn Thr Arg Leu Gly Gln Gly
                165                 170                 175

Val Pro Leu Val Gly Leu Val Val Glu Gly Gly Pro Asn Val Val Ser
                180                 185                 190

Ile Val Leu Glu Tyr Leu Gln Glu Glu Pro Ile Pro Val Val Ile
            195                 200                 205

Cys Asp Gly Ser Gly Arg Ala Ser Asp Ile Leu Ser Phe Ala His Lys
210                 215                 220

Tyr Cys Glu Glu Gly Gly Ile Ile Asn Glu Ser Leu Arg Glu Gln Leu
225                 230                 235                 240

Leu Val Thr Ile Gln Lys Thr Phe Asn Tyr Asn Lys Ala Gln Ser His
                245                 250                 255

Gln Leu Phe Ala Ile Ile Met Glu Cys Met Lys Lys Glu Leu Val
            260                 265                 270

Thr Val Phe Arg Met Gly Ser Glu Gly Gln Gln Asp Ile Glu Met Ala
            275                 280                 285

Ile Leu Thr Ala Leu Leu Lys Gly Thr Asn Val Ser Ala Pro Asp Gln
        290                 295                 300

Leu Ser Leu Ala Leu Ala Trp Asn Arg Val Asp Ile Ala Arg Ser Gln
305                 310                 315                 320

Ile Phe Val Phe Gly Pro His Trp Thr Pro Leu Gly Ser Leu Ala Pro
                325                 330                 335

Pro Thr Asp Ser Lys Ala Thr Glu Lys Glu Lys Lys Pro Pro Met Ala
            340                 345                 350

Thr Thr Lys Gly Gly Arg Gly Lys Gly Lys Gly Lys Lys Lys Gly Lys
        355                 360                 365

Val Lys Glu Glu Val Glu Glu Thr Asp Pro Arg Lys Ile Glu Leu
    370                 375                 380

Leu Asn Trp Val Asn Ala Leu Glu Gln Ala Met Leu Asp Ala Leu Val
385                 390                 395                 400

Leu Asp Arg Val Asp Phe Val Lys Leu Leu Ile Glu Asn Gly Val Asn
                405                 410                 415

Met Gln His Phe Leu Thr Ile Pro Arg Leu Glu Glu Leu Tyr Asn Thr
            420                 425                 430

Arg Leu Gly Pro Pro Asn Thr Leu His Leu Leu Val Arg Asp Val Lys
        435                 440                 445

Lys Ser Asn Leu Pro Pro Asp Tyr His Ile Ser Leu Ile Asp Ile Gly
        450                 455                 460

Leu Val Leu Glu Tyr Leu Met Gly Gly Ala Tyr Arg Cys Asn Tyr Thr
465                 470                 475                 480

Arg Lys Asn Phe Arg Thr Leu Tyr Asn Asn Leu Phe Gly Pro Lys Arg
                485                 490                 495

Pro Lys Ala Leu Lys Leu Leu Gly Met Glu Asp Asp Glu Pro Pro Ala
            500                 505                 510

Lys Gly Lys Lys Lys Lys Lys Lys Lys Glu Glu Glu Ile Asp Ile
        515                 520                 525
```

-continued

```
Asp Val Asp Asp Pro Ala Val Ser Arg Phe Gln Tyr Pro Phe His Glu
530                 535                 540

Leu Met Val Trp Ala Val Leu Met Lys Arg Gln Lys Met Ala Val Phe
545                 550                 555                 560

Leu Trp Gln Arg Gly Glu Glu Ser Met Ala Lys Ala Leu Val Ala Cys
                565                 570                 575

Lys Leu Tyr Lys Ala Met Ala His Glu Ser Ser Glu Ser Asp Leu Val
            580                 585                 590

Asp Asp Ile Ser Gln Asp Leu Asp Asn Asn Ser Lys Asp Phe Gly Gln
        595                 600                 605

Leu Ala Leu Glu Leu Leu Asp Gln Ser Tyr Lys His Asp Glu Gln Ile
    610                 615                 620

Ala Met Lys Leu Leu Thr Tyr Glu Leu Lys Asn Trp Ser Asn Ser Thr
625                 630                 635                 640

Cys Leu Lys Leu Ala Val Ala Ala Lys His Arg Asp Phe Ile Ala His
                645                 650                 655

Thr Cys Ser Gln Met Leu Leu Thr Asp Met Trp Met Gly Arg Leu Arg
            660                 665                 670

Met Arg Lys Asn Pro Gly Leu Lys Val Ile Met Gly Ile Leu Leu Pro
        675                 680                 685

Pro Thr Ile Leu Phe Leu Glu Phe Arg Thr Tyr Asp Asp Phe Ser Tyr
    690                 695                 700

Gln Thr Ser Lys Glu Asn Glu Asp Gly Lys Glu Lys Glu Glu Glu Asn
705                 710                 715                 720

Thr Asp Ala Asn Ala Asp Ala Gly Ser Arg Lys Gly Asp Glu Glu Asn
                725                 730                 735

Glu His Lys Lys Gln Arg Ser Ile Pro Ile Gly Thr Lys Ile Cys Glu
            740                 745                 750

Phe Tyr Asn Ala Pro Ile Val Lys Phe Trp Phe Tyr Thr Ile Ser Tyr
        755                 760                 765

Leu Gly Tyr Leu Leu Leu Phe Asn Tyr Val Ile Leu Val Arg Met Asp
    770                 775                 780

Gly Trp Pro Ser Leu Gln Glu Trp Ile Val Ile Ser Tyr Ile Val Ser
785                 790                 795                 800

Leu Ala Leu Glu Lys Ile Arg Glu Ile Leu Met Ser Glu Pro Gly Lys
                805                 810                 815

Leu Ser Gln Lys Ile Lys Val Trp Leu Gln Glu Tyr Trp Asn Ile Thr
            820                 825                 830

Asp Leu Val Ala Ile Ser Thr Phe Met Ile Gly Ala Ile Leu Arg Leu
        835                 840                 845

Gln Asn Gln Pro Tyr Met Gly Tyr Gly Arg Val Ile Tyr Cys Val Asp
    850                 855                 860

Ile Ile Phe Trp Tyr Ile Arg Val Leu Asp Ile Phe Gly Val Asn Lys
865                 870                 875                 880

Tyr Leu Gly Pro Tyr Val Met Met Ile Gly Lys Met Met Ile Asp Met
                885                 890                 895

Leu Tyr Phe Val Val Ile Met Leu Val Val Leu Met Ser Phe Gly Val
            900                 905                 910

Ala Arg Gln Ala Ile Leu His Pro Glu Glu Lys Pro Ser Trp Lys Leu
        915                 920                 925

Ala Arg Asn Ile Phe Tyr Met Pro Tyr Trp Met Ile Tyr Gly Glu Val
    930                 935                 940
```

```
Phe Ala Asp Gln Ile Asp Leu Tyr Ala Met Glu Ile Asn Pro Pro Cys
945                 950                 955                 960

Gly Glu Asn Leu Tyr Asp Glu Glu Gly Lys Arg Leu Pro Pro Cys Ile
                965                 970                 975

Pro Gly Ala Trp Leu Thr Pro Ala Leu Met Ala Cys Tyr Leu Leu Val
            980                 985                 990

Ala Asn Ile Leu Leu Val Asn Leu  Leu Ile Ala Val Phe  Asn Asn Thr
        995                 1000                1005

Phe Phe Glu Val Lys Ser Ile  Ser Asn Gln Val Trp  Lys Phe Gln
1010                1015                1020

Arg Tyr Gln Leu Ile Met Thr  Phe His Asp Arg Pro  Val Leu Pro
1025                1030                1035

Pro Pro Met Ile Ile Leu Ser  His Ile Tyr Ile Ile  Ile Met Arg
1040                1045                1050

Leu Ser Gly Arg Cys Arg Lys  Lys Arg Glu Gly Asp  Gln Glu Glu
1055                1060                1065

Arg Asp Arg Gly Leu Lys Leu  Phe Leu Ser Asp Glu  Glu Leu Lys
1070                1075                1080

Arg Leu His Glu Phe Glu Glu  Gln Cys Val Gln Glu  His Phe Arg
1085                1090                1095

Glu Lys Glu Asp Glu Gln Gln  Ser Ser Ser Asp Glu  Arg Ile Arg
1100                1105                1110

Val Thr Ser Glu Arg Val Glu  Asn Met Ser Met Arg  Leu Glu Glu
1115                1120                1125

Ile Asn Glu Arg Glu Thr Phe  Met Lys Thr Ser Leu  Gln Thr Val
1130                1135                1140

Asp Leu Arg Leu Ala Gln Leu  Glu Glu Leu Ser Asn  Arg Met Val
1145                1150                1155

Asn Ala Leu Glu Asn Leu Ala  Gly Ile Asp Arg Ser  Asp Leu Ile
1160                1165                1170

Gln Ala Arg Ser Arg Ala Ser  Ser Glu Cys Glu Ala  Thr Tyr Leu
1175                1180                1185

Leu Arg Gln Ser Ser Ile Asn  Ser Ala Asp Gly Tyr  Ser Leu Tyr
1190                1195                1200

Arg Tyr His Phe Asn Gly Glu  Glu Leu Leu Phe Glu  Asp Thr Ser
1205                1210                1215

Leu Ser Thr Ser Pro Gly Thr  Gly Val Arg Lys Lys  Thr Cys Ser
1220                1225                1230

Phe Arg Ile Lys Glu Glu Lys  Asp Val Lys Thr His  Leu Val Pro
1235                1240                1245

Glu Cys Gln Asn Ser Leu His  Leu Ser Leu Gly Thr  Ser Thr Ser
1250                1255                1260

Ala Thr Pro Asp Gly Ser His  Leu Ala Val Asp Asp  Leu Lys Asn
1265                1270                1275

Ala Glu Glu Ser Lys Leu Gly  Pro Asp Ile Gly Ile  Ser Lys Glu
1280                1285                1290

Asp Asp Glu Arg Gln Thr Asp  Ser Lys Lys Glu Glu  Thr Ile Ser
1295                1300                1305

Pro Ser Leu Asn Lys Thr Val  Ile His Gly Gln Asp  Lys Ser
1310                1315                1320

Asp Val Gln Asn Thr Gln Leu  Thr Val Glu Thr Thr  Asn Ile Glu
1325                1330                1335
```

```
Gly Thr Ile Ser Tyr Pro Leu Glu Glu Thr Lys Ile Thr Arg Tyr
            1340                1345                1350

Phe Pro Asp Glu Thr Ile Asn Ala Cys Lys Thr Met Lys Ser Arg
            1355                1360                1365

Ser Phe Val Tyr Ser Arg Gly Arg Lys Leu Val Gly Gly Val Asn
            1370                1375                1380

Gln Asp Val Glu Tyr Ser Ser Ile Thr Asp Gln Gln Leu Thr Thr
            1385                1390                1395

Glu Trp Gln Cys Gln Val Gln Lys Ile Thr Arg Ser His Ser Thr
            1400                1405                1410

Asp Ile Pro Tyr Ile Val Ser Glu Ala Ala Val Gln Ala Glu Gln
            1415                1420                1425

Lys Glu Gln Phe Ala Asp Met Gln Asp Glu His His Val Ala Glu
            1430                1435                1440

Ala Ile Pro Arg Ile Pro Arg Leu Ser Leu Thr Ile Thr Asp Arg
            1445                1450                1455

Asn Gly Met Glu Asn Leu Leu Ser Val Lys Pro Asp Gln Thr Leu
            1460                1465                1470

Gly Phe Pro Ser Leu Arg Ser Lys Ser Leu His Gly His Pro Arg
            1475                1480                1485

Asn Val Lys Ser Ile Gln Gly Lys Leu Asp Arg Ser Gly His Ala
            1490                1495                1500

Ser Ser Val Ser Ser Leu Val Ile Val Ser Gly Met Thr Ala Glu
            1505                1510                1515

Glu Lys Lys Val Lys Lys Glu Lys Ala Ser Thr Glu Thr Glu Cys
            1520                1525                1530

<210> SEQ ID NO 261
<211> LENGTH: 8
<212> TYPE: PRT
<213> ORGANISM: bacteriophage T7

<400> SEQUENCE: 261

Asp Tyr Lys Asp Asp Asp Asp Lys
1               5

<210> SEQ ID NO 262
<211> LENGTH: 733
<212> TYPE: DNA
<213> ORGANISM: homo sapiens

<400> SEQUENCE: 262
gggatccgga gcccaaatct tctgacaaaa ctcacacatg cccaccgtgc ccagcacctg      60
aattcgaggg tgcaccgtca gtcttcctct ccccccaaa  acccaaggac accctcatga     120
tctcccggac tcctgaggtc acatgcgtgg tggtggacgt aagccacgaa gaccctgagg     180
tcaagttcaa ctggtacgtg gacggcgtgg aggtgcataa tgccaagaca aagccgcggg     240
aggagcagta caacagcacg taccgtgtgg tcagcgtcct caccgtcctg caccaggact     300
ggctgaatgg caaggagtac aagtgcaagg tctccaacaa agccctccca ccccccatcg     360
agaaaaccat ctccaaagcc aaagggcagc ccgagaacc  acaggtgtac accctgcccc     420
catcccggga tgagctgacc aagaaccagg tcagcctgac ctgcctggtc aaaggcttct     480
atccaagcga catcgccgtg gagtgggaga gcaatgggca gccggagaac aactacaaga     540
ccacgcctcc cgtgctggac tccgacggct ccttcttcct ctacagcaag ctcaccgtgg     600
acaagagcag gtggcagcag gggaacgtct tctcatgctc cgtgatgcat gaggctctgc     660
```

```
acaaccacta cacgcagaag agcctctccc tgtctccggg taaatgagtg cgacggccgc    720
gactctagag gat                                                      733

<210> SEQ ID NO 263
<211> LENGTH: 35
<212> TYPE: DNA
<213> ORGANISM: Homo sapiens

<400> SEQUENCE: 263
gcagcagcgg ccgctggtta aagattatta taagc                              35

<210> SEQ ID NO 264
<211> LENGTH: 35
<212> TYPE: DNA
<213> ORGANISM: Homo sapiens

<400> SEQUENCE: 264
gcagcagtcg actagttgca tatcatcttc tgggg                              35

<210> SEQ ID NO 265
<211> LENGTH: 38
<212> TYPE: DNA
<213> ORGANISM: Homo sapiens

<400> SEQUENCE: 265
gcagcagcgg ccgcatgatt atcctatcta agtcccag                           38

<210> SEQ ID NO 266
<211> LENGTH: 37
<212> TYPE: DNA
<213> ORGANISM: Homo sapiens

<400> SEQUENCE: 266
gcagcagtcg acgggatgcc ggcctccagc caggctc                            37

<210> SEQ ID NO 267
<211> LENGTH: 23
<212> TYPE: DNA
<213> ORGANISM: Homo sapiens

<400> SEQUENCE: 267
agaaaataca ctgccgctca aga                                           23

<210> SEQ ID NO 268
<211> LENGTH: 17
<212> TYPE: DNA
<213> ORGANISM: Homo sapiens

<400> SEQUENCE: 268
gttgggaccg ccttcca                                                  17

<210> SEQ ID NO 269
<211> LENGTH: 19
<212> TYPE: DNA
<213> ORGANISM: Homo sapiens

<400> SEQUENCE: 269
cccacgaccg gcacgcctt                                                19

<210> SEQ ID NO 270
<211> LENGTH: 38
<212> TYPE: DNA
<213> ORGANISM: Homo sapiens
```

<400> SEQUENCE: 270
cgggatccac gatgggagtt gacaagatct cagcctcc    38

<210> SEQ ID NO 271
<211> LENGTH: 67
<212> TYPE: DNA
<213> ORGANISM: Homo sapiens

<400> SEQUENCE: 271
atagttagcg gccgcttaag cgtaatctgg aacatcgtat gggtatagtt gcatatcatc    60
ttctggg    67

<210> SEQ ID NO 272
<211> LENGTH: 23
<212> TYPE: DNA
<213> ORGANISM: Homo sapiens

<400> SEQUENCE: 272
caggtgcagc tggtgcagtc tgg    23

<210> SEQ ID NO 273
<211> LENGTH: 23
<212> TYPE: DNA
<213> ORGANISM: Homo sapiens

<400> SEQUENCE: 273
caggtcaact taagggagtc tgg    23

<210> SEQ ID NO 274
<211> LENGTH: 23
<212> TYPE: DNA
<213> ORGANISM: Homo sapiens

<400> SEQUENCE: 274
gaggtgcagc tggtggagtc tgg    23

<210> SEQ ID NO 275
<211> LENGTH: 23
<212> TYPE: DNA
<213> ORGANISM: Homo sapiens

<400> SEQUENCE: 275
caggtgcagc tgcaggagtc ggg    23

<210> SEQ ID NO 276
<211> LENGTH: 23
<212> TYPE: DNA
<213> ORGANISM: Homo sapiens

<400> SEQUENCE: 276
gaggtgcagc tgttgcagtc tgc    23

<210> SEQ ID NO 277
<211> LENGTH: 23
<212> TYPE: DNA
<213> ORGANISM: Homo sapiens

<400> SEQUENCE: 277
caggtacagc tgcagcagtc agg    23

<210> SEQ ID NO 278
<211> LENGTH: 24
<212> TYPE: DNA
<213> ORGANISM: Homo sapiens

<400> SEQUENCE: 278
tgaggagacg gtgaccaggg tgcc                                            24

<210> SEQ ID NO 279
<211> LENGTH: 24
<212> TYPE: DNA
<213> ORGANISM: Homo sapiens

<400> SEQUENCE: 279
tgaagagacg gtgaccattg tccc                                            24

<210> SEQ ID NO 280
<211> LENGTH: 24
<212> TYPE: DNA
<213> ORGANISM: Homo sapiens

<400> SEQUENCE: 280
tgaggagacg gtgaccaggg ttcc                                            24

<210> SEQ ID NO 281
<211> LENGTH: 24
<212> TYPE: DNA
<213> ORGANISM: Homo sapiens

<400> SEQUENCE: 281
tgaggagacg gtgaccgtgg tccc                                            24

<210> SEQ ID NO 282
<211> LENGTH: 23
<212> TYPE: DNA
<213> ORGANISM: Homo sapiens

<400> SEQUENCE: 282
gacatccaga tgacccagtc tcc                                             23

<210> SEQ ID NO 283
<211> LENGTH: 23
<212> TYPE: DNA
<213> ORGANISM: Homo sapiens

<400> SEQUENCE: 283
gatgttgtga tgactcagtc tcc                                             23

<210> SEQ ID NO 284
<211> LENGTH: 23
<212> TYPE: DNA
<213> ORGANISM: Homo sapiens

<400> SEQUENCE: 284
gatattgtga tgactcagtc tcc                                             23

<210> SEQ ID NO 285
<211> LENGTH: 23
<212> TYPE: DNA
<213> ORGANISM: Homo sapiens

<400> SEQUENCE: 285
gaaattgtgt tgacgcagtc tcc                                             23

<210> SEQ ID NO 286
<211> LENGTH: 23
<212> TYPE: DNA
<213> ORGANISM: Homo sapiens

<400> SEQUENCE: 286
gacatcgtga tgacccagtc tcc                                               23

<210> SEQ ID NO 287
<211> LENGTH: 23
<212> TYPE: DNA
<213> ORGANISM: Homo sapiens

<400> SEQUENCE: 287
gaaacgacac tcacgcagtc tcc                                               23

<210> SEQ ID NO 288
<211> LENGTH: 23
<212> TYPE: DNA
<213> ORGANISM: Homo sapiens

<400> SEQUENCE: 288
gaaattgtgc tgactcagtc tcc                                               23

<210> SEQ ID NO 289
<211> LENGTH: 23
<212> TYPE: DNA
<213> ORGANISM: Homo sapiens

<400> SEQUENCE: 289
cagtctgtgt tgacgcagcc gcc                                               23

<210> SEQ ID NO 290
<211> LENGTH: 23
<212> TYPE: DNA
<213> ORGANISM: Homo sapiens

<400> SEQUENCE: 290
cagtctgccc tgactcagcc tgc                                               23

<210> SEQ ID NO 291
<211> LENGTH: 23
<212> TYPE: DNA
<213> ORGANISM: Homo sapiens

<400> SEQUENCE: 291
tcctatgtgc tgactcagcc acc                                               23

<210> SEQ ID NO 292
<211> LENGTH: 23
<212> TYPE: DNA
<213> ORGANISM: Homo sapiens

<400> SEQUENCE: 292
tcttctgagc tgactcagga ccc                                               23

<210> SEQ ID NO 293
<211> LENGTH: 23
<212> TYPE: DNA
<213> ORGANISM: Homo sapiens

<400> SEQUENCE: 293
cacgttatac tgactcaacc gcc                                               23

```
<210> SEQ ID NO 294
<211> LENGTH: 23
<212> TYPE: DNA
<213> ORGANISM: Homo sapiens

<400> SEQUENCE: 294
caggctgtgc tcactcagcc gtc                                          23

<210> SEQ ID NO 295
<211> LENGTH: 23
<212> TYPE: DNA
<213> ORGANISM: Homo sapiens

<400> SEQUENCE: 295
aattttatgc tgactcagcc cca                                          23

<210> SEQ ID NO 296
<211> LENGTH: 24
<212> TYPE: DNA
<213> ORGANISM: Homo sapiens

<400> SEQUENCE: 296
acgtttgatt tccaccttgg tccc                                         24

<210> SEQ ID NO 297
<211> LENGTH: 24
<212> TYPE: DNA
<213> ORGANISM: Homo sapiens

<400> SEQUENCE: 297
acgtttgatc tccagcttgg tccc                                         24

<210> SEQ ID NO 298
<211> LENGTH: 24
<212> TYPE: DNA
<213> ORGANISM: Homo sapiens

<400> SEQUENCE: 298
acgtttgata tccactttgg tccc                                         24

<210> SEQ ID NO 299
<211> LENGTH: 24
<212> TYPE: DNA
<213> ORGANISM: Homo sapiens

<400> SEQUENCE: 299
acgtttgatc tccaccttgg tccc                                         24

<210> SEQ ID NO 300
<211> LENGTH: 24
<212> TYPE: DNA
<213> ORGANISM: Homo sapiens

<400> SEQUENCE: 300
acgtttaatc tccagtcgtg tccc                                         24

<210> SEQ ID NO 301
<211> LENGTH: 23
<212> TYPE: DNA
<213> ORGANISM: Homo sapiens

<400> SEQUENCE: 301
cagtctgtgt tgacgcagcc gcc                                          23
```

<210> SEQ ID NO 302
<211> LENGTH: 23
<212> TYPE: DNA
<213> ORGANISM: Homo sapiens

<400> SEQUENCE: 302
cagtctgccc tgactcagcc tgc                                    23

<210> SEQ ID NO 303
<211> LENGTH: 23
<212> TYPE: DNA
<213> ORGANISM: Homo sapiens

<400> SEQUENCE: 303
tcctatgtgc tgactcagcc acc                                    23

<210> SEQ ID NO 304
<211> LENGTH: 23
<212> TYPE: DNA
<213> ORGANISM: Homo sapiens

<400> SEQUENCE: 304
tcttctgagc tgactcagga ccc                                    23

<210> SEQ ID NO 305
<211> LENGTH: 23
<212> TYPE: DNA
<213> ORGANISM: Homo sapiens

<400> SEQUENCE: 305
cacgttatac tgactcaacc gcc                                    23

<210> SEQ ID NO 306
<211> LENGTH: 23
<212> TYPE: DNA
<213> ORGANISM: Homo sapiens

<400> SEQUENCE: 306
caggctgtgc tcactcagcc gtc                                    23

<210> SEQ ID NO 307
<211> LENGTH: 23
<212> TYPE: DNA
<213> ORGANISM: Homo sapiens

<400> SEQUENCE: 307
aattttatgc tgactcagcc cca                                    23

<210> SEQ ID NO 308
<211> LENGTH: 24
<212> TYPE: DNA
<213> ORGANISM: Homo sapiens

<400> SEQUENCE: 308
gaggatgagg agagctatga caca                                   24

<210> SEQ ID NO 309
<211> LENGTH: 22
<212> TYPE: DNA
<213> ORGANISM: Homo sapiens

<400> SEQUENCE: 309 cccctttgcac tcataacgtc ag                                    22

```
<210> SEQ ID NO 310
<211> LENGTH: 29
<212> TYPE: DNA
<213> ORGANISM: Homo sapiens

<400> SEQUENCE: 310
aaacacacag tcatcatagg gcagctcgt                                               29

<210> SEQ ID NO 311
<211> LENGTH: 25
<212> TYPE: DNA
<213> ORGANISM: Artificial Sequence
<220> FEATURE:
<223> OTHER INFORMATION: Synthesized Oligonucleotide

<400> SEQUENCE: 311
ccuugacagu cucccacacu gacag                                                   25

<210> SEQ ID NO 312
<211> LENGTH: 204
<212> TYPE: PRT
<213> ORGANISM: Homo sapiens

<400> SEQUENCE: 312
```

Val Lys Asp Lys Asp Pro Val Val Cys Glu Gly Thr Gly Arg Ala
1               5                   10                  15

Ala Asp Leu Leu Ala Phe Thr His Lys His Leu Ala Asp Glu Gly Met
            20                  25                  30

Leu Arg Pro Gln Val Lys Glu Glu Ile Ile Cys Met Ile Gln Asn Thr
        35                  40                  45

Phe Asn Phe Ser Leu Lys Gln Ser Lys His Leu Phe Gln Ile Leu Met
    50                  55                  60

Glu Cys Met Val His Arg Asp Cys Ile Thr Ile Phe Asp Ala Asp Ser
65                  70                  75                  80

Glu Glu Gln Gln Asp Leu Asp Leu Ala Ile Leu Thr Ala Leu Leu Lys
                85                  90                  95

Gly Thr Asn Leu Ser Ala Ser Glu Gln Leu Asn Leu Ala Met Ala Trp
            100                 105                 110

Asp Arg Val Asp Ile Ala Lys Lys His Ile Leu Ile Tyr Glu Gln His
        115                 120                 125

Trp Lys Pro Asp Ala Leu Glu Gln Ala Met Ser Asp Ala Leu Val Met
    130                 135                 140

Asp Arg Val Asp Phe Val Lys Leu Leu Ile Glu Tyr Gly Val Asn Leu
145                 150                 155                 160

His Arg Phe Leu Thr Ile Pro Arg Leu Glu Glu Leu Tyr Asn Thr Lys
                165                 170                 175

Gln Gly Pro Thr Asn Thr Leu His His Leu Val Gly Asp Val Lys
            180                 185                 190

Gln His Thr Leu Leu Ser Gly Tyr Arg Ile Thr Leu
        195                 200

```
<210> SEQ ID NO 313
<211> LENGTH: 17
<212> TYPE: PRT
<213> ORGANISM: Homo sapiens
```

-continued

```
<400> SEQUENCE: 313

Lys Ser Pro Thr Asp Thr Phe Gly Thr Ile Asn Phe Gln Asp Gly Glu
1               5                   10                  15

His

<210> SEQ ID NO 314
<211> LENGTH: 24
<212> TYPE: PRT
<213> ORGANISM: Homo sapiens

<400> SEQUENCE: 314

Asp His Leu Leu His Leu Met Leu Lys Glu Trp Met Glu Leu Pro Lys
1               5                   10                  15

Leu Val Ile Ser Val His Gly Gly
            20

<210> SEQ ID NO 315
<211> LENGTH: 22
<212> TYPE: PRT
<213> ORGANISM: Homo sapiens

<400> SEQUENCE: 315

Phe Ser Gln Gly Leu Val Lys Ala Ala Glu Thr Thr Gly Ala Trp Ile
1               5                   10                  15

Ile Thr Glu Gly Ile Asn
            20

<210> SEQ ID NO 316
<211> LENGTH: 20
<212> TYPE: PRT
<213> ORGANISM: Homo sapiens

<400> SEQUENCE: 316

Ser Leu Arg Lys Ile Trp Thr Val Gly Ile Pro Pro Trp Gly Val Ile
1               5                   10                  15

Glu Asn Gln Arg
            20

<210> SEQ ID NO 317
<211> LENGTH: 19
<212> TYPE: PRT
<213> ORGANISM: Homo sapiens

<400> SEQUENCE: 317

Thr Val Leu His Leu Cys Leu Arg Glu Ile Gln Gln Gln Arg Ala Ala
1               5                   10                  15

Gln Lys Leu

<210> SEQ ID NO 318
<211> LENGTH: 16
<212> TYPE: PRT
<213> ORGANISM: Homo sapiens

<400> SEQUENCE: 318

Met Thr Gly Glu Phe Arg Lys Tyr Asn Asn Asn Gly Asp Glu Ile
1               5                   10                  15

<210> SEQ ID NO 319
<211> LENGTH: 35
<212> TYPE: PRT
<213> ORGANISM: Homo sapiens
```

```
<400> SEQUENCE: 319

Met Leu Ala Phe Ser His Trp Thr Tyr Glu Tyr Thr Arg Gly Glu Leu
1               5                   10                  15

Leu Val Leu Asp Leu Gln Gly Val Gly Glu Asn Leu Thr Asp Pro Ser
            20                  25                  30

Val Ile Lys
        35

<210> SEQ ID NO 320
<211> LENGTH: 22
<212> TYPE: PRT
<213> ORGANISM: Homo sapiens

<400> SEQUENCE: 320

Ala Lys His His Cys Asn Ser Cys Cys Arg Lys Leu Lys Leu Pro Asp
1               5                   10                  15

Leu Lys Arg Asn Asp Tyr
            20

<210> SEQ ID NO 321
<211> LENGTH: 158
<212> TYPE: PRT
<213> ORGANISM: Homo sapiens

<400> SEQUENCE: 321

Gly Lys Asp Val Val Cys Leu Tyr Gln Thr Leu Asp Asn Pro Leu Ser
1               5                   10                  15

Lys Leu Thr Thr Leu Asn Ser Met His Ser His Phe Ile Leu Ser Asp
            20                  25                  30

Asp Gly Thr Val Gly Lys Tyr Gly Asn Glu Met Lys Leu Arg Arg Asn
        35                  40                  45

Leu Glu Lys Tyr Leu Ser Leu Gln Lys Ile His Cys Arg Ser Arg Gln
    50                  55                  60

Gly Val Pro Val Gly Leu Val Glu Gly Gly Pro Asn Val Ile
65                  70                  75                  80

Leu Ser Val Trp Glu Thr Val Lys Asp Lys Asp Pro Val Val Val Cys
                85                  90                  95

Glu Gly Thr Gly Arg Ala Ala Asp Leu Leu Ala Phe Thr His Lys His
            100                 105                 110

Leu Ala Asp Glu Gly Met Leu Arg Pro Gln Val Lys Glu Glu Ile Ile
        115                 120                 125

Cys Met Ile Gln Asn Thr Phe Asn Phe Ser Leu Lys Gln Ser Lys His
    130                 135                 140

Leu Phe Gln Ile Leu Met Glu Cys Met Val His Arg Asp Cys
145                 150                 155

<210> SEQ ID NO 322
<211> LENGTH: 26
<212> TYPE: PRT
<213> ORGANISM: Homo sapiens

<400> SEQUENCE: 322

Glu Tyr Thr Arg Gly Glu Leu Leu Val Leu Asp Leu Gln Gly Val Gly
1               5                   10                  15

Glu Asn Leu Thr Asp Pro Ser Val Ile Lys
            20                  25
```

```
<210> SEQ ID NO 323
<211> LENGTH: 16
<212> TYPE: PRT
<213> ORGANISM: Homo sapiens

<400> SEQUENCE: 323

Tyr Pro Tyr Asn Asp Leu Leu Val Trp Ala Val Leu Met Lys Arg Gln
1               5                   10                  15

<210> SEQ ID NO 324
<211> LENGTH: 19
<212> TYPE: PRT
<213> ORGANISM: Homo sapiens

<400> SEQUENCE: 324

Met Ala Met Phe Phe Trp Gln His Gly Glu Glu Ala Thr Val Lys Ala
1               5                   10                  15

Val Ile Ala

<210> SEQ ID NO 325
<211> LENGTH: 22
<212> TYPE: PRT
<213> ORGANISM: Homo sapiens

<400> SEQUENCE: 325

Asn Trp Ser Asn Ser Thr Cys Leu Lys Leu Ala Val Ser Gly Gly Leu
1               5                   10                  15

Arg Pro Phe Val Ser His
            20

<210> SEQ ID NO 326
<211> LENGTH: 26
<212> TYPE: PRT
<213> ORGANISM: Homo sapiens

<400> SEQUENCE: 326

Gln Met Leu Leu Thr Asp Met Trp Met Gly Arg Leu Lys Met Arg Lys
1               5                   10                  15

Asn Ser Trp Leu Lys Ile Ile Ile Ser Ile
            20                  25

<210> SEQ ID NO 327
<211> LENGTH: 17
<212> TYPE: PRT
<213> ORGANISM: Homo sapiens

<400> SEQUENCE: 327

Leu Lys Pro Gly Gln Val Phe Ile Val Lys Ser Phe Leu Pro Glu Val
1               5                   10                  15

Val

<210> SEQ ID NO 328
<211> LENGTH: 46
<212> TYPE: PRT
<213> ORGANISM: Homo sapiens

<400> SEQUENCE: 328

Lys Ile Phe Gln Glu Ser Thr Val Leu His Leu Cys Leu Arg Glu Ile
1               5                   10                  15
```

-continued

Gln Gln Gln Arg Ala Ala Gln Lys Leu Ile Tyr Thr Phe Asn Gln Val
            20                  25                  30

Lys Pro Gln Thr Ile Pro Tyr Thr Pro Arg Phe Leu Glu Val
        35                  40                  45

<210> SEQ ID NO 329
<211> LENGTH: 30
<212> TYPE: PRT
<213> ORGANISM: Homo sapiens

<400> SEQUENCE: 329

Tyr Cys His Ser Ala Asn Gln Trp Leu Thr Ile Glu Lys Tyr Met Thr
1               5                   10                  15

Gly Glu Phe Arg Lys Tyr Asn Asn Asn Gly Asp Glu Ile
            20                  25                  30

<210> SEQ ID NO 330
<211> LENGTH: 39
<212> TYPE: PRT
<213> ORGANISM: Homo sapiens

<400> SEQUENCE: 330

Pro Thr Asn Thr Leu Glu Glu Leu Met Leu Ala Phe Ser His Trp Thr
1               5                   10                  15

Tyr Glu Tyr Thr Arg Gly Glu Leu Leu Val Leu Asp Leu Gln Gly Val
            20                  25                  30

Gly Glu Asn Leu Thr Asp Pro
        35

<210> SEQ ID NO 331
<211> LENGTH: 19
<212> TYPE: PRT
<213> ORGANISM: Homo sapiens

<400> SEQUENCE: 331

Thr Val Leu His Leu Cys Leu Arg Glu Ile Gln Gln Gln Arg Ala Ala
1               5                   10                  15

Gln Lys Leu

<210> SEQ ID NO 332
<211> LENGTH: 16
<212> TYPE: PRT
<213> ORGANISM: Homo sapiens

<400> SEQUENCE: 332

Met Thr Gly Glu Phe Arg Lys Tyr Asn Asn Asn Gly Asp Glu Ile
1               5                   10                  15

<210> SEQ ID NO 333
<211> LENGTH: 35
<212> TYPE: PRT
<213> ORGANISM: Homo sapiens

<400> SEQUENCE: 333

Met Leu Ala Phe Ser His Trp Thr Tyr Glu Tyr Thr Arg Gly Glu Leu
1               5                   10                  15

Leu Val Leu Asp Leu Gln Gly Val Gly Glu Asn Leu Thr Asp Pro Ser
            20                  25                  30

Val Ile Lys
        35

```
<210> SEQ ID NO 334
<211> LENGTH: 22
<212> TYPE: PRT
<213> ORGANISM: Homo sapiens

<400> SEQUENCE: 334

Ala Lys His His Cys Asn Ser Cys Cys Arg Lys Leu Lys Leu Pro Asp
1               5                   10                  15

Leu Lys Arg Asn Asp Tyr
            20

<210> SEQ ID NO 335
<211> LENGTH: 20
<212> TYPE: PRT
<213> ORGANISM: Homo sapiens

<400> SEQUENCE: 335

Glu Tyr Thr Arg Gly Glu Leu Leu Val Leu Asp Leu Gln Gly Val Gly
1               5                   10                  15

Glu Asn Leu Thr
            20
```

US 7,541,434 B2

POLYPEPTIDE FOR A TRP CHANNEL FAMILY MEMBER, TRP-PLIK2, AND SPLICE VARIANTS

This application is a divisional application of non-provisional application U.S. Ser. No. 10/153,244, filed May 22, 2002, now U.S. Pat. No. 7,223,557, which claims benefit to provisional application U.S. Ser. No. 60/292,599 filed May 22, 2001; and to provisional application U.S. Ser. No. 60/362,944, filed Mar. 8, 2002. The entire teachings of the referenced applications are incorporated herein by reference.

FIELD OF THE INVENTION

The present invention provides novel polynucleotides encoding TRP-PLIK2 polypeptides, fragments and homologues thereof. The present invention also provides polynucleotides encoding variants and splice variants of TRP-PLIK2 polypeptides, TRP-PLIK2b, TRP-PLIK2c, and TRP-PLIK2d, respectively. Also provided are vectors, host cells, antibodies, and recombinant and synthetic methods for producing said polypeptides. The invention further relates to diagnostic and therapeutic methods for applying these novel TRP-PLIK2, TRP-PLIK2b, TRP-PLIK2c, and TRP-PLIK2d polypeptides to the diagnosis, treatment, and/or prevention of various diseases and/or disorders related to these polypeptides. The invention further relates to screening methods for identifying agonists and antagonists of the polynucleotides and polypeptides of the present invention.

BACKGROUND OF THE INVENTION

Intracellular $Ca^{2+}$ plays a pivotal role in various cell functions, ranging from exocytosis and contraction to gene expression and cell differentiation, proliferation and apoptosis. Human mutations in the genes involved in intracellular $Ca^{2+}$ handling result in visual defects, diabetes mellitus, disorders in the skin, skeletal-muscle, nervous, cardiac and vascular systems (reviewed by Missiaen et al., 2000). In addition to the well characterized voltage-dependent $Ca^{2+}$ channels, $Ca^{2+}$ pumps and $Ca^{2+}$-permeable ligand-gated channels, TRPC (Transient Receptor Potential Channels) is an emerging class of $Ca^{2+}$-permeable cation channel superfamily. All of the channels in this family contain a six-trans-membrane domain although various cellular mechanisms have been implicated in their functions (reviewed by Harteneck et al., 2000).

The first member of this family, dTRP, was identified from Drosophila mutants trp whose photoreceptors failed to generate a sustained receptor potential in response to intense sustained light. The mutant fly showed a reduced $Ca^{2+}$ selectivity of the light response and the channel activity of dTRP depended on PLC activation was also demonstrated. Later, many mammalian homologues have been cloned and based on their homology, they are divided into three subfamilies: short (s), osm (o) and long (l). The sTRPC subfamily includes TRP1-7. Although the specific physiological function of each isoform remains to be assigned, it is generally believed that they may be involved in $Ca^{2+}$ entry after activation of receptors coupling to PLC. The TRP2 is specifically expressed in vomeronasal organ and involved in pheromone sensory signaling (Liman, et al., 1999). TRP1 and TRP6 are functioned in vascular smooth muscle cells and may play a role in controlling smooth muscle tone, arteriosclerosis and neointimal hyperplasia (Inoue et al., 2001; Xu & Beech, 2001). It has been shown that TRP4−/− mice lack an endothelial store-operated $Ca^{2+}$ current, which leads to reduced agonist-dependent vasorelaxation (Freichel et al., 2001).

The first member of oTRPC Subfamily is OSM-9 cloned from C. elegans. It is involved in responses to odorants, high osmotic strength, and mechanical stimulation. Recently, several mammalian homologues including vanilloid receptor (VR1) and vanilloid receptor-like receptor (VRL-1), which may have functions in pain and heat perception (Caterina, 1999; Caterina et al., 2000). VR1 has also been shown to be the receptor of anandamide and mediating its vasodilation effect (Zygmunt et al., 1999). OTRPC4 is an osmotically activated channel and a candidate osmoreceptor, may be involved in regulation of cellular volume (Strotmann et al., 2000). CaT1 & ECaC1 may be the calcium-release-activated calcium channel and involved in $Ca^{2+}$ reabsorption in intestine and kidney (Peng, et al, 1999; Yu et al., 2001).

The function of the lTRPC is less clear. The cloned mammalian lTRPC includes melastatin1/MLSN1/LTRPC1, MTR1/LTRPC5, TRPC7/LTRPC2 and TRP-P8. It is known that melastatin 1 is down regulated in metastatic melanomas (Duncan et al., 1998) and MTR1 is associated with Beckwith-Wiedemann syndrome and a predisposition to neoplasias (Prawitt et al., 2000). TRPC7 is mapped to the chromosome region linked to bipolar affective disorder, nonsyndromic hereditary deafness, Knobloch syndrome and holosencephaly (Nagamine et al., 1998). TRP-P8 is a prostate-specific gene and up-regulated in prostate cancer and other malignancies (Tsavaler et al., 2001). A recently cloned TRP-PLIK/hSOC-2/hCRAC-1 exhibits a very interesting feature in that it is a bi-functional protein with kinase and ion channel activities (Runnels et al., 2001). Additionally, a very long TRPC homologue NOMPC was found in Drosophila and C. elegans. NOMPC was identified as a mechanosensitive channel that can detect sound, pressure or movement changes (Walker et al., 2000).

Characterization of the TRP-PLIK2 polypeptide of the present invention led to the determination that it is involved in the modulation of the NFkB pathway, either directly or indirectly.

The fate of a cell in multicellular organisms often requires choosing between life and death. This process of cell suicide, known as programmed cell death or apoptosis, occurs during a number of events in an organisms life cycle, such as for example, in development of an embryo, during the course of an immunological response, or in the demise of cancerous cells after drug treatment, among others. The final outcome of cell survival versus apoptosis is dependent on the balance of two counteracting events, the onset and speed of caspase cascade activation (essentially a protease chain reaction), and the delivery of antiapoptotic factors which block the caspase activity (Aggarwal B. B. Biochem. Pharmacol. 60, 1033-1039, (2000); Thornberry, N. A. and Lazebnik, Y. Science 281, 1312-1316, (1998)).

The production of antiapoptotic proteins is controlled by the transcriptional factor complex NF-kB. For example, exposure of cells to the protein tumor necrosis factor (TNF) can signal both cell death and survival, an event playing a major role in the regulation of immunological and inflammatory responses (Ghosh, S., May, M. J., Kopp, E. B. Annu. Rev. Immunol. 16, 225-260, (1998); Silverman, N. and Maniatis, T., Genes & Dev. 15, 2321-2342, (2001); Baud, V. and Karin, M., Trends Cell Biol. 11, 372-377, (2001)). The anti-apoptotic activity of NF-kB is also crucial to oncogenesis and to chemo- and radio-resistance in cancer (Baldwin, A. S., J. Clin. Inves. 107, 241-246, (2001)).

Nuclear Factor-kB (NF-kB), is composed of dimeric complexes of p50 (NF-kB1) or p52 (NF-kB2) usually associated with members of the Rel family (p65, c-Rel, Rel B) which have potent transactivation domains. Different combinations of NF-kB/Rel proteins bind distinct kB sites to regulate the transcription of different genes. Early work involving NF-kB suggested its expression was limited to specific cell types, particularly in stimulating the transcription of genes encoding kappa immunoglobulins in B lymphocytes. However, it has been discovered that NF-kB is, in fact, present and inducible in many, if not all, cell types and that it acts as an intracellular messenger capable of playing a broad role in gene regulation as a mediator of inducible signal transduction. Specifically, it has been demonstrated that NF-kB plays a central role in regulation of intercellular signals in many cell types. For example, NF-kB has been shown to positively regulate the human beta-interferon (beta-IFN) gene in many, if not all, cell types. Moreover, NF-kB has also been shown to serve the important function of acting as an intracellular transducer of external influences.

The transcription factor NF-kB is sequestered in an inactive form in the cytoplasm as a complex with its inhibitor, IkB, the most prominent member of this class being IkBa. A number of factors are known to serve the role of stimulators of NF-kB activity, such as, for example, TNF. After TNF exposure, the inhibitor is phosphorylated and proteolytically removed, releasing NF-kB into the nucleus and allowing its transcriptional activity. Numerous genes are upregulated by this transcription factor, among them IkBa. The newly synthesized IkBa protein inhibits NF-kB, effectively shutting down further transcriptional activation of its downstream effectors. However, as mentioned above, the IkBa protein may only inhibit NF-kB in the absence of IkBa stimuli, such as TNF stimulation, for example. Other agents that are known to stimulate NF-kB release, and thus NF-kB activity, are bacterial lipopolysaccharide, extracellular polypeptides, chemical agents, such as phorbol esters, which stimulate intracellular phosphokinases, inflammatory cytokines, IL-1, oxidative and fluid mechanical stresses, and Ionizing Radiation (Basu, S., Rosenzweig, K, R., Youmell, M., Price, B, D, Biochem, Biophys, Res, Commun., 247(1):79-83, (1998)). Therefore, as a general rule, the stronger the insulting stimulus, the stronger the resulting NF-kB activation, and the higher the level of IkBa transcription. As a consequence, measuring the level of IkBa RNA can be used as a marker for antiapoptotic events, and indirectly, for the onset and strength of pro-apoptotic events.

Using the above examples, it is clear the availability of a novel cloned transient receptor potential channel family provides an opportunity for adjunct or replacement therapy, and are useful for the identification of transient receptor potential channel agonists, or stimulators (which might stimulate and/ or bias transient receptor potential channel function), as well as, in the identification of transient receptor potential channel inhibitors. All of which might be therapeutically useful under different circumstances.

The present invention also relates to recombinant vectors, which include the isolated nucleic acid molecules of the present invention, and to host cells containing the recombinant vectors, as well as to methods of making such vectors and host cells, in addition to their use in the production of TRP-PLIK2, TRP-PLIK2b, TRP-PLIK2c, and TRP-PLIK2d polypeptides using recombinant techniques. Synthetic methods for producing the polypeptides and polynucleotides of the present invention are provided. Also provided are diagnostic methods for detecting diseases, disorders, and/or conditions related to the TRP-PLIK2, TRP-PLIK2b, TRP-PLIK2c, and TRP-PLIK2d polypeptides and polynucleotides, and therapeutic methods for treating such diseases, disorders, and/or conditions. The invention further relates to screening methods for identifying binding partners of the polypeptides.

BRIEF SUMMARY OF THE INVENTION

The present invention provides isolated nucleic acid molecules, that comprise, or alternatively consist of, a polynucleotide encoding the TRP-PLIK2 protein having the amino acid sequence shown in FIGS. 1A-G (SEQ ID NO:2) or the amino acid sequence encoded by the cDNA clone, TRP-PLIK2 (also referred to as LTRPC6, BAC57, AL354795, and/or gene 95) deposited as ATCC® Deposit Number PTA-4175 on Mar. 21, 2002.

The present invention provides isolated nucleic acid molecules, that comprise, or alternatively consist of, a polynucleotide encoding the TRP-PLIK2b protein having the amino acid sequence shown in FIGS. 2A-G (SEQ ID NO:4) or the amino acid sequence encoded by the cDNA clone, TRP-PLIK2b (also referred to as LTRPC6, BAC57, AL354795, and/or gene 95 splice variant).

The present invention provides isolated nucleic acid molecules, that comprise, or alternatively consist of, a polynucleotide encoding the TRP-PLIK2c protein having the amino acid sequence shown in FIGS. 3A-G (SEQ ID NO:6) or the amino acid sequence encoded by the cDNA clone, TRP-PLIK2c (also referred to as LTRPC6, BAC57, AL354795, and/or gene 95 splice variant).

The present invention provides isolated nucleic acid molecules, that comprise, or alternatively consist of, a polynucleotide encoding the TRP-PLIK2d protein having the amino acid sequence shown in FIGS. 4A-G (SEQ ID NO:8) or the amino acid sequence encoded by the cDNA clone, TRP-PLIK2d (also referred to as LTRPC6, BAC57, AL354795, and/or gene 95 splice variant).

The present invention also relates to recombinant vectors, which include the isolated nucleic acid molecules of the present invention, and to host cells containing the recombinant vectors, as well as to methods of making such vectors and host cells, in addition to their use in the production of TRP-PLIK2, TRP-PLIK2b, TRP-PLIK2c, and TRP-PLIK2d polynucleotides or polypeptides using recombinant techniques. Synthetic methods for producing the polypeptides and polynucleotides of the present invention are provided. Also provided are diagnostic methods for detecting diseases, disorders, and/or conditions related to the TRP-PLIK2, TRP-PLIK2b, TRP-PLIK2c, and TRP-PLIK2d polypeptides and polynucleotides, and therapeutic methods for treating such diseases, disorders, and/or conditions. The invention further relates to screening methods for identifying binding partners of the polypeptides.

The invention further provides an isolated TRP-PLIK2 polypeptide having an amino acid sequence encoded by a polynucleotide described herein.

The invention further provides an isolated TRP-PLIK2b polypeptide having an amino acid sequence encoded by a polynucleotide described herein.

The invention further provides an isolated TRP-PLIK2c polypeptide having an amino acid sequence encoded by a polynucleotide described herein.

The invention further provides an isolated TRP-PLIK2d polypeptide having an amino acid sequence encoded by a polynucleotide described herein.

The invention further relates to a polynucleotide encoding a polypeptide fragment of SEQ ID NO:2, 4, 6, 8, and/or 98, or a polypeptide fragment encoded by the cDNA sequence included in the deposited clone, which is hybridizable to SEQ ID NO:1, 3, 5, 7, and/or 97.

The invention further relates to a polynucleotide encoding a polypeptide domain of SEQ ID NO:2, 4, 6, 8, and/or 98 or a polypeptide domain encoded by the cDNA sequence included in the deposited clone, which is hybridizable to SEQ ID NO:1, 3, 5, 7, and/or 97.

The invention further relates to a polynucleotide encoding a polypeptide epitope of SEQ ID NO:2, 4, 6, 8, and/or 98 or a polypeptide epitope encoded by the cDNA sequence included in the deposited clone, which is hybridizable to SEQ ID NO:1, 3, 5, 7, and/or 97.

The invention further relates to a polynucleotide encoding a polypeptide of SEQ ID NO:2, 4, 6, 8, and/or 98 or the cDNA sequence included in the deposited clone, which is hybridizable to SEQ ID NO:1, 3, 5, 7, and/or 97, having biological activity.

The invention further relates to a polynucleotide which is a variant of SEQ ID NO:1, 3, 5, 7, and/or 97.

The invention further relates to a polynucleotide which is an allelic variant of SEQ ID NO:1, 3, 5, 7, and/or 97.

The invention further relates to a polynucleotide which encodes a species homologue of the SEQ ID NO:2, 4, 6, 8, and/or 98.

The invention further relates to a polynucleotide which represents the complimentary sequence (antisense) of SEQ ID NO:1, 3, 5, 7, and/or 97.

The invention further relates to a polynucleotide capable of hybridizing under stringent conditions to any one of the polynucleotides specified herein, wherein said polynucleotide does not hybridize under stringent conditions to a nucleic acid molecule having a nucleotide sequence of only A residues or of only T residues.

The invention further relates to an isolated nucleic acid molecule of SEQ ID NO:2, 4, 6, 8, and/or 98, wherein the polynucleotide fragment comprises a nucleotide sequence encoding an transient potential receptor protein.

The invention further relates to an isolated nucleic acid molecule of SEQ ID NO:1, 3, 5, 7, and/or 97, wherein the polynucleotide fragment comprises a nucleotide sequence encoding the sequence identified as SEQ ID NO:2, 4, 6, 8, and/or 98 or the polypeptide encoded by the cDNA sequence included in the deposited clone, which is hybridizable to SEQ ID NO:1, 3, 5, 7, and/or 97.

The invention further relates to an isolated nucleic acid molecule of SEQ ID NO:1, 3, 5, 7, and/or 97, wherein the polynucleotide fragment comprises the entire nucleotide sequence of SEQ ID NO:1, 3, 5, 7, and/or 97 or the cDNA sequence included in the deposited clone, which is hybridizable to SEQ ID NO:1, 3, 5, 7, and/or 97.

The invention further relates to an isolated nucleic acid molecule of SEQ ID NO:1, 3, 5, 7, and/or 97, wherein the nucleotide sequence comprises sequential nucleotide deletions from either the C-terminus or the N-terminus.

The invention further relates to an isolated polypeptide comprising an amino acid sequence that comprises a polypeptide fragment of SEQ ID NO:2, 4, 6, 8, and/or 98 or the encoded sequence included in the deposited clone.

The invention further relates to a polypeptide fragment of SEQ ID NO:2, 4, 6, 8, and/or 98 or the encoded sequence included in the deposited clone, having biological activity.

The invention further relates to a polypeptide domain of SEQ ID NO:2, 4, 6, 8, and/or 98 or the encoded sequence included in the deposited clone.

The invention further relates to a polypeptide epitope of SEQ ID NO:2, 4, 6, 8, and/or 98 or the encoded sequence included in the deposited clone.

The invention further relates to a full length protein of SEQ ID NO:2, 4, 6, 8, and/or 98 or the encoded sequence included in the deposited clone.

The invention further relates to a variant of SEQ ID NO:2, 4, 6, 8, and/or 98.

The invention further relates to an allelic variant of SEQ ID NO:2, 4, 6, 8, and/or 98. The invention further relates to a species homologue of SEQ ID NO:2, 4, 6, 8, and/or 98.

The invention further relates to the isolated polypeptide of SEQ ID NO:2, 4, 6, 8, and/or 98, wherein the full length protein comprises sequential amino acid deletions from either the C-terminus or the N-terminus.

The invention further relates to an isolated antibody that binds specifically to the isolated polypeptide of SEQ ID NO:2, 4, 6, 8, and/or 98.

The invention further relates to a method for preventing, treating, or ameliorating a medical condition, comprising administering to a mammalian subject a therapeutically effective amount of the polypeptide of SEQ ID NO:2, 4, 6, 8, and/or 98 or the polynucleotide of SEQ ID NO:1, 3, 5, 7, and/or 97.

The invention further relates to a method of diagnosing a pathological condition or a susceptibility to a pathological condition in a subject comprising the steps of (a) determining the presence or absence of a mutation in the polynucleotide of SEQ ID NO:1, 3, 5, 7, and/or 97; and (b) diagnosing a pathological condition or a susceptibility to a pathological condition based on the presence or absence of said mutation.

The invention further relates to a method of diagnosing a pathological condition or a susceptibility to a pathological condition in a subject comprising the steps of (a) determining the presence or amount of expression of the polypeptide of SEQ ID NO:2, 4, 6, 8, and/or 98 in a biological sample; and diagnosing a pathological condition or a susceptibility to a pathological condition based on the presence or amount of expression of the polypeptide.

The invention further relates to a method for identifying a binding partner to the polypeptide of SEQ ID NO:2, 4, 6, 8, and/or 98 comprising the steps of (a) contacting the polypeptide of SEQ ID NO:2, 4, 6, 8, and/or 98 with a binding partner; and (b) determining whether the binding partner effects an activity of the polypeptide.

The invention further relates to a gene corresponding to the cDNA sequence of SEQ ID NO:1, 3, 5, 7, and/or 97.

The invention further relates to a method of identifying an activity in a biological assay, wherein the method comprises the steps of expressing SEQ ID NO:1, 3, 5, 7, and/or 97 in a cell, (b) isolating the supernatant; (c) detecting an activity in a biological assay; and (d) identifying the protein in the supernatant having the activity.

The invention further relates to a process for making polynucleotide sequences encoding gene products having altered SEQ ID NO:2, 4, 6, 8, and/or 98 activity comprising the steps of (a) shuffling a nucleotide sequence of SEQ ID NO:1, 3, 5, 7, and/or 97, (b) expressing the resulting shuffled nucleotide sequences and, (c) selecting for altered activity as compared to the activity of the gene product of said unmodified nucleotide sequence.

The invention further relates to a shuffled polynucleotide sequence produced by a shuffling process, wherein said shuffled DNA molecule encodes a gene product having enhanced tolerance to an inhibitor of SEQ ID NO:2, 4, 6, 8, and/or 98 activity.

The invention further relates to a method for preventing, treating, or ameliorating a medical condition with the polypeptide provided as SEQ ID NO:2, 4, 6, 8, and/or 98, in addition to, its encoding nucleic acid, wherein the medical condition is a gastrointestinal disorder.

The invention further relates to a method for preventing, treating, or ameliorating a medical condition with the polypeptide provided as SEQ ID NO:2, 4, 6, 8, and/or 98, in addition to, its encoding nucleic acid, wherein the medical condition is a metabolic disorder.

The invention further relates to a method for preventing, treating, or ameliorating a medical condition with the polypeptide provided as SEQ ID NO:2, 4, 6, 8, and/or 98, in addition to, its encoding nucleic acid, wherein the medical condition is an immune disorder The invention further relates to a method for preventing, treating, or ameliorating a medical condition with the polypeptide provided as SEQ ID NO:2, 4, 6, 8, and/or 98, in addition to, its encoding nucleic acid, wherein the medical condition is a hematopoietic disorder.

The invention further relates to a method for preventing, treating, or ameliorating a medical condition with the polypeptide provided as SEQ ID NO:2, 4, 6, 8, and/or 98, in addition to, its encoding nucleic acid, wherein the medical condition is a inflammatory disorder.

The invention further relates to a method for preventing, treating, or ameliorating a medical condition with the polypeptide provided as SEQ ID NO:2, 4, 6, 8, and/or 98, in addition to, its encoding nucleic acid, wherein the medical condition is a renal disorder.

The invention further relates to a method for preventing, treating, or ameliorating a medical condition with the polypeptide provided as SEQ ID NO:2, 4, 6, 8, and/or 98, in addition to, its encoding nucleic acid, wherein the medical condition is a reproductive disorder.

The invention further relates to a method for preventing, treating, or ameliorating a medical condition with the polypeptide provided as SEQ ID NO:2, 4, 6, 8, and/or 98, in addition to, its encoding nucleic acid, wherein the medical condition is a hepatic disorder.

The invention further relates to a method for preventing, treating, or ameliorating a medical condition with the polypeptide provided as SEQ ID NO:2, 4, 6, 8, and/or 98, in addition to, its encoding nucleic acid, wherein the medical condition is a disorder related to hyper transient receptor potential activity.

The invention further relates to a method for preventing, treating, or ameliorating a medical condition with the polypeptide provided as SEQ ID NO:2, 4, 6, 8, and/or 98, in addition to, its encoding nucleic acid, wherein the medical condition is prostate cancer.

The invention further relates to a method for preventing, treating, or ameliorating a medical condition with the polypeptide provided as SEQ ID NO:2, 4, 6, 8, and/or 98, in addition to, its encoding nucleic acid, wherein the medical condition is amyotrophic lateral sclerosis with frontotemporal dementia, early-onset pulverulent cataract, infantile nephronophthisis, hypomagnesemia with secondary hypocalcemia, familial hemophagocytic lymphohistiocytosis, neuronal degeneration, neurogenic inflammation, allergy, immunodeficiency/excessive immune activation, visual defects, hearing disorder, pain, cancer, hypertension, other cardiovascular diseases, diseases associated with disturbances in $Ca^{2+}$ homeostasis including osteoporosis, hypercalciuric stone disease, and chronic renal failure The invention further relates to a method of identifying a compound that modulates the biological activity of TRP-PLIK2, comprising the steps of, (a) combining a candidate modulator compound with TRP-PLIK2 having the sequence set forth in one or more of SEQ ID NO:2, 4, 6, 8, and/or 98; and measuring an effect of the candidate modulator compound on the activity of TRP-PLIK2.

The invention further relates to a method of identifying a compound that modulates the biological activity of a transient receptor potential protein, comprising the steps of, (a) combining a candidate modulator compound with a host cell expressing TRP-PLIK2 having the sequence as set forth in SEQ ID NO:2, 4, 6, 8, and/or 98; and, (b) measuring an effect of the candidate modulator compound on the activity of the expressed TRP-PLIK2.

The invention further relates to a method of identifying a compound that modulates the biological activity of TRP-PLIK2, comprising the steps of, (a) combining a candidate modulator compound with a host cell containing a vector described herein, wherein TRP-PLIK2 is expressed by the cell; and, (b) measuring an effect of the candidate modulator compound on the activity of the expressed TRP-PLIK2.

The invention further relates to a method of screening for a compound that is capable of modulating the biological activity of TRP-PLIK2, comprising the steps of: (a) providing a host cell described herein; (b) determining the biological activity of TRP-PLIK2 in the absence of a modulator compound; (c) contacting the cell with the modulator compound; and (d) determining the biological activity of TRP-PLIK2 in the presence of the modulator compound; wherein a difference between the activity of TRP-PLIK2 in the presence of the modulator compound and in the absence of the modulator compound indicates a modulating effect of the compound.

The invention further relates to a compound that modulates the biological activity of human TRP-PLIK2 as identified by the methods described herein.

The present invention also relates to an isolated polynucleotide consisting of a portion of the human TRP-PLIK2 gene consisting of at least 8 bases, specifically excluding GENBANK® Accession Nos. BI754451, BB593693, BM472126, BE465471, AW645658, BB650718, AI390333, AW916907, BJ028793, and/or BE305668.

The present invention also relates to an isolated polynucleotide consisting of a nucleotide sequence encoding a fragment of the human TRP-PLIK2 protein, wherein said fragment displays one or more functional activities specifically excluding GENBANK® Accession Nos. BI754451, BB593693, BM472126, BE465471, AW645658, BB650718, AI390333, AW916907, BJ028793, and/or BE305668.

The present invention also relates to the polynucleotide of SEQ ID NO:1, 3, 5, 7, and/or 97 consisting of at least 10 to 50 bases, wherein said at least 10 to 50 bases specifically exclude the polynucleotide sequence of GENBANK® Accession Nos. BI754451, BB593693, BM472126, BE465471, AW645658, BB650718, AI390333, AW916907, BJ028793, and/or BE305668.

The present invention also relates to the polynucleotide of SEQ ID NO:1, 3, 5, 7, and/or 97 consisting of at least 15 to 100 bases, wherein said at least 15 to 100 bases specifically exclude the polynucleotide sequence of GENBANK® Accession Nos. BI754451, BB593693, BM472126, BE465471, AW645658, BB650718, AI390333, AW916907, BJ028793, and/or BE305668.

The present invention also relates to the polynucleotide of SEQ ID NO:1, 3, 5, 7, and/or 97 consisting of at least 100 to 1000 bases, wherein said at least 100 to 1000 bases specifically exclude the polynucleotide sequence of GENBANK® Accession Nos. BI754451, BB593693, BM472126, BE465471, AW645658, BB650718, AI390333, AW916907, BJ028793, and/or BE305668.

The present invention also relates to an isolated polypeptide fragment of the human TRP-PLIK2 protein, wherein said polypeptide fragment does not consist of the polypeptide encoded by the polynucleotide sequence of GENBANK® Accession Nos. BI754451, BB593693, BM472126, BE465471, AW645658, BB650718, AI390333, AW916907, BJ028793, and/or BE305668.

BRIEF DESCRIPTION OF THE FIGURES/DRAWINGS

FIGS. 1A-G show the polynucleotide sequence (SEQ ID NO:1) and deduced amino acid sequence (SEQ ID NO:2) of the novel human transient receptor potential channel member, TRP-PLIK2, of the present invention. The standard one-letter abbreviation for amino acids is used to illustrate the deduced amino acid sequence. The polynucleotide sequence contains a sequence of 6054 nucleotides (SEQ ID NO:1), encoding a polypeptide of 2017 amino acids (SEQ ID NO:2). An analysis of the TRP-PLIK2 polypeptide determined that it comprised the following features: six transmembrane domains (TM1 thru TM6) located from about amino acid 740 to about amino acid 757 (TM1), from about amino acid 834 to about amino acid 851 (TM2), from about amino acid 908 to about amino acid 920 (TM3), from about amino acid 934 to about amino acid 951 (TM4), from about amino acid 968 to about amino acid 985 (TM5), and/or from about amino acid 1043 to about amino acid 1062 (TM6) of SEQ ID NO:2 represented by double underlining; a predicted TRP domain (LWKYNR) located from about amino acid 1078 to about amino acid 1083 of SEQ ID NO:2 represented by light shading; a predicted nucleotide binding domain located from about amino acid 1945 to about amino acid 1950 of SEQ ID NO:2 represented by dark shading; a predicted zinc finger domain located at about amino acid 1960 to about amino acid 1970 of SEQ ID NO:2 represented by dotted underlining; a predicted ion transport signature domain located at about amino acid 904 to about amino acid 1064 of SEQ ID NO:2 represented by italics; conserved cysteine residues located at amino acid 21, 34, 38, 41, 47, 49, 311, 367, 637, 702, 719, 938, 1028, 1034, 1114, 1148, 1822, 1861, 1963, 1966, and 1967 of SEQ ID NO:2 represented in bold. Conservation of cysteines at key amino acid residues is indicative of conserved structural features, which may correlate with conservation of protein function and/or activity.

FIGS. 2A-G show the polynucleotide sequence (SEQ ID NO:3) and deduced amino acid sequence (SEQ ID NO:4) of the novel human transient receptor potential channel member splice variant, TRP-PLIK2b, of the present invention. The standard one-letter abbreviation for amino acids is used to illustrate the deduced amino acid sequence. The polynucleotide sequence contains a sequence of 5913 nucleotides (SEQ ID NO:3), encoding a polypeptide of 1970 amino acids (SEQ ID NO:4). An analysis of the TRP-PLIK2b polypeptide determined that it comprised the following features: six transmembrane domains (TM1 thru TM6) located from about amino acid 693 to about amino acid 710 (TM1), from about amino acid 787 to about amino acid 804 (TM2), from about amino acid 861 to about amino acid 873 (TM3), from about amino acid 887 to about amino acid 904 (TM4), from about amino acid 921 to about amino acid 938 (TM5), and/or from about amino acid 996 to about amino acid 1015 (TM6) of SEQ ID NO:4 represented by double underlining; a predicted TRP domain (LWKYNR) located from about amino acid 1031 to about amino acid 1036 of SEQ ID NO:4 represented by light shading; a predicted nucleotide binding domain located from about amino acid 1898 to about amino acid 1903 of SEQ ID NO:4 represented by dark shading; a predicted zinc finger domain located at about amino acid 1913 to about amino acid 1923 of SEQ ID NO:2 represented by dotted underlining; a predicted ion transport signature domain located at about amino acid 857 to about amino acid 1017 of SEQ ID NO:4 represented by italics; conserved cysteine residues located at amino acid 21, 34, 38, 41, 47, 49, 311, 367, 590, 655, 672, 891, 981, 987, 1067, 1101, 1775, 1814, 1915, 1919, and 1920 of SEQ ID NO:4 represented in bold. Conservation of cysteines at key amino acid residues is indicative of conserved structural features, which may correlate with conservation of protein function and/or activity.

FIGS. 3A-G show the polynucleotide sequence (SEQ ID NO:5) and deduced amino acid sequence (SEQ ID NO:6) of the novel human transient receptor potential channel member splice variant, TRP-PLIK2c, of the present invention. The standard one-letter abbreviation for amino acids is used to illustrate the deduced amino acid sequence. The polynucleotide sequence contains a sequence of 5820 nucleotides (SEQ ID NO:5), encoding a polypeptide of 1939 amino acids (SEQ ID NO:6). An analysis of the TRP-PLIK2c polypeptide determined that it comprised the following features: six transmembrane domains (TM1 thru TM6) located from about amino acid 662 to about amino acid 679 (TM1), from about amino acid 756 to about amino acid 773 (TM2), from about amino acid 830 to about amino acid 842 (TM3), from about amino acid 856 to about amino acid 873 (TM4), from about amino acid 890 to about amino acid 907 (TM5), and/or from about amino acid 965 to about amino acid 984 (TM6) of SEQ ID NO:6 represented by double underlining; a predicted TRP domain (LWKYNR) located from about amino acid 1000 to about amino acid 1005 of SEQ ID NO:6 represented by light shading; a predicted nucleotide binding domain located from about amino acid 1867 to about amino acid 1872 of SEQ ID NO:6 represented by dark shading; a predicted zinc finger domain located at about amino acid 1882 to about amino acid 1892 of SEQ ID NO:2 represented by dotted underlining; a predicted ion transport signature domain located at about amino acid 826 to about amino acid 986 of SEQ ID NO:6 represented by italics; conserved cysteine residues located at amino acid 21, 34, 38, 41, 47, 49, 311, 367, 590, 655, 672, 891, 981, 987, 1067, 1101, 1775, 1814, 1915, 1919, and 1920 of SEQ ID NO:6 represented in bold. Conservation of cysteines at key amino acid residues is indicative of conserved structural features, which may correlate with conservation of protein function and/or activity.

FIGS. 4A-G show the polynucleotide sequence (SEQ ID NO:7) and deduced amino acid sequence (SEQ ID NO:8) of the novel human transient receptor potential channel member splice variant, TRP-PLIK2d, of the present invention. The standard one-letter abbreviation for amino acids is used to illustrate the deduced amino acid sequence. The polynucleotide sequence contains a sequence of 5925 nucleotides (SEQ ID NO:7), encoding a polypeptide of 1974 amino acids (SEQ ID NO:8). An analysis of the TRP-PLIK2d polypeptide determined that it comprised the following features: six transmembrane domains (TM1 thru TM6) located from about amino acid 740 to about amino acid 757 (TM1), from about amino acid 834 to about amino acid 845 (TM2), from about amino acid 861 to about amino acid 880 (TM3), from about amino acid 892 to about amino acid 909 (TM4), from about amino acid 925 to about amino acid 946 (TM5), and/or from about amino acid 996 to about amino acid 1026 (TM6) of SEQ ID NO:8 represented by double underlining; a predicted TRP domain (LWKYNR) located from about amino acid 1035 to about amino acid 1040 of SEQ ID NO:8 represented by light shading; a predicted nucleotide binding domain located from about amino acid 1902 to about amino acid 1907 of SEQ ID NO:8 represented by dark shading; a predicted zinc finger domain located at about amino acid 1917 to about amino acid 1927 of SEQ ID NO:2 represented by dotted underlining; a predicted ion transport signature domain located at about amino acid 904 to about amino acid 959 of SEQ ID NO:8 represented by italics; conserved cysteine residues located at amino acid 21, 34, 38, 41, 47, 49, 311, 367, 637, 702, 719, 895, 985, 991, 1071, 1105, 1779, 1818, 1920, 1923, and 1924 of SEQ ID NO:8 represented in bold. Conservation of cysteines at key amino acid residues is indicative of conserved structural features, which may correlate with conservation of protein function and/or activity.

FIGS. 5A-F show the regions of identity and similarity between the TRP-PLIK2, TRP-PLIK2b, TRP-PLIK2c, and TRP-PLIK2d polypeptides of the present invention to another member of human transient receptor potential channel family, specifically, the human channel-kinase 1 protein, also known as the human CHAK1 or TRP-PLIK1 protein (CHAK1; GENBANK® Accession No. gi|AF346629; SEQ ID NO:9); and the human melastatin 1 protein (Melastatin1; GENBANK® Accession No. gi|3243075; SEQ ID NO:260). The alignment was created using the CLUSTALW algorithm described elsewhere herein using default parameters (CLUSTALW parameters: gap opening penalty: 10; gap extension penalty: 0.5; gap separation penalty range: 8; percent identity for alignment delay: 40%; and transition, weighting: 0). The darkly shaded amino acids represent regions of matching identity. The lightly shaded amino acids represent regions of matching similarity. Dots between residues indicate gapped regions for the aligned polypeptides.

FIGS. 6A-E shows the regions of identity between the TRP-PLIK2 polypeptide (SEQ ID NO:2) of the present invention to its predicted splice variants TRP-PLIK2b (SEQ ID NO:4), TRP-PLIK2c (SEQ ID NO:6), and TRP-PLIK2d (SEQ ID NO:8) polypeptides of the present invention. The alignment was created using the CLUSTALW algorithm described elsewhere herein using default parameters (CLUSTALW parameters: gap opening penalty: 10; gap extension penalty: 0.5; gap separation penalty range: 8; percent identity for alignment delay: 40%; and transition, weighting: 0). The darkly shaded amino acids represent regions of matching identity. The lightly shaded amino acids represent regions of matching similarity. Dots between residues indicate gapped regions for the aligned polypeptides.

FIG. 7 shows an expression profile of the novel human transient receptor potential channel family member, TRP-PLIK2 (SEQ ID NO:2). The figure illustrates the relative expression level of TRP-PLIK2 amongst various mRNA tissue sources. As shown, transcripts corresponding to TRP-PLIK2 expressed predominately in bone marrow, kidney, and testis tissue. The TRP-PLIK2 polypeptide was also expressed significantly in liver, and to a lesser extent, in small intestine, spinal cord, prostate, uterus, lung, lymph node, stomach, heart, brain, thymus, and pancrease. Expression data was obtained by measuring the steady state TRP-PLIK2 mRNA levels by RT-PCR using the PCR primer pair provided as SEQ ID NO:27 and 28 as described herein.

Figure 8:
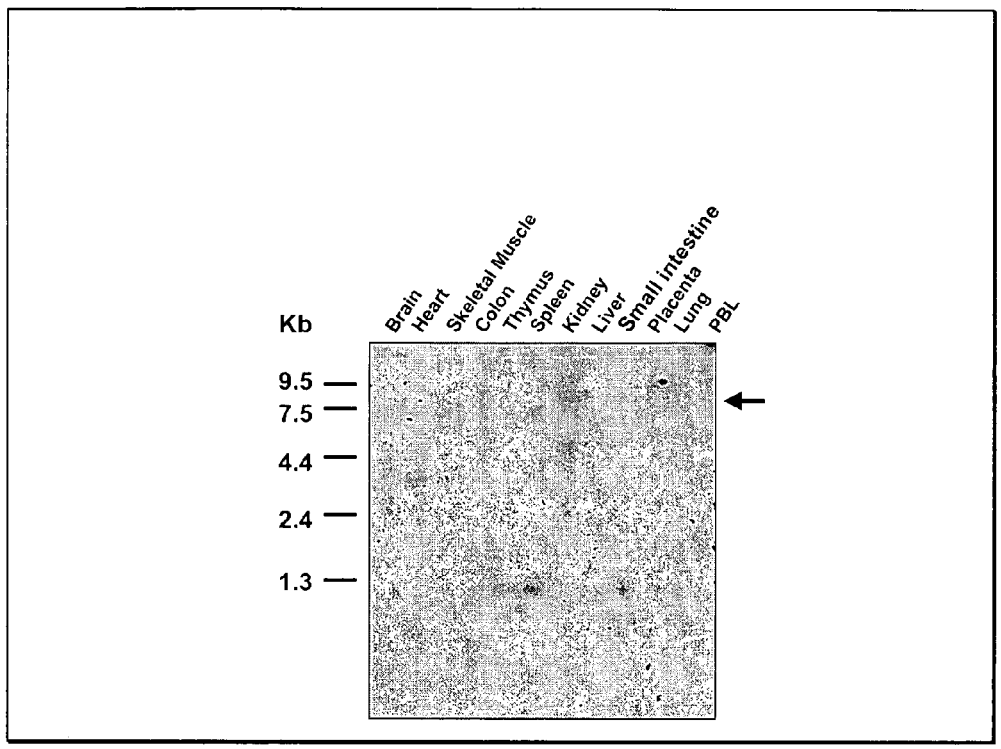

FIG. 8 shows an expression profile of the novel human transient receptor potential channel family member, TRP-PLIK2 (SEQ ID NO:2). The figure illustrates the relative expression level of TRP-PLIK2 amongst various mRNA tissue, and cell sources. As shown, transcripts corresponding to TRP-PLIK2 expressed predominately in kidney tissue. The TRP-PLIK2 polypeptide was also expressed significantly in brain, and skeletal muscle. Expression data was obtained by probing a Northern blot using a TRP-PLIK2 507-bp PCR amplified fragment as described herein.

FIG. 9 shows a table illustrating the percent identity and percent similarity between the TRP-PLIK2, TRP-PLIK2b, TRP-PLIK2c, and TRP-PLIK2d polypeptides of the present invention with the human CHAK1 protein (CHAK1; GENBANK® Accession No. gi|AF346629; SEQ ID NO:9); and the human melastatin 1 protein (Melastatin1; GENBANK® Accession No. gi|3243075; SEQ ID NO:260). The percent identity and percent similarity values were determined based upon the GAP® algorithm (GCG suite of programs; and Henikoff, S, and Henikoff, J. G., Proc. Natl. Acad. Sci. USA 89: 10915-10919 (1992)).

FIGS. 10A-B shows the polynucleotide sequences from the human bac AL354795 used to design primers for cloning the TRP-PLIK2, TRP-PLIK2b, TRP-PLIK2c, and TRP-PLIK2d polynucleotides of the present invention as described herein.

FIGS. 11A-C show a partial polynucleotide sequence (SEQ ID NO:97) and partial deduced amino acid sequence (SEQ ID NO:98) of the novel human transient receptor potential channel member, TRP-PLIK2, of the present invention. The standard one-letter abbreviation for amino acids is used to illustrate the deduced amino acid sequence. The polynucleotide sequence contains a sequence of 1933 nucleotides (SEQ ID NO:97), encoding a polypeptide of 496 amino acids (SEQ ID NO:98).

Figure 12:
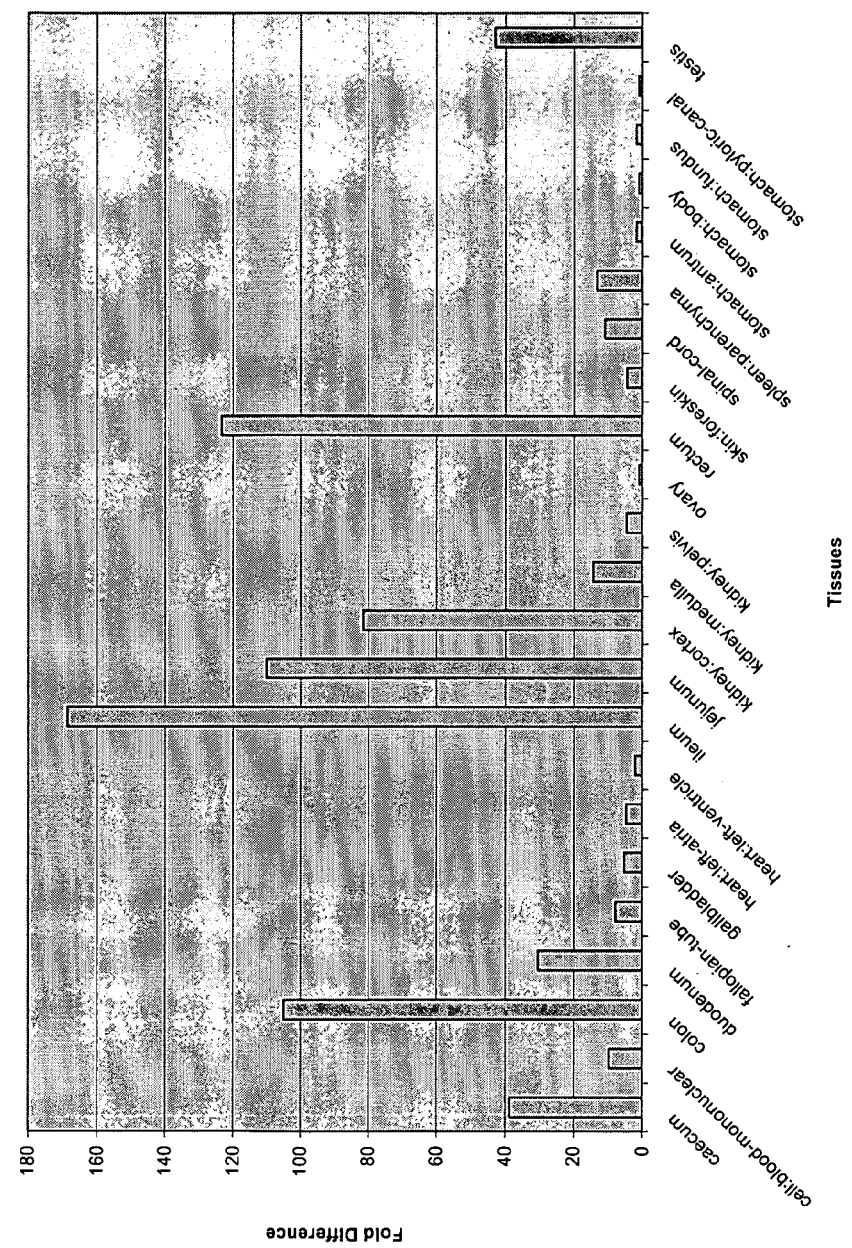

FIG. 12 shows an expanded expression profile of the novel human transient receptor potential channel member, TRP-PLIK2. The figure illustrates the relative expression level of TRP-PLIK2 amongst various mRNA tissue sources. As shown, the TRP-PLIK2 polypeptide was expressed predominately in the lower gastrointestinal tract, specifically the ileum, the rectum, the colon, the jejunum, duodenum, with minor transcript levels observed in the stomach. Expression of TRP-PLIK2 was also significantly expressed in the kidney, particularly in the cortex, followed by the medulla, and to a lesser extent in the testis. Expression data was obtained by measuring the steady state TRP-PLIK2 mRNA levels by quantitative PCR using the PCR primer pair provided as SEQ ID NO:267 and 268, and TAQMAN® probe (SEQ ID NO:269) as described in Example 4 herein.

Figure 13:
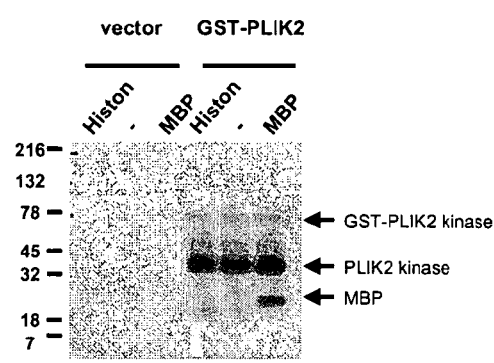

FIG. 13 shows the results of a kinase assay for the TRP-PLIK2-GST fusion protein polypeptide designed to measure the level of incorporated $P^{32}$ in either MBP or Histon protein substrates. GST fusion vector lacking the TRP-PLIK2 kinase domain was used as a control ("Vector"). The TRP-PLIK2-GST fusion protein is represented as "GST-PLIK2 kinase", the TRP-PLIK2 kinase domain is represented as "PLIK2 kinase", and "MBP" represents the MBP protein. As shown, predicted TRP-PLIK2 kinase domain was determined to have kinase activity as demonstrated by the phosphorylated MBP protein. Moreover, TRP-PLIK2 was also determined to be capable of autophosphorylation as demonstrated by the intense phosphorylation of the TRP-PLIK2 kinase domain ("PLIK2 kinase"). The TRP-PLIK2-GST fusion protein contained only the predicted kinase domain of the TRP-PLIK2 polypeptide as described in Example 5 herein.

Figure 14:
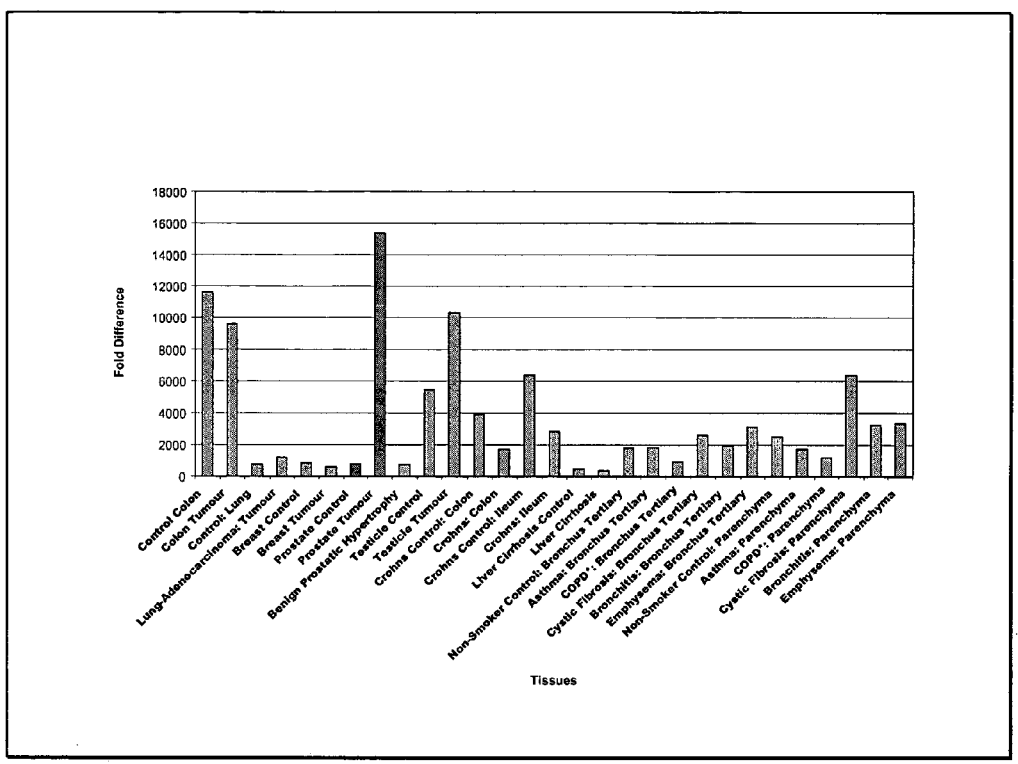

FIG. 14 shows an expanded expression profile of the novel human transient receptor potential channel member, TRP-PLIK2. The figure illustrates the relative expression level of TRP-PLIK2 amongst various normal and tumor mRNA tissue sources. As shown, the TRP-PLIK2 polypeptide was differentially expressed to the greatest extent in prostate tumor tissue relative to normal prostate tissue (approximately 20 fold difference). Expression of TRP-PLIK2 was also significantly differentially expressed in the testicular tumors relative to normal testicular tissue. Expression data was obtained by measuring the steady state TRP-PLIK2 mRNA levels by quantitative PCR using the PCR primer pair provided as SEQ ID NO:267 and 268, and TAQMAN® probe (SEQ ID NO:269) as described in Example 4 herein.

Figure 15:
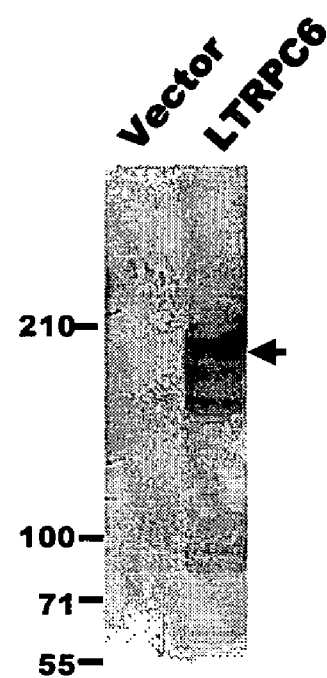

FIG. 15 shows the results of an immunoprecipitation assay for the HA tagged TRP-PLIK2-GST fusion protein polypeptide designed to prove TRP-PLIK2 is expressed in HEK cells. GST fusion vector lacking the encoding TRP-PLIK2 polynucleotide sequence was used as a control ("Vector"). The HA tagged TRP-PLIK2-GST fusion protein is represented as "LTRPC6". The immunoprecipitation experiments were performed as described in Example 5 herein.

Table I provides a summary of the novel polypeptides and their encoding polynucleotides of the present invention.

Table II illustrates the preferred hybridization conditions for the polynucleotides of the present invention. Other hybridization conditions may be known in the art or are described elsewhere herein.

Table III provides a summary of various conservative substitutions encompassed by the present invention.

DETAILED DESCRIPTION OF THE INVENTION

The present invention may be understood more readily by reference to the following detailed description of the preferred embodiments of the invention and the Examples included herein. All references to "TRP-PLIK2" shall be construed to apply to "TRP-PLIK2", "TRP-PLIK2b", "TRP-PLIK2c", and/or "TRP-PLIK2d" unless otherwise specified herein.

The invention provides a novel human sequence that potentially encodes a novel human transient receptor potential channel family member called TRP-PLIK2, in addition to, its splice variants TRP-PLIK2b, TRP-PLIK2c, and TRP-PLIK2d. TRP-PLIK2 shares significant homologue with other transient receptor potential channel family members, such as human CHAK1. Transcripts for TRP-PLIK2 were found predominately in the kidney, gastrointestinal tract, bone marrow, and testis suggesting that the invention potentially modulates leukocyte proliferation, differentiation, migration, and activation in these tissues. Therefore, the polynucleotide of the present invention has been tentatively named TRP-PLIK2.

In the present invention, "isolated" refers to material removed from its original environment (e.g., the natural environment if it is naturally occurring), and thus is altered "by the hand of man" from its natural state. For example, an isolated polynucleotide could be part of a vector or a composition of matter, or could be contained within a cell, and still be "isolated" because that vector, composition of matter, or particular cell is not the original environment of the polynucleotide. The term "isolated" does not refer to genomic or cDNA libraries, whole cell total or mRNA preparations, genomic DNA preparations (including those separated by electrophoresis and transferred onto blots), sheared whole cell genomic DNA preparations or other compositions where the art demonstrates no distinguishing features of the polynucleotide/sequences of the present invention.

In specific embodiments, the polynucleotides of the invention are at least 15, at least 30, at least 50, at least 100, at least 125, at least 500, or at least 1000 continuous nucleotides but are less than or equal to 300 kb, 200 kb, 100 kb, 50 kb, 15 kb, 10 kb, 7.5 kb, 5 kb, 2.5 kb, 2.0 kb, or 1 kb, in length. In a further embodiment, polynucleotides of the invention comprise a portion of the coding sequences, as disclosed herein, but do not comprise all or a portion of any intron. In another embodiment, the polynucleotides comprising coding sequences do not contain coding sequences of a genomic flanking gene (i.e., 5' or 3' to the gene of interest in the genome). In other embodiments, the polynucleotides of the invention do not contain the coding sequence of more than 1000, 500, 250, 100, 50, 25, 20, 15, 10, 5, 4, 3, 2, or 1 genomic flanking gene(s).

As used herein, a "polynucleotide" refers to a molecule having a nucleic acid sequence contained in SEQ ID NO:1, SEQ ID NO:3, SEQ ID NO:5, SEQ ID NO:7, SEQ ID NO:97 or the cDNA contained within the clone deposited with the ATCC®. For example, the polynucleotide can contain the nucleotide sequence of the full length cDNA sequence, including the 5' and 3' untranslated sequences, the coding region, with or without a signal sequence, the secreted protein coding region, as well as fragments, epitopes, domains, and variants of the nucleic acid sequence. Moreover, as used herein, a "polypeptide" refers to a molecule having the translated amino acid sequence generated from the polynucleotide as broadly defined.

In the present invention, the full length sequence identified as SEQ ID NO:1, SEQ ID NO:3, SEQ ID NO:5, SEQ ID NO:7 and, SEQ ID NO:97 was often generated by overlapping sequences contained in multiple clones (contig analysis). A representative clone containing all or most of the sequence for SEQ ID NO:1, SEQ ID NO:3, SEQ ID NO:5, SEQ ID NO:7, or SEQ ID NO:97 was deposited with the American Type Culture Collection ("ATCC"). As shown in Table 1, each clone is identified by a cDNA Clone ID (Identifier) and the ATCC® Deposit Number. The ATCC® is located at 10801 University Boulevard, Manassas, Va. 20110-2209, USA. The ATCC® deposit was made pursuant to the terms of the Budapest Treaty on the international recognition of the deposit of microorganisms for purposes of patent procedure. The deposited clone is inserted in the pCR4 Blunt-TOPO plasmid (Invitrogen) as described herein.

Unless otherwise indicated, all nucleotide sequences determined by sequencing a DNA molecule herein were determined using an automated DNA sequencer (such as the Model 373, preferably a Model 3700, from Applied Biosystems, Inc.), and all amino acid sequences of polypeptides encoded by DNA molecules determined herein were predicted by translation of a DNA sequence determined above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded bt the sequenced DNA molecule, beginning at the point of such an insertion or deletion.

Using the information provided herein, such as the nucleotide sequence in FIGS. 1A-G (SEQ ID NO: 1), a nucleic acid molecule of the present invention encoding the TRP-PLIK2 polypeptide may be obtained using standard cloning and screening procedures, such as those for cloning cDNAs using mRNA as starting material. Illustrative of the invention, the nucleic acid molecule described in FIGS. 1A-G (SEQ ID NO:1) was discovered in a cDNA library derived from brain, fetal brain, heart, fetal heart, kidney and fetal kidney.

Using the information provided herein, such as the nucleotide sequence in FIGS. 2A-G (SEQ ID NO:3), a nucleic acid molecule of the present invention encoding the TRP-PLIK2b polypeptide may be obtained using standard cloning and screening procedures, such as those for cloning cDNAs using mRNA as starting material. Illustrative of the invention, the nucleic acid molecule described in FIGS. 2A-G (SEQ ID NO:3) was discovered in a cDNA library derived from brain, fetal brain, heart, fetal heart, kidney and fetal kidney.

Using the information provided herein, such as the nucleotide sequence in FIGS. 3A-G (SEQ ID NO:5), a nucleic acid molecule of the present invention encoding the TRP-PLIK2c polypeptide may be obtained using standard cloning and screening procedures, such as those for cloning cDNAs using mRNA as starting material. Illustrative of the invention, the nucleic acid molecule described in FIGS. 3A-G (SEQ ID NO:5) was discovered in a cDNA library derived from brain, fetal brain, heart, fetal heart, kidney and fetal kidney.

Using the information provided herein, such as the nucleotide sequence in FIGS. 4A-G (SEQ ID NO:7), a nucleic acid molecule of the present invention encoding the TRP-PLIK2d polypeptide may be obtained using standard cloning and screening procedures, such as those for cloning cDNAs using mRNA as starting material. Illustrative of the invention, the nucleic acid molecule described in FIGS. 4A-G (SEQ ID NO:7) was discovered in a cDNA library derived from brain, fetal brain, heart, fetal heart, kidney and fetal kidney.

A "polynucleotide" of the present invention also includes those polynucleotides capable of hybridizing, under stringent hybridization conditions, to sequences contained in SEQ ID NO:1, SEQ ID NO:3, SEQ ID NO:5, SEQ ID NO:7, SEQ ID NO:97, the complements thereof, to polynucleotide sequences encoding the sequences contained in SEQ ID NO:2, SEQ ID NO:4, SEQ ID NO:6, SEQ ID NO:8, SEQ ID NO:98, the complements thereof, or the cDNA within the clone deposited with the ATCC®. "Stringent hybridization conditions" refers to an overnight incubation at 42 degree C. in a solution comprising 50% formamide, 5×SSC (750 mM NaCl, 75 mM trisodium citrate), 50 mM sodium phosphate (pH 7.6), 5×Denhardt's solution, 10% dextran sulfate, and 20 μg/ml denatured, sheared salmon sperm DNA, followed by washing the filters in 0.1×SSC at about 65 degree C.

Also contemplated are nucleic acid molecules that hybridize to the polynucleotides of the present invention at lower stringency hybridization conditions. Changes in the stringency of hybridization and signal detection are primarily accomplished through the manipulation of formamide concentration (lower percentages of formamide result in lowered stringency); salt conditions, or temperature. For example, lower stringency conditions include an overnight incubation at 37 degree C. in a solution comprising 6×SSPE (20× SSPE=3M NaCl; 0.2M NaH2PO4; 0.02M EDTA, pH 7.4), 0.5% SDS, 30% formamide, 100 ug/ml salmon sperm blocking DNA; followed by washes at 50 degree C. with 1×SSPE, 0.1% SDS. In addition, to achieve even lower stringency, washes performed following stringent hybridization can be done at higher salt concentrations (e.g. 5×SSC).

Note that variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility.

Of course, a polynucleotide which hybridizes only to polyA+ sequences (such as any 3' terminal polyA+ tract of a cDNA shown in the sequence listing), or to a complementary stretch of T (or U) residues, would not be included in the definition of "polynucleotide," since such a polynucleotide would hybridize to any nucleic acid molecule containing a poly (A) stretch or the complement thereof (e.g., practically any double-stranded cDNA clone generated using oligo dT as a primer).

The polynucleotide of the present invention can be composed of any polyribonucleotide or polydeoxyribonucleotide, which may be unmodified RNA or DNA or modified RNA or DNA. For example, polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, the polynucleotide can be composed of triple-stranded regions comprising RNA or DNA or both RNA and DNA. A polynucleotide may also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

The polypeptide of the present invention can be composed of amino acids joined to each other by peptide bonds or modified peptide bonds, i.e., peptide isosteres, and may contain amino acids other than the 20 gene-encoded amino acids. The polypeptides may be modified by either natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched, for example, as a result of ubiquitination, and they may be cyclic, with or without branching. Cyclic, branched, and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, Proteins—Structure and Molecular Properties, 2nd Ed., T. E. Creighton, W. H. Freeman and Company, New York (1993); Posttranslational Covalent Modification of Proteins, B. C. Johnson, Ed., Academic Press, New York, pgs. 1-12 (1983); Seifter et al., Meth Enzymol 182:626-646 (1990); Rattan et al., Ann NY Acad Sci 663:48-62 (1992).)

"SEQ ID NO:X" refer to polynucleotide sequences, while "SEQ ID NO:Y" refer to polypeptide sequences, all sequences being identified by an integer specified in Table 1 herein.

"A polypeptide having biological activity" refers to polypeptides exhibiting activity similar, but not necessarily identical to, an activity of a polypeptide of the present invention, including mature forms, as measured in a particular biological assay, with or without dose dependency. In the case where dose dependency does exist, it need not be identical to that of the polypeptide, but rather substantially similar to the dose-dependence in a given activity as compared to the polypeptide of the present invention (i.e., the candidate polypeptide will exhibit greater activity or not more than about 25-fold less and, preferably, not more than about ten-fold less activity, and most preferably, not more than about three-fold less activity relative to the polypeptide of the present invention.)

The term "organism" as referred to herein is meant to encompass any organism referenced herein, though preferably to eukaryotic organisms, more preferably to mammals, and most preferably to humans.

The present invention encompasses the identification of proteins, nucleic acids, or other molecules, that bind to polypeptides and polynucleotides of the present invention (for example, in a receptor-ligand interaction). The polynucleotides of the present invention can also be used in interaction trap assays (such as, for example, that described by Ozenberger and Young (Mol Endocrinol., 9(10):1321-9, (1995); and Ann. N.Y. Acad. Sci., 7; 766:279-81, (1995)).

The polynucleotide and polypeptides of the present invention are useful as probes for the identification and isolation of full-length cDNAs and/or genomic DNA which correspond to the polynucleotides of the present invention, as probes to hybridize and discover novel, related DNA sequences, as probes for positional cloning of this or a related sequence, as probe to "subtract-out" known sequences in the process of discovering other novel polynucleotides, as probes to quantify gene expression, and as probes for microarrays.

In addition, polynucleotides and polypeptides of the present invention may comprise one, two, three, four, five, six, seven, eight, or more membrane domains.

Also, in preferred embodiments the present invention provides methods for further refining the biological function of the polynucleotides and/or polypeptides of the present invention.

Specifically, the invention provides methods for using the polynucleotides and polypeptides of the invention to identify orthologs, homologs, paralogs, variants, and/or allelic variants of the invention. Also provided are methods of using the polynucleotides and polypeptides of the invention to identify the entire coding region of the invention, non-coding regions of the invention, regulatory sequences of the invention, and secreted, mature, pro-, prepro-, forms of the invention (as applicable).

In preferred embodiments, the invention provides methods for identifying the glycosylation sites inherent in the polynucleotides and polypeptides of the invention, and the subsequent alteration, deletion, and/or addition of said sites for a number of desirable characteristics which include, but are not limited to, augmentation of protein folding, inhibition of protein aggregation, regulation of intracellular trafficking to organelles, increasing resistance to proteolysis, modulation of protein antigenicity, and mediation of intercellular adhesion.

In further preferred embodiments, methods are provided for evolving the polynucleotides and polypeptides of the present invention using molecular evolution techniques in an effort to create and identify novel variants with desired structural, functional, and/or physical characteristics.

The present invention further provides for other experimental methods and procedures currently available to derive functional assignments. These procedures include but are not limited to spotting of clones on arrays, micro-array technology, PCR based methods (e.g., quantitative PCR), anti-sense methodology, gene knockout experiments, and other procedures that could use sequence information from clones to build a primer or a hybrid partner.

As used herein the terms "modulate" or "modulates" refer to an increase or decrease in the amount, quality or effect of a particular activity, DNA, RNA, or protein.

Polynucleotides and Polypeptides of the Invention

Features of the Polypeptide Encoded by Gene No:1

The polypeptide of this gene provided as SEQ ID NO:2 (FIGS. 1A-G), encoded by the polynucleotide sequence according to SEQ ID NO:1 (FIGS. 1A-G), and/or encoded by the polynucleotide contained within the deposited clone, TRP-PLIK2, has significant homology at the nucleotide and amino acid level to the human channel-kinase 1 protein, also known as the human CHAK1 or TRP-PLIK1 protein (CHAK1; GENBANK® Accession No. gi|AF346629; SEQ ID NO:9); and the human melastatin 1 protein (Melastatin1; GENBANK® Accession No. gi|3243075; SEQ ID NO:260). An alignment of the TRP-PLIK2 polypeptide with this protein is provided in FIGS. 5A-F.

The TRP-PLIK2 polypeptide was determined to share 58.0% identity and 66.0% similarity with the human CHAK1 or TRP-PLIK1 protein (CHAK1; GENBANK® Accession No. gi|AF346629; SEQ ID NO:9); and was determined to share 48.1% identity and 58.6% similarity with the human melastatin 1 protein (Melastatin1; GENBANK® Accession No. gi|3243075; SEQ ID NO:260) as shown in FIG. 9.

The CHAK1 protein is believed to represent a member of a new class of protein kinases referred to as alpha kinases (Curr. Biol. 9 (2), R43-R45 (1999)). These kinases represent a novel type of signaling molecule comprising both a catalytic protein kinase domain, in addition to, an ion channel domain.

The melastatin1 protein is believed to be negatively associated with the incidence of melanoma based upon its inverse correlative expression in highly aggressive melanomas (Genomics 54 (1), 116-123 (1998)). Thus, overexpression of melastatin1 could represent a novel therapeutic in the treatment of melanoma and potentially other cancers.

Based upon the observed homology, the polypeptide of the present invention is expected to share at least some biological activity with other transient receptor potential channel family members, more specifically with the CHAK1 and melastatin1 proteins, in addition to, other transient receptor potential channel family members referenced elsewhere herein or otherwise known in the art.

Consistent with the TRP-PLIK2 polypeptide representing a novel transient receptor potential channel family member, the predicted TRP-PLIK2 kinase domain polypeptide was determined to possess kinase activity as shown in FIG. 13 and described in Example 5. Demonstration of kinase activity was determined by creating and purifying a TRP-PLIK2 kinase domain/GST fusion protein, and subjecting it to a kinase assay. The results also demonstrated that the TRP-PLIK2-

GST fusion protein could be autophosphorylated and phosphorylate substrate polypeptides. MBP was determined to represent a preferred substrate over Histon, as described in Example 5. Evidence of autophosphorylation activity is demonstrated by the intense phosphorylation of the PLIK2 kinase domain band ("PLIK2 kinase"), in addition to the phosphorylation of the TRP-PLIK2-GST fusion protein band ("GST-PLIK2 kinase").

Most of the known transient receptor potential channel family members, possess one or more transmembrane domains. Likewise, the TRP-PLIK2 polypeptide has been determined to comprise six transmembrane domains (TM1-TM6) as shown in FIGS. 1A-G. The transmembrane domains are located from about amino acid 740 to about amino acid 757 (TM1), from about amino acid 834 to about amino acid 851 (TM2), from about amino acid 908 to about amino acid 920 (TM3), from about amino acid 934 to about amino acid 951 (TM4), from about amino acid 968 to about amino acid 985 (TM5), and/or from about amino acid 1043 to about amino acid 1062 (TM6) of SEQ ID NO:2. In this context, the term "about" may be construed to mean 1, 2, 3, 4, 5, 6, 7, 8, 9, or 10 amino acids beyond the N-Terminus and/or C-terminus of the above referenced polypeptide.

In preferred embodiments, the following transmembrane domain polypeptides are encompassed by the present invention: LKIIISIILPPTILTLEF (SEQ ID NO:45), IVKFWFYT-MAYLAFLMLF (SEQ ID NO:46), TETVAIGLFSAGF (SEQ ID NO:47), RLIYCIDIIFWFSRLLDF (SEQ ID NO:48), MTANMFYIVIIMAIVLLS (SEQ ID NO:49), and/or FLQAVYLFVQYIIMVNLLIA (SEQ ID NO:50). Polynucleotides encoding these polypeptides are also provided. The present invention also encompasses the use of the TRP-PLIK2 transmembrane polypeptides as immunogenic and/or antigenic epitopes as described elsewhere herein.

In preferred embodiments, the present invention encompasses the use of N-terminal deletions, C-terminal deletions, or any combination of N-terminal and C-terminal deletions of any one or more of the TRP-PLIK2 TM1 thru TM6 transmembrane domain polypeptides as antigenic and/or immunogenic epitopes.

In preferred embodiments, the present invention also encompasses the use of N-terminal deletions, C-terminal deletions, or any combination of N-terminal and C-terminal deletions of any one or more of the amino acids intervening (i.e., ion channel extracellular or intracellular loops) the TRP-PLIK2 TM1 thru TM6 transmembrane domain polypeptides as antigenic and/or immunogenic epitopes.

The TRP-PLIK2 polypeptide was determined to comprise several conserved cysteines, at amino acid 21, 34, 38, 41, 47, 49, 311, 367, 637, 702, 719, 938, 1028, 1034, 1114, 1148, 1822, 1861, 1963, 1966, and 1967 of SEQ ID No: 2 (FIGS. 1A-D). Conservation of cysteines at key amino acid residues is indicative of conserved structural features, which may correlate with conservation of protein function and/or activity.

In confirmation of the TRP-PLIK2 representing a member of the transient receptor channel family, the TRP-PLIK2 polypeptide was determined to comprise a predicted TRP domain (LWKYNR) located from about amino acid 1078 to about amino acid 1083 of SEQ ID NO:2. In this context, the term "about" may be construed to mean 1, 2, 3, 4, 5, 6, 7, 8, 9, or 10 amino acids beyond the N-Terminus and/or C-terminus of the above referenced polypeptide.

In further confirmation of the TRP-PLIK2 representing a member of the transient receptor channel family, the TRP-PLIK2 polypeptide was determined to comprise a predicted ion transport signature domain located at about amino acid 904 to about amino acid 1064 of SEQ ID NO:2. In this context, the term "about" may be construed to mean 1, 2, 3, 4, 5, 6, 7, 8, 9, or 10 amino acids beyond the N-Terminus and/or C-terminus of the above referenced polypeptide.

The TRP-PLIK2 polypeptide was determined to comprise a predicted nucleotide binding domain located from about amino acid 1945 to about amino acid 1950 of SEQ ID NO:2. In this context, the term "about" may be construed to mean 1, 2, 3, 4, 5, 6, 7, 8, 9, or 10 amino acids beyond the N-Terminus and/or C-terminus of the above referenced polypeptide.

In addition, the TRP-PLIK2 polypeptide was determined to comprise a predicted zinc finger domain located at about amino acid 1960 to about amino acid 1970 of SEQ ID NO:2. In this context, the term "about" may be construed to mean 1, 2, 3, 4, 5, 6, 7, 8, 9, or 10 amino acids beyond the N-Terminus and/or C-terminus of the above referenced polypeptide.

TRP-PLIK2 polypeptides and polynucleotides are useful for diagnosing diseases related to the over and/or under expression of TRP-PLIK2 by identifying mutations in the TRP-PLIK2 gene using TRP-PLIK2 sequences as probes or by determining TRP-PLIK2 protein or mRNA expression levels. TRP-PLIK2 polypeptides will be useful in screens for compounds that affect the activity of the protein. TRP-PLIK2 peptides can also be used for the generation of specific antibodies and as bait in yeast two hybrid screens to find proteins the specifically interact with TRP-PLIK2.

Expression profiling designed to measure the steady state mRNA levels encoding the TRP-PLIK2 polypeptide showed predominately high expression levels in bone marrow, kidney, and testis. The TRP-PLIK2 polypeptide was also significantly expressioned in liver, and to a lesser extent, in small intestine, spinal cord, prostate, uterus, lung, lymph node, stomach, heart, brain, thymus, and pancrease (as shown in FIG. 7).

Expanded analysis of TRP-PLIK2 expression levels by TAQMAN® quantitative PCR (see FIG. 12) confirmed that the TRP-PLIK2 polypeptide is expressed in kidney, colon, and testis (FIG. 7). TRP-PLIK2 mRNA was expressed predominately in the lower gastrointestinal tract, specifically the ileum, the rectum, the colon, the jejunum, and to a lesser extent in the duodenum and stomach. Significant expression was observed in the kidney, particularly in the cortex, followed by the medulla, and to a lesser extent in the testis, pelvis, and bone marrow (mononuclear cells).

Furthermore, an expanded analysis of TRP-PLIK2 expression levels in various tumor and normal tissues by TAQMAN® quantitative PCR (see FIG. 14) showed TRP-PLIK2 mRNA was differentially expressed to the greatest extent in prostate tumor tissue relative to normal prostate tissue (approximately 20 fold difference). Significant differential expression was also observed in the testicular tumor tissue relative to normal testicular tissue.

Characterization of the TRP-PLIK2 polypeptide of the present invention using antisense oligonucleotides directed against a portion of the TRP-PLIK2 encoding sequence led to the determination that it is involved in the modulation of the NFkB pathway, either directly or indirectly.

The upregulation of IkBa due to the downregulation of TRP-PLIK2 places this transient receptor potential protein into a signalling pathway potentially involved in apoptotic events. This gives the opportunity to regulate downstream events via the activity of the protein TRP-PLIK2 with antisense polynucleotides, polypeptides or low molecular chemicals with the potential of achieving a therapeutic effect in cancer, autoimmune diseases. In addition to cancer and immunological disorders, NF-kB has significant roles in other diseases (Baldwin, A. S., J. Clin Invest. 107: 3-6 (2001)). NF-kB is a key factor in the pathophysiology of ischemia-reperfusion injury and heart failure (Valen, G., Yan. Z Q, Hansson, G K, J. Am. Coll. Cardiol. 38, 307-14 (2001)). Furthermore, NF-kB has been found to be activated in experimental renal disease (Guijarro C, Egido J., Kidney Int. 59, 415-425 (2001)). As TRP-PLIK2 is highly expressed in kidney there is the potential of an involvement in renal diseases.

In preferred embodiments, TRP-PLIK2 polynucleotides and polypeptides, including fragments thereof, are useful for treating, diagnosing, and/or ameliorating proliferative disorders, cancers, ischemia-reperfusion injury, heart failure, immuno compromised conditions, HIV infection, and renal diseases.

Moreover, TRP-PLIK2 polynucleotides and polypeptides, including fragments thereof, are useful for increasing NF-kB activity, increasing apoptotic events, and/or decreasing IkBa expression or activity levels.

In preferred embodiments, antagonists directed against TRP-PLIK2 are useful for treating, diagnosing, and/or ameliorating autoimmune disorders, disorders related to hyper immune activity, inflammatory conditions, disorders related to aberrant acute phase responses, hypercongenital conditions, birth defects, necrotic lesions, wounds, organ transplant rejection, conditions related to organ transplant rejection, disorders related to aberrant signal transduction, proliferating disorders, cancers, HIV, and HIV propagation in cells infected with other viruses.

Moreover, antagonists directed against TRP-PLIK2 are useful for decreasing NF-kB activity, decreasing apoptotic events, and/or increasing IkBa expression or activity levels.

In preferred embodiments, agonists directed against TRP-PLIK2 are useful for treating, diagnosing, and/or ameliorating autoimmune disorders, disorders related to hyper immune activity, hypercongenital conditions, birth defects, necrotic lesions, wounds, disorders related to aberrant signal transduction, immuno compromised conditions, HIV infection, proliferating disorders, and/or cancers.

Moreover, agonists directed against TRP-PLIK2 are useful for increasing NF-kB activity, increasing apoptotic events, and/or decreasing IkBa expression or activity levels.

The strong homology to transient receptor potential channels (TRP), combined with the predominate localized expression in the lower gastrointestinal tract, specifically the ileum, the rectum, the colon, the jejunum, and to a lesser extent in the duodenum and stomach, suggests the TRP-PLIK2 polynucleotides and polypeptides may be useful in treating, diagnosing, prognosing, and/or preventing gastrointestinal diseases and/or disorders, which include, but are not limited to, ulcers, irritable bowel syndrome, inflammatory bowel disease, diarrhea, traveler's diarrhea, drug-related diarrhea polyps, absorption disorders, constipation, diverticulitis, vascular disease of the intestines, intestinal obstruction, intestinal infections, ulcerative colitis, Shigellosis, cholera, Crohn's Disease, amebiasis, enteric fever, Whipple's Disease, peritonitis, intraabdominal abscesses, hereditary hemochromatosis, gastroenteritis, viral gastroenteritis, food poisoning, mesenteric ischemia, mesenteric infarction, in addition to, metabolic diseases and/or disorders.

Moreover, polynucleotides and polypeptides, including fragments and/or antagonists thereof, have uses which include, directly or indirectly, treating, preventing, diagnosing, and/or prognosing susceptibility to the following, non-limiting, gastrointestinal infections: *Salmonella infection, E. coli infection, E. coli* O157:H7 infection, Shiga Toxin-producing *E. coli infection, Campylobacter* infection (e.g., *Campylobacter fetus, Campylobacter upsaliensis, Campylobacter hyointestinalis, Campylobacter lari, Campylobacter jejuni, Campylobacter concisus, Campylobacter mucosalis, Campylobacter sputorum, Campylobacter rectus, Campylobacter curvus, Campylobacter sputorum*, etc.), *Heliobacter* infection (e.g., *Heliobacter cinaedi, Heliobacter fennelliae*, etc.) *Yersinia enterocolitica* infection, *Vibrio* sp. Infection (e.g., *Vibrio mimicus, Vibrio parahaemolyticus, Vibrio fluvialis, Vibrio furnissii, Vibrio hollisae, Vibrio vulnificus, Vibrio alginolyticus, Vibrio metschnikovii, Vibrio damsela, Vibrio cincinnatiensis*, etc.) *Aeromonas* infection (e.g., *Aeromonas hydrophila, Aeromonas sobira, Aeromonas caviae*, etc.), *Plesiomonas shigelliodes* infection, *Giardia* infection (e.g., *Giardia lamblia*, etc.), *Cryptosporidium* infection, *Listeria* infection, *Entamoeba histolytica* infection, Rotavirus infection, Norwalk virus infection, *Clostridium difficile* infection, *Clostriudium perfringens* infection, *Staphylococcus* infection, *Bacillus* infection, in addition to any other gastrointestinal disease and/or disorder implicated by the causative agents listed above or elsewhere herein.

The strong homology to human transient receptor potential channels (TRP), combined with the localized expression in kidney tissue suggests the TRP-PLIK2 polynucleotides and polypeptides may be useful in treating, diagnosing, prognosing, and/or preventing renal diseases and/or disorders, which include, but are not limited to: nephritis, renal failure, nephrotic syndrome, urinary tract infection, hematuria, proteinuria, oliguria, polyuria, nocturia, edema, hypertension, electrolyte disorders, sterile pyuria, renal osteodystrophy, large kidneys, renal transport defects, nephrolithiasis, azotemia, anuria, urinary retention, slowing of urinary stream, large prostate, flank tenderness, full bladder sensation after voiding, enuresis, dysuria, bacteriuria, kidney stones, glomerulonephritis, vasculitis, hemolytic uremic syndromes, thrombotic thrombocytopenic purpura, malignant hypertension, casts, tubulointerstitial kidney diseases, renal tubular acidosis, pyelonephritis, hydronephritis, nephrotic syndrome, crush syndrome, and/or renal colic, in addition to Wilm's Tumor Disease, and congenital kidney abnormalities such as horseshoe kidney, polycystic kidney, and Falconi's syndrome for example.

Several known TRP family members have been identified that are expressed significantly in kidney tissue. These TRP family members include, for example, Trp12 (Wissenbach, U., Bodding, M., Freichel, M., Flockerzi, V, Lett., 485(2-3): 127-34, (2000)); OTRPC4 (Strotmann, R., Harteneck, C., Nunnenmacher, K., Schultz, G., Plant, T, D, Nat, Cell, Biol., 2(10):695-702, (2000)); polycystin-L2 (Guo, L., Schreiber, T, H., Weremowicz, S., Morton, C, C., Lee, C., Zhou, J. Genomics., 64(3):241-51, (2000)); and EcaC (Hoenderop, J. G., van, der, Kemp, A, W., Hartog, A., van, de, Graaf, S, F., van, Os, C, H., Willems, P, H., Bindels, R, J. J. Biol, Chem., 274(13):8375-8, (1999)).

Thus, the TRP-PLIK2 polynucleotides and polypeptides are expected to share at least some biological activity with TRP family members expressed in kidney cells and tissues, particularly those specifically referenced herein.

The strong homology to human transient receptor potential channels (TRP), combined with the localized expression in bone marrow tissue suggests the TRP-PLIK2 polynucleotides and polypeptides may be useful in treating, diagnosing, prognosing, and/or preventing immune diseases and/or disorders. Representative uses are described in the "Immune Activity", "Chemotaxis", and "Infectious Disease" sections below, and elsewhere herein. Briefly, the strong expression in immune tissue indicates a role in regulating the proliferation; survival; differentiation; and/or activation of hematopoietic cell lineages, including blood stem cells.

The TRP-PLIK2 polypeptide may also be useful as a preventative agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's disease, and scleroderma. The TRP-PLIK2 polypeptide may be useful for modulating cytokine production, antigen presentation, or other processes, such as for boosting immune responses, etc.

Moreover, the protein may represent a factor that influences the differentiation or behavior of other blood cells, or that recruits hematopoietic cells to sites of injury. Thus, this gene product is thought to be useful in the expansion of stem cells and committed progenitors of various blood lineages, and in the differentiation and/or proliferation of various cell types. Furthermore, the protein may also be used to determine biological activity, raise antibodies, as tissuemarkers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Significantly, TRP-PLIK2 is believed to represent the first TRP family member expressed in bone marrow tissue.

The strong homology to human transient receptor potential channels (TRP), combined with the localized expression in testis tissue emphasizes the potential utility for TRP-PLIK2 polynucleotides and polypeptides in treating, diagnosing, prognosing, and/or preventing testicular, in addition to reproductive disorders.

In preferred embodiments, TRP-PLIK2 polynucleotides and polypeptides including agonists, antagonists, and/or fragments thereof, have uses which include treating, diagnosing, prognosing, and/or preventing the following, non-limiting, diseases or disorders of the testis: spermatogenesis, infertility, Klinefelter's syndrome, XX male, epididymitis, genital warts, germinal cell aplasia, cryptorchidism, varicocele, immotile cilia syndrome, and viral orchitis. The TRP-PLIK2 polynucleotides and polypeptides including agonists, antagonists, and/or fragments thereof, may also have uses related to modulating testicular development, embryogenesis, reproduction, and in ameliorating, treating, and/or preventing testicular proliferative disorders (e.g., cancers, which include, for example, choriocarcinoma, Nonseminoma, seminona, and testicular germ cell tumors).

Likewise, the localized expression in testis tissue also emphasizes the potential utility for TRP-PLIK2 polynucleotides and polypeptides in treating, diagnosing, prognosing, and/or preventing metabolic diseases and disorders which include the following, not limiting examples: premature puberty, incomplete puberty, Kallman syndrome, Cushing's syndrome, hyperprolactinemia, hemochromatosis, congenital adrenal hyperplasia, FSH deficiency, and granulomatous disease, for example.

This gene product may also be useful in assays designed to identify binding agents, as such agents (antagonists) are useful as male contraceptive agents. The testes are also a site of active gene expression of transcripts that is expressed, particularly at low levels, in other tissues of the body. Therefore, this gene product may be expressed in other specific tissues or organs where it may play related functional roles in other processes, such as hematopoiesis, inflammation, bone formation, and kidney function, to name a few possible target indications.

Several known TRP family members have been identified that are expressed significantly in testis tissue. These TRP family members include, for example, polycystin-L2 (Guo, L., Schreiber, T, H., Weremowicz, S., Morton, C, C., Lee, C., Zhou, J. Genomics., 64(3):241-51, (2000)); TRP7 (Okada, T., Inoue, R., Yamazaki, K., Maeda, A., Kurosaki, T., Yamakuni, T., Tanaka, I., Shimizu, S., Ikenaka, K., Imoto, K., Mori, Y, J. Biol, Chem., 274(39):27359-70, (1999)); btrp2 (Wissenbach, U., Schroth, G., Philipp, S., Flockerzi, V, Lett., 429(1):61-6, (1998)); Htrp-1 (Zhu, X., Chu, P, B., Peyton, M., Bienbaumer, L, Lett., 373(3):193-8, (1995)); and TRPC1 (Wes, P, D., Chevesich, J., Jeromin, A., Rosenberg, C., Stetten, G., Montell, C, Proc, Natl, Acad, Sci, U.S.A., 92(21):9652-6, (1995)).

Thus, the TRP-PLIK2 polynucleotides and polypeptides are expected to share at least some biological activity with TRP family members expressed in testis cells and tissues, particularly those specifically referenced herein.

The predominate differential expression of TRP-PLIK2 in prostate tumor relative to normal prostate tissue strongly suggests TRP-PLIK2 polynucleotides and polypeptides including agonists, antagonists, and/or fragments thereof, have uses which include treating, diagnosing, prognosing, and/or preventing prostate cancers and/or proliferative conditions.

Alternatively, the tissue distribution in liver indicates the protein product of this clone would be useful for the detection and treatment of liver disorders and cancers. Representative uses are described in the "Hyperproliferative Disorders", "Infectious Disease", and "Binding Activity" sections below, and elsewhere herein. Briefly, the protein can be used for the detection, treatment, and/or prevention of hepatoblastoma, jaundice, hepatitis, liver metabolic diseases and conditions that are attributable to the differentiation of hepatocyte progenitor cells, cirrhosis, hepatic cysts, pyrogenic abscess, amebic abscess, hydatid cyst, cystadenocarcinoma, adenoma, focal nodular hyperplasia, hemangioma, hepatocellular carcinoma, cholangiocarcinoma, angiosarcoma, and granulomatous liver disease.

Moreover, polynucleotides and polypeptides, including fragments and/or antagonists thereof, have uses which include, directly or indirectly, treating, preventing, diagnosing, and/or prognosing the following, non-limiting, hepatic infections: liver disease caused by sepsis infection, liver disease caused by bacteremia, liver disease caused by Pneomococcal pneumonia infection, liver disease caused by Toxic shock syndrome, liver disease caused by Listeriosis, liver disease caused by Legionnaires' disease, liver disease caused by Brucellosis infection, liver disease caused by *Neisseria gonorrhoeae* infection, liver disease caused by *Yersinia* infection, liver disease caused by Salmonellosis, liver disease caused by Nocardiosis, liver disease caused by Spirochete infection, liver disease caused by *Treponema pallidum* infection, liver disease caused by *Brrelia burgdorferi* infection, liver disease caused by *Leptospirosis*, liver disease caused by *Coxiella burnetii* infection, liver disease caused by *Rickettsia richettsii* infection, liver disease caused by *Chlamydia trachomatis* infection, liver disease caused by *Chlamydia psittaci* infection, in addition to any other hepatic disease and/or disorder implicated by the causative agents listed above or elsewhere herein.

As described elsewhere herein, transient receptor potential channel family members have been implicated in modulating cell proliferation, differentiation, migration, activation, exocytosis, muscle contraction, gene expression, apoptosis. signalling, pheromone sensory signaling, smooth muscle tone, pain perception, heat perception, osmosensitivity, and mechanosensitivity. Moreover, transient receptor potential channel family members have been implicated in disorders of the skin, skeletal-muscle, nervous, cardiac, and vascular systems, in addition to the following, non-limiting diseases and disorders, which include, for example, arteriosclerosis, neointimal hyperplasia, metastatic melanomas, bipolar disorder, nonsyndromic hereditary deafness, Knobloch syndrome, holosencephaly, and various malignancies including prostate cancer.

In preferred embodiments, TRP-PLIK2 polynucleotides and polypeptides of the present invention, including agonists and/or fragments thereof, have uses that include, modulating cell proliferation, differentiation, migration, activation, exocytosis, muscle contraction, gene expression, apoptosis. signalling, pheromone sensory signaling, smooth muscle tone, pain perception, heat perception, osmosenstivity, and mechanosensitivity.

In more preferred embodiments, TRP-PLIK2 polynucleotides and polypeptides of the present invention, including agonists and/or fragments thereof, have uses that include, treating, ameliorating, preventing, detecting, and/or prognosing various diseases and disorders, particularly the following, non-limiting examples, disorders of the skin, skeletal-muscle, nervous, cardiac, and vascular systems, in addition to the following, non-limiting diseases and disorders, which include, for example, arteriosclerosis, neointimal hyperplasia, metastatic melanomas, bipolar disorder, nonsyndromic hereditary deafness, Knobloch syndrome, holosencephaly, and various malignancies including prostate cancer.

TRP-PLIK2 polynucleotides and polypeptides of the present invention, including agonists and/or fragments may be involved in intracellular $Ca^{2+}$ homeostasis which affects various aspects of biological functions including mechano-regulation, pain transduction, vasorelaxation, gene expression, cell cycle and proliferation/apoptosis. Since TRP-PLIK2 is dominantly expressed in bone marrow, it may particularly play an important role in regulating cytosolic $Ca^{2+}$ in immune system.

The TRP-PLIK2 gene maps to chromosome 9q21.2-22.1. This region is linked to amyotrophic lateral sclerosis with frontotemporal dementia, early-onset pulverulent cataract, infantile nephronophthisis, hypomagnesemia with secondary hypocalcemia and familial hemophagocytic lymphohistiocytosis. Therefore, agonists and/or antagonists of the novel TRP-PLIK2 can be used to treat diseases including various forms of neuronal degeneration, neurogenic inflammation, allergy, immunodeficiency/excessive immune activation, visual defects, hearing disorder, pain, cancer, hypertension and other cardiovascular diseases. In addition, the therapeutics may be useful in the treatment of diseases associated with disturbances in $Ca^{2+}$ homeostasis including osteoporosis, hypercalciuric stone disease, and chronic renal failure.

In addition, TRP-PLIK2 polynucleotides and polypeptides of the present invention, including agonists and/or fragments thereof, have uses that include modulating intracellular Ca++ ion concentrations, Ca++ ion flux, stored intracellular Ca++ ion concentrations, Ca++ ion pump activity, Ca++ ion flow into cell, Ca++ ion flow out of cells, the activation of Ca++ sensitive proteins, the activation of Ca++ sensitive signaling pathways, the activation of kinase-activatible proteins, and the activation of kinase-dependent signaling pathways.

The TRP-PLIK2 polynucleotides and polypeptides of the present invention, including agonists and/or fragments thereof, have uses that include modulating proliferation, differentiation, migration, and activation in various cells, tissues, and organisms, and particularly in mammalian bone marrow, kidney, testis, liver, small intestine, spinal cord, prostate, uterus, lung, lymph node, stomach, heart, brain, thymus, and pancreas, preferably human. TRP-PLIK2 polynucleotides and polypeptides of the present invention, including agonists and/or fragments thereof, may be useful in diagnosing, treating, prognosing, and/or preventing immune, hematopoietic, renal, reproductive, hepatic, and/or proliferative diseases or disorders, particularly of the immune system.

In addition, antagonists of the TRP-PLIK2 polynucleotides and polypeptides may have uses that include diagnosing, treating, prognosing, and/or preventing diseases or disorders related to transient receptor potential channel activity, which may include immune, hematopoietic, renal, reproductive, hepatic, and/or proliferative diseases or disorders.

Although it is believed the encoded polypeptide may share at least some biological activities with transient receptor potential channel family members, particularly those from CHAK1, a number of methods of determining the exact biological function of this clone are either known in the art or are described elsewhere herein. Briefly, the function of this clone may be determined by applying microarray methodology. Nucleic acids corresponding to the TRP-PLIK2 polynucleotides, in addition to, other clones of the present invention, may be arrayed on microchips for expression profiling. Depending on which polynucleotide probe is used to hybridize to the slides, a change in expression of a specific gene may provide additional insight into the function of this gene based upon the conditions being studied. For example, an observed increase or decrease in expression levels when the polynucleotide probe used comes from tissue that has been treated with known immunoglobulin inhibitors, which include, but are not limited to the drugs listed herein or otherwise known in the art, might indicate a function in modulating immunoglobulin function, for example. In the case of TRP-PLIK2, bone marrow, kidney, testis, liver, small intestine, spinal cord, prostate, uterus, lung, lymph node, stomach, heart, brain, thymus, and/or pancrease, should be used to extract RNA to prepare the probe.

In addition, the function of the protein may be assessed by applying quantitative PCR methodology, for example. Real time quantitative PCR would provide the capability of following the expression of the TRP-PLIK2 gene throughout development, for example. Quantitative PCR methodology requires only a nominal amount of tissue from each developmentally important step is needed to perform such experiments. Therefore, the application of quantitative PCR methodology to refining the biological function of this polypeptide is encompassed by the present invention. Also encompassed by the present invention are quantitative PCR probes corresponding to the polynucleotide sequence provided as SEQ ID NO:1 (FIGS. 1A-G).

The function of the protein may also be assessed through complementation assays in yeast. For example, in the case of the TRP-PLIK2, transforming yeast deficient in transient receptor potential channel activity with TRP-PLIK2 and assessing their ability to grow would provide convincing evidence the TRP-PLIK2 polypeptide has transient receptor potential channel activity. Additional assay conditions and methods that may be used in assessing the function of the polynucleotides and polypeptides of the present invention are known in the art, some of which are disclosed elsewhere herein.

Alternatively, the biological function of the encoded polypeptide may be determined by disrupting a homologue of this polypeptide in Mice and/or rats and observing the resulting phenotype.

Moreover, the biological function of this polypeptide may be determined by the application of antisense and/or sense methodology and the resulting generation of transgenic mice and/or rats. Expressing a particular gene in either sense or antisense orientation in a transgenic mouse or rat could lead to respectively higher or lower expression levels of that particular gene. Altering the endogenous expression levels of a gene can lead to the observation of a particular phenotype that can then be used to derive indications on the function of the gene. The gene can be either over-expressed or under expressed in every cell of the organism at all times using a strong ubiquitous promoter, or it could be expressed in one or more discrete parts of the organism using a well characterized tissue-specific promoter (e.g., a bone marrow, kidney, testis, liver, small intestine, spinal cord, prostate, uterus, lung, lymph node, stomach, heart, brain, thymus, and/or pancrease-specific promoter), or it can be expressed at a specified time of development using an inducible and/or a developmentally regulated promoter.

In the case of TRP-PLIK2 transgenic mice or rats, if no phenotype is apparent in normal growth conditions, observing the organism under diseased conditions (immune, hematopoietic, renal, reproductive, hepatic, or proliferative disorders, etc.) may lead to understanding the function of the gene. Therefore, the application of antisense and/or sense methodology to the creation of transgenic mice or rats to refine the biological function of the polypeptide is encompassed by the present invention.

In preferred embodiments, the following N-terminal TRP-PLIK2 deletion polypeptides are encompassed by the present invention: M1-L2017, I2-L2017, I3-L2017, L4-L2017, S5-L2017, K6-L2017, S7-L2017, Q8-L2017, K9-L2017, S10-L2017, W11-L2017, I12-L2017, K13-L2017, G14-L2017, V15-L2017, F16-L2017, D17-L2017, K18-L2017, R19-L2017, E20-L2017, C21-L2017, S22-L2017, T23-L2017, I24-L2017, I25-L2017, P26-L2017, S27-L2017, S28-L2017, K29-L2017, N30-L2017, P31-L2017, H32-L2017, R33-L2017, C34-L2017, T35-L2017, P36-L2017, V37-L2017, C38-L2017, Q39-L2017, V40-L2017, C41-L2017, Q42-L2017, N43-L2017, L44-L2017, I45-L2017, R46-L2017, C47-L2017, Y48-L2017, C49-L2017, G50-L2017, R51-L2017, L52-L2017, I53-L2017, G54-L2017, D55-L2017, H56-L2017, A57-L2017, G58-L2017, I59-L2017, D60-L2017, Y61-L2017, S62-L2017, W63-L2017, T64-L2017, I65-L2017, S66-L2017, A67-L2017, G68-L2017, K69-L2017, G70-L2017, K71-L2017, E72-L2017, S73-L2017, E74-L2017, Q75-L2017, W76-L2017, S77-L2017, V78-L2017, E79-L2017, K80-L2017, H81-L2017, T82-L2017, T83-L2017, K84-L2017, S85-L2017, P86-L2017, T87-L2017, D88-L2017, T89-L2017, F90-L2017, G91-L2017, T92-L2017, I93-L2017, N94-L2017, F95-L2017, Q96-L2017, D97-L2017, G98-L2017, E99-L2017, H100-L2017, T101-L2017, H102-L2017, H103-L2017, A104-L2017, K105-L2017, Y106-L2017, I107-L2017, R108-L2017, T109-L2017, S110-L2017, Y111-L2017, D112-L2017, T113-L2017, K114-L2017, L115-L2017, D116-L2017, H117-L2017, L118-L2017, L119-L2017, H120-L2017, L121-L2017, M122-L2017, L123-L2017, K124-L2017, E125-L2017, W126-L2017, K127-L2017, M128-L2017, E129-L2017, L130-L2017, P131-L2017, K132-L2017, L133-L2017, V134-L2017, I135-L2017, S136-L2017, V137-L2017, H138-L2017, G139-L2017, G140-L2017, I141-L2017, Q142-L2017, N143-L2017, F144-L2017, T145-L2017, M146-L2017, P147-L2017, S148-L2017, K149-L2017, F150-L2017, K151-L2017, E152-L2017, I153-L2017, F154-L2017, S155-L2017, Q156-L2017, G157-L2017, L158-L2017, V159-L2017, K160-L2017, A161-L2017, A162-L2017, E163-L2017, T164-L2017, T165-L2017, G166-L2017, A167-L2017, W168-L2017, I169-L2017, I170-L2017, T171-L2017, E172-L2017, G173-L2017, I174-L2017, N175-L2017, T176-L2017, G177-L2017, V178-L2017, S179-L2017, K180-L2017, H181-L2017, V182-L2017, G183-L2017, D184-L2017, A185-L2017, L186-L2017, K187-L2017, S188-L2017, H189-L2017, S190-L2017, S191-L2017, H192-L2017, S193-L2017, L194-L2017, R195-L2017, K196-L2017, I197-L2017, W198-L2017, T199-L2017, V200-L2017, G201-L2017, I202-L2017, P203-L2017, P204-L2017, W205-L2017, G206-L2017, V207-L2017, I208-L2017, E209-L2017, N210-L2017, Q21-L2017, R212-L2017, D213-L2017, L214-L2017, I215-L2017, G216-L2017, K217-L2017, D218-L2017, V219-L2017, V220-L2017, C221-L2017, L222-L2017, Y223-L2017, Q224-L2017, T225-L2017, L226-L2017, D227-L2017, N228-L2017, P229-L2017, L230-L2017, S231-L2017, K232-L2017, L233-L2017, T234-L2017, T235-L2017, L236-L2017, N237-L2017, S238-L2017, M239-L2017, H240-L2017, S241-L2017, H242-L2017, F243-L2017, I244-L2017, L245-L2017, S246-L2017, D247-L2017, D248-L2017, G249-L2017, T250-L2017, V251-L2017, G252-L2017, K253-L2017, Y254-L2017, G255-L2017, N256-L2017, E257-L2017, M258-L2017, K259-L2017, L260-L2017, R261-L2017, R262-L2017, N263-L2017, L264-L2017, E265-L2017, K266-L2017, Y267-L2017, L268-L2017, S269-L2017, L270-L2017, Q271-L2017, K272-L2017, I273-L2017, H274-L2017, C275-L2017, R276-L2017, S277-L2017, R278-L2017, Q279-L2017, G280-L2017, V281-L2017, P282-L2017, V283-L2017, V284-L2017, G285-L2017, L286-L2017, V287-L2017, V288-L2017, E289-L2017, G290-L2017, G291-L2017, P292-L2017, N293-L2017, V294-L2017, I295-L2017, L296-L2017, S297-L2017, V298-L2017, W299-L2017, E300-L2017, T301-L2017, V302-L2017, K303-L2017, D304-L2017, K305-L2017, D306-L2017, P307-L2017, V308-L2017, V309-L2017, V310-L2017, C311-L2017, E312-L2017, G313-L2017, T314-L2017, G315-L2017, R316-L2017, A317-L2017, A318-L2017, D319-L2017, L320-L2017, L321-L2017, A322-L2017, F323-L2017, T324-L2017, H325-L2017, K326-L2017, H327-L2017, L328-L2017, A329-L2017, D330-L2017, E331-L2017, G332-L2017, M333-L2017, L334-L2017, R335-L2017, P336-L2017, Q337-L2017, V338-L2017, K339-L2017, E340-L2017, E341-L2017, I342-L2017, I343-L2017, C344-L2017, M345-L2017, I346-L2017, Q347-L2017, N348-L2017, T349-L2017, F350-L2017, N351-L2017, F352-L2017, S353-L2017, L354-L2017, K355-L2017, Q356-L2017, S357-L2017, K358-L2017, H359-L2017, L360-L2017, F361-L2017, Q362-L2017, I363-L2017, L364-L2017, M365-L2017, E366-L2017, C367-L2017, M368-L2017, V369-L2017, H370-L2017, R371-L2017, D372-L2017, C373-L2017, I374-L2017, T375-L2017, I376-L2017, F377-L2017, D378-L2017, A379-L2017, D380-L2017, S381-L2017, E382-L2017, E383-L2017, Q384-L2017, Q385-L2017, D386-L2017, L387-L2017, D388-L2017, L389-L2017, A390-L2017, I391-L2017, L392-L2017, T393-L2017, A394-L2017, L395-L2017, L396-L2017, K397-L2017, G398-L2017, T399-L2017, N400-L2017, L401-L2017, S402-L2017, A403-L2017, S404-L2017, E405-L2017, Q406-L2017, L407-L2017, N408-L2017, L409-L2017, A410-L2017, M411-L2017, A412-L2017, W413-L2017, D414-L2017, R415-L2017, V416-L2017, D417-L2017, I418-L2017, A419-L2017, K420-L2017, K421-L2017, H422-L2017, I423-L2017, L424-L2017, I425-L2017, Y426-L2017, E427-L2017, Q428-L2017, H429-L2017, W430-L2017, K431-L2017, P432-L2017, D433-L2017, A434-L2017, L435-L2017, E436-

L2017, Q437-L2017, A438-L2017, M439-L2017, S440-L2017, D441-L2017, A442-L2017, L443-L2017, V444-L2017, M445-L2017, D446-L2017, R447-L2017, V448-L2017, D449-L2017, F450-L2017, V451-L2017, K452-L2017, L453-L2017, L454-L2017, I455-L2017, E456-L2017, Y457-L2017, G458-L2017, V459-L2017, N460-L2017, L461-L2017, H462-L2017, R463-L2017, F464-L2017, L465-L2017, T466-L2017, I467-L2017, P468-L2017, R469-L2017, L470-L2017, E471-L2017, E472-L2017, L473-L2017, Y474-L2017, N475-L2017, T476-L2017, K477-L2017, Q478-L2017, G479-L2017, P480-L2017, T481-L2017, N482-L2017, T483-L2017, L484-L2017, L485-L2017, H486-L2017, H487-L2017, L488-L2017, V489-L2017, Q490-L2017, D491-L2017, V492-L2017, K493-L2017, Q494-L2017, H495-L2017, T496-L2017, L497-L2017, L498-L2017, S499-L2017, G500-L2017, Y501-L2017, R502-L2017, I503-L2017, T504-L2017, L505-L2017, I506-L2017, D507-L2017, I508-L2017, G509-L2017, L510-L2017, V511-L2017, V512-L2017, E513-L2017, Y514-L2017, L515-L2017, I516-L2017, G517-L2017, R518-L2017, A519-L2017, Y520-L2017, R521-L2017, S522-L2017, N523-L2017, Y524-L2017, T525-L2017, R526-L2017, K527-L2017, H528-L2017, F529-L2017, R530-L2017, A531-L2017, L532-L2017, Y533-L2017, N534-L2017, N535-L2017, L536-L2017, Y537-L2017, R538-L2017, K539-L2017, Y540-L2017, K541-L2017, H542-L2017, Q543-L2017, R544-L2017, H545-L2017, S546-L2017, S547-L2017, G548-L2017, N549-L2017, R550-L2017, N551-L2017, E552-L2017, S553-L2017, A554-L2017, E555-L2017, S556-L2017, T557-L2017, L558-L2017, H559-L2017, S560-L2017, Q561-L2017, F562-L2017, I563-L2017, R564-L2017, T565-L2017, A566-L2017, Q567-L2017, P568-L2017, Y569-L2017, K570-L2017, F571-L2017, K572-L2017, E573-L2017, K574-L2017, S575-L2017, I576-L2017, V577-L2017, L578-L2017, H579-L2017, K580-L2017, S581-L2017, R582-L2017, K583-L2017, K584-L2017, S585-L2017, K586-L2017, E587-L2017, Q588-L2017, N589-L2017, V590-L2017, S591-L2017, D592-L2017, D593-L2017, P594-L2017, E595-L2017, S596-L2017, T597-L2017, G598-L2017, F599-L2017, L600-L2017, Y601-L2017, P602-L2017, Y603-L2017, N604-L2017, D605-L2017, L606-L2017, L607-L2017, V608-L2017, W609-L2017, A610-L2017, V611-L2017, L612-L2017, M613-L2017, K614-L2017, R615-L2017, Q616-L2017, K617-L2017, M618-L2017, A619-L2017, M620-L2017, F621-L2017, F622-L2017, W623-L2017, Q624-L2017, H625-L2017, G626-L2017, E627-L2017, E628-L2017, A629-L2017, T630-L2017, V631-L2017, K632-L2017, A633-L2017, V634-L2017, I635-L2017, A636-L2017, C637-L2017, I638-L2017, L639-L2017, Y640-L2017, R641-L2017, A642-L2017, M643-L2017, A644-L2017, H645-L2017, E646-L2017, A647-L2017, K648-L2017, E649-L2017, S650-L2017, H651-L2017, M652-L2017, V653-L2017, D654-L2017, D655-L2017, A656-L2017, S657-L2017, E658-L2017, E659-L2017, L660-L2017, K661-L2017, N662-L2017, Y663-L2017, S664-L2017, K665-L2017, Q666-L2017, F667-L2017, G668-L2017, Q669-L2017, L670-L2017, A671-L2017, L672-L2017, D673-L2017, L674-L2017, L675-L2017, E676-L2017, K677-L2017, A678-L2017, F679-L2017, K680-L2017, Q681-L2017, N682-L2017, E683-L2017, R684-L2017, M685-L2017, A686-L2017, M687-L2017, T688-L2017, L689-L2017, L690-L2017, T691-L2017, Y692-L2017, E693-L2017, L694-L2017, R695-L2017, N696-L2017, W697-L2017, S698-L2017, N699-L2017, S700-L2017, T701-L2017, C702-L2017, L703-L2017, K704-L2017, L705-L2017, A706-L2017, V707-L2017, S708-L2017, G709-L2017, G710-L2017, L711-L2017, R712-L2017, P713-L2017, F714-L2017, V715-L2017, S716-L2017, H717-L2017, T718-L2017, C719-L2017, T720-L2017, Q721-L2017, M722-L2017, L723-L2017, L724-L2017, T725-L2017, D726-L2017, M727-L2017, W728-L2017, M729-L2017, G730-L2017, R731-L2017, L732-L2017, K733-L2017, M734-L2017, R735-L2017, K736-L2017, N737-L2017, S738-L2017, W739-L2017, L740-L2017, K741-L2017, I742-L2017, I743-L2017, I744-L2017, S745-L2017, I746-L2017, I747-L2017, L748-L2017, P749-L2017, P750-L2017, T751-L2017, I752-L2017, L753-L2017, T754-L2017, L755-L2017, E756-L2017, F757-L2017, K758-L2017, S759-L2017, K760-L2017, A761-L2017, E762-L2017, M763-L2017, S764-L2017, H765-L2017, V766-L2017, P767-L2017, Q768-L2017, S769-L2017, Q770-L2017, D771-L2017, F772-L2017, Q773-L2017, F774-L2017, M775-L2017, W776-L2017, Y777-L2017, Y778-L2017, S779-L2017, D780-L2017, Q781-L2017, N782-L2017, A783-L2017, S784-L2017, S785-L2017, S786-L2017, K787-L2017, E788-L2017, S789-L2017, A790-L2017, S791-L2017, V792-L2017, K793-L2017, E794-L2017, Y795-L2017, D796-L2017, L797-L2017, E798-L2017, R799-L2017, G800-L2017, H801-L2017, D802-L2017, E803-L2017, K804-L2017, L805-L2017, D806-L2017, E807-L2017, N808-L2017, Q809-L2017, H810-L2017, F811-L2017, G812-L2017, L813-L2017, E814-L2017, S815-L2017, G816-L2017, H817-L2017, Q818-L2017, H819-L2017, L820-L2017, P821-L2017, W822-L2017, T823-L2017, R824-L2017, K825-L2017, V826-L2017, Y827-L2017, E828-L2017, F829-L2017, Y830-L2017, S831-L2017, A832-L2017, P833-L2017, I834-L2017, V835-L2017, K836-L2017, F837-L2017, W838-L2017, F839-L2017, Y840-L2017, T841-L2017, M842-L2017, A843-L2017, Y844-L2017, L845-L2017, A846-L2017, F847-L2017, L848-L2017, M849-L2017, L850-L2017, F851-L2017, T852-L2017, Y853-L2017, T854-L2017, V855-L2017, L856-L2017, V857-L2017, E858-L2017, M859-L2017, Q860-L2017, P861-L2017, Q862-L2017, P863-L2017, S864-L2017, V865-L2017, Q866-L2017, E867-L2017, W868-L2017, L869-L2017, V870-L2017, S871-L2017, I872-L2017, Y873-L2017, I874-L2017, F875-L2017, T876-L2017, N877-L2017, A878-L2017, I879-L2017, E880-L2017, V881-L2017, V882-L2017, R883-L2017, E884-L2017, I885-L2017, C886-L2017, I887-L2017, S888-L2017, E889-L2017, P890-L2017, G891-L2017, K892-L2017, F893-L2017, T894-L2017, Q895-L2017, K896-L2017, V897-L2017, K898-L2017, V899-L2017, W900-L2017, I901-L2017, S902-L2017, E903-L2017, Y904-L2017, W905-L2017, N906-L2017, L907-L2017, T908-L2017, E909-L2017, T910-L2017, V911-L2017, A912-L2017, I913-L2017, G914-L2017, L915-L2017, F916-L2017, S917-L2017, A918-L2017, G919-L2017, F920-L2017, V921-L2017, L922-L2017, R923-L2017, W924-L2017, G925-L2017, D926-L2017, P927-L2017, P928-L2017, F929-L2017, H930-L2017, T931-L2017, A932-L2017, G933-L2017, R934-L2017, L935-L2017, I936-L2017, Y937-L2017, C938-L2017, I939-L2017, D940-L2017, I941-L2017, I942-L2017, F943-L2017, W944-L2017, F945-L2017, S946-L2017, R947-L2017, L948-L2017, L949-L2017, D950-L2017, F951-L2017, F952-L2017, A953-L2017, V954-L2017, N955-L2017, Q956-L2017, H957-L2017, A958-L2017, G959-L2017, P960-L2017, Y961-L2017, V962-L2017, T963-L2017, M964-L2017, I965-L2017, A966-L2017, K967-L2017, M968-L2017, T969-L2017, A970-L2017, N971-L2017, M972-L2017, F973-

L2017, Y974-L2017, I975-L2017, V976-L2017, I977-L2017, I978-L2017, M979-L2017, A980-L2017, I981-L2017, V982-L2017, L983-L2017, L984-L2017, S985-L2017, F986-L2017, G987-L2017, V988-L2017, A989-L2017, R990-L2017, K991-L2017, A992-L2017, I993-L2017, L994-L2017, S995-L2017, P996-L2017, K997-L2017, E998-L2017, P999-L2017, P1000-L2017, S1001-L2017, W1002-L2017, S1003-L2017, L1004-L2017, A1005-L2017, R1006-L2017, D1007-L2017, I1008-L2017, V1009-L2017, F1010-L2017, E1011-L2017, P1012-L2017, Y1013-L2017, W1014-L2017, M1015-L2017, I1016-L2017, Y1017-L2017, G1018-L2017, E1019-L2017, V1020-L2017, Y1021-L2017, A1022-L2017, G1023-L2017, E1024-L2017, I1025-L2017, D1026-L2017, V1027-L2017, C1028-L2017, S1029-L2017, S1030-L2017, Q1031-L2017, P1032-L2017, S1033-L2017, C1034-L2017, P1035-L2017, P1036-L2017, G1037-L2017, S1038-L2017, F1039-L2017, L1040-L2017, T1041-L2017, P1042-L2017, F1043-L2017, L1044-L2017, Q1045-L2017, A1046-L2017, V1047-L2017, Y1048-L2017, L1049-L2017, F1050-L2017, V1051-L2017, Q1052-L2017, Y1053-L2017, I1054-L2017, I1055-L2017, M1056-L2017, V1057-L2017, N1058-L2017, L1059-L2017, L1060-L2017, I1061-L2017, A1062-L2017, F1063-L2017, F1064-L2017, N1065-L2017, N1066-L2017, V1067-L2017, Y1068-L2017, L1069-L2017, D1070-L2017, M1071-L2017, E1072-L2017, S1073-L2017, I1074-L2017, S1075-L2017, N1076-L2017, N1077-L2017, L1078-L2017, W1079-L2017, K1080-L2017, Y1081-L2017, N1082-L2017, R1083-L2017, Y1084-L2017, R1085-L2017, Y1086-L2017, I1087-L2017, M1088-L2017, T1089-L2017, Y1090-L2017, H1091-L2017, E1092-L2017, K1093-L2017, P1094-L2017, W1095-L2017, L1096-L2017, P1097-L2017, P1098-L2017, P1099-L2017, L1100-L2017, I1101-L2017, L1102-L2017, L1103-L2017, S1104-L2017, H1105-L2017, V1106-L2017, G1107-L2017, L1108-L2017, L1109-L2017, L1100-L2017, R1111-L2017, R1112-L2017, L1113-L2017, C1114-L2017, C1115-L2017, H1116-L2017, R1117-L2017, A1118-L2017, P1119-L2017, H1120-L2017, D1121-L2017, Q1122-L2017, E1123-L2017, E1124-L2017, G1125-L2017, D1126-L2017, V1127-L2017, G1128-L2017, L1129-L2017, K1130-L2017, L1131-L2017, Y1132-L2017, L1133-L2017, S1134-L2017, K1135-L2017, E1136-L2017, D1137-L2017, L1138-L2017, K1139-L2017, K1140-L2017, L1141-L2017, H1142-L2017, D1143-L2017, F1144-L2017, E1145-L2017, E1146-L2017, Q1147-L2017, C1148-L2017, V1149-L2017, E1150-L2017, K1151-L2017, Y1152-L2017, F1153-L2017, H1154-L2017, E1155-L2017, K1156-L2017, M1157-L2017, E1158-L2017, D1159-L2017, V1160-L2017, N1161-L2017, C1162-L2017, S1163-L2017, C1164-L2017, E1165-L2017, E1166-L2017, R1167-L2017, I1168-L2017, R1169-L2017, V1170-L2017, T1171-L2017, S1172-L2017, E1173-L2017, R1174-L2017, V1175-L2017, T1176-L2017, E1177-L2017, M1178-L2017, Y1179-L2017, F1180-L2017, Q1181-L2017, L1182-L2017, K1183-L2017, E1184-L2017, M1185-L2017, N1186-L2017, E1187-L2017, K1188-L2017, V1189-L2017, S1190-L2017, F1191-L2017, I1192-L2017, K1193-L2017, D1194-L2017, S1195-L2017, L1196-L2017, L1197-L2017, S1198-L2017, L1199-L2017, D1200-L2017, S1201-L2017, Q1202-L2017, V1203-L2017, G1204-L2017, H1205-L2017, L1206-L2017, Q1207-L2017, D1208-L2017, L1209-L2017, S1210-L2017, A1211-L2017, L1212-L2017, T1213-L2017, V1214-L2017, D1215-L2017, T1216-L2017, L1217-L2017, K1218-L2017, V1219-L2017, L1220-L2017, S1221-L2017, A1222-L2017, V1223-L2017, D1224-L2017, T1225-L2017, L1226-L2017, Q1227-L2017, E1228-L2017, D1229-L2017, E1230-L2017, A1231-L2017, L1232-L2017, L1233-L2017, A1234-L2017, K1235-L2017, R1236-L2017, K1237-L2017, H1238-L2017, S1239-L2017, T1240-L2017, C1241-L2017, K1242-L2017, K1243-L2017, L1244-L2017, P1245-L2017, H1246-L2017, S1247-L2017, W1248-L2017, S1249-L2017, N1250-L2017, V1251-L2017, I1252-L2017, C1253-L2017, A1254-L2017, E1255-L2017, V1256-L2017, L1257-L2017, G1258-L2017, S1259-L2017, M1260-L2017, E1261-L2017, I1262-L2017, A1263-L2017, G1264-L2017, E1265-L2017, K1266-L2017, K1267-L2017, Y1268-L2017, Q1269-L2017, Y1270-L2017, Y1271-L2017, S1272-L2017, M1273-L2017, P1274-L2017, S1275-L2017, S1276-L2017, L1277-L2017, L1278-L2017, R1279-L2017, S1280-L2017, L1281-L2017, A1282-L2017, G1283-L2017, G1284-L2017, R1285-L2017, H1286-L2017, P1287-L2017, P1288-L2017, R1289-L2017, V1290-L2017, Q1291-L2017, R1292-L2017, G1293-L2017, A1294-L2017, L1295-L2017, L1296-L2017, E1297-L2017, I1298-L2017, T1299-L2017, N1300-L2017, S1301-L2017, K1302-L2017, R1303-L2017, E1304-L2017, A1305-L2017, T1306-L2017, N1307-L2017, V1308-L2017, R1309-L2017, N1310-L2017, D1311-L2017, Q1312-L2017, E1313-L2017, R1314-L2017, Q1315-L2017, E1316-L2017, T1317-L2017, Q1318-L2017, S1319-L2017, S1320-L2017, I1321-L2017, V1322-L2017, V1323-L2017, S1324-L2017, G1325-L2017, V1326-L2017, S1327-L2017, P1328-L2017, N1329-L2017, R1330-L2017, Q1331-L2017, A1332-L2017, H1333-L2017, S1334-L2017, K1335-L2017, Y1336-L2017, G1337-L2017, Q1338-L2017, F1339-L2017, L1340-L2017, L1341-L2017, V1342-L2017, P1343-L2017, S1344-L2017, N1345-L2017, L1346-L2017, K1347-L2017, R1348-L2017, V1349-L2017, P1350-L2017, F1351-L2017, S1352-L2017, A1353-L2017, E1354-L2017, T1355-L2017, V1356-L2017, L1357-L2017, P1358-L2017, L1359-L2017, S1360-L2017, R1361-L2017, P1362-L2017, S1363-L2017, V1364-L2017, P1365-L2017, D1366-L2017, V1367-L2017, L1368-L2017, A1369-L2017, T1370-L2017, E1371-L2017, Q1372-L2017, D1373-L2017, I1374-L2017, Q1375-L2017, T1376-L2017, E1377-L2017, V1378-L2017, L1379-L2017, V1380-L2017, H1381-L2017, L1382-L2017, T1383-L2017, G1384-L2017, Q1385-L2017, T1386-L2017, P1387-L2017, V1388-L2017, V1389-L2017, S1390-L2017, D1391-L2017, W1392-L2017, A1393-L2017, S1394-L2017, V1395-L2017, D1396-L2017, E1397-L2017, P1398-L2017, K1399-L2017, E1400-L2017, K1401-L2017, H1402-L2017, E1403-L2017, P1404-L2017, I1405-L2017, A1406-L2017, H1407-L2017, L1408-L2017, L1409-L2017, D1410-L2017, G1411-L2017, Q1412-L2017, D1413-L2017, K1414-L2017, A1415-L2017, E1416-L2017, Q1417-L2017, V1418-L2017, L1419-L2017, P1420-L2017, T1421-L2017, L1422-L2017, S1423-L2017, C1424-L2017, T1425-L2017, P1426-L2017, E1427-L2017, P1428-L2017, M1429-L2017, T1430-L2017, M1431-L2017, S1432-L2017, S1433-L2017, P1434-L2017, L1435-L2017, S1436-L2017, Q1437-L2017, A1438-L2017, K1439-L2017, I1440-L2017, M1441-L2017, Q1442-L2017, T1443-L2017, G1444-L2017, G1445-L2017, G1446-L2017, Y1447-L2017, V1448-L2017, N1449-L2017, W1450-L2017, A1451-L2017, F1452-L2017, S1453-L2017, E1454-L2017, G1455-L2017, D1456-L2017, E1457-L2017, T1458-L2017, G1459-L2017, V1460-L2017, F1461-L2017, S1462-L2017, I1463-L2017, K1464-L2017, K1465-L2017, K1466-L2017, W1467-L2017, Q1468-L2017, T1469-L2017, C1470-L2017, L1471-L2017, P1472-L2017, S1473-L2017, T1474-L2017, C1475-L2017, D1476-L2017, S1477-L2017, D1478-L2017, S1479-L2017, S1480-L2017, R1481-L2017, S1482-L2017, E1483-L2017, Q1484-L2017, H1485-L2017, Q1486-L2017, K1487-L2017, Q1488-L2017, A1489-L2017, Q1490-L2017, D1491-L2017, S1492-L2017, S1493-L2017, L1494-L2017, S1495-L2017, D1496-L2017,

N1497-L2017, S1498-L2017, T1499-L2017, R1500-L2017, S1501-L2017, A1502-L2017, Q1503-L2017, S1504-L2017, S1505-L2017, E1506-L2017, C1507-L2017, S1508-L2017, E1509-L2017, V1510-L2017, G1511-L2017, P1512-L2017, W1513-L2017, L1514-L2017, Q1515-L2017, P1516-L2017, N1517-L2017, T1518-L2017, S1519-L2017, F1520-L2017, W1521-L2017, I1522-L2017, N1523-L2017, P1524-L2017, L1525-L2017, R1526-L2017, R1527-L2017, Y1528-L2017, R1529-L2017, P1530-L2017, F1531-L2017, A1532-L2017, R1533-L2017, S1534-L2017, H1535-L2017, S1536-L2017, F1537-L2017, R1538-L2017, F1539-L2017, H1540-L2017, K1541-L2017, E1542-L2017, E1543-L2017, K1544-L2017, L1545-L2017, M1546-L2017, K1547-L2017, I1548-L2017, C1549-L2017, K1550-L2017, I1551-L2017, K1552-L2017, N1553-L2017, L1554-L2017, S1555-L2017, G1556-L2017, S1557-L2017, S1558-L2017, E1559-L2017, I1560-L2017, G1561-L2017, Q1562-L2017, G1563-L2017, A1564-L2017, W1565-L2017, V1566-L2017, K1567-L2017, A1568-L2017, K1569-L2017, M1570-L2017, L1571-L2017, T1572-L2017, K1573-L2017, D1574-L2017, R1575-L2017, R1576-L2017, L1577-L2017, S1578-L2017, K1579-L2017, K1580-L2017, K1581-L2017, K1582-L2017, N1583-L2017, T1584-L2017, Q1585-L2017, G1586-L2017, L1587-L2017, Q1588-L2017, V1589-L2017, P1590-L2017, I1591-L2017, I1592-L2017, T1593-L2017, V1594-L2017, N1595-L2017, A1596-L2017, C1597-L2017, S1598-L2017, Q1599-L2017, S1600-L2017, D1601-L2017, Q1602-L2017, L1603-L2017, N1604-L2017, P1605-L2017, E1606-L2017, P1607-L2017, G1608-L2017, E1609-L2017, N1610-L2017, S1611-L2017, I1612-L2017, S1613-L2017, E1614-L2017, E1615-L2017, E1616-L2017, Y1617-L2017, S1618-L2017, K1619-L2017, N1620-L2017, W1621-L2017, F1622-L2017, T1623-L2017, V1624-L2017, S1625-L2017, K1626-L2017, F1627-L2017, S1628-L2017, H1629-L2017, T1630-L2017, G1631-L2017, V1632-L2017, E1633-L2017, P1634-L2017, Y1635-L2017, I1636-L2017, H1637-L2017, Q1638-L2017, K1639-L2017, M1640-L2017, K1641-L2017, T1642-L2017, K1643-L2017, E1644-L2017, I1645-L2017, G1646-L2017, Q1647-L2017, C1648-L2017, A1649-L2017, I1650-L2017, Q1651-L2017, I1652-L2017, S1653-L2017, D1654-L2017, Y1655-L2017, L1656-L2017, K1657-L2017, Q1658-L2017, S1659-L2017, Q1660-L2017, E1661-L2017, D1662-L2017, L1663-L2017, S1664-L2017, K1665-L2017, N1666-L2017, S1667-L2017, L1668-L2017, W1669-L2017, N1670-L2017, S1671-L2017, R1672-L2017, S1673-L2017, T1674-L2017, N1675-L2017, L1676-L2017, N1677-L2017, R1678-L2017, N1679-L2017, S1680-L2017, L1681-L2017, L1682-L2017, K1683-L2017, S1684-L2017, S1685-L2017, I1686-L2017, G1687-L2017, V1688-L2017, D1689-L2017, K1690-L2017, I1691-L2017, S1692-L2017, A1693-L2017, S1694-L2017, L1695-L2017, K1696-L2017, S1697-L2017, P1698-L2017, Q1699-L2017, E1700-L2017, P1701-L2017, H1702-L2017, H1703-L2017, H1704-L2017, Y1705-L2017, S1706-L2017, A1707-L2017, I1708-L2017, E1709-L2017, R1710-L2017, N1711-L2017, N1712-L2017, L1713-L2017, M1714-L2017, R1715-L2017, L1716-L2017, S1717-L2017, Q1718-L2017, T1719-L2017, I1720-L2017, P1721-L2017, F1722-L2017, T1723-L2017, P1724-L2017, V1725-L2017, Q1726-L2017, L1727-L2017, F1728-L2017, A1729-L2017, G1730-L2017, E1731-L2017, E1732-L2017, I1733-L2017, T1734-L2017, V1735-L2017, Y1736-L2017, R1737-L2017, L1738-L2017, E1739-L2017, E1740-L2017, S1741-L2017, S1742-L2017, P1743-L2017, L1744-L2017, N1745-L2017, L1746-L2017, D1747-L2017, K1748-L2017, S1749-L2017, M1750-L2017, S1751-L2017, S1752-L2017, W1753-L2017, S1754-L2017, Q1755-L2017, R1756-L2017, G1757-L2017, R1758-L2017, A1759-L2017, A1760-L2017, M1761-L2017, I1762-L2017, Q1763-L2017, V1764-L2017, L1765-L2017, S1766-L2017, R1767-L2017, E1768-L2017, E1769-L2017, M1770-L2017, D1771-L2017, G1772-L2017, G1773-L2017, L1774-L2017, R1775-L2017, K1776-L2017, A1777-L2017, M1778-L2017, R1779-L2017, V1780-L2017, V1781-L2017, S1782-L2017, T1783-L2017, W1784-L2017, S1785-L2017, E1786-L2017, D1787-L2017, D1788-L2017, I1789-L2017, L1790-L2017, K1791-L2017, P1792-L2017, G1793-L2017, Q1794-L2017, V1795-L2017, F1796-L2017, I1797-L2017, V1798-L2017, K1799-L2017, S1800-L2017, F1801-L2017, L1802-L2017, P1803-L2017, E1804-L2017, V1805-L2017, V1806-L2017, R1807-L2017, T1808-L2017, W1809-L2017, H1810-L2017, K1811-L2017, I1812-L2017, F1813-L2017, Q1814-L2017, E1815-L2017, S1816-L2017, T1817-L2017, V1818-L2017, L1819-L2017, H1820-L2017, L1821-L2017, C1822-L2017, L1823-L2017, R1824-L2017, E1825-L2017, I1826-L2017, Q1827-L2017, Q1828-L2017, Q1829-L2017, R1830-L2017, A1831-L2017, A1832-L2017, Q1833-L2017, K1834-L2017, L1835-L2017, I1836-L2017, Y1837-L2017, T1838-L2017, F1839-L2017, N1840-L2017, Q1841-L2017, V1842-L2017, K1843-L2017, P1844-L2017, Q1845-L2017, T1846-L2017, I1847-L2017, P1848-L2017, Y1849-L2017, T1850-L2017, P1851-L2017, R1852-L2017, F1853-L2017, L1854-L2017, E1855-L2017, V1856-L2017, F1857-L2017, L1858-L2017, I1859-L2017, Y1860-L2017, C1861-L2017, H1862-L2017, S1863-L2017, A1864-L2017, N1865-L2017, Q1866-L2017, W1867-L2017, L1868-L2017, T1869-L2017, I1870-L2017, E1871-L2017, K1872-L2017, Y1873-L2017, M1874-L2017, T1875-L2017, G1876-L2017, E1877-L2017, F1878-L2017, R1879-L2017, K1880-L2017, Y1881-L2017, N1882-L2017, N1883-L2017, N1884-L2017, N1885-L2017, G1886-L2017, D1887-L2017, E1888-L2017, I1889-L2017, T1890-L2017, P1891-L2017, T1892-L2017, N1893-L2017, T1894-L2017, L1895-L2017, E1896-L2017, E1897-L2017, L1898-L2017, M1899-L2017, L1900-L2017, A1901-L2017, F1902-L2017, S1903-L2017, H1904-L2017, W1905-L2017, T1906-L2017, Y1907-L2017, E1908-L2017, Y1909-L2017, T1910-L2017, R1911-L2017, G1912-L2017, E1913-L2017, L1914-L2017, L1915-L2017, V1916-L2017, L1917-L2017, D1918-L2017, L1919-L2017, Q1920-L2017, G1921-L2017, V1922-L2017, G1923-L2017, E1924-L2017, N1925-L2017, L1926-L2017, T1927-L2017, D1928-L2017, P1929-L2017, S1930-L2017, V1931-L2017, I1932-L2017, K1933-L2017, P1934-L2017, E1935-L2017, V1936-L2017, K1937-L2017, Q1938-L2017, S1939-L2017, R1940-L2017, G1941-L2017, M1942-L2017, V1943-L2017, F1944-L2017, G1945-L2017, P1946-L2017, A1947-L2017, N1948-L2017, L1949-L2017, G1950-L2017, E1951-L2017, D1952-L2017, A1953-L2017, I1954-L2017, R1955-L2017, N1956-L2017, F1957-L2017, I1958-L2017, A1959-L2017, K1960-L2017, H1961-L2017, H1962-L2017, C1963-L2017, N1964-L2017, S1965-L2017, C1966-L2017, C1967-L2017, R1968-L2017, K1969-L2017, L1970-L2017, K1971-L2017, L1972-L2017, P1973-L2017, D1974-L2017, L1975-L2017, K1976-L2017, R1977-L2017, N1978-L2017, D1979-L2017, Y1980-L2017, S1981-L2017, P1982-L2017, E1983-L2017, R1984-L2017, I1985-L2017, N1986-L2017, S1987-L2017, T1988-L2017, F1989-L2017, G1990-L2017, L1991-L2017, E1992-L2017, I1993-L2017, K1994-L2017, I1995-L2017, E1996-L2017, S1997-L2017, A1998-L2017, E1999-L2017, E2000-L2017, P2001-L2017, P2002-L2017, A2003-L2017, R2004-L2017, E2005-L2017, T2006-L2017, G2007-L2017, R2008-L2017, N2009-L2017, S2010-L2017, and/or P2011-L2017 of SEQ ID NO:2. Polynucleotide sequences encoding these polypeptides are also provided. The present invention also encompasses the use of these N-terminal TRP-PLIK2 deletion polypeptides as immunogenic and/or antigenic epitopes as described elsewhere herein.

In preferred embodiments, the following C-terminal TRP-PLIK2 deletion polypeptides are encompassed by the present invention: M1-L2017, M1-Q2016, M1-M2015, M1-D2014, M1-D2013, M1-E2012, M1-P2011, M1-S2010, M1-N2009, M1-R2008, M1-G2007, M1-T2006, M1-E2005, M1-R2004, M1-A2003, M1-P2002, M1-P2001, M1-E2000, M1-E1999, M1-A1998, M1-S1997, M1-E1996, M1-I1995, M1-K1994, M1-I1993, M1-E1992, M1-L1991, M1-G1990, M1-F1989, M1-T1988, M1-S1987, M1-N1986, M1-I1985, M1-R1984, M1-E1983, M1-P1982, M1-S1981, M1-Y1980, M1-D1979, M1-N1978, M1-R1977, M1-K1976, M1-L1975, M1-D1974, M1-P1973, M1-L1972, M1-K1971, M1-L1970, M1-K1969, M1-R1968, M1-C1967, M1-C1966, M1-S1965, M1-N1964, M1-C1963, M1-H1962, M1-H1961, M1-K1960, M1-A1959, M1-I1958, M1-F1957, M1-N1956, M1-R1955, M1-I1954, M1-A1953, M1-D1952, M1-E1951, M1-G1950, M1-L1949, M1-N1948, M1-A1947, M1-P1946, M1-G1945, M1-F1944, M1-V1943, M1-M1942, M1-G1941, M1-R1940, M1-S1939, M1-Q1938, M1-K1937, M1-V1936, M1-E1935, M1-P1934, M1-K1933, M1-I1932, M1-V1931, M1-S1930, M1-P1929, M1-D1928, M1-T1927, M1-L1926, M1-N1925, M1-E1924, M1-G1923, M1-V1922, M1-G1921, M1-Q1920, M1-L1919, M1-D1918, M1-L1917, M1-V1916, M1-L1915, M1-L1914, M1-E1913, M1-G1912, M1-R1911, M1-T1910, M1-Y1909, M1-E1908, M1-Y1907, M1-T1906, M1-W1905, M1-H1904, M1-S1903, M1-F1902, M1-A1901, M1-L1900, M1-M1899, M1-L1898, M1-E1897, M1-E1896, M1-L1895, M1-T1894, M1-N1893, M1-T1892, M1-P1891, M1-T1890, M1-I1889, M1-E1888, M1-D1887, M1-G1886, M1-N1885, M1-N1884, M1-N1883, M1-N1882, M1-Y1881, M1-K1880, M1-R1879, M1-F1878, M1-E1877, M1-G1876, M1-T1875, M1-M1874, M1-Y1873, M1-K1872, M1-E1871, M1-I1870, M1-T1869, M1-L1868, M1-W1867, M1-Q1866, M1-N1865, M1-A1864, M1-S1863, M1-H1862, M1-C1861, M1-Y1860, M1-I1859, M1-L1858, M1-F1857, M1-V1856, M1-E1855, M1-L1854, M1-F1853, M1-R1852, M1-P1851, M1-T1850, M1-Y1849, M1-P1848, M1-I1847, M1-T1846, M1-Q1845, M1-P1844, M1-K1843, M1-V1842, M1-Q1841, M1-N1840, M1-F1839, M1-T1838, M1-Y1837, M1-I1836, M1-L1835, M1-H1834, M1-Q1833, M1-A1832, M1-A1831, M1-R1830, M1-Q1829, M1-Q1828, M1-Q1827, M1-I1826, M1-E1825, M1-R1824, M1-L1823, M1-C1822, M1-L1821, M1-H1820, M1-L1819, M1-V1818, M1-T1817, M1-S1816, M1-E1815, M1-Q1814, M1-F1813, M1-I1812, M1-K1811, M1-H1810, M1-W1809, M1-T1808, M1-R1807, M1-V1806, M1-V1805, M1-E1804, M1-P1803, M1-L1802, M1-F1801, M1-S1800, M1-K1799, M1-V1798, M1-I1797, M1-F1796, M1-V1795, M1-Q1794, M1-G1793, M1-P1792, M1-K1791, M1-L1790, M1-I1789, M1-D1788, M1-D1787, M1-E1786, M1-S1785, M1-W1784, M1-T1783, M1-S1782, M1-V1781, M1-V1780, M1-R1779, M1-M1778, M1-A1777, M1-K1776, M1-R1775, M1-L1774, M1-G1773, M1-G1772, M1-D1771, M1-M1770, M1-E1769, M1-E1768, M1-R1767, M1-S1766, M1-L1765, M1-V1764, M1-Q1763, M1-I1762, M1-M1761, M1-A1760, M1-A1759, M1-R1758, M1-G1757, M1-R1756, M1-Q1755, M1-S1754, M1-W1753, M1-S1752, M1-S1751, M1-M1750, M1-S1749, M1-K1748, M1-D1747, M1-L1746, M1-N1745, M1-L1744, M1-P1743, M1-S1742, M1-S1741, M1-E1740, M1-E1739, M1-L1738, M1-R1737, M1-Y1736, M1-V1735, M1-T1734, M1-I1733, M1-E1732, M1-E1731, M1-G1730, M1-A1729, M1-F1728, M1-L1727, M1-Q1726, M1-V1725, M1-P1724, M1-T1723, M1-F1722, M1-P1721, M1-I1720, M1-T1719, M1-Q1718, M1-S1717, M1-L1716, M1-R1715, M1-M1714, M1-L1713, M1-N1712, M1-N1711, M1-R1710, M1-E1709, M1-I1708, M1-A1707, M1-T1706, M1-Y1705, M1-H1704, M1-H1703, M1-H1702, M1-P1701, M1-E1700, M1-Q1699, M1-P1698, M1-S1697, M1-K1696, M1-L1695, M1-S1694, M1-A1693, M1-S1692, M1-I1691, M1-K1690, M1-D1689, M1-V1688, M1-G1687, M1-I1686, M1-S1685, M1-S1684, M1-K1683, M1-L1682, M1-L1681, M1-S1680, M1-N1679, M1-R1678, M1-N1677, M1-L1676, M1-N1675, M1-T1674, M1-S1673, M1-R1672, M1-S1671, M1-N1670, M1-W1669, M1-L1668, M1-S1667, M1-N1666, M1-K1665, M1-S1664, M1-L1663, M1-D1662, M1-E1661, M1-Q1660, M1-S1659, M1-Q1658, M1-K1657, M1-L1656, M1-Y1655, M1-D1654, M1-S1653, M1-I1652, M1-Q1651, M1-I1650, M1-A1649, M1-C1648, M1-Q1647, M1-G1646, M1-I1645, M1-E1644, M1-K1643, M1-T1642, M1-K1641, M1-M1640, M1-K1639, M1-Q1638, M1-H1637, M1-I1636, M1-Y1635, M1-P1634, M1-E1633, M1-V1632, M1-G1631, M1-T1630, M1-H1629, M1-S1628, M1-F1627, M1-K1626, M1-S1625, M1-V1624, M1-T1623, M1-F1622, M1-W1621, M1-N1620, M1-K1619, M1-S1618, M1-Y1617, M1-E1616, M1-E1615, M1-E1614, M1-S1613, M1-I1612, M1-S1611, M1-N1610, M1-E1609, M1-G1608, M1-P1607, M1-E1606, M1-P1605, M1-N1604, M1-L1603, M1-Q1602, M1-D1601, M1-S1600, M1-Q1599, M1-S1598, M1-C1597, M1-A1596, M1-N1595, M1-V1594, M1-T1593, M1-I1592, M1-I1591, M1-P1590, M1-V1589, M1-Q1588, M1-L1587, M1-G1586, M1-Q1585, M1-T1584, M1-N1583, M1-K1582, M1-K1581, M1-K1580, M1-K1579, M1-S1578, M1-L1577, M1-R1576, M1-R1575, M1-D1574, M1-K1573, M1-T1572, M1-L1571, M1-M1570, M1-K1569, M1-A1568, M1-K1567, M1-V1566, M1-W1565, M1-A1564, M1-G1563, M1-Q1562, M1-G1561, M1-I1560, M1-E1559, M1-S1558, M1-S1557, M1-G1556, M1-S1555, M1-L1554, M1-N1553, M1-K1552, M1-I1551, M1-K1550, M1-C1549, M1-I1548, M1-K1547, M1-M1546, M1-L1545, M1-K1544, M1-E1543, M1-E1542, M1-K1541, M1-H1540, M1-F1539, M1-R1538, M1-F1537, M1-S1536, M1-H1535, M1-S1534, M1-R1533, M1-A1532, M1-F1531, M1-P1530, M1-R1529, M1-Y1528, M1-R1527, M1-R1526, M1-L1525, M1-P1524, M1-N1523, M1-I1522, M1-W1521, M1-F1520, M1-S1519, M1-T1518, M1-N1517, M1-P1516, M1-Q1515, M1-L1514, M1-W1513, M1-P1512, M1-G1511, M1-V1510, M1-E1509, M1-S1508, M1-C1507, M1-E1506, M1-S1505, M1-S1504, M1-Q1503, M1-A1502, M1-S1501, M1-R1500, M1-T1499, M1-S1498, M1-N1497, M1-D1496, M1-S1495, M1-L1494, M1-S1493, M1-S1492, M1-D1491, M1-Q1490, M1-A1489, M1-Q1488, M1-K1487, M1-Q1486, M1-H1485, M1-Q1484, M1-E1483, M1-S1482, M1-R1481, M1-S1480, M1-S1479, M1-D1478, M1-S1477, M1-D1476, M1-C1475, M1-T1474, M1-S1473, M1-P1472, M1-L1471, M1-C1470, M1-T1469, M1-Q1468, M1-W1467, M1-K1466, M1-K1465, M1-K1464, M1-I1463, M1-S1462, M1-F1461, M1-V1460, M1-G1459, M1-T1458, M1-E1457, M1-D1456, M1-G1455, M1-E1454, M1-S1453, M1-F1452, M1-A1451, M1-W1450, M1-N1449, M1-V1448, M1-Y1447, M1-G1446, M1-G1445, M1-G1444, M1-T1443, M1-Q1442, M1-M1441, M1-I1440, M1-K1439, M1-A1438, M1-Q1437, M1-S1436, M1-L1435, M1-P1434, M1-S1433, M1-S1432, M1-M1431, M1-T1430, M1-M1429, M1-P1428, M1-E1427, M1-P1426, M1-T1425, M1-C1424, M1-S1423, M1-L1422, M1-T1421, M1-P1420, M1-L1419, M1-V1418, M1-Q1417, M1-E1416, M1-A1415, M1-K1414, M1-D1413, M1-Q1412, M1-G1411, M1-D1410, M1-L1409, M1-L1408, M1-H1407, M1-A1406, M1-I1405, M1-P1404, M1-E1403, M1-H1402, M1-K1401, M1-E1400, M1-K1399, M1-P1398, M1-E1397, M1-D1396, M1-V1395, M1-S1394, M1-A1393, M1-W1392, M1-D1391, M1-S1390, M1-V1389, M1-V1388, M1-P1387, M1-T1386, M1-Q1385, M1-G1384, M1-T1383, M1-L1382, M1-H1381, M1-V1380, M1-L1379, M1-V1378, M1-E1377, M1-T1376, M1-Q1375, M1-I1374, M1-D1373, M1-Q1372, M1-E1371, M1-T1370, M1-A1369, M1-L1368, M1-V1367, M1-D1366, M1-P1365, M1-V1364, M1-S1363, M1-P1362, M1-R1361, M1-S1360, M1-L1359, M1-P1358, M1-L1357, M1-V1356, M1-T1355, M1-E1354, M1-A1353, M1-S1352, M1-F1351, M1-P1350, M1-V1349, M1-R1348, M1-K1347, M1-L1346, M1-N1345, M1-S1344, M1-P1343, M1-V1342, M1-L1341, M1-L1340, M1-F1339, M1-Q1338, M1-G1337, M1-Y1336, M1-K1335, M1-S1334, M1-H1333, M1-A1332, M1-Q1331, M1-R1330, M1-N1329, M1-P1328, M1-S1327, M1-V1326, M1-G1325, M1-S1324, M1-V1323, M1-V1322, M1-I1321, M1-S1320, M1-S1319, M1-Q1318, M1-T1317, M1-E1316, M1-Q1315, M1-R1314, M1-E1313, M1-Q1312, M1-D1311, M1-N1310, M1-R1309, M1-V1308, M1-N1307, M1-T1306, M1-A1305, M1-E1304, M1-R1303, M1-K1302, M1-S1301, M1-N1300, M1-T1299, M1-I1298, M1-E1297, M1-L1296, M1-L1295, M1-A1294, M1-G1293, M1-R1292, M1-Q1291, M1-V1290, M1-R1289, M1-P1288, M1-P1287, M1-H1286, M1-R1285, M1-G1284, M1-G1283, M1-A1282, M1-L1281, M1-S1280, M1-R1279, M1-L1278, M1-L1277, M1-S1276, M1-S1275, M1-P1274, M1-M1273, M1-S1272, M1-Y1271, M1-Y1270, M1-Q1269, M1-Y1268, M1-K1267, M1-K1266, M1-E1265, M1-G1264, M1-A1263, M1-I1262, M1-E1261, M1-M1260, M1-S1259, M1-G1258, M1-L1257, M1-V1256, M1-E1255, M1-A1254, M1-C1253, M1-I1252, M1-V1251, M1-N1250, M1-S1249, M1-W1248, M1-S1247, M1-H1246, M1-P1245, M1-L1244, M1-K1243, M1-K1242, M1-C1241, M1-T1240, M1-S1239, M1-H1238, M1-K1237, M1-R1236, M1-K1235, M1-A1234, M1-L1233, M1-L1232, M1-A1231, M1-E1230, M1-D1229, M1-E1228, M1-Q1227, M1-L1226, M1-T1225, M1-D1224, M1-V1223, M1-A1222, M1-S1221, M1-L1220, M1-V1219, M1-K1218, M1-L1217, M1-T1216, M1-D1215, M1-V1214, M1-T1213, M1-L1212, M1-A1211, M1-S1210, M1-L1209, M1-D1208, M1-Q1207, M1-L1206, M1-H1205, M1-G1204, M1-V1203, M1-Q1202, M1-S1201, M1-D1200, M1-L1199, M1-S1198, M1-L1197, M1-L1196, M1-S1195, M1-D1194, M1-K1193, M1-I1192, M1-F1191, M1-S1190, M1-V1189, M1-K1188, M1-E1187, M1-N1186, M1-M1185, M1-E1184, M1-K1183, M1-L1182, M1-Q1181, M1-F1180, M1-Y1179, M1-M1178, M1-E1177, M1-T1176, M1-V1175, M1-R1174, M1-E1173, M1-S1172, M1-T1171, M1-V1170, M1-R1169, M1-I1168, M1-R1167, M1-E1166, M1-E1165, M1-C1164, M1-S1163, M1-C1162, M1-N1161, M1-V1160, M1-D1159, M1-E1158, M1-M1157, M1-K1156, M1-E1155, M1-H1154, M1-F1153, M1-Y1152, M1-K1151, M1-E1150, M1-V1149, M1-C1148, M1-Q1147, M1-E1146, M1-E1145, M1-F1144, M1-D1143, M1-H1142, M1-L1141, M1-K1140, M1-K1139, M1-L1138, M1-D1137, M1-E1136, M1-K1135, M1-S1134, M1-L1133, M1-Y1132, M1-L1131, M1-K1130, M1-L1129, M1-G1128, M1-V1127, M1-D1126, M1-G1125, M1-E1124, M1-E1123, M1-Q1122, M1-D1121, M1-H1120, M1-P1119, M1-A1118, M1-R1117, M1-H1116, M1-C1115, M1-C1114, M1-L1113, M1-R1112, M1-R1111, M1-L1110, M1-L1109, M1-L1108, M1-G1107, M1-V1106, M1-H1105, M1-S1104, M1-L1103, M1-L1102, M1-I1101, M1-L1100, M1-P1099, M1-P1098, M1-P1097, M1-L1096, M1-W1095, M1-P1094, M1-K1093, M1-E1092, M1-H1091, M1-Y1090, M1-T1089, M1-M1088, M1-I1087, M1-Y1086, M1-R1085, M1-Y1084, M1-R1083, M1-N1082, M1-Y1081, M1-K1080, M1-W1079, M1-L1078, M1-N1077, M1-N1076, M1-S1075, M1-I1074, M1-S1073, M1-E1072, M1-M1071, M1-D1070, M1-L1069, M1-Y1068, M1-V1067, M1-N1066, M1-N1065, M1-F1064, M1-F1063, M1-A1062, M1-I1061, M1-L1060, M1-L1059, M1-N1058, M1-V1057, M1-M1056, M1-I1055, M1-I1054, M1-Y1053, M1-Q1052, M1-V1051, M1-F1050, M1-L1049, M1-Y1048, M1-V1047, M1-A1046, M1-Q1045, M1-L1044, M1-F1043, M1-P1042, M1-T1041, M1-L1040, M1-F1039, M1-S1038, M1-G1037, M1-P1036, M1-P1035, M1-C1034, M1-S1033, M1-P1032, M1-Q1031, M1-S1030, M1-S1029, M1-C1028, M1-V1027, M1-D1026, M1-I1025, M1-E1024, M1-G1023, M1-A1022, M1-Y1021, M1-V1020, M1-E1019, M1-G1018, M1-Y1017, M1-I1016, M1-M1015, M1-W1014, M1-Y1013, M1-P1012, M1-E1011, M1-F1010, M1-V1009, M1-I1008, M1-D1007, M1-R1006, M1-A1005, M1-L1004, M1-S1003, M1-W1002, M1-S1001, M1-P1000, M1-P999, M1-E998, M1-K997, M1-P996, M1-S995, M1-L994, M1-I993, M1-A992, M1-K991, M1-R990, M1-A989, M1-V988, M1-G987, M1-F986, M1-S985, M1-L984, M1-L983, M1-V982, M1-I981, M1-A980, M1-M979, M1-I978, M1-I977, M1-V976, M1-I975, M1-Y974, M1-F973, M1-M972, M1-N971, M1-A970, M1-T969, M1-M968, M1-K967, M1-A966, M1-I965, M1-M964, M1-T963, M1-V962, M1-Y961, M1-P960, M1-G959, M1-A958, M1-H957, M1-Q956, M1-N955, M1-V954, M1-A953, M1-F952, M1-F951, M1-D950, M1-L949, M1-L948, M1-R947, M1-S946, M1-F945, M1-W944, M1-F943, M1-I942, M1-I941, M1-D940, M1-I939, M1-C938, M1-Y937, M1-I936, M1-L935, M1-R934, M1-G933, M1-A932, M1-T931, M1-H930, M1-F929, M1-P928, M1-P927, M1-D926, M1-G925, M1-W924, M1-R923, M1-L922, M1-V921, M1-F920, M1-G919, M1-A918, M1-S917, M1-F916, M1-L915, M1-G914, M1-I913, M1-A912, M1-V911, M1-T910, M1-E909, M1-T908, M1-L907, M1-N906, M1-W905, M1-Y904, M1-E903, M1-S902, M1-I901, M1-W900, M1-V899, M1-K898, M1-V897, M1-K896, M1-Q895, M1-T894, M1-F893, M1-K892, M1-G891, M1-P890, M1-E889, M1-S888, M1-I887, M1-C886, M1-I885, M1-E884, M1-R883, M1-V882, M1-V881, M1-E880, M1-I879, M1-A878, M1-N877, M1-T876, M1-F875, M1-I874, M1-Y873, M1-I872, M1-S871, M1-V870, M1-L869, M1-W868, M1-E867, M1-Q866, M1-V865, M1-S864, M1-P863, M1-Q862, M1-P861, M1-Q860, M1-M859, M1-E858, M1-V857, M1-L856, M1-V855, M1-T854, M1-Y853, M1-T852, M1-F851, M1-L850, M1-M849, M1-L848, M1-F847, M1-A846, M1-L845, M1-Y844, M1-A843, M1-M842, M1-T841, M1-Y840, M1-F839, M1-W838, M1-F837, M1-K836, M1-V835, M1-I834, M1-P833, M1-A832, M1-S831, M1-Y830, M1-F829, M1-E828, M1-Y827, M1-V826, M1-K825, M1-R824, M1-T823, M1-W822, M1-P821, M1-L820, M1-H819, M1-Q818, M1-H817, M1-G816, M1-S815, M1-E814, M1-L813, M1-G812, M1-F811, M1-H810, M1-Q809, M1-N808, M1-E807, M1-D806, M1-L805, M1-K804, M1-E803, M1-D802, M1-H801, M1-G800, M1-R799, M1-E798, M1-L797, M1-D796, M1-Y795, M1-E794, M1-K793, M1-V792, M1-S791, M1-A790, M1-S789, M1-E788, M1-K787, M1-S786, M1-S785, M1-S784, M1-A783, M1-N782, M1-Q781, M1-D780, M1-S779, M1-Y778, M1-Y777, M1-W776, M1-M775, M1-F774, M1-Q773, M1-F772, M1-D771, M1-Q770, M1-S769, M1-Q768, M1-P767, M1-V766, M1-H765, M1-S764, M1-M763, M1-E762, M1-A761, M1-K760, M1-S759, M1-K758, M1-F757, M1-E756, M1-L755, M1-T754, M1-L753, M1-I752, M1-T751, M1-P750, M1-P749, M1-L748, M1-I747, M1-I746, M1-S745, M1-I744, M1-I743, M1-I742, M1-K741, M1-L740, M1-W739, M1-S738, M1-N737, M1-K736, M1-R735, M1-M734, M1-K733, M1-L732,
M1-R731, M1-G730, M1-M729, M1-W728, M1-M727,
M1-D726, M1-T725, M1-T724, M1-L723, M1-M722,
M1-Q721, M1-T720, M1-C719, M1-T718, M1-H717,
M1-S716, M1-V715, M1-F714, M1-P713, M1-R712,
M1-L711, M1-G710, M1-G709, M1-S708, M1-V707,
M1-A706, M1-L705, M1-K704, M1-L703, M1-C702,
M1-T701, M1-S700, M1-N699, M1-S698, M1-W697,
M1-N696, M1-R695, M1-L694, M1-E693, M1-Y692,
M1-T691, M1-L690, M1-L689, M1-T688, M1-M687,
M1-A686, M1-M685, M1-R684, M1-E683, M1-N682,
M1-Q681, M1-K680, M1-F679, M1-A678, M1-K677,
M1-E676, M1-L675, M1-L674, M1-D673, M1-L672,
M1-A671, M1-L670, M1-Q669, M1-G668, M1-F667,
M1-Q666, M1-K665, M1-S664, M1-Y663, M1-N662,
M1-K661, M1-L660, M1-E659, M1-E658, M1-S657,
M1-A656, M1-D655, M1-D654, M1-V653, M1-M652,
M1-H651, M1-S650, M1-E649, M1-K648, M1-A647,
M1-E646, M1-H645, M1-A644, M1-M643, M1-A642,
M1-R641, M1-Y640, M1-L639, M1-I638, M1-C637,
M1-A636, M1-I635, M1-V634, M1-A633, M1-K632,
M1-V631, M1-T630, M1-A629, M1-E628, M1-E627,
M1-G626, M1-M625, M1-Q624, M1-W623, M1-F622,
M1-F621, M1-M620, M1-A619, M1-M618, M1-K617,
M1-Q616, M1-R615, M1-K614, M1-M613, M1-L612,
M1-V611, M1-A610, M1-W609, M1-V608, M1-L607,
M1-L606, M1-D605, M1-N604, M1-Y603, M1-P602,
M1-Y601, M1-L600, M1-F599, M1-G598, M1-T597,
M1-S596, M1-E595, M1-P594, M1-D593, M1-D592,
M1-S591, M1-V590, M1-N589, M1-Q588, M1-E587,
M1-K586, M1-S585, M1-K584, M1-K583, M1-R582,
M1-S581, M1-K580, M1-H579, M1-L578, M1-V577,
M1-I576, M1-S575, M1-K574, M1-E573, M1-K572,
M1-F571, M1-K570, M1-Y569, M1-P568, M1-Q567,
M1-A566, M1-T565, M1-R564, M1-I563, M1-F562,
M1-Q561, M1-S560, M1-H559, M1-L558, M1-T557,
M1-S556, M1-E555, M1-A554, M1-S553, M1-E552,
M1-N551, M1-R550, M1-N549, M1-G548, M1-S547,
M1-S546, M1-H545, M1-R544, M1-Q543, M1-H542,
M1-K541, M1-Y540, M1-K539, M1-R538, M1-Y537,
M1-L536, M1-N535, M1-N534, M1-Y533, M1-L532,
M1-A531, M1-R530, M1-F529, M1-H528, M1-K527,
M1-R526, M1-T525, M1-Y524, M1-N523, M1-S522,
M1-R521, M1-Y520, M1-A519, M1-R518, M1-G517,
M1-I516, M1-L515, M1-Y514, M1-E513, M1-V512,
M1-V511, M1-L510, M1-G509, M1-I508, M1-D507,
M1-I506, M1-L505, M1-T504, M1-I503, M1-R502,
M1-Y501, M1-G500, M1-S499, M1-L498, M1-L497,
M1-T496, M1-H495, M1-Q494, M1-K493, M1-V492,
M1-D491, M1-Q490, M1-V489, M1-L488, M1-H487,
M1-H486, M1-L485, M1-L484, M1-T483, M1-N482,
M1-T481, M1-P480, M1-G479, M1-Q478, M1-K477,
M1-T476, M1-N475, M1-Y474, M1-L473, M1-E472,
M1-E471, M1-L470, M1-R469, M1-P468, M1-I467,
M1-T466, M1-L465, M1-F464, M1-R463, M1-H462,
M1-L461, M1-N460, M1-V459, M1-G458, M1-Y457,
M1-E456, M1-I455, M1-L454, M1-L453, M1-K452,
M1-V451, M1-F450, M1-D449, M1-V448, M1-R447,
M1-D446, M1-M445, M1-V444, M1-L443, M1-A442,
M1-D441, M1-S440, M1-M439, M1-A438, M1-Q437,
M1-E436, M1-L435, M1-A434, M1-D433, M1-P432,
M1-K431, M1-W430, M1-H429, M1-Q428, M1-E427,
M1-Y426, M1-I425, M1-L424, M1-I423, M1-H422,
M1-K421, M1-K420, M1-A419, M1-I418, M1-D417,
M1-V416, M1-R415, M1-D414, M1-W413, M1-A412,
M1-M411, M1-A410, M1-L409, M1-N408, M1-L407,
M1-Q406, M1-E405, M1-S404, M1-A403, M1-S402,
M1-L401, M1-N400, M1-T399, M1-G398, M1-K397,
M1-L396, M1-L395, M1-A394, M1-T393, M1-L392,
M1-I391, M1-A390, M1-L389, M1-D388, M1-L387,
M1-D386, M1-Q385, M1-Q384, M1-E383, M1-E382,
M1-S381, M1-D380, M1-A379, M1-D378, M1-F377,
M1-I376, M1-T375, M1-I374, M1-C373, M1-D372,
M1-R371, M1-H370, M1-V369, M1-M368, M1-C367,
M1-E366, M1-M365, M1-L364, M1-I363, M1-Q362,
M1-F361, M1-L360, M1-H359, M1-K358, M1-S357,
M1-Q356, M1-K355, M1-L354, M1-S353, M1-F352,
M1-N351, M1-F350, M1-T349, M1-N348, M1-Q347,
M1-I346, M1-M345, M1-C344, M1-I343, M1-I342,
M1-E341, M1-E340, M1-K339, M1-V338, M1-Q337,
M1-P336, M1-R335, M1-L334, M1-M333, M1-G332,
M1-E331, M1-D330, M1-A329, M1-L328, M1-H327,
M1-K326, M1-H325, M1-T324, M1-F323, M1-A322,
M1-L321, M1-L320, M1-D319, M1-A318, M1-A317,
M1-R316, M1-G315, M1-T314, M1-G313, M1-E312,
M1-C311, M1-V310, M1-V309, M1-V308, M1-P307,
M1-D306, M1-K305, M1-D304, M1-K303, M1-V302,
M1-T301, M1-E300, M1-W299, M1-V298, M1-S297,
M1-L296, M1-I295, M1-V294, M1-N293, M1-P292,
M1-G291, M1-G290, M1-E289, M1-V288, M1-V287,
M1-L286, M1-G285, M1-V284, M1-V283, M1-P282,
M1-V281, M1-G280, M1-Q279, M1-R278, M1-S277,
M1-R276, M1-C275, M1-H274, M1-I273, M1-K272,
M1-Q271, M1-L270, M1-S269, M1-L268, M1-Y267,
M1-K266, M1-E265, M1-L264, M1-N263, M1-R262,
M1-R261, M1-L260, M1-K259, M1-M258, M1-E257,
M1-N256, M1-G255, M1-Y254, M1-K253, M1-G252,
M1-V251, M1-T250, M1-G249, M1-D248, M1-D247,
M1-S246, M1-L245, M1-I244, M1-F243, M1-H242,
M1-S241, M1-H240, M1-M239, M1-S238, M1-N237,
M1-L236, M1-T235, M1-T234, M1-L233, M1-K232,
M1-S231, M1-L230, M1-P229, M1-N228, M1-D227,
M1-L226, M1-T225, M1-Q224, M1-Y223, M1-L222,
M1-C221, M1-V220, M1-V219, M1-D218, M1-K217,
M1-G216, M1-I215, M1-L214, M1-D213, M1-R212,
M1-Q211, M1-N210, M1-E209, M1-I208, M1-V207,
M1-G206, M1-W205, M1-P204, M1-P203, M1-I202,
M1-G201, M1-V200, M1-T199, M1-W198, M1-I197,
M1-K196, M1-R195, M1-L194, M1-S193, M1-H192,
M1-S191, M1-S190, M1-H189, M1-S188, M1-K187,
M1-L186, M1-A185, M1-D184, M1-G183, M1-V182,
M1-H181, M1-K180, M1-S179, M1-V178, M1-G177,
M1-T176, M1-N175, M1-I174, M1-G173, M1-E172,
M1-T171, M1-I170, M1-I169, M1-W168, M1-A167,
M1-G166, M1-T165, M1-T164, M1-E163, M1-A162,
M1-A161, M1-K160, M1-V159, M1-L158, M1-G157,
M1-Q156, M1-S155, M1-F154, M1-I153, M1-E152,
M1-K151, M1-F150, M1-K149, M1-S148, M1-P147,
M1-M146, M1-T145, M1-F144, M1-N143, M1-Q142,
M1-I141, M1-G140, M1-G139, M1-H138, M1-V137,
M1-S136, M1-I135, M1-V134, M1-L133, M1-K132,
M1-P131, M1-L130, M1-E129, M1-M128, M1-K127,
M1-W126, M1-E125, M1-K124, M1-L123, M1-M122,
M1-L121, M1-H120, M1-L119, M1-L118, M1-H117,
M1-D116, M1-L115, M1-K114, M1-T113, M1-D112,
M1-Y111, M1-S110, M1-T109, M1-R108, M1-I107,
M1-Y106, M1-K105, M1-A104, M1-H103, M1-H102,
M1-T101, M1-H100, M1-E99, M1-G98, M1-D97, M1-Q96,
M1-F95, M1-N94, M1-I93, M1-T92, M1-G91, M1-F90,
M1-T89, M1-D88, M1-T87, M1-P86, M1-S85, M1-K84,
M1-T83, M1-T82, M1-H81, M1-K80, M1-E79, M1-V78,
M1-S77, M1-W76, M1-Q75, M1-E74, M1-S73, M1-E72,
M1-K71, M1-G70, M1-K69, M1-A68, M1-A67, M1-S66,
M1-I65, M1-T64, M1-W63, M1-S62, M1-Y61, M1-D60, M1-I59, M1-G58, M1-A57, M1-H56, M1-D55, M1-G54, M1-I53, M1-L52, M1-R51, M1-G50, M1-C49, M1-Y48, M1-C47, M1-R46, M1-I45, M1-L44, M1-N43, M1-Q42, M1-C41, M1-V40, M1-Q39, M1-C38, M1-V37, M1-P36, M1-T35, M1-C34, M1-R33, M1-H32, M1-P31, M1-N30, M1-K29, M1-S28, M1-S27, M1-P26, M1-I25, M1-I24, M1-T23, M1-S22, M1-C21, M1-E20, M1-R19, M1-K18, M1-D17, M1-F16, M1-V15, M1-G14, M1-K13, M1-I12, M1-W11, M1-S10, M1-K9, M1-Q8, and/or M1-S7 of SEQ ID NO:2. Polynucleotide sequences encoding these polypeptides are also provided. The present invention also encompasses the use of these C-terminal TRP-PLIK2 deletion polypeptides as immunogenic and/or antigenic epitopes as described elsewhere herein.

Alternatively, preferred polypeptides of the present invention may comprise polypeptide sequences corresponding to, for example, internal regions of the TRP-PLIK2 polypeptide (e.g., any combination of both N- and C-terminal TRP-PLIK2 polypeptide deletions) of SEQ ID NO:2. For example, internal regions could be defined by the equation: amino acid NX to amino acid CX, wherein NX refers to any N-terminal deletion polypeptide amino acid of TRP-PLIK2 (SEQ ID NO:2), and where CX refers to any C-terminal deletion polypeptide amino acid of TRP-PLIK2 (SEQ ID NO:2). Polynucleotides encoding these polypeptides are also provided. The present invention also encompasses the use of these polypeptides as an immunogenic and/or antigenic epitope as described elsewhere herein.

The TRP-PLIK2 polypeptides of the present invention were determined to comprise several phosphorylation sites based upon the Motif algorithm (Genetics Computer Group, Inc.). The phosphorylation of such sites may regulate some biological activity of the TRP-PLIK2 polypeptide. For example, phosphorylation at specific sites may be involved in regulating the proteins ability to associate or bind to other molecules (e.g., proteins, ligands, substrates, DNA, etc.). In the present case, phosphorylation may modulate the ability of the TRP-PLIK2 polypeptide to associate with other potassium channel alpha subunits, beta subunits, or its ability to modulate potassium channel function.

The TRP-PLIK2 polypeptide was predicted to comprise twenty nine PKC phosphorylation sites using the Motif algorithm (Genetics Computer Group, Inc.). In vivo, protein kinase C exhibits a preference for the phosphorylation of serine or threonine residues. The PKC phosphorylation sites have the following consensus pattern: [ST]-x-[RK], where S or T represents the site of phosphorylation and 'x' an intervening amino acid residue. Additional information regarding PKC phosphorylation sites can be found in Woodget J. R., Gould K. L., Hunter T., Eur. J. Biochem. 161:177-184 (1986), and Kishimoto A., Nishiyama K., Nakanishi H., Uratsuji Y., Nomura H., Takeyama Y., Nishizuka Y., J. Biol. Chem. . . . 260:12492-12499 (1985); which are hereby incorporated by reference herein.

In preferred embodiments, the following PKC phosphorylation site polypeptides are encompassed by the present invention: IILSKSQKSWIKG (SEQ ID NO:51), STIIPSSKNPHRC (SEQ ID NO:52), SVEKHTTKSPTDT (SEQ ID NO:53), SHSSHSLRKIWTV (SEQ ID NO:54), LSVWETVKDKDPV (SEQ ID NO:55), VVCEGTGRAADLL (SEQ ID NO:56), DLLAFTHKHLADE (SEQ ID NO:57), NTFNFSLKQSKHL (SEQ ID NO:58), YRSNYTRKHFRAL (SEQ ID NO:59), IVLHKSRKKSKEQ (SEQ ID NO:60), HGEEATVKAVIAC (SEQ ID NO:61), DQNASSSKESASV (SEQ ID NO:62), SKESASVKEYDLE (SEQ ID NO:63), QHLPWTRKVYEFY (SEQ ID NO:64), EPGKFTQKVKVWI (SEQ ID NO:65), RKAIL-SPKEPPSW (SEQ ID NO:66), RIRVTSERVTEMY (SEQ ID NO:67), ALTVDTLKVLSAV (SEQ ID NO:68), KRKHSTCKKLPHS (SEQ ID NO:69), LEITNSKREATNV (SEQ ID NO:70), ETGVFSIKKKWQT (SEQ ID NO:71), TCDSDSSRSEQHQ (SEQ ID NO:72), SLSDNSTRSAQSS (SEQ ID NO:73), FARSHSFRFHKEE (SEQ ID NO:74), KDRRLSKKKKNTQ (SEQ ID NO:75), DKISASLKSPQEP (SEQ ID NO:76), SMSSWSQRGRAAM (SEQ ID NO:77), QTIPYTPRFLEVF (SEQ ID NO:78), and/or PPARETGRNSPED (SEQ ID NO:79). Polynucleotides encoding these polypeptides are also provided. The present invention also encompasses the use of these TRP-PLIK2 PKC phosphorylation site polypeptides as immunogenic and/or antigenic epitopes as described elsewhere herein.

The present invention also encompasses immunogenic and/or antigenic epitopes of the TRP-PLIK2 polypeptide.

The TRP-PLIK2 polypeptide has been shown to comprise seventeen glycosylation sites according to the Motif algorithm (Genetics Computer Group, Inc.). As discussed more specifically herein, protein glycosylation is thought to serve a variety of functions including: augmentation of protein folding, inhibition of protein aggregation, regulation of intracellular trafficking to organelles, increasing resistance to proteolysis, modulation of protein antigenicity, and mediation of intercellular adhesion.

Asparagine phosphorylation sites have the following consensus pattern, N-{P}-[ST]-{P}, wherein N represents the glycosylation site. However, it is well known that that potential N-glycosylation sites are specific to the consensus sequence Asn-Xaa-Ser/Thr. However, the presence of the consensus tripeptide is not sufficient to conclude that an asparagine residue is glycosylated, due to the fact that the folding of the protein plays an important role in the regulation of N-glycosylation. It has been shown that the presence of proline between Asn and Ser/Thr will inhibit N-glycosylation; this has been confirmed by a recent statistical analysis of glycosylation sites, which also shows that about 50% of the sites that have a proline C-terminal to Ser/Thr are not glycosylated. Additional information relating to asparagine glycosylation may be found in reference to the following publications, which are hereby incorporated by reference herein: Marshall R. D., Annu. Rev. Biochem. 41:673-702 (1972); Pless D. D., Lennarz W. J., Proc. Natl. Acad. Sci. U.S.A. 74:134-138 (1977); Bause E., Biochem. J. 209:331-336 (1983); Gavel Y., von Heijne G., Protein Eng. 3:433-442 (1990); and Miletich J. P., Broze G. J. Jr., J. Biol. Chem. . . . 265:11397-11404 (1990).

In preferred embodiments, the following asparagine glycosylation site polypeptides are encompassed by the present invention: HGGIQNFTMPSKFK (SEQ ID NO:80), IQNTFNFSLKQSKH (SEQ ID NO:81), LLKGTNLSASEQLN (SEQ ID NO:82), RAYRSNYTRKHFRA (SEQ ID NO:83), SSGNRNESAESTLH (SEQ ID NO:84), KSKEQNVSDDPEST (SEQ ID NO:85), SEELKNYSKQFGQL (SEQ ID NO:86), TYELRNWSNSTCLK (SEQ ID NO:87), LRNWSNSTCLKLAV (SEQ ID NO:88), YYSDQNASSSKESA (SEQ ID NO:89), ISEYWNLTETVAIG (SEQ ID NO:90), KMEDVNCSCEERIR (SEQ ID NO:91), SSLSDNSTRSAQSS (SEQ ID NO:92), PWLQPNTSFWINPL (SEQ ID NO:93), ICKIKNLSGSSEIG (SEQ ID NO:94), QGVGENLTDPSVIK (SEQ ID NO:95), and/or SPERINSTFGLEIK (SEQ ID NO:96). Polynucleotides encoding these polypeptides are also provided. The present invention also encompasses the use of these TRP-PLIK2 asparagine glycosylation site polypeptides as immunogenic and/or antigenic epitopes as described elsewhere herein.

Many polynucleotide sequences, such as EST sequences, are publicly available and accessible through sequence databases. Some of these sequences are related to SEQ ID NO: 1 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides consisting of a nucleotide sequence described by the general formula of a-b, where a is any integer between 1 to 6040 of SEQ ID NO:1, b is an integer between 15 to 6054, where both a and b correspond to the positions of nucleotide residues shown in SEQ ID NO:1, and where b is greater than or equal to a+14.

In one embodiment, a TRP-PLIK2 polypeptide comprises a portion of the amino sequence depicted in FIGS. 1A-G. In another embodiment, a TRP-PLIK2 polypeptide comprises at least 4, 5, 6, 7, 8, 9, 10, 11, 12, 13, 14, 15, 16, 17, 18, 19 or 20 amino acids of the amino sequence depicted in FIGS. 1A-G. In further embodiments, the following TRP-PLIK2 polypeptide fragments are specifically excluded from the present invention:

VKDKDPVVVCEGTGRAADLLAFTHKHLADEGMLR (SEQ ID NO:312)
PQVKEEIICMIQNTFNFSLKQSKHLFQILMECMV
HRDCITIFDADSEEQQDLDLAILTALLKGTNLSA
SEQLNLAMAWDRVDIAKKHILIYEQHWKPDALEQ
AMSDALVMDRVDFVKLLIEYGVNLHRFLTIPRLE
ELYNTKQGPTNTLLHHLVQDVKQHTLLSGYRIT
L;

| | |
|---|---|
| KSPTDTFGTINFQDGEH; | (SEQ ID NO:313) |
| DHLLHLMLKEWMELPKLVISVHGG; | (SEQ ID NO:314) |
| FSQGLVKAAETTGAWIITEGIN; | (SEQ ID NO:315) |
| SLRKIWTVGIPPWGVIENQR; | (SEQ ID NO:316) |
| TVLHLCLREIQQQRAAQKL, | (SEQ ID NO:317) |
| MTGEFRKYNNNNGDEI, | (SEQ ID NO:318) |
| MLAFSHWTYEYTRGELLVLDLQGVGENLTDPSVI K, | (SEQ ID NO:319) |
| AKHHCNSCCRKLKLPDLKRNDY, | (SEQ ID NO:320) |
| GKDVVCLYQTLDNPLSKLTTLNSMHSHFILSDDG | (SEQ ID NO:321) |

TVGKYGNEMKLRRNLEKYLSLQKIHCRSRQGVPV
VGLVVEGGPNVILSVWETVKDKDPVVVCEGTGRA
ADLLAFTHKHLADEGMLRPQVKEEIICMIQNTFN
FSLKQSKHLFQILMECMVHRDC,

| | |
|---|---|
| EYTRGELLVLDLQGVGENLTDPSVIK, | (SEQ ID NO:322) |
| YPYNDLLVWAVLMKRQ, | (SEQ ID NO:323) |
| MAMFFWQHGEEATVKAVIA, | (SEQ ID NO:324) |
| NWSNSTCLKLAVSGGLRPFVSH, | (SEQ ID NO:325) |
| QMLLTDMWMGRLKMRKNSWLKIIISI, | (SEQ ID NO:326) |
| LKPGQVFIVKSFLPEVV, | (SEQ ID NO:327) |
| KIFQESTVLHLCLREIQQQRAAQKLIYTFNQVKP QTIPYTPRFLEV, | (SEQ ID NO:328) |
| YCHSANQWLTIEKYMTGEFRKYNNNNGDEI, | (SEQ ID NO:329) |
| PTNTLEELMLAFSHWTYEYTRGELLVLDLQGVGE NLTDP, | (SEQ ID NO:330) |
| TVLHLCLREIQQQRAAQKL, | (SEQ ID NO:331) |
| MTGEFRKYNNNNGDEI, | (SEQ ID NO:332) |
| MLAFSHWTYEYTRGELLVLDLQGVGENLTDPSVI K, | (SEQ ID NO:333) |
| AKHHCNSCCRKLKLPDLKRNDY, | (SEQ ID NO:334) | and/or

| | |
|---|---|
| EYTRGELLVLDLQGVGENLT. | (SEQ ID NO:335) |

Features of the Polypeptide Encoded by Gene No:2

The polypeptide of this gene provided as SEQ ID NO:4 (FIGS. 2A-G), encoded by the polynucleotide sequence according to SEQ ID NO:3 (FIGS. 2A-G), and/or encoded by the polynucleotide contained within the deposited clone, TRP-PLIK2b, has significant homology at the nucleotide and amino acid level to the human channel-kinase 1 protein, also known as the human CHAK1 or TRP-PLIKB1 protein (CHAK1; GENBANK® Accession No. gi|AF346629; SEQ ID NO:9); and the human melastatin 1 protein (Melastatin1; GENBANK® Accession No. gi|3243075; SEQ ID NO:260). An alignment of the TRP-PLIK2b polypeptide with this protein is provided in FIGS. 5A-F.

The TRP-PLIK2b polypeptide was determined to share 58.1% identity and 66.1% similarity with the human CHAK1 or TRP-PLIKB1 protein (CHAK1; GENBANK® Accession No. gi|AF346629; SEQ ID NO:9); and was determined to share 47.2% identity and 57.9% similarity with the human melastatin 1 protein (Melastatin1; GENBANK® Accession No. gi|3243075; SEQ ID NO:260) as shown in FIG. 9.

The CHAK1 protein is believed to represent a member of a new class of protein kinases referred to as alpha kinases (Curr. Biol. 9 (2), R43-R45 (1999)). These kinases represent a novel type of signaling molecule comprising both a catalytic protein kinase domain, in addition to, an ion channel domain.

The melastatin1 protein is believed to be negatively associated with the incidence of melanoma based upon its inverse correlative expression in highly aggressive melanomas (Genomics 54 (1), 116-123 (1998)). Thus, overexpression of melastatin1 could represent a novel therapeutic in the treatment of melanoma and potentially other cancers.

Based upon the observed homology, the polypeptide of the present invention is expected to share at least some biological activity with other transient receptor potential channel family members, more specifically with the CHAK1 and melastatin1 proteins, in addition to, other transient receptor potential channel family members referenced elsewhere herein or otherwise known in the art.

The TRP-PLIK2b (SEQ ID NO:4) polypeptide represents a novel splice variant form of the TRP-PLIK2 (SEQ ID NO:2) polypeptide of the present invention.

Most of the known transient receptor potential channel family members, possess one or more transmembrane domains. Likewise, the TRP-PLIK2b polypeptide has been determined to comprise six transmembrane domains (TM1-TM6) as shown in FIGS. 2A-G. The transmembrane domains are located from about amino acid 693 to about amino acid 710 (TM1), from about amino acid 787 to about amino acid 804 (TM2), from about amino acid 861 to about amino acid 873 (TM3), from about amino acid 887 to about amino acid 904 (TM4), from about amino acid 921 to about amino acid 938 (TM5), and/or from about amino acid 996 to about amino acid 1015 (TM6) of SEQ ID NO:4. In this context, the term "about" may be construed to mean 1, 2, 3, 4, 5, 6, 7, 8, 9, or 10 amino acids beyond the N-Terminus and/or C-terminus of the above referenced polypeptide.

In preferred embodiments, the following transmembrane domain polypeptides are encompassed by the present invention: LKIIISIILPPTILTLEF (SEQ ID NO:109), IVKFW-FYTMAYLAFLMLF (SEQ ID NO:110), TETVAIGLF-SAGF (SEQ ID NO:111), RLIYCIDIIFWFSRLLDF (SEQ ID NO:112), MTANMFYIVIIMAIVLLS (SEQ ID NO:113), and/or FLQAVYLFVQYIIMVNLLIA (SEQ ID NO:114). Polynucleotides encoding these polypeptides are also provided. The present invention also encompasses the use of the TRP-PLIK2b transmembrane polypeptides as immunogenic and/or antigenic epitopes as described elsewhere herein.

In preferred embodiments, the present invention encompasses the use of N-terminal deletions, C-terminal deletions, or any combination of N-terminal and C-terminal deletions of any one or more of the TRP-PLIK2b TM1 thru TM6 transmembrane domain polypeptides as antigenic and/or immunogenic epitopes.

In preferred embodiments, the present invention also encompasses the use of N-terminal deletions, C-terminal deletions, or any combination of N-terminal and C-terminal deletions of any one or more of the amino acids intervening (i.e., ion channel extracellular or intracellular loops) the TRP-PLIK2b TM1 thru TM6 transmembrane domain polypeptides as antigenic and/or immunogenic epitopes.

The TRP-PLIK2b polypeptide was determined to comprise several conserved cysteines, at amino acid 21, 34, 38, 41, 47, 49, 311, 367, 590, 655, 672, 891, 981, 987, 1067, 1101, 1775, 1814, 1915, 1919, and 1920 of SEQ ID No:4 (FIGS. 2A-G). Conservation of cysteines at key amino acid residues is indicative of conserved structural features, which may correlate with conservation of protein function and/or activity.

In confirmation of the TRP-PLIK2b representing a member of the transient receptor channel family, the TRP-PLIK2b polypeptide was determined to comprise a predicted TRP domain (LWKYNR) located from about amino acid 1031 to about amino acid 1036 of SEQ ID NO:4. In this context, the term "about" may be construed to mean 1, 2, 3, 4, 5, 6, 7, 8, 9, or 10 amino acids beyond the N-Terminus and/or C-terminus of the above referenced polypeptide.

In further confirmation of the TRP-PLIK2b representing a member of the transient receptor channel family, the TRP-PLIK2b polypeptide was determined to comprise a predicted ion transport signature domain located at about amino acid 857 to about amino acid 1017 of SEQ ID NO:4. In this context, the term "about" may be construed to mean 1, 2, 3, 4, 5, 6, 7, 8, 9, or 10 amino acids beyond the N-Terminus and/or C-terminus of the above referenced polypeptide.

The TRP-PLIK2b polypeptide was determined to comprise a predicted nucleotide binding domain located from about amino acid 1898 to about amino acid 1903 of SEQ ID NO:4. In this context, the term "about" may be construed to mean 1, 2, 3, 4, 5, 6, 7, 8, 9, or 10 amino acids beyond the N-Terminus and/or C-terminus of the above referenced polypeptide.

In addition, the TRP-PLIK2b polypeptide was determined to comprise a predicted zinc finger domain located at about amino acid 1913 to about amino acid 1923 of SEQ ID NO:4. In this context, the term "about" may be construed to mean 1, 2, 3, 4, 5, 6, 7, 8, 9, or 10 amino acids beyond the N-Terminus and/or C-terminus of the above referenced polypeptide.

TRP-PLIK2b polypeptides and polynucleotides are useful for diagnosing diseases related to the over and/or under expression of TRP-PLIK2b by identifying mutations in the TRP-PLIK2b gene using TRP-PLIK2b sequences as probes or by determining TRP-PLIK2b protein or mRNA expression levels. TRP-PLIK2b polypeptides will be useful in screens for compounds that affect the activity of the protein. TRP-PLIK2b peptides can also be used for the generation of specific antibodies and as bait in yeast two hybrid screens to find proteins the specifically interact with TRP-PLIK2b.

Expression profiling designed to measure the steady state mRNA levels encoding the TRP-PLIK2 polypeptide showed predominately high expression levels in bone marrow, kidney, and testis. The TRP-PLIK2 polypeptide was also significantly expressioned in liver, and to a lesser extent, in small intestine, spinal cord, prostate, uterus, lung, lymph node, stomach, heart, brain, thymus, and pancrease (as shown in FIG. 7). The tissue expression of TRP-PLIK2b may follow the same pattern as for the TRP-PLIK2 polypeptide of the present invention.

Expanded analysis of TRP-PLIK2 expression levels by TAQMAN® quantitative PCR (see FIG. 12) confirmed that the TRP-PLIK2 polypeptide is expressed in kidney, colon, and testis (FIG. 7). TRP-PLIK2 mRNA was expressed predominately in the lower gastrointestinal tract, specifically the ileum, the rectum, the colon, the jejunum, and to a lesser extent in the duodenum and stomach. Significant expression was observed in the kidney, particularly in the cortex, followed by the medulla, and to a lesser extent in the testis, pelvis, and bone marrow (mononuclear cells).

Furthermore, an expanded analysis of TRP-PLIK2 expression levels in various tumor and normal tissues by TAQMAN® quantitative PCR (see FIG. 14) showed TRP-PLIK2 mRNA was differentially expressed to the greatest extent in prostate tumor tissue relative to normal prostate tissue (approximately 20 fold difference). Significant differential expression was also observed in the testicular tumor tissue relative to normal testicular tissue.

Characterization of the TRP-PLIK2 polypeptide of the present invention using antisense oligonucleotides directed against a portion of the TRP-PLIK2 encoding sequence led to the determination that it is involved in the modulation of the NFkB pathway, either directly or indirectly.

The upregulation of IkBa due to the downregulation of TRP-PLIK2 places this transient receptor potential protein into a signalling pathway potentially involved in apoptotic events. This gives the opportunity to regulate downstream events via the activity of the protein TRP-PLIK2 with antisense polynucleotides, polypeptides or low molecular chemicals with the potential of achieving a therapeutic effect in cancer, autoimmune diseases. In addition to cancer and immunological disorders, NF-kB has significant roles in other diseases (Baldwin, A. S., J. Clin Invest. 107: 3-6 (2001)). NF-kB is a key factor in the pathophysiology of ischemia-reperfusion injury and heart failure (Valen, G., Yan. Z Q, Hansson, G K, J. Am. Coll. Cardiol. 38, 307-14 (2001)). Furthermore, NF-kB has been found to be activated in experimental renal disease (Guijarro C, Egido J., Kidney Int. 59, 415-425 (2001)). As TRP-PLIK2 is highly expressed in kidney there is the potential of an involvement in renal diseases.

In preferred embodiments, TRP-PLIK2b polynucleotides and polypeptides, including fragments thereof, are useful for treating, diagnosing, and/or ameliorating proliferative disorders, cancers, ischemia-reperfusion injury, heart failure, immuno compromised conditions, HIV infection, and renal diseases.

Moreover, TRP-PLIK2b polynucleotides and polypeptides, including fragments thereof, are useful for increasing NF-kB activity, increasing apoptotic events, and/or decreasing IkBa expression or activity levels.

In preferred embodiments, antagonists directed against TRP-PLIK2b are useful for treating, diagnosing, and/or ameliorating autoimmune disorders, disorders related to hyper immune activity, inflammatory conditions, disorders related to aberrant acute phase responses, hypercongenital conditions, birth defects, necrotic lesions, wounds, organ transplant rejection, conditions related to organ transplant rejection, disorders related to aberrant signal transduction, proliferating disorders, cancers, HIV, and HIV propagation in cells infected with other viruses.

Moreover, antagonists directed against TRP-PLIK2b are useful for decreasing NF-kB activity, decreasing apoptotic events, and/or increasing IkBa expression or activity levels.

In preferred embodiments, agonists directed against TRP-PLIK2b are useful for treating, diagnosing, and/or ameliorating autoimmune disorders, disorders related to hyper immune activity, hypercongenital conditions, birth defects, necrotic lesions, wounds, disorders related to aberrant signal transduction, immuno compromised conditions, HIV infection, proliferating disorders, and/or cancers.

Moreover, agonists directed against TRP-PLIK2b are useful for increasing NF-kB activity, increasing apoptotic events, and/or decreasing IkBa expression or activity levels.

The strong homology to transient receptor potential channels (TRP), combined with the predominate localized expression of the TRP-PLIK2 polypeptide in the lower gastrointestinal tract, specifically the ileum, the rectum, the colon, the jejunum, and to a lesser extent in the duodenum and stomach, suggests the TRP-PLIK2b polynucleotides and polypeptides may be useful in treating, diagnosing, prognosing, and/or preventing gastrointestinal diseases and/or disorders, which include, but are not limited to, ulcers, irritable bowel syndrome, inflammatory bowel disease, diarrhea, traveler's diarrhea, drug-related diarrhea polyps, absorption disorders, constipation, diverticulitis, vascular disease of the intestines, intestinal obstruction, intestinal infections, ulcerative colitis, Shigellosis, cholera, Crohn's Disease, amebiasis, enteric fever, Whipple's Disease, peritonitis, intraabdominal abscesses, hereditary hemochromatosis, gastroenteritis, viral gastroenteritis, food poisoning, mesenteric ischemia, mesenteric infarction, in addition to, metabolic diseases and/or disorders.

Moreover, polynucleotides and polypeptides, including fragments and/or antagonists thereof, have uses which include, directly or indirectly, treating, preventing, diagnosing, and/or prognosing susceptibility to the following, non-limiting, gastrointestinal infections: *Salmonella* infection, *E. coli* infection, *E. coli* O157:H7 infection, Shiga Toxin-producing *E. coli* infection, *Campylobacter* infection (e.g., *Campylobacter fetus, Campylobacter upsaliensis, Campylobacter hyointestinalis, Campylobacter lari, Campylobacter jejuni, Campylobacter concisus, Campylobacter mucosalis, Campylobacter sputorum, Campylobacter rectus, Campylobacter curvus, Campylobacter sputorum*, etc.), *Heliobacter* infection (e.g., *Heliobacter cinaedi, Heliobacter fennelliae*, etc.) *Yersinia enterocolitica* infection, *Vibrio* sp. Infection (e.g., *Vibrio mimicus, Vibrio parahaemolyticus, Vibrio fluvialis, Vibrio furnissii, Vibrio hollisae, Vibrio vulnificus, Vibrio alginolyticus, Vibrio metschnikovii, Vibrio damsela, Vibrio cincinnatiensis,* etc.) *Aeromonas* infection (e.g., *Aeromonas hydrophila, Aeromonas sobira, Aeromonas caviae,* etc.), *Plesiomonas shigelliodes* infection, *Giardia* infection (e.g., *Giardia lamblia,* etc.), *Cryptosporidium* infection, *Listeria* infection, *Entamoeba histolytica* infection, Rotavirus infection, Norwalk virus infection, *Clostridium difficile* infection, *Clostriudium perfringens* infection, *Staphylococcus* infection, *Bacillus* infection, in addition to any other gastrointestinal disease and/or disorder implicated by the causative agents listed above or elsewhere herein.

The strong homology to human transient receptor potential channels (TRP), combined with the localized expression of the TRP-PLIK2 polypeptide in kidney tissue suggests the TRP-PLIK2b polynucleotides and polypeptides may be useful in treating, diagnosing, prognosing, and/or preventing renal diseases and/or disorders, which include, but are not limited to: nephritis, renal failure, nephrotic syndrome, urinary tract infection, hematuria, proteinuria, oliguria, polyuria, nocturia, edema, hypertension, electrolyte disorders, sterile pyuria, renal osteodystrophy, large kidneys, renal transport defects, nephrolithiasis, azotemia, anuria, urinary retention, slowing of urinary stream, large prostate, flank tenderness, full bladder sensation after voiding, enuresis, dysuria, bacteriuria, kidney stones, glomerulonephritis, vasculitis, hemolytic uremic syndromes, thrombotic thrombocytopenic purpura, malignant hypertension, casts, tubulointerstitial kidney diseases, renal tubular acidosis, pyelonephritis, hydronephritis, nephrotic syndrome, crush syndrome, and/or renal colic, in addition to Wilm's Tumor Disease, and congenital kidney abnormalities such as horse-shoe kidney, polycystic kidney, and Falconi's syndrome for example.

Several known TRP family members have been identified that are expressed significantly in kidney tissue. These TRP family members include, for example, Trp12 (Wissenbach, U., Bodding, M., Freichel, M., Flockerzi, V, Lett., 485(2-3): 127-34, (2000)); OTRPC4 (Strotmann, R., Harteneck, C., Nunnenmacher, K., Schultz, G., Plant, T, D, Nat, Cell, Biol., 2(10):695-702, (2000)); polycystin-L2 (Guo, L., Schreiber, T, H., Weremowicz, S., Morton, C, C., Lee, C., Zhou, J. Genomics., 64(3):241-51, (2000)); and EcaC (Hoenderop, J. G., van, der, Kemp, A, W., Hartog, A., van, de, Graaf, S, F., van, Os, C, H., Willems, P, H., Bindels, R, J. J. Biol, Chem., 274(13):8375-8, (1999)).

Thus, the TRP-PLIK2b polynucleotides and polypeptides are expected to share at least some biological activity with TRP family members expressed in kidney cells and tissues, particularly those specifically referenced herein.

The strong homology to human transient receptor potential channels (TRP), combined with the localized expression of the TRP-PLIK2 polypeptide in bone marrow tissue suggests the TRP-PLIK2b polynucleotides and polypeptides may be useful in treating, diagnosing, prognosing, and/or preventing immune diseases and/or disorders. Representative uses are described in the "Immune Activity", "Chemotaxis", and "Infectious Disease" sections below, and elsewhere herein. Briefly, the strong expression in immune tissue indicates a role in regulating the proliferation; survival; differentiation; and/or activation of hematopoietic cell lineages, including blood stem cells.

The TRP-PLIK2b polypeptide may also be useful as a preventative agent for to immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's disease, and scleroderma. The TRP-PLIK2 polypeptide may be useful for modulating cytokine production, antigen presentation, or other processes, such as for boosting immune responses, etc.

Moreover, the protein may represent a factor that influences the differentiation or behavior of other blood cells, or that recruits hematopoietic cells to sites of injury. Thus, this gene product is thought to be useful in the expansion of stem cells and committed progenitors of various blood lineages, and in the differentiation and/or proliferation of various cell types. Furthermore, the protein may also be used to determine biological activity, raise antibodies, as tissuemarkers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Significantly, TRP-PLIK2b is believed to represent the first TRP family member expressed in bone marrow tissue.

The strong homology to human transient receptor potential channels (TRP), combined with the localized expression of TRP-PLIK in testis tissue emphasizes the potential utility for TRP-PLIK2b polynucleotides and polypeptides in treating, diagnosing, prognosing, and/or preventing testicular, in addition to reproductive disorders.

In preferred embodiments, TRP-PLIK2b polynucleotides and polypeptides including agonists, antagonists, and/or fragments thereof, have uses which include treating, diagnosing, prognosing, and/or preventing the following, non-limiting, diseases or disorders of the testis: spermatogenesis, infertility, Klinefelter's syndrome, XX male, epididymitis, genital warts, germinal cell aplasia, cryptorchidism, varicocele, immotile cilia syndrome, and viral orchitis. The TRP-PLIK2b polynucleotides and polypeptides including agonists, antagonists, and/or fragments thereof, may also have uses related to modulating testicular development, embryogenesis, reproduction, and in ameliorating, treating, and/or preventing testicular proliferative disorders (e.g., cancers, which include, for example, choriocarcinoma, Nonseminoma, seminona, and testicular germ cell tumors).

Likewise, the localized expression in testis tissue also emphasizes the potential utility for TRP-PLIK2b polynucleotides and polypeptides in treating, diagnosing, prognosing, and/or preventing metabolic diseases and disorders which include the following, not limiting examples: premature puberty, incomplete puberty, Kallman syndrome, Cushing's syndrome, hyperprolactinemia, hemochromatosis, congenital adrenal hyperplasia, FSH deficiency, and granulomatous disease, for example.

This gene product may also be useful in assays designed to identify binding agents, as such agents (antagonists) are useful as male contraceptive agents. The testes are also a site of active gene expression of transcripts that is expressed, particularly at low levels, in other tissues of the body. Therefore, this gene product may be expressed in other specific tissues or organs where it may play related functional roles in other processes, such as hematopoiesis, inflammation, bone formation, and kidney function, to name a few possible target indications.

Several known TRP family members have been identified that are expressed significantly in testis tissue. These TRP family members include, for example, polycystin-L2 (Guo, L., Schreiber, T, H., Weremowicz, S., Morton, C, C., Lee, C., Zhou, J. Genomics., 64(3):241-51, (2000)); TRP7 (Okada, T., Inoue, R., Yamazaki, K., Maeda, A., Kurosaki, T., Yamakuni, T., Tanaka, I., Shimizu, S., Ikenaka, K., Imoto, K., Mori, Y, J. Biol, Chem., 274(39):27359-70, (1999)); btrp2 (Wissenbach, U., Schroth, G., Philipp, S., Flockerzi, V, Lett., 429(1):61-6, (1998)); Htrp-1 (Zhu, X., Chu, P, B., Peyton, M., Birnbaumer, L, Lett., 373(3):193-8, (1995)); and TRPC1 (Wes, P, D., Chevesich, J., Jeromin, A., Rosenberg, C., Stetten, G., Montell, C, Proc, Natl, Acad, Sci, U.S.A., 92(21):9652-6, (1995)).

Thus, the TRP-PLIK2b polynucleotides and polypeptides are expected to share at least some biological activity with TRP family members expressed in testis cells and tissues, particularly those specifically referenced herein.

The predominate differential expression of TRP-PLIK2 in prostate tumor relative to normal prostate tissue strongly suggests TRP-PLIK2b polynucleotides and polypeptides including agonists, antagonists, and/or fragments thereof, have uses which include treating, diagnosing, prognosing, and/or preventing prostate cancers and/or proliferative conditions.

Alternatively, the tissue distribution of TRP-PLIK2 in liver indicates the protein product of the TRP-PLIK2b clone would be useful for the detection and treatment of liver disorders and cancers. Representative uses are described in the "Hyperproliferative Disorders", "Infectious Disease", and "Binding Activity" sections below, and elsewhere herein. Briefly, the protein can be used for the detection, treatment, and/or prevention of hepatoblastoma, jaundice, hepatitis, liver metabolic diseases and conditions that are attributable to the differentiation of hepatocyte progenitor cells, cirrhosis, hepatic cysts, pyrogenic abscess, amebic abscess, hydatid cyst, cystadenocarcinoma, adenoma, focal nodular hyperplasia, hemangioma, hepatocellular carcinoma, cholangiocarcinoma, angiosarcoma, and granulomatous liver disease.

Moreover, polynucleotides and polypeptides, including fragments and/or antagonists thereof, have uses which include, directly or indirectly, treating, preventing, diagnosing, and/or prognosing the following, non-limiting, hepatic infections: liver disease caused by sepsis infection, liver disease caused by bacteremia, liver disease caused by Pneomococcal pneumonia infection, liver disease caused by Toxic shock syndrome, liver disease caused by Listeriosis, liver disease caused by Legionnaires' disease, liver disease caused by Brucellosis infection, liver disease caused by *Neisseria gonorrhoeae* infection, liver disease caused by *Yersinia* infection, liver disease caused by Salmonellosis, liver disease caused by Nocardiosis, liver disease caused by Spirochete infection, liver disease caused by *Treponema pallidum* infection, liver disease caused by *Brrelia burgdorferi* infection, liver disease caused by Leptospirosis, liver disease caused by *Coxiella burnetii* infection, liver disease caused by *Rickettsia richettsii* infection, liver disease caused by *Chlamydia trachomatis* infection, liver disease caused by *Chlamydia psittaci* infection, in addition to any other hepatic disease and/or disorder implicated by the causative agents listed above or elsewhere herein.

As described elsewhere herein, transient receptor potential channel family members have been implicated in modulating cell proliferation, differentiation, migration, activation, exocytosis, muscle contraction, gene expression, apoptosis. signalling, pheromone sensory signaling, smooth muscle tone, pain perception, heat perception, osmosenstivity, and mechanosensitivity. Moreover, transient receptor potential channel family members have been implicated in disorders of the skin, skeletal-muscle, nervous, cardiac, and vascular systems, in addition to the following, non-limiting diseases and disorders, which include, for example, arteriosclerosis, neointimal hyperplasia, metastatic melanomas, bipolar disorder, nonsyndromic hereditary deafness, Knobloch syndrome, holosencephaly, and various malignancies including prostate cancer.

In preferred embodiments, TRP-PLIK2b polynucleotides and polypeptides of the present invention, including agonists and/or fragments thereof, have uses that include, modulating cell proliferation, differentiation, migration, activation, exocytosis, muscle contraction, gene expression, apoptosis. signalling, pheromone sensory signaling, smooth muscle tone, pain perception, heat perception, osmosenstivity, and mechanosensitivity.

In more preferred embodiments, TRP-PLIK2b polynucleotides and polypeptides of the present invention, including agonists and/or fragments thereof, have uses that include, treating, ameliorating, preventing, detecting, and/or prognosing various diseases and disorders, particularly the following, non-limiting examples, disorders of the skin, skeletal-muscle, nervous, cardiac, and vascular systems, in addition to the following, non-limiting diseases and disorders, which include, for example, arteriosclerosis, neointimal hyperplasia, metastatic melanomas, bipolar disorder, nonsyndromic hereditary deafness, Knobloch syndrome, holosencephaly, and various malignancies including prostate cancer.

TRP-PLIK2b polynucleotides and polypeptides of the present invention, including agonists and/or fragments may be involved in intracellular $Ca^{2+}$ homeostasis which affects various aspects of biological functions including mechano-regulation, pain transduction, vasorelaxation, gene expression, cell cycle and proliferation/apoptosis. Since TRP-PLIK2 is dominantly expressed in bone marrow, the TRP-PLIK2b splice variant may play an important role in regulating cytosolic $Ca^{2+}$ in immune system.

The TRP-PLIK2 gene maps to chromosome 9q21.2-22.1. This region is linked to amyotrophic lateral sclerosis with frontotemporal dementia, early-onset pulverulent cataract, infantile nephronophthisis, hypomagnesemia with secondary hypocalcemia and familial hemophagocytic lymphohistiocytosis. Therefore, agonists and/or antagonists of the novel TRP-PLIK2b splice variant can be used to treat diseases including various forms of neuronal degeneration, neurogenic inflammation, allergy, immunodeficiency/excessive immune activation, visual defects, hearing disorder, pain, cancer, hypertension and other cardiovascular diseases. In addition, the therapeutics may be useful in the treatment of diseases associated with disturbances in $Ca^{2+}$ homeostasis including osteoporosis, hypercalciuric stone disease, and chronic renal failure.

In addition, TRP-PLIK2b polynucleotides and polypeptides of the present invention, including agonists and/or fragments thereof, have uses that include modulating intracellular Ca++ ion concentrations, Ca++ ion flux, stored intracellular Ca++ ion concentrations, Ca++ ion pump activity, Ca++ ion flow into cell, Ca++ ion flow out of cells, the activation of Ca++ sensitive proteins, the activation of Ca++ sensitive signaling pathways, the activation of kinase-activatible proteins, and the activation of kinase-dependent signaling pathways.

The TRP-PLIK2b polynucleotides and polypeptides of the present invention, including agonists and/or fragments thereof, have uses that include modulating proliferation, differentiation, migration, and activation in various cells, tissues, and organisms, and particularly in mammalian bone marrow, kidney, testis, liver, small intestine, spinal cord, prostate, uterus, lung, lymph node, stomach, heart, brain, thymus, and pancreas, preferably human. TRP-PLIK2b polynucleotides and polypeptides of the present invention, including agonists and/or fragments thereof, may be useful in diagnosing, treating, prognosing, and/or preventing immune, hematopoietic, renal, reproductive, hepatic, and/or proliferative diseases or disorders, particularly of the immune system.

In addition, antagonists of the TRP-PLIK2b polynucleotides and polypeptides may have uses that include diagnosing, treating, prognosing, and/or preventing diseases or disorders related to transient receptor potential channel activity, which may include immune, hematopoietic, renal, reproductive, hepatic, and/or proliferative diseases or disorders.

Although it is believed the encoded polypeptide may share at least some biological activities with transient receptor potential channel family members, particularly those from CHAK1, a number of methods of determining the exact biological function of this clone are either known in the art or are described elsewhere herein. Briefly, the function of this clone may be determined by applying microarray methodology. Nucleic acids corresponding to the TRP-PLIK2b polynucleotides, in addition to, other clones of the present invention, may be arrayed on microchips for expression profiling. Depending on which polynucleotide probe is used to hybridize to the slides, a change in expression of a specific gene may provide additional insight into the function of this gene based upon the conditions being studied. For example, an observed increase or decrease in expression levels when the polynucleotide probe used comes from tissue that has been treated with known immunoglobulin inhibitors, which include, but are not limited to the drugs listed herein or otherwise known in the art, might indicate a function in modulating immunoglobulin function, for example. In the case of TRP-PLIK2b, bone marrow, kidney, testis, liver, small intestine, spinal cord, prostate, uterus, lung, lymph node, stomach, heart, brain, thymus, and/or pancrease, should be used to extract RNA to prepare the probe.

In addition, the function of the protein may be assessed by applying quantitative PCR methodology, for example. Real time quantitative PCR would provide the capability of following the expression of the TRP-PLIK2b gene throughout development, for example. Quantitative PCR methodology requires only a nominal amount of tissue from each developmentally important step is needed to perform such experiments. Therefore, the application of quantitative PCR methodology to refining the biological function of this polypeptide is encompassed by the present invention. Also encompassed by the present invention are quantitative PCR probes corresponding to the polynucleotide sequence provided as SEQ ID NO:3 (FIGS. 2A-G).

The function of the protein may also be assessed through complementation assays in yeast. For example, in the case of the TRP-PLIK2b, transforming yeast deficient in transient receptor potential channel activity with TRP-PLIK2b and assessing their ability to grow would provide convincing evidence the TRP-PLIK2b polypeptide has transient receptor potential channel activity. Additional assay conditions and methods that may be used in assessing the function of the polynucleotides and polypeptides of the present invention are known in the art, some of which are disclosed elsewhere herein.

Alternatively, the biological function of the encoded polypeptide may be determined by disrupting a homologue of this polypeptide in Mice and/or rats and observing the resulting phenotype.

Moreover, the biological function of this polypeptide may be determined by the application of antisense and/or sense methodology and the resulting generation of transgenic mice and/or rats. Expressing a particular gene in either sense or antisense orientation in a transgenic mouse or rat could lead to respectively higher or lower expression levels of that particular gene. Altering the endogenous expression levels of a gene can lead to the observation of a particular phenotype that can then be used to derive indications on the function of the gene. The gene can be either over-expressed or under expressed in every cell of the organism at all times using a strong ubiquitous promoter, or it could be expressed in one or more discrete parts of the organism using a well characterized tissue-specific promoter (e.g., a bone marrow, kidney, testis, liver, small intestine, spinal cord, prostate, uterus, lung, lymph node, stomach, heart, brain, thymus, and/or pancrease-specific promoter), or it can be expressed at a specified time of development using an inducible and/or a developmentally regulated promoter.

In the case of TRP-PLIK2b transgenic mice or rats, if no phenotype is apparent in normal growth conditions, observing the organism under diseased conditions (immune, hematopoietic, renal, reproductive, hepatic, or proliferative disorders, etc.) may lead to understanding the function of the gene. Therefore, the application of antisense and/or sense methodology to the creation of transgenic mice or rats to refine the biological function of the polypeptide is encompassed by the present invention.

In preferred embodiments, the following N-terminal TRP-PLIK2b deletion polypeptides are encompassed by the present invention: M1-L1970, I2-L1970, I3-L1970, L4-L1970, S5-L1970, K6-L1970, S7-L1970, Q8-L1970, K9-L1970, S10-L1970, W11-L1970, I12-L1970, K13-L1970, G14-L1970, V15-L1970, F16-L1970, D17-L1970, K18-L1970, R19-L1970, E20-L1970, C21-L1970, S22-L1970, T23-L1970, I24-L1970, I25-L1970, P26-L1970, S27-L1970, S28-L1970, K29-L1970, N30-L1970, P31-L1970, H32-L1970, R33-L1970, C34-L1970, T35-L1970, P36-L1970, V37-L1970, C38-L1970, Q39-L1970, V40-L1970, C41-L1970, Q42-L1970, N43-L1970, L44-L1970, I45-L1970, R46-L1970, C47-L1970, Y48-L1970, C49-L1970, G50-L1970, R51-L1970, L52-L1970, I53-L1970, G54-L1970, D55-L1970, H56-L1970, A57-L1970, G58-L1970, I59-L1970, D60-L1970, Y61-L1970, S62-L1970, W63-L1970, T64-L1970, I65-L1970, S66-L1970, A67-L1970, A68-L1970, K69-L1970, G70-L1970, K71-L1970, E72-L1970, S73-L1970, E74-L1970, Q75-L1970, W76-L1970, S77-L1970, V78-L1970, E79-L1970, K80-L1970, H81-L1970, T82-L1970, T83-L1970, K84-L1970, S85-L1970, P86-L1970, T87-L1970, D88-L1970, T89-L1970, F90-L1970, G91-L1970, T92-L1970, I93-L1970, N94-L1970, F95-L1970, Q96-L1970, D97-L1970, G98-L1970, E99-L1970, H100-L1970, T101-L1970, H102-L1970, H103-L1970, A104-L1970, K105-L1970, Y106-L1970, I107-L1970, R108-L1970, T109-L1970, S110-L1970, Y111-L1970, D112-L1970, T113-L1970, K114-L1970, L115-L1970, D116-L1970, H117-L1970, L118-L1970, L119-L1970, H120-L1970, L121-L1970, M122-L1970, L123-L1970, K124-L1970, E125-L1970, W126-L1970, K127-L1970, M128-L1970, E129-L1970, L130-L1970, P131-L1970, K132-L1970, L133-L1970, V134-L1970, I135-L1970, S136-L1970, V137-L1970, H138-L1970, G139-L1970, G140-L1970, I141-L1970, Q142-L1970, N143-L1970, F144-L1970, T145-L1970, M146-L1970, P147-L1970, S148-L1970, K149-L1970, F150-L1970, K151-L1970, E152-L1970, I153-L1970, F154-L1970, S155-L1970, Q156-L1970, G157-L1970, L158-L1970, V159-L1970, K160-L1970, A161-L1970, A162-L1970, E163-L1970, T164-L1970, T165-L1970, G166-L1970, A167-L1970, W168-L1970, I169-L1970, I170-L1970, T171-L1970, E172-L1970, G173-L1970, I174-L1970, N175-L1970, T176-L1970, G177-L1970, V178-L1970, S179-L1970, K180-L1970, H181-L1970, V182-L1970, G183-L1970, D184-L1970, A185-L1970, L186-L1970, K187-L1970, S188-L1970, H189-L1970, S190-L1970, S191-L1970, H192-L1970, S193-L1970, L194-L1970, R195-L1970, K196-L1970, I197-L1970, W198-L1970, T199-L1970, V200-L1970, G201-L1970, I202-L1970, P203-L1970, P204-L1970, W205-L1970, G206-L1970, V207-L1970, I208-L1970, E209-L1970, N210-L1970, Q211-L1970, R212-L1970, D213-L1970, L214-L1970, I215-L1970, G216-L1970, K217-L1970, D218-L1970, V219-L1970, V220-L1970, C221-L1970, L222-L1970, Y223-L1970, Q224-L1970, T225-L1970, L226-L1970, D227-L1970, N228-L1970, P229-L1970, L230-L1970, S231-L1970, K232-L1970, L233-L1970, T234-L1970, T235-L1970, L236-L1970, N237-L1970, S238-L1970, M239-L1970, H240-L1970, S241-L1970, H242-L1970, F243-L1970, I244-L1970, L245-L1970, S246-L1970, D247-L1970, D248-L1970, G249-L1970, T250-L1970, V251-L1970, G252-L1970, K253-L1970, Y254-L1970, G255-L1970, N256-L1970, E257-L1970, M258-L1970, K259-L1970, L260-L1970, R261-L1970, R262-L1970, N263-L1970, L264-L1970, E265-L1970, K266-L1970, Y267-L1970, L268-L1970, S269-L1970, L270-L1970, Q271-L1970, K272-L1970, I273-L1970, H274-L1970, C275-L1970, R276-L1970, S277-L1970, R278-L1970, Q279-L1970, G280-L1970, V281-L1970, P282-L1970, V283-L1970, V284-L1970, G285-L1970, L286-L1970, V287-L1970, V288-L1970, E289-L1970, G290-L1970, G291-L1970, P292-L1970, N293-L1970, V294-L1970, I295-L1970, L296-L1970, S297-L1970, V298-L1970, W299-L1970, E300-L1970, T301-L1970, V302-L1970, K303-L1970, D304-L1970, K305-L1970, D306-L1970, P307-L1970, V308-L1970, V309-L1970, V310-L1970, C311-L1970, E312-L1970, G313-L1970, T314-L1970, G315-L1970, R316-L1970, A317-L1970, A318-L1970, D319-L1970, L320-L1970, L321-L1970, A322-L1970, F323-L1970, T324-L1970, H325-L1970, K326-L1970, H327-L1970, L328-L1970, A329-L1970, D330-L1970, E331-L1970, G332-L1970, M333-L1970, L334-L1970, R335-L1970, P336-L1970, Q337-L1970, V338-L1970, K339-L1970, E340-L1970, E341-L1970, I342-L1970, I343-L1970, C344-L1970, M345-L1970, I346-L1970, Q347-L1970, N348-L1970, T349-L1970, F350-L1970, N351-L1970, F352-L1970, S353-L1970, L354-L1970, K355-L1970, Q356-L1970, S357-L1970, K358-L1970, H359-L1970, L360-L1970, F361-L1970, Q362-L1970, I363-L1970, L364-L1970, M365-L1970, E366-L1970, C367-L1970, M368-L1970, V369-L1970, H370-L1970, R371-L1970, D372-L1970, C373-L1970, I374-L1970, T375-L1970, I376-L1970, F377-L1970, D378-L1970, A379-L1970, D380-L1970, S381-L1970, E382-L1970, E383-L1970, Q384-L1970, Q385-L1970, D386-L1970, L387-L1970, D388-L1970, L389-L1970, A390-L1970, I391-L1970, L392-L1970, T393-L1970, A394-L1970, L395-L1970, L396-L1970, K397-L1970, G398-L1970, T399-L1970, N400-L1970, L401-L1970, S402-L1970, A403-L1970, S404-L1970, E405-L1970, Q406-L1970, L407-L1970, N408-L1970, L409-L1970, A410-L1970, M411-L1970, A412-L1970, W413-L1970, D414-L1970, R415-L1970, V416-L1970, D417-L1970, I418-L1970, A419-L1970, K420-L1970, K421-L1970, H422-L1970, I423-L1970, L424-L1970, I425-L1970, Y426-L1970, E427-L1970, Q428-L1970, H429-L1970, W430-L1970, K431-L1970, P432-L1970, D433-L1970, A434-L1970, L435-L1970, E436-L1970, Q437-L1970, A438-L1970, M439-L1970, S440-L1970, D441-L1970, A442-L1970, L443-

L1970, V444-L1970, M445-L1970, D446-L1970, R447-L1970, V448-L1970, D449-L1970, F450-L1970, V451-L1970, K452-L1970, L453-L1970, L454-L1970, I455-L1970, E456-L1970, Y457-L1970, G458-L1970, V459-L1970, N460-L1970, L461-L1970, H462-L1970, R463-L1970, F464-L1970, L465-L1970, T466-L1970, I467-L1970, P468-L1970, R469-L1970, L470-L1970, E471-L1970, E472-L1970, L473-L1970, Y474-L1970, N475-L1970, T476-L1970, K477-L1970, Q478-L1970, G479-L1970, P480-L1970, T481-L1970, N482-L1970, T483-L1970, L484-L1970, L485-L1970, H486-L1970, H487-L1970, L488-L1970, V489-L1970, Q490-L1970, D491-L1970, V492-L1970, K493-L1970, Q494-L1970, and/or H495-L1970, of SEQ ID NO:4. Polynucleotide sequences encoding these polypeptides are also provided. The present invention also encompasses the use of these N-terminal TRP-PLIK2b deletion polypeptides as immunogenic and/or antigenic epitopes as described elsewhere herein.

In preferred embodiments, the following C-terminal TRP-PLIK2b deletion polypeptides are encompassed by the present invention: M1-L1970, M1-Q1969, M1-M1968, M1-D1967, M1-D1966, M1-E1965, M1-P1964, M1-S1963, M1-N1962, M1-R1961, M1-G1960, M1-T1959, M1-E1958, M1-R1957, M1-A1956, M1-P1955, M1-P1954, M1-E1953, M1-E1952, M1-A1951, M1-S1950, M1-E1949, M1-I1948, M1-K1947, M1-I1946, M1-E1945, M1-L1944, M1-G1943, M1-F1942, M1-T1941, M1-S1940, M1-N1939, M1-I1938, M1-R1937, M1-E1936, M1-P1935, M1-S1934, M1-Y1933, M1-D1932, M1-N1931, M1-R1930, M1-K1929, M1-L1928, M1-D1927, M1-P1926, M1-L1925, M1-K1924, M1-L1923, M1-K1922, M1-R1921, M1-C1920, M1-C1919, M1-S1918, M1-N1917, M1-C1916, M1-H1915, M1-H1914, M1-K1913, M1-A1912, M1-I1911, M1-F1910, M1-N1909, M1-R1908, M1-I1907, M1-A1906, M1-D1905, M1-E1904, M1-G1903, M1-L1902, M1-N1901, M1-A1900, M1-P1899, M1-G1898, M1-F1897, M1-V1896, M1-M1895, M1-G1894, M1-R1893, M1-S1892, M1-Q1891, M1-K1890, M1-V1889, M1-E1888, M1-P1887, M1-K1886, M1-I1885, M1-V1884, M1-S1883, M1-P1882, M1-D1881, M1-T1880, M1-L1879, M1-N1878, M1-E1877, M1-G1876, M1-V1875, M1-G1874, M1-Q1873, M1-L1872, M1-D1871, M1-L1870, M1-V1869, M1-L1868, M1-L1867, M1-E1866, M1-G1865, M1-R1864, M1-T1863, M1-Y1862, M1-E1861, M1-Y1860, M1-T1859, M1-W1858, M1-H1857, M1-S1856, M1-F1855, M1-A1854, M1-L1853, M1-M1852, M1-L1851, M1-E1850, M1-E1849, M1-L1848, M1-T1847, M1-N1846, M1-T1845, M1-P1844, M1-T1843, M1-I1842, M1-E1841, M1-D1840, M1-G1839, M1-N1838, M1-N1837, M1-N1836, M1-N1835, M1-Y1834, M1-K1833, M1-R1832, M1-F1831, M1-E1830, M1-G1829, M1-T1828, M1-M1827, M1-Y1826, M1-K1825, M1-E1824, M1-I1823, M1-T1822, M1-L1821, M1-W1820, M1-Q1819, M1-N1818, M1-A1817, M1-S1816, M1-H1815, M1-C1814, M1-Y1813, M1-I1812, M1-L1811, M1-F1810, M1-V1809, M1-E1808, M1-L1807, M1-F1806, M1-R1805, M1-P1804, M1-T1803, M1-Y1802, M1-P1801, M1-I1800, M1-T1799, M1-Q1798, M1-P1797, M1-K1796, M1-V1795, M1-Q1794, M1-N1793, M1-F1792, M1-T1791, M1-Y1790, M1-I1789, M1-L1788, M1-K1787, M1-Q1786, M1-A1785, M1-A1784, M1-R1783, M1-Q1782, M1-Q1781, M1-Q1780, M1-I1779, M1-E1778, M1-R1777, M1-L1776, M1-C1775, M1-L1774, M1-H1773, M1-L1772, M1-V1771, M1-T1770, M1-S1769, M1-E1768, M1-Q1767, M1-F1766, M1-I1765, M1-K1764, M1-H1763, M1-W1762, M1-T1761, M1-R1760, M1-V1759, M1-V1758, M1-E1757, M1-P1756, M1-L1755, M1-F1754, M1-S1753, M1-K1752, M1-V1751, M1-I1750, M1-F1749, M1-V1748, M1-Q1747, M1-G1746, M1-P1745, M1-K1744, M1-L1743, M1-I1742, M1-D1741, M1-D1740, M1-E1739, M1-S1738, M1-W1737, M1-T1736, M1-S1735, M1-V1734, M1-V1733, M1-R1732, M1-M1731, M1-A1730, M1-K1729, M1-R1728, M1-L1727, M1-G1726, M1-G1725, M1-D1724, M1-M1723, M1-E1722, M1-E1721, M1-R1720, M1-S1719, M1-L1718, M1-V1717, M1-Q1716, M1-I1715, M1-M1714, M1-A1713, M1-A1712, M1-R1711, M1-G1710, M1-R1709, M1-Q1708, M1-S1707, M1-W1706, M1-S1705, M1-S1704, M1-M1703, M1-S1702, M1-K1701, M1-D1700, M1-L1699, M1-N1698, M1-L1697, M1-P1696, M1-S1695, M1-S1694, M1-E1693, M1-E1692, M1-L1691, M1-R1690, M1-Y1689, M1-V1688, M1-T1687, M1-I1686, M1-E1685, M1-E1684, M1-G1683, M1-A1682, M1-F1681, M1-L1680, M1-Q1679, M1-V1678, M1-P1677, M1-T1676, M1-F1675, M1-P1674, M1-I1673, M1-T1672, M1-Q1671, M1-S1670, M1-L1669, M1-R1668, M1-M1667, M1-L1666, M1-N1665, M1-N1664, M1-R1663, M1-E1662, M1-I1661, M1-A1660, M1-S1659, M1-Y1658, M1-H1657, M1-H1656, M1-H1655, M1-P1654, M1-E1653, M1-Q1652, M1-P1651, M1-S1650, M1-K1649, M1-L1648, M1-S1647, M1-A1646, M1-S1645, M1-I1644, M1-K1643, M1-D1642, M1-V1641, M1-G1640, M1-I1639, M1-S1638, M1-S1637, M1-K1636, M1-L1635, M1-L1634, M1-S1633, M1-N1632, M1-R1631, M1-N1630, M1-L1629, M1-N1628, M1-T1627, M1-S1626, M1-R1625, M1-S1624, M1-N1623, M1-W1622, M1-L1621, M1-S1620, M1-N1619, M1-K1618, M1-S1617, M1-L1616, M1-D1615, M1-E1614, M1-Q1613, M1-S1612, M1-Q1611, M1-K1610, M1-L1609, M1-Y1608, M1-D1607, M1-S1606, M1-I1605, M1-Q1604, M1-I1603, M1-A1602, M1-C1601, M1-Q1600, M1-G1599, M1-I1598, M1-E1597, M1-K1596, M1-T1595, M1-K1594, M1-M1593, M1-K1592, M1-Q1591, M1-H1590, M1-I1589, M1-Y1588, M1-P1587, M1-E1586, M1-V1585, M1-G1584, M1-T1583, M1-H1582, M1-S1581, M1-F1580, M1-K1579, M1-S1578, M1-V1577, M1-T1576, M1-F1575, M1-W1574, M1-N1573, M1-K1572, M1-S1571, M1-Y1570, M1-E1569, M1-E1568, M1-E1567, M1-S1566, M1-I1565, M1-S1564, M1-N1563, M1-E1562, M1-G1561, M1-P1560, M1-E1559, M1-P1558, M1-N1557, M1-L1556, M1-Q1555, M1-D1554, M1-S1553, M1-Q1552, M1-S1551, M1-C1550, M1-A1549, M1-N1548, M1-V1547, M1-T1546, M1-I1545, M1-I1544, M1-P1543, M1-V1542, M1-Q1541, M1-L1540, M1-G1539, M1-Q1538, M1-T1537, M1-N1536, M1-K1535, M1-K1534, M1-K1533, M1-K1532, M1-S1531, M1-L1530, M1-R1529, M1-R1528, M1-D1527, M1-K1526, M1-T1525, M1-L1524, M1-M1523, M1-K1522, M1-A1521, M1-K1520, M1-V1519, M1-W1518, M1-A1517, M1-G1516, M1-Q1515, M1-G1514, M1-I1513, M1-E1512, M1-S1511, M1-S1510, M1-G1509, M1-S1508, M1-L1507, M1-N1506, M1-K1505, M1-I1504, M1-K1503, M1-C1502, M1-I1501, M1-K1500, M1-M1499, M1-L1498, M1-K1497, M1-E1496, M1-E1495, M1-K1494, M1-H1493, M1-F1492, M1-R1491, M1-F1490, M1-S1489, M1-H1488, M1-S1487, M1-R1486, M1-A1485, M1-F1484, M1-P1483, M1-R1482, M1-Y1481, M1-R1480, M1-R1479, M1-L1478, M1-P1477, M1-N1476, M1-I1475, M1-W1474, M1-F1473, M1-S1472, M1-T1471, M1-N1470, M1-P1469, M1-Q1468, M1-L1467, M1-W1466, M1-P1465, M1-G1464, M1-V1463, M1-E1462, M1-S1461, M1-C1460, M1-E1459, M1-S1458, M1-S1457, M1-Q1456, M1-A1455, M1-S1454, M1-R1453, M1-T1452, M1-S1451, M1-N1450, M1-D1449, M1-S1448, M1-L1447, M1-S1446, M1-S1445, M1-D1444, M1-Q1443, M1-A1442, M1-Q1441, M1-K1440, M1-Q1439, M1-H1438, M1-Q1437, M1-E1436, M1-S1435, M1-R1434, M1-S1433, M1-S1432, M1-D1431, M1-S1430, M1-D1429, M1-C1428, M1-T1427, M1-S1426, M1-P1425, M1-L1424, M1-C1423, M1-T1422, M1-Q1421, M1-W1420, M1-K1419, M1-K1418, M1-K1417, M1-I1416, M1-S1415, M1-F1414, M1-V1413, M1-G1412, M1-T1411, M1-E1410, M1-D1409, M1-G1408, M1-E1407, M1-S1406, M1-F1405, M1-A1404, M1-W1403, M1-N1402, M1-V1401, M1-Y1400, M1-G1399, M1-G1398, M1-G1397, M1-T1396, M1-Q1395, M1-M1394, M1-I1393, M1-K1392, M1-A1391, M1-Q1390, M1-S1389, M1-L1388, M1-P1387, M1-S1386, M1-S1385, M1-M1384, M1-T1383, M1-M1382, M1-P1381, M1-E1380, M1-P1379, M1-T1378, M1-C1377, M1-S1376, M1-L1375, M1-T1374, M1-P1373, M1-L1372, M1-V1371, M1-Q1370, M1-E1369, M1-A1368, M1-K1367, M1-D1366, M1-Q1365, M1-G1364, M1-D1363, M1-L1362, M1-L1361, M1-H1360, M1-A1359, M1-I1358, M1-P1357, M1-E1356, M1-H1355, M1-K1354, M1-E1353, M1-K1352, M1-P1351, M1-E1350, M1-D1349, M1-V1348, M1-S1347, M1-A1346, M1-W1345, M1-D1344, M1-S1343, M1-V1342, M1-V1341, M1-P1340, M1-T1339, M1-Q1338, M1-G1337, M1-T1336, M1-L1335, M1-H1334, M1-V1333, M1-L1332, M1-V1331, M1-E1330, M1-T1329, M1-Q1328, M1-I1327, M1-D1326, M1-Q1325, M1-E1324, M1-T1323, M1-A1322, M1-L1321, M1-V1320, M1-D1319, M1-P1318, M1-V1317, M1-S1316, M1-P1315, M1-R1314, M1-S1313, M1-L1312, M1-P1311, M1-L1310, M1-V1309, M1-T1308, M1-E1307, M1-A1306, M1-S1305, M1-F1304, M1-P1303, M1-V1302, M1-R1301, M1-K1300, M1-L1299, M1-N1298, M1-S1297, M1-P1296, M1-V1295, M1-L1294, M1-L1293, M1-F1292, M1-Q1291, M1-G1290, M1-Y1289, M1-K1288, M1-S1287, M1-H1286, M1-A1285, M1-Q1284, M1-R1283, M1-N1282, M1-P1281, M1-S1280, M1-V1279, M1-G1278, M1-S1277, M1-V1276, M1-V1275, M1-I1274, M1-S1273, M1-S1272, M1-Q1271, M1-T1270, M1-E1269, M1-Q1268, M1-R1267, M1-E1266, M1-Q1265, M1-D1264, M1-N1263, M1-R1262, M1-V1261, M1-N1260, M1-T1259, M1-A1258, M1-E1257, M1-R1256, M1-K1255, M1-S1254, M1-N1253, M1-T1252, M1-I1251, M1-E1250, M1-L1249, M1-L1248, M1-A1247, M1-G1246, M1-R1245, M1-Q1244, M1-V1243, M1-R1242, M1-P1241, M1-P1240, M1-H1239, M1-R1238, M1-G1237, M1-G1236, M1-A1235, M1-L1234, M1-S1233, M1-R1232, M1-L1231, M1-L1230, M1-S1229, M1-S1228, M1-P1227, M1-M1226, M1-S1225, M1-Y1224, M1-Y1223, M1-Q1222, M1-Y1221, M1-K1220, M1-K1219, M1-E1218, M1-G1217, M1-A1216, M1-I1215, M1-E1214, M1-M1213, M1-S1212, M1-G1211, M1-L1210, M1-V1209, M1-E1208, M1-A1207, M1-C1206, M1-I1205, M1-V1204, M1-N1203, M1-S1202, M1-W1201, M1-S1200, M1-H1199, M1-P1198, M1-L1197, M1-K1196, M1-K1195, M1-C1194, M1-T1193, M1-S1192, M1-H1191, M1-K1190, M1-R1189, M1-K1188, M1-A1187, M1-L1186, M1-L1185, M1-A1184, M1-E1183, M1-D1182, M1-E1181, M1-Q1180, M1-L179, M1-T1178, M1-D1177, M1-V1176, M1-A1175, M1-S1174, M1-L1173, M1-V1172, M1-K1171, M1-L1170, M1-T1169, M1-D1168, M1-V1167, M1-T1166, M1-L1165, M1-A1164, M1-S1163, M1-L1162, M1-D1161, M1-Q1160, M1-L1159, M1-H1158, M1-G1157, M1-V1156, M1-Q155, M1-S1154, M1-D1153, M1-L1152, M1-S1151, M1-L1150, M1-L1149, M1-S1148, M1-D1147, M1-K1146, M1-I1145, M1-F1144, M1-S1143, M1-V1142, M1-K1141, M1-E1140, M1-N1139, M1-M1138, M1-E1137, M1-K1136, M1-L1135, M1-Q1134, M1-F1133, M1-Y1132, M1-M131, M1-E1130, M1-T1129, M1-V1128, M1-R1127, M1-E1126, M1-S1125, M1-T1124, M1-V1123, M1-R1122, M1-I1121, M1-R1120, M1-E1119, M1-E1118, M1-C1117, M1-S1116, M1-C1115, M1-N1114, M1-V1113, M1-D1112, M1-E1111, M1-M1110, M1-K1109, M1-E1108, M1-H1107, M1-F1106, M1-Y1105, M1-K1104, M1-E1103, M1-V1102, M1-C1101, M1-Q1100, M1-E1099, M1-E1098, M1-F1097, M1-D1096, M1-H1095, M1-L1094, M1-K1093, M1-K1092, M1-L1091, M1-D1090, M1-E1089, M1-K1088, M1-S1087, M1-L1086, M1-Y1085, M1-L1084, M1-K1083, M1-L1082, M1-G1081, M1-V1080, M1-D1079, M1-G1078, M1-E1077, M1-E1076, M1-Q1075, M1-D1074, M1-H1073, M1-P1072, M1-A1071, M1-R1070, M1-H1069, M1-C1068, M1-C1067, M1-L1066, M1-R1065, M1-R1064, M1-L1063, M1-L1062, M1-L1061, M1-G1060, M1-V1059, M1-H1058, M1-S1057, M1-L1056, M1-L1055, M1-I1054, M1-L1053, M1-P1052, M1-P1051, M1-P1050, M1-L1049, M1-W1048, M1-P1047, M1-K1046, M1-E1045, M1-H1044, M1-Y1043, M1-T1042, M1-M1041, M1-I1040, M1-Y1039, M1-R1038, M1-Y1037, M1-R1036, M1-N1035, M1-Y1034, M1-K1033, M1-W1032, M1-L1031, M1-N1030, M1-N1029, M1-S1028, M1-I1027, M1-S1026, M1-E1025, M1-M1024, M1-D1023, M1-L1022, M1-Y1021, M1-V1020, M1-N1019, M1-N1018, M1-F1017, M1-F1016, M1-A1015, M1-I1014, M1-L1013, M1-L1012, M1-N1011, M1-V1010, M1-M1009, M1-I1008, M1-I1007, M1-Y1006, M1-Q1005, M1-V1004, M1-F1003, M1-L1002, M1-Y1001, M1-V1000, M1-A999, M1-Q998, M1-L997, M1-F996, M1-P995, M1-T994, M1-L993, M1-F992, M1-S991, M1-G990, M1-P989, M1-P988, M1-C987, M1-S986, M1-P985, M1-Q984, M1-S983, M1-S982, M1-C981, M1-V980, M1-D979, M1-I978, M1-E977, M1-G976, M1-A975, M1-Y974, M1-V973, M1-E972, M1-G971, M1-Y970, M1-I969, M1-M968, M1-W967, M1-Y966, M1-P965, M1-E964, M1-F963, M1-V962, M1-I961, M1-D960, M1-R959, M1-A958, M1-L957, M1-S956, M1-W955, M1-S954, M1-P953, M1-P952, M1-E951, M1-K950, M1-P949, M1-S948, M1-L947, M1-I946, M1-A945, M1-K944, M1-R943, M1-A942, M1-V941, M1-G940, M1-F939, M1-S938, M1-L937, M1-L936, M1-V935, M1-I934, M1-A933, M1-M932, M1-I931, M1-I930, M1-V929, M1-I928, M1-Y927, M1-F926, M1-M925, M1-N924, M1-A923, M1-T922, M1-M921, M1-K920, M1-A919, M1-I918, M1-M917, M1-T916, M1-V915, M1-Y914, M1-P913, M1-G912, M1-A911, M1-H910, M1-Q909, M1-N908, M1-V907, M1-A906, M1-F905, M1-F904, M1-D903, M1-L902, M1-L901, M1-R900, M1-S899, M1-F898, M1-W897, M1-F896, M1-I895, M1-I894, M1-D893, M1-I892, M1-C891, M1-Y890, M1-I889, M1-L888, M1-R887, M1-G886, M1-A885, M1-T884, M1-H883, M1-F882, M1-P881, M1-P880, M1-D879, M1-G878, M1-W877, M1-R876, M1-L875, M1-V874, M1-F873, M1-G872, M1-A871, M1-S870, M1-F869, M1-L868, M1-G867, M1-I866, M1-A865, M1-V864, M1-T863, M1-E862, M1-T861, M1-L860, M1-N859, M1-W858, M1-Y857, M1-E856, M1-S855, M1-I854, M1-W853, M1-V852, M1-K851, M1-V850, M1-K849, M1-Q848, M1-T847, M1-F846, M1-K845, M1-G844, M1-P843, M1-E842, M1-S841, M1-I840, M1-C839, M1-I838, M1-E837, M1-R836, M1-V835, M1-V834, M1-E833, M1-I832, M1-A831, M1-N830, M1-T829, M1-F828, M1-I827, M1-Y826, M1-I825, M1-S824, M1-V823, M1-L822, M1-W821, M1-E820, M1-Q819, M1-V818, M1-S817, M1-P816, M1-Q815, M1-P814, M1-Q813, M1-M812, M1-E811, M1-V810, M1-L809, M1-V808, M1-T807, M1-Y806, M1-T805, M1-F804, M1-L803, M1-M802, M1-L801, M1-F800, M1-A799, M1-L798, M1-Y797, M1-A796, M1-M795, M1-T794, M1-Y793, M1-F792, M1-W791, M1-F790, M1-K789, M1-V788, M1-I787, M1-P786, M1-A785, M1-S784, M1-Y783, M1-F782, M1-E781, M1-Y780, M1-V779, M1-W778, M1-R777, M1-T776, M1-P774, M1-L773, M1-H772, M1-Q771, M1-H770, M1-G769, M1-S768, M1-E767, M1-L766, M1-G765, M1-F764, M1-H763, M1-Q762, M1-N761, M1-E760, M1-D759, M1-L758, M1-K757, M1-E756, M1-D755, M1-H754, M1-G753, M1-R752, M1-E751, M1-L750, M1-D749, M1-Y748, M1-E747, M1-K746, M1-V745, M1-S744, M1-A743, M1-S742, M1-E741, M1-K740, M1-S739, M1-S738, M1-S737, M1-A736, M1-N735, M1-Q734, M1-D733, M1-S732, M1-Y731, M1-Y730, M1-W729, M1-M728, M1-F727, M1-Q726, M1-F725, M1-D724, M1-Q723, M1-S722, M1-Q721, M1-P720, M1-V719, M1-H718, M1-S717, M1-M716, M1-E715, M1-A714, M1-K713, M1-S712, M1-K711, M1-F710, M1-E709, M1-L708, M1-T707, M1-L706, M1-I705, M1-T704, M1-P703, M1-P702, M1-L701, M1-I700, M1-I699, M1-S698, M1-I697, M1-I696, M1-I695, M1-K694, M1-L693, M1-W692, M1-S691, M1-N690, M1-K689, M1-R688, M1-M687, M1-K686, M1-L685, M1-R684, M1-G683, M1-M682, M1-W681, M1-M680, M1-D679, M1-T678, M1-L677, M1-L676, M1-M675, M1-Q674, M1-T673, M1-C672, M1-T671, M1-H670, M1-S669, M1-V668, M1-F667, M1-P666, M1-R665, M1-L664, M1-G663, M1-G662, M1-S661, M1-V660, M1-A659, M1-L658, M1-K657, M1-L656, M1-C655, M1-T654, M1-S653, M1-N652, M1-S651, M1-W650, M1-N649, M1-R648, M1-L647, M1-E646, M1-Y645, M1-T644, M1-L643, M1-L642, M1-T641, M1-M640, M1-A639, M1-M638, M1-R637, M1-E636, M1-N635, M1-Q634, M1-K633, M1-F632, M1-A631, M1-K630, M1-E629, M1-L628, M1-L627, M1-D626, M1-L625, M1-A624, M1-L623, M1-Q622, M1-G621, M1-F620, M1-Q619, M1-K618, M1-S617, M1-Y616, M1-N615, M1-K614, M1-L613, M1-E612, M1-E611, M1-S610, M1-A609, M1-D608, M1-D607, M1-V606, M1-M605, M1-H604, M1-S603, M1-E602, M1-K601, M1-A600, M1-E599, M1-H598, M1-A597, M1-M596, M1-A595, M1-R594, M1-Y593, M1-L592, M1-I591, M1-C590, M1-A589, M1-I588, M1-V587, M1-A586, M1-K585, M1-V584, M1-T583, M1-A582, M1-E581, M1-E580, M1-G579, M1-H578, M1-Q577, M1-W576, M1-F575, M1-F574, M1-M573, M1-A572, M1-M571, M1-K570, M1-Q569, M1-R568, M1-K567, M1-M566, M1-L565, M1-V564, M1-A563, M1-W562, M1-V561, M1-L560, M1-L559, M1-D558, M1-N557, M1-Y556, M1-P555, M1-Y554, M1-L553, M1-F552, M1-G551, M1-T550, M1-S549, M1-E548, M1-P547, M1-D546, M1-D545, M1-S544, M1-V543, M1-N542, M1-Q541, M1-E540, M1-K539, M1-S538, M1-K537, M1-K536, M1-R535, M1-S534, M1-K533, M1-H532, M1-L531, M1-V530, M1-I529, M1-S528, M1-K527, M1-E526, M1-K525, M1-F524, M1-K523, M1-Y522, M1-P521, M1-Q520, M1-A519, M1-T518, M1-R517, M1-I516, M1-F515, M1-Q514, M1-S513, M1-H512, M1-L511, M1-T510, M1-S509, M1-E508, M1-A507, M1-S506, M1-E505, M1-N504, M1-R503, M1-N502, M1-G501, M1-S500, M1-S499, M1-H498, M1-R497, and/or M1-Q496 of SEQ ID NO:4. Polynucleotide sequences encoding these polypeptides are also provided. The present invention also encompasses the use of these C-terminal TRP-PLIK2b deletion polypeptides as immunogenic and/or antigenic epitopes as described elsewhere herein.

Alternatively, preferred polypeptides of the present invention may comprise polypeptide sequences corresponding to, for example, internal regions of the TRP-PLIK2b polypeptide (e.g., any combination of both N- and C-terminal TRP-PLIK2b polypeptide deletions) of SEQ ID NO:4. For example, internal regions could be defined by the equation: amino acid NX to amino acid CX, wherein NX refers to any N-terminal deletion polypeptide amino acid of TRP-PLIK2b (SEQ ID NO:4), and where CX refers to any C-terminal deletion polypeptide amino acid of TRP-PLIK2b (SEQ ID NO:4). Polynucleotides encoding these polypeptides are also provided. The present invention also encompasses the use of these polypeptides as an immunogenic and/or antigenic epitope as described elsewhere herein.

The TRP-PLIK2b polypeptides of the present invention were determined to comprise several phosphorylation sites based upon the Motif algorithm (Genetics Computer Group, Inc.). The phosphorylation of such sites may regulate some biological activity of the TRP-PLIK2b polypeptide. For example, phosphorylation at specific sites may be involved in regulating the proteins ability to associate or bind to other molecules (e.g., proteins, ligands, substrates, DNA, etc.). In the present case, phosphorylation may modulate the ability of the TRP-PLIK2b polypeptide to associate with other potassium channel alpha subunits, beta subunits, or its ability to modulate potassium channel function.

The TRP-PLIK2b polypeptide was predicted to comprise twenty eight PKC phosphorylation sites using the Motif algorithm (Genetics Computer Group, Inc.). In vivo, protein kinase C exhibits a preference for the phosphorylation of serine or threonine residues. The PKC phosphorylation sites have the following consensus pattern: [ST]-x-[RK], where S or T represents the site of phosphorylation and 'x' an intervening amino acid residue. Additional information regarding PKC phosphorylation sites can be found in Woodget J. R., Gould K. L., Hunter T., Eur. J. Biochem. 161:177-184 (1986), and Kishimoto A., Nishiyama K., Nakanishi H., Uratsuji Y., Nomura H., Takeyama Y., Nishizuka Y., J. Biol. Chem. . . . 260:12492-12499 (1985); which are hereby incorporated by reference herein.

In preferred embodiments, the following PKC phosphorylation site polypeptides are encompassed by the present invention: IILSKSQKSWIKG (SEQ ID NO:115), STIIPSSKNPHRC (SEQ ID NO:116), SVEKHTTKSPTDT (SEQ ID NO:117), SHSSHSLRKIWTV (SEQ ID NO:118), LSVWETVKDKDPV (SEQ ID NO:119), VVCEGTGRAADLL (SEQ ID NO:120), DLLAFTHKHLADE (SEQ ID NO:121), NTFNFSLKQSKHL (SEQ ID NO:122), IVLHKSRKKSKEQ (SEQ ID NO:123), HGEEATVKAVIAC (SEQ ID NO:124), DQNASSSKESASV (SEQ ID NO:125), SKESASVKEYDLE (SEQ ID NO:126), QHLPWTRKVYEFY (SEQ ID NO:127), EPGKFTQKVKVWI (SEQ ID NO:128), RKAILSPKEPPSW (SEQ ID NO:129), RIRVTSERVTEMY (SEQ ID NO:130), ALTVDTLKVLSAV (SEQ ID NO:131), KRKHSTCKKLPHS (SEQ ID NO:132), LEITNSKREATNV (SEQ ID NO:133), ETGVFSIKKKWQT (SEQ ID NO:134), TCDSDSSRSEQHQ (SEQ ID NO:135), SLSDNSTRSAQSS (SEQ ID NO:136), FARSHSFRFHKEE (SEQ ID NO:137), KDRRLSKKKKNTQ (SEQ ID NO:138), DKISASLKSPQEP (SEQ ID NO:139), SMSSWSQRGRAAM (SEQ ID NO:140), QTIPYTPRFLEVF (SEQ ID NO:141), and/or PPARETGRNSPED (SEQ ID NO:142). Polynucleotides encoding these polypeptides are also provided. The present invention also encompasses the use of these TRP-PLIK2b PKC phosphorylation site polypeptides as immunogenic and/or antigenic epitopes as described elsewhere herein.

The present invention also encompasses immunogenic and/or antigenic epitopes of the TRP-PLIK2b polypeptide.

The TRP-PLIK2b polypeptide has been shown to comprise sixteen glycosylation sites according to the Motif algorithm (Genetics Computer Group, Inc.). As discussed more specifically herein, protein glycosylation is thought to serve a variety of functions including: augmentation of protein folding, inhibition of protein aggregation, regulation of intracellular trafficking to organelles, increasing resistance to proteolysis, modulation of protein antigenicity, and mediation of intercellular adhesion.

Asparagine phosphorylation sites have the following consensus pattern, N-{P}-[ST]-{P}, wherein N represents the glycosylation site. However, it is well known that that potential N-glycosylation sites are specific to the consensus sequence Asn-Xaa-Ser/Thr. However, the presence of the consensus tripeptide is not sufficient to conclude that an asparagine residue is glycosylated, due to the fact that the folding of the protein plays an important role in the regulation of N-glycosylation. It has been shown that the presence of proline between Asn and Ser/Thr will inhibit N-glycosylation; this has been confirmed by a recent statistical analysis of glycosylation sites, which also shows that about 50% of the sites that have a proline C-terminal to Ser/Thr are not glycosylated. Additional information relating to asparagine glycosylation may be found in reference to the following publications, which are hereby incorporated by reference herein: Marshall R. D., Annu. Rev. Biochem. 41:673-702 (1972); Pless D. D., Lennarz W. J., Proc. Natl. Acad. Sci. U.S.A. 74:134-138 (1977); Bause E., Biochem. J. 209:331-336 (1983); Gavel Y., von Heijne G., Protein Eng. 3:433-442 (1990); and Miletich J. P., Broze G. J. Jr., J. Biol. Chem. . . . 265:11397-11404 (1990).

In preferred embodiments, the following asparagine glycosylation site polypeptides are encompassed by the present invention: HGGIQNFTMPSKFK (SEQ ID NO:143), IQNTFNFSLKQSKH (SEQ ID NO:144), LLKGTNLSASEQLN (SEQ ID NO:145), SSGNRNESAESTLH (SEQ ID NO:146), KSKEQNVSDDPEST (SEQ ID NO:147), SEELKNYSKQFGQL (SEQ ID NO:148), TYELRNWSNSTCLK (SEQ ID NO:149), LRNWSNSTCLKLAV (SEQ ID NO:150), YYSDQNASSSKESA (SEQ ID NO:151), ISEYWNLTETVAIG (SEQ ID NO:152), KMEDVNCSCEERIR (SEQ ID NO:153), SSLSDNSTRSAQSS (SEQ ID NO:154), PWLQPNTSFWINPL (SEQ ID NO:155), ICKIKNLSGSSEIG (SEQ ID NO:156), QGVGENLTDPSVIK (SEQ ID NO:157), and/or SPERINSTFGLEIK (SEQ ID NO:158). Polynucleotides encoding these polypeptides are also provided. The present invention also encompasses the use of these TRP-PLIK2b asparagine glycosylation site polypeptides as immunogenic and/or antigenic epitopes as described elsewhere herein.

Many polynucleotide sequences, such as EST sequences, are publicly available and accessible through sequence databases. Some of these sequences are related to SEQ ID NO:3 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides consisting of a nucleotide sequence described by the general formula of a-b, where a is any integer between 1 to 5899 of SEQ ID NO:3, b is an integer between 15 to 5913, where both a and b correspond to the positions of nucleotide residues shown in SEQ ID NO:3, and where b is greater than or equal to a+14.

Features of the Polypeptide Encoded by Gene No:3

The polypeptide of this gene provided as SEQ ID NO:6 (FIGS. 3A-G), encoded by the polynucleotide sequence according to SEQ ID NO:5 (FIGS. 3A-G), and/or encoded by the polynucleotide contained within the deposited clone, TRP-PLIK2c, has significant homology at the nucleotide and amino acid level to the human channel-kinase 1 protein, also known as the human CHAK1 or TRP-PLIKB1 protein (CHAK1; GENBANK® Accession No. gi|AF346629; SEQ ID NO:9); and the human melastatin 1 protein (Melastatin1; GENBANK® Accession No. gi|3243075; SEQ ID NO:260). An alignment of the TRP-PLIK2c polypeptide with this protein is provided in FIGS. 5A-F.

The TRP-PLIK2c polypeptide was determined to share 58.5% identity and 66.5% similarity with the human CHAK1 or TRP-PLIKB1 protein (CHAK1; GENBANK® Accession No. gi|AF346629; SEQ ID NO:9); and was determined to share 47.8% identity and 58.7% similarity with the human melastatin 1 protein (Melastatin1; GENBANK® Accession No. gi|3243075; SEQ ID NO:260) as shown in FIG. 9.

The CHAK1 protein is believed to represent a member of a new class of protein kinases referred to as alpha kinases (Curr. Biol. 9 (2), R43-R45 (1999)). These kinases represent a novel type of signaling molecule comprising both a catalytic protein kinase domain, in addition to, an ion channel domain.

The melastatin1 protein is believed to be negatively associated with the incidence of melanoma based upon its inverse correlative expression in highly aggressive melanomas (Genomics 54 (1), 116-123 (1998)). Thus, overexpression of melastatin1 could represent a novel therapeutic in the treatment of melanoma and potentially other cancers.

Based upon the observed homology, the polypeptide of the present invention is expected to share at least some biological activity with other transient receptor potential channel family members, more specifically with the CHAK1 and melastatin1 proteins, in addition to, other transient receptor potential channel family members referenced elsewhere herein or otherwise known in the art.

The TRP-PLIK2c (SEQ ID NO:6) polypeptide represents a novel splice variant form of the TRP-PLIK2 (SEQ ID NO:2) polypeptide of the present invention.

Most of the known transient receptor potential channel family members, possess one or more transmembrane domains. Likewise, the TRP-PLIK2c polypeptide has been determined to comprise six transmembrane domains (TM1-TM6) as shown in FIGS. 3A-G. The transmembrane domains are located from about amino acid 662 to about amino acid 679 (TM1), from about amino acid 756 to about amino acid 773 (TM2), from about amino acid 830 to about amino acid 842 (TM3), from about amino acid 856 to about amino acid 873 (TM4), from about amino acid 890 to about amino acid 907 (TM5), and/or from about amino acid 965 to about amino acid 984 (TM6) of SEQ ID NO:6. In this context, the term "about" may be construed to mean 1, 2, 3, 4, 5, 6, 7, 8, 9, or 10 amino acids beyond the N-Terminus and/or C-terminus of the above referenced polypeptide.

In preferred embodiments, the following transmembrane domain polypeptides are encompassed by the present invention: LKIIISIILPPTILTLEF (SEQ ID NO:159), IVKFWFYTMAYLAFLMLF (SEQ ID NO:160), TETVAIGLFSAGF (SEQ ID NO:161), RLIYCIDIIFWFSRLLDF (SEQ ID NO:162), MTANMFYIVIIMAIVLLS (SEQ ID NO:163), and/or FLQAVYLFVQYIIMVNLLIA (SEQ ID NO:164). Polynucleotides encoding these polypeptides are also provided. The present invention also encompasses the use of the TRP-PLIK2c transmembrane polypeptides as immunogenic and/or antigenic epitopes as described elsewhere herein.

In preferred embodiments, the present invention encompasses the use of N-terminal deletions, C-terminal deletions, or any combination of N-terminal and C-terminal deletions of any one or more of the TRP-PLIK2c TM1 thru TM6 transmembrane domain polypeptides as antigenic and/or immunogenic epitopes.

In preferred embodiments, the present invention also encompasses the use of N-terminal deletions, C-terminal deletions, or any combination of N-terminal and C-terminal deletions of any one or more of the amino acids intervening (i.e., ion channel extracellular or intracellular loops) the TRP-PLIK2c TM1 thru TM6 transmembrane domain polypeptides as antigenic and/or immunogenic epitopes.

The TRP-PLIK2c polypeptide was determined to comprise several conserved cysteines, at amino acid 21, 34, 38, 41, 47, 49, 311, 367, 590, 655, 672, 891, 981, 987, 1067, 1101, 1775, 1814, 1915, 1919, and 1920 of SEQ ID No: 6 (FIGS. 3A-G). Conservation of cysteines at key amino acid residues is indicative of conserved structural features, which may correlate with conservation of protein function and/or activity.

In confirmation of the TRP-PLIK2c representing a member of the transient receptor channel family, the TRP-PLIK2c polypeptide was determined to comprise a predicted TRP domain (LWKYNR) located from about amino acid 1000 to about amino acid 1005 of SEQ ID NO:6. In this context, the term "about" may be construed to mean 1, 2, 3, 4, 5, 6, 7, 8, 9, or 10 amino acids beyond the N-Terminus and/or C-terminus of the above referenced polypeptide.

In further confirmation of the TRP-PLIK2c representing a member of the transient receptor channel family, the TRP-PLIK2c polypeptide was determined to comprise a predicted ion transport signature domain located at about amino acid 826 to about amino acid 986 of SEQ ID NO:6. In this context, the term "about" may be construed to mean 1, 2, 3, 4, 5, 6, 7, 8, 9, or 10 amino acids beyond the N-Terminus and/or C-terminus of the above referenced polypeptide.

The TRP-PLIK2c polypeptide was determined to comprise a predicted nucleotide binding domain located from about amino acid 1867 to about amino acid 1872 of SEQ ID NO:6. In this context, the term "about" may be construed to mean 1, 2, 3, 4, 5, 6, 7, 8, 9, or 10 amino acids beyond the N-Terminus and/or C-terminus of the above referenced polypeptide.

In addition, the TRP-PLIK2c polypeptide was determined to comprise a predicted zinc finger domain located at about amino acid 1882 to about amino acid 1892 of SEQ ID NO:6. In this context, the term "about" may be construed to mean 1, 2, 3, 4, 5, 6, 7, 8, 9, or 10 amino acids beyond the N-Terminus and/or C-terminus of the above referenced polypeptide.

TRP-PLIK2c polypeptides and polynucleotides are useful for diagnosing diseases related to the over and/or under expression of TRP-PLIK2c by identifying mutations in the TRP-PLIK2c gene using TRP-PLIK2c sequences as probes or by determining TRP-PLIK2c protein or mRNA expression levels. TRP-PLIK2c polypeptides will be useful in screens for compounds that affect the activity of the protein. TRP-PLIK2c peptides can also be used for the generation of specific antibodies and as bait in yeast two hybrid screens to find proteins the specifically interact with TRP-PLIK2c.

Expression profiling designed to measure the steady state mRNA levels encoding the TRP-PLIK2 polypeptide showed predominately high expression levels in bone marrow, kidney, and testis. The TRP-PLIK2 polypeptide was also significantly expressioned in liver, and to a lesser extent, in small intestine, spinal cord, prostate, uterus, lung, lymph node, stomach, heart, brain, thymus, and pancrease (as shown in FIG. 7). The tissue expression of TRP-PLIK2c may follow the same pattern as for the TRP-PLIK2 polypeptide of the present invention.

Expanded analysis of TRP-PLIK2 expression levels by TAQMAN® quantitative PCR (see FIG. 12) confirmed that the TRP-PLIK2 polypeptide is expressed in kidney, colon, and testis (FIG. 7). TRP-PLIK2 mRNA was expressed predominately in the lower gastrointestinal tract, specifically the ileum, the rectum, the colon, the jejunum, and to a lesser extent in the duodenum and stomach. Significant expression was observed in the kidney, particularly in the cortex, followed by the medulla, and to a lesser extent in the testis, pelvis, and bone marrow (mononuclear cells).

Furthermore, an expanded analysis of TRP-PLIK2 expression levels in various tumor and normal tissues by TAQ-MAN® quantitative PCR (see FIG. 14) showed TRP-PLIK2 mRNA was differentially expressed to the greatest extent in prostate tumor tissue relative to normal prostate tissue (approximately 20 fold difference). Significant differential expression was also observed in the testicular tumor tissue relative to normal testicular tissue.

Characterization of the TRP-PLIK2 polypeptide of the present invention using antisense oligonucleotides directed against a portion of the TRP-PLIK2 encoding sequence led to the determination that it is involved in the modulation of the NFkB pathway, either directly or indirectly.

The upregulation of IkBa due to the downregulation of TRP-PLIK2 places this transient receptor potential protein into a signalling pathway potentially involved in apoptotic events. This gives the opportunity to regulate downstream events via the activity of the protein TRP-PLIK2 with antisense polynucleotides, polypeptides or low molecular chemicals with the potential of achieving a therapeutic effect in cancer, autoimmune diseases. In addition to cancer and immunological disorders, NF-kB has significant roles in other diseases (Baldwin, A. S., J. Clin Invest. 107: 3-6 (2001)). NF-kB is a key factor in the pathophysiology of ischemia-reperfusion injury and heart failure (Valen, G., Yan. Z Q, Hansson, G K, J. Am. Coll. Cardiol. 38, 307-14 (2001)). Furthermore, NF-kB has been found to be activated in experimental renal disease (Guijarro C, Egido J., Kidney Int. 59, 415-425 (2001)). As TRP-PLIK2 is highly expressed in kidney there is the potential of an involvement in renal diseases.

In preferred embodiments, TRP-PLIK2c polynucleotides and polypeptides, including fragments thereof, are useful for treating, diagnosing, and/or ameliorating proliferative disorders, cancers, ischemia-reperfusion injury, heart failure, immuno compromised conditions, HIV infection, and renal diseases.

Moreover, TRP-PLIK2c polynucleotides and polypeptides, including fragments thereof, are useful for increasing NF-kB activity, increasing apoptotic events, and/or decreasing IkBa expression or activity levels.

In preferred embodiments, antagonists directed against TRP-PLIK2c are useful for treating, diagnosing, and/or ameliorating autoimmune disorders, disorders related to hyper immune activity, inflammatory conditions, disorders related to aberrant acute phase responses, hypercongenital conditions, birth defects, necrotic lesions, wounds, organ transplant rejection, conditions related to organ transplant rejection, disorders related to aberrant signal transduction, proliferating disorders, cancers, HIV, and HIV propagation in cells infected with other viruses.

Moreover, antagonists directed against TRP-PLIK2c are useful for decreasing NF-kB activity, decreasing apoptotic events, and/or increasing IkBa expression or activity levels.

In preferred embodiments, agonists directed against TRP-PLIK2c are useful for treating, diagnosing, and/or ameliorating autoimmune disorders, disorders related to hyper immune activity, hypercongenital conditions, birth defects, necrotic lesions, wounds, disorders related to aberrant signal transduction, immuno compromised conditions, HIV infection, proliferating disorders, and/or cancers.

Moreover, agonists directed against TRP-PLIK2c are useful for increasing NF-kB activity, increasing apoptotic events, and/or decreasing IkBa expression or activity levels.

The strong homology to transient receptor potential channels (TRP), combined with the predominate localized expression of the TRP-PLIK2 polypeptide in the lower gastrointestinal tract, specifically the ileum, the rectum, the colon, the jejunum, and to a lesser extent in the duodenum and stomach, suggests the TRP-PLIK2c polynucleotides and polypeptides may be useful in treating, diagnosing, prognosing, and/or preventing gastrointestinal diseases and/or disorders, which include, but are not limited to, ulcers, irritable bowel syndrome, inflammatory bowel disease, diarrhea, traveler's diarrhea, drug-related diarrhea polyps, absorption disorders, constipation, diverticulitis, vascular disease of the intestines, intestinal obstruction, intestinal infections, ulcerative colitis, Shigellosis, cholera, Crohn's Disease, amebiasis, enteric fever, Whipple's Disease, peritonitis, intraabdominal abscesses, hereditary hemochromatosis, gastroenteritis, viral gastroenteritis, food poisoning, mesenteric ischemia, mesenteric infarction, in addition to, metabolic diseases and/or disorders.

Moreover, polynucleotides and polypeptides, including fragments and/or antagonists thereof, have uses which include, directly or indirectly, treating, preventing, diagnosing, and/or prognosing susceptibility to the following, non-limiting, gastrointestinal infections: *Salmonella* infection, *E. coli* infection, *E. coli* O157:H7 infection, Shiga Toxin-producing *E. coli* infection, *Campylobacter* infection (e.g., *Campylobacter fetus, Campylobacter upsaliensis, Campylobacter hyointestinalis, Campylobacter lari, Campylobacter jejuni, Campylobacter concisus, Campylobacter mucosalis, Campylobacter sputorum, Campylobacter rectus, Campylobacter curvus, Campylobacter sputorum*, etc.), *Heliobacter* infection (e.g., *Heliobacter cinaedi, Heliobacter fennelliae*, etc.) *Yersinia enterocolitica* infection, *Vibrio* sp. Infection (e.g., *Vibrio mimicus, Vibrio parahaemolyticus, Vibrio fluvialis, Vibrio furnissii, Vibrio hollisae, Vibrio vulnificus, Vibrio alginolyticus, Vibrio metschnikovii, Vibrio damsela, Vibrio cincinnatiensis*, etc.) *Aeromonas* infection (e.g., *Aeromonas hydrophila, Aeromonas sobira, Aeromonas caviae*, etc.), *Plesiomonas shigelliodes* infection, *Giardia* infection (e.g., *Giardia lamblia*, etc.), *Cryptosporidium* infection, *Listeria* infection, *Entamoeba histolytica* infection, Rotavirus infection, Norwalk virus infection, *Clostridium difficile* infection, *Clostriudium perfringens* infection, *Staphylococcus* infection, *Bacillus* infection, in addition to any other gastrointestinal disease and/or disorder implicated by the causative agents listed above or elsewhere herein.

The strong homology to human transient receptor potential channels (TRP), combined with the localized expression of the TRP-PLIK2 polypeptide in kidney tissue suggests the TRP-PLIK2c polynucleotides and polypeptides may be useful in treating, diagnosing, prognosing, and/or preventing renal diseases and/or disorders, which include, but are not limited to: nephritis, renal failure, nephrotic syndrome, urinary tract infection, hematuria, proteinuria, oliguria, polyuria, nocturia, edema, hypertension, electrolyte disorders, sterile pyuria, renal osteodystrophy, large kidneys, renal transport defects, nephrolithiasis, azotemia, anuria, urinary retention, slowing of urinary stream, large prostate, flank tenderness, full bladder sensation after voiding, enuresis, dysuria, bacteriuria, kidney stones, glomerulonephritis, vasculitis, hemolytic uremic syndromes, thrombotic thrombocytopenic purpura, malignant hypertension, casts, tubulointerstitial kidney diseases, renal tubular acidosis, pyelonephritis, hydronephritis, nephrotic syndrome, crush syndrome, and/or renal colic, in addition to Wilm's Tumor Disease, and congenital kidney abnormalities such as horseshoe kidney, polycystic kidney, and Falconi's syndrome for example.

Several known TRP family members have been identified that are expressed significantly in kidney tissue. These TRP family members include, for example, Trp12 (Wissenbach, U., Bodding, M., Freichel, M., Flockerzi, V, Lett., 485(2-3): 127-34, (2000)); OTRPC4 (Strotmann, R., Harteneck, C., Nunnenmacher, K., Schultz, G., Plant, T, D, Nat, Cell, Biol., 2(10):695-702, (2000)); polycystin-L2 (Guo, L., Schreiber, T, H., Weremowicz, S., Morton, C, C., Lee, C., Zhou, J. Genomics., 64(3):241-51, (2000)); and EcaC (Hoenderop, J. G., van, der, Kemp, A, W., Hartog, A., van, de, Graaf, S, F., van, Os, C, H., Willems, P, H., Bindels, R, J. J. Biol, Chem., 274(13):8375-8, (1999)).

Thus, the TRP-PLIK2c polynucleotides and polypeptides are expected to share at least some biological activity with TRP family members expressed in kidney cells and tissues, particularly those specifically referenced herein.

The strong homology to human transient receptor potential channels (TRP), combined with the localized expression of the TRP-PLIK2 polypeptide in bone marrow tissue suggests the TRP-PLIK2c polynucleotides and polypeptides may be useful in treating, diagnosing, prognosing, and/or preventing immune diseases and/or disorders. Representative uses are described in the "Immune Activity", "Chemotaxis", and "Infectious Disease" sections below, and elsewhere herein. Briefly, the strong expression in immune tissue indicates a role in regulating the proliferation; survival; differentiation; and/or activation of hematopoietic cell lineages, including blood stem cells.

The TRP-PLIK2c polypeptide may also be useful as a preventative agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's disease, and scleroderma. The TRP-PLIK2 polypeptide may be useful for modulating cytokine production, antigen presentation, or other processes, such as for boosting immune responses, etc.

Moreover, the protein may represent a factor that influences the differentiation or behavior of other blood cells, or that recruits hematopoietic cells to sites of injury. Thus, this gene product is thought to be useful in the expansion of stem cells and committed progenitors of various blood lineages, and in the differentiation and/or proliferation of various cell types. Furthermore, the protein may also be used to determine biological activity, raise antibodies, as tissuemarkers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Significantly, TRP-PLIK2c is believed to represent the first TRP family member expressed in bone marrow tissue.

The strong homology to human transient receptor potential channels (TRP), combined with the localized expression of TRP-PLIK in testis tissue emphasizes the potential utility for TRP-PLIK2c polynucleotides and polypeptides in treating, diagnosing, prognosing, and/or preventing testicular, in addition to reproductive disorders.

In preferred embodiments, TRP-PLIK2c polynucleotides and polypeptides including agonists, antagonists, and/or fragments thereof, have uses which include treating, diagnosing, prognosing, and/or preventing the following, non-limiting, diseases or disorders of the testis: spermatogenesis, infertility, Klinefelter's syndrome, XX male, epididymitis, genital warts, germinal cell aplasia, cryptorchidism, varicocele, immotile cilia syndrome, and viral orchitis. The TRP-PLIK2c polynucleotides and polypeptides including agonists, antagonists, and/or fragments thereof, may also have uses related to modulating testicular development, embryogenesis, reproduction, and in ameliorating, treating, and/or preventing testicular proliferative disorders (e.g., cancers, which include, for example, choriocarcinoma, Nonseminoma, seminona, and testicular germ cell tumors).

Likewise, the localized expression in testis tissue also emphasizes the potential utility for TRP-PLIK2c polynucleotides and polypeptides in treating, diagnosing, prognosing, and/or preventing metabolic diseases and disorders which include the following, not limiting examples: premature puberty, incomplete puberty, Kallman syndrome, Cushing's syndrome, hyperprolactinemia, hemochromatosis, congenital adrenal hyperplasia, FSH deficiency, and granulomatous disease, for example.

This gene product may also be useful in assays designed to identify binding agents, as such agents (antagonists) are useful as male contraceptive agents. The testes are also a site of active gene expression of transcripts that is expressed, particularly at low levels, in other tissues of the body. Therefore, this gene product may be expressed in other specific tissues or organs where it may play related functional roles in other processes, such as hematopoiesis, inflammation, bone formation, and kidney function, to name a few possible target indications.

Several known TRP family members have been identified that are expressed significantly in testis tissue. These TRP family members include, for example, polycystin-L2 (Guo, L., Schreiber, T, H., Weremowicz, S., Morton, C, C., Lee, C., Zhou, J. Genomics., 64(3):241-51, (2000)); TRP7 (Okada, T., Inoue, R., Yamazaki, K., Maeda, A., Kurosaki, T., Yamakuni, T., Tanaka, I., Shimizu, S., Ikenaka, K., Imoto, K., Mori, Y, J. Biol, Chem., 274(39):27359-70, (1999)); btrp2 (Wissenbach, U., Schroth, G., Philipp, S., Flockerzi, V, Lett., 429(1):61-6, (1998)); Htrp-1 (Zhu, X., Chu, P, B., Peyton, M., Birnbaumer, L, Lett., 373(3):193-8, (1995)); and TRPC1 (Wes, P, D., Chevesich, J., Jeromin, A., Rosenberg, C., Stetten, G., Montell, C, Proc, Natl, Acad, Sci, U.S.A., 92(21):9652-6, (1995)).

Thus, the TRP-PLIK2c polynucleotides and polypeptides are expected to share at least some biological activity with TRP family members expressed in testis cells and tissues, particularly those specifically referenced herein.

The predominate differential expression of TRP-PLIK2 in prostate tumor relative to normal prostate tissue strongly suggests TRP-PLIK2c polynucleotides and polypeptides including agonists, antagonists, and/or fragments thereof, have uses which include treating, diagnosing, prognosing, and/or preventing prostate cancers and/or proliferative conditions.

Alternatively, the tissue distribution of TRP-PLIK2 in liver indicates the protein product of the TRP-PLIK2c clone would be useful for the detection and treatment of liver disorders and cancers. Representative uses are described in the "Hyperproliferative Disorders", "Infectious Disease", and "Binding Activity" sections below, and elsewhere herein. Briefly, the protein can be used for the detection, treatment, and/or prevention of hepatoblastoma, jaundice, hepatitis, liver metabolic diseases and conditions that are attributable to the differentiation of hepatocyte progenitor cells, cirrhosis, hepatic cysts, pyrogenic abscess, amebic abscess, hydatid cyst, cystadenocarcinoma, adenoma, focal nodular hyperplasia, hemangioma, hepatocellular carcinoma, cholangiocarcinoma, angiosarcoma, and granulomatous liver disease.

Moreover, polynucleotides and polypeptides, including fragments and/or antagonists thereof, have uses which include, directly or indirectly, treating, preventing, diagnosing, and/or prognosing the following, non-limiting, hepatic infections: liver disease caused by sepsis infection, liver disease caused by bacteremia, liver disease caused by Pneomococcal pneumonia infection, liver disease caused by Toxic shock syndrome, liver disease caused by Listeriosis, liver disease caused by Legionnaries' disease, liver disease caused by Brucellosis infection, liver disease caused by *Neisseria gonorrhoeae* infection, liver disease caused by *Yersinia* infection, liver disease caused by Salmonellosis, liver disease caused by Nocardiosis, liver disease caused by Spirochete infection, liver disease caused by *Treponema pallidum* infection, liver disease caused by Brrelia burgdorferi infection, liver disease caused by Leptospirosis, liver disease caused by *Coxiella burnetii* infection, liver disease caused by *Rickettsia richettsii* infection, liver disease caused by *Chlamydia trachomatis* infection, liver disease caused by *Chlamydia psittaci* infection, in addition to any other hepatic disease and/or disorder implicated by the causative agents listed above or elsewhere herein.

As described elsewhere herein, transient receptor potential channel family members have been implicated in modulating cell proliferation, differentiation, migration, activation, exocytosis, muscle contraction, gene expression, apoptosis. signalling, pheromone sensory signaling, smooth muscle tone, pain perception, heat perception, osmosenstivity, and mechanosensitivity. Moreover, transient receptor potential channel family members have been implicated in disorders of the skin, skeletal-muscle, nervous, cardiac, and vascular systems, in addition to the following, non-limiting diseases and disorders, which include, for example, arteriosclerosis, neointimal hyperplasia, metastatic melanomas, bipolar disorder, nonsyndromic hereditary deafness, Knobloch syndrome, holosencephaly, and various malignancies including prostate cancer.

In preferred embodiments, TRP-PLIK2c polynucleotides and polypeptides of the present invention, including agonists and/or fragments thereof, have uses that include, modulating cell proliferation, differentiation, migration, activation, exocytosis, muscle contraction, gene expression, apoptosis. signalling, pheromone sensory signaling, smooth muscle tone, pain perception, heat perception, osmosenstivity, and mechanosensitivity.

In more preferred embodiments, TRP-PLIK2c polynucleotides and polypeptides of the present invention, including agonists and/or fragments thereof, have uses that include, treating, ameliorating, preventing, detecting, and/or prognosing various diseases and disorders, particularly the following, non-limiting examples, disorders of the skin, skeletal-muscle, nervous, cardiac, and vascular systems, in addition to the following, non-limiting diseases and disorders, which include, for example, arteriosclerosis, neointimal hyperplasia, metastatic melanomas, bipolar disorder, nonsyndromic hereditary deafness, Knobloch syndrome, holosencephaly, and various malignancies including prostate cancer.

TRP-PLIK2c polynucleotides and polypeptides of the present invention, including agonists and/or fragments may be involved in intracellular $Ca^{2+}$ homeostasis which affects various aspects of biological functions including mechano-regulation, pain transduction, vasorelaxation, gene expression, cell cycle and proliferation/apoptosis. Since TRP-PLIK2 is dominantly expressed in bone marrow, the TRP- PLIK2c splice variant may play an important role in regulating cytosolic Ca²⁺ in immune system.

The TRP-PLIK2 gene maps to chromosome 9q21.2-22.1. This region is linked to amyotrophic lateral sclerosis with frontotemporal dementia, early-onset pulverulent cataract, infantile nephronophthisis, hypomagnesemia with secondary hypocalcemia and familial hemophagocytic lymphohistiocytosis. Therefore, agonists and/or antagonists of the novel TRP-PLIK2c splice variant can be used to treat diseases including various forms of neuronal degeneration, neurogenic inflammation, allergy, immunodeficiency/excessive immune activation, visual defects, hearing disorder, pain, cancer, hypertension and other cardiovascular diseases. In addition, the therapeutics may be useful in the treatment of diseases associated with disturbances in Ca²⁺ homeostasis including osteoporosis, hypercalciuric stone disease, and chronic renal failure.

In addition, TRP-PLIK2c polynucleotides and polypeptides of the present invention, including agonists and/or fragments thereof, have uses that include modulating intracellular Ca++ ion concentrations, Ca++ ion flux, stored intracellular Ca++ ion concentrations, Ca++ ion pump activity, Ca++ ion flow into cell, Ca++ ion flow out of cells, the activation of Ca++ sensitive proteins, the activation of Ca++ sensitive signaling pathways, the activation of kinase-activatible proteins, and the activation of kinase-dependent signaling pathways.

The TRP-PLIK2c polynucleotides and polypeptides of the present invention, including agonists and/or fragments thereof, have uses that include modulating proliferation, differentiation, migration, and activation in various cells, tissues, and organisms, and particularly in mammalian bone marrow, kidney, testis, liver, small intestine, spinal cord, prostate, uterus, lung, lymph node, stomach, heart, brain, thymus, and pancreas, preferably human. TRP-PLIK2c polynucleotides and polypeptides of the present invention, including agonists and/or fragments thereof, may be useful in diagnosing, treating, prognosing, and/or preventing immune, hematopoietic, renal, reproductive, hepatic, and/or proliferative diseases or disorders, particularly of the immune system.

In addition, antagonists of the TRP-PLIK2c polynucleotides and polypeptides may have uses that include diagnosing, treating, prognosing, and/or preventing diseases or disorders related to transient receptor potential channel activity, which may include immune, hematopoietic, renal, reproductive, hepatic, and/or proliferative diseases or disorders.

Although it is believed the encoded polypeptide may share at least some biological activities with transient receptor potential channel family members, particularly those from CHAK1, a number of methods of determining the exact biological function of this clone are either known in the art or are described elsewhere herein. Briefly, the function of this clone may be determined by applying microarray methodology. Nucleic acids corresponding to the TRP-PLIK2c polynucleotides, in addition to, other clones of the present invention, may be arrayed on microchips for expression profiling. Depending on which polynucleotide probe is used to hybridize to the slides, a change in expression of a specific gene may provide additional insight into the function of this gene based upon the conditions being studied. For example, an observed increase or decrease in expression levels when the polynucleotide probe used comes from tissue that has been treated with known immunoglobulin inhibitors, which include, but are not limited to the drugs listed herein or otherwise known in the art, might indicate a function in modulating immunoglobulin function, for example. In the case of TRP-PLIK2c, bone marrow, kidney, testis, liver, small intestine, spinal cord, prostate, uterus, lung, lymph node, stomach, heart, brain, thymus, and/or pancrease, should be used to extract RNA to prepare the probe.

In addition, the function of the protein may be assessed by applying quantitative PCR methodology, for example. Real time quantitative PCR would provide the capability of following the expression of the TRP-PLIK2c gene throughout development, for example. Quantitative PCR methodology requires only a nominal amount of tissue from each developmentally important step is needed to perform such experiments. Therefore, the application of quantitative PCR methodology to refining the biological function of this polypeptide is encompassed by the present invention. Also encompassed by the present invention are quantitative PCR probes corresponding to the polynucleotide sequence provided as SEQ ID NO:5 (FIGS. 3A-G).

The function of the protein may also be assessed through complementation assays in yeast. For example, in the case of the TRP-PLIK2c, transforming yeast deficient in transient receptor potential channel activity with TRP-PLIK2c and assessing their ability to grow would provide convincing evidence the TRP-PLIK2c polypeptide has transient receptor potential channel activity. Additional assay conditions and methods that may be used in assessing the function of the polynucleotides and polypeptides of the present invention are known in the art, some of which are disclosed elsewhere herein.

Alternatively, the biological function of the encoded polypeptide may be determined by disrupting a homologue of this polypeptide in Mice and/or rats and observing the resulting phenotype.

Moreover, the biological function of this polypeptide may be determined by the application of antisense and/or sense methodology and the resulting generation of transgenic mice and/or rats. Expressing a particular gene in either sense or antisense orientation in a transgenic mouse or rat could lead to respectively higher or lower expression levels of that particular gene. Altering the endogenous expression levels of a gene can lead to the observation of a particular phenotype that can then be used to derive indications on the function of the gene. The gene can be either over-expressed or under expressed in every cell of the organism at all times using a strong ubiquitous promoter, or it could be expressed in one or more discrete parts of the organism using a well characterized tissue-specific promoter (e.g., a bone marrow, kidney, testis, liver, small intestine, spinal cord, prostate, uterus, lung, lymph node, stomach, heart, brain, thymus, and/or pancrease-specific promoter), or it can be expressed at a specified time of development using an inducible and/or a developmentally regulated promoter.

In the case of TRP-PLIK2c transgenic mice or rats, if no phenotype is apparent in normal growth conditions, observing the organism under diseased conditions (immune, hematopoietic, renal, reproductive, hepatic, or proliferative disorders, etc.) may lead to understanding the function of the gene. Therefore, the application of antisense and/or sense methodology to the creation of transgenic mice or rats to refine the biological function of the polypeptide is encompassed by the present invention.

In preferred embodiments, the following N-terminal TRP-PLIK2c deletion polypeptides are encompassed by the present invention: M1-L1939, I2-L1939, I3-L1939, L4-L1939, S5-L1939, K6-L1939, S7-L1939, Q8-L1939, K9-L1939, S10-L1939, W11-L1939, I12-L1939, K13-L1939, G14-L1939, V15-L1939, F16-L1939, D17-L1939, K18-L1939, R19-L1939, E20-L1939, C21-L1939, S22-L1939, T23-L1939, I24-L1939, I25-L1939, P26-L1939, S27-L1939, S28-L1939, K29-L1939, N30-L1939, P31-L1939, H32-L1939, R33-L1939, C34-L1939, T35-L1939, P36-L1939, V37-L1939, C38-L1939, Q39-L1939, V40-L1939, C41-L1939, Q42-L1939, N43-L1939, L44-L1939, I45-L1939, R46-L1939, C47-L1939, Y48-L1939, C49-L1939, G50-L1939, R51-L1939, L52-L1939, I53-L1939, G54-L1939, D55-L1939, H56-L1939, A57-L1939, G58-L1939, I59-L1939, D60-L1939, Y61-L1939, S62-L1939, W63-L1939, T64-L1939, I65-L1939, S66-L1939, A67-L1939, A68-L1939, K69-L1939, G70-L1939, K71-L1939, E72-L1939, S73-L1939, E74-L1939, Q75-L1939, W76-L1939, S77-L1939, V78-L1939, E79-L1939, K80-L1939, H81-L1939, T82-L1939, T83-L1939, K84-L1939, S85-L1939, P86-L1939, T87-L1939, D88-L1939, T89-L1939, F90-L1939, G91-L1939, T92-L1939, I93-L1939, N94-L1939, F95-L1939, Q96-L1939, D97-L1939, G98-L1939, E99-L1939, H100-L1939, T101-L1939, H102-L1939, H103-L1939, A104-L1939, K105-L1939, Y106-L1939, I107-L1939, R108-L1939, T109-L1939, S110-L1939, Y111-L1939, D112-L1939, T113-L1939, K114-L1939, L115-L1939, D116-L1939, H117-L1939, L118-L1939, L119-L1939, H120-L1939, L121-L1939, M122-L1939, L123-L1939, K124-L1939, E125-L1939, W126-L1939, K127-L1939, M128-L1939, E129-L1939, L130-L1939, P131-L1939, K132-L1939, L133-L1939, V134-L1939, I135-L1939, S136-L1939, V137-L1939, H138-L1939, G139-L1939, G140-L1939, I141-L1939, Q142-L1939, N143-L1939, F144-L1939, T145-L1939, M146-L1939, P147-L1939, S148-L1939, K149-L1939, F150-L1939, K151-L1939, E152-L1939, I153-L1939, F154-L1939, S155-L1939, Q156-L1939, G157-L1939, L158-L1939, V159-L1939, K160-L1939, A161-L1939, A162-L1939, E163-L1939, T164-L1939, T165-L1939, G166-L1939, A167-L1939, W168-L1939, I169-L1939, I170-L1939, T171-L1939, E172-L1939, G173-L1939, I174-L1939, N175-L1939, T176-L1939, G177-L1939, V178-L1939, S179-L1939, K180-L1939, H181-L1939, V182-L1939, G183-L1939, D184-L1939, A185-L1939, L186-L1939, K187-L1939, S188-L1939, H189-L1939, S190-L1939, S191-L1939, H192-L1939, S193-L1939, L194-L1939, R195-L1939, K196-L1939, I197-L1939, W198-L1939, T199-L1939, V200-L1939, G201-L1939, I202-L1939, P203-L1939, P204-L1939, W205-L1939, G206-L1939, V207-L1939, I208-L1939, E209-L1939, N210-L1939, Q211-L1939, R212-L1939, D213-L1939, L214-L1939, I215-L1939, G216-L1939, K217-L1939, D218-L1939, V219-L1939, V220-L1939, C221-L1939, L222-L1939, Y223-L1939, Q224-L1939, T225-L1939, L226-L1939, D227-L1939, N228-L1939, P229-L1939, L230-L1939, S231-L1939, K232-L1939, L233-L1939, T234-L1939, T235-L1939, L236-L1939, N237-L1939, S238-L1939, M239-L1939, H240-L1939, S241-L1939, H242-L1939, F243-L1939, I244-L1939, L245-L1939, S246-L1939, D247-L1939, D248-L1939, G249-L1939, T250-L1939, V251-L1939, G252-L1939, K253-L1939, Y254-L1939, G255-L1939, N256-L1939, E257-L1939, M258-L1939, K259-L1939, L260-L1939, R261-L1939, R262-L1939, N263-L1939, L264-L1939, E265-L1939, K266-L1939, Y267-L1939, L268-L1939, S269-L1939, L270-L1939, Q271-L1939, K272-L1939, I273-L1939, H274-L1939, C275-L1939, R276-L1939, S277-L1939, R278-L1939, Q279-L1939, G280-L1939, V281-L1939, P282-L1939, V283-L1939, V284-L1939, G285-L1939, L286-L1939, V287-L1939, V288-L1939, E289-L1939, G290-L1939, G291-L1939, P292-L1939, N293-L1939, V294-L1939, I295-L1939, L296-L1939, S297-L1939, V298-L1939, W299-L1939, E300-L1939, T301-L1939, V302-L1939, K303-L1939, D304-L1939, K305-L1939, D306-L1939, P307-L1939, V308-L1939, V309-L1939, V310-L1939, C311-L1939, E312-L1939, G313-L1939, T314-L1939, G315-L1939, R316-L1939, A317-L1939, A318-L1939, D319-L1939, L320-L1939, L321-L1939, A322-L1939, F323-L1939, T324-L1939, H325-L1939, K326-L1939, H327-L1939, L328-L1939, A329-L1939, D330-L1939, E331-L1939, G332-L1939, M333-L1939, L334-L1939, R335-L1939, P336-L1939, Q337-L1939, V338-L1939, K339-L1939, E340-L1939, E341-L1939, I342-L1939, I343-L1939, C344-L1939, M345-L1939, I346-L1939, Q347-L1939, N348-L1939, T349-L1939, F350-L1939, N351-L1939, F352-L1939, S353-L1939, L354-L1939, K355-L1939, Q356-L1939, S357-L1939, K358-L1939, H359-L1939, L360-L1939, F361-L1939, Q362-L1939, I363-L1939, L364-L1939, M365-L1939, E366-L1939, C367-L1939, M368-L1939, V369-L1939, H370-L1939, R371-L1939, D372-L1939, C373-L1939, I374-L1939, T375-L1939, I376-L1939, F377-L1939, D378-L1939, A379-L1939, D380-L1939, S381-L1939, E382-L1939, E383-L1939, Q384-L1939, Q385-L1939, D386-L1939, L387-L1939, D388-L1939, L389-L1939, A390-L1939, I391-L1939, L392-L1939, T393-L1939, A394-L1939, L395-L1939, L396-L1939, K397-L1939, G398-L1939, T399-L1939, N400-L1939, L401-L1939, S402-L1939, A403-L1939, S404-L1939, E405-L1939, Q406-L1939, L407-L1939, N408-L1939, L409-L1939, A410-L1939, M411-L1939, A412-L1939, W413-L1939, D414-L1939, R415-L1939, V416-L1939, D417-L1939, I418-L1939, A419-L1939, K420-L1939, K421-L1939, H422-L1939, I423-L1939, L424-L1939, I425-L1939, Y426-L1939, E427-L1939, Q428-L1939, H429-L1939, W430-L1939, K431-L1939, P432-L1939, D433-L1939, A434-L1939, L435-L1939, E436-L1939, Q437-L1939, A438-L1939, M439-L1939, S440-L1939, D441-L1939, A442-L1939, L443-L1939, V444-L1939, M445-L1939, D446-L1939, R447-L1939, V448-L1939, D449-L1939, F450-L1939, V451-L1939, K452-L1939, L453-L1939, L454-L1939, I455-L1939, E456-L1939, Y457-L1939, G458-L1939, V459-L1939, N460-L1939, L461-L1939, H462-L1939, R463-L1939, F464-L1939, L465-L1939, T466-L1939, I467-L1939, P468-L1939, R469-L1939, L470-L1939, E471-L1939, E472-L1939, L473-L1939, Y474-L1939, N475-L1939, T476-L1939, K477-L1939, Q478-L1939, G479-L1939, P480-L1939, T481-L1939, N482-L1939, T483-L1939, L484-L1939, L485-L1939, H486-L1939, H487-L1939, L488-L1939, V489-L1939, Q490-L1939, D491-L1939, V492-L1939, K493-L1939, and/or Q494-L1939 of SEQ ID NO:6. Polynucleotide sequences encoding these polypeptides are also provided. The present invention also encompasses the use of these N-terminal TRP-PLIK2c deletion polypeptides as immunogenic and/or antigenic epitopes as described elsewhere herein.

In preferred embodiments, the following C-terminal TRP-PLIK2c deletion polypeptides are encompassed by the present invention: M1-L1939, M1-Q1938, M1-M1937, M1-D1936, M1-D1935, M1-E1934, M1-P1933, M1-S1932, M1-N1931, M1-R1930, M1-G1929, M1-T1928, M1-E1927, M1-R1926, M1-A1925, M1-P1924, M1-P1923, M1-E1922, M1-E1921, M1-A1920, M1-S1919, M1-E1918, M1-I1917, M1-K1916, M1-I1915, M1-E1914, M1-L1913, M1-G1912, M1-F1911, M1-T1910, M1-S1909, M1-N1908, M1-I1907, M1-R1906, M1-E1905, M1-P1904, M1-S1903, M1-Y1902, M1-D1901, M1-N1900, M1-R1899, M1-K1898, M1-L1897, M1-D1896, M1-P1895, M1-L1894, M1-K1893, M1-L1892, M1-K1891, M1-R1890, M1-C1889, M1-C1888, M1-S1887, M1-N1886, M1-C1885, M1-H1884, M1-H1883, M1-K1882, M1-A1881, M1-I1880, M1-F1879, M1-N1878, M1-R1877, M1-I1876, M1-A1875, M1-D1874, M1-E1873, M1-G1872, M1-L1871, M1-N1870, M1-A1869, M1-P1868, M1-G1867, M1-F1866, M1-V1865, M1-M1864, M1-G1863, M1-R1862, M1-S1861, M1-Q1860, M1-K1859, M1-V1858, M1-E1857, M1-P1856, M1-K1855, M1-I1854, M1-V1853, M1-S1852, M1-P1851, M1-D1850, M1-T1849, M1-L1848, M1-N1847, M1-E1846, M1-G1845, M1-V1844, M1-G1843, M1-Q1842, M1-L1841, M1-D1840, M1-L1839, M1-V1838, M1-L1837, M1-L1836, M1-E1835, M1-G1834, M1-R1833, M1-T1832, M1-Y1831, M1-E1830, M1-Y1829, M1-T1828, M1-W1827, M1-H1826, M1-S1825, M1-F1824, M1-A1823, M1-L1822, M1-M1821, M1-L1820, M1-E1819, M1-E1818, M1-L1817, M1-T1816, M1-N1815, M1-T1814, M1-P1813, M1-T1812, M1-I1811, M1-E1810, M1-D1809, M1-G1808, M1-N1807, M1-N1806, M1-N1805, M1-N1804, M1-Y1803, M1-K1802, M1-R1801, M1-F1800, M1-E1799, M1-G1798, M1-T1797, M1-M1796, M1-Y1795, M1-K1794, M1-E1793, M1-I1792, M1-T1791, M1-L1790, M1-W1789, M1-Q1788, M1-N1787, M1-A1786, M1-S1785, M1-H1784, M1-C1783, M1-Y1782, M1-I1781, M1-L1780, M1-F1779, M1-V1778, M1-E1777, M1-L1776, M1-F1775, M1-R1774, M1-P1773, M1-T1772, M1-Y1771, M1-P1770, M1-I1769, M1-M1768, M1-Q1767, M1-P1766, M1-K1765, M1-V1764, M1-Q1763, M1-N1762, M1-F1761, M1-T1760, M1-Y1759, M1-I1758, M1-L1757, M1-K1756, M1-Q1755, M1-A1754, M1-A1753, M1-R1752, M1-Q1751, M1-Q1750, M1-Q1749, M1-I1748, M1-E1747, M1-R1746, M1-L1745, M1-C1744, M1-L1743, M1-H1742, M1-L1741, M1-V1740, M1-T1739, M1-S1738, M1-E1737, M1-Q1736, M1-F1735, M1-I1734, M1-K1733, M1-H1732, M1-W1731, M1-T1730, M1-R1729, M1-V1728, M1-V1727, M1-E1726, M1-P1725, M1-L1724, M1-F1723, M1-S1722, M1-K1721, M1-V1720, M1-I1719, M1-F1718, M1-V1717, M1-Q1716, M1-G1715, M1-P1714, M1-K1713, M1-L1712, M1-I1711, M1-D1710, M1-D1709, M1-E1708, M1-S1707, M1-W1706, M1-T1705, M1-S1704, M1-V1703, M1-V1702, M1-R1701, M1-M1700, M1-A1699, M1-K1698, M1-R1697, M1-L1696, M1-G1695, M1-G1694, M1-D1693, M1-M1692, M1-E1691, M1-E1690, M1-R1689, M1-S1688, M1-L1687, M1-V1686, M1-Q1685, M1-I1684, M1-M1683, M1-A1682, M1-A1681, M1-R1680, M1-G1679, M1-R1678, M1-Q1677, M1-S1676, M1-W1675, M1-S1674, M1-S1673, M1-M1672, M1-S1671, M1-K1670, M1-D1669, M1-L1668, M1-N1667, M1-L1666, M1-P1665, M1-S1664, M1-S1663, M1-E1662, M1-E1661, M1-L1660, M1-R1659, M1-Y1658, M1-V1657, M1-T1656, M1-I1655, M1-E1654, M1-E1653, M1-G1652, M1-A1651, M1-F1650, M1-L1649, M1-Q1648, M1-V1647, M1-P1646, M1-T1645, M1-F1644, M1-P1643, M1-I1642, M1-T1641, M1-Q1640, M1-S1639, M1-L1638, M1-R1637, M1-M1636, M1-L1635, M1-N1634, M1-N1633, M1-R1632, M1-E1631, M1-I1630, M1-A1629, M1-S1628, M1-Y1627, M1-H1626, M1-H1625, M1-H1624, M1-P1623, M1-E1622, M1-Q1621, M1-P1620, M1-S1619, M1-K1618, M1-L1617, M1-S1616, M1-A1615, M1-S1614, M1-I1613, M1-K1612, M1-D1611, M1-V1610, M1-G1609, M1-I1608, M1-S1607, M1-S1606, M1-K1605, M1-L1604, M1-L1603, M1-S1602, M1-N1601, M1-R1600, M1-N1599, M1-L1598, M1-N1597, M1-T1596, M1-S1595, M1-R1594, M1-S1593, M1-N1592, M1-W1591, M1-L1590, M1-S1589, M1-N1588, M1-K1587, M1-S1586, M1-L1585, M1-D1584, M1-E1583, M1-Q1582, M1-S1581, M1-Q1580, M1-K1579, M1-L1578, M1-Y1577, M1-D1576, M1-S1575, M1-I1574, M1-Q1573, M1-I1572, M1-A1571, M1-C1570, M1-Q1569, M1-S1568, M1-I1567, M1-E1566, M1-K1565, M1-T1564, M1-K1563, M1-M1562, M1-K1561, M1-Q1560, M1-H1559, M1-I1558, M1-Y1557, M1-P1556, M1-E1555, M1-V1554, M1-G1553, M1-T1552, M1-H1551, M1-S1550, M1-F1549, M1-K1548, M1-S1547, M1-V1546, M1-T1545, M1-F1544, M1-W1543, M1-N1542, M1-K1541, M1-S1540, M1-Y1539, M1-E1538, M1-E1537, M1-E1536, M1-S1535, M1-I1534, M1-S1533, M1-N1532, M1-E1531, M1-G1530, M1-P1529, M1-E1528, M1-P1527, M1-N1526, M1-L1525, M1-Q1524, M1-D1523, M1-S1522, M1-Q1521, M1-S1520, M1-C1519, M1-A1518, M1-N1517, M1-V1516, M1-T1515, M1-I1514, M1-I1513, M1-P1512, M1-V1511, M1-Q1510, M1-L1509, M1-G1508, M1-Q1507, M1-T1506, M1-N1505, M1-K1504, M1-K1503, M1-K1502, M1-K1501, M1-S1500, M1-L1499, M1-R1498, M1-R1497, M1-D1496, M1-K1495, M1-T1494, M1-L1493, M1-M1492, M1-K1491, M1-A1490, M1-K1489, M1-V1488, M1-W1487, M1-A1486, M1-G1485, M1-Q1484, M1-G1483, M1-I1482, M1-E1481, M1-S1480, M1-S1479, M1-G1478, M1-S1477, M1-L1476, M1-N1475, M1-K1474, M1-I1473, M1-K1472, M1-C1471, M1-I1470, M1-K1469, M1-M1468, M1-L1467, M1-K1466, M1-E1465, M1-E1464, M1-K1463, M1-H1462, M1-F1461, M1-R1460, M1-F1459, M1-S1458, M1-H1457, M1-S1456, M1-R1455, M1-A1454, M1-F1453, M1-P1452, M1-R1451, M1-Y1450, M1-W1449, M1-R1448, M1-L1447, M1-P1446, M1-N1445, M1-I1444, M1-W1443, M1-F1442, M1-S1441, M1-T1440, M1-N1439, M1-P1438, M1-Q1437, M1-L1436, M1-W1435, M1-P1434, M1-G1433, M1-V1432, M1-E1431, M1-S1430, M1-C1429, M1-E1428, M1-S1427, M1-S1426, M1-Q1425, M1-A1424, M1-S1423, M1-R1422, M1-T1421, M1-S1420, M1-N1419, M1-D1418, M1-S1417, M1-L1416, M1-S1415, M1-S1414, M1-D1413, M1-Q1412, M1-A1411, M1-Q1410, M1-K1409, M1-Q1408, M1-H1407, M1-Q1406, M1-E1405, M1-S1404, M1-R1403, M1-S1402, M1-S1401, M1-D1400, M1-S1399, M1-D1398, M1-C1397, M1-T1396, M1-S1395, M1-P1394, M1-L1393, M1-C1392, M1-T1391, M1-Q1390, M1-W1389, M1-K1388, M1-K1387, M1-K1386, M1-I1385, M1-S1384, M1-F1383, M1-V1382, M1-G1381, M1-T1380, M1-E1379, M1-D1378, M1-G1377, M1-E1376, M1-S1375, M1-F1374, M1-A1373, M1-W1372, M1-N1371, M1-V1370, M1-Y1369, M1-G1368, M1-G1367, M1-G1366, M1-T1365, M1-Q1364, M1-M1363, M1-I1362, M1-K1361, M1-A1360, M1-Q1359, M1-S1358, M1-L1357, M1-P1356, M1-S1355, M1-S1354, M1-M1353, M1-T1352, M1-M1351, M1-P1350, M1-E1349, M1-P1348, M1-M1347, M1-C1346, M1-S1345, M1-L1344, M1-T1343, M1-P1342, M1-L1341, M1-V1340, M1-Q1339, M1-E1338, M1-A1337, M1-K1336, M1-D1335, M1-Q1334, M1-G1333, M1-D1332, M1-L1331, M1-L1330, M1-H1329, M1-A1328, M1-I1327, M1-P1326, M1-E1325, M1-H1324, M1-K1323, M1-E1322, M1-K1321, M1-P1320, M1-E1319, M1-D1318, M1-V1317, M1-S1316, M1-A1315, M1-W1314, M1-D1313, M1-S1312, M1-V1311, M1-V1310, M1-P1309, M1-T1308, M1-Q1307, M1-G1306, M1-T1305, M1-L1304, M1-H1303, M1-V1302, M1-L1301, M1-V1300, M1-E1299, M1-T1298, M1-Q1297, M1-I1296, M1-D1295, M1-Q1294, M1-E1293, M1-T1292, M1-A1291, M1-L1290, M1-V1289, M1-D1288, M1-P1287, M1-V1286, M1-S1285, M1-P1284, M1-R1283, M1-S1282, M1-L1281, M1-P1280, M1-L1279, M1-V1278, M1-T1277, M1-E1276, M1-A1275, M1-S1274, M1-F1273, M1-P1272, M1-V1271, M1-R1270, M1-K1269, M1-L1268, M1-N1267, M1-S1266, M1-P1265, M1-V1264, M1-L1263, M1-L1262, M1-F1261, M1-Q1260, M1-G1259, M1-Y1258, M1-K1257, M1-S1256, M1-H1255, M1-A1254, M1-Q1253, M1-R1252, M1-N1251, M1-P1250, M1-V1249, M1-V1248, M1-G1247, M1-S1246, M1-V1245, M1-V1244, M1-I1243, M1-S1242, M1-S1241, M1-Q1240, M1-T1239, M1-E1238, M1-Q1237, M1-R1236, M1-E1235, M1-Q1234, M1-D1233, M1-N1232, M1-R1231, M1-V1230, M1-N1229, M1-T1228, M1-A1227, M1-E1226, M1-R1225, M1-K1224, M1-S1223, M1-N1222, M1-T1221, M1-I1220, M1-E1219, M1-L1218, M1-L1217, M1-A1216, M1-G1215, M1-R1214, M1-Q1213, M1-V1212, M1-R1211, M1-P1210, M1-P1209, M1-H1208, M1-R1207, M1-G1206, M1-G1205, M1-A1204, M1-L1203, M1-S1202, M1-R1201, M1-L1200, M1-L1199, M1-S1198, M1-S1197, M1-P1196, M1-M1195, M1-S1194, M1-Y1193, M1-Y1192, M1-Q1191, M1-Y1190, M1-K1189, M1-K1188, M1-E1187, M1-G1186, M1-A1185, M1-I1184, M1-E1183, M1-M1182, M1-S1181, M1-G1180, M1-L1179, M1-V1178, M1-E1177, M1-A1176, M1-C1175, M1-I1174, M1-V1173, M1-N1172, M1-S1171, M1-W1170, M1-S1169, M1-H1168, M1-P1167, M1-L1166, M1-K1165, M1-K1164, M1-C1163, M1-T1162, M1-S1161, M1-H1160, M1-K1159, M1-R1158, M1-K1157, M1-A1156, M1-L1155, M1-L1154, M1-A1153, M1-E1152, M1-D1151, M1-E1150, M1-Q1149, M1-L1148, M1-T1147, M1-D1146, M1-V1145, M1-A1144, M1-S1143, M1-L1142, M1-V1141, M1-K1140, M1-L1139, M1-T1138, M1-D1137, M1-V1136, M1-T1135, M1-L1134, M1-A1133, M1-S1132, M1-L1131, M1-D1130, M1-Q1129, M1-L1128, M1-H1127, M1-G1126, M1-V1125, M1-Q1124, M1-S1123, M1-D1122, M1-L1121, M1-S1120, M1-L1119, M1-L1118, M1-S1117, M1-D1116, M1-K1115, M1-I1114, M1-F1113, M1-S1112, M1-V1111, M1-K1110, M1-E1109, M1-N1108, M1-M1107, M1-E1106, M1-K1105, M1-L1104, M1-Q1103, M1-F1102, M1-Y1101, M1-M1100, M1-E1099, M1-T1098, M1-V1097, M1-R1096, M1-E1095, M1-S1094, M1-T1093, M1-V1092, M1-R1091, M1-I1090, M1-R1089, M1-E1088, M1-E1087, M1-C1086, M1-S1085, M1-C1084, M1-N1083, M1-V1082, M1-D1081, M1-E1080, M1-M1079, M1-K1078, M1-E1077, M1-H1076, M1-F1075, M1-Y1074, M1-K1073, M1-E1072, M1-V1071, M1-C1070, M1-Q1069, M1-E1068, M1-E1067, M1-F1066, M1-D1065, M1-H1064, M1-L1063, M1-K1062, M1-K1061, M1-L1060, M1-D1059, M1-E1058, M1-K1057, M1-S1056, M1-L1055, M1-Y1054, M1-L1053, M1-K1052, M1-L1051, M1-G1050, M1-V1049, M1-D1048, M1-G1047, M1-E1046, M1-E1045, M1-Q1044, M1-D1043, M1-H1042, M1-P1041, M1-A1040, M1-R1039, M1-H1038, M1-C1037, M1-C1036, M1-L1035, M1-R1034, M1-R1033, M1-L1032, M1-L1031, M1-L1030, M1-G1029, M1-V1028, M1-H1027, M1-S1026, M1-L1025, M1-L1024, M1-I1023, M1-L1022, M1-P1021, M1-P1020, M1-P1019, M1-L1018, M1-W1017, M1-P1016, M1-K1015, M1-E1014, M1-H1013, M1-Y1012, M1-T1011, M1-M1010, M1-I1009, M1-Y1008, M1-R1007, M1-Y1006, M1-R1005, M1-N1004, M1-Y1003, M1-K1002, M1-W1001, M1-L1000, M1-N999, M1-N998, M1-S997, M1-I996, M1-S995, M1-E994, M1-M993, M1-D992, M1-L991, M1-Y990, M1-V989, M1-N988, M1-N987, M1-F986, M1-F985, M1-A984, M1-I983, M1-L982, M1-L981, M1-N980, M1-V979, M1-M978, M1-I977, M1-I976, M1-Y975, M1-Q974, M1-V973, M1-F972, M1-L971, M1-Y970, M1-V969, M1-A968, M1-Q967, M1-L966, M1-F965, M1-P964, M1-T963, M1-L962, M1-F961, M1-S960, M1-G959, M1-P958, M1-P957, M1-C956, M1-S955, M1-P954, M1-Q953, M1-S952, M1-S951, M1-C950, M1-V949, M1-D948, M1-I947, M1-E946, M1-G945, M1-A944, M1-Y943, M1-V942, M1-E941, M1-G940, M1-Y939, M1-I938, M1-M937, M1-W936, M1-Y935, M1-P934, M1-E933, M1-F932, M1-V931, M1-I930, M1-D929, M1-R928, M1-A927, M1-L926, M1-S925, M1-W924, M1-S923, M1-P922, M1-P921, M1-E920, M1-K919, M1-P918, M1-Y917, M1-L916, M1-I915, M1-A914, M1-K913, M1-R912, M1-A911, M1-V910, M1-G909, M1-F908, M1-S907, M1-L906, M1-L905, M1-V904, M1-I903, M1-A902, M1-M901, M1-I900, M1-I899, M1-V898, M1-I897, M1-Y896, M1-F895, M1-M894, M1-N893, M1-A892, M1-T891, M1-M890, M1-K889, M1-A888, M1-I887, M1-M886, M1-T885, M1-V884, M1-Y883, M1-P882, M1-G881, M1-A880, M1-H879, M1-Q878, M1-N877, M1-V876, M1-A875, M1-F874, M1-F873, M1-D872, M1-L871, M1-L870, M1-R869, M1-S868, M1-F867, M1-W866, M1-F865, M1-I864, M1-I863, M1-D862, M1-I861, M1-C860, M1-Y859, M1-I858, M1-L857, M1-R856, M1-G855, M1-A854, M1-T853, M1-H852, M1-F851, M1-P850, M1-P849, M1-D848, M1-G847, M1-W846, M1-R845, M1-L844, M1-V843, M1-F842, M1-G841, M1-A840, M1-S839, M1-F838, M1-L837, M1-G836, M1-I835, M1-A834, M1-V833, M1-T832, M1-E831, M1-T830, M1-L829, M1-N828, M1-W827, M1-Y826, M1-E825, M1-S824, M1-I823, M1-W822, M1-V821, M1-K820, M1-V819, M1-K818, M1-Q817, M1-T816, M1-F815, M1-K814, M1-G813, M1-P812, M1-E811, M1-S810, M1-I809, M1-C808, M1-I807, M1-E806, M1-R805, M1-V804, M1-V803, M1-E802, M1-I801, M1-A800, M1-N799, M1-T798, M1-F797, M1-I796, M1-Y795, M1-I794, M1-S793, M1-V792, M1-L791, M1-W790, M1-E789, M1-Q788, M1-V787, M1-S786, M1-P785, M1-Q784, M1-P783, M1-Q782, M1-M781, M1-E780, M1-V779, M1-L778, M1-V777, M1-T776, M1-Y775, M1-T774, M1-F773, M1-L772, M1-M771, M1-L770, M1-F769, M1-A768, M1-L767, M1-Y766, M1-A765, M1-M764, M1-T763, M1-Y762, M1-F761, M1-W760, M1-F759, M1-K758, M1-V757, M1-I756, M1-P755, M1-A754, M1-S753, M1-Y752, M1-F751, M1-E750, M1-Y749, M1-V748, M1-K747, M1-R746, M1-T745, M1-W744, M1-P743, M1-L742, M1-H741, M1-Q740, M1-H739, M1-G738, M1-S737, M1-E736, M1-L735, M1-G734, M1-F733, M1-H732, M1-Q731, M1-N730, M1-E729, M1-D728, M1-L727, M1-K726, M1-E725, M1-D724, M1-H723, M1-G722, M1-R721, M1-E720, M1-L719, M1-D718, M1-Y717, M1-E716, M1-K715, M1-V714, M1-S713, M1-A712, M1-S711, M1-E710, M1-K709, M1-S708, M1-S707, M1-S706, M1-A705, M1-N704, M1-Q703, M1-D702, M1-S701, M1-Y700, M1-Y699, M1-W698, M1-M697, M1-F696, M1-Q695, M1-F694, M1-D693, M1-Q692, M1-S691, M1-Q690, M1-P689, M1-V688, M1-H687, M1-S686, M1-M685, M1-E684, M1-A683, M1-K682, M1-S681, M1-K680, M1-F679, M1-E678, M1-L677, M1-T676, M1-L675, M1-I674, M1-T673, M1-P672, M1-P671, M1-L670, M1-I669, M1-I668, M1-S667, M1-I666, M1-I665, M1-I664, M1-K663, M1-L662, M1-W661, M1-S660, M1-N659, M1-K658, M1-R657, M1-M656, M1-K655, M1-L654, M1-R653, M1-G652, M1-M651, M1-W650, M1-M649, M1-D648, M1-T647, M1-L646, M1-L645, M1-M644, M1-Q643, M1-T642, M1-C641, M1-T640, M1-H639, M1-S638, M1-V637, M1-F636, M1-P635, M1-R634, M1-L633, M1-G632, M1-G631, M1-S630, M1-V629, M1-A628, M1-L627, M1-K626, M1-L625, M1-C624, M1-T623, M1-S622, M1-N621, M1-S620, M1-W619, M1-N618, M1-R617, M1-L616, M1-E615, M1-Y614, M1-T613, M1-L612, M1-L611, M1-T610, M1-M609, M1-A608, M1-M607, M1-R606, M1-E605, M1-N604, M1-Q603, M1-K602, M1-F601, M1-A600, M1-K599, M1-E598, M1-L597, M1-L596, M1-D595, M1-L594, M1-A593, M1-L592, M1-Q591, M1-G590, M1-F589, M1-Q588, M1-K587, M1-S586, M1-Y585, M1-N584, M1-K583, M1-L582, M1-E581, M1-E580, M1-S579, M1-A578, M1-S577, M1-D576, M1-V575, M1-M574, M1-H573, M1-S572, M1-E571, M1-K570, M1-A569, M1-E568, M1-H567, M1-A566, M1-M565, M1-A564, M1-R563, M1-Y562, M1-L561, M1-I560, M1-C559, M1-A558, M1-I557, M1-V556, M1-A555, M1-K554, M1-V553, M1-T552, M1-A551, M1-E550, M1-E549, M1-G548, M1-H547, M1-Q546, M1-W545, M1-F544, M1-F543, M1-M542, M1-A541, M1-M540, M1-K539, M1-Q538, M1-R537, M1-K536, M1-M535, M1-L534, M1-V533, M1-A532, M1-W531, M1-V530, M1-L529, M1-L528, M1-D527, M1-N526, M1-Y525, M1-P524, M1-Y523, M1-L522, M1-F521, M1-G520, M1-T519, M1-S518, M1-E517, M1-P516, M1-D515, M1-D514, M1-S513, M1-V512, M1-N511, M1-Q510, M1-E509, M1-K508, M1-S507, M1-K506, M1-K505, M1-R504, M1-S503, M1-K502, M1-H501, M1-L500, M1-V499, M1-I498, M1-S497, M1-K496, and/or M1-E495 of SEQ ID NO:6. Polynucleotide sequences encoding these polypeptides are also provided. The present invention also encompasses the use of these C-terminal TRP-PLIK2c deletion polypeptides as immunogenic and/or antigenic epitopes as described elsewhere herein.

Alternatively, preferred polypeptides of the present invention may comprise polypeptide sequences corresponding to, for example, internal regions of the TRP-PLIK2c polypeptide (e.g., any combination of both N- and C-terminal TRP-PLIK2c polypeptide deletions) of SEQ ID NO:6. For example, internal regions could be defined by the equation: amino acid NX to amino acid CX, wherein NX refers to any N-terminal deletion polypeptide amino acid of TRP-PLIK2c (SEQ ID NO:6), and where CX refers to any C-terminal deletion polypeptide amino acid of TRP-PLIK2c (SEQ ID NO:6). Polynucleotides encoding these polypeptides are also provided. The present invention also encompasses the use of these polypeptides as an immunogenic and/or antigenic epitope as described elsewhere herein.

The TRP-PLIK2c polypeptides of the present invention were determined to comprise several phosphorylation sites based upon the Motif algorithm (Genetics Computer Group, Inc.). The phosphorylation of such sites may regulate some biological activity of the TRP-PLIK2c polypeptide. For example, phosphorylation at specific sites may be involved in regulating the proteins ability to associate or bind to other molecules (e.g., proteins, ligands, substrates, DNA, etc.). In the present case, phosphorylation may modulate the ability of the TRP-PLIK2c polypeptide to associate with other potassium channel alpha subunits, beta subunits, or its ability to modulate potassium channel function.

The TRP-PLIK2c polypeptide was predicted to comprise twenty eight PKC phosphorylation sites using the Motif algorithm (Genetics Computer Group, Inc.). In vivo, protein kinase C exhibits a preference for the phosphorylation of serine or threonine residues. The PKC phosphorylation sites have the following consensus pattern: [ST]-x-[RK], where S or T represents the site of phosphorylation and 'x' an intervening amino acid residue. Additional information regarding PKC phosphorylation sites can be found in Woodget J. R., Gould K. L., Hunter T., Eur. J. Biochem. 161:177-184 (1986), and Kishimoto A., Nishiyama K., Nakanishi H., Uratsuji Y., Nomura H., Takeyama Y., Nishizuka Y., J. Biol. Chem. . . . 260:12492-12499 (1985); which are hereby incorporated by reference herein.

In preferred embodiments, the following PKC phosphorylation site polypeptides are encompassed by the present invention: IILSKSQKSWIKG (SEQ ID NO:165), STIIPSSKNPHRC (SEQ ID NO:166), SVEKHTTKSPTDT (SEQ ID NO:167), SHSSHSLRKIWTV (SEQ ID NO:168), LSVWETVKDKDPV (SEQ ID NO:169), VVCEGTGRAADLL (SEQ ID NO:170), DLLAFTHKHLADE (SEQ ID NO:171), NTFNFSLKQSKHL (SEQ ID NO:172), IVLHKSRKKSKEQ (SEQ ID NO:173), HGEEATVKAVIAC (SEQ ID NO:174), DQNASSSKESASV (SEQ ID NO:175), SKESASVKEYDLE (SEQ ID NO:176), QHLPWTRKVYEFY (SEQ ID NO:177), EPGKFTQKVKVWI (SEQ ID NO:178), RKAILSPKEPPSW (SEQ ID NO:179), RIRVTSERVTEMY (SEQ ID NO:180), ALTVDTLKVLSAV (SEQ ID NO:181), KRKHSTCKKLPHS (SEQ ID NO:182), LEITNSKREATNV (SEQ ID NO:183), ETGVFSIKKKWQT (SEQ ID NO:184), TCDSDSSRSEQHQ (SEQ ID NO:185), SLSDNSTRSAQSS (SEQ ID NO:186), FARSHSFRFHKEE (SEQ ID NO:187), KDRRLSKKKKNTQ (SEQ ID NO:188), DKISASLKSPQEP (SEQ ID NO:189), SMSSWSQRGRAAM (SEQ ID NO:190), QTIPYTPRFLEVF (SEQ ID NO:191), and/or PPARETGRNSPED (SEQ ID NO:192). Polynucleotides encoding these polypeptides are also provided. The present invention also encompasses the use of these TRP-PLIK2c PKC phosphorylation site polypeptides as immunogenic and/or antigenic epitopes as described elsewhere herein.

The present invention also encompasses immunogenic and/or antigenic epitopes of the TRP-PLIK2c polypeptide.

The TRP-PLIK2c polypeptide has been shown to comprise fifteen glycosylation sites according to the Motif algorithm (Genetics Computer Group, Inc.). As discussed more specifically herein, protein glycosylation is thought to serve a variety of functions including: augmentation of protein folding, inhibition of protein aggregation, regulation of intracellular trafficking to organelles, increasing resistance to proteolysis, modulation of protein antigenicity, and mediation of intercellular adhesion.

Asparagine phosphorylation sites have the following consensus pattern, N-{P}-[ST]-{P}, wherein N represents the glycosylation site. However, it is well known that that potential N-glycosylation sites are specific to the consensus sequence Asn-Xaa-Ser/Thr. However, the presence of the consensus tripeptide is not sufficient to conclude that an asparagine residue is glycosylated, due to the fact that the folding of the protein plays an important role in the regulation of N-glycosylation. It has been shown that the presence of proline between Asn and Ser/Thr will inhibit N-glycosylation; this has been confirmed by a recent statistical analysis of glycosylation sites, which also shows that about 50% of the sites that have a proline C-terminal to Ser/Thr are not glycosylated. Additional information relating to asparagine glycosylation may be found in reference to the following publications, which are hereby incorporated by reference herein: Marshall R. D., Annu. Rev. Biochem. 41:673-702 (1972); Pless D. D., Lennarz W. J., Proc. Natl. Acad. Sci. U.S.A. 74:134-138 (1977); Bause E., Biochem. J. 209:331-336 (1983); Gavel Y., von Heijne G., Protein Eng. 3:433-442 (1990); and Miletich J. P., Broze G. J. Jr., J. Biol. Chem. . . . 265:11397-11404 (1990).

In preferred embodiments, the following asparagine glycosylation site polypeptides are encompassed by the present invention: HGGIQNFTMPSKFK (SEQ ID NO:193), IQNTFNFSLKQSKH (SEQ ID NO:194), LLKGTNLSASEQLN (SEQ ID NO:195), KSKEQNVSDDPEST (SEQ ID NO:196), SEELKNYSKQFGQL (SEQ ID NO:197), TYELRNWSNSTCLK (SEQ ID NO:198), LRNWSNSTCLKLAV (SEQ ID NO:199), YYSDQNASSSKESA (SEQ ID NO:200), ISEYWNLTETVAIG (SEQ ID NO:201), KMEDVNCSCEERIR (SEQ ID NO:202), SSLSDNSTRSAQSS (SEQ ID NO:203), PWLQPNTSFWINPL (SEQ ID NO:204), ICKIKNLSGSSEIG (SEQ ID NO:205), QGVGENLTDPSVIK (SEQ ID NO:206), and/or SPERINSTFGLEIK (SEQ ID NO:207). Polynucleotides encoding these polypeptides are also provided. The present invention also encompasses the use of these TRP-PLIK2c asparagine glycosylation site polypeptides as immunogenic and/or antigenic epitopes as described elsewhere herein.

Many polynucleotide sequences, such as EST sequences, are publicly available and accessible through sequence databases. Some of these sequences are related to SEQ ID NO:5 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides consisting of a nucleotide sequence described by the general formula of a-b, where a is any integer between 1 to 5806 of SEQ ID NO:5, b is an integer between 15 to 5820, where both a and b correspond to the positions of nucleotide residues shown in SEQ ID NO:5, and where b is greater than or equal to a+14.

Features of the Polypeptide Encoded by Gene No:4

The polypeptide of this gene provided as SEQ ID NO:8 (FIGS. 4A-G), encoded by the polynucleotide sequence according to SEQ ID NO:7 (FIGS. 4A-G), and/or encoded by the polynucleotide contained within the deposited clone, TRP-PLIK2d, has significant homology at the nucleotide and amino acid level to the human channel-kinase 1 protein, also known as the human CHAK1 or TRP-PLIKB1 protein (CHAK1; GENBANK® Accession No. gi|AF346629; SEQ ID NO:9); and the human melastatin 1 protein (Melastatin1; GENBANK® Accession No. gi|3243075; SEQ ID NO:260). An alignment of the TRP-PLIK2d polypeptide with this protein is provided in FIGS. 5A-F.

The TRP-PLIK2d polypeptide was determined to share 57.9% identity and 65.7% similarity with the human CHAK1 or TRP-PLIKB1 protein (CHAK1; GENBANK® Accession No. gi|AF346629; SEQ ID NO:9); and was determined to share 48.0% identity and 58.4% similarity with the human melastatin 1 protein (Melastatin1; GENBANK® Accession No. gi|3243075; SEQ ID NO:260) as shown in FIG. 9.

The CHAK1 protein is believed to represent a member of a new class of protein kinases referred to as alpha kinases (Curr. Biol. 9 (2), R43-R45 (1999)). These kinases represent a novel type of signaling molecule comprising both a catalytic protein kinase domain, in addition to, an ion channel domain.

The melastatin1 protein is believed to be negatively associated with the incidence of melanoma based upon its inverse correlative expression in highly aggressive melanomas (Genomics 54 (1), 116-123 (1998)). Thus, overexpression of melastatin1 could represent a novel therapeutic in the treatment of melanoma and potentially other cancers.

Based upon the observed homology, the polypeptide of the present invention is expected to share at least some biological activity with other transient receptor potential channel family members, more specifically with the CHAK1 and melastatin1 proteins, in addition to, other transient receptor potential channel family members referenced elsewhere herein or otherwise known in the art.

The TRP-PLIK2d (SEQ ID NO:8) polypeptide represents a novel splice variant form of the TRP-PLIK2 (SEQ ID NO:2) polypeptide of the present invention.

Most of the known transient receptor potential channel family members, possess one or more transmembrane domains. Likewise, the TRP-PLIK2d polypeptide has been determined to comprise six transmembrane domains (TM1-TM6) as shown in FIGS. 4A-G. The transmembrane domains are located from about amino acid 740 to about amino acid 757 (TM1), from about amino acid 834 to about amino acid 845 (TM2), from about amino acid 861 to about amino acid 880 (TM3), from about amino acid 892 to about amino acid 909 (TM4), from about amino acid 925 to about amino acid 946 (TM5), and/or from about amino acid 996 to about amino acid 1026 (TM6) of SEQ ID NO:8. In this context, the term "about" may be construed to mean 1, 2, 3, 4, 5, 6, 7, 8, 9, or 10 amino acids beyond the N-Terminus and/or C-terminus of the above referenced polypeptide.

In preferred embodiments, the following transmembrane domain polypeptides are encompassed by the present invention: LKIIISIILPPTILTLEF (SEQ ID NO:208), IVKFW-FYTICIS (SEQ ID NO:209), YWNLTETVAIGLFSAG-FVLR (SEQ ID NO:210), LIYCIDIIFWFSRLLDFF (SEQ ID NO:211), MTANMFYIVIIMAIVLLSFGVA (SEQ ID NO:212), and/or FLTPFLQAVYLFVQYIIMVNLLIAFFN-NVYL (SEQ ID NO:213). Polynucleotides encoding these polypeptides are also provided. The present invention also encompasses the use of the TRP-PLIK2d transmembrane polypeptides as immunogenic and/or antigenic epitopes as described elsewhere herein.

In preferred embodiments, the present invention encompasses the use of N-terminal deletions, C-terminal deletions, or any combination of N-terminal and C-terminal deletions of any one or more of the TRP-PLIK2d TM1 thru TM6 transmembrane domain polypeptides as antigenic and/or immunogenic epitopes.

In preferred embodiments, the present invention also encompasses the use of N-terminal deletions, C-terminal deletions, or any combination of N-terminal and C-terminal deletions of any one or more of the amino acids intervening (i.e., ion channel extracellular or intracellular loops) the TRP-PLIK2d TM1 thru TM6 transmembrane domain polypeptides as antigenic and/or immunogenic epitopes.

The TRP-PLIK2d polypeptide was determined to comprise several conserved cysteines, at amino acid 21, 34, 38, 41, 47, 49, 311, 367, 637, 702, 719, 895. 985, 991, 1071, 1105, 1779, 1818, 1920, 1923, and 1924 of SEQ ID No:8 (FIGS. 4A-G). Conservation of cysteines at key amino acid residues is indicative of conserved structural features, which may correlate with conservation of protein function and/or activity.

In confirmation of the TRP-PLIK2d representing a member of the transient receptor channel family, the TRP-PLIK2d polypeptide was determined to comprise a predicted TRP domain (LWKYNR) located from about amino acid 1035 to about amino acid 1040 of SEQ ID NO:8. In this context, the term "about" may be construed to mean 1, 2, 3, 4, 5, 6, 7, 8, 9, or 10 amino acids beyond the N-Terminus and/or C-terminus of the above referenced polypeptide.

In further confirmation of the TRP-PLIK2d representing a member of the transient receptor channel family, the TRP-PLIK2d polypeptide was determined to comprise a predicted ion transport signature domain located at about amino acid 904 to about amino acid 959 of SEQ ID NO:8. In this context, the term "about" may be construed to mean 1, 2, 3, 4, 5, 6, 7, 8, 9, or 10 amino acids beyond the N-Terminus and/or C-terminus of the above referenced polypeptide.

The TRP-PLIK2d polypeptide was determined to comprise a predicted nucleotide binding domain located from about amino acid 1902 to about amino acid 1907 of SEQ ID NO:8. In this context, the term "about" may be construed to mean 1, 2, 3, 4, 5, 6, 7, 8, 9, or 10 amino acids beyond the N-Terminus and/or C-terminus of the above referenced polypeptide.

In addition, the TRP-PLIK2d polypeptide was determined to comprise a predicted zinc finger domain located at about amino acid 1917 to about amino acid 1927 of SEQ ID NO:8.

In this context, the term "about" may be construed to mean 1, 2, 3, 4, 5, 6, 7, 8, 9, or 10 amino acids beyond the N-Terminus and/or C-terminus of the above referenced polypeptide.

TRP-PLIK2d polypeptides and polynucleotides are useful for diagnosing diseases related to the over and/or under expression of TRP-PLIK2d by identifying mutations in the TRP-PLIK2d gene using TRP-PLIK2d sequences as probes or by determining TRP-PLIK2d protein or mRNA expression levels. TRP-PLIK2d polypeptides will be useful in screens for compounds that affect the activity of the protein. TRP-PLIK2d peptides can also be used for the generation of specific antibodies and as bait in yeast two hybrid screens to find proteins the specifically interact with TRP-PLIK2d.

Expression profiling designed to measure the steady state mRNA levels encoding the TRP-PLIK2 polypeptide showed predominately high expression levels in bone marrow, kidney, and testis. The TRP-PLIK2 polypeptide was also significantly expressioned in liver, and to a lesser extent, in small intestine, spinal cord, prostate, uterus, lung, lymph node, stomach, heart, brain, thymus, and pancrease (as shown in FIG. 7). The tissue expression of TRP-PLIK2d may follow the same pattern as for the TRP-PLIK2 polypeptide of the present invention.

Expanded analysis of TRP-PLIK2 expression levels by TAQMAN® quantitative PCR (see FIG. 12) confirmed that the TRP-PLIK2 polypeptide is expressed in kidney, colon, and testis (FIG. 7). TRP-PLIK2 mRNA was expressed predominately in the lower gastrointestinal tract, specifically the ileum, the rectum, the colon, the jejunum, and to a lesser extent in the duodenum and stomach. Significant expression was observed in the kidney, particularly in the cortex, followed by the medulla, and to a lesser extent in the testis, pelvis, and bone marrow (mononuclear cells).

Furthermore, an expanded analysis of TRP-PLIK2 expression levels in various tumor and normal tissues by TAQMAN® quantitative PCR (see FIG. 14) showed TRP-PLIK2 mRNA was differentially expressed to the greatest extent in prostate tumor tissue relative to normal prostate tissue (approximately 20 fold difference). Significant differential expression was also observed in the testicular tumor tissue relative to normal testicular tissue.

In preferred embodiments, TRP-PLIK2d polynucleotides and polypeptides, including fragments thereof, are useful for treating, diagnosing, and/or ameliorating proliferative disorders, cancers, ischemia-reperfusion injury, heart failure, immuno compromised conditions, HIV infection, and renal diseases.

Moreover, TRP-PLIK2d polynucleotides and polypeptides, including fragments thereof, are useful for increasing NF-kB activity, increasing apoptotic events, and/or decreasing IkBa expression or activity levels.

In preferred embodiments, antagonists directed against TRP-PLIK2d are useful for treating, diagnosing, and/or ameliorating autoimmune disorders, disorders related to hyper immune activity, inflammatory conditions, disorders related to aberrant acute phase responses, hypercongenital conditions, birth defects, necrotic lesions, wounds, organ transplant rejection, conditions related to organ transplant rejection, disorders related to aberrant signal transduction, proliferating disorders, cancers, HIV, and HIV propagation in cells infected with other viruses.

Moreover, antagonists directed against TRP-PLIK2d are useful for decreasing NF-kB activity, decreasing apoptotic events, and/or increasing IkBa expression or activity levels.

In preferred embodiments, agonists directed against TRP-PLIK2d are useful for treating, diagnosing, and/or ameliorating autoimmune disorders, disorders related to hyper immune activity, hypercongenital conditions, birth defects, necrotic lesions, wounds, disorders related to aberrant signal transduction, immuno compromised conditions, HIV infection, proliferating disorders, and/or cancers.

Moreover, agonists directed against TRP-PLIK2d are useful for increasing NF-kB activity, increasing apoptotic events, and/or decreasing IkBa expression or activity levels.

The strong homology to transient receptor potential channels (TRP), combined with the predominate localized expression of the TRP-PLIK2 polypeptide in the lower gastrointestinal tract, specifically the ileum, the rectum, the colon, the jejunum, and to a lesser extent in the duodenum and stomach, suggests the TRP-PLIK2d polynucleotides and polypeptides may be useful in treating, diagnosing, prognosing, and/or preventing gastrointestinal diseases and/or disorders, which include, but are not limited to, ulcers, irritable bowel syndrome, inflammatory bowel disease, diarrhea, traveler's diarrhea, drug-related diarrhea polyps, absorption disorders, constipation, diverticulitis, vascular disease of the intestines, intestinal obstruction, intestinal infections, ulcerative colitis, Shigellosis, cholera, Crohn's Disease, amebiasis, enteric fever, Whipple's Disease, peritonitis, intraabdominal abscesses, hereditary hemochromatosis, gastroenteritis, viral gastroenteritis, food poisoning, mesenteric ischemia, mesenteric infarction, in addition to, metabolic diseases and/or disorders.

Moreover, polynucleotides and polypeptides, including fragments and/or antagonists thereof, have uses which include, directly or indirectly, treating, preventing, diagnosing, and/or prognosing susceptibility to the following, non-limiting, gastrointestinal infections: *Salmonella infection*, *E. coli infection*, *E. coli O157:H7 infection*, Shiga Toxin-producing *E. coli* infection, *Campylobacter* infection (e.g., *Campylobacter fetus, Campylobacter upsaliensis, Campylobacter hyointestinalis, Campylobacter lari, Campylobacter jejuni, Campylobacter concisus, Campylobacter mucosalis, Campylobacter sputorum, Campylobacter rectus, Campylobacter curvus, Campylobacter sputorum*, etc.), *Heliobacter* infection (e.g., *Heliobacter cinaedi, Heliobacter fennelliae*, etc.) *Yersinia enterocolitica* infection, *Vibrio* sp. Infection (e.g., *Vibrio mimicus, Vibrio parahaemolyticus, Vibrio fluvialis, Vibrio furnissii, Vibrio hollisae, Vibrio vulnificus, Vibrio alginolyticus, Vibrio metschnikovii, Vibrio damsela, Vibrio cincinnatiensis*, etc.) *Aeromonas* infection (e.g., *Aeromonas hydrophila, Aeromonas sobira, Aeromonas caviae*, etc.), *Plesiomonas shigelliodes* infection, *Giardia* infection (e.g., *Giardia lamblia*, etc.), *Cryptosporidium* infection, *Listeria* infection, *Entamoeba histolytica* infection, Rotavirus infection, Norwalk virus infection, *Clostridium difficile* infection, *Clostriudium perfringens* infection, *Staphylococcus* infection, *Bacillus* infection, in addition to any other gastrointestinal disease and/or disorder implicated by the causative agents listed above or elsewhere herein.

The strong homology to human transient receptor potential channels (TRP), combined with the localized expression of the TRP-PLIK2 polypeptide in kidney tissue suggests the TRP-PLIK2d polynucleotides and polypeptides may be useful in treating, diagnosing, prognosing, and/or preventing renal diseases and/or disorders, which include, but are not limited to: nephritis, renal failure, nephrotic syndrome, urinary tract infection, hematuria, proteinuria, oliguria, polyuria, nocturia, edema, hypertension, electrolyte disorders, sterile pyuria, renal osteodystrophy, large kidneys, renal transport defects, nephrolithiasis, azotemia, anuria, urinary retention, slowing of urinary stream, large prostate, flank tenderness, full bladder sensation after voiding, enuresis, dysuria, bacteriuria, kidney stones, glomerulonephritis, vasculitis, hemolytic uremic syndromes, thrombotic thrombocytopenic purpura, malignant hypertension, casts, tubulointerstitial kidney diseases, renal tubular acidosis, pyelonephritis, hydronephritis, nephrotic syndrome, crush syndrome, and/or renal colic, in addition to Wilm's Tumor Disease, and congenital kidney abnormalities such as horseshoe kidney, polycystic kidney, and Falconi's syndrome for example.

Several known TRP family members have been identified that are expressed significantly in kidney tissue. These TRP family members include, for example, Trp12 (Wissenbach, U., Bodding, M., Freichel, M., Flockerzi, V, Lett., 485(2-3): 127-34, (2000)); OTRPC4 (Strotmann, R., Harteneck, C., Nunnenmacher, K., Schultz, G., Plant, T, D, Nat, Cell, Biol., 2(10):695-702, (2000)); polycystin-L2 (Guo, L., Schreiber, T, H., Weremowicz, S., Morton, C, C., Lee, C., Zhou, J. Genomics., 64(3):241-51, (2000)); and EcaC (Hoenderop, J. G., van, der, Kemp, A, W., Hartog, A., van, de, Graaf, S, F., van, Os, C, H., Willems, P, H., Bindels, R, J. J. Biol, Chem., 274(13):8375-8, (1999)).

Thus, the TRP-PLIK2d polynucleotides and polypeptides are expected to share at least some biological activity with TRP family members expressed in kidney cells and tissues, particularly those specifically referenced herein.

The strong homology to human transient receptor potential channels (TRP), combined with the localized expression of the TRP-PLIK2 polypeptide in bone marrow tissue suggests the TRP-PLIK2d polynucleotides and polypeptides may be useful in treating, diagnosing, prognosing, and/or preventing immune diseases and/or disorders. Representative uses are described in the "Immune Activity", "Chemotaxis", and "Infectious Disease" sections below, and elsewhere herein. Briefly, the strong expression in immune tissue indicates a role in regulating the proliferation; survival; differentiation; and/or activation of hematopoietic cell lineages, including blood stem cells.

The TRP-PLIK2d polypeptide may also be useful as a preventative agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's disease, and scleroderma. The TRP-PLIK2 polypeptide may be useful for modulating cytokine production, antigen presentation, or other processes, such as for boosting immune responses, etc.

Moreover, the protein may represent a factor that influences the differentiation or behavior of other blood cells, or that recruits hematopoietic cells to sites of injury. Thus, this gene product is thought to be useful in the expansion of stem cells and committed progenitors of various blood lineages, and in the differentiation and/or proliferation of various cell types. Furthermore, the protein may also be used to determine biological activity, raise antibodies, as tissuemarkers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Significantly, TRP-PLIK2d is believed to represent the first TRP family member expressed in bone marrow tissue.

The strong homology to human transient receptor potential channels (TRP), combined with the localized expression of TRP-PLIK in testis tissue emphasizes the potential utility for TRP-PLIK2d polynucleotides and polypeptides in treating, diagnosing, prognosing, and/or preventing testicular, in addition to reproductive disorders.

In preferred embodiments, TRP-PLIK2d polynucleotides and polypeptides including agonists, antagonists, and/or fragments thereof, have uses which include treating, diagnosing, prognosing, and/or preventing the following, non-limiting, diseases or disorders of the testis: spermatogenesis, infertility, Klinefelter's syndrome, XX male, epididymitis, genital warts, germinal cell aplasia, cryptorchidism, varicocele, immotile cilia syndrome, and viral orchitis. The TRP-PLIK2d polynucleotides and polypeptides including agonists, antagonists, and/or fragments thereof, may also have uses related to modulating testicular development, embryogenesis, reproduction, and in ameliorating, treating, and/or preventing testicular proliferative disorders (e.g., cancers, which include, for example, choriocarcinoma, Nonseminoma, seminona, and testicular germ cell tumors).

Likewise, the localized expression in testis tissue also emphasizes the potential utility for TRP-PLIK2d polynucleotides and polypeptides in treating, diagnosing, prognosing, and/or preventing metabolic diseases and disorders which include the following, not limiting examples: premature puberty, incomplete puberty, Kallman syndrome, Cushing's syndrome, hyperprolactinemia, hemochromatosis, congenital adrenal hyperplasia, FSH deficiency, and granulomatous disease, for example.

This gene product may also be useful in assays designed to identify binding agents, as such agents (antagonists) are useful as male contraceptive agents. The testes are also a site of active gene expression of transcripts that is expressed, particularly at low levels, in other tissues of the body. Therefore, this gene product may be expressed in other specific tissues or organs where it may play related functional roles in other processes, such as hematopoiesis, inflammation, bone formation, and kidney function, to name a few possible target indications.

Several known TRP family members have been identified that are expressed significantly in testis tissue. These TRP family members include, for example, polycystin-L2 (Guo, L., Schreiber, T, H., Weremowicz, S., Morton, C, C., Lee, C., Zhou, J. Genomics., 64(3):241-51, (2000)); TRP7 (Okada, T., Inoue, R., Yamazaki, K., Maeda, A., Kurosaki, T., Yamakuni, T., Tanaka, I., Shimizu, S., Ikenaka, K., Imoto, K., Mori, Y, J. Biol, Chem., 274(39):27359-70, (1999)); btrp2 (Wissenbach, U., Schroth, G., Philipp, S., Flockerzi, V, Lett., 429(1):61-6, (1998)); Htrp-1 (Zhu, X., Chu, P, B., Peyton, M., Birnbaumer, L, Lett., 373(3):193-8, (1995)); and TRPC1 (Wes, P, D., Chevesich, J., Jeromin, A., Rosenberg, C., Stetten, G., Montell, C, Proc, Natl, Acad, Sci, U.S.A., 92(21):9652-6, (1995)).

Thus, the TRP-PLIK2d polynucleotides and polypeptides are expected to share at least some biological activity with TRP family members expressed in testis cells and tissues, particularly those specifically referenced herein.

The predominate differential expression of TRP-PLIK2 in prostate tumor relative to normal prostate tissue strongly suggests TRP-PLIK2d polynucleotides and polypeptides including agonists, antagonists, and/or fragments thereof, have uses which include treating, diagnosing, prognosing, and/or preventing prostate cancers and/or proliferative conditions.

Alternatively, the tissue distribution of TRP-PLIK2 in liver indicates the protein product of the TRP-PLIK2d clone would be useful for the detection and treatment of liver disorders and cancers. Representative uses are described in the "Hyperproliferative Disorders", "Infectious Disease", and "Binding Activity" sections below, and elsewhere herein. Briefly, the protein can be used for the detection, treatment, and/or prevention of hepatoblastoma, jaundice, hepatitis, liver metabolic diseases and conditions that are attributable to the differentiation of hepatocyte progenitor cells, cirrhosis, hepatic cysts, pyrogenic abscess, amebic abscess, hydatid cyst, cystadenocarcinoma, adenoma, focal nodular hyperplasia, hemangioma, hepatocellular carcinoma, cholangiocarcinoma, angiosarcoma, and granulomatous liver disease.

Moreover, polynucleotides and polypeptides, including fragments and/or antagonists thereof, have uses which include, directly or indirectly, treating, preventing, diagnosing, and/or prognosing the following, non-limiting, hepatic infections: liver disease caused by sepsis infection, liver disease caused by bacteremia, liver disease caused by Pneomococcal pneumonia infection, liver disease caused by Toxic shock syndrome, liver disease caused by Listeriosis, liver disease caused by Legionnaries' disease, liver disease caused by Brucellosis infection, liver disease caused by *Neisseria gonorrhoeae* infection, liver disease caused by *Yersinia* infection, liver disease caused by Salmonellosis, liver disease caused by Nocardiosis, liver disease caused by Spirochete infection, liver disease caused by *Treponema pallidum* infection, liver disease caused by Brrelia burgdorferi infection, liver disease caused by Leptospirosis, liver disease caused by *Coxiella burnetii* infection, liver disease caused by *Rickettsia richettsii* infection, liver disease caused by *Chlamydia trachomatis* infection, liver disease caused by *Chlamydia psittaci* infection, in addition to any other hepatic disease and/or disorder implicated by the causative agents listed above or elsewhere herein.

As described elsewhere herein, transient receptor potential channel family members have been implicated in modulating cell proliferation, differentiation, migration, activation, exocytosis, muscle contraction, gene expression, apoptosis. signalling, pheromone sensory signaling, smooth muscle tone, pain perception, heat perception, osmosenstivity, and mechanosensitivity. Moreover, transient receptor potential channel family members have been implicated in disorders of the skin, skeletal-muscle, nervous, cardiac, and vascular systems, in addition to the following, non-limiting diseases and disorders, which include, for example, arteriosclerosis, neointimal hyperplasia, metastatic melanomas, bipolar disorder, nonsyndromic hereditary deafness, Knobloch syndrome, holosencephaly, and various malignancies including prostate cancer.

In preferred embodiments, TRP-PLIK2d polynucleotides and polypeptides of the present invention, including agonists and/or fragments thereof, have uses that include, modulating cell proliferation, differentiation, migration, activation, exocytosis, muscle contraction, gene expression, apoptosis. signalling, pheromone sensory signaling, smooth muscle tone, pain perception, heat perception, osmosenstivity, and mechanosensitivity.

In more preferred embodiments, TRP-PLIK2d polynucleotides and polypeptides of the present invention, including agonists and/or fragments thereof, have uses that include, treating, ameliorating, preventing, detecting, and/or prognosing various diseases and disorders, particularly the following, non-limiting examples, disorders of the skin, skeletal-muscle, nervous, cardiac, and vascular systems, in addition to the following, non-limiting diseases and disorders, which include, for example, arteriosclerosis, neointimal hyperplasia, metastatic melanomas, bipolar disorder, nonsyndromic hereditary deafness, Knobloch syndrome, holosencephaly, and various malignancies including prostate cancer.

TRP-PLIK2d polynucleotides and polypeptides of the present invention, including agonists and/or fragments may be involved in intracellular $Ca^{2+}$ homeostasis which affects various aspects of biological functions including mechanoregulation, pain transduction, vasorelaxation, gene expression, cell cycle and proliferation/apoptosis. Since TRP-PLIK2 is dominantly expressed in bone marrow, the TRP-PLIK2d splice variant may play an important role in regulating cytosolic $Ca^{2+}$ in immune system.

The TRP-PLIK2 gene maps to chromosome 9q21.2-22.1. This region is linked to amyotrophic lateral sclerosis with frontotemporal dementia, early-onset pulverulent cataract, infantile nephronophthisis, hypomagnesemia with secondary hypocalcemia and familial hemophagocytic lymphohistiocytosis. Therefore, agonists and/or antagonists of the novel TRP-PLIK2d splice variant can be used to treat diseases including various forms of neuronal degeneration, neurogenic inflammation, allergy, immunodeficiency/excessive immune activation, visual defects, hearing disorder, pain, cancer, hypertension and other cardiovascular diseases. In addition, the therapeutics may be useful in the treatment of diseases associated with disturbances in $Ca^{2+}$ homeostasis including osteoporosis, hypercalciuric stone disease, and chronic renal failure.

In addition, TRP-PLIK2d polynucleotides and polypeptides of the present invention, including agonists and/or fragments thereof, have uses that include modulating intracellular Ca++ ion concentrations, Ca++ ion flux, stored intracellular Ca++ ion concentrations, Ca++ ion pump activity, Ca++ ion flow into cell, Ca++ ion flow out of cells, the activation of Ca++ sensitive proteins, the activation of Ca++ sensitive signaling pathways, the activation of kinase-activatible proteins, and the activation of kinase-dependent signaling pathways.

The TRP-PLIK2d polynucleotides and polypeptides of the present invention, including agonists and/or fragments thereof, have uses that include modulating proliferation, differentiation, migration, and activation in various cells, tissues, and organisms, and particularly in mammalian bone marrow, kidney, testis, liver, small intestine, spinal cord, prostate, uterus, lung, lymph node, stomach, heart, brain, thymus, and pancreas, preferably human. TRP-PLIK2d polynucleotides and polypeptides of the present invention, including agonists and/or fragments thereof, may be useful in diagnosing, treating, prognosing, and/or preventing immune, hematopoietic, renal, reproductive, hepatic, and/or proliferative diseases or disorders, particularly of the immune system.

In addition, antagonists of the TRP-PLIK2d polynucleotides and polypeptides may have uses that include diagnosing, treating, prognosing, and/or preventing diseases or disorders related to transient receptor potential channel activity, which may include immune, hematopoietic, renal, reproductive, hepatic, and/or proliferative diseases or disorders.

Although it is believed the encoded polypeptide may share at least some biological activities with transient receptor potential channel family members, particularly those from CHAK1, a number of methods of determining the exact biological function of this clone are either known in the art or are described elsewhere herein. Briefly, the function of this clone may be determined by applying microarray methodology. Nucleic acids corresponding to the TRP-PLIK2d polynucleotides, in addition to, other clones of the present invention, may be arrayed on microchips for expression profiling. Depending on which polynucleotide probe is used to hybridize to the slides, a change in expression of a specific gene may provide additional insight into the function of this gene based upon the conditions being studied. For example, an observed increase or decrease in expression levels when the polynucleotide probe used comes from tissue that has been treated with known immunoglobulin inhibitors, which include, but are not limited to the drugs listed herein or otherwise known in the art, might indicate a function in modulating immunoglobulin function, for example. In the case of TRP-PLIK2d, bone marrow, kidney, testis, liver, small intestine, spinal cord, prostate, uterus, lung, lymph node, stomach, heart, brain, thymus, and/or pancrease, should be used to extract RNA to prepare the probe.

In addition, the function of the protein may be assessed by applying quantitative PCR methodology, for example. Real time quantitative PCR would provide the capability of following the expression of the TRP-PLIK2d gene throughout development, for example. Quantitative PCR methodology requires only a nominal amount of tissue from each developmentally important step is needed to perform such experiments. Therefore, the application of quantitative PCR methodology to refining the biological function of this polypeptide is encompassed by the present invention. Also encompassed by the present invention are quantitative PCR probes corresponding to the polynucleotide sequence provided as SEQ ID NO:7 (FIGS. 4A-G).

The function of the protein may also be assessed through complementation assays in yeast. For example, in the case of the TRP-PLIK2d, transforming yeast deficient in transient receptor potential channel activity with TRP-PLIK2d and assessing their ability to grow would provide convincing evidence the TRP-PLIK2d polypeptide has transient receptor potential channel activity. Additional assay conditions and methods that may be used in assessing the function of the polynucleotides and polypeptides of the present invention are known in the art, some of which are disclosed elsewhere herein.

Alternatively, the biological function of the encoded polypeptide may be determined by disrupting a homologue of this polypeptide in Mice and/or rats and observing the resulting phenotype.

Moreover, the biological function of this polypeptide may be determined by the application of antisense and/or sense methodology and the resulting generation of transgenic mice and/or rats. Expressing a particular gene in either sense or antisense orientation in a transgenic mouse or rat could lead to respectively higher or lower expression levels of that particular gene. Altering the endogenous expression levels of a gene can lead to the observation of a particular phenotype that can then be used to derive indications on the function of the gene. The gene can be either over-expressed or under expressed in every cell of the organism at all times using a strong ubiquitous promoter, or it could be expressed in one or more discrete parts of the organism using a well characterized tissue-specific promoter (e.g., a bone marrow, kidney, testis, liver, small intestine, spinal cord, prostate, uterus, lung, lymph node, stomach, heart, brain, thymus, and/or pancrease-specific promoter), or it can be expressed at a specified time of development using an inducible and/or a developmentally regulated promoter.

In the case of TRP-PLIK2d transgenic mice or rats, if no phenotype is apparent in normal growth conditions, observing the organism under diseased conditions (immune, hematopoietic, renal, reproductive, hepatic, or proliferative disorders, etc.) may lead to understanding the function of the gene. Therefore, the application of antisense and/or sense methodology to the creation of transgenic mice or rats to refine the biological function of the polypeptide is encompassed by the present invention.

In preferred embodiments, the following N-terminal TRP-PLIK2d deletion polypeptides are encompassed by the present invention: M1-L1974, I2-L1974, I3-L1974, L4-L1974, S5-L1974, K6-L1974, S7-L1974, Q8-L1974, K9-L1974, S10-L1974, W11-L1974, I12-L1974, K13-L1974, G14-L1974, V15-L1974, F16-L1974, D17-L1974, K18-L1974, R19-L1974, E20-L1974, C21-L1974, S22-L1974, T23-L1974, I24-L1974, I25-L1974, P26-L1974, S27-L1974, S28-L1974, K29-L1974, N30-L1974, P31-L1974, H32-L1974, R33-L1974, C34-L1974, T35-L1974, P36-L1974, V37-L1974, C38-L1974, Q39-L1974, V40-L1974, C41-L1974, Q42-L1974, N43-L1974, L44-L1974, I45-L1974, R46-L1974, C47-L1974, Y48-L1974, C49-L1974, G50-L1974, R51-L1974, L52-L1974, I53-L1974, G54-L1974, D55-L1974, H56-L1974, A57-L1974, G58-L1974, I59-L1974, D60-L1974, Y61-L1974, S62-L1974, W63-L1974, T64-L1974, I65-L1974, S66-L1974, A67-L1974, A68-L1974, K69-L1974, G70-L1974, K71-L1974, E72-L1974, S73-L1974, E74-L1974, Q75-L1974, W76-L1974, S77-L1974, V78-L1974, E79-L1974, K80-L1974, H81-L1974, T82-L1974, T83-L1974, K84-L1974, S85-L1974, P86-L1974, T87-L1974, D88-L1974, T89-L1974, F90-L1974, G91-L1974, T92-L1974, I93-L1974, N94-L1974, F95-L1974, Q96-L1974, D97-L1974, G98-L1974, E99-L1974, H100-L1974, T101-L1974, H102-L1974, H103-L1974, A104-L1974, K105-L1974, Y106-L1974, I107-L1974, R108-L1974, T109-L1974, S110-L1974, Y111-L1974, D112-L1974, T113-L1974, K114-L1974, L115-L1974, D116-L1974, H117-L1974, L118-L1974, L119-L1974, H120-L1974, L121-L1974, M122-L1974, L123-L1974, K124-L1974, E125-L1974, W126-L1974, K127-L1974, M128-L1974, E129-L1974, L130-L1974, P131-L1974, K132-L1974, L133-L1974, V134-L1974, I135-L1974, S136-L1974, V137-L1974, H138-L1974, G139-L1974, G140-L1974, I141-L1974, Q142-L1974, N143-L1974, F144-L1974, T145-L1974, M146-L1974, P147-L1974, S148-L1974, K149-L1974, F150-L1974, K151-L1974, E152-L1974, I153-L1974, F154-L1974, S155-L1974, Q156-L1974, G157-L1974, L158-L1974, V159-L1974, K160-L1974, A161-L1974, A162-L1974, E163-L1974, T164-L1974, T165-L1974, G166-L1974, A167-L1974, W168-L1974, I169-L1974, I170-L1974, T171-L1974, E172-L1974, G173-L1974, I174-L1974, N175-L1974, T176-L1974, G177-L1974, V178-L1974, S179-L1974, K180-L1974, H181-L1974, V182-L1974, G183-L1974, D184-L1974, A185-L1974, L186-L1974, K187-L1974, S188-L1974, H189-L1974, S190-L1974, S191-L1974, H192-L1974, S193-L1974, L194-L1974, R195-L1974, K196-L1974, I197-L1974, W198-L1974, T199-L1974, V200-L1974, G201-L1974, I202-L1974, P203-L1974, P204-L1974, W205-L1974, G206-L1974, V207-L1974, I208-L1974, E209-L1974, N210-L1974, Q211-L1974, R212-L1974, D213-L1974, L214-L1974, I215-L1974, G216-L1974, K217-L1974, D218-L1974, V219-L1974, V220-L1974, C221-L1974, L222-L1974, Y223-L1974, Q224-L1974, T225-L1974, L226-L1974, D227-L1974, N228-L1974, P229-L1974, L230-L1974, S231-L1974, K232-L1974, L233-L1974, T234-L1974, T235-L1974, L236-L1974, N237-L1974, S238-L1974, M239-L1974, H240-L1974, S241-L1974, H242-L1974, F243-L1974, I244-L1974, L245-L1974, S246-L1974, D247-L1974, D248-L1974, G249-L1974, T250-L1974, V251-L1974, G252-L1974, K253-L1974, Y254-L1974, G255-L1974, N256-L1974, E257-L1974, M258-L1974, K259-L1974, L260-L1974, R261-L1974, R262-L1974, N263-L1974, L264-L1974, E265-L1974, K266-L1974, Y267-L1974, L268-L1974, S269-L1974, L270-L1974, Q271-L1974, K272-L1974, I273-L1974, H274-L1974, C275-L1974, R276-L1974, S277-L1974, R278-L1974, Q279-

L1974, G280-L1974, V281-L1974, P282-L1974, V283-L1974, V284-L1974, G285-L1974, L286-L1974, V287-L1974, V288-L1974, E289-L1974, G290-L1974, G291-L1974, P292-L1974, N293-L1974, V294-L1974, I295-L1974, L296-L1974, S297-L1974, V298-L1974, W299-L1974, E300-L1974, T301-L1974, V302-L1974, K303-L1974, D304-L1974, K305-L1974, D306-L1974, P307-L1974, V308-L1974, V309-L1974, V310-L1974, C311-L1974, E312-L1974, G313-L1974, T314-L1974, G315-L1974, R316-L1974, A317-L1974, A318-L1974, D319-L1974, L320-L1974, L321-L1974, A322-L1974, F323-L1974, T324-L1974, H325-L1974, K326-L1974, H327-L1974, L328-L1974, A329-L1974, D330-L1974, E331-L1974, G332-L1974, M333-L1974, L334-L1974, R335-L1974, P336-L1974, Q337-L1974, V338-L1974, K339-L1974, E340-L1974, E341-L1974, I342-L1974, I343-L1974, C344-L1974, M345-L1974, I346-L1974, Q347-L1974, N348-L1974, T349-L1974, F350-L1974, N351-L1974, F352-L1974, S353-L1974, L354-L1974, K355-L1974, Q356-L1974, S357-L1974, K358-L1974, H359-L1974, L360-L1974, F361-L1974, Q362-L1974, I363-L1974, L364-L1974, M365-L1974, E366-L1974, C367-L1974, M368-L1974, V369-L1974, H370-L1974, R371-L1974, D372-L1974, C373-L1974, I374-L1974, T375-L1974, I376-L1974, F377-L1974, D378-L1974, A379-L1974, D380-L1974, S381-L1974, E382-L1974, E383-L1974, Q384-L1974, Q385-L1974, D386-L1974, L387-L1974, D388-L1974, L389-L1974, A390-L1974, I391-L1974, L392-L1974, T393-L1974, A394-L1974, L395-L1974, L396-L1974, K397-L1974, G398-L1974, T399-L1974, N400-L1974, L401-L1974, S402-L1974, A403-L1974, S404-L1974, E405-L1974, Q406-L1974, L407-L1974, N408-L1974, L409-L1974, A410-L1974, M411-L1974, A412-L1974, W413-L1974, D414-L1974, R415-L1974, V416-L1974, D417-L1974, I418-L1974, A419-L1974, K420-L1974, K421-L1974, H422-L1974, I423-L1974, L424-L1974, I425-L1974, Y426-L1974, E427-L1974, Q428-L1974, H429-L1974, W430-L1974, K431-L1974, P432-L1974, D433-L1974, A434-L1974, L435-L1974, E436-L1974, Q437-L1974, A438-L1974, M439-L1974, S440-L1974, D441-L1974, A442-L1974, L443-L1974, V444-L1974, M445-L1974, D446-L1974, R447-L1974, V448-L1974, D449-L1974, F450-L1974, V451-L1974, K452-L1974, L453-L1974, L454-L1974, I455-L1974, E456-L1974, Y457-L1974, G458-L1974, V459-L1974, N460-L1974, L461-L1974, H462-L1974, R463-L1974, F464-L1974, L465-L1974, T466-L1974, I467-L1974, P468-L1974, R469-L1974, L470-L1974, E471-L1974, E472-L1974, L473-L1974, Y474-L1974, N475-L1974, T476-L1974, K477-L1974, Q478-L1974, G479-L1974, P480-L1974, T481-L1974, N482-L1974, T483-L1974, L484-L1974, L485-L1974, H486-L1974, H487-L1974, L488-L1974, V489-L1974, Q490-L1974, D491-L1974, V492-L1974, K493-L1974, Q494-L1974, H495-L1974, T496-L1974, L497-L1974, L498-L1974, S499-L1974, G500-L1974, Y501-L1974, R502-L1974, I503-L1974, T504-L1974, L505-L1974, I506-L1974, D507-L1974, I508-L1974, G509-L1974, L510-L1974, V511-L1974, V512-L1974, E513-L1974, Y514-L1974, L515-L1974, I516-L1974, G517-L1974, R518-L1974, A519-L1974, Y520-L1974, R521-L1974, S522-L1974, N523-L1974, Y524-L1974, T525-L1974, R526-L1974, K527-L1974, H528-L1974, F529-L1974, R530-L1974, A531-L1974, L532-L1974, Y533-L1974, N534-L1974, N535-L1974, L536-L1974, Y537-L1974, R538-L1974, K539-L1974, Y540-L1974, K541-L1974, H542-L1974, Q543-L1974, R544-L1974, H545-L1974, S546-L1974, S547-L1974, G548-L1974, N549-L1974, R550-L1974, N551-L1974, E552-L1974, S553-L1974, A554-L1974, E555-L1974, S556-L1974, T557-L1974, L558-L1974, H559-L1974, S560-L1974, Q561-L1974, F562-L1974, I563-L1974, R564-L1974, T565-L1974, A566-L1974, Q567-L1974, P568-L1974, Y569-L1974, K570-L1974, F571-L1974, K572-L1974, E573-L1974, K574-L1974, S575-L1974, I576-L1974, V577-L1974, L578-L1974, H579-L1974, K580-L1974, S581-L1974, R582-L1974, K583-L1974, K584-L1974, S585-L1974, K586-L1974, E587-L1974, Q588-L1974, N589-L1974, V590-L1974, S591-L1974, D592-L1974, D593-L1974, P594-L1974, E595-L1974, S596-L1974, T597-L1974, G598-L1974, F599-L1974, L600-L1974, Y601-L1974, P602-L1974, Y603-L1974, N604-L1974, D605-L1974, L606-L1974, L607-L1974, V608-L1974, W609-L1974, A610-L1974, V611-L1974, L612-L1974, M613-L1974, K614-L1974, R615-L1974, Q616-L1974, K617-L1974, M618-L1974, A619-L1974, M620-L1974, F621-L1974, F622-L1974, W623-L1974, Q624-L1974, H625-L1974, G626-L1974, E627-L1974, E628-L1974, A629-L1974, T630-L1974, V631-L1974, K632-L1974, A633-L1974, V634-L1974, I635-L1974, A636-L1974, C637-L1974, I638-L1974, L639-L1974, Y640-L1974, R641-L1974, A642-L1974, M643-L1974, A644-L1974, H645-L1974, E646-L1974, A647-L1974, K648-L1974, E649-L1974, S650-L1974, H651-L1974, M652-L1974, V653-L1974, D654-L1974, D655-L1974, A656-L1974, S657-L1974, E658-L1974, E659-L1974, L660-L1974, K661-L1974, N662-L1974, Y663-L1974, S664-L1974, K665-L1974, Q666-L1974, F667-L1974, G668-L1974, Q669-L1974, L670-L1974, A671-L1974, L672-L1974, D673-L1974, L674-L1974, L675-L1974, E676-L1974, K677-L1974, A678-L1974, F679-L1974, K680-L1974, Q681-L1974, N682-L1974, E683-L1974, R684-L1974, M685-L1974, A686-L1974, M687-L1974, T688-L1974, L689-L1974, L690-L1974, T691-L1974, Y692-L1974, E693-L1974, L694-L1974, R695-L1974, N696-L1974, W697-L1974, S698-L1974, N699-L1974, S700-L1974, T701-L1974, C702-L1974, L703-L1974, K704-L1974, L705-L1974, A706-L1974, V707-L1974, S708-L1974, G709-L1974, G710-L1974, L711-L1974, R712-L1974, P713-L1974, F714-L1974, V715-L1974, S716-L1974, H717-L1974, T718-L1974, C719-L1974, T720-L1974, Q721-L1974, M722-L1974, L723-L1974, L724-L1974, T725-L1974, D726-L1974, M727-L1974, W728-L1974, M729-L1974, G730-L1974, R731-L1974, L732-L1974, K733-L1974, M734-L1974, R735-L1974, K736-L1974, N737-L1974, S738-L1974, W739-L1974, L740-L1974, K741-L1974, I742-L1974, I743-L1974, I744-L1974, S745-L1974, I746-L1974, I747-L1974, L748-L1974, P749-L1974, P750-L1974, T751-L1974, I752-L1974, L753-L1974, T754-L1974, L755-L1974, E756-L1974, F757-L1974, K758-L1974, S759-L1974, K760-L1974, A761-L1974, E762-L1974, M763-L1974, S764-L1974, H765-L1974, V766-L1974, P767-L1974, Q768-L1974, S769-L1974, Q770-L1974, D771-L1974, F772-L1974, Q773-L1974, F774-L1974, M775-L1974, W776-L1974, Y777-L1974, Y778-L1974, S779-L1974, D780-L1974, Q781-L1974, N782-L1974, A783-L1974, S784-L1974, S785-L1974, S786-L1974, K787-L1974, E788-L1974, S789-L1974, A790-L1974, S791-L1974, V792-L1974, K793-L1974, E794-L1974, Y795-L1974, D796-L1974, L797-L1974, E798-L1974, R799-L1974, G800-L1974, H801-L1974, D802-L1974, E803-L1974, K804-L1974, L805-L1974, D806-L1974, E807-L1974, N808-L1974, Q809-L1974, H810-L1974, F811-L1974, G812-L1974, L813-L1974, E814-L1974, S815-L1974, G816-

L1974, H817-L1974, Q818-L1974, H819-L1974, L820-L1974, P821-L1974, W822-L1974, T823-L1974, R824-L1974, K825-L1974, V826-L1974, Y827-L1974, E828-L1974, F829-L1974, Y830-L1974, S831-L1974, A832-L1974, P833-L1974, I834-L1974, V835-L1974, K836-L1974, F837-L1974, W838-L1974, F839-L1974, Y840-L1974, and/or T841-L1974 of SEQ ID NO:8. Polynucleotide sequences encoding these polypeptides are also provided. The present invention also encompasses the use of these N-terminal TRP-PLIK2d deletion polypeptides as immunogenic and/or antigenic epitopes as described elsewhere herein.

In preferred embodiments, the following C-terminal TRP-PLIK2d deletion polypeptides are encompassed by the present invention: M1-L1974, M1-Q1973, M1-M1972, M1-D1971, M1-D1970, M1-E1969, M1-P1968, M1-S1967, M1-N1966, M1-R1965, M1-G1964, M1-T1963, M1-E1962, M1-R1961, M1-A1960, M1-P1959, M1-P1958, M1-E1957, M1-E1956, M1-A1955, M1-S1954, M1-E1953, M1-I1952, M1-K1951, M1-I1950, M1-E1949, M1-L1948, M1-G1947, M1-F1946, M1-T1945, M1-S1944, M1-N1943, M1-I1942, M1-R1941, M1-E1940, M1-P1939, M1-S1938, M1-Y1937, M1-D1936, M1-N1935, M1-R1934, M1-K1933, M1-L1932, M1-D1931, M1-P1930, M1-L1929, M1-K1928, M1-L1927, M1-K1926, M1-R1925, M1-C1924, M1-C1923, M1-S1922, M1-N1921, M1-C1920, M1-H1919, M1-H1918, M1-K1917, M1-A1916, M1-I1915, M1-F1914, M1-N1913, M1-R1912, M1-I1911, M1-A1910, M1-D1909, M1-E1908, M1-G1907, M1-L1906, M1-N1905, M1-A1904, M1-P1903, M1-G1902, M1-F1901, M1-V1900, M1-M1899, M1-G1898, M1-R1897, M1-S1896, M1-Q1895, M1-K1894, M1-V1893, M1-E1892, M1-P1891, M1-K1890, M1-I1889, M1-V1888, M1-S1887, M1-P1886, M1-D1885, M1-T1884, M1-L1883, M1-N1882, M1-E1881, M1-G1880, M1-V1879, M1-G1878, M1-Q1877, M1-L1876, M1-D1875, M1-L1874, M1-V1873, M1-L1872, M1-L1871, M1-E1870, M1-G1869, M1-R1868, M1-T1867, M1-Y1866, M1-E1865, M1-Y1864, M1-T1863, M1-W1862, M1-H1861, M1-S1860, M1-F1859, M1-A1858, M1-L1857, M1-M1856, M1-L1855, M1-E1854, M1-E1853, M1-L1852, M1-T1851, M1-N1850, M1-T1849, M1-P1848, M1-T1847, M1-I1846, M1-E1845, M1-D1844, M1-G1843, M1-N1842, M1-N1841, M1-N1840, M1-N1839, M1-Y1838, M1-K1837, M1-R1836, M1-F1835, M1-E1834, M1-G1833, M1-T1832, M1-M1831, M1-Y1830, M1-K1829, M1-E1828, M1-I1827, M1-T1826, M1-L1825, M1-W1824, M1-Q1823, M1-N1822, M1-A1821, M1-S1820, M1-H1819, M1-C1818, M1-Y1817, M1-I1816, M1-L1815, M1-F1814, M1-V1813, M1-E1812, M1-L1811, M1-F1810, M1-R1809, M1-P1808, M1-T1807, M1-Y1806, M1-P1805, M1-I1804, M1-T1803, M1-Q1802, M1-P1801, M1-K1800, M1-V1799, M1-Q1798, M1-N1797, M1-F1796, M1-T1795, M1-Y1794, M1-I1793, M1-L1792, M1-K1791, M1-Q1790, M1-A1789, M1-A1788, M1-R1787, M1-Q1786, M1-Q1785, M1-Q1784, M1-I1783, M1-E1782, M1-R1781, M1-L1780, M1-C1779, M1-L1778, M1-H1777, M1-L1776, M1-V1775, M1-T1774, M1-S1773, M1-E1772, M1-Q1771, M1-F1770, M1-I1769, M1-K1768, M1-H1767, M1-W1766, M1-T1765, M1-R1764, M1-V1763, M1-V1762, M1-E1761, M1-P1760, M1-L1759, M1-F1758, M1-S1757, M1-K1756, M1-V1755, M1-I1754, M1-F1753, M1-V1752, M1-Q1751, M1-G1750, M1-P1749, M1-K1748, M1-L1747, M1-I1746, M1-D1745, M1-D1744, M1-E1743, M1-S1742, M1-W1741, M1-T1740, M1-S1739, M1-V1738, M1-V1737, M1-R1736, M1-M1735, M1-A1734, M1-K1733, M1-R1732, M1-L1731, M1-G1730, M1-G1729, M1-D1728, M1-M1727, M1-E1726, M1-E1725, M1-R1724, M1-S1723, M1-L1722, M1-V1721, M1-Q1720, M1-I1719, M1-M1718, M1-A1717, M1-A1716, M1-R1715, M1-G1714, M1-R1713, M1-Q1712, M1-S1711, M1-W1710, M1-S1709, M1-S1708, M1-M1707, M1-S1706, M1-K1705, M1-D1704, M1-L1703, M1-N1702, M1-L1701, M1-P1700, M1-S1699, M1-S1698, M1-E1697, M1-E1696, M1-L1695, M1-R1694, M1-Y1693, M1-V1692, M1-T1691, M1-I1690, M1-E1689, M1-E1688, M1-G1687, M1-A1686, M1-F1685, M1-L1684, M1-Q1683, M1-V1682, M1-P1681, M1-T1680, M1-F1679, M1-P1678, M1-I1677, M1-T1676, M1-Q1675, M1-S1674, M1-L1673, M1-R1672, M1-M1671, M1-L1670, M1-N1669, M1-N1668, M1-R1667, M1-E1666, M1-I1665, M1-A1664, M1-S1663, M1-Y1662, M1-H1661, M1-H1660, M1-H1659, M1-P1658, M1-E1657, M1-Q1656, M1-P1655, M1-S1654, M1-K1653, M1-L1652, M1-S1651, M1-A1650, M1-S1649, M1-I1648, M1-K1647, M1-D1646, M1-V1645, M1-G1644, M1-I1643, M1-S1642, M1-S1641, M1-K1640, M1-L1639, M1-L1638, M1-S1637, M1-N1636, M1-R1635, M1-N1634, M1-L1633, M1-N1632, M1-T1631, M1-S1630, M1-R1629, M1-S1628, M1-N1627, M1-W1626, M1-L1625, M1-S1624, M1-N1623, M1-K1622, M1-S1621, M1-L1620, M1-D1619, M1-E1618, M1-Q1617, M1-S1616, M1-Q1615, M1-K1614, M1-L1613, M1-Y1612, M1-D1611, M1-S1610, M1-I1609, M1-Q1608, M1-I1607, M1-A1606, M1-C1605, M1-Q1604, M1-G1603, M1-I1602, M1-E1601, M1-K1600, M1-T1599, M1-K1598, M1-M1597, M1-K1596, M1-Q1595, M1-H1594, M1-I1593, M1-Y1592, M1-P1591, M1-E1590, M1-V1589, M1-G1588, M1-T1587, M1-H1586, M1-S1585, M1-F1584, M1-K1583, M1-S1582, M1-V1581, M1-T1580, M1-F1579, M1-W1578, M1-N1577, M1-K1576, M1-S1575, M1-Y1574, M1-E1573, M1-E1572, M1-E1571, M1-S1570, M1-I1569, M1-S1568, M1-N1567, M1-E1566, M1-G1565, M1-P1564, M1-E1563, M1-P1562, M1-N1561, M1-L1560, M1-Q1559, M1-D1558, M1-S1557, M1-Q1556, M1-S1555, M1-C1554, M1-A1553, M1-N1552, M1-V1551, M1-T1550, M1-I1549, M1-I1548, M1-P1547, M1-V1546, M1-Q1545, M1-L1544, M1-G1543, M1-Q1542, M1-T1541, M1-N1540, M1-K1539, M1-K1538, M1-K1537, M1-K1536, M1-S1535, M1-L1534, M1-R1533, M1-R1532, M1-D1531, M1-K1530, M1-T1529, M1-L1528, M1-M1527, M1-K1526, M1-A1525, M1-K1524, M1-V1523, M1-W1522, M1-A1521, M1-G1520, M1-Q1519, M1-G1518, M1-I1517, M1-E1516, M1-S1515, M1-S1514, M1-G1513, M1-S1512, M1-L1511, M1-N1510, M1-K1509, M1-I1508, M1-K1507, M1-C1506, M1-I1505, M1-K1504, M1-M1503, M1-L1502, M1-K1501, M1-E1500, M1-E1499, M1-K1498, M1-H1497, M1-F1496, M1-R1495, M1-F1494, M1-S1493, M1-H1492, M1-S1491, M1-R1490, M1-A1489, M1-F1488, M1-P1487, M1-R1486, M1-Y1485, M1-R1484, M1-R1483, M1-L1482, M1-P1481, M1-N1480, M1-I1479, M1-W1478, M1-F1477, M1-S1476, M1-T1475, M1-N1474, M1-P1473, M1-Q1472, M1-L1471, M1-W1470, M1-P1469, M1-G1468, M1-V1467, M1-E1466, M1-S1465, M1-C1464, M1-E1463, M1-S1462, M1-S1461, M1-Q1460, M1-A1459, M1-S1458, M1-R1457, M1-T1456, M1-S1455, M1-N1454, M1-D1453, M1-S1452, M1-L1451, M1-S1450, M1-S1449, M1-D1448, M1-Q1447, M1-A1446, M1-Q1445, M1-K1444, M1-Q1443, M1-H1442, M1-Q1441, M1-E1440, M1-S1439, M1-R1438, M1-S1437, M1-S1436, M1-D1435, M1-S1434, M1-D1433, M1-C1432, M1-T1431, M1-S1430, M1-P1429, M1-L1428, M1-C1427, M1-T1426, M1-Q1425, M1-W1424, M1-K1423, M1-K1422, M1-K1421, M1-I1420, M1-S1419, M1-F1418, M1-V1417, M1-G1416, M1-T1415, M1-E1414, M1-D1413, M1-G1412, M1-E1411, M1-S1410, M1-F1409, M1-A1408, M1-W1407, M1-N1406, M1-V1405, M1-Y1404, M1-G1403, M1-G1402, M1-G1401, M1-T1400, M1-Q1399, M1-M1398, M1-I1397, M1-K1396, M1-A1395, M1-Q1394, M1-S1393, M1-L1392, M1-P1391, M1-S1390, M1-S1389, M1-M1388, M1-T1387, M1-M1386, M1-P1385, M1-E1384, M1-P1383, M1-T1382, M1-C1381, M1-S1380, M1-L1379, M1-T1378, M1-P1377, M1-L1376, M1-V1375, M1-Q1374, M1-E1373, M1-A1372, M1-K1371, M1-D1370, M1-Q1369, M1-G1368, M1-D1367, M1-L1366, M1-L1365, M1-H1364, M1-A1363, M1-I1362, M1-P1361, M1-E1360, M1-H1359, M1-K1358, M1-E1357, M1-K1356, M1-P1355, M1-E1354, M1-D1353, M1-V1352, M1-S1351, M1-A1350, M1-W1349, M1-D1348, M1-S1347, M1-V1346, M1-V1345, M1-P1344, M1-T1343, M1-Q1342, M1-G1341, M1-T1340, M1-L1339, M1-H1338, M1-V1337, M1-L1336, M1-V1335, M1-E1334, M1-T1333, M1-Q1332, M1-I1331, M1-D1330, M1-Q1329, M1-E1328, M1-T1327, M1-A1326, M1-L1325, M1-V1324, M1-D1323, M1-P1322, M1-V1321, M1-S1320, M1-P1319, M1-R1318, M1-S1317, M1-L1316, M1-P1315, M1-L1314, M1-V1313, M1-T1312, M1-E1311, M1-A1310, M1-S1309, M1-F1308, M1-P1307, M1-V1306, M1-R1305, M1-K1304, M1-L1303, M1-N1302, M1-S1301, M1-P1300, M1-V1299, M1-L1298, M1-L1297, M1-F1296, M1-Q1295, M1-G1294, M1-Y1293, M1-K1292, M1-S1291, M1-H1290, M1-A1289, M1-Q1288, M1-R1287, M1-N1286, M1-P1285, M1-S1284, M1-V1283, M1-G1282, M1-S1281, M1-V1280, M1-V1279, M1-I1278, M1-S1277, M1-S1276, M1-Q1275, M1-T1274, M1-E1273, M1-Q1272, M1-R1271, M1-E1270, M1-Q1269, M1-D1268, M1-N1267, M1-R1266, M1-V1265, M1-N1264, M1-T1263, M1-A1262, M1-E1261, M1-R1260, M1-K1259, M1-S1258, M1-N1257, M1-T1256, M1-I1255, M1-E1254, M1-L1253, M1-L1252, M1-A1251, M1-G1250, M1-R1249, M1-Q1248, M1-V1247, M1-R1246, M1-P1245, M1-P1244, M1-H1243, M1-R1242, M1-G1241, M1-G1240, M1-A1239, M1-L1238, M1-S1237, M1-R1236, M1-L1235, M1-L1234, M1-S1233, M1-S1232, M1-P1231, M1-M1230, M1-S1229, M1-Y1228, M1-Y1227, M1-Q1226, M1-Y1225, M1-K1224, M1-K1223, M1-E1222, M1-G1221, M1-A1220, M1-I1219, M1-E1218, M1-M1217, M1-S1216, M1-G1215, M1-L1214, M1-V1213, M1-E1212, M1-A1211, M1-C1210, M1-I1209, M1-V1208, M1-N1207, M1-S1206, M1-W1205, M1-S1204, M1-H1203, M1-P1202, M1-L1201, M1-K1200, M1-K1199, M1-C1198, M1-T1197, M1-S1196, M1-H1195, M1-K1194, M1-R1193, M1-K1192, M1-A1191, M1-L1190, M1-L1189, M1-A1188, M1-E1187, M1-D1186, M1-E1185, M1-Q1184, M1-L1183, M1-T1182, M1-D1181, M1-V1180, M1-A1179, M1-S1178, M1-L1177, M1-V1176, M1-K1175, M1-L1174, M1-T1173, M1-D1172, M1-V1171, M1-T1170, M1-L1169, M1-A1168, M1-S1167, M1-L1166, M1-D1165, M1-Q1164, M1-L1163, M1-H1162, M1-G1161, M1-V1160, M1-Q1159, M1-S1158, M1-D1157, M1-L1156, M1-S155, M1-L1154, M1-L1153, M1-S1152, M1-D1151, M1-K1150, M1-I1149, M1-F1148, M1-S1147, M1-V1146, M1-K1145, M1-E1144, M1-N1143, M1-M1142, M1-E1141, M1-K1140, M1-L1139, M1-Q1138, M1-F1137, M1-Y1136, M1-M1135, M1-E1134, M1-T1133, M1-V1132, M1-R131, M1-E1130, M1-S1129, M1-T1128, M1-V1127, M1-R1126, M1-I1125, M1-R1124, M1-E1123, M1-E1122, M1-C1121, M1-S1120, M1-C1119, M1-N1118, M1-V1117, M1-D1116, M1-E1115, M1-M1114, M1-K1113, M1-E112, M1-H1111, M1-F1110, M1-Y1109, M1-K1108, M1-E1107, M1-V1106, M1-C1105, M1-Q1104, M1-E1103, M1-E1102, M1-F1101, M1-D1100, M1-H1099, M1-L1098, M1-K1097, M1-K1096, M1-L1095, M1-D1094, M1-E1093, M1-K1092, M1-S1091, M1-L1090, M1-Y1089, M1-L1088, M1-K1087, M1-L1086, M1-G1085, M1-V1084, M1-D1083, M1-G1082, M1-E1081, M1-E1080, M1-Q1079, M1-D1078, M1-H1077, M1-P1076, M1-A1075, M1-R1074, M1-H1073, M1-C1072, M1-C1071, M1-L1070, M1-R1069, M1-R1068, M1-L1067, M1-L1066, M1-L1065, M1-G1064, M1-V1063, M1-H1062, M1-S1061, M1-L1060, M1-L1059, M1-I1058, M1-L1057, M1-P1056, M1-P1055, M1-P1054, M1-L1053, M1-W1052, M1-P1051, M1-K1050, M1-E1049, M1-H1048, M1-Y1047, M1-T1046, M1-M1045, M1-I1044, M1-Y1043, M1-R1042, M1-Y1041, M1-R1040, M1-N1039, M1-Y1038, M1-K1037, M1-W1036, M1-L1035, M1-N1034, M1-N1033, M1-S1032, M1-I1031, M1-S1030, M1-E1029, M1-M1028, M1-D1027, M1-L1026, M1-Y1025, M1-V1024, M1-N1023, M1-N1022, M1-F1021, M1-F1020, M1-A1019, M1-I1018, M1-L1017, M1-L1016, M1-N1015, M1-V1014, M1-M1013, M1-I1012, M1-I1011, M1-Y1010, M1-Q1009, M1-V1008, M1-F1007, M1-L1006, M1-Y1005, M1-V1004, M1-A1003, M1-Q1002, M1-L1001, M1-F1000, M1-P999, M1-T998, M1-L997, M1-F996, M1-S995, M1-G994, M1-P993, M1-P992, M1-C991, M1-S990, M1-P989, M1-Q988, M1-S987, M1-S986, M1-C985, M1-V984, M1-D983, M1-I982, M1-E981, M1-G980, M1-A979, M1-Y978, M1-V977, M1-E976, M1-G975, M1-Y974, M1-I973, M1-M972, M1-W971, M1-Y970, M1-P969, M1-E968, M1-F967, M1-V966, M1-I965, M1-D964, M1-R963, M1-A962, M1-L961, M1-S960, M1-W959, M1-S958, M1-P957, M1-P956, M1-E955, M1-K954, M1-P953, M1-S952, M1-L951, M1-I950, M1-A949, M1-K948, M1-R947, M1-A946, M1-V945, M1-G944, M1-F943, M1-S942, M1-L941, M1-L940, M1-V939, M1-I938, M1-A937, M1-M936, M1-I935, M1-I934, M1-V933, M1-I932, M1-Y931, M1-F930, M1-M929, M1-N928, M1-A927, M1-T926, M1-M925, M1-K924, M1-A923, M1-I922, M1-M921, M1-T920, M1-V919, M1-Y918, M1-P917, M1-G916, M1-A915, M1-H914, M1-Q913, M1-N912, M1-V911, M1-A910, M1-F909, M1-F908, M1-D907, M1-L906, M1-L905, M1-R904, M1-S903, M1-F902, M1-W901, M1-F900, M1-I899, M1-I898, M1-D897, M1-I896, M1-C895, M1-Y894, M1-I893, M1-L892, M1-R891, M1-G890, M1-A889, M1-T888, M1-H887, M1-F886, M1-P885, M1-P884, M1-D883, M1-G882, M1-W881, M1-R880, M1-L879, M1-V878, M1-F877, M1-G876, M1-A875, M1-S874, M1-F873, M1-L872, M1-G871, M1-I870, M1-A869, M1-V868, M1-T867, M1-E866, M1-T865, M1-L864, M1-N863, M1-W862, M1-Y861, M1-E860, M1-S859, M1-I858, M1-W857, M1-V856, M1-K855, M1-V854, M1-K853, M1-Q852, M1-T851, M1-F850, M1-K849, M1-G848, M1-P847, M1-E846, M1-S845, M1-I844, M1-C843, and/or M1-I842 of SEQ ID NO:8. Polynucleotide sequences encoding these polypeptides are also provided. The present invention also encompasses the use of these C-terminal TRP-PLIK2d deletion polypeptides as immunogenic and/or antigenic epitopes as described elsewhere herein.

Alternatively, preferred polypeptides of the present invention may comprise polypeptide sequences corresponding to, for example, internal regions of the TRP-PLIK2d polypeptide (e.g., any combination of both N- and C-terminal TRP-PLIK2d polypeptide deletions) of SEQ ID NO:8. For example, internal regions could be defined by the equation: amino acid NX to amino acid CX, wherein NX refers to any N-terminal deletion polypeptide amino acid of TRP-PLIK2d (SEQ ID NO:8), and where CX refers to any C-terminal deletion polypeptide amino acid of TRP-PLIK2d (SEQ ID NO:8). Polynucleotides encoding these polypeptides are also provided. The present invention also encompasses the use of these polypeptides as an immunogenic and/or antigenic epitope as described elsewhere herein.

The TRP-PLIK2d polypeptides of the present invention were determined to comprise several phosphorylation sites based upon the Motif algorithm (Genetics Computer Group, Inc.). The phosphorylation of such sites may regulate some biological activity of the TRP-PLIK2d polypeptide. For example, phosphorylation at specific sites may be involved in regulating the proteins ability to associate or bind to other molecules (e.g., proteins, ligands, substrates, DNA, etc.). In the present case, phosphorylation may modulate the ability of the TRP-PLIK2d polypeptide to associate with other potassium channel alpha subunits, beta subunits, or its ability to modulate potassium channel function.

The TRP-PLIK2d polypeptide was predicted to comprise twenty nine PKC phosphorylation sites using the Motif algorithm (Genetics Computer Group, Inc.). In vivo, protein kinase C exhibits a preference for the phosphorylation of serine or threonine residues. The PKC phosphorylation sites have the following consensus pattern: [ST]-x-[RK], where S or T represents the site of phosphorylation and 'x' an intervening amino acid residue. Additional information regarding PKC phosphorylation sites can be found in Woodget J. R., Gould K. L., Hunter T., Eur. J. Biochem. 161:177-184 (1986), and Kishimoto A., Nishiyama K., Nakanishi H., Uratsuji Y., Nomura H., Takeyama Y., Nishizuka Y., J. Biol. Chem. . . . 260:12492-12499 (1985); which are hereby incorporated by reference herein.

In preferred embodiments, the following PKC phosphorylation site polypeptides are encompassed by the present invention: IILSKSQKSWIKG (SEQ ID NO:214), STIIPSSKNPHRC (SEQ ID NO:215), SVEKHTTKSPTDT (SEQ ID NO:216), SHSSHSLRKIWTV (SEQ ID NO:217), LSVWETVKDKDPV (SEQ ID NO:218), VVCEGTGRAADLL (SEQ ID NO:219), DLLAFTHKHLADE (SEQ ID NO:220), NTFNFSLKQSKHL (SEQ ID NO:221), YRSNYTRKHFRAL (SEQ ID NO:222), IVLHKSRKKSKEQ (SEQ ID NO:223), HGEEATVKAVIAC (SEQ ID NO:224), DQNASSSKESASV (SEQ ID NO:225), SKESASVKEYDLE (SEQ ID NO:226), QHLPWTRKVYEFY (SEQ ID NO:227), EPGKFTQKVKVWI (SEQ ID NO:228), RKAILSPKEPPSW (SEQ ID NO:229), RIRVTSERVTEMY (SEQ ID NO:230), ALTVDTLKVLSAV (SEQ ID NO:231), KRKHSTCKKLPHS (SEQ ID NO:232), LEITNSKREATNV (SEQ ID NO:233), ETGVFSIKKKWQT (SEQ ID NO:234), TCDSDSSRSEQHQ (SEQ ID NO:235), SLSDNSTRSAQSS (SEQ ID NO:236), FARSHSFRFHKEE (SEQ ID NO:237), KDRRLSKKKKNTQ (SEQ ID NO:238), DKISASLKSPQEP (SEQ ID NO:239), SMSSWSQRGRAAM (SEQ ID NO:240), QTIPYTPRFLEVF (SEQ ID NO:241), and/or PPARETGRNSPED (SEQ ID NO:242). Polynucleotides encoding these polypeptides are also provided. The present invention also encompasses the use of these TRP-PLIK2d PKC phosphorylation site polypeptides as immunogenic and/or antigenic epitopes as described elsewhere herein.

The present invention also encompasses immunogenic and/or antigenic epitopes of the TRP-PLIK2d polypeptide.

The TRP-PLIK2d polypeptide has been shown to comprise seventeen glycosylation sites according to the Motif algorithm (Genetics Computer Group, Inc.). As discussed more specifically herein, protein glycosylation is thought to serve a variety of functions including: augmentation of protein folding, inhibition of protein aggregation, regulation of intracellular trafficking to organelles, increasing resistance to proteolysis, modulation of protein antigenicity, and mediation of intercellular adhesion.

Asparagine phosphorylation sites have the following consensus pattern, N-{P}-[ST]-{P}, wherein N represents the glycosylation site. However, it is well known that that potential N-glycosylation sites are specific to the consensus sequence Asn-Xaa-Ser/Thr. However, the presence of the consensus tripeptide is not sufficient to conclude that an asparagine residue is glycosylated, due to the fact that the folding of the protein plays an important role in the regulation of N-glycosylation. It has been shown that the presence of proline between Asn and Ser/Thr will inhibit N-glycosylation; this has been confirmed by a recent statistical analysis of glycosylation sites, which also shows that about 50% of the sites that have a proline C-terminal to Ser/Thr are not glycosylated. Additional information relating to asparagine glycosylation may be found in reference to the following publications, which are hereby incorporated by reference herein: Marshall R. D., Annu. Rev. Biochem. 41:673-702 (1972); Pless D. D., Lennarz W. J., Proc. Natl. Acad. Sci. U.S.A. 74:134-138 (1977); Bause E., Biochem. J. 209:331-336 (1983); Gavel Y., von Heijne G., Protein Eng. 3:433-442 (1990); and Miletich J. P., Broze G. J. Jr., J. Biol. Chem. . . . 265:11397-11404 (1990).

In preferred embodiments, the following asparagine glycosylation site polypeptides are encompassed by the present invention: HGGIQNFTMPSKFK (SEQ ID NO:243), IQNTFNFSLKQSKH (SEQ ID NO:244), LLKGTNLSASEQLN (SEQ ID NO:245), RAYRSNYTRKHFRA (SEQ ID NO:246), SSGNRNESAESTLH (SEQ ID NO:247), KSKEQNVSDDPEST (SEQ ID NO:248), SEELKNYSKQFGQL (SEQ ID NO:249), TYELRNWSNSTCLK (SEQ ID NO:250), LRNWSNSTCLKLAV (SEQ ID NO:251), YYSDQNASSSKESA (SEQ ID NO:252), ISEYWNLTETVAIG (SEQ ID NO:253), KMEDVNCSCEERIR (SEQ ID NO:254), SSLSDNSTRSAQSS (SEQ ID NO:255), PWLQPNTSFWINPL (SEQ ID NO:256), ICKIKNLSGSSEIG (SEQ ID NO:257), QGVGENLTDPSVIK (SEQ ID NO:258), and/or SPERINSTFGLEIK (SEQ ID NO:259). Polynucleotides encoding these polypeptides are also provided. The present invention also encompasses the use of these TRP-PLIK2d asparagine glycosylation site polypeptides as immunogenic and/or antigenic epitopes as described elsewhere herein.

Many polynucleotide sequences, such as EST sequences, are publicly available and accessible through sequence databases. Some of these sequences are related to SEQ ID NO:7 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides consisting of a nucleotide sequence described by the general formula of a-b, where a is any integer between 1 to 5911 of SEQ ID NO:7, b is an integer between 15 to 5925, where both a and b correspond to the positions of nucleotide residues shown in SEQ ID NO:7, and where b is greater than or equal to a+14.

TABLE I

| Gene No. | CDNA CloneID | ATCC ® Deposit No. Z and Date | Vector | NT SEQ ID. No. X | Total NT Seq of Clone | 5' NT of Start Codon of ORF | 3' NT of ORF | AA Seq ID No. Y | Total AA of ORF |
|---|---|---|---|---|---|---|---|---|---|
| 1. | TRP-PLIK2 (LTRPC6, gene 95; AL354795; BAC57) | PTA-4175 Mar. 21, 2002 | pCR4 Blunt-TOPO | 1 | 6054 | 1 | 6051 | 2 | 2017 |

TABLE I-continued

| Gene No. | CDNA CloneID | ATCC ® Deposit No. Z and Date | Vector | NT SEQ ID. No. X | Total NT Seq of Clone | 5' NT of Start Codon of ORF | 3' NT of ORF | AA Seq ID No. Y | Total AA of ORF |
|---|---|---|---|---|---|---|---|---|---|
| 2 | TRP-PLIK2b (LTRPC6, gene 95; AL354795; BAC57 splice variant) | N/A | pCR4 Blunt-TOPO | 3 | 5913 | 1 | 5910 | 4 | 1970 |
| 3. | TRP-PLIK2c (LTRPC6, gene 95; AL354795; BAC57 splice variant) | N/A | pCR4 Blunt-TOPO | 5 | 5820 | 1 | 5817 | 6 | 1939 |
| 4. | TRP-PLIK2d (LTRPC6, gene 95; AL354795; BAC57 splice variant) | N/A | pCR4 Blunt-TOPO | 7 | 5925 | 1 | 5922 | 8 | 1974 |

Table 1 summarizes the information corresponding to each "Gene No." described above. The nucleotide sequence identified as "NT SEQ ID NO:X" was assembled from partially homologous ("overlapping") sequences obtained from the "cDNA clone ID" identified in Table 1 and, in some cases, from additional related DNA clones. The overlapping sequences were assembled into a single contiguous sequence of high redundancy (usually several overlapping sequences at each nucleotide position), resulting in a final sequence identified as SEQ ID NO:X.

The cDNA Clone ID was deposited on the date and given the corresponding deposit number listed in "ATCC® Deposit No:PTA-4175 and Date." "Vector" refers to the type of vector contained in the cDNA Clone ID.

"Total NT Seq. Of Clone" refers to the total number of nucleotides in the clone contig identified by "Gene No." The deposited clone may contain all or most of the sequence of SEQ ID NO:X. The nucleotide position of SEQ ID NO:X of the putative start codon (methionine) is identified as "5' NT of Start Codon of ORF."

The translated amino acid sequence, beginning with the methionine, is identified as "AA SEQ ID NO:Y," although other reading frames can also be easily translated using known molecular biology techniques. The polypeptides produced by these alternative open reading frames are specifically contemplated by the present invention.

The total number of amino acids within the open reading frame of SEQ ID NO:Y is identified as "Total AA of ORF".

SEQ ID NO:X (where X may be any of the polynucleotide sequences disclosed in the sequence listing) and the translated SEQ ID NO:Y (where Y may be any of the polypeptide sequences disclosed in the sequence listing) are sufficiently accurate and otherwise suitable for a variety of uses well known in the art and described further herein. For instance, SEQ ID NO:1, 3, 5, 7, and/or 97 is useful for designing nucleic acid hybridization probes that will detect nucleic acid sequences contained in SEQ ID NO:1, 3, 5, 7, and/or 97 or the cDNA contained in the deposited clone. These probes will also hybridize to nucleic acid molecules in biological samples, thereby enabling a variety of forensic and diagnostic methods of the invention. Similarly, polypeptides identified from SEQ ID NO:2, 4, 6, 8, and/or 98 may be used, for example, to generate antibodies which bind specifically to proteins containing the polypeptides and the proteins encoded by the cDNA clones identified in Table 1.

Nevertheless, DNA sequences generated by sequencing reactions can contain sequencing errors. The errors exist as misidentified nucleotides, or as insertions or deletions of nucleotides in the generated DNA sequence. The erroneously inserted or deleted nucleotides may cause frame shifts in the reading frames of the predicted amino acid sequence. In these cases, the predicted amino acid sequence diverges from the actual amino acid sequence, even though the generated DNA sequence may be greater than 99.9% identical to the actual DNA sequence (for example, one base insertion or deletion in an open reading frame of over 1000 bases).

Accordingly, for those applications requiring precision in the nucleotide sequence or the amino acid sequence, the present invention provides not only the generated nucleotide sequence identified as SEQ ID NO:1, 3, 5, 7, and/or 97 and the predicted translated amino acid sequence identified as SEQ ID NO:2, 4, 6, 8, and/or 98, but also a sample of plasmid DNA containing a cDNA of the invention deposited with the ATCC®, as set forth in Table 1. The nucleotide sequence of each deposited clone can readily be determined by sequencing the deposited clone in accordance with known methods. The predicted amino acid sequence can then be verified from such deposits. Moreover, the amino acid sequence of the protein encoded by a particular clone can also be directly determined by peptide sequencing or by expressing the protein in a suitable host cell containing the deposited cDNA, collecting the protein, and determining its sequence.

The present invention also relates to the genes corresponding to SEQ ID NO:1, 3, 5, 7, and/or 97, SEQ ID NO:2, 4, 6, 8, and/or 98, or the deposited clone. The corresponding gene can be isolated in accordance with known methods using the sequence information disclosed herein. Such methods include preparing probes or primers from the disclosed sequence and identifying or amplifying the corresponding gene from appropriate sources of genomic material.

Also provided in the present invention are species homologs, allelic variants, and/or orthologs. The skilled artisan could, using procedures well-known in the art, obtain the polynucleotide sequence corresponding to full-length genes (including, but not limited to the full-length coding region), allelic variants, splice variants, orthologs, and/or species homologues of genes corresponding to SEQ ID NO:1, 3, 5, 7, and/or 97, SEQ ID NO:2, 4, 6, 8, and/or 98, or a deposited clone, relying on the sequence from the sequences disclosed herein or the clones deposited with the ATCC®. For example, allelic variants and/or species homologues may be isolated and identified by making suitable probes or primers which correspond to the 5', 3', or internal regions of the sequences provided herein and screening a suitable nucleic acid source for allelic variants and/or the desired homologue.

The polypeptides of the invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

The polypeptides may be in the form of the protein, or may be a part of a larger protein, such as a fusion protein (see below). It is often advantageous to include an additional amino acid sequence which contains secretory or leader sequences, pro-sequences, sequences which aid in purification, such as multiple histidine residues, or an additional sequence for stability during recombinant production.

The polypeptides of the present invention are preferably provided in an isolated form, and preferably are substantially purified. A recombinantly produced version of a polypeptide, can be substantially purified using techniques described herein or otherwise known in the art, such as, for example, by the one-step method described in Smith and Johnson, Gene 67:31-40 (1988). Polypeptides of the invention also can be purified from natural, synthetic or recombinant sources using protocols described herein or otherwise known in the art, such as, for example, antibodies of the invention raised against the full-length form of the protein.

The present invention provides a polynucleotide comprising, or alternatively consisting of, the sequence identified as SEQ ID NO:1, 3, 5, 7, and/or 97, and/or a cDNA provided in ATCC® Deposit No. Z. The present invention also provides a polypeptide comprising, or alternatively consisting of, the sequence identified as SEQ ID NO:2, 4, 6, 8, and/or 98, and/or a polypeptide encoded by the cDNA provided in ATCC® Deposit No:PTA-4175. The present invention also provides polynucleotides encoding a polypeptide comprising, or alternatively consisting of the polypeptide sequence of SEQ ID NO:2, 4, 6, 8, and/or 98, and/or a polypeptide sequence encoded by the cDNA contained in ATCC® Deposit No:PTA-4175.

Preferably, the present invention is directed to a polynucleotide comprising, or alternatively consisting of, the sequence identified as SEQ ID NO:1, 3, 5, 7, and/or 97, and/or a cDNA provided in ATCC® Deposit No.: that is less than, or equal to, a polynucleotide sequence that is 5 mega basepairs, 1 mega basepairs, 0.5 mega basepairs, 0.1 mega basepairs, 50,000 basepairs, 20,000 basepairs, or 10,000 basepairs in length.

The present invention encompasses polynucleotides with sequences complementary to those of the polynucleotides of the present invention disclosed herein. Such sequences may be complementary to the sequence disclosed as SEQ ID NO:1, 3, 5, 7, and/or 97, the sequence contained in a deposit, and/or the nucleic acid sequence encoding the sequence disclosed as SEQ ID NO:2, 4, 6, 8, and/or 98.

The present invention also encompasses polynucleotides capable of hybridizing, preferably under reduced stringency conditions, more preferably under stringent conditions, and most preferably under highly stringent conditions, to polynucleotides described herein. Examples of stringency conditions are shown in Table 2 below: highly stringent conditions are those that are at least as stringent as, for example, conditions A-F; stringent conditions are at least as stringent as, for example, conditions G-L; and reduced stringency conditions are at least as stringent as, for example, conditions M-R.

TABLE 2

| Stringency Condition | Polynucleotide Hybrid± | Hybrid Length (bp)‡ | Hyridization Temperature and Buffer† | Wash Temperature and Buffer† |
|---|---|---|---|---|
| A | DNA:DNA | > or equal to 50 | 65° C.; 1xSSC - or- 42° C.; 1xSSC, 50% formamide | 65° C.; 0.3xSSC |
| B | DNA:DNA | <50 | Tb*; 1xSSC | Tb*; 1xSSC |
| C | DNA:RNA | > or equal to 50 | 67° C.; 1xSSC - or- 45° C.; 1xSSC, 50% formamide | 67° C.; 0.3xSSC |
| D | DNA:RNA | <50 | Td*; 1xSSC | Td*; 1xSSC |
| E | RNA:RNA | > or equal to 50 | 70° C.; 1xSSC - or- 50° C.; 1xSSC, 50% formamide | 70° C.; 0.3xSSC |
| F | RNA:RNA | <50 | Tf*; 1xSSC | Tf*; 1xSSC |
| G | DNA:DNA | > or equal to 50 | 65° C.; 4xSSC - or- 45° C.; 4xSSC, 50% formamide | 65° C.; 1xSSC |
| H | DNA:DNA | <50 | Th*; 4xSSC | Th*; 4xSSC |
| I | DNA:RNA | > or equal to 50 | 67° C.; 4xSSC - or- 45° C.; 4xSSC, 50% formamide | 67° C.; 1xSSC |
| J | DNA:RNA | <50 | Tj*; 4xSSC | Tj*; 4xSSC |
| K | RNA:RNA | > or equal to 50 | 70° C.; 4xSSC - or- 40° C.; 6xSSC, 50% formamide | 67° C.; 1xSSC |
| L | RNA:RNA | <50 | Tl*; 2xSSC | Tl*; 2xSSC |
| M | DNA:DNA | > or equal to 50 | 50° C.; 4xSSC - or- 40° C. 6xSSC, 50% formamide | 50° C.; 2xSSC |
| N | DNA:DNA | <50 | Tn*; 6xSSC | Tn*; 6xSSC |
| O | DNA:RNA | > or equal to 50 | 55° C.; 4xSSC - or- 42° C.; 6xSSC, 50% formamide | 55° C.; 2xSSC |
| P | DNA:RNA | <50 | Tp*; 6xSSC | Tp*; 6xSSC |
| Q | RNA:RNA | > or equal to 50 | 60° C.; 4xSSC - or- 45° C.; 6xSSC, 50% formamide | 60° C.; 2xSSC |
| R | RNA:RNA | <50 | Tr*; 4xSSC | Tr*; 4xSSC |

‡The "hybrid length" is the anticipated length for the hybridized region(s) of the hybridizing polynucleotides. When hybridizing a polynucletotide of unknown sequence, the hybrid is assumed to be that of the hybridizing polynucleotide of the present invention. When polynucleotides of known sequence are hybridized, the hybrid length can be determined by aligning the sequences of the polynucleotides and identifying the region or regions of optimal sequence complementarity. Methods of aligning two or more polynucleotide sequences and/or determining the percent identity between two polynucleotide sequences are well known in the art (e.g., MegAlign program of the DNA*Star suite of programs, etc).
†SSPE (1xSSPE is 0.15 M NaCl, 10 mM NaH2PO4, and 1.25 mM EDTA, pH 7.4) can be substituted for SSC (1xSSC is 0.15 M NaCl and 15 mM sodium citrate) in the hybridization and wash buffers; washes are performed for 15 minutes after hybridization is complete. The hydridizations and washes may additionally include 5X Denhardt's reagent, .5-1.0% SDS, 100 ug/ml denatured, fragmented salmon sperm DNA, 0.5% sodium pyrophosphate, and up to 50% formamide.
*Tb – Tr: The hybridization temperature for hybrids anticipated to be less than 50 base pairs in length should be 5-10° C. less than the melting temperature Tm of the hybrids there Tm is determined according to the following equations. For hybrids less than 18 base pairs in length, Tm(° C.) = 2(# of A + T bases) + 4(# of G + C bases). For hybrids between 18 and 49 base pairs in length, Tm(° C.) = 81.5 + 16.6(log$_{10}$[Na+]) + 0.41(% G + C) − (600/N), where N is the number of bases in the hybrid, and [Na+] is the concentration of sodium ions in the hybridization buffer ([NA+] for 1xSSC = .165 M).
±The present invention encompasses the substitution of any one, or more DNA or RNA hybrid partners with either a PNA, or a modified polynucleotide. Such modified polynucleotides are known in the art and are more particularly described elsewhere herein.

Additional examples of stringency conditions for polynucleotide hybridization are provided, for example, in Sambrook, J., E. F. Fritsch, and T. Maniatis, 1989, Molecular Cloning: A Laboratory Manual, Cold Spring Harbor Laboratory Press, Cold Spring Harbor, N.Y., chapters 9 and 11, and Current Protocols in Molecular Biology, 1995, F. M., Ausubel et al., eds, John Wiley and Sons, Inc., sections 2.10 and 6.3-6.4, which are hereby incorporated by reference herein.

Preferably, such hybridizing polynucleotides have at least 70% sequence identity (more preferably, at least 80% identity; and most preferably at least 90% or 95% identity) with the polynucleotide of the present invention to which they hybridize, where sequence identity is determined by comparing the sequences of the hybridizing polynucleotides when aligned so as to maximize overlap and identity while minimizing sequence gaps. The determination of identity is well known in the art, and discussed more specifically elsewhere herein.

The invention encompasses the application of PCR methodology to the polynucleotide sequences of the present invention, the clone deposited with the ATCC®, and/or the cDNA encoding the polypeptides of the present invention. PCR techniques for the amplification of nucleic acids are described in U.S. Pat. No. 4,683,195 and Saiki et al., Science, 239:487-491 (1988). PCR, for example, may include the following steps, of denaturation of template nucleic acid (if double-stranded), annealing of primer to target, and polymerization. The nucleic acid probed or used as a template in the amplification reaction may be genomic DNA, cDNA, RNA, or a PNA. PCR may be used to amplify specific sequences from genomic DNA, specific RNA sequence, and/or cDNA transcribed from mRNA. References for the general use of PCR techniques, including specific method parameters, include Mullis et al., Cold Spring Harbor Symp. Quant. Biol., 51:263, (1987), Ehrlich (ed), PCR Technology, Stockton Press, NY, 1989; Ehrlich et al., Science, 252:1643-1650, (1991); and "PCR Protocols, A Guide to Methods and Applications", Eds., Innis et al., Academic Press, New York, (1990).

Polynucleotide and Polypeptide Variants

The present invention also encompasses variants (e.g., allelic variants, orthologs, etc.) of the polynucleotide sequence disclosed herein in SEQ ID NO:1, 3, 5, 7, and/or 97, the complementary strand thereto, and/or the cDNA sequence contained in the deposited clone.

The present invention also encompasses variants of the polypeptide sequence, and/or fragments therein, disclosed in SEQ ID NO:2, 4, 6, 8, and/or 98, a polypeptide encoded by the polynucleotide sequence in SEQ ID NO:1, 3, 5, 7, and/or 97, and/or a polypeptide encoded by a cDNA in the deposited clone.

"Variant" refers to a polynucleotide or polypeptide differing from the polynucleotide or polypeptide of the present invention, but retaining essential properties thereof. Generally, variants are overall closely similar, and, in many regions, identical to the polynucleotide or polypeptide of the present invention.

Thus, one aspect of the invention provides an isolated nucleic acid molecule comprising, or alternatively consisting of, a polynucleotide having a nucleotide sequence selected from the group consisting of: (a) a nucleotide sequence encoding a TRP-PLIK2 related polypeptide having an amino acid sequence as shown in the sequence listing and described in SEQ ID NO:1, 3, 5, 7, and/or 97 or the cDNA contained in ATCC® Deposit No:PTA-4175; (b) a nucleotide sequence encoding a mature TRP-PLIK2 related polypeptide having the amino acid sequence as shown in the sequence listing and described in SEQ ID NO:1, 3, 5, 7, and/or 97 or the cDNA contained in ATCC® Deposit No:PTA-4175; (c) a nucleotide sequence encoding a biologically active fragment of a TRP-PLIK2 related polypeptide having an amino acid sequence shown in the sequence listing and described in SEQ ID NO:1, 3, 5, 7, and/or 97 or the cDNA contained in ATCC® Deposit No:PTA-4175; (d) a nucleotide sequence encoding an antigenic fragment of a TRP-PLIK2 related polypeptide having an amino acid sequence shown in the sequence listing and described in SEQ ID NO:1, 3, 5, 7, and/or 97 or the cDNA contained in ATCC® Deposit No:PTA-4175; (e) a nucleotide sequence encoding a TRP-PLIK2 related polypeptide comprising the complete amino acid sequence encoded by a human cDNA plasmid contained in SEQ ID NO:1, 3, 5, 7, and/or 97 or the cDNA contained in ATCC® Deposit No:PTA-4175; (f) a nucleotide sequence encoding a mature TRP-PLIK2 related polypeptide having an amino acid sequence encoded by a human cDNA plasmid contained in SEQ ID NO:1, 3, 5, 7, and/or 97 or the cDNA contained in ATCC® Deposit No:PTA-4175; (g) a nucleotide sequence encoding a biologically active fragment of a TRP-PLIK2 related polypeptide having an amino acid sequence encoded by a human cDNA plasmid contained in SEQ ID NO:1, 3, 5, 7, and/or 97 or the cDNA contained in ATCC® Deposit No:PTA-4175; (h) a nucleotide sequence encoding an antigenic fragment of a TRP-PLIK2 related polypeptide having an amino acid sequence encoded by a human cDNA plasmid contained in SEQ ID NO:1, 3, 5, 7, and/or 97 or the cDNA contained in ATCC® Deposit No:PTA-4175; (I) a nucleotide sequence complimentary to any of the nucleotide sequences in (a), (b), (c), (d), (e), (f), (g), or (h), above.

The present invention is also directed to polynucleotide sequences which comprise, or alternatively consist of, a polynucleotide sequence which is at least about 80%, 85%, 90%, 91%, 92%, 93%, 94%, 95%, 95.9%, 96%, 97%, 97.4%, 97.6%, 98%, 99%, 99.1%, 99.2%, 99.3%, 99.4%, 99.5%, 99.6%, 99.7%, 99.8%, or 99.9% identical to, for example, any of the nucleotide sequences in (a), (b), (c), (d), (e), (f), (g), or (h), above. Polynucleotides encoded by these nucleic acid molecules are also encompassed by the invention. In another embodiment, the invention encompasses nucleic acid molecule which comprise, or alternatively, consist of a polynucleotide which hybridizes under stringent conditions, or alternatively, under lower stringency conditions, to a polynucleotide in (a), (b), (c), (d), (e), (f), (g), or (h), above. Polynucleotides which hybridize to the complement of these nucleic acid molecules under stringent hybridization conditions or alternatively, under lower stringency conditions, are also encompassed by the invention, as are polypeptides encoded by these polypeptides.

Another aspect of the invention provides an isolated nucleic acid molecule comprising, or alternatively, consisting of, a polynucleotide having a nucleotide sequence selected from the group consisting of: (a) a nucleotide sequence encoding a TRP-PLIK2 related polypeptide having an amino acid sequence as shown in the sequence listing and described in Table 1; (b) a nucleotide sequence encoding a mature TRP-PLIK2 related polypeptide having the amino acid sequence as shown in the sequence listing and described in Table 1; (c) a nucleotide sequence encoding a biologically active fragment of a TRP-PLIK2 related polypeptide having an amino acid sequence as shown in the sequence listing and described in Table 1; (d) a nucleotide sequence encoding an antigenic fragment of a TRP-PLIK2 related polypeptide having an amino acid sequence as shown in the sequence listing and described in Table 1; (e) a nucleotide sequence encoding a TRP-PLIK2 related polypeptide comprising the complete amino acid sequence encoded by a human cDNA in a cDNA plasmid contained in the ATCC® Deposit and described in Table 1; (f) a nucleotide sequence encoding a mature TRP-PLIK2 related polypeptide having an amino acid sequence encoded by a human cDNA in a cDNA plasmid contained in the ATCC® Deposit and described in Table 1: (g) a nucleotide sequence encoding a biologically active fragment of a TRP-PLIK2 related polypeptide having an amino acid sequence encoded by a human cDNA in a cDNA plasmid contained in the ATCC® Deposit and described in Table 1; (h) a nucleotide sequence encoding an antigenic fragment of a TRP-PLIK2 related polypeptide having an amino acid sequence encoded by a human cDNA in a cDNA plasmid contained in the ATCC® deposit and described in Table 1; (i) a nucleotide sequence complimentary to any of the nucleotide sequences in (a), (b), (c), (d), (e), (f), (g), or (h) above.

The present invention is also directed to nucleic acid molecules which comprise, or alternatively, consist of, a nucleotide sequence which is at least about 80%, 85%, 90%, 91%, 92%, 93%, 94%, 95%, 95.9%, 96%, 97%, 97.4%, 97.6%, 98%, 99%, 99.1%, 99.2%, 99.3%, 99.4%, 99.5%, 99.6%, 99.7%, 99.8%, or 99.9% identical to, for example, any of the nucleotide sequences in (a), (b), (c), (d), (e), (f), (g), or (h), above.

The present invention encompasses polypeptide sequences which comprise, or alternatively consist of, an amino acid sequence which is at least about 80%, 85%, 90%, 91%, 92%, 93%, 94%, 95%, 95.8%, 96%, 97%, 97.2%, 97.5%, 98%, 99%, 99.1%, 99.2%, 99.3%, 99.4%, 99.5%, 99.6%, 99.7%, 99.8%, or 99.9% identical to, the following non-limited examples, the polypeptide sequence identified as SEQ ID NO:2, 4, 6, 8, and/or 98, the polypeptide sequence encoded by a cDNA provided in the deposited clone, and/or polypeptide fragments of any of the polypeptides provided herein. Polynucleotides encoded by these nucleic acid molecules are also encompassed by the invention. In another embodiment, the invention encompasses nucleic acid molecule which comprise, or alternatively, consist of a polynucleotide which hybridizes under stringent conditions, or alternatively, under lower stringency conditions, to a polynucleotide in (a), (b), (c), (d), (e), (f), (g), or (h), above. Polynucleotides which hybridize to the complement of these nucleic acid molecules under stringent hybridization conditions or alternatively, under lower stringency conditions, are also encompassed by the invention, as are polypeptides encoded by these polypeptides.

The present invention is also directed to polypeptides which comprise, or alternatively consist of, an amino acid sequence which is at least about 80%, 85%, 90%, 91%, 92%, 93%, 94%, 95%, 95.8%, 96%, 97%, 97.2%, 97.5%, 98%, 99%, 99.1%, 99.2%, 99.3%, 99.4%, 99.5%, 99.6%, 99.7%, 99.8%, or 99.9% identical to, for example, the polypeptide sequence shown in SEQ ID NO:2, 4, 6, 8, and/or 98, a polypeptide sequence encoded by the nucleotide sequence in SEQ ID NO:1, 3, 5, 7, and/or 97, a polypeptide sequence encoded by the cDNA in cDNA plasmid: Z, and/or polypeptide fragments of any of these polypeptides (e.g., those fragments described herein). Polynucleotides which hybridize to the complement of the nucleic acid molecules encoding these polypeptides under stringent hybridization conditions or alternatively, under lower stringency conditions, are also encompasses by the present invention, as are the polypeptides encoded by these polynucleotides.

By a nucleic acid having a nucleotide sequence at least, for example, 95% "identical" to a reference nucleotide sequence of the present invention, it is intended that the nucleotide sequence of the nucleic acid is identical to the reference sequence except that the nucleotide sequence may include up to five point mutations per each 100 nucleotides of the reference nucleotide sequence encoding the polypeptide. In other words, to obtain a nucleic acid having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. The query sequence may be an entire sequence referenced in Table 1, the ORF (open reading frame), or any fragment specified as described herein.

As a practical matter, whether any particular nucleic acid molecule or polypeptide is at least about 80%, 85%, 90%, 91%, 92%, 93%, 94%, 95%, 95.8%, 95.9%, 96%, 97%, 97.2%, 97.4%, 97.5%, 97.6%, 98%, 99%, 99.1%, 99.2%, 99.3%, 99.4%, 99.5%, 99.6%, 99.7%, 99.8%, or 99.9% identical to a nucleotide sequence of the present invention can be determined conventionally using known computer programs. A preferred method for determining the best overall match between a query sequence (a sequence of the present invention) and a subject sequence, also referred to as a global sequence alignment, can be determined using the CLUSTALW computer program (Thompson, J. D., et al., Nucleic Acids Research, 2(22):4673-4680, (1994)), which is based on the algorithm of Higgins, D. G., et al., Computer Applications in the Biosciences (CABIOS), 8(2):189-191, (1992). In a sequence alignment the query and subject sequences are both DNA sequences. An RNA sequence can be compared by converting U's to T's. However, the CLUSTALW algorithm automatically converts U's to T's when comparing RNA sequences to DNA sequences. The result of said global sequence alignment is in percent identity. Preferred parameters used in a CLUSTALW alignment of DNA sequences to calculate percent identity via pairwise alignments are: Matrix=IUB, k-tuple=1, Number of Top Diagonals=5, Gap Penalty=3, Gap Open Penalty 10, Gap Extension Penalty=0.1, Scoring Method=Percent, Window Size=5 or the length of the subject nucleotide sequence, whichever is shorter. For multiple alignments, the following CLUSTALW parameters are preferred: Gap Opening Penalty=10; Gap Extension Parameter=0.05; Gap Separation Penalty Range=8; End Gap Separation Penalty=Off; % Identity for Alignment Delay=40%; Residue Specific Gaps: Off; Hydrophilic Residue Gap=Off; and Transition Weighting=0. The pairwise and multiple alignment parameters provided for CLUSTALW above represent the default parameters as provided with the AlignX software program (VECTOR NTI® suite of programs, version 6.0).

The present invention encompasses the application of a manual correction to the percent identity results, in the instance where the subject sequence is shorter than the query sequence because of 5' or 3' deletions, not because of internal deletions. If only the local pairwise percent identity is required, no manual correction is needed. However, a manual correction may be applied to determine the global percent identity from a global polynucleotide alignment. Percent identity calculations based upon global polynucleotide alignments are often preferred since they reflect the percent identity between the polynucleotide molecules as a whole (i.e., including any polynucleotide overhangs, not just overlapping regions), as opposed to, only local matching polynucleotides. Manual corrections for global percent identity determinations are required since the CLUSTALW program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/ aligned is determined by results of the CLUSTALW sequence alignment. This percentage is then subtracted from the percent identity, calculated by the above CLUSTALW program using the specified parameters, to arrive at a final percent identity score. This corrected score may be used for the purposes of the present invention. Only bases outside the 5' and 3' bases of the subject sequence, as displayed by the CLUSTALW alignment, which are not matched/aligned with the query sequence, are calculated for the purposes of manually adjusting the percent identity score.

For example, a 90 base subject sequence is aligned to a 100 base query sequence to determine percent identity. The deletions occur at the 5' end of the subject sequence and therefore, the CLUSTALW alignment does not show a matched/alignment of the first 10 bases at 5' end. The 10 unpaired bases represent 10% of the sequence (number of bases at the 5' and 3' ends not matched/total number of bases in the query sequence) so 10% is subtracted from the percent identity score calculated by the CLUSTALW program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by CLUSTALW is not manually corrected. Once again, only bases 5' and 3' of the subject sequence which are not matched/aligned with the query sequence are manually corrected for. No other manual corrections are required for the purposes of the present invention.

By a polypeptide having an amino acid sequence at least, for example, 95% "identical" to a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence may be inserted, deleted, or substituted with another amino acid. These alterations of the reference sequence may occur at the amino- or carboxy-terminal positions of the reference amino acid sequence or anywhere between those terminal positions, interspersed either individually among residues in the reference sequence or in one or more contiguous groups within the reference sequence.

As a practical matter, whether any particular polypeptide is at least about 80%, 85%, 90%, 91%, 92%, 93%, 94%, 95%, 95.8%, 96%, 97%, 97.2%, 97.5%, 98%, 99%, 99.1%, 99.2%, 99.3%, 99.4%, 99.5%, 99.6%, 99.7%, 99.8%, or 99.9% identical to, for instance, an amino acid sequence referenced in Table 1 (SEQ ID NO:2) or to the amino acid sequence encoded by cDNA contained in a deposited clone, can be determined conventionally using known computer programs. A preferred method for determining the best overall match between a query sequence (a sequence of the present invention) and a subject sequence, also referred to as a global sequence alignment, can be determined using the CLUSTALW computer program (Thompson, J. D., et al., Nucleic Acids Research, 2(22):4673-4680, (1994)), which is based on the algorithm of Higgins, D. G., et al., Computer Applications in the Biosciences (CABIOS), 8(2):189-191, (1992). In a sequence alignment the query and subject sequences are both amino acid sequences. The result of said global sequence alignment is in percent identity. Preferred parameters used in a CLUSTALW alignment of DNA sequences to calculate percent identity via pairwise alignments are: Matrix=BLOSUM, k-tuple=1, Number of Top Diagonals=5, Gap Penalty=3, Gap Open Penalty 10, Gap Extension Penalty=0.1, Scoring Method=Percent, Window Size=5 or the length of the subject nucleotide sequence, whichever is shorter. For multiple alignments, the following CLUSTALW parameters are preferred: Gap Opening Penalty=10; Gap Extension Parameter=0.05; Gap Separation Penalty Range=8; End Gap Separation Penalty=Off; % Identity for Alignment Delay=40%; Residue Specific Gaps: Off; Hydrophilic Residue Gap=Off; and Transition Weighting=0. The pairwise and multiple alignment parameters provided for CLUSTALW above represent the default parameters as provided with the AlignX software program (VECTOR NTI® suite of programs, version 6.0).

The present invention encompasses the application of a manual correction to the percent identity results, in the instance where the subject sequence is shorter than the query sequence because of N- or C-terminal deletions, not because of internal deletions. If only the local pairwise percent identity is required, no manual correction is needed. However, a manual correction may be applied to determine the global percent identity from a global polypeptide alignment. Percent identity calculations based upon global polypeptide alignments are often preferred since they reflect the percent identity between the polypeptide molecules as a whole (i.e., including any polypeptide overhangs, not just overlapping regions), as opposed to, only local matching polypeptides. Manual corrections for global percent identity determinations are required since the CLUSTALW program does not account for N- and C-terminal truncations of the subject sequence when calculating percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. Whether a residue is matched/aligned is determined by results of the CLUSTALW sequence alignment. This percentage is then subtracted from the percent identity, calculated by the above CLUSTALW program using the specified parameters, to arrive at a final percent identity score. This final percent identity score is what may be used for the purposes of the present invention. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence.

For example, a 90 amino acid residue subject sequence is aligned with a 100 residue query sequence to determine percent identity. The deletion occurs at the N-terminus of the subject sequence and therefore, the CLUSTALW alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the CLUSTALW program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence, which are not matched/aligned with the query. In this case the percent identity calculated by CLUSTALW is not manually corrected. Once again, only residue positions outside the N- and C-terminal ends of the subject sequence, as displayed in the CLUSTALW alignment, which are not matched/aligned with the query sequence are manually corrected for. No other manual corrections are required for the purposes of the present invention.

In addition to the above method of aligning two or more polynucleotide or polypeptide sequences to arrive at a percent identity value for the aligned sequences, it may be desirable in some circumstances to use a modified version of the CLUSTALW algorithm which takes into account known structural features of the sequences to be aligned, such as for example, the SWISS-PROT® designations for each sequence. The result of such a modified CLUSTALW algorithm may provide a more accurate value of the percent identity for two polynucleotide or polypeptide sequences. Support for such a modified version of CLUSTALW is provided within the CLUSTALW algorithm and would be readily appreciated to one of skill in the art of bioinformatics.

The variants may contain alterations in the coding regions, non-coding regions, or both. Especially preferred are polynucleotide variants containing alterations which produce silent substitutions, additions, or deletions, but do not alter the properties or activities of the encoded polypeptide. Nucleotide variants produced by silent substitutions due to the degeneracy of the genetic code are preferred. Moreover, variants in which 5-10, 1-5, or 1-2 amino acids are substituted, deleted, or added in any combination are also preferred. Polynucleotide variants can be produced for a variety of reasons, e.g., to optimize codon expression for a particular host (change codons in the mRNA to those preferred by a bacterial host such as E. coli).

Naturally occurring variants are called "allelic variants," and refer to one of several alternate forms of a gene occupying a given locus on a chromosome of an organism. (Genes II, Lewin, B., ed., John Wiley & Sons, New York (1985).) These allelic variants can vary at either the polynucleotide and/or polypeptide level and are included in the present invention. Alternatively, non-naturally occurring variants may be produced by mutagenesis techniques or by direct synthesis.

Using known methods of protein engineering and recombinant DNA technology, variants may be generated to improve or alter the characteristics of the polypeptides of the present invention. For instance, one or more amino acids can be deleted from the N-terminus or C-terminus of the protein without substantial loss of biological function. The authors of Ron et al., J. Biol. Chem. 268: 2984-2988 (1993), reported variant KGF proteins having heparin binding activity even after deleting 3, 8, or 27 amino-terminal amino acid residues. Similarly, Interferon gamma exhibited up to ten times higher activity after deleting 8-10 amino acid residues from the carboxy terminus of this protein (Dobeli et al., J. Biotechnology 7:199-216 (1988)).

Moreover, ample evidence demonstrates that variants often retain a biological activity similar to that of the naturally occurring protein. For example, Gayle and coworkers (J. Biol. Chem. . . . 268:22105-22111 (1993)) conducted extensive mutational analysis of human cytokine IL-1a. They used random mutagenesis to generate over 3,500 individual IL-1a mutants that averaged 2.5 amino acid changes per variant over the entire length of the molecule. Multiple mutations were examined at every possible amino acid position. The investigators found that "[m]ost of the molecule could be altered with little effect on either [binding or biological activity]." In fact, only 23 unique amino acid sequences, out of more than 3,500 nucleotide sequences examined, produced a protein that significantly differed in activity from wild-type.

Furthermore, even if deleting one or more amino acids from the N-terminus or C-terminus of a polypeptide results in modification or loss of one or more biological functions, other biological activities may still be retained. For example, the ability of a deletion variant to induce and/or to bind antibodies which recognize the protein will likely be retained when less than the majority of the residues of the protein are removed from the N-terminus or C-terminus. Whether a particular polypeptide lacking N- or C-terminal residues of a protein retains such immunogenic activities can readily be determined by routine methods described herein and otherwise known in the art.

Alternatively, such N-terminus or C-terminus deletions of a polypeptide of the present invention may, in fact, result in a significant increase in one or more of the biological activities of the polypeptide(s). For example, biological activity of many polypeptides are governed by the presence of regulatory domains at either one or both termini. Such regulatory domains effectively inhibit the biological activity of such polypeptides in lieu of an activation event (e.g., binding to a cognate ligand or receptor, phosphorylation, proteolytic processing, etc.). Thus, by eliminating the regulatory domain of a polypeptide, the polypeptide may effectively be rendered biologically active in the absence of an activation event.

The invention further includes polypeptide variants that show substantial biological activity. Such variants include deletions, insertions, inversions, repeats, and substitutions selected according to general rules known in the art so as have little effect on activity. For example, guidance concerning how to make phenotypically silent amino acid substitutions is provided in Bowie et al., Science 247:1306-1310 (1990), wherein the authors indicate that there are two main strategies for studying the tolerance of an amino acid sequence to change.

The first strategy exploits the tolerance of amino acid substitutions by natural selection during the process of evolution. By comparing amino acid sequences in different species, conserved amino acids can be identified. These conserved amino acids are likely important for protein function. In contrast, the amino acid positions where substitutions have been tolerated by natural selection indicates that these positions are not critical for protein function. Thus, positions tolerating amino acid substitution could be modified while still maintaining biological activity of the protein.

The second strategy uses genetic engineering to introduce amino acid changes at specific positions of a cloned gene to identify regions critical for protein function. For example, site directed mutagenesis or alanine-scanning mutagenesis (introduction of single alanine mutations at every residue in the molecule) can be used. (Cunningham and Wells, Science 244:1081-1085 (1989).) The resulting mutant molecules can then be tested for biological activity.

As the authors state, these two strategies have revealed that proteins are surprisingly tolerant of amino acid substitutions. The authors further indicate which amino acid changes are likely to be permissive at certain amino acid positions in the protein. For example, most buried (within the tertiary structure of the protein) amino acid residues require nonpolar side chains, whereas few features of surface side chains are generally conserved.

The invention encompasses polypeptides having a lower degree of identity but having sufficient similarity so as to perform one or more of the same functions performed by the polypeptide of the present invention. Similarity is determined by conserved amino acid substitution. Such substitutions are those that substitute a given amino acid in a polypeptide by another amino acid of like characteristics (e.g., chemical properties). According to Cunningham et al above, such conservative substitutions are likely to be phenotypically silent. Additional guidance concerning which amino acid changes are likely to be phenotypically silent are found in Bowie et al., Science 247:1306-1310 (1990).

Tolerated conservative amino acid substitutions of the present invention involve replacement of the aliphatic or hydrophobic amino acids Ala, Val, Leu and Ile; replacement of the hydroxyl residues Ser and Thr; replacement of the acidic residues Asp and Glu; replacement of the amide residues Asn and Gln, replacement of the basic residues Lys, Arg, and His; replacement of the aromatic residues Phe, Tyr, and Trp, and replacement of the small-sized amino acids Ala, Ser, Thr, Met, and Gly.

In addition, the present invention also encompasses the conservative substitutions provided in Table III below.

TABLE III

| For Amino Acid | Code | Replace with any of: |
|---|---|---|
| Alanine | A | D-Ala, Gly, beta-Ala, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, β-Ala, Acp |
| Isoleucine | I | D-Ile, Val, D-Val, Leu, D-Leu, Met, D-Met |
| Leucine | L | D-Leu, Val, D-Val, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |
| Phenylalanine | F | D-Phe, Tyr, D-Thr, L-Dopa, His, D-His, Trp, D-Trp, Trans-3,4, or 5-phenylproline, cis-3,4, or 5-phenylproline |
| Proline | P | D-Pro, L-1-thioazolidine-4-carboxylic acid, D- or L-1-oxazolidine-4-carboxylic acid |
| Serine | S | D-Ser, Thr, D-Thr, allo-Thr, Met, D-Met, Met(O), D-Met(O), L-Cys, D-Cys |
| Threonine | T | D-Thr, Ser, D-Ser, allo-Thr, Met, D-Met, Met(O), D-Met(O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met |

Aside from the uses described above, such amino acid substitutions may also increase protein or peptide stability. The invention encompasses amino acid substitutions that contain, for example, one or more non-peptide bonds (which replace the peptide bonds) in the protein or peptide sequence. Also included are substitutions that include amino acid residues other than naturally occurring L-amino acids, e.g., D-amino acids or non-naturally occurring or synthetic amino acids, e.g., β or γ amino acids.

Both identity and similarity can be readily calculated by reference to the following publications: Computational Molecular Biology, Lesk, A. M., ed., Oxford University Press, New York, 1988; Biocomputing: Informatics and Genome Projects, Smith, D. W., ed., Academic Press, New York, 1993; Informatics Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991.

In addition, the present invention also encompasses substitution of amino acids based upon the probability of an amino acid substitution resulting in conservation of function. Such probabilities are determined by aligning multiple genes with related function and assessing the relative penalty of each substitution to proper gene function. Such probabilities are often described in a matrix and are used by some algorithms (e.g., BLAST, CLUSTALW, GAP, etc.) in calculating percent similarity wherein similarity refers to the degree by which one amino acid may substitute for another amino acid without lose of function. An example of such a matrix is the PAM250 or BLOSUM62 matrix.

Aside from the canonical chemically conservative substitutions referenced above, the invention also encompasses substitutions which are typically not classified as conservative, but that may be chemically conservative under certain circumstances. Analysis of enzymatic catalysis for proteases, for example, has shown that certain amino acids within the active site of some enzymes may have highly perturbed pKa's due to the unique microenvironment of the active site. Such perturbed pKa's could enable some amino acids to substitute for other amino acids while conserving enzymatic structure and function. Examples of amino acids that are known to have amino acids with perturbed pKa's are the Glu-35 residue of Lysozyme, the Ile-16 residue of Chymotrypsin, the His-159 residue of Papain, etc. The conservation of function relates to either anomalous protonation or anomalous deprotonation of such amino acids, relative to their canonical, non-perturbed pKa. The pKa perturbation may enable these amino acids to actively participate in general acid-base catalysis due to the unique ionization environment within the enzyme active site. Thus, substituting an amino acid capable of serving as either a general acid or general base within the microenvironment of an enzyme active site or cavity, as may be the case, in the same or similar capacity as the wild-type amino acid, would effectively serve as a conservative amino substitution.

Besides conservative amino acid substitution, variants of the present invention include, but are not limited to, the following: (i) substitutions with one or more of the non-conserved amino acid residues, where the substituted amino acid residues may or may not be one encoded by the genetic code, or (ii) substitution with one or more of amino acid residues having a substituent group, or (iii) fusion of the mature polypeptide with another compound, such as a compound to increase the stability and/or solubility of the polypeptide (for example, polyethylene glycol), or (iv) fusion of the polypeptide with additional amino acids, such as, for example, an IgG Fc fusion region peptide, or leader or secretory sequence, or a sequence facilitating purification. Such variant polypeptides are deemed to be within the scope of those skilled in the art from the teachings herein.

For example, polypeptide variants containing amino acid substitutions of charged amino acids with other charged or neutral amino acids may produce proteins with improved characteristics, such as less aggregation. Aggregation of pharmaceutical formulations both reduces activity and increases clearance due to the aggregate's immunogenic activity. (Pinckard et al., Clin. Exp. Immunol. 2:331-340 (1967); Robbins et al., Diabetes 36: 838-845 (1987); Cleland et al., Crit. Rev. Therapeutic Drug Carrier Systems 10:307-377 (1993).)

Moreover, the invention further includes polypeptide variants created through the application of molecular evolution ("DNA Shuffling") methodology to the polynucleotide disclosed as SEQ ID NO:1, 3, 5, 7, and/or 97, the sequence of the clone submitted in a deposit, and/or the cDNA encoding the polypeptide disclosed as SEQ ID NO:2, 4, 6, 8, and/or 98. Such DNA Shuffling technology is known in the art and more particularly described elsewhere herein (e.g., WPC, Stemmer, PNAS, 91:10747, (1994)), and in the Examples provided herein).

A further embodiment of the invention relates to a polypeptide which comprises the amino acid sequence of the present invention having an amino acid sequence which contains at least one amino acid substitution, but not more than 50 amino acid substitutions, even more preferably, not more than 40 amino acid substitutions, still more preferably, not more than 30 amino acid substitutions, and still even more preferably, not more than 20 amino acid substitutions. Of course, in order of ever-increasing preference, it is highly preferable for a peptide or polypeptide to have an amino acid sequence which comprises the amino acid sequence of the present invention, which contains at least one, but not more than 10, 9, 8, 7, 6, 5, 4, 3, 2 or 1 amino acid substitutions. In specific embodiments, the number of additions, substitutions, and/or deletions in the amino acid sequence of the present invention or fragments thereof (e.g., the mature form and/or other fragments described herein), is 1-5, 5-10, 5-25, 5-50, 10-50 or 50-150, conservative amino acid substitutions are preferable.

Polynucleotide and Polypeptide Fragments

The present invention is directed to polynucleotide fragments of the polynucleotides of the invention, in addition to polypeptides encoded therein by said polynucleotides and/or fragments.

In the present invention, a "polynucleotide fragment" refers to a short polynucleotide having a nucleic acid sequence which: is a portion of that contained in a deposited clone, or encoding the polypeptide encoded by the cDNA in a deposited clone; is a portion of that shown in SEQ ID NO:1, 3, 5, 7, and/or 97 or the complementary strand thereto, or is a portion of a polynucleotide sequence encoding the polypeptide of SEQ ID NO:2, 4, 6, 8, and/or 98. The nucleotide fragments of the invention are preferably at least about 15 nt, and more preferably at least about 20 nt, still more preferably at least about 30 nt, and even more preferably, at least about 40 nt, at least about 50 nt, at least about 75 nt, or at least about 150 nt in length. A fragment "at least 20 nt in length," for example, is intended to include 20 or more contiguous bases from the cDNA sequence contained in a deposited clone or the nucleotide sequence shown in SEQ ID NO:1, 3, 5, 7, and/or 97. In this context "about" includes the particularly recited value, a value larger or smaller by several (5, 4, 3, 2, or 1) nucleotides, at either terminus, or at both termini. These nucleotide fragments have uses that include, but are not limited to, as diagnostic probes and primers as discussed herein. Of course, larger fragments (e.g., 50, 150, 500, 600, 2000 nucleotides) are preferred.

Moreover, representative examples of polynucleotide fragments of the invention, include, for example, fragments comprising, or alternatively consisting of, a sequence from about nucleotide number 1-50, 51-100, 101-150, 151-200, 201-250, 251-300, 301-350, 351-400, 401-450, 451-500, 501-550, 551-600, 651-700, 701-750, 751-800, 800-850, 851-900, 901-950, 951-1000, 1001-1050, 1051-1100, 1101-1150, 1151-1200, 1201-1250, 1251-1300, 1301-1350, 1351-1400, 1401-1450, 1451-1500, 1501-1550, 1551-1600, 1601-1650, 1651-1700, 1701-1750, 1751-1800, 1801-1850, 1851-1900, 1901-1950, 1951-2000, or 2001 to the end of SEQ ID NO:1, 3, 5, 7, and/or 97, or the complementary strand thereto, or the cDNA contained in a deposited clone. In this context "about" includes the particularly recited ranges, and ranges larger or smaller by several (5, 4, 3, 2, or 1) nucleotides, at either terminus or at both termini. Preferably, these fragments encode a polypeptide which has biological activity. More preferably, these polynucleotides can be used as probes or primers as discussed herein. Also encompassed by the present invention are polynucleotides which hybridize to these nucleic acid molecules under stringent hybridization conditions or lower stringency conditions, as are the polypeptides encoded by these polynucleotides.

In the present invention, a "polypeptide fragment" refers to an amino acid sequence which is a portion of that contained in SEQ ID NO:2, 4, 6, 8, and/or 98 or encoded by the cDNA contained in a deposited clone. Protein (polypeptide) fragments may be "free-standing," or comprised within a larger polypeptide of which the fragment forms a part or region, most preferably as a single continuous region. Representative examples of polypeptide fragments of the invention, include, for example, fragments comprising, or alternatively consisting of, from about amino acid number 1-20, 21-40, 41-60, 61-80, 81-100, 102-120, 121-140, 141-160, or 161 to the end of the coding region. Moreover, polypeptide fragments can be about 20, 30, 40, 50, 60, 70, 80, 90, 100, 110, 120, 130, 140, or 150 amino acids in length. In this context "about" includes the particularly recited ranges or values, and ranges or values larger or smaller by several (5, 4, 3, 2, or 1) amino acids, at either extreme or at both extremes. Polynucleotides encoding these polypeptides are also encompassed by the invention.

Preferred polypeptide fragments include the full-length protein. Further preferred polypeptide fragments include the full-length protein having a continuous series of deleted residues from the amino or the carboxy terminus, or both. For example, any number of amino acids, ranging from 1-60, can be deleted from the amino terminus of the full-length polypeptide. Similarly, any number of amino acids, ranging from 1-30, can be deleted from the carboxy terminus of the full-length protein. Furthermore, any combination of the above amino and carboxy terminus deletions are preferred. Similarly, polynucleotides encoding these polypeptide fragments are also preferred.

Also preferred are polypeptide and polynucleotide fragments characterized by structural or functional domains, such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions. Polypeptide fragments of SEQ ID NO:2, 4, 6, 8, and/or 98 falling within conserved domains are specifically contemplated by the present invention. Moreover, polynucleotides encoding these domains are also contemplated.

Other preferred polypeptide fragments are biologically active fragments. Biologically active fragments are those exhibiting activity similar, but not necessarily identical, to an activity of the polypeptide of the present invention. The biological activity of the fragments may include an improved desired activity, or a decreased undesirable activity. Polynucleotides encoding these polypeptide fragments are also encompassed by the invention.

In a preferred embodiment, the functional activity displayed by a polypeptide encoded by a polynucleotide fragment of the invention may be one or more biological activities typically associated with the full-length polypeptide of the invention. Illustrative of these biological activities includes the fragments ability to bind to at least one of the same antibodies which bind to the full-length protein, the fragments ability to interact with at lease one of the same proteins which bind to the full-length, the fragments ability to elicit at least one of the same immune responses as the full-length protein (i.e., to cause the immune system to create antibodies specific to the same epitope, etc.), the fragments ability to bind to at least one of the same polynucleotides as the full-length protein, the fragments ability to bind to a receptor of the full-length protein, the fragments ability to bind to a ligand of the full-length protein, and the fragments ability to multimerize with the full-length protein. However, the skilled artisan would appreciate that some fragments may have biological activities which are desirable and directly inapposite to the biological activity of the full-length protein. The functional activity of polypeptides of the invention, including fragments, variants, derivatives, and analogs thereof can be determined by numerous methods available to the skilled artisan, some of which are described elsewhere herein.

The present invention encompasses polypeptides comprising, or alternatively consisting of, an epitope of the polypeptide having an amino acid sequence of SEQ ID NO:2, 4, 6, 8, and/or 98, or an epitope of the polypeptide sequence encoded by a polynucleotide sequence contained in ATCC® deposit No. Z or encoded by a polynucleotide that hybridizes to the complement of the sequence of SEQ ID NO:1, 3, 5, 7, and/or 97 or contained in ATCC® deposit No. Z under stringent hybridization conditions or lower stringency hybridization conditions as defined supra. The present invention further encompasses polynucleotide sequences encoding an epitope of a polypeptide sequence of the invention (such as, for example, the sequence disclosed in SEQ ID NO:1), polynucleotide sequences of the complementary strand of a polynucleotide sequence encoding an epitope of the invention, and polynucleotide sequences which hybridize to the complementary strand under stringent hybridization conditions or lower stringency hybridization conditions defined supra.

The term "epitopes," as used herein, refers to portions of a polypeptide having antigenic or immunogenic activity in an animal, preferably a mammal, and most preferably in a human. In a preferred embodiment, the present invention encompasses a polypeptide comprising an epitope, as well as the polynucleotide encoding this polypeptide. An "immunogenic epitope," as used herein, is defined as a portion of a protein that elicits an antibody response in an animal, as determined by any method known in the art, for example, by the methods for generating antibodies described infra. (See, for example, Geysen et al., Proc. Natl. Acad. Sci. USA 81:3998-4002 (1983)). The term "antigenic epitope," as used herein, is defined as a portion of a protein to which an antibody can immunospecifically bind its antigen as determined by any method well known in the art, for example, by the immunoassays described herein. Immunospecific binding excludes non-specific binding but does not necessarily exclude cross-reactivity with other antigens. Antigenic epitopes need not necessarily be immunogenic.

Fragments which function as epitopes may be produced by any conventional means. (See, e.g., Houghten, Proc. Natl. Acad. Sci. USA 82:5131-5135 (1985), further described in U.S. Pat. No. 4,631,211).

In the present invention, antigenic epitopes preferably contain a sequence of at least 4, at least 5, at least 6, at least 7, more preferably at least 8, at least 9, at least 10, at least 11, at least 12, at least 13, at least 14, at least 15, at least 20, at least 25, at least 30, at least 40, at least 50, and, most preferably, between about 15 to about 30 amino acids. Preferred polypeptides comprising immunogenic or antigenic epitopes are at least 10, 15, 20, 25, 30, 35, 40, 45, 50, 55, 60, 65, 70, 75, 80, 85, 90, 95, or 100 amino acid residues in length, or longer. Additional non-exclusive preferred antigenic epitopes include the antigenic epitopes disclosed herein, as well as portions thereof. Antigenic epitopes are useful, for example, to raise antibodies, including monoclonal antibodies, that specifically bind the epitope. Preferred antigenic epitopes include the antigenic epitopes disclosed herein, as well as any combination of two, three, four, five or more of these antigenic epitopes. Antigenic epitopes can be used as the target molecules in immunoassays. (See, for instance, Wilson et al., Cell 37:767-778 (1984); Sutcliffe et al., Science 219:660-666 (1983)).

Similarly, immunogenic epitopes can be used, for example, to induce antibodies according to methods well known in the art. (See, for instance, Sutcliffe et al., supra; Wilson et al., supra; Chow et al., Proc. Natl. Acad. Sci. USA 82:910-914; and Bittle et al., J. Gen. Virol. 66:2347-2354 (1985). Preferred immunogenic epitopes include the immunogenic epitopes disclosed herein, as well as any combination of two, three, four, five or more of these immunogenic epitopes. The polypeptides comprising one or more immunogenic epitopes may be presented for eliciting an antibody response together with a carrier protein, such as an albumin, to an animal system (such as rabbit or mouse), or, if the polypeptide is of sufficient length (at least about 25 amino acids), the polypeptide may be presented without a carrier. However, immunogenic epitopes comprising as few as 8 to 10 amino acids have been shown to be sufficient to raise antibodies capable of binding to, at the very least, linear epitopes in a denatured polypeptide (e.g., in Western blotting).

Epitope-bearing polypeptides of the present invention may be used to induce antibodies according to methods well known in the art including, but not limited to, in vivo immunization, in vitro immunization, and phage display methods. See, e.g., Sutcliffe et al., supra; Wilson et al., supra, and Bittle et al., J. Gen. Virol., 66:2347-2354 (1985). If in vivo immunization is used, animals may be immunized with free peptide; however, anti-peptide antibody titer may be boosted by coupling the peptide to a macromolecular carrier, such as keyhole limpet hemacyanin (KLH) or tetanus toxoid. For instance, peptides containing cysteine residues may be coupled to a carrier using a linker such as maleimidobenzoyl-N-hydroxysuccinimide ester (MBS), while other peptides may be coupled to carriers using a more general linking agent such as glutaraldehyde. Animals such as rabbits, rats and mice are immunized with either free or carrier-coupled peptides, for instance, by intraperitoneal and/or intradermal injection of emulsions containing about 100 µg of peptide or carrier protein and Freund's adjuvant or any other adjuvant known for stimulating an immune response. Several booster injections may be needed, for instance, at intervals of about two weeks, to provide a useful titer of anti-peptide antibody which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

As one of skill in the art will appreciate, and as discussed above, the polypeptides of the present invention comprising an immunogenic or antigenic epitope can be fused to other polypeptide sequences. For example, the polypeptides of the present invention may be fused with the constant domain of immunoglobulins (IgA, IgE, IgG, IgM), or portions thereof (CH1, CH2, CH3, or any combination thereof and portions thereof) resulting in chimeric polypeptides. Such fusion proteins may facilitate purification and may increase half-life in vivo. This has been shown for chimeric proteins consisting of the first two domains of the human CD4-polypeptide and various domains of the constant regions of the heavy or light chains of mammalian immunoglobulins. See, e.g., EP 394, 827; Traunecker et al., Nature, 331:84-86 (1988). Enhanced delivery of an antigen across the epithelial barrier to the immune system has been demonstrated for antigens (e.g., insulin) conjugated to an FcRn binding partner such as IgG or Fc fragments (see, e.g., PCT Publications WO 96/22024 and WO 99/04813). IgG Fusion proteins that have a disulfide-linked dimeric structure due to the IgG portion disulfide bonds have also been found to be more efficient in binding and neutralizing other molecules than monomeric polypeptides or fragments thereof alone. See, e.g., Fountoulakis et al., J. Biochem., 270:3958-3964 (1995). Nucleic acids encoding the above epitopes can also be recombined with a gene of interest as an epitope tag (e.g., the hemagglutinin ("HA") tag or flag tag) to aid in detection and purification of the expressed polypeptide. For example, a system described by Janknecht et al. allows for the ready purification of non-denatured fusion proteins expressed in human cell lines (Janknecht et al., 1991, Proc. Natl. Acad. Sci. USA 88:8972-897). In this system, the gene of interest is subcloned into a vaccinia recombination plasmid such that the open reading frame of the gene is translationally fused to an amino-terminal tag consisting of six histidine residues. The tag serves as a matrix binding domain for the fusion protein. Extracts from cells infected with the recombinant vaccinia virus are loaded onto Ni2+ nitriloacetic acid-agarose column and histidine-tagged proteins can be selectively eluted with imidazole-containing buffers.

Additional fusion proteins of the invention may be generated through the techniques of gene-shuffling, motif-shuffling, exon-shuffling, and/or codon-shuffling (collectively referred to as "DNA shuffling"). DNA shuffling may be employed to modulate the activities of polypeptides of the invention, such methods can be used to generate polypeptides with altered activity, as well as agonists and antagonists of the polypeptides. See, generally, U.S. Pat. Nos. 5,605,793; 5,811,238; 5,830,721; 5,834,252; and 5,837,458, and Patten et al., Curr. Opinion Biotechnol. 8:724-33 (1997); Harayama, Trends Biotechnol. 16(2):76-82 (1998); Hansson, et al., J. Mol. Biol. 287:265-76 (1999); and Lorenzo and Blasco, Biotechniques 24(2):308-13 (1998) (each of these patents and publications are hereby incorporated by reference in its entirety). In one embodiment, alteration of polynucleotides corresponding to SEQ ID NO:1, 3, 5, 7, and/or 97 and the polypeptides encoded by these polynucleotides may be achieved by DNA shuffling. DNA shuffling involves the assembly of two or more DNA segments by homologous or site-specific recombination to generate variation in the polynucleotide sequence. In another embodiment, polynucleotides of the invention, or the encoded polypeptides, may be altered by being subjected to random mutagenesis by error-prone PCR, random nucleotide insertion or other methods prior to recombination. In another embodiment, one or more components, motifs, sections, parts, domains, fragments, etc., of a polynucleotide encoding a polypeptide of the invention may be recombined with one or more components, motifs, sections, parts, domains, fragments, etc. of one or more heterologous molecules.

Antibodies

Further polypeptides of the invention relate to antibodies and T-cell antigen receptors (TCR) which immunospecifically bind a polypeptide, polypeptide fragment, or variant of SEQ ID NO:2, 4, 6, 8, and/or 98, and/or an epitope, of the present invention (as determined by immunoassays well known in the art for assaying specific antibody-antigen binding). Antibodies of the invention include, but are not limited to, polyclonal, monoclonal, monovalent, bispecific, heteroconjugate, multispecific, human, humanized or chimeric antibodies, single chain antibodies, Fab fragments, F(ab') fragments, fragments produced by a Fab expression library, anti-idiotypic (anti-Id) antibodies (including, e.g., anti-Id antibodies to antibodies of the invention), and epitope-binding fragments of any of the above. The term "antibody," as used herein, refers to immunoglobulin molecules and immunologically active portions of immunoglobulin molecules, i.e., molecules that contain an antigen binding site that immunospecifically binds an antigen. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule. Moreover, the term "antibody" (Ab) or "monoclonal antibody" (Mab) is meant to include intact molecules, as well as, antibody fragments (such as, for example, Fab and F(ab')2 fragments) which are capable of specifically binding to protein. Fab and F(ab')2 fragments lack the Fc fragment of intact antibody, clear more rapidly from the circulation of the animal or plant, and may have less non-specific tissue binding than an intact antibody (Wahl et al., J. Nucl. Med. . . . 24:316-325 (1983)). Thus, these fragments are preferred, as well as the products of a FAB or other immunoglobulin expression library. Moreover, antibodies of the present invention include chimeric, single chain, and humanized antibodies.

Most preferably the antibodies are human antigen-binding antibody fragments of the present invention and include, but are not limited to, Fab, Fab' and F(ab')2, Fd, single-chain Fvs (scFv), single-chain antibodies, disulfide-linked Fvs (sdFv) and fragments comprising either a VL or VH domain. Antigen-binding antibody fragments, including single-chain antibodies, may comprise the variable region(s) alone or in combination with the entirety or a portion of the following: hinge region, CH1, CH2, and CH3 domains. Also included in the invention are antigen-binding fragments also comprising any combination of variable region(s) with a hinge region, CH1, CH2, and CH3 domains. The antibodies of the invention may be from any animal origin including birds and mammals. Preferably, the antibodies are human, murine (e.g., mouse and rat), donkey, ship rabbit, goat, guinea pig, camel, horse, or chicken. As used herein, "human" antibodies include antibodies having the amino acid sequence of a human immunoglobulin and include antibodies isolated from human immunoglobulin libraries or from animals transgenic for one or more human immunoglobulin and that do not express endogenous immunoglobulins, as described infra and, for example in, U.S. Pat. No. 5,939,598 by Kucherlapati et al.

The antibodies of the present invention may be monospecific, bispecific, trispecific or of greater multispecificity. Multispecific antibodies may be specific for different epitopes of a polypeptide of the present invention or may be specific for both a polypeptide of the present invention as well as for a heterologous epitope, such as a heterologous polypeptide or solid support material. See, e.g., PCT publications WO 93/17715; WO 92/08802; WO 91/00360; WO 92/05793; Tutt, et al., J. Immunol. 147:60-69 (1991); U.S. Pat. Nos. 4,474,893; 4,714,681; 4,925,648; 5,573,920; 5,601,819; Kostelny et al., J. Immunol. 148:1547-1553 (1992).

Antibodies of the present invention may be described or specified in terms of the epitope(s) or portion(s) of a polypeptide of the present invention which they recognize or specifically bind. The epitope(s) or polypeptide portion(s) may be specified as described herein, e.g., by N-terminal and C-terminal positions, by size in contiguous amino acid residues, or listed in the Tables and Figures. Antibodies which specifically bind any epitope or polypeptide of the present invention may also be excluded. Therefore, the present invention includes antibodies that specifically bind polypeptides of the present invention, and allows for the exclusion of the same.

Antibodies of the present invention may also be described or specified in terms of their cross-reactivity. Antibodies that do not bind any other analog, ortholog, or homologue of a polypeptide of the present invention are included. Antibodies that bind polypeptides with at least 95%, at least 90%, at least 85%, at least 80%, at least 75%, at least 70%, at least 65%, at least 60%, at least 55%, and at least 50% identity (as calculated using methods known in the art and described herein) to a polypeptide of the present invention are also included in the present invention. In specific embodiments, antibodies of the present invention cross-react with murine, rat and/or rabbit homologues of human proteins and the corresponding epitopes thereof. Antibodies that do not bind polypeptides with less than 95%, less than 90%, less than 85%, less than 80%, less than 75%, less than 70%, less than 65%, less than 60%, less than 55%, and less than 50% identity (as calculated using methods known in the art and described herein) to a polypeptide of the present invention are also included in the present invention. In a specific embodiment, the above-described cross-reactivity is with respect to any single specific antigenic or immunogenic polypeptide, or combination(s) of 2, 3, 4, 5, or more of the specific antigenic and/or immunogenic polypeptides disclosed herein. Further included in the present invention are antibodies which bind polypeptides encoded by polynucleotides which hybridize to a polynucleotide of the present invention under stringent hybridization conditions (as described herein). Antibodies of the present invention may also be described or specified in terms of their binding affinity to a polypeptide of the invention. Preferred binding affinities include those with a dissociation constant or Kd less than $5\times10^{-2}$ M, $10^{-2}$ M, $5\times10^{-3}$ M, $10^{-3}$ M, $5\times10^{-4}$ M, $10^{-4}$ M, $5\times10^{-5}$ M, $10^{-5}$ M, $5\times10^{-6}$ M, $10^{-6}$ M, $5\times10^{-7}$ M, $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, or $10^{-15}$ M.

The invention also provides antibodies that competitively inhibit binding of an antibody to an epitope of the invention as determined by any method known in the art for determining competitive binding, for example, the immunoassays described herein. In preferred embodiments, the antibody competitively inhibits binding to the epitope by at least 95%, at least 90%, at least 85%, at least 80%, at least 75%, at least 70%, at least 60%, or at least 50%.

Antibodies of the present invention may act as agonists or antagonists of the polypeptides of the present invention. For example, the present invention includes antibodies which disrupt the receptor/ligand interactions with the polypeptides of the invention either partially or fully. Preferably, antibodies of the present invention bind an antigenic epitope disclosed herein, or a portion thereof. The invention features both receptor-specific antibodies and ligand-specific antibodies. The invention also features receptor-specific antibodies which do not prevent ligand binding but prevent receptor activation. Receptor activation (i.e., signaling) may be determined by techniques described herein or otherwise known in the art. For example, receptor activation can be determined by detecting the phosphorylation (e.g., tyrosine or serine/threonine) of the receptor or its substrate by immunoprecipitation followed by western blot analysis (for example, as described supra). In specific embodiments, antibodies are provided that inhibit ligand activity or receptor activity by at least 95%, at least 90%, at least 85%, at least 80%, at least 75%, at least 70%, at least 60%, or at least 50% of the activity in absence of the antibody.

The invention also features receptor-specific antibodies which both prevent ligand binding and receptor activation as well as antibodies that recognize the receptor-ligand complex, and, preferably, do not specifically recognize the unbound receptor or the unbound ligand. Likewise, included in the invention are neutralizing antibodies which bind the ligand and prevent binding of the ligand to the receptor, as well as antibodies which bind the ligand, thereby preventing receptor activation, but do not prevent the ligand from binding the receptor. Further included in the invention are antibodies which activate the receptor. These antibodies may act as receptor agonists, i.e., potentiate or activate either all or a subset of the biological activities of the ligand-mediated receptor activation, for example, by inducing dimerization of the receptor. The antibodies may be specified as agonists, antagonists or inverse agonists for biological activities comprising the specific biological activities of the peptides of the invention disclosed herein. The above antibody agonists can be made using methods known in the art. See, e.g., PCT publication WO 96/40281; U.S. Pat. No. 5,811,097; Deng et al., Blood 92(6):1981-1988 (1998); Chen et al., Cancer Res. 58(16):3668-3678 (1998); Harrop et al., J. Immunol. 161(4): 1786-1794 (1998); Zhu et al., Cancer Res. 58(15):3209-3214 (1998); Yoon et al., J. Immunol. 160(7):3170-3179 (1998); Prat et al., J. Cell. Sci. 111(Pt2):237-247 (1998); Pitard et al., J. Immunol. Methods 205(2):177-190 (1997); Liautard et al., Cytokine 9(4):233-241 (1997); Carlson et al., J. Biol. Chem. 272(17):11295-11301 (1997); Taryman et al., Neuron 14(4): 755-762 (1995); Muller et al., Structure 6(9):1153-1167 (1998); Bartunek et al., Cytokine 8(1):14-20 (1996) (which are all incorporated by reference herein in their entireties).

Antibodies of the present invention may be used, for example, but not limited to, to purify, detect, and target the polypeptides of the present invention, including both in vitro and in vivo diagnostic and therapeutic methods. For example, the antibodies have use in immunoassays for qualitatively and quantitatively measuring levels of the polypeptides of the present invention in biological samples. See, e.g., Harlow et al., Antibodies: A Laboratory Manual, (Cold Spring Harbor Laboratory Press, 2nd ed. 1988) (incorporated by reference herein in its entirety).

As discussed in more detail below, the antibodies of the present invention may be used either alone or in combination with other compositions. The antibodies may further be recombinantly fused to a heterologous polypeptide at the N- or C-terminus or chemically conjugated (including covalently and non-covalently conjugations) to polypeptides or other compositions. For example, antibodies of the present invention may be recombinantly fused or conjugated to molecules useful as labels in detection assays and effector molecules such as heterologous polypeptides, drugs, radionucleotides, or toxins. See, e.g., PCT publications WO 92/08495; WO 91/14438; WO 89/12624; U.S. Pat. No. 5,314,995; and EP 396,387B1.

The antibodies of the invention include derivatives that are modified, i.e., by the covalent attachment of any type of molecule to the antibody such that covalent attachment does not prevent the antibody from generating an anti-idiotypic response. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

The antibodies of the present invention may be generated by any suitable method known in the art.

The antibodies of the present invention may comprise polyclonal antibodies. Methods of preparing polyclonal antibodies are known to the skilled artisan (Harlow, et al., Antibodies: A Laboratory Manual, (Cold spring Harbor Laboratory Press, $2^{nd}$ ed. (1988); and Current Protocols, Chapter 2; which are hereby incorporated herein by reference in its entirety). In a preferred method, a preparation of the TRP-PLIK2 polypeptides, TRP-PLIK2b, TRP-PLIK2c, and/or TRP-PLIK2d protein is prepared and purified to render it substantially free of natural contaminants. Such a preparation is then introduced into an animal in order to produce polyclonal antisera of greater specific activity. For example, a polypeptide of the invention can be administered to various host animals including, but not limited to, rabbits, mice, rats, etc. to induce the production of sera containing polyclonal antibodies specific for the antigen. The administration of the polypeptides of the present invention may entail one or more injections of an immunizing agent and, if desired, an adjuvant. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*. Such adjuvants are also well known in the art. For the purposes of the invention, "immunizing agent" may be defined as a polypeptide of the invention, including fragments, variants, and/or derivatives thereof, in addition to fusions with heterologous polypeptides and other forms of the polypeptides described herein.

Typically, the immunizing agent and/or adjuvant will be injected in the mammal by multiple subcutaneous or intraperitoneal injections, though they may also be given intramuscularly, and/or through IV). The immunizing agent may include polypeptides of the present invention or a fusion protein or variants thereof. Depending upon the nature of the polypeptides (i.e., percent hydrophobicity, percent hydrophilicity, stability, net charge, isoelectric point etc.), it may be useful to conjugate the immunizing agent to a protein known to be immunogenic in the mammal being immunized. Such conjugation includes either chemical conjugation by derivitizing active chemical functional groups to both the polypeptide of the present invention and the immunogenic protein such that a covalent bond is formed, or through fusion-protein based methodology, or other methods known to the skilled artisan. Examples of such immunogenic proteins include, but are not limited to keyhole limpet hemocyanin, serum albumin, bovine thyroglobulin, and soybean trypsin inhibitor. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*. Additional examples of adjuvants which may be employed includes the MPL-TDM adjuvant (monophosphoryl lipid A, synthetic trehalose dicorynomycolate). The immunization protocol may be selected by one skilled in the art without undue experimentation.

The antibodies of the present invention may comprise monoclonal antibodies. Monoclonal antibodies may be prepared using hybridoma methods, such as those described by Kohler and Milstein, Nature, 256:495 (1975) and U.S. Pat. No. 4,376,110, by Harlow, et al., Antibodies: A Laboratory Manual, (Cold spring Harbor Laboratory Press, $2^{nd}$ ed. (1988), by Hammerling, et al., Monoclonal Antibodies and T-Cell Hybridomas (Elsevier, N.Y., pp. 563-681 (1981); Köhler et al., Eur. J. Immunol. 6:511 (1976); Köhler et al., Eur. J. Immunol. 6:292 (1976), or other methods known to the artisan. Other examples of methods which may be employed for producing monoclonal antibodies includes, but are not limited to, the human B-cell hybridoma technique (Kosbor et al., 1983, Immunology Today 4:72; Cole et al., 1983, Proc. Natl. Acad. Sci. USA 80:2026-2030), and the EBV-hybridoma technique (Cole et al., 1985, Monoclonal Antibodies And Cancer Therapy, Alan R. Liss, Inc., pp. 77-96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In a hybridoma method, a mouse, a humanized mouse, a mouse with a human immune system, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include polypeptides of the present invention or a fusion protein thereof. Preferably, the immunizing agent consists of an TRP-PLIK2 polypeptides, TRP-PLIK2b, TRP-PLIK2c, and/or TRP-PLIK2d polypeptide or, more preferably, with a TRP-PLIK2 polypeptides, TRP-PLIK2b, TRP-PLIK2c, and/or TRP-PLIK2d polypeptide-expressing cell. Such cells may be cultured in any suitable tissue culture medium; however, it is preferable to culture cells in Earle's modified Eagle's medium supplemented with 10% fetal bovine serum (inactivated at about 56 degrees C.), and supplemented with about 10 g/l of nonessential amino acids, about 1,000 U/ml of penicillin, and about 100 ug/ml of streptomycin. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, Monoclonal Antibodies: Principles and Practice, Academic Press, (1986), pp. 59-103). Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. More preferred are the parent myeloma cell line (SP2O) as provided by the ATCC®. As inferred throughout the specification, human myeloma and mouse-human heteromyeloma cell lines also have been described for the production of human monoclonal antibodies (Kozbor, J. Immunol., 133:3001 (1984); Brodeur et al., Monoclonal Antibody Production Techniques and Applications, Marcel Dekker, Inc., New York, (1987) pp. 51-63).

The culture medium in which the hybridoma cells are cultured can then be assayed for the presence of monoclonal antibodies directed against the polypeptides of the present invention. Preferably, the binding specificity of monoclonal antibodies produced by the hybridoma cells is determined by immunoprecipitation or by an in vitro binding assay, such as radioimmunoassay (RIA) or enzyme-linked immunoabsorbant assay (ELISA). Such techniques are known in the art and within the skill of the artisan. The binding affinity of the monoclonal antibody can, for example, be determined by the Scatchard analysis of Munson and Pollart, Anal. Biochem., 107:220 (1980).

After the desired hybridoma cells are identified, the clones may be subcloned by limiting dilution procedures and grown by standard methods (Goding, supra, and/or according to Wands et al. (Gastroenterology 80:225-232 (1981)). Suitable culture media for this purpose include, for example, Dulbecco's Modified Eagle's Medium and RPMI-1640. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-sepharose, hydroxyapatite chromatography, gel exclusion chromatography, gel electrophoresis, dialysis, or affinity chromatography.

The skilled artisan would acknowledge that a variety of methods exist in the art for the production of monoclonal antibodies and thus, the invention is not limited to their sole production in hybridomas. For example, the monoclonal antibodies may be made by recombinant DNA methods, such as those described in U.S. Pat. No. 4,816,567. In this context, the term "monoclonal antibody" refers to an antibody derived from a single eukaryotic, phage, or prokaryotic clone. The DNA encoding the monoclonal antibodies of the invention can be readily isolated and sequenced using conventional procedures (e.g., by using oligonucleotide probes that are capable of binding specifically to genes encoding the heavy and light chains of murine antibodies, or such chains from human, humanized, or other sources). The hybridoma cells of the invention serve as a preferred source of such DNA. Once isolated, the DNA may be placed into expression vectors, which are then transformed into host cells such as Simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences (U.S. Pat. No. 4,816,567; Morrison et al, supra) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art. Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling, et al., in: Monoclonal Antibodies and T-Cell Hybridomas 563-681 (Elsevier, N.Y., 1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art and are discussed in detail in the Examples described herein. In a non-limiting example, mice can be immunized with a polypeptide of the invention or a cell expressing such peptide. Once an immune response is detected, e.g., antibodies specific for the antigen are detected in the mouse serum, the mouse spleen is harvested and splenocytes isolated. The splenocytes are then fused by well known techniques to any suitable myeloma cells, for example cells from cell line SP20 available from the ATCC®. Hybridomas are selected and cloned by limited dilution. The hybridoma clones are then assayed by methods known in the art for cells that secrete antibodies capable of binding a polypeptide of the invention. Ascites fluid, which generally contains high levels of antibodies, can be generated by immunizing mice with positive hybridoma clones.

Accordingly, the present invention provides methods of generating monoclonal antibodies as well as antibodies produced by the method comprising culturing a hybridoma cell secreting an antibody of the invention wherein, preferably, the hybridoma is generated by fusing splenocytes isolated from a mouse immunized with an antigen of the invention with myeloma cells and then screening the hybridomas resulting from the fusion for hybridoma clones that secrete an antibody able to bind a polypeptide of the invention.

Antibody fragments which recognize specific epitopes may be generated by known techniques. For example, Fab and F(ab')2 fragments of the invention may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain.

For example, the antibodies of the present invention can also be generated using various phage display methods known in the art. In phage display methods, functional antibody domains are displayed on the surface of phage particles which carry the polynucleotide sequences encoding them. In a particular embodiment, such phage can be utilized to display antigen binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make the antibodies of the present invention include those disclosed in Brinkman et al., J. Immunol. Methods 182:41-50 (1995); Ames et al., J. Immunol. Methods 184:177-186 (1995); Kettleborough et al., Eur. J. Immunol. 24:952-958 (1994); Persic et al., Gene 187 9-18 (1997); Burton et al., Advances in Immunology 57:191-280 (1994); PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described in detail below. For example, techniques to recombinantly produce Fab, Fab' and F(ab')2 fragments can also be employed using methods known in the art such as those disclosed in PCT publication WO 92/22324; Mullinax et al., BioTechniques 12(6):864-869 (1992); and Sawai et al., AJRI 34:26-34 (1995); and Better et al., Science 240:1041-1043 (1988) (said references incorporated by reference in their entireties). Examples of techniques which can be used to produce single-chain Fvs and antibodies include those described in U.S. Pat. Nos. 4,946,778 and 5,258,498; Huston et al., Methods in Enzymology 203:46-88 (1991); Shu et al., PNAS 90:7995-7999 (1993); and Skerra et al., Science 240: 1038-1040 (1988).

For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See e.g., Morrison, Science 229:1202 (1985); Oi et al., BioTechniques 4:214 (1986); Gillies et al., (1989) J. Immunol. Methods 125:191-202; Cabilly et al., Taniguchi et al., EP 171496B1; Morrison et al., EP 173494; Neuberger et al., WO 8601533; Robinson et al., WO 8702671; Boulianne et al., Nature 312:643 (1984); Neuberger et al., Nature 314:268 (1985); U.S. Pat. Nos. 5,807,715; 4,816,567; and 4,816,397, which are incorporated herein by reference in their entirety. Humanized antibodies are antibody molecules from non-human species antibody that binds the desired antigen having one or more complementarity determining regions (CDRs) from the non-human species and a framework regions from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., Nature 332:323 (1988), which are incorporated herein by reference in their entireties.) Antibodies can be humanized using a variety of techniques known in the art including, for example, CDR-grafting (EP 239,400B1; PCT publication WO 91/09967; U.S. Pat. Nos. 5,225,539; 5,530,101; and 5,585,089), veneering or resurfacing (EP 592,106B1; EP 519,596B1; Padlan, Molecular Immunology 28(4/5):489-498 (1991); Studnicka et al., Protein Engineering 7(6):805-814 (1994); Roguska. et al., PNAS 91:969-973 (1994)), and chain shuffling (U.S. Pat. No. 5,565,332). Generally, a humanized antibody has one or more amino acid residues introduced into it from a source that is non-human. These non-human amino acid residues are often referred to as "import" residues, which are typically taken from an "import" variable domain. Humanization can be essentially performed following the methods of Winter and co-workers (Jones et al., Nature, 321:522-525 (1986); Riechmann et al., Nature, 332:323-327 (1988); Verhoeyen et al., Science, 239:1534-1536 (1988), by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possible some FR residues are substituted from analogous sites in rodent antibodies.

In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin (Jones et al., Nature, 321:522-525 (1986); Riechmann et al., Nature 332:323-329 (1988)1 and Presta, Curr. Op. Struct. Biol., 2:593-596 (1992).

Completely human antibodies are particularly desirable for therapeutic treatment of human patients. Human antibodies can be made by a variety of methods known in the art including phage display methods described above using antibody libraries derived from human immunoglobulin sequences. See also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741; each of which is incorporated herein by reference in its entirety. The techniques of cole et al., and Boerder et al., are also available for the preparation of human monoclonal antibodies (cole et al., Monoclonal Antibodies and Cancer Therapy, Alan R. Riss, (1985); and Boerner et al., J. Immunol., 147(1):86-95, (1991)).

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar, Int. Rev. Immunol. 13:65-93 (1995). For a detailed discussion of this technology for producing human antibodies and human monoclonal antibodies and protocols for producing such antibodies, see, e.g., PCT publications WO 98/24893; WO 92/01047; WO 96/34096; WO 96/33735; European Patent No. 0 598 877; U.S. Pat. Nos. 5,413,923; 5,625,126; 5,633,425; 5,569,825; 5,661,016; 5,545,806; 5,814,318; 5,885,793; 5,916,771; and 5,939,598, which are incorporated by reference herein in their entirety. In addition, companies such as Abgenix, Inc. (Freemont, Calif.), Genpharm (San Jose, Calif.), and Medarex, Inc. (Princeton, N.J.) can be engaged to provide human antibodies directed against a selected antigen using technology similar to that described above.

Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and creation of an antibody repertoire. This approach is described, for example, in U.S. Pat. Nos. 5,545,807; 5,545,806; 5,569,825; 5,625,126; 5,633,425; 5,661,106, and in the following scientific publications: Marks et al., Biotechnol., 10:779-783 (1992); Lonberg et al., Nature 368:856-859 (1994); Fishwild et al., Nature Biotechnol., 14:845-51 (1996); Neuberger, Nature Biotechnol., 14:826 (1996); Lonberg and Huszer, Intern. Rev. Immunol., 13:65-93 (1995).

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., Bio/technology 12:899-903 (1988)).

Further, antibodies to the polypeptides of the invention can, in turn, be utilized to generate anti-idiotype antibodies that "mimic" polypeptides of the invention using techniques well known to those skilled in the art. (See, e.g., Greenspan & Bona, FASEB J. 7(5):437-444; (1989) and Nissinoff, J. Immunol. 147(8):2429-2438 (1991)). For example, antibodies which bind to and competitively inhibit polypeptide multimerization and/or binding of a polypeptide of the invention to a ligand can be used to generate anti-idiotypes that "mimic" the polypeptide multimerization and/or binding domain and, as a consequence, bind to and neutralize polypeptide and/or its ligand. Such neutralizing anti-idiotypes or Fab fragments of such anti-idiotypes can be used in therapeutic regimens to neutralize polypeptide ligand. For example, such anti-idiotypic antibodies can be used to bind a polypeptide of the invention and/or to bind its ligands/receptors, and thereby block its biological activity.

Such anti-idiotypic antibodies capable of binding to the TRP-PLIK2 polypeptides, TRP-PLIK2b, TRP-PLIK2c, and/or TRP-PLIK2d polypeptide can be produced in a two-step procedure. Such a method makes use of the fact that antibodies are themselves antigens, and therefore, it is possible to obtain an antibody that binds to a second antibody. In accordance with this method, protein specific antibodies are used to immunize an animal, preferably a mouse. The splenocytes of such an animal are then used to produce hybridoma cells, and the hybridoma cells are screened to identify clones that produce an antibody whose ability to bind to the protein-specific antibody can be blocked by the polypeptide. Such antibodies comprise anti-idiotypic antibodies to the protein-specific antibody and can be used to immunize an animal to induce formation of further protein-specific antibodies.

The antibodies of the present invention may be bispecific antibodies. Bispecific antibodies are monoclonal, Preferably human or humanized, antibodies that have binding specificities for at least two different antigens. In the present invention, one of the binding specificities may be directed towards a polypeptide of the present invention, the other may be for any other antigen, and preferably for a cell-surface protein, receptor, receptor subunit, tissue-specific antigen, virally derived protein, virally encoded envelope protein, bacterially derived protein, or bacterial surface protein, etc.

Methods for making bispecific antibodies are known in the art. Traditionally, the recombinant production of bispecific antibodies is based on the co-expression of two immunoglobulin heavy-chain/light-chain pairs, where the two heavy chains have different specificities (Milstein and Cuello, Nature, 305:537-539 (1983). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker et al., EMBO J., 10:3655-3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transformed into a suitable host organism. For further details of generating bispecific antibodies see, for example Suresh et al., Meth. In Enzym., 121:210 (1986).

Heteroconjugate antibodies are also contemplated by the present invention. Heteroconjugate antibodies are composed of two covalently joined antibodies. Such antibodies have, for example, been proposed to target immune system cells to unwanted cells (U.S. Pat. No. 4,676,980), and for the treatment of HIV infection (WO 91/00360; WO 92/20373; and EP03089B1). It is contemplated that the antibodies may be prepared in vitro using known methods in synthetic protein chemistry, including those involving crosslinking agents. For example, immunotoxins may be constructed using a disulfide exchange reaction or by forming a thioester bond. Examples of suitable reagents for this purpose include iminothiolate and methyl-4-mercaptobutyrimidate and those disclosed, for example, in U.S. Pat. No. 4,676,980.

Polynucleotides Encoding Antibodies

The invention further provides polynucleotides comprising a nucleotide sequence encoding an antibody of the invention and fragments thereof. The invention also encompasses polynucleotides that hybridize under stringent or lower stringency hybridization conditions, e.g., as defined supra, to polynucleotides that encode an antibody, preferably, that specifically binds to a polypeptide of the invention, preferably, an antibody that binds to a polypeptide having the amino acid sequence of SEQ ID NO:2, 4, 6, 8, and/or 98.

The polynucleotides may be obtained, and the nucleotide sequence of the polynucleotides determined, by any method known in the art. For example, if the nucleotide sequence of the antibody is known, a polynucleotide encoding the antibody may be assembled from chemically synthesized oligonucleotides (e.g., as described in Kutmeier et al., BioTechniques 17:242 (1994)), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody may be generated from nucleic acid from a suitable source. If a clone containing a nucleic acid encoding a particular antibody is not available, but the sequence of the antibody molecule is known, a nucleic acid encoding the immunoglobulin may be chemically synthesized or obtained from a suitable source (e.g., an antibody cDNA library, or a cDNA library generated from, or nucleic acid, preferably poly A+ RNA, isolated from, any tissue or cells expressing the antibody, such as hybridoma cells selected to express an antibody of the invention) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence and corresponding amino acid sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, NY, which are both incorporated by reference herein in their entireties), to generate antibodies having a different amino acid sequence, for example to create amino acid substitutions, deletions, and/or insertions.

In a specific embodiment, the amino acid sequence of the heavy and/or light chain variable domains may be inspected to identify the sequences of the complementarity determining regions (CDRs) by methods that are well know in the art, e.g., by comparison to known amino acid sequences of other heavy and light chain variable regions to determine the regions of sequence hypervariability. Using routine recombinant DNA techniques, one or more of the CDRs may be inserted within framework regions, e.g., into human framework regions to humanize a non-human antibody, as described supra. The framework regions may be naturally occurring or consensus framework regions, and preferably human framework regions (see, e.g., Chothia et al., J. Mol. Biol. 278: 457-479 (1998) for a listing of human framework regions). Preferably, the polynucleotide generated by the combination of the framework regions and CDRs encodes an antibody that specifically binds a polypeptide of the invention. Preferably, as discussed supra, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and within the skill of the art.

In addition, techniques developed for the production of "chimeric antibodies" (Morrison et al., Proc. Natl. Acad. Sci. 81:851-855 (1984); Neuberger et al., Nature 312:604-608 (1984); Takeda et al., Nature 314:452-454 (1985)) by splicing genes from a mouse antibody molecule of appropriate antigen specificity together with genes from a human antibody molecule of appropriate biological activity can be used. As described supra, a chimeric antibody is a molecule in which different portions are derived from different animal species, such as those having a variable region derived from a murine mAb and a human immunoglobulin constant region, e.g., humanized antibodies.

Alternatively, techniques described for the production of single chain antibodies (U.S. Pat. No. 4,946,778; Bird, Science 242:423-42 (1988); Huston et al., Proc. Natl. Acad. Sci. USA 85:5879-5883 (1988); and Ward et al., Nature 334:544-54 (1989)) can be adapted to produce single chain antibodies. Single chain antibodies are formed by linking the heavy and light chain fragments of the Fv region via an amino acid bridge, resulting in a single chain polypeptide. Techniques for the assembly of functional Fv fragments in E. coli may also be used (Skerra et al., Science 242:1038-1041 (1988)).

More preferably, a clone encoding an antibody of the present invention may be obtained according to the method described in the Example section herein.

Methods of Producing Antibodies

The antibodies of the invention can be produced by any method known in the art for the synthesis of antibodies, in particular, by chemical synthesis or preferably, by recombinant expression techniques.

Recombinant expression of an antibody of the invention, or fragment, derivative or analog thereof, (e.g., a heavy or light chain of an antibody of the invention or a single chain antibody of the invention), requires construction of an expression vector containing a polynucleotide that encodes the antibody. Once a polynucleotide encoding an antibody molecule or a heavy or light chain of an antibody, or portion thereof (preferably containing the heavy or light chain variable domain), of the invention has been obtained, the vector for the production of the antibody molecule may be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, or a heavy or light chain thereof, or a heavy or light chain variable domain, operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464) and the variable domain of the antibody may be cloned into such a vector for expression of the entire heavy or light chain.

The expression vector is transferred to a host cell by conventional techniques and the transfected cells are then cultured by conventional techniques to produce an antibody of the invention. Thus, the invention includes host cells containing a polynucleotide encoding an antibody of the invention, or a heavy or light chain thereof, or a single chain antibody of the invention, operably linked to a heterologous promoter. In preferred embodiments for the expression of double-chained antibodies, vectors encoding both the heavy and light chains may be co-expressed in the host cell for expression of the entire immunoglobulin molecule, as detailed below.

A variety of host-expression vector systems may be utilized to express the antibody molecules of the invention. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., Gene 45:101 (1986); Cockett et al., Bio/Technology 8:2 (1990)).

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited to, the *E. coli* expression vector pUR278 (Ruther et al., EMBO J. 2:1791 (1983)), in which the antibody coding sequence may be ligated individually into the vector in frame with the lac Z coding region so that a fusion protein is produced; pIN vectors (Inouye & Inouye, Nucleic Acids Res. 13:3101-3109 (1985); Van Heeke & Schuster, J. Biol. Chem. 24:5503-5509 (1989)); and the like. pGEX vectors may also be used to express foreign polypeptides as fusion proteins with glutathione S-transferase (GST). In general, such fusion proteins are soluble and can easily be purified from lysed cells by adsorption and binding to matrix glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts. (e.g., see Logan & Shenk, Proc. Natl. Acad. Sci. USA 81:355-359 (1984)). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., Methods in Enzymol. 153:51-544 (1987)).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 3T3, W138, and in particular, breast cancer cell lines such as, for example, BT483, Hs578T, HTB2, BT20 and T47D, and normal mammary gland cell line such as, for example, CRL7030 and Hs578Bst.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compounds that interact directly or indirectly with the antibody molecule.

A number of selection systems may be used, including but not limited to the herpes simplex virus thymidine kinase (Wigler et al., Cell 11:223 (1977)), hypoxanthine-guanine phosphoribosyltransferase (Szybalska & Szybalski, Proc. Natl. Acad. Sci. USA 48:202 (1992)), and adenine phosphoribosyltransferase (Lowy et al., Cell 22:817 (1980)) genes can be employed in tk–, hgprt– or aprt– cells, respectively. Also, antimetabolite resistance can be used as the basis of selection for the following genes: dhfr, which confers resistance to methotrexate (Wigler et al., Natl. Acad. Sci. USA 77:357 (1980); O'Hare et al., Proc. Natl. Acad. Sci. USA 78:1527 (1981)); gpt, which confers resistance to mycophenolic acid (Mulligan & Berg, Proc. Natl. Acad. Sci. USA 78:2072 (1981)); neo, which confers resistance to the aminoglycoside G-418 Clinical Pharmacy 12:488-505; Wu and Wu, Biotherapy 3:87-95 (1991); Tolstoshev, Ann. Rev. Pharmacol. Toxicol. 32:573-596 (1993); Mulligan, Science 260:926-932 (1993); and Morgan and Anderson, Ann. Rev. Biochem. 62:191-217 (1993); May, 1993, TIB TECH 11(5):155-215); and hygro, which confers resistance to hygromycin (Santerre et al., Gene 30:147 (1984)). Methods commonly known in the art of recombinant DNA technology may be routinely applied to select the desired recombinant clone, and such methods are described, for example, in Ausubel et al. (eds.), Current Protocols in Molecular Biology, John Wiley & Sons, NY (1993); Kriegler, Gene Transfer and Expression, A Laboratory Manual, Stockton Press, NY (1990); and in Chapters 12 and 13, Dracopoli et al. (eds), Current Protocols in Human Genetics, John Wiley & Sons, NY (1994); Colberre-Garapin et al., J. Mol. Biol. 150:1 (1981), which are incorporated by reference herein in their entireties.

The expression levels of an antibody molecule can be increased by vector amplification (for a review, see Bebbington and Hentschel, The use of vectors based on gene amplification for the expression of cloned genes in mammalian cells in DNA cloning, Vol. 3. (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., Mol. Cell. Biol. 3:257 (1983)).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes, and is capable of expressing, both heavy and light chain polypeptides. In such situations, the light chain should be placed before the heavy chain to avoid an excess of toxic free heavy chain (Proudfoot, Nature 322:52 (1986); Kohler, Proc. Natl. Acad. Sci. USA 77:2197 (1980)). The coding sequences for the heavy and light chains may comprise cDNA or genomic DNA.

Once an antibody molecule of the invention has been produced by an animal, chemically synthesized, or recombinantly expressed, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. In addition, the antibodies of the present invention or fragments thereof can be fused to heterologous polypeptide sequences described herein or otherwise known in the art, to facilitate purification.

The present invention encompasses antibodies recombinantly fused or chemically conjugated (including both covalently and non-covalently conjugations) to a polypeptide (or portion thereof, preferably at least 10, 20, 30, 40, 50, 60, 70, 80, 90 or 100 amino acids of the polypeptide) of the present invention to generate fusion proteins. The fusion does not necessarily need to be direct, but may occur through linker sequences. The antibodies may be specific for antigens other than polypeptides (or portion thereof, preferably at least 10, 20, 30, 40, 50, 60, 70, 80, 90 or 100 amino acids of the polypeptide) of the present invention. For example, antibodies may be used to target the polypeptides of the present invention to particular cell types, either in vitro or in vivo, by fusing or conjugating the polypeptides of the present invention to antibodies specific for particular cell surface receptors. Antibodies fused or conjugated to the polypeptides of the present invention may also be used in in vitro immunoassays and purification methods using methods known in the art. See e.g., Harbor et al., supra, and PCT publication WO 93/21232; EP 439,095B1; Naramura et al., Immunol. Lett. 39:91-99 (1994); U.S. Pat. No. 5,474,981; Gillies et al., PNAS 89:1428-1432 (1992); Fell et al., J. Immunol. 146:2446-2452 (1991), which are incorporated by reference in their entireties.

The present invention further includes compositions comprising the polypeptides of the present invention fused or conjugated to antibody domains other than the variable regions. For example, the polypeptides of the present invention may be fused or conjugated to an antibody Fc region, or portion thereof. The antibody portion fused to a polypeptide of the present invention may comprise the constant region, hinge region, CH1 domain, CH2 domain, and CH3 domain or any combination of whole domains or portions thereof. The polypeptides may also be fused or conjugated to the above antibody portions to form multimers. For example, Fc portions fused to the polypeptides of the present invention can form dimers through disulfide bonding between the Fc portions. Higher multimeric forms can be made by fusing the polypeptides to portions of IgA and IgM. Methods for fusing or conjugating the polypeptides of the present invention to antibody portions are known in the art. See, e.g., U.S. Pat. Nos. 5,336,603; 5,622,929; 5,359,046; 5,349,053; 5,447,851; 5,112,946; EP 307,434B1; EP 367,166; PCT publications WO 96/04388; WO 91/06570; Ashkenazi et al., Proc. Natl. Acad. Sci. USA 88:10535-10539 (1991); Zheng et al., J. Immunol. 154:5590-5600 (1995); and Vil et al., Proc. Natl. Acad. Sci. USA 89:11337-11341 (1992) (said references incorporated by reference in their entireties).

As discussed, supra, the polypeptides corresponding to a polypeptide, polypeptide fragment, or a variant of SEQ ID NO:2, 4, 6, 8, and/or 98 may be fused or conjugated to the above antibody portions to increase the in vivo half life of the polypeptides or for use in immunoassays using methods known in the art. Further, the polypeptides corresponding to SEQ ID NO:2, 4, 6, 8, and/or 98 may be fused or conjugated to the above antibody portions to facilitate purification. One reported example describes chimeric proteins consisting of the first two domains of the human CD4-polypeptide and various domains of the constant regions of the heavy or light chains of mammalian immunoglobulins. (EP 394,827; Traunecker et al., Nature 331:84-86 (1988). The polypeptides of the present invention fused or conjugated to an antibody having disulfide-linked dimeric structures (due to the IgG) may also be more efficient in binding and neutralizing other molecules, than the monomeric secreted protein or protein fragment alone. (Fountoulakis et al., J. Biochem. 270:3958-3964 (1995)). In many cases, the Fc part in a fusion protein is beneficial in therapy and diagnosis, and thus can result in, for example, improved pharmacokinetic properties. (EP A 232, 262). Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5. (See, Bennett et al., J. Molecular Recognition 8:52-58 (1995); Johanson et al., J. Biol. Chem. 270: 9459-9471 (1995).

Moreover, the antibodies or fragments thereof of the present invention can be fused to marker sequences, such as a peptide to facilitate purification. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821-824 (1989), for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., Cell 37:767 (1984)) and the "flag" tag.

The present invention further encompasses antibodies or fragments thereof conjugated to a diagnostic or therapeutic agent. The antibodies can be used diagnostically to, for example, monitor the development or progression of a tumor as part of a clinical testing procedure to, e.g., determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the antibody (or fragment thereof) or indirectly, through an intermediate (such as, for example, a linker known in the art) using techniques known in the art. See, for example, U.S. Pat. No. 4,741,900 for metal ions which can be conjugated to antibodies for use as diagnostics according to the present invention. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and acquorin; and examples of suitable radioactive material include 125I, 131I, 111In or 99Tc.

Further, an antibody or fragment thereof may be conjugated to a therapeutic moiety such as a cytotoxin, e.g., a cytostatic or cytocidal agent, a therapeutic agent or a radioactive metal ion, e.g., alpha-emitters such as, for example, 213Bi. A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicine, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologues thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thiotepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the therapeutic agent or drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, a-interferon, β-interferon, nerve growth factor, platelet derived growth factor, tissue plasminogen activator, an apoptotic agent, e.g., TNF-alpha, TNF-beta, AIM I (See, International Publication No. WO 97/33899), AIM II (See, International Publication No. WO 97/34911), Fas Ligand (Takahashi et al., Int. Immunol., 6:1567-1574 (1994)), VEGI (See, International Publication No. WO 99/23105), a thrombotic agent or an anti-angiogenic agent, e.g., angiostatin or endostatin; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Techniques for conjugating such therapeutic moiety to antibodies are well known, see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev. 62:119-58 (1982).

Alternatively, an antibody can be conjugated to a second antibody to form an antibody heteroconjugate as described by Segal in U.S. Pat. No. 4,676,980, which is incorporated herein by reference in its entirety.

An antibody, with or without a therapeutic moiety conjugated to it, administered alone or in combination with cytotoxic factor(s) and/or cytokine(s) can be used as a therapeutic.

The present invention also encompasses the creation of synthetic antibodies directed against the polypeptides of the present invention. One example of synthetic antibodies is described in Radrizzani, M., et al., Medicina, (Aires), 59(6): 753-8, (1999)). Recently, a new class of synthetic antibodies has been described and are referred to as molecularly imprinted polymers (MIPs) (Semorex, Inc.). Antibodies, peptides, and enzymes are often used as molecular recognition elements in chemical and biological sensors. However, their lack of stability and signal transduction mechanisms limits their use as sensing devices. Molecularly imprinted polymers (MIPs) are capable of mimicking the function of biological receptors but with less stability constraints. Such polymers provide high sensitivity and selectivity while maintaining excellent thermal and mechanical stability. MIPs have the ability to bind to small molecules and to target molecules such as organics and proteins' with equal or greater potency than that of natural antibodies. These "super" MIPs have higher affinities for their target and thus require lower concentrations for efficacious binding.

During synthesis, the MIPs are imprinted so as to have complementary size, shape, charge and functional groups of the selected target by using the target molecule itself (such as a polypeptide, antibody, etc.), or a substance having a very similar structure, as its "print" or "template." MIPs can be derivatized with the same reagents afforded to antibodies. For example, fluorescent 'super' MIPs can be coated onto beads or wells for use in highly sensitive separations or assays, or for use in high throughput screening of proteins.

Moreover, MIPs based upon the structure of the polypeptide(s) of the present invention may be useful in screening for compounds that bind to the polypeptide(s) of the invention. Such a MIP would serve the role of a synthetic "receptor" by minimicking the native architecture of the polypeptide. In fact, the ability of a MIP to serve the role of a synthetic receptor has already been demonstrated for the estrogen receptor (Ye, L., Yu, Y., Mosbach, K, Analyst., 126(6):760-5, (2001); Dickert, F, L., Hayden, O., Halikias, K, P, Analyst., 126(6):766-71, (2001)). A synthetic receptor may either be mimicked in its entirety (e.g., as the entire protein), or mimicked as a series of short peptides corresponding to the protein (Rachkov, A., Minoura, N, Biochim, Biophys, Acta., 1544(1-2):255-66, (2001)). Such a synthetic receptor MIPs may be employed in any one or more of the screening methods described elsewhere herein.

MIPs have also been shown to be useful in "sensing" the presence of its mimicked molecule (Cheng, Z., Wang, E., Yang, X, Biosens, Bioelectron., 16(3):179-85, (2001); Jenkins, A, L., Yin, R., Jensen, J, L, Analyst., 126(6):798-802, (2001); Jenkins, A, L., Yin, R., Jensen, J, L, Analyst., 126(6): 798-802, (2001)). For example, a MIP designed using a polypeptide of the present invention may be used in assays designed to identify, and potentially quantitate, the level of said polypeptide in a sample. Such a MIP may be used as a substitute for any component described in the assays, or kits, provided herein (e.g., ELISA, etc.).

A number of methods may be employed to create MIPs to a specific receptor, ligand, polypeptide, peptide, organic molecule. Several preferred methods are described by Esteban et al in J. Anal, Chem., 370(7):795-802, (2001), which is hereby incorporated herein by reference in its entirety in addition to any references cited therein. Additional methods are known in the art and are encompassed by the present invention, such as for example, Hart, B, R., Shea, K, J. J. Am. Chem., Soc., 123(9):2072-3, (2001); and Quaglia, M., Chenon, K., Hall, A, J., De, Lorenzi, E., Sellergren, B, J. Am. Chem., Soc., 123 (10):2146-54, (2001); which are hereby incorporated by reference in their entirety herein.

Uses for Antibodies Directed Against Polypeptides of the Invention

The antibodies of the present invention have various utilities. For example, such antibodies may be used in diagnostic assays to detect the presence or quantification of the polypeptides of the invention in a sample. Such a diagnostic assay may be comprised of at least two steps. The first, subjecting a sample with the antibody, wherein the sample is a tissue (e.g., human, animal, etc.), biological fluid (e.g., blood, urine, sputum, semen, amniotic fluid, saliva, etc.), biological extract (e.g., tissue or cellular homogenate, etc.), a protein microchip (e.g., See Arenkov P, et al., Anal Biochem., 278(2):123-131 (2000)), or a chromatography column, etc. And a second step involving the quantification of antibody bound to the substrate. Alternatively, the method may additionally involve a first step of attaching the antibody, either covalently, electrostatically, or reversibly, to a solid support, and a second step of subjecting the bound antibody to the sample, as defined above and elsewhere herein.

Various diagnostic assay techniques are known in the art, such as competitive binding assays, direct or indirect sandwich assays and immunoprecipitation assays conducted in either heterogeneous or homogenous phases (Zola, Monoclonal Antibodies: A Manual of Techniques, CRC Press, Inc., (1987), pp 147-158). The antibodies used in the diagnostic assays can be labeled with a detectable moiety. The detectable moiety should be capable of producing, either directly or indirectly, a detectable signal. For example, the detectable moiety may be a radioisotope, such as 2H, 14C, 32P, or 125I, a florescent or chemiluminescent compound, such as fluorescein isothiocyanate, rhodamine, or luciferin, or an enzyme, such as alkaline phosphatase, beta-galactosidase, green fluorescent protein, or horseradish peroxidase. Any method known in the art for conjugating the antibody to the detectable moiety may be employed, including those methods described by Hunter et al., Nature, 144:945 (1962); Dafvid et al., Biochem., 13:1014 (1974); Pain et al., J. Immunol. Metho., 40:219 (1981); and Nygren, J. Histochem. And Cytochem., 30:407 (1982).

Antibodies directed against the polypeptides of the present invention are useful for the affinity purification of such polypeptides from recombinant cell culture or natural sources. In this process, the antibodies against a particular polypeptide are immobilized on a suitable support, such as a SEPHADEX® resin or filter paper, using methods well known in the art. The immobilized antibody then is contacted with a sample containing the polypeptides to be purified, and thereafter the support is washed with a suitable solvent that will remove substantially all the material in the sample except for the desired polypeptides, which are bound to the immobilized antibody. Finally, the support is washed with another suitable solvent that will release the desired polypeptide from the antibody.

Immunophenotyping

The antibodies of the invention may be utilized for immunophenotyping of cell lines and biological samples. The translation product of the gene of the present invention may be useful as a cell specific marker, or more specifically as a cellular marker that is differentially expressed at various stages of differentiation and/or maturation of particular cell types. Monoclonal antibodies directed against a specific epitope, or combination of epitopes, will allow for the screening of cellular populations expressing the marker. Various techniques can be utilized using monoclonal antibodies to screen for cellular populations expressing the marker(s), and include magnetic separation using antibody-coated magnetic beads, "panning" with antibody attached to a solid matrix (i.e., plate), and flow cytometry (See, e.g., U.S. Pat. No. 5,985,660; and Morrison et al., Cell, 96:737-49 (1999)).

These techniques allow for the screening of particular populations of cells, such as might be found with hematological malignancies (i.e. minimal residual disease (MRD) in acute leukemic patients) and "non-self" cells in transplantations to prevent Graft-versus-Host Disease (GVHD). Alternatively, these techniques allow for the screening of hematopoietic stem and progenitor cells capable of undergoing proliferation and/or differentiation, as might be found in human umbilical cord blood.

Assays for Antibody Binding

The antibodies of the invention may be assayed for immunospecific binding by any method known in the art. The immunoassays which can be used include but are not limited to competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al, eds, 1994, Current Protocols in Molecular Biology, Vol. 1, John Wiley & Sons, Inc., New York, which is incorporated by reference herein in its entirety). Exemplary immunoassays are described briefly below (but are not intended by way of limitation).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% TRASYLOL®) supplemented with protein phosphatase and/or protease inhibitors (e.g., EDTA, PMSF, aprotinin, sodium vanadate), adding the antibody of interest to the cell lysate, incubating for a period of time (e.g., 1-4 hours) at 4° C., adding protein A and/or protein G sepharose beads to the cell lysate, incubating for about an hour or more at 4° C., washing the beads in lysis buffer and resuspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al, eds, 1994, Current Protocols in Molecular Biology, Vol. 1, John Wiley & Sons, Inc., New York at 10.16.1.

Western blot analysis generally comprises preparing protein samples, electrophoresis of the protein samples in a polyacrylamide gel (e.g., 8%-20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., 32P or 125I) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al, eds, 1994, Current Protocols in Molecular Biology, Vol. 1, John Wiley & Sons, Inc., New York at 10.8.1.

ELISAs comprise preparing antigen, coating the well of a 96 well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art. For further discussion regarding ELISAs see, e.g., Ausubel et al, eds, 1994, Current Protocols in Molecular Biology, Vol. 1, John Wiley & Sons, Inc., New York at 11.2.1.

The binding affinity of an antibody to an antigen and the off-rate of an antibody-antigen interaction can be determined by competitive binding assays. One example of a competitive binding assay is a radioimmunoassay comprising the incubation of labeled antigen (e.g., 3H or 125I) with the antibody of interest in the presence of increasing amounts of unlabeled antigen, and the detection of the antibody bound to the labeled antigen. The affinity of the antibody of interest for a particular antigen and the binding off-rates can be determined from the data by scatchard plot analysis. Competition with a second antibody can also be determined using radioimmunoassays. In this case, the antigen is incubated with antibody of interest conjugated to a labeled compound (e.g., 3H or 125I) in the presence of increasing amounts of an unlabeled second antibody.

Therapeutic Uses of Antibodies

The present invention is further directed to antibody-based therapies which involve administering antibodies of the invention to an animal, preferably a mammal, and most preferably a human, patient for treating one or more of the disclosed diseases, disorders, or conditions. Therapeutic compounds of the invention include, but are not limited to, antibodies of the invention (including fragments, analogs and derivatives thereof as described herein) and nucleic acids encoding antibodies of the invention (including fragments, analogs and derivatives thereof and anti-idiotypic antibodies as described herein). The antibodies of the invention can be used to treat, inhibit or prevent diseases, disorders or conditions associated with aberrant expression and/or activity of a polypeptide of the invention, including, but not limited to, any one or more of the diseases, disorders, or conditions described herein. The treatment and/or prevention of diseases, disorders, or conditions associated with aberrant expression and/or activity of a polypeptide of the invention includes, but is not limited to, alleviating symptoms associated with those diseases, disorders or conditions. Antibodies of the invention may be provided in pharmaceutically acceptable compositions as known in the art or as described herein.

A summary of the ways in which the antibodies of the present invention may be used therapeutically includes binding polynucleotides or polypeptides of the present invention locally or systemically in the body or by direct cytotoxicity of the antibody, e.g. as mediated by complement (CDC) or by effector cells (ADCC). Some of these approaches are described in more detail below. Armed with the teachings provided herein, one of ordinary skill in the art will know how to use the antibodies of the present invention for diagnostic, monitoring or therapeutic purposes without undue experimentation.

The antibodies of this invention may be advantageously utilized in combination with other monoclonal or chimeric antibodies, or with lymphokines or hematopoietic growth factors (such as, e.g., IL-2, IL-3 and IL-7), for example, which serve to increase the number or activity of effector cells which interact with the antibodies.

The antibodies of the invention may be administered alone or in combination with other types of treatments (e.g., radiation therapy, chemotherapy, hormonal therapy, immunotherapy and anti-tumor agents). Generally, administration of products of a species origin or species reactivity (in the case of antibodies) that is the same species as that of the patient is preferred. Thus, in a preferred embodiment, human antibodies, fragments derivatives, analogs, or nucleic acids, are administered to a human patient for therapy or prophylaxis.

It is preferred to use high affinity and/or potent in vivo inhibiting and/or neutralizing antibodies against polypeptides or polynucleotides of the present invention, fragments or regions thereof, for both immunoassays directed to and therapy of disorders related to polynucleotides or polypeptides, including fragments thereof, of the present invention. Such antibodies, fragments, or regions, will preferably have an affinity for polynucleotides or polypeptides of the invention, including fragments thereof. Preferred binding affinities include those with a dissociation constant or Kd less than $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, $10^{-5}$ M, $5 \times 10^{-6}$ M, $10^{-6}$ M, $5 \times 10^{-7}$ M, $10^{-7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, and $10^{-15}$ M.

Antibodies directed against polypeptides of the present invention are useful for inhibiting allergic reactions in animals. For example, by administering a therapeutically acceptable dose of an antibody, or antibodies, of the present invention, or a cocktail of the present antibodies, or in combination with other antibodies of varying sources, the animal may not elicit an allergic response to antigens.

Likewise, one could envision cloning the gene encoding an antibody directed against a polypeptide of the present invention, said polypeptide having the potential to elicit an allergic and/or immune response in an organism, and transforming the organism with said antibody gene such that it is expressed (e.g., constitutively, inducibly, etc.) in the organism. Thus, the organism would effectively become resistant to an allergic response resulting from the ingestion or presence of such an immune/allergic reactive polypeptide. Moreover, such a use of the antibodies of the present invention may have particular utility in preventing and/or ameliorating autoimmune diseases and/or disorders, as such conditions are typically a result of antibodies being directed against endogenous proteins. For example, in the instance where the polypeptide of the present invention is responsible for modulating the immune response to auto-antigens, transforming the organism and/or individual with a construct comprising any of the promoters disclosed herein or otherwise known in the art, in addition, to a polynucleotide encoding the antibody directed against the polypeptide of the present invention could effective inhibit the organisms immune system from eliciting an immune response to the auto-antigen(s). Detailed descriptions of therapeutic and/or gene therapy applications of the present invention are provided elsewhere herein.

Alternatively, antibodies of the present invention could be produced in a plant (e.g., cloning the gene of the antibody directed against a polypeptide of the present invention, and transforming a plant with a suitable vector comprising said gene for constitutive expression of the antibody within the plant), and the plant subsequently ingested by an animal, thereby conferring temporary immunity to the animal for the specific antigen the antibody is directed towards (See, for example, U.S. Pat. Nos. 5,914,123 and 6,034,298).

In another embodiment, antibodies of the present invention, preferably polyclonal antibodies, more preferably monoclonal antibodies, and most preferably single-chain antibodies, can be used as a means of inhibiting gene expression of a particular gene, or genes, in a human, mammal, and/or other organism. See, for example, International Publication Number WO 00/05391, published Feb. 3, 2000, to Dow Agrosciences LLC. The application of such methods for the antibodies of the present invention are known in the art, and are more particularly described elsewhere herein.

In yet another embodiment, antibodies of the present invention may be useful for multimerizing the polypeptides of the present invention. For example, certain proteins may confer enhanced biological activity when present in a multimeric state (i.e., such enhanced activity may be due to the increased effective concentration of such proteins whereby more protein is available in a localized location).

Antibody-Based Gene Therapy

In a specific embodiment, nucleic acids comprising sequences encoding antibodies or functional derivatives thereof, are administered to treat, inhibit or prevent a disease or disorder associated with aberrant expression and/or activity of a polypeptide of the invention, by way of gene therapy. Gene therapy refers to therapy performed by the administration to a subject of an expressed or expressible nucleic acid. In this embodiment of the invention, the nucleic acids produce their encoded protein that mediates a therapeutic effect.

Any of the methods for gene therapy available in the art can be used according to the present invention. Exemplary methods are described below.

For general reviews of the methods of gene therapy, see Goldspiel et al., Clinical Pharmacy 12:488-505 (1993); Wu and Wu, Biotherapy 3:87-95 (1991); Tolstoshev, Ann. Rev.

Pharmacol. Toxicol. 32:573-596 (1993); Mulligan, Science 260:926-932 (1993); and Morgan and Anderson, Ann. Rev. Biochem. 62:191-217 (1993); May, TIBTECH 11(5):155-215 (1993). Methods commonly known in the art of recombinant DNA technology which can be used are described in Ausubel et al. (eds.), Current Protocols in Molecular Biology, John Wiley & Sons, NY (1993); and Kriegler, Gene Transfer and Expression, A Laboratory Manual, Stockton Press, NY (1990).

In a preferred aspect, the compound comprises nucleic acid sequences encoding an antibody, said nucleic acid sequences being part of expression vectors that express the antibody or fragments or chimeric proteins or heavy or light chains thereof in a suitable host. In particular, such nucleic acid sequences have promoters operably linked to the antibody coding region, said promoter being inducible or constitutive, and, optionally, tissue-specific. In another particular embodiment, nucleic acid molecules are used in which the antibody coding sequences and any other desired sequences are flanked by regions that promote homologous recombination at a desired site in the genome, thus providing for intrachromosomal expression of the antibody encoding nucleic acids (Koller and Smithies, Proc. Natl. Acad. Sci. USA 86:8932-8935 (1989); Zijlstra et al., Nature 342:435-438 (1989). In specific embodiments, the expressed antibody molecule is a single chain antibody; alternatively, the nucleic acid sequences include sequences encoding both the heavy and light chains, or fragments thereof, of the antibody.

Delivery of the nucleic acids into a patient may be either direct, in which case the patient is directly exposed to the nucleic acid or nucleic acid-carrying vectors, or indirect, in which case, cells are first transformed with the nucleic acids in vitro, then transplanted into the patient. These two approaches are known, respectively, as in vivo or ex vivo gene therapy.

In a specific embodiment, the nucleic acid sequences are directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retrovirals or other viral vectors (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, J. Biol. Chem. 262:4429-4432 (1987)) (which can be used to target cell types specifically expressing the receptors), etc. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180; WO 92/22635; WO92/20316; WO93/14188, WO 93/20221). Alternatively, the nucleic acid can be introduced intracellularly and incorporated within host cell DNA for expression, by homologous recombination (Koller and Smithies, Proc. Natl. Acad. Sci. USA 86:8932-8935 (1989); Zijlstra et al., Nature 342:435-438 (1989)).

In a specific embodiment, viral vectors that contains nucleic acid sequences encoding an antibody of the invention are used. For example, a retroviral vector can be used (see Miller et al., Meth. Enzymol. 217:581-599 (1993)). These retroviral vectors contain the components necessary for the correct packaging of the viral genome and integration into the host cell DNA. The nucleic acid sequences encoding the antibody to be used in gene therapy are cloned into one or more vectors, which facilitates delivery of the gene into a patient. More detail about retroviral vectors can be found in Boesen et al., Biotherapy 6:291-302 (1994), which describes the use of a retroviral vector to deliver the mdr1 gene to hematopoietic stem cells in order to make the stem cells more resistant to chemotherapy. Other references illustrating the use of retroviral vectors in gene therapy are: Clowes et al., J. Clin. Invest. 93:644-651 (1994); Kiem et al., Blood 83:1467-1473 (1994); Salmons and Gunzberg, Human Gene Therapy 4:129-141 (1993); and Grossman and Wilson, Curr. Opin. in Genetics and Devel. 3:110-114 (1993).

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, Current Opinion in Genetics and Development 3:499-503 (1993) present a review of adenovirus-based gene therapy. Bout et al., Human Gene Therapy 5:3-10 (1994) demonstrated the use of adenovirus vectors to transfer genes to the respiratory epithelia of rhesus monkeys. Other instances of the use of adenoviruses in gene therapy can be found in Rosenfeld et al., Science 252:431-434 (1991); Rosenfeld et al., Cell 68:143-155 (1992); Mastrangeli et al., J. Clin. Invest. 91:225-234 (1993); PCT Publication WO94/12649; and Wang, et al., Gene Therapy 2:775-783 (1995). In a preferred embodiment, adenovirus vectors are used.

Adeno-associated virus (AAV) has also been proposed for use in gene therapy (Walsh et al., Proc. Soc. Exp. Biol. Med. 204:289-300 (1993); U.S. Pat. No. 5,436,146).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler and Behr, Meth. Enzymol. 217:599-618 (1993); Cohen et al., Meth. Enzymol. 217:618-644 (1993); Cline, Pharmac. Ther. 29:69-92m (1985) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as Tlymphocytes, Blymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a preferred embodiment, the cell used for gene therapy is autologous to the patient.

In an embodiment in which recombinant cells are used in gene therapy, nucleic acid sequences encoding an antibody are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention (see e.g. PCT Publication WO 94/08598; Stemple and Anderson, Cell 71:973-985 (1992); Rheinwald, Meth. Cell Bio. 21A:229 (1980); and Pittelkow and Scott, Mayo Clinic Proc. 61:771 (1986)).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription. Demonstration of Therapeutic or Prophylactic Activity The compounds or pharmaceutical compositions of the invention are preferably tested in vitro, and then in vivo for the desired therapeutic or prophylactic activity, prior to use in humans. For example, in vitro assays to demonstrate the therapeutic or prophylactic utility of a compound or pharmaceutical composition include, the effect of a compound on a cell line or a patient tissue sample. The effect of the compound or composition on the cell line and/or tissue sample can be determined utilizing techniques known to those of skill in the art including, but not limited to, rosette formation assays and cell lysis assays. In accordance with the invention, in vitro assays which can be used to determine whether administration of a specific compound is indicated, include in vitro cell culture assays in which a patient tissue sample is grown in culture, and exposed to or otherwise administered a compound, and the effect of such compound upon the tissue sample is observed.

Therapeutic/Prophylactic Administration and Compositions

The invention provides methods of treatment, inhibition and prophylaxis by administration to a subject of an effective amount of a compound or pharmaceutical composition of the invention, preferably an antibody of the invention. In a preferred aspect, the compound is substantially purified (e.g., substantially free from substances that limit its effect or produce undesired side-effects). The subject is preferably an animal, including but not limited to animals such as cows, pigs, horses, chickens, cats, dogs, etc., and is preferably a mammal, and most preferably human.

Formulations and methods of administration that can be employed when the compound comprises a nucleic acid or an immunoglobulin are described above; additional appropriate formulations and routes of administration can be selected from among those described herein below.

Various delivery systems are known and can be used to administer a compound of the invention, e.g., encapsulation in liposomes, microparticles, microcapsules, recombinant cells capable of expressing the compound, receptor-mediated endocytosis (see, e.g., Wu and Wu, J. Biol. Chem. 262:4429-4432 (1987)), construction of a nucleic acid as part of a retroviral or other vector, etc. Methods of introduction include but are not limited to intradermal, intramuscular, intraperitoneal, intravenous, subcutaneous, intranasal, epidural, and oral routes. The compounds or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compounds or compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compounds or compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as silastic membranes, or fibers. Preferably, when administering a protein, including an antibody, of the invention, care must be taken to use materials to which the protein does not absorb.

In another embodiment, the compound or composition can be delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.)

In yet another embodiment, the compound or composition can be delivered in a controlled release system. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J., Macromol. Sci. Rev. Macromol. Chem. 23:61 (1983); see also Levy et al., Science 228:190 (1985); During et al., Ann. Neurol. 25:351 (1989); Howard et al., J. Neurosurg. 71:105 (1989)). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115-138 (1984)).

Other controlled release systems are discussed in the review by Langer (Science 249:1527-1533 (1990)).

In a specific embodiment where the compound of the invention is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., Proc. Natl. Acad. Sci. USA 88:1864-1868 (1991)), etc. Alternatively, a nucleic acid can be introduced intracellularly and incorporated within host cell DNA for expression, by homologous recombination.

The present invention also provides pharmaceutical compositions. Such compositions comprise a therapeutically effective amount of a compound, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The amount of the compound of the invention which will be effective in the treatment, inhibition and prevention of a disease or disorder associated with aberrant expression and/or activity of a polypeptide of the invention can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

For antibodies, the dosage administered to a patient is typically 0.1 mg/kg to 100 mg/kg of the patient's body weight. Preferably, the dosage administered to a patient is between 0.1 mg/kg and 20 mg/kg of the patient's body weight, more preferably 1 mg/kg to 10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the invention may be reduced by enhancing uptake and tissue penetration (e.g., into the brain) of the antibodies by modifications such as, for example, lipidation.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

Diagnosis and Imaging with Antibodies

Labeled antibodies, and derivatives and analogs thereof, which specifically bind to a polypeptide of interest can be used for diagnostic purposes to detect, diagnose, or monitor diseases, disorders, and/or conditions associated with the aberrant expression and/or activity of a polypeptide of the invention. The invention provides for the detection of aberrant expression of a polypeptide of interest, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of aberrant expression.

The invention provides a diagnostic assay for diagnosing a disorder, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of a particular disorder. With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Antibodies of the invention can be used to assay protein levels in a biological sample using classical immunohistological methods known to those of skill in the art (e.g., see Jalkanen, et al., J. Cell. Biol. 101:976-985 (1985); Jalkanen, et al., J. Cell Biol. 105:3087-3096 (1987)). Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase; radioisotopes, such as iodine ($125I$, $121I$), carbon ($14C$), sulfur ($35S$), tritium ($3H$), indium ($112In$), and technetium ($99Tc$); luminescent labels, such as luminol; and fluorescent labels, such as fluorescein and rhodamine, and biotin.

One aspect of the invention is the detection and diagnosis of a disease or disorder associated with aberrant expression of a polypeptide of interest in an animal, preferably a mammal and most preferably a human. In one embodiment, diagnosis comprises: a) administering (for example, parenterally, subcutaneously, or intraperitoneally) to a subject an effective amount of a labeled molecule which specifically binds to the polypeptide of interest; b) waiting for a time interval following the administering for permitting the labeled molecule to preferentially concentrate at sites in the subject where the polypeptide is expressed (and for unbound labeled molecule to be cleared to background level); c) determining background level; and d) detecting the labeled molecule in the subject, such that detection of labeled molecule above the background level indicates that the subject has a particular disease or disorder associated with aberrant expression of the polypeptide of interest. Background level can be determined by various methods including, comparing the amount of labeled molecule detected to a standard value previously determined for a particular system.

It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of 99mTc. The labeled antibody or antibody fragment will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).

Depending on several variables, including the type of label used and the mode of administration, the time interval following the administration for permitting the labeled molecule to preferentially concentrate at sites in the subject and for unbound labeled molecule to be cleared to background level is 6 to 48 hours or 6 to 24 hours or 6 to 12 hours. In another embodiment the time interval following administration is 5 to 20 days or 5 to 10 days.

In an embodiment, monitoring of the disease or disorder is carried out by repeating the method for diagnosing the disease or disease, for example, one month after initial diagnosis, six months after initial diagnosis, one year after initial diagnosis, etc.

Presence of the labeled molecule can be detected in the patient using methods known in the art for in vivo scanning. These methods depend upon the type of label used. Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (Thurston et al., U.S. Pat. No. 5,441,050). In another embodiment, the molecule is labeled with a fluorescent compound and is detected in the patient using a fluorescence responsive scanning instrument. In another embodiment, the molecule is labeled with a positron emitting metal and is detected in the patent using positron emission-tomography. In yet another embodiment, the molecule is labeled with a paramagnetic label and is detected in a patient using magnetic resonance imaging (MRI).

Kits

The present invention provides kits that can be used in the above methods. In one embodiment, a kit comprises an antibody of the invention, preferably a purified antibody, in one or more containers. In a specific embodiment, the kits of the present invention contain a substantially isolated polypeptide comprising an epitope which is specifically immunoreactive with an antibody included in the kit. Preferably, the kits of the present invention further comprise a control antibody which does not react with the polypeptide of interest. In another specific embodiment, the kits of the present invention contain a means for detecting the binding of an antibody to a polypeptide of interest (e.g., the antibody may be conjugated to a detectable substrate such as a fluorescent compound, an enzymatic substrate, a radioactive compound or a luminescent compound, or a second antibody which recognizes the first antibody may be conjugated to a detectable substrate).

In another specific embodiment of the present invention, the kit is a diagnostic kit for use in screening serum containing antibodies specific against proliferative and/or cancerous polynucleotides and polypeptides. Such a kit may include a control antibody that does not react with the polypeptide of interest. Such a kit may include a substantially isolated polypeptide antigen comprising an epitope which is specifically immunoreactive with at least one anti-polypeptide antigen antibody. Further, such a kit includes means for detecting the binding of said antibody to the antigen (e.g., the antibody may be conjugated to a fluorescent compound such as fluorescein or rhodamine which can be detected by flow cytometry). In specific embodiments, the kit may include a recombinantly produced or chemically synthesized polypeptide antigen. The polypeptide antigen of the kit may also be attached to a solid support.

In a more specific embodiment the detecting means of the above-described kit includes a solid support to which said polypeptide antigen is attached. Such a kit may also include a non-attached reporter-labeled anti-human antibody. In this embodiment, binding of the antibody to the polypeptide antigen can be detected by binding of the said reporter-labeled antibody.

In an additional embodiment, the invention includes a diagnostic kit for use in screening serum containing antigens of the polypeptide of the invention. The diagnostic kit includes a substantially isolated antibody specifically immunoreactive with polypeptide or polynucleotide antigens, and means for detecting the binding of the polynucleotide or polypeptide antigen to the antibody. In one embodiment, the antibody is attached to a solid support. In a specific embodiment, the antibody may be a monoclonal antibody. The detecting means of the kit may include a second, labeled monoclonal antibody. Alternatively, or in addition, the detecting means may include a labeled, competing antigen.

In one diagnostic configuration, test serum is reacted with a solid phase reagent having a surface-bound antigen obtained by the methods of the present invention. After binding with specific antigen antibody to the reagent and removing unbound serum components by washing, the reagent is reacted with reporter-labeled anti-human antibody to bind reporter to the reagent in proportion to the amount of bound anti-antigen antibody on the solid support. The reagent is again washed to remove unbound labeled antibody, and the amount of reporter associated with the reagent is determined. Typically, the reporter is an enzyme which is detected by incubating the solid phase in the presence of a suitable fluorometric, luminescent or colorimetric substrate (Sigma, St. Louis, Mo.).

The solid surface reagent in the above assay is prepared by known techniques for attaching protein material to solid support material, such as polymeric beads, dip sticks, 96-well plate or filter material. These attachment methods generally include non-specific adsorption of the protein to the support or covalent attachment of the protein, typically through a free amine group, to a chemically reactive group on the solid support, such as an activated carboxyl, hydroxyl, or aldehyde group. Alternatively, streptavidin coated plates can be used in conjunction with biotinylated antigen(s).

Thus, the invention provides an assay system or kit for carrying out this diagnostic method. The kit generally includes a support with surface-bound recombinant antigens, and a reporter-labeled anti-human antibody for detecting surface-bound anti-antigen antibody.

Fusion Proteins

Any polypeptide of the present invention can be used to generate fusion proteins. For example, the polypeptide of the present invention, when fused to a second protein, can be used as an antigenic tag. Antibodies raised against the polypeptide of the present invention can be used to indirectly detect the second protein by binding to the polypeptide. Moreover, because certain proteins target cellular locations based on trafficking signals, the polypeptides of the present invention can be used as targeting molecules once fused to other proteins.

Examples of domains that can be fused to polypeptides of the present invention include not only heterologous signal sequences, but also other heterologous functional regions. The fusion does not necessarily need to be direct, but may occur through linker sequences.

Moreover, fusion proteins may also be engineered to improve characteristics of the polypeptide of the present invention. For instance, a region of additional amino acids, particularly charged amino acids, may be added to the N-terminus of the polypeptide to improve stability and persistence during purification from the host cell or subsequent handling and storage. Peptide moieties may be added to the polypeptide to facilitate purification. Such regions may be removed prior to final preparation of the polypeptide. Similarly, peptide cleavage sites can be introduced in-between such peptide moieties, which could additionally be subjected to protease activity to remove said peptide(s) from the protein of the present invention. The addition of peptide moieties, including peptide cleavage sites, to facilitate handling of polypeptides are familiar and routine techniques in the art.

Moreover, polypeptides of the present invention, including fragments, and specifically epitopes, can be combined with parts of the constant domain of immunoglobulins (IgA, IgE, IgG, IgM) or portions thereof (CH1, CH2, CH3, and any combination thereof, including both entire domains and portions thereof), resulting in chimeric polypeptides. These fusion proteins facilitate purification and show an increased half-life in vivo. One reported example describes chimeric proteins consisting of the first two domains of the human CD4-polypeptide and various domains of the constant regions of the heavy or light chains of mammalian immunoglobulins. (EP A 394,827; Traunecker et al., Nature 331:84-86 (1988).) Fusion proteins having disulfide-linked dimeric structures (due to the IgG) can also be more efficient in binding and neutralizing other molecules, than the monomeric secreted protein or protein fragment alone. (Fountoulakis et al., J. Biochem. 270:3958-3964 (1995).)

Similarly, EP-A-O 464 533B1 (Canadian counterpart 2045869) discloses fusion proteins comprising various portions of the constant region of immunoglobulin molecules together with another human protein or part thereof. In many cases, the Fc part in a fusion protein is beneficial in therapy and diagnosis, and thus can result in, for example, improved pharmacokinetic properties. (EP-A 0232 262.) Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5. (See, D. Bennett et al., J. Molecular Recognition 8:52-58 (1995); K. Johanson et al., J. Biol. Chem. 270:9459-9471 (1995).)

Moreover, the polypeptides of the present invention can be fused to marker sequences (also referred to as "tags"). Due to the availability of antibodies specific to such "tags", purification of the fused polypeptide of the invention, and/or its identification is significantly facilitated since antibodies specific to the polypeptides of the invention are not required. Such purification may be in the form of an affinity purification whereby an anti-tag antibody or another type of affinity matrix (e.g., anti-tag antibody attached to the matrix of a flow-thru column) that binds to the epitope tag is present. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821-824 (1989), for instance, hexa-histidine provides for convenient purification of the fusion protein. Another peptide tag useful for purification, the "HA" tag, corresponds to an epitope derived from the influenza hemagglutinin protein. (Wilson et al., Cell 37:767 (1984)).

The skilled artisan would acknowledge the existence of other "tags" which could be readily substituted for the tags referred to supra for purification and/or identification of polypeptides of the present invention (Jones C., et al., J Chromatogr A. 707(1):3-22 (1995)). For example, the c-myc tag and the 8F9, 3C7, 6E10, G4m B7 and 9E10 antibodies thereto (Evan et al., Molecular and Cellular Biology 5:3610-3616 (1985)); the Herpes Simplex virus glycoprotein D (gD) tag and its antibody (Paborsky et al., Protein Engineering, 3(6): 547-553 (1990), the Flag-peptide—i.e., the octapeptide sequence DYKDDDDK (SEQ ID NO:261), (Hopp et al., Biotech. 6:1204-1210 (1988); the KT3 epitope peptide (Martin et al., Science, 255:192-194 (1992)); a-tubulin epitope peptide (Skinner et al., J. Biol. Chem., 266:15136-15166, (1991)); the T7 gene 10 protein peptide tag (Lutz-Freyermuth et al., Proc. Natl. Sci. USA, 87:6363-6397 (1990)), the FITC epitope (Zymed, Inc.), the GFP epitope (Zymed, Inc.), and the Rhodamine epitope (Zymed, Inc.).

The present invention also encompasses the attachment of up to nine codons encoding a repeating series of up to nine arginine amino acids to the coding region of a polynucleotide of the present invention. The invention also encompasses chemically derivitizing a polypeptide of the present invention with a repeating series of up to nine arginine amino acids. Such a tag, when attached to a polypeptide, has recently been shown to serve as a universal pass, allowing compounds access to the interior of cells without additional derivitization or manipulation (Wender, P., et al., unpublished data).

Protein fusions involving polypeptides of the present invention, including fragments and/or variants thereof, can be used for the following, non-limiting examples, subcellular localization of proteins, determination of protein-protein interactions via immunoprecipitation, purification of proteins via affinity chromatography, functional and/or structural characterization of protein. The present invention also encompasses the application of hapten specific antibodies for any of the uses referenced above for epitope fusion proteins. For example, the polypeptides of the present invention could be chemically derivatized to attach hapten molecules (e.g., DNP, (Zymed, Inc.)). Due to the availability of monoclonal antibodies specific to such haptens, the protein could be readily purified using immunoprecipation, for example.

Polypeptides of the present invention, including fragments and/or variants thereof, in addition to, antibodies directed against such polypeptides, fragments, and/or variants, may be fused to any of a number of known, and yet to be determined, toxins, such as ricin, saporin (Mashiba H, et al., Ann. N.Y. Acad. Sci. 1999; 886:233-5), or HC toxin (Tonukari N J, et al., Plant Cell. 2000 February; 12(2):237-248), for example. Such fusions could be used to deliver the toxins to desired tissues for which a ligand or a protein capable of binding to the polypeptides of the invention exists.

The invention encompasses the fusion of antibodies directed against polypeptides of the present invention, including variants and fragments thereof, to said toxins for delivering the toxin to specific locations in a cell, to specific tissues, and/or to specific species. Such bifunctional antibodies are known in the art, though a review describing additional advantageous fusions, including citations for methods of production, can be found in P. J. Hudson, Curr. Opp. In. Imm. 11:548-557, (1999); this publication, in addition to the references cited therein, are hereby incorporated by reference in their entirety herein. In this context, the term "toxin" may be expanded to include any heterologous protein, a small molecule, radionucleotides, cytotoxic drugs, liposomes, adhesion molecules, glycoproteins, ligands, cell or tissue-specific ligands, enzymes, of bioactive agents, biological response modifiers, anti-fungal agents, hormones, steroids, vitamins, peptides, peptide analogs, anti-allergenic agents, anti-tubercular agents, anti-viral agents, antibiotics, anti-protozoan agents, chelates, radioactive particles, radioactive ions, X-ray contrast agents, monoclonal antibodies, polyclonal antibodies and genetic material. In view of the present disclosure, one skilled in the art could determine whether any particular "toxin" could be used in the compounds of the present invention. Examples of suitable "toxins" listed above are exemplary only and are not intended to limit the "toxins" that may be used in the present invention.

Thus, any of these above fusions can be engineered using the polynucleotides or the polypeptides of the present invention.

Vectors, Host Cells, and Protein Production

The present invention also relates to vectors containing the polynucleotide of the present invention, host cells, and the production of polypeptides by recombinant techniques. The vector may be, for example, a phage, plasmid, viral, or retroviral vector. Retroviral vectors may be replication competent or replication defective. In the latter case, viral propagation generally will occur only in complementing host cells.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The polynucleotide insert should be operatively linked to an appropriate promoter, such as the phage lambda PL promoter, the E. coli lac, trp, phoA and tac promoters, the SV40 early and late promoters and promoters of retroviral LTRs, to name a few. Other suitable promoters will be known to the skilled artisan. The expression constructs will further contain sites for transcription initiation, termination, and, in the transcribed region, a ribosome binding site for translation. The coding portion of the transcripts expressed by the constructs will preferably include a translation initiating codon at the beginning and a termination codon (UAA, UGA or UAG) appropriately positioned at the end of the polypeptide to be translated.

As indicated, the expression vectors will preferably include at least one selectable marker. Such markers include dihydrofolate reductase, G418 or neomycin resistance for eukaryotic cell culture and tetracycline, kanamycin or ampicillin resistance genes for culturing in E. coli and other bacteria. Representative examples of appropriate hosts include, but are not limited to, bacterial cells, such as E. coli, Streptomyces and Salmonella typhimurium cells; fungal cells, such as yeast cells (e.g., Saccharomyces cerevisiae or Pichia pastoris (ATCC® Accession No. 201178)); insect cells such as Drosophila S2 and Spodoptera Sf9 cells; animal cells such as CHO, COS, 293, and Bowes melanoma cells; and plant cells. Appropriate culture mediums and conditions for the above-described host cells are known in the art.

Among vectors preferred for use in bacteria include pQE70, pQE60 and pQE-9, available from QIAGEN, Inc.; PBLUESCRIPT® vectors, Phagescript vectors, pNH8A, pNH16a, pNH18A, pNH46A, available from Stratagene Cloning Systems, Inc.; and ptrc99a, pKK223-3, pKK233-3, pDR540, pRIT5 available from Pharmacia Biotech, Inc. Among preferred eukaryotic vectors are pWLNEO, pSV2CAT, pOG44, pXT1 and pSG available from Stratagene; and pSVK3, pBPV, pMSG and pSVL available from Pharmacia. Preferred expression vectors for use in yeast systems include, but are not limited to pYES2, pYD1, pTEF1/Zeo, pYES2/GS, pPICZ, pGAPZ, pGAPZalph, pPIC9, pPIC3.5, pHIL-D2, pHIL-S1, pPIC3.5K, pPIC9K, and PAO815 (all available from Invitrogen, Carlsbad, Calif.). Other suitable vectors will be readily apparent to the skilled artisan.

Introduction of the construct into the host cell can be effected by calcium phosphate transfection, DEAE-dextran mediated transfection, cationic lipid-mediated transfection, electroporation, transduction, infection, or other methods. Such methods are described in many standard laboratory manuals, such as Davis et al., Basic Methods In Molecular Biology (1986). It is specifically contemplated that the polypeptides of the present invention may in fact be expressed by a host cell lacking a recombinant vector.

A polypeptide of this invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification.

Polypeptides of the present invention, and preferably the secreted form, can also be recovered from: products purified from natural sources, including bodily fluids, tissues and cells, whether directly isolated or cultured; products of chemical synthetic procedures; and products produced by recombinant techniques from a prokaryotic or eukaryotic host, including, for example, bacterial, yeast, higher plant, insect, and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes. Thus, it is well known in the art that the N-terminal methionine encoded by the translation initiation codon generally is removed with high efficiency from any protein after translation in all eukaryotic cells. While the N-terminal methionine on most proteins also is efficiently removed in most prokaryotes, for some proteins, this prokaryotic removal process is inefficient, depending on the nature of the amino acid to which the N-terminal methionine is covalently linked.

In one embodiment, the yeast *Pichia pastoris* is used to express the polypeptide of the present invention in a eukaryotic system. *Pichia pastoris* is a methylotrophic yeast which can metabolize methanol as its sole carbon source. A main step in the methanol metabolization pathway is the oxidation of methanol to formaldehyde using O2. This reaction is catalyzed by the enzyme alcohol oxidase. In order to metabolize methanol as its sole carbon source, *Pichia pastoris* must generate high levels of alcohol oxidase due, in part, to the relatively low affinity of alcohol oxidase for O2. Consequently, in a growth medium depending on methanol as a main carbon source, the promoter region of one of the two alcohol oxidase genes (AOX1) is highly active. In the presence of methanol, alcohol oxidase produced from the AOX1 gene comprises up to approximately 30% of the total soluble protein in *Pichia pastoris*. See, Ellis, S. B., et al., Mol. Cell. Biol. 5:1111-21 (1985); Koutz, P. J, et al., Yeast 5:167-77 (1989); Tschopp, J. F., et al., Nucl. Acids Res. 15:3859-76 (1987). Thus, a heterologous coding sequence, such as, for example, a polynucleotide of the present invention, under the transcriptional regulation of all or part of the AOX1 regulatory sequence is expressed at exceptionally high levels in *Pichia* yeast grown in the presence of methanol.

In one example, the plasmid vector pPIC9K is used to express DNA encoding a polypeptide of the invention, as set forth herein, in a Pichea yeast system essentially as described in "*Pichia* Protocols: Methods in Molecular Biology," D. R. Higgins and J. Cregg, eds. The Humana Press, Totowa, N.J., 1998. This expression vector allows expression and secretion of a protein of the invention by virtue of the strong AOX1 promoter linked to the *Pichia pastoris* alkaline phosphatase (PHO) secretory signal peptide (i.e., leader) located upstream of a multiple cloning site.

Many other yeast vectors could be used in place of pPIC9K, such as, pYES2, pYD1, pTEF1/Zeo, pYES2/GS, pPICZ, pGAPZ, pGAPZalpha, pPIC9, pPIC3.5, pHIL-D2, pHIL-S1, pPIC3.5K, and PAO815, as one skilled in the art would readily appreciate, as long as the proposed expression construct provides appropriately located signals for transcription, translation, secretion (if desired), and the like, including an in-frame AUG, as required.

In another embodiment, high-level expression of a heterologous coding sequence, such as, for example, a polynucleotide of the present invention, may be achieved by cloning the heterologous polynucleotide of the invention into an expression vector such as, for example, pGAPZ or pGAPZalpha, and growing the yeast culture in the absence of methanol.

In addition to encompassing host cells containing the vector constructs discussed herein, the invention also encompasses primary, secondary, and immortalized host cells of vertebrate origin, particularly mammalian origin, that have been engineered to delete or replace endogenous genetic material (e.g., coding sequence), and/or to include genetic material (e.g., heterologous polynucleotide sequences) that is operably associated with the polynucleotides of the invention, and which activates, alters, and/or amplifies endogenous polynucleotides. For example, techniques known in the art may be used to operably associate heterologous control regions (e.g., promoter and/or enhancer) and endogenous polynucleotide sequences via homologous recombination, resulting in the formation of a new transcription unit (see, e.g., U.S. Pat. No. 5,641,670, issued Jun. 24, 1997; U.S. Pat. No. 5,733,761, issued Mar. 31, 1998; International Publication No. WO 96/29411, published Sep. 26, 1996; International Publication No. WO 94/12650, published Aug. 4, 1994; Koller et al., Proc. Natl. Acad. Sci. USA 86:8932-8935 (1989); and Zijlstra et al., Nature 342:435-438 (1989), the disclosures of each of which are incorporated by reference in their entireties).

In addition, polypeptides of the invention can be chemically synthesized using techniques known in the art (e.g., see Creighton, 1983, Proteins: Structures and Molecular Principles, W.H. Freeman & Co., N.Y., and Hunkapiller et al., Nature, 310:105-111 (1984)). For example, a polypeptide corresponding to a fragment of a polypeptide sequence of the invention can be synthesized by use of a peptide synthesizer. Furthermore, if desired, nonclassical amino acids or chemical amino acid analogs can be introduced as a substitution or addition into the polypeptide sequence. Non-classical amino acids include, but are not limited to, to the D-isomers of the common amino acids, 2,4-diaminobutyric acid, a-amino isobutyric acid, 4-aminobutyric acid, Abu, 2-amino butyric acid, g-Abu, e-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, b-alanine, fluoro-amino acids, designer amino acids such as b-methyl amino acids, Ca-methyl amino acids, Na-methyl amino acids, and amino acid analogs in general. Furthermore, the amino acid can be D (dextrorotary) or L (levorotary).

The invention encompasses polypeptides which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited, to specific chemical cleavage by cyanogen bromide, trypsin, chymotrypsin, papain, V8 protease, NaBH4; acetylation, formylation, oxidation, reduction; metabolic synthesis in the presence of tunicamycin; etc.

Additional post-translational modifications encompassed by the invention include, for example, e.g., N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of prokaryotic host cell expression. The polypeptides may also be modified with a detectable label, such as an enzymatic, fluorescent, isotopic or affinity label to allow for detection and isolation of the protein, the addition of epitope tagged peptide fragments (e.g., FLAG, HA, GST, thioredoxin, maltose binding protein, etc.), attachment of affinity tags such as biotin and/or streptavidin, the covalent attachment of chemical moieties to the amino acid backbone, N- or C-terminal processing of the polypeptides ends (e.g., proteolytic processing), deletion of the N-terminal methionine residue, etc.

Also provided by the invention are chemically modified derivatives of the polypeptides of the invention which may provide additional advantages such as increased solubility, stability and circulating time of the polypeptide, or decreased immunogenicity (see U.S. Pat. No. 4,179,337). The chemical moieties for derivitization may be selected from water soluble polymers such as polyethylene glycol, ethylene glycol/propylene glycol copolymers, carboxymethylcellulose, dextran, polyvinyl alcohol and the like. The polypeptides may be modified at random positions within the molecule, or at predetermined positions within the molecule and may include one, two, three or more attached chemical moieties.

The invention further encompasses chemical derivitization of the polypeptides of the present invention, preferably where the chemical is a hydrophilic polymer residue. Exemplary hydrophilic polymers, including derivatives, may be those that include polymers in which the repeating units contain one or more hydroxy groups (polyhydroxy polymers), including, for example, poly(vinyl alcohol); polymers in which the repeating units contain one or more amino groups (polyamine polymers), including, for example, peptides, polypeptides, proteins and lipoproteins, such as albumin and natural lipoproteins; polymers in which the repeating units contain one or more carboxy groups (polycarboxy polymers), including, for example, carboxymethylcellulose, alginic acid and salts thereof, such as sodium and calcium alginate, glycosaminoglycans and salts thereof, including salts of hyaluronic acid, phosphorylated and sulfonated derivatives of carbohydrates, genetic material, such as interleukin-2 and interferon, and phosphorothioate oligomers; and polymers in which the repeating units contain one or more saccharide moieties (polysaccharide polymers), including, for example, carbohydrates.

The molecular weight of the hydrophilic polymers may vary, and is generally about 50 to about 5,000,000, with polymers having a molecular weight of about 100 to about 50,000 being preferred. The polymers may be branched or unbranched. More preferred polymers have a molecular weight of about 150 to about 10,000, with molecular weights of 200 to about 8,000 being even more preferred.

For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog).

Additional preferred polymers which may be used to derivatize polypeptides of the invention, include, for example, poly(ethylene glycol) (PEG), poly(vinylpyrrolidone), polyoxomers, polysorbate and poly(vinyl alcohol), with PEG polymers being particularly preferred. Preferred among the PEG polymers are PEG polymers having a molecular weight of from about 100 to about 10,000. More preferably, the PEG polymers have a molecular weight of from about 200 to about 8,000, with PEG 2,000, PEG 5,000 and PEG 8,000, which have molecular weights of 2,000, 5,000 and 8,000, respectively, being even more preferred. Other suitable hydrophilic polymers, in addition to those exemplified above, will be readily apparent to one skilled in the art based on the present disclosure. Generally, the polymers used may include polymers that can be attached to the polypeptides of the invention via alkylation or acylation reactions.

The polyethylene glycol molecules (or other chemical moieties) should be attached to the protein with consideration of effects on functional or antigenic domains of the protein. There are a number of attachment methods available to those skilled in the art, e.g., EP 0 401 384B1, herein incorporated by reference (coupling PEG to G-CSF), see also Malik et al., Exp. Hematol. 20:1028-1035 (1992) (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues glutamic acid residues and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group.

One may specifically desire proteins chemically modified at the N-terminus. Using polyethylene glycol as an illustration of the present composition, one may select from a variety of polyethylene glycol molecules (by molecular weight, branching, etc.), the proportion of polyethylene glycol molecules to protein (polypeptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective proteins chemically modified at the N-terminus modification may be accomplished by reductive alkylation which exploits differential reactivity of different types of primary amino groups (lysine versus the N-terminus) available for derivatization in a particular protein. Under the appropriate reaction conditions, substantially selective derivatization of the protein at the N-terminus with a carbonyl group containing polymer is achieved.

As with the various polymers exemplified above, it is contemplated that the polymeric residues may contain functional groups in addition, for example, to those typically involved in linking the polymeric residues to the polypeptides of the present invention. Such functionalities include, for example, carboxyl, amine, hydroxy and thiol groups. These functional groups on the polymeric residues can be further reacted, if desired, with materials that are generally reactive with such functional groups and which can assist in targeting specific tissues in the body including, for example, diseased tissue. Exemplary materials which can be reacted with the additional functional groups include, for example, proteins, including antibodies, carbohydrates, peptides, glycopeptides, glycolipids, lectins, and nucleosides.

In addition to residues of hydrophilic polymers, the chemical used to derivatize the polypeptides of the present invention can be a saccharide residue. Exemplary saccharides which can be derived include, for example, monosaccharides or sugar alcohols, such as erythrose, threose, ribose, arabinose, xylose, lyxose, fructose, sorbitol, mannitol and sedoheptulose, with preferred monosaccharides being fructose, mannose, xylose, arabinose, mannitol and sorbitol; and disaccharides, such as lactose, sucrose, maltose and cellobiose. Other saccharides include, for example, inositol and ganglioside head groups. Other suitable saccharides, in addition to those exemplified above, will be readily apparent to one skilled in the art based on the present disclosure. Generally, saccharides which may be used for derivitization include saccharides that can be attached to the polypeptides of the invention via alkylation or acylation reactions.

Moreover, the invention also encompasses derivitization of the polypeptides of the present invention, for example, with lipids (including cationic, anionic, polymerized, charged, synthetic, saturated, unsaturated, and any combination of the above, etc.). stabilizing agents.

The invention encompasses derivitization of the polypeptides of the present invention, for example, with compounds that may serve a stabilizing function (e.g., to increase the polypeptides half-life in solution, to make the polypeptides more water soluble, to increase the polypeptides hydrophilic or hydrophobic character, etc.). Polymers useful as stabilizing materials may be of natural, semi-synthetic (modified natural) or synthetic origin. Exemplary natural polymers include naturally occurring polysaccharides, such as, for example, arabinans, fructans, fucans, galactans, galacturonans, glucans, mannans, xylans (such as, for example, inulin), levan, fucoidan, carrageenan, galactocarolose, pectic acid, pectins, including amylose, pullulan, glycogen, amylopectin, cellulose, dextran, dextrin, dextrose, glucose, polyglucose, polydextrose, pustulan, chitin, agarose, keratin, chondroitin, dermatan, hyaluronic acid, alginic acid, xanthin gum, starch and various other natural homopolymer or heteropolymers, such as those containing one or more of the following aldoses, ketoses, acids or amines: erythrose, threose, ribose, arabinose, xylose, lyxose, allose, altrose, glucose, dextrose, mannose, gulose, idose, galactose, talose, erythrulose, ribulose, xylulose, psicose, fructose, sorbose, tagatose, mannitol, sorbitol, lactose, sucrose, trehalose, maltose, cellobiose, glycine, serine, threonine, cysteine, tyrosine, asparagine, glutamine, aspartic acid, glutamic acid, lysine, arginine, histidine, glucuronic acid, gluconic acid, glucaric acid, galacturonic acid, mannuronic acid, glucosamine, galactosamine, and neuraminic acid, and naturally occurring derivatives thereof. Accordingly, suitable polymers include, for example, proteins, such as albumin, polyalginates, and polylactide-coglycolide polymers. Exemplary semi-synthetic polymers include carboxymethylcellulose, hydroxymethylcellulose, hydroxypropylmethylcellulose, methylcellulose, and methoxycellulose. Exemplary synthetic polymers include polyphosphazenes, hydroxyapatites, fluoroapatite polymers, polyethylenes (such as, for example, polyethylene glycol (including for example, the class of compounds referred to as PLURONIC®, commercially available from BASF, Parsippany, N.J.), polyoxyethylene, and polyethylene terephthalate), polypropylenes (such as, for example, polypropylene glycol), polyurethanes (such as, for example, polyvinyl alcohol (PVA), polyvinyl chloride and polyvinylpyrrolidone), polyamides including nylon, polystyrene, polylactic acids, fluorinated hydrocarbon polymers, fluorinated carbon polymers (such as, for example, polytetrafluoroethylene), acrylate, methacrylate, and polymethylmethacrylate, and derivatives thereof. Methods for the preparation of derivatized polypeptides of the invention which employ polymers as stabilizing compounds will be readily apparent to one skilled in the art, in view of the present disclosure, when coupled with information known in the art, such as that described and referred to in Unger, U.S. Pat. No. 5,205,290, the disclosure of which is hereby incorporated by reference herein in its entirety.

Moreover, the invention encompasses additional modifications of the polypeptides of the present invention. Such additional modifications are known in the art, and are specifically provided, in addition to methods of derivitization, etc., in U.S. Pat. No. 6,028,066, which is hereby incorporated in its entirety herein.

The polypeptides of the invention may be in monomers or multimers (i.e., dimers, trimers, tetramers and higher multimers). Accordingly, the present invention relates to monomers and multimers of the polypeptides of the invention, their preparation, and compositions (preferably, Therapeutics) containing them. In specific embodiments, the polypeptides of the invention are monomers, dimers, trimers or tetramers. In additional embodiments, the multimers of the invention are at least dimers, at least trimers, or at least tetramers.

Multimers encompassed by the invention may be homomers or heteromers. As used herein, the term homomer, refers to a multimer containing only polypeptides corresponding to the amino acid sequence of SEQ ID NO:2, 4, 6, 8, and/or 98 or encoded by the cDNA contained in a deposited clone (including fragments, variants, splice variants, and fusion proteins, corresponding to these polypeptides as described herein). These homomers may contain polypeptides having identical or different amino acid sequences. In a specific embodiment, a homomer of the invention is a multimer containing only polypeptides having an identical amino acid sequence. In another specific embodiment, a homomer of the invention is a multimer containing polypeptides having different amino acid sequences. In specific embodiments, the multimer of the invention is a homodimer (e.g., containing polypeptides having identical or different amino acid sequences) or a homotrimer (e.g., containing polypeptides having identical and/or different amino acid sequences). In additional embodiments, the homomeric multimer of the invention is at least a homodimer, at least a homotrimer, or at least a homotetramer.

As used herein, the term heteromer refers to a multimer containing one or more heterologous polypeptides (i.e., polypeptides of different proteins) in addition to the polypeptides of the invention. In a specific embodiment, the multimer of the invention is a heterodimer, a heterotrimer, or a heterotetramer. In additional embodiments, the heteromeric multimer of the invention is at least a heterodimer, at least a heterotrimer, or at least a heterotetramer.

Multimers of the invention may be the result of hydrophobic, hydrophilic, ionic and/or covalent associations and/or may be indirectly linked, by for example, liposome formation. Thus, in one embodiment, multimers of the invention, such as, for example, homodimers or homotrimers, are formed when polypeptides of the invention contact one another in solution. In another embodiment, heteromultimers of the invention, such as, for example, heterotrimers or heterotetramers, are formed when polypeptides of the invention contact antibodies to the polypeptides of the invention (including antibodies to the heterologous polypeptide sequence in a fusion protein of the invention) in solution. In other embodiments, multimers of the invention are formed by covalent associations with and/or between the polypeptides of the invention. Such covalent associations may involve one or more amino acid residues contained in the polypeptide sequence (e.g., that recited in the sequence listing, or contained in the polypeptide encoded by a deposited clone). In one instance, the covalent associations are cross-linking between cysteine residues located within the polypeptide sequences which interact in the native (i.e., naturally occurring) polypeptide. In another instance, the covalent associations are the consequence of chemical or recombinant manipulation. Alternatively, such covalent associations may involve one or more amino acid residues contained in the heterologous polypeptide sequence in a fusion protein of the invention.

In one example, covalent associations are between the heterologous sequence contained in a fusion protein of the invention (see, e.g., U.S. Pat. No. 5,478,925). In a specific example, the covalent associations are between the heterologous sequence contained in an Fc fusion protein of the invention (as described herein). In another specific example, covalent associations of fusion proteins of the invention are between heterologous polypeptide sequence from another protein that is capable of forming covalently associated multimers, such as for example, osteoprotegerin (see, e.g., International Publication NO: WO 98/49305, the contents of which are herein incorporated by reference in its entirety). In another embodiment, two or more polypeptides of the invention are joined through peptide linkers. Examples include those peptide linkers described in U.S. Pat. No. 5,073,627 (hereby incorporated by reference). Proteins comprising multiple polypeptides of the invention separated by peptide linkers may be produced using conventional recombinant DNA technology.

Another method for preparing multimer polypeptides of the invention involves use of polypeptides of the invention fused to a leucine zipper or isoleucine zipper polypeptide sequence. Leucine zipper and isoleucine zipper domains are polypeptides that promote multimerization of the proteins in which they are found. Leucine zippers were originally identified in several DNA-binding proteins (Landschulz et al., Science 240:1759, (1988)), and have since been found in a variety of different proteins. Among the known leucine zippers are naturally occurring peptides and derivatives thereof that dimerize or trimerize. Examples of leucine zipper domains suitable for producing soluble multimeric proteins of the invention are those described in PCT application WO 94/10308, hereby incorporated by reference. Recombinant fusion proteins comprising a polypeptide of the invention fused to a polypeptide sequence that dimerizes or trimerizes in solution are expressed in suitable host cells, and the resulting soluble multimeric fusion protein is recovered from the culture supernatant using techniques known in the art.

Trimeric polypeptides of the invention may offer the advantage of enhanced biological activity. Preferred leucine zipper moieties and isoleucine moieties are those that preferentially form trimers. One example is a leucine zipper derived from lung surfactant protein D (SPD), as described in Hoppe et al. (FEBS Letters 344:191, (1994)) and in U.S. patent application Ser. No. 08/446,922 (now U.S. Pat. No. 5,716,805), hereby incorporated by reference. Other peptides derived from naturally occurring trimeric proteins may be employed in preparing trimeric polypeptides of the invention.

In another example, proteins of the invention are associated by interactions between Flag® polypeptide sequence contained in fusion proteins of the invention containing Flag® polypeptide sequence. In a further embodiment, associations proteins of the invention are associated by interactions between heterologous polypeptide sequence contained in Flag® fusion proteins of the invention and anti-Flag® antibody.

The multimers of the invention may be generated using chemical techniques known in the art. For example, polypeptides desired to be contained in the multimers of the invention may be chemically cross-linked using linker molecules and linker molecule length optimization techniques known in the art (see, e.g., U.S. Pat. No. 5,478,925, which is herein incorporated by reference in its entirety). Additionally, multimers of the invention may be generated using techniques known in the art to form one or more inter-molecule cross-links between the cysteine residues located within the sequence of the polypeptides desired to be contained in the multimer (see, e.g., U.S. Pat. No. 5,478,925, which is herein incorporated by reference in its entirety). Further, polypeptides of the invention may be routinely modified by the addition of cysteine or biotin to the C terminus or N-terminus of the polypeptide and techniques known in the art may be applied to generate multimers containing one or more of these modified polypeptides (see, e.g., U.S. Pat. No. 5,478,925, which is herein incorporated by reference in its entirety). Additionally, techniques known in the art may be applied to generate liposomes containing the polypeptide components desired to be contained in the multimer of the invention (see, e.g., U.S. Pat. No. 5,478,925, which is herein incorporated by reference in its entirety).

Alternatively, multimers of the invention may be generated using genetic engineering techniques known in the art. In one embodiment, polypeptides contained in multimers of the invention are produced recombinantly using fusion protein technology described herein or otherwise known in the art (see, e.g., U.S. Pat. No. 5,478,925, which is herein incorporated by reference in its entirety). In a specific embodiment, polynucleotides coding for a homodimer of the invention are generated by ligating a polynucleotide sequence encoding a polypeptide of the invention to a sequence encoding a linker polypeptide and then further to a synthetic polynucleotide encoding the translated product of the polypeptide in the reverse orientation from the original C-terminus to the N-terminus (lacking the leader sequence) (see, e.g., U.S. Pat. No. 5,478,925, which is herein incorporated by reference in its entirety). In another embodiment, recombinant techniques described herein or otherwise known in the art are applied to generate recombinant polypeptides of the invention which contain a transmembrane domain (or hydrophobic or signal peptide) and which can be incorporated by membrane reconstitution techniques into liposomes (see, e.g., U.S. Pat. No. 5,478,925, which is herein incorporated by reference in its entirety).

In addition, the polynucleotide insert of the present invention could be operatively linked to "artificial" or chimeric promoters and transcription factors. Specifically, the artificial promoter could comprise, or alternatively consist, of any combination of cis-acting DNA sequence elements that are recognized by trans-acting transcription factors. Preferably, the cis acting DNA sequence elements and trans-acting transcription factors are operable in mammals. Further, the trans-acting transcription factors of such "artificial" promoters could also be "artificial" or chimeric in design themselves and could act as activators or repressors to said "artificial" promoter.

Uses of the Polynucleotides

Each of the polynucleotides identified herein can be used in numerous ways as reagents. The following description should be considered exemplary and utilizes known techniques.

The polynucleotides of the present invention are useful for chromosome identification. There exists an ongoing need to identify new chromosome markers, since few chromosome marking reagents, based on actual sequence data (repeat polymorphisms), are presently available. Each polynucleotide of the present invention can be used as a chromosome marker.

Briefly, sequences can be mapped to chromosomes by preparing PCR primers (preferably 15-25 bp) from the sequences shown in SEQ ID NO:1, 3, 5, 7, and/or 97. Primers can be selected using computer analysis so that primers do not span more than one predicted exon in the genomic DNA. These primers are then used for PCR screening of somatic cell hybrids containing individual human chromosomes. Only those hybrids containing the human gene corresponding to the SEQ ID NO:1, 3, 5, 7, and/or 97 will yield an amplified fragment.

Similarly, somatic hybrids provide a rapid method of PCR mapping the polynucleotides to particular chromosomes. Three or more clones can be assigned per day using a single thermal cycler. Moreover, sublocalization of the polynucleotides can be achieved with panels of specific chromosome fragments. Other gene mapping strategies that can be used include in situ hybridization, prescreening with labeled flow-sorted chromosomes, and preselection by hybridization to construct chromosome specific-cDNA libraries.

Precise chromosomal location of the polynucleotides can also be achieved using fluorescence in situ hybridization (FISH) of a metaphase chromosomal spread. This technique uses polynucleotides as short as 500 or 600 bases; however, polynucleotides 2,000-4,000 bp are preferred. For a review of this technique, see Verma et al., "Human Chromosomes: a Manual of Basic Techniques," Pergamon Press, New York (1988).

For chromosome mapping, the polynucleotides can be used individually (to mark a single chromosome or a single site on that chromosome) or in panels (for marking multiple sites and/or multiple chromosomes). Preferred polynucleotides correspond to the noncoding regions of the cDNAs because the coding sequences are more likely conserved within gene families, thus increasing the chance of cross hybridization during chromosomal mapping.

Once a polynucleotide has been mapped to a precise chromosomal location, the physical position of the polynucleotide can be used in linkage analysis. Linkage analysis establishes coinheritance between a chromosomal location and presentation of a particular disease. Disease mapping data are known in the art. Assuming 1 megabase mapping resolution and one gene per 20 kb, a cDNA precisely localized to a chromosomal region associated with the disease could be one of 50-500 potential causative genes.

Thus, once coinheritance is established, differences in the polynucleotide and the corresponding gene between affected and unaffected organisms can be examined. First, visible structural alterations in the chromosomes, such as deletions or translocations, are examined in chromosome spreads or by PCR. If no structural alterations exist, the presence of point mutations are ascertained. Mutations observed in some or all affected organisms, but not in normal organisms, indicates that the mutation may cause the disease. However, complete sequencing of the polypeptide and the corresponding gene from several normal organisms is required to distinguish the mutation from a polymorphism. If a new polymorphism is identified, this polymorphic polypeptide can be used for further linkage analysis.

Furthermore, increased or decreased expression of the gene in affected organisms as compared to unaffected organisms can be assessed using polynucleotides of the present invention. Any of these alterations (altered expression, chromosomal rearrangement, or mutation) can be used as a diagnostic or prognostic marker.

Thus, the invention also provides a diagnostic method useful during diagnosis of a disorder, involving measuring the expression level of polynucleotides of the present invention in cells or body fluid from an organism and comparing the measured gene expression level with a standard level of polynucleotide expression level, whereby an increase or decrease in the gene expression level compared to the standard is indicative of a disorder.

By "measuring the expression level of a polynucleotide of the present invention" is intended qualitatively or quantitatively measuring or estimating the level of the polypeptide of the present invention or the level of the mRNA encoding the polypeptide in a first biological sample either directly (e.g., by determining or estimating absolute protein level or mRNA level) or relatively (e.g., by comparing to the polypeptide level or mRNA level in a second biological sample). Preferably, the polypeptide level or mRNA level in the first biological sample is measured or estimated and compared to a standard polypeptide level or mRNA level, the standard being taken from a second biological sample obtained from an individual not having the disorder or being determined by averaging levels from a population of organisms not having a disorder. As will be appreciated in the art, once a standard polypeptide level or mRNA level is known, it can be used repeatedly as a standard for comparison.

By "biological sample" is intended any biological sample obtained from an organism, body fluids, cell line, tissue culture, or other source which contains the polypeptide of the present invention or mRNA. As indicated, biological samples include body fluids (such as the following non-limiting examples, sputum, amniotic fluid, urine, saliva, breast milk, secretions, interstitial fluid, blood, serum, spinal fluid, etc.) which contain the polypeptide of the present invention, and other tissue sources found to express the polypeptide of the present invention. Methods for obtaining tissue biopsies and body fluids from organisms are well known in the art. Where the biological sample is to include mRNA, a tissue biopsy is the preferred source.

The method(s) provided above may Preferably be applied in a diagnostic method and/or kits in which polynucleotides and/or polypeptides are attached to a solid support. In one exemplary method, the support may be a "gene chip" or a "biological chip" as described in U.S. Pat. Nos. 5,837,832, 5,874,219, and 5,856,174. Further, such a gene chip with polynucleotides of the present invention attached may be used to identify polymorphisms between the polynucleotide sequences, with polynucleotides isolated from a test subject. The knowledge of such polymorphisms (i.e. their location, as well as, their existence) would be beneficial in identifying disease loci for many disorders, including proliferative diseases and conditions. Such a method is described in U.S. Pat. Nos. 5,858,659 and 5,856,104. The US patents referenced supra are hereby incorporated by reference in their entirety herein.

The present invention encompasses polynucleotides of the present invention that are chemically synthesized, or reproduced as peptide nucleic acids (PNA), or according to other methods known in the art. The use of PNAs would serve as the preferred form if the polynucleotides are incorporated onto a solid support, or gene chip. For the purposes of the present invention, a peptide nucleic acid (PNA) is a polyamide type of DNA analog and the monomeric units for adenine, guanine, thymine and cytosine are available commercially (Perceptive Biosystems). Certain components of DNA, such as phosphorus, phosphorus oxides, or deoxyribose derivatives, are not present in PNAs. As disclosed by P. E. Nielsen, M. Egholm, R. H. Berg and O. Buchardt, Science 254, 1497 (1991); and M. Egholm, O. Buchardt, L. Christensen, C. Behrens, S. M. Freier, D. A. Driver, R. H. Berg, S. K. Kim, B. Norden, and P. E. Nielsen, Nature 365, 666 (1993), PNAs bind specifically and tightly to complementary DNA strands and are not degraded by nucleases. In fact, PNA binds more strongly to DNA than DNA itself does. This is probably because there is no electrostatic repulsion between the two strands, and also the polyamide backbone is more flexible. Because of this, PNA/DNA duplexes bind under a wider range of stringency conditions than DNA/DNA duplexes, making it easier to perform multiplex hybridization. Smaller probes can be used than with DNA due to the stronger binding characteristics of PNA:DNA hybrids. In addition, it is more likely that single base mismatches can be determined with PNA/DNA hybridization because a single mismatch in a PNA/DNA 15-mer lowers the melting point (T.sub.m) by 8°-20° C., vs. 4°-16° C. for the DNA/DNA 15-mer duplex. Also, the absence of charge groups in PNA means that hybridization can be done at low ionic strengths and reduce possible interference by salt during the analysis.

In addition to the foregoing, a polynucleotide can be used to control gene expression through triple helix formation or antisense DNA or RNA. Antisense techniques are discussed, for example, in Okano, J. Neurochem. 56: 560 (1991); "Oligodeoxynucleotides as Antisense Inhibitors of Gene Expression, CRC Press, Boca Raton, Fla. (1988). Triple helix formation is discussed in, for instance Lee et al., Nucleic Acids Research 6: 3073 (1979); Cooney et al., Science 241: 456 (1988); and Dervan et al., Science 251: 1360 (1991). Both methods rely on binding of the polynucleotide to a complementary DNA or RNA. For these techniques, preferred polynucleotides are usually oligonucleotides 20 to 40 bases in length and complementary to either the region of the gene involved in transcription (triple helix—see Lee et al., Nucl. Acids Res. 6:3073 (1979); Cooney et al., Science 241:456 (1988); and Dervan et al., Science 251:1360 (1991)) or to the mRNA itself (antisense—Okano, J. Neurochem. 56:560 (1991); Oligodeoxy-nucleotides as Antisense Inhibitors of Gene Expression, CRC Press, Boca Raton, Fla. (1988).) Triple helix formation optimally results in a shut-off of RNA transcription from DNA, while antisense RNA hybridization blocks translation of an mRNA molecule into polypeptide. Both techniques are effective in model systems, and the information disclosed herein can be used to design antisense or triple helix polynucleotides in an effort to treat or prevent disease.

The present invention encompasses the addition of a nuclear localization signal, operably linked to the 5' end, 3' end, or any location therein, to any of the oligonucleotides, antisense oligonucleotides, triple helix oligonucleotides, ribozymes, PNA oligonucleotides, and/or polynucleotides, of the present invention. See, for example, G. Cutrona, et al., Nat. Biotech., 18:300-303, (2000); which is hereby incorporated herein by reference.

Polynucleotides of the present invention are also useful in gene therapy. One goal of gene therapy is to insert a normal gene into an organism having a defective gene, in an effort to correct the genetic defect. The polynucleotides disclosed in the present invention offer a means of targeting such genetic defects in a highly accurate manner. Another goal is to insert a new gene that was not present in the host genome, thereby producing a new trait in the host cell. In one example, polynucleotide sequences of the present invention may be used to construct chimeric RNA/DNA oligonucleotides corresponding to said sequences, specifically designed to induce host cell mismatch repair mechanisms in an organism upon systemic injection, for example (Bartlett, R. J., et al., Nat. Biotech, 18:615-622 (2000), which is hereby incorporated by reference herein in its entirety). Such RNA/DNA oligonucleotides could be designed to correct genetic defects in certain host strains, and/or to introduce desired phenotypes in the host (e.g., introduction of a specific polymorphism within an endogenous gene corresponding to a polynucleotide of the present invention that may ameliorate and/or prevent a disease symptom and/or disorder, etc.). Alternatively, the polynucleotide sequence of the present invention may be used to construct duplex oligonucleotides corresponding to said sequence, specifically designed to correct genetic defects in certain host strains, and/or to introduce desired phenotypes into the host (e.g., introduction of a specific polymorphism within an endogenous gene corresponding to a polynucleotide of the present invention that may ameliorate and/or prevent a disease symptom and/or disorder, etc). Such methods of using duplex oligonucleotides are known in the art and are encompassed by the present invention (see EP1007712, which is hereby incorporated by reference herein in its entirety).

The polynucleotides are also useful for identifying organisms from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identifying personnel. This method does not suffer from the current limitations of "Dog Tags" which can be lost, switched, or stolen, making positive identification difficult. The polynucleotides of the present invention can be used as additional DNA markers for RFLP.

The polynucleotides of the present invention can also be used as an alternative to RFLP, by determining the actual base-by-base DNA sequence of selected portions of an organisms genome. These sequences can be used to prepare PCR primers for amplifying and isolating such selected DNA, which can then be sequenced. Using this technique, organisms can be identified because each organism will have a unique set of DNA sequences. Once an unique ID database is established for an organism, positive identification of that organism, living or dead, can be made from extremely small tissue samples. Similarly, polynucleotides of the present invention can be used as polymorphic markers, in addition to, the identification of transformed or non-transformed cells and/or tissues.

There is also a need for reagents capable of identifying the source of a particular tissue. Such need arises, for example, when presented with tissue of unknown origin. Appropriate reagents can comprise, for example, DNA probes or primers specific to particular tissue prepared from the sequences of the present invention. Panels of such reagents can identify tissue by species and/or by organ type. In a similar fashion, these reagents can be used to screen tissue cultures for contamination. Moreover, as mentioned above, such reagents can be used to screen and/or identify transformed and non-transformed cells and/or tissues.

In the very least, the polynucleotides of the present invention can be used as molecular weight markers on Southern gels, as diagnostic probes for the presence of a specific mRNA in a particular cell type, as a probe to "subtract-out" known sequences in the process of discovering novel polynucleotides, for selecting and making oligomers for attachment to a "gene chip" or other support, to raise anti-DNA antibodies using DNA immunization techniques, and as an antigen to elicit an immune response.

Uses of the Polypeptides

Each of the polypeptides identified herein can be used in numerous ways. The following description should be considered exemplary and utilizes known techniques.

A polypeptide of the present invention can be used to assay protein levels in a biological sample using antibody-based techniques. For example, protein expression in tissues can be studied with classical immunohistological methods. (Jalkanen, M., et al., J. Cell. Biol. 101:976-985 (1985); Jalkanen, M., et al., J. Cell. Biol. 105:3087-3096 (1987).) Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase, and radioisotopes, such as iodine (125I, 121I), carbon (14C), sulfur (35S), tritium (3H), indium (112In), and technetium (99mTc), and fluorescent labels, such as fluorescein and rhodamine, and biotin.

In addition to assaying protein levels in a biological sample, proteins can also be detected in vivo by imaging. Antibody labels or markers for in vivo imaging of protein include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which may be incorporated into the antibody by labeling of nutrients for the relevant hybridoma.

A protein-specific antibody or antibody fragment which has been labeled with an appropriate detectable imaging moiety, such as a radioisotope (for example, 131I, 112In, 99mTc), a radio-opaque substance, or a material detectable by nuclear magnetic resonance, is introduced (for example, parenterally, subcutaneously, or intraperitoneally) into the mammal. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of 99mTc. The labeled antibody or antibody fragment will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).)

Thus, the invention provides a diagnostic method of a disorder, which involves (a) assaying the expression of a polypeptide of the present invention in cells or body fluid of an individual; (b) comparing the level of gene expression with a standard gene expression level, whereby an increase or decrease in the assayed polypeptide gene expression level compared to the standard expression level is indicative of a disorder. With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Moreover, polypeptides of the present invention can be used to treat, prevent, and/or diagnose disease. For example, patients can be administered a polypeptide of the present invention in an effort to replace absent or decreased levels of the polypeptide (e.g., insulin), to supplement absent or decreased levels of a different polypeptide (e.g., hemoglobin S for hemoglobin B, SOD, catalase, DNA repair proteins), to inhibit the activity of a polypeptide (e.g., an oncogene or tumor suppressor), to activate the activity of a polypeptide (e.g., by binding to a receptor), to reduce the activity of a membrane bound receptor by competing with it for free ligand (e.g., soluble TNF receptors used in reducing inflammation), or to bring about a desired response (e.g., blood vessel growth inhibition, enhancement of the immune response to proliferative cells or tissues).

Similarly, antibodies directed to a polypeptide of the present invention can also be used to treat, prevent, and/or diagnose disease. For example, administration of an antibody directed to a polypeptide of the present invention can bind and reduce overproduction of the polypeptide. Similarly, administration of an antibody can activate the polypeptide, such as by binding to a polypeptide bound to a membrane (receptor).

At the very least, the polypeptides of the present invention can be used as molecular weight markers on SDS-PAGE gels or on molecular sieve gel filtration columns using methods well known to those of skill in the art. Polypeptides can also be used to raise antibodies, which in turn are used to measure protein expression from a recombinant cell, as a way of assessing transformation of the host cell. Moreover, the polypeptides of the present invention can be used to test the following biological activities.

Gene Therapy Methods

Another aspect of the present invention is to gene therapy methods for treating or preventing disorders, diseases and conditions. The gene therapy methods relate to the introduction of nucleic acid (DNA, RNA and antisense DNA or RNA) sequences into an animal to achieve expression of a polypeptide of the present invention. This method requires a polynucleotide which codes for a polypeptide of the invention that operatively linked to a promoter and any other genetic elements necessary for the expression of the polypeptide by the target tissue. Such gene therapy and delivery techniques are known in the art, see, for example, WO90/11092, which is herein incorporated by reference.

Thus, for example, cells from a patient may be engineered with a polynucleotide (DNA or RNA) comprising a promoter operably linked to a polynucleotide of the invention ex vivo, with the engineered cells then being provided to a patient to be treated with the polypeptide. Such methods are well-known in the art. For example, see Belldegrun et al., J. Natl. Cancer Inst., 85:207-216 (1993); Ferrantini et al., Cancer Research, 53:107-1112 (1993); Ferrantini et al., J. Immunology 153: 4604-4615 (1994); Kaido, T., et al., Int. J. Cancer 60: 221-229 (1995); Ogura et al., Cancer Research 50: 5102-5106 (1990); Santodonato, et al., Human Gene Therapy 7:1-10 (1996); Santodonato, et al., Gene Therapy 4:1246-1255

(1997); and Zhang, et al., Cancer Gene Therapy 3: 31-38 (1996)), which are herein incorporated by reference. In one embodiment, the cells which are engineered are arterial cells. The arterial cells may be reintroduced into the patient through direct injection to the artery, the tissues surrounding the artery, or through catheter injection.

As discussed in more detail below, the polynucleotide constructs can be delivered by any method that delivers injectable materials to the cells of an animal, such as, injection into the interstitial space of tissues (heart, muscle, skin, lung, liver, and the like). The polynucleotide constructs may be delivered in a pharmaceutically acceptable liquid or aqueous carrier.

In one embodiment, the polynucleotide of the invention is delivered as a naked polynucleotide. The term "naked" polynucleotide, DNA or RNA refers to sequences that are free from any delivery vehicle that acts to assist, promote or facilitate entry into the cell, including viral sequences, viral particles, liposome formulations, lipofectin or precipitating agents and the like. However, the polynucleotides of the invention can also be delivered in liposome formulations and lipofectin formulations and the like can be prepared by methods well known to those skilled in the art. Such methods are described, for example, in U.S. Pat. Nos. 5,593,972, 5,589,466, and 5,580,859, which are herein incorporated by reference.

The polynucleotide vector constructs of the invention used in the gene therapy method are preferably constructs that will not integrate into the host genome nor will they contain sequences that allow for replication. Appropriate vectors include pWLNEO, pSV2CAT, pOG44, pXT1 and pSG available from Stratagene; pSVK3, pBPV, pMSG and pSVL available from Pharmacia; and pEF1/V5, pcDNA3.1, and pRc/CMV2 available from Invitrogen. Other suitable vectors will be readily apparent to the skilled artisan.

Any strong promoter known to those skilled in the art can be used for driving the expression of polynucleotide sequence of the invention. Suitable promoters include adenoviral promoters, such as the adenoviral major late promoter; or heterologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs; the b-actin promoter; and human growth hormone promoters. The promoter also may be the native promoter for the polynucleotides of the invention.

Unlike other gene therapy techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for periods of up to six months.

The polynucleotide construct of the invention can be delivered to the interstitial space of tissues within the an animal, including of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular, fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. Delivery to the interstitial space of muscle tissue is preferred for the reasons discussed below. They may be conveniently delivered by injection into the tissues comprising these cells. They are preferably delivered to and expressed in persistent, non-dividing cells which are differentiated, although delivery and expression may be achieved in non-differentiated or less completely differentiated cells, such as, for example, stem cells of blood or skin fibroblasts. In vivo muscle cells are particularly competent in their ability to take up and express polynucleotides.

For the naked nucleic acid sequence injection, an effective dosage amount of DNA or RNA will be in the range of from about 0.05 mg/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and may depend on the condition being treated and the route of administration.

The preferred route of administration is by the parenteral route of injection into the interstitial space of tissues. However, other parenteral routes may also be used, such as, inhalation of an aerosol formulation particularly for delivery to lungs or bronchial tissues, throat or mucous membranes of the nose. In addition, naked DNA constructs can be delivered to arteries during angioplasty by the catheter used in the procedure.

The naked polynucleotides are delivered by any method known in the art, including, but not limited to, direct needle injection at the delivery site, intravenous injection, topical administration, catheter infusion, and so-called "gene guns". These delivery methods are known in the art.

The constructs may also be delivered with delivery vehicles such as viral sequences, viral particles, liposome formulations, lipofectin, precipitating agents, etc. Such methods of delivery are known in the art.

In certain embodiments, the polynucleotide constructs of the invention are complexed in a liposome preparation. Liposomal preparations for use in the instant invention include cationic (positively charged), anionic (negatively charged) and neutral preparations. However, cationic liposomes are particularly preferred because a tight charge complex can be formed between the cationic liposome and the polyanionic nucleic acid. Cationic liposomes have been shown to mediate intracellular delivery of plasmid DNA (Felgner et al., Proc. Natl. Acad. Sci. USA, 84:7413-7416 (1987), which is herein incorporated by reference); mRNA (Malone et al., Proc. Natl. Acad. Sci. USA, 86:6077-6081 (1989), which is herein incorporated by reference); and purified transcription factors (Debs et al., J. Biol. Chem., 265:10189-10192 (1990), which is herein incorporated by reference), in functional form.

Cationic liposomes are readily available. For example, N[1-2,3-dioleyloxy)propyl]-N,N,N-triethylammonium (DOTMA) liposomes are particularly useful and are available under the trademark Lipofectin, from GIBCO BRL, Grand Island, N.Y. (See, also, Felgner et al., Proc. Natl. Acad. Sci. USA, 84:7413-7416 (1987), which is herein incorporated by reference). Other commercially available liposomes include transfectace (DDAB/DOPE) and DOTAP/DOPE (Boehringer).

Other cationic liposomes can be prepared from readily available materials using techniques well known in the art. See, e.g. PCT Publication NO: WO 90/11092 (which is herein incorporated by reference) for a description of the synthesis of DOTAP (1,2-bis(oleoyloxy)-3-(trimethylammonio)propane) liposomes. Preparation of DOTMA liposomes is explained in the literature, see, e.g., Felgner et al., Proc. Natl. Acad. Sci. USA, 84:7413-7417, which is herein incorporated by reference.

Similar methods can be used to prepare liposomes from other cationic lipid materials. Similarly, anionic and neutral liposomes are readily available, such as from Avanti Polar Lipids (Birmingham, Ala.), or can be easily prepared using readily available materials. Such materials include phosphatidyl, choline, cholesterol, phosphatidyl ethanolamine, dioleoylphosphatidyl choline (DOPC), dioleoylphosphatidyl glycerol (DOPG), dioleoylphosphatidyl ethanolamine (DOPE), among others. These materials can also be mixed with the DOTMA and DOTAP starting materials in appropriate ratios. Methods for making liposomes using these materials are well known in the art.

For example, commercially dioleoylphosphatidyl choline (DOPC), dioleoylphosphatidyl glycerol (DOPG), and dioleoylphosphatidyl ethanolamine (DOPE) can be used in various combinations to make conventional liposomes, with or without the addition of cholesterol. Thus, for example, DOPG/DOPC vesicles can be prepared by drying 50 mg each of DOPG and DOPC under a stream of nitrogen gas into a sonication vial. The sample is placed under a vacuum pump overnight and is hydrated the following day with deionized water. The sample is then sonicated for 2 hours in a capped vial, using a Heat Systems model 350 sonicator equipped with an inverted cup (bath type) probe at the maximum setting while the bath is circulated at 15EC. Alternatively, negatively charged vesicles can be prepared without sonication to produce multilamellar vesicles or by extrusion through nucleopore membranes to produce unilamellar vesicles of discrete size. Other methods are known and available to those of skill in the art.

The liposomes can comprise multilamellar vesicles (MLVs), small unilamellar vesicles (SUVs), or large unilamellar vesicles (LUVs), with SUVs being preferred. The various liposome-nucleic acid complexes are prepared using methods well known in the art. See, e.g., Straubinger et al., Methods of Immunology, 101:512-527 (1983), which is herein incorporated by reference. For example, MLVs containing nucleic acid can be prepared by depositing a thin film of phospholipid on the walls of a glass tube and subsequently hydrating with a solution of the material to be encapsulated. SUVs are prepared by extended sonication of MLVs to produce a homogeneous population of unilamellar liposomes. The material to be entrapped is added to a suspension of preformed MLVs and then sonicated. When using liposomes containing cationic lipids, the dried lipid film is resuspended in an appropriate solution such as sterile water or an isotonic buffer solution such as 10 mM Tris/NaCl, sonicated, and then the preformed liposomes are mixed directly with the DNA. The liposome and DNA form a very stable complex due to binding of the positively charged liposomes to the cationic DNA. SUVs find use with small nucleic acid fragments. LUVs are prepared by a number of methods, well known in the art. Commonly used methods include Ca2+-EDTA chelation (Papahadjopoulos et al., Biochim. Biophys. Acta, 394: 483 (1975); Wilson et al., Cell, 17:77 (1979)); ether injection (Deamer et al., Biochim. Biophys. Acta, 443:629 (1976); Ostro et al., Biochem. Biophys. Res. Commun., 76:836 (1977); Fraley et al., Proc. Natl. Acad. Sci. USA, 76:3348 (1979)); detergent dialysis (Enoch et al., Proc. Natl. Acad. Sci. USA, 76:145 (1979)); and reverse-phase evaporation (REV) (Fraley et al., J. Biol. Chem., 255:10431 (1980); Szoka et al., Proc. Natl. Acad. Sci. USA, 75:145 (1978); Schaefer-Ridder et al., Science, 215:166 (1982)), which are herein incorporated by reference.

Generally, the ratio of DNA to liposomes will be from about 10:1 to about 1:10. Preferably, the ration will be from about 5:1 to about 1:5. More preferably, the ration will be about 3:1 to about 1:3. Still more preferably, the ratio will be about 1:1.

U.S. Pat. No. 5,676,954 (which is herein incorporated by reference) reports on the injection of genetic material, complexed with cationic liposomes carriers, into mice. U.S. Pat. Nos. 4,897,355, 4,946,787, 5,049,386, 5,459,127, 5,589,466, 5,693,622, 5,580,859, 5,703,055, and international publication NO: WO 94/9469 (which are herein incorporated by reference) provide cationic lipids for use in transfecting DNA into cells and mammals. U.S. Pat. Nos. 5,589,466, 5,693,622, 5,580,859, 5,703,055, and international publication NO: WO 94/9469 (which are herein incorporated by reference) provide methods for delivering DNA-cationic lipid complexes to mammals.

In certain embodiments, cells are engineered, ex vivo or in vivo, using a retroviral particle containing RNA which comprises a sequence encoding polypeptides of the invention. Retroviruses from which the retroviral plasmid vectors may be derived include, but are not limited to, Moloney Murine Leukemia Virus, spleen necrosis virus, Rous sarcoma Virus, Harvey Sarcoma Virus, avian leukosis virus, gibbon ape leukemia virus, human immunodeficiency virus, Myeloproliferative Sarcoma Virus, and mammary tumor virus.

The retroviral plasmid vector is employed to transduce packaging cell lines to form producer cell lines. Examples of packaging cells which may be transfected include, but are not limited to, the PE501, PA317, R-2, R-AM, PA12, T19-14X, VT-19-17-H2, RCRE, RCRIP, GP+E-86, GP+envAm12, and DAN cell lines as described in Miller, Human Gene Therapy, 1:5-14 (1990), which is incorporated herein by reference in its entirety. The vector may transduce the packaging cells through any means known in the art. Such means include, but are not limited to, electroporation, the use of liposomes, and CaPO4 precipitation. In one alternative, the retroviral plasmid vector may be encapsulated into a liposome, or coupled to a lipid, and then administered to a host.

The producer cell line generates infectious retroviral vector particles which include polynucleotide encoding polypeptides of the invention. Such retroviral vector particles then may be employed, to transduce eukaryotic cells, either in vitro or in vivo. The transduced eukaryotic cells will express polypeptides of the invention.

In certain other embodiments, cells are engineered, ex vivo or in vivo, with polynucleotides of the invention contained in an adenovirus vector. Adenovirus can be manipulated such that it encodes and expresses polypeptides of the invention, and at the same time is inactivated in terms of its ability to replicate in a normal lytic viral life cycle. Adenovirus expression is achieved without integration of the viral DNA into the host cell chromosome, thereby alleviating concerns about insertional mutagenesis. Furthermore, adenoviruses have been used as live enteric vaccines for many years with an excellent safety profile (Schwartz et al., Am. Rev. Respir. Dis., 109:233-238 (1974)). Finally, adenovirus mediated gene transfer has been demonstrated in a number of instances including transfer of alpha-1-antitrypsin and CFTR to the lungs of cotton rats (Rosenfeld et al., Science, 252:431-434 (1991); Rosenfeld et al., Cell, 68:143-155 (1992)). Furthermore, extensive studies to attempt to establish adenovirus as a causative agent in human cancer were uniformly negative (Green et al. Proc. Natl. Acad. Sci. USA, 76:6606 (1979)).

Suitable adenoviral vectors useful in the present invention are described, for example, in Kozarsky and Wilson, Curr. Opin. Genet. Devel., 3:499-503 (1993); Rosenfeld et al., Cell, 68:143-155 (1992); Engelhardt et al., Human Genet. Ther., 4:759-769 (1993); Yang et al., Nature Genet., 7:362-369 (1994); Wilson et al., Nature, 365:691-692 (1993); and U.S. Pat. No. 5,652,224, which are herein incorporated by reference. For example, the adenovirus vector Ad2 is useful and can be grown in human 293 cells. These cells contain the E1 region of adenovirus and constitutively express E1a and E1b, which complement the defective adenoviruses by providing the products of the genes deleted from the vector. In addition to Ad2, other varieties of adenovirus (e.g., Ad3, Ad5, and Ad7) are also useful in the present invention.

Preferably, the adenoviruses used in the present invention are replication deficient. Replication deficient adenoviruses require the aid of a helper virus and/or packaging cell line to form infectious particles. The resulting virus is capable of infecting cells and can express a polynucleotide of interest which is operably linked to a promoter, but cannot replicate in most cells. Replication deficient adenoviruses may be deleted in one or more of all or a portion of the following genes: E1a, E1b, E3, E4, E2a, or L1 through L5.

In certain other embodiments, the cells are engineered, ex vivo or in vivo, using an adeno-associated virus (AAV). AAVs are naturally occurring defective viruses that require helper viruses to produce infectious particles (Muzyczka, Curr. Topics in Microbiol. Immunol., 158:97 (1992)). It is also one of the few viruses that may integrate its DNA into non-dividing cells. Vectors containing as little as 300 base pairs of AAV can be packaged and can integrate, but space for exogenous DNA is limited to about 4.5 kb. Methods for producing and using such AAVs are known in the art. See, for example, U.S. Pat. Nos. 5,139,941, 5,173,414, 5,354,678, 5,436,146, 5,474,935, 5,478,745, and 5,589,377.

For example, an appropriate AAV vector for use in the present invention will include all the sequences necessary for DNA replication, encapsidation, and host-cell integration. The polynucleotide construct containing polynucleotides of the invention is inserted into the AAV vector using standard cloning methods, such as those found in Sambrook et al., Molecular Cloning: A Laboratory Manual, Cold Spring Harbor Press (1989). The recombinant AAV vector is then transfected into packaging cells which are infected with a helper virus, using any standard technique, including lipofection, electroporation, calcium phosphate precipitation, etc. Appropriate helper viruses include adenoviruses, cytomegaloviruses, vaccinia viruses, or herpes viruses. Once the packaging cells are transfected and infected, they will produce infectious AAV viral particles which contain the polynucleotide construct of the invention. These viral particles are then used to transduce eukaryotic cells, either ex vivo or in vivo. The transduced cells will contain the polynucleotide construct integrated into its genome, and will express the desired gene product.

Another method of gene therapy involves operably associating heterologous control regions and endogenous polynucleotide sequences (e.g. encoding the polypeptide sequence of interest) via homologous recombination (see, e.g., U.S. Pat. No. 5,641,670, issued Jun. 24, 1997; International Publication NO: WO 96/29411, published Sep. 26, 1996; International Publication NO: WO 94/12650, published Aug. 4, 1994; Koller et al., Proc. Natl. Acad. Sci. USA, 86:8932-8935 (1989); and Zijlstra et al., Nature, 342:435-438 (1989). This method involves the activation of a gene which is present in the target cells, but which is not normally expressed in the cells, or is expressed at a lower level than desired.

Polynucleotide constructs are made, using standard techniques known in the art, which contain the promoter with targeting sequences flanking the promoter. Suitable promoters are described herein. The targeting sequence is sufficiently complementary to an endogenous sequence to permit homologous recombination of the promoter-targeting sequence with the endogenous sequence. The targeting sequence will be sufficiently near the 5' end of the desired endogenous polynucleotide sequence so the promoter will be operably linked to the endogenous sequence upon homologous recombination.

The promoter and the targeting sequences can be amplified using PCR. Preferably, the amplified promoter contains distinct restriction enzyme sites on the 5' and 3' ends. Preferably, the 3, end of the first targeting sequence contains the same restriction enzyme site as the 5' end of the amplified promoter and the 5' end of the second targeting sequence contains the same restriction site as the 3' end of the amplified promoter. The amplified promoter and targeting sequences are digested and ligated together.

The promoter-targeting sequence construct is delivered to the cells, either as naked polynucleotide, or in conjunction with transfection-facilitating agents, such as liposomes, viral sequences, viral particles, whole viruses, lipofection, precipitating agents, etc., described in more detail above. The P promoter-targeting sequence can be delivered by any method, included direct needle injection, intravenous injection, topical administration, catheter infusion, particle accelerators, etc. The methods are described in more detail below.

The promoter-targeting sequence construct is taken up by cells. Homologous recombination between the construct and the endogenous sequence takes place, such that an endogenous sequence is placed under the control of the promoter. The promoter then drives the expression of the endogenous sequence.

The polynucleotides encoding polypeptides of the present invention may be administered along with other polynucleotides encoding angiogenic proteins. Angiogenic proteins include, but are not limited to, acidic and basic fibroblast growth factors, VEGF-1, VEGF-2 (VEGF-C), VEGF-3 (VEGF-B), epidermal growth factor alpha and beta, platelet-derived endothelial cell growth factor, platelet-derived growth factor, tumor necrosis factor alpha, hepatocyte growth factor, insulin like growth factor, colony stimulating factor, macrophage colony stimulating factor, granulocyte/macrophage colony stimulating factor, and nitric oxide synthase.

Preferably, the polynucleotide encoding a polypeptide of the invention contains a secretory signal sequence that facilitates secretion of the protein. Typically, the signal sequence is positioned in the coding region of the polynucleotide to be expressed towards or at the 5' end of the coding region. The signal sequence may be homologous or heterologous to the polynucleotide of interest and may be homologous or heterologous to the cells to be transfected. Additionally, the signal sequence may be chemically synthesized using methods known in the art.

Any mode of administration of any of the above-described polynucleotides constructs can be used so long as the mode results in the expression of one or more molecules in an amount sufficient to provide a therapeutic effect. This includes direct needle injection, systemic injection, catheter infusion, biolistic injectors, particle accelerators (i.e., "gene guns"), gelfoam sponge depots, other commercially available depot materials, osmotic pumps (e.g., ALZA® minipumps), oral or suppositorial solid (tablet or pill) pharmaceutical formulations, and decanting or topical applications during surgery. For example, direct injection of naked calcium phosphate-precipitated plasmid into rat liver and rat spleen or a protein-coated plasmid into the portal vein has resulted in gene expression of the foreign gene in the rat livers. (Kaneda et al., Science, 243:375 (1989)).

A preferred method of local administration is by direct injection. Preferably, a recombinant molecule of the present invention complexed with a delivery vehicle is administered by direct injection into or locally within the area of arteries. Administration of a composition locally within the area of arteries refers to injecting the composition centimeters and preferably, millimeters within arteries.

Another method of local administration is to contact a polynucleotide construct of the present invention in or around a surgical wound. For example, a patient can undergo surgery and the polynucleotide construct can be coated on the surface of tissue inside the wound or the construct can be injected into areas of tissue inside the wound.

Therapeutic compositions useful in systemic administration, include recombinant molecules of the present invention complexed to a targeted delivery vehicle of the present invention. Suitable delivery vehicles for use with systemic administration comprise liposomes comprising ligands for targeting the vehicle to a particular site.

Preferred methods of systemic administration, include intravenous injection, aerosol, oral and percutaneous (topical) delivery. Intravenous injections can be performed using methods standard in the art. Aerosol delivery can also be performed using methods standard in the art (see, for example, Stribling et al., Proc. Natl. Acad. Sci. USA, 189: 11277-11281 (1992), which is incorporated herein by reference). Oral delivery can be performed by complexing a polynucleotide construct of the present invention to a carrier capable of withstanding degradation by digestive enzymes in the gut of an animal. Examples of such carriers, include plastic capsules or tablets, such as those known in the art. Topical delivery can be performed by mixing a polynucleotide construct of the present invention with a lipophilic reagent (e.g., DMSO) that is capable of passing into the skin.

Determining an effective amount of substance to be delivered can depend upon a number of factors including, for example, the chemical structure and biological activity of the substance, the age and weight of the animal, the precise condition requiring treatment and its severity, and the route of administration. The frequency of treatments depends upon a number of factors, such as the amount of polynucleotide constructs administered per dose, as well as the health and history of the subject. The precise amount, number of doses, and timing of doses will be determined by the attending physician or veterinarian. Therapeutic compositions of the present invention can be administered to any animal, preferably to mammals and birds. Preferred mammals include humans, dogs, cats, mice, rats, rabbits sheep, cattle, horses and pigs, with humans being particularly preferred.

Biological Activities

The polynucleotides or polypeptides, or agonists or antagonists of the present invention can be used in assays to test for one or more biological activities. If these polynucleotides and polypeptides do exhibit activity in a particular assay, it is likely that these molecules may be involved in the diseases associated with the biological activity. Thus, the polynucleotides or polypeptides, or agonists or antagonists could be used to treat the associated disease.

Immune Activity

The polynucleotides or polypeptides, or agonists or antagonists of the present invention may be useful in treating, preventing, and/or diagnosing diseases, disorders, and/or conditions of the immune system, by activating or inhibiting the proliferation, differentiation, or mobilization (chemotaxis) of immune cells. Immune cells develop through a process called hematopoiesis, producing myeloid (platelets, red blood cells, neutrophils, and macrophages) and lymphoid (B and T lymphocytes) cells from pluripotent stem cells. The etiology of these immune diseases, disorders, and/or conditions may be genetic, somatic, such as cancer or some autoimmune diseases, disorders, and/or conditions, acquired (e.g., by chemotherapy or toxins), or infectious. Moreover, a polynucleotides or polypeptides, or agonists or antagonists of the present invention can be used as a marker or detector of a particular immune system disease or disorder.

A polynucleotides or polypeptides, or agonists or antagonists of the present invention may be useful in treating, preventing, and/or diagnosing diseases, disorders, and/or conditions of hematopoietic cells. A polynucleotides or polypeptides, or agonists or antagonists of the present invention could be used to increase differentiation and proliferation of hematopoietic cells, including the pluripotent stem cells, in an effort to treat or prevent those diseases, disorders, and/or conditions associated with a decrease in certain (or many) types hematopoietic cells. Examples of immunologic deficiency syndromes include, but are not limited to: blood protein diseases, disorders, and/or conditions (e.g. agammaglobulinemia, dysgammaglobulinemia), ataxia telangiectasia, common variable immunodeficiency, Digeorge Syndrome, HIV infection, HTLV-BLV infection, leukocyte adhesion deficiency syndrome, lymphopenia, phagocyte bactericidal dysfunction, severe combined immunodeficiency (SCIDs), Wiskott-Aldrich Disorder, anemia, thrombocytopenia, or hemoglobinuria.

Moreover, a polynucleotides or polypeptides, or agonists or antagonists of the present invention could also be used to modulate hemostatic (the stopping of bleeding) or thrombolytic activity (clot formation). For example, by increasing hemostatic or thrombolytic activity, a polynucleotides or polypeptides, or agonists or antagonists of the present invention could be used to treat or prevent blood coagulation diseases, disorders, and/or conditions (e.g., afibrinogenemia, factor deficiencies), blood platelet diseases, disorders, and/or conditions (e.g. thrombocytopenia), or wounds resulting from trauma, surgery, or other causes. Alternatively, a polynucleotides or polypeptides, or agonists or antagonists of the present invention that can decrease hemostatic or thrombolytic activity could be used to inhibit or dissolve clotting. These molecules could be important in the treatment or prevention of heart attacks (infarction), strokes, or scarring.

A polynucleotides or polypeptides, or agonists or antagonists of the present invention may also be useful in treating, preventing, and/or diagnosing autoimmune diseases, disorders, and/or conditions. Many autoimmune diseases, disorders, and/or conditions result from inappropriate recognition of self as foreign material by immune cells. This inappropriate recognition results in an immune response leading to the destruction of the host tissue. Therefore, the administration of a polynucleotides or polypeptides, or agonists or antagonists of the present invention that inhibits an immune response, particularly the proliferation, differentiation, or chemotaxis of T-cells, may be an effective therapy in preventing autoimmune diseases, disorders, and/or conditions.

Examples of autoimmune diseases, disorders, and/or conditions that can be treated, prevented, and/or diagnosed or detected by the present invention include, but are not limited to: Addison's Disease, hemolytic anemia, antiphospholipid syndrome, rheumatoid arthritis, dermatitis, allergic encephalomyelitis, glomerulonephritis, Goodpasture's Syndrome, Graves' Disease, Multiple Sclerosis, Myasthenia Gravis, Neuritis, Ophthalmia, Bullous Pemphigoid, Pemphigus, Polyendocrinopathies, Purpura, Reiter's Disease, Stiff-Man Syndrome, Autoimmune Thyroiditis, Systemic Lupus Erythematosus, Autoimmune Pulmonary Inflammation, Guillain-Barre Syndrome, insulin dependent diabetes mellitis, and autoimmune inflammatory eye disease.

Similarly, allergic reactions and conditions, such as asthma (particularly allergic asthma) or other respiratory problems, may also be treated, prevented, and/or diagnosed by polynucleotides or polypeptides, or agonists or antagonists of the present invention. Moreover, these molecules can be used to treat anaphylaxis, hypersensitivity to an antigenic molecule, or blood group incompatibility.

A polynucleotides or polypeptides, or agonists or antagonists of the present invention may also be used to treat, prevent, and/or diagnose organ rejection or graft-versus-host disease (GVHD). Organ rejection occurs by host immune cell destruction of the transplanted tissue through an immune response. Similarly, an immune response is also involved in GVHD, but, in this case, the foreign transplanted immune cells destroy the host tissues. The administration of a polynucleotides or polypeptides, or agonists or antagonists of the present invention that inhibits an immune response, particularly the proliferation, differentiation, or chemotaxis of T-cells, may be an effective therapy in preventing organ rejection or GVHD.

Similarly, a polynucleotides or polypeptides, or agonists or antagonists of the present invention may also be used to modulate inflammation. For example, the polypeptide or polynucleotide or agonists or antagonist may inhibit the proliferation and differentiation of cells involved in an inflammatory response. These molecules can be used to treat, prevent, and/or diagnose inflammatory conditions, both chronic and acute conditions, including chronic prostatitis, granulomatous prostatitis and malacoplakia, inflammation associated with infection (e.g., septic shock, sepsis, or systemic inflammatory response syndrome (SIRS)), ischemia-reperfusion injury, endotoxin lethality, arthritis, complement-mediated hyperacute rejection, nephritis, cytokine or chemokine induced lung injury, inflammatory bowel disease, Crohn's disease, or resulting from over production of cytokines (e.g., TNF or IL-1.)

Hyperproliferative Disorders

A polynucleotides or polypeptides, or agonists or antagonists of the invention can be used to treat, prevent, and/or diagnose hyperproliferative diseases, disorders, and/or conditions, including neoplasms. A polynucleotides or polypeptides, or agonists or antagonists of the present invention may inhibit the proliferation of the disorder through direct or indirect interactions. Alternatively, a polynucleotides or polypeptides, or agonists or antagonists of the present invention may proliferate other cells which can inhibit the hyperproliferative disorder.

For example, by increasing an immune response, particularly increasing antigenic qualities of the hyperproliferative disorder or by proliferating, differentiating, or mobilizing T-cells, hyperproliferative diseases, disorders, and/or conditions can be treated, prevented, and/or diagnosed. This immune response may be increased by either enhancing an existing immune response, or by initiating a new immune response. Alternatively, decreasing an immune response may also be a method of treating, preventing, and/or diagnosing hyperproliferative diseases, disorders, and/or conditions, such as a chemotherapeutic agent.

Examples of hyperproliferative diseases, disorders, and/or conditions that can be treated, prevented, and/or diagnosed by polynucleotides or polypeptides, or agonists or antagonists of the present invention include, but are not limited to neoplasms located in the: colon, abdomen, bone, breast, digestive system, liver, pancreas, peritoneum, endocrine glands (adrenal, parathyroid, pituitary, testicles, ovary, thymus, thyroid), eye, head and neck, nervous (central and peripheral), lymphatic system, pelvic, skin, soft tissue, spleen, thoracic, and urogenital.

Similarly, other hyperproliferative diseases, disorders, and/or conditions can also be treated, prevented, and/or diagnosed by a polynucleotides or polypeptides, or agonists or antagonists of the present invention. Examples of such hyperproliferative diseases, disorders, and/or conditions include, but are not limited to: hypergammaglobulinemia, lymphoproliferative diseases, disorders, and/or conditions, paraproteinemias, purpura, sarcoidosis, Sezary Syndrome, Waldenstron's Macroglobulinemia, Gaucher's Disease, histiocytosis, and any other hyperproliferative disease, besides neoplasia, located in an organ system listed above.

One preferred embodiment utilizes polynucleotides of the present invention to inhibit aberrant cellular division, by gene therapy using the present invention, and/or protein fusions or fragments thereof.

Thus, the present invention provides a method for treating or preventing cell proliferative diseases, disorders, and/or conditions by inserting into an abnormally proliferating cell a polynucleotide of the present invention, wherein said polynucleotide represses said expression.

Another embodiment of the present invention provides a method of treating or preventing cell-proliferative diseases, disorders, and/or conditions in individuals comprising administration of one or more active gene copies of the present invention to an abnormally proliferating cell or cells. In a preferred embodiment, polynucleotides of the present invention is a DNA construct comprising a recombinant expression vector effective in expressing a DNA sequence encoding said polynucleotides. In another preferred embodiment of the present invention, the DNA construct encoding the polynucleotides of the present invention is inserted into cells to be treated utilizing a retrovirus, or more Preferably an adenoviral vector (See G J. Nabel, et. al., PNAS 1999 96: 324-326, which is hereby incorporated by reference). In a most preferred embodiment, the viral vector is defective and will not transform non-proliferating cells, only proliferating cells. Moreover, in a preferred embodiment, the polynucleotides of the present invention inserted into proliferating cells either alone, or in combination with or fused to other polynucleotides, can then be modulated via an external stimulus (i.e. magnetic, specific small molecule, chemical, or drug administration, etc.), which acts upon the promoter upstream of said polynucleotides to induce expression of the encoded protein product. As such the beneficial therapeutic affect of the present invention may be expressly modulated (i.e. to increase, decrease, or inhibit expression of the present invention) based upon said external stimulus.

Polynucleotides of the present invention may be useful in repressing expression of oncogenic genes or antigens. By "repressing expression of the oncogenic genes" is intended the suppression of the transcription of the gene, the degradation of the gene transcript (pre-message RNA), the inhibition of splicing, the destruction of the messenger RNA, the prevention of the post-translational modifications of the protein, the destruction of the protein, or the inhibition of the normal function of the protein.

For local administration to abnormally proliferating cells, polynucleotides of the present invention may be administered by any method known to those of skill in the art including, but not limited to transfection, electroporation, microinjection of cells, or in vehicles such as liposomes, lipofectin, or as naked polynucleotides, or any other method described throughout the specification. The polynucleotide of the present invention may be delivered by known gene delivery systems such as, but not limited to, retroviral vectors (Gilboa, J. Virology 44:845 (1982); Hocke, Nature 320:275 (1986); Wilson, et al., Proc. Natl. Acad. Sci. U.S.A. 85:3014), vaccinia virus system (Chakrabarty et al., Mol. Cell Biol. 5:3403 (1985) or other efficient DNA delivery systems (Yates et al., Nature 313:812 (1985)) known to those skilled in the art. These references are exemplary only and are hereby incorporated by reference. In order to specifically deliver or transfect cells which are abnormally proliferating and spare non-dividing cells, it is preferable to utilize a retrovirus, or adenoviral (as described in the art and elsewhere herein) delivery system known to those of skill in the art. Since host DNA replication is required for retroviral DNA to integrate and the retrovirus will be unable to self replicate due to the lack of the retrovirus genes needed for its life cycle. Utilizing such a retroviral delivery system for polynucleotides of the present invention will target said gene and constructs to abnormally proliferating cells and will spare the non-dividing normal cells.

The polynucleotides of the present invention may be delivered directly to cell proliferative disorder/disease sites in internal organs, body cavities and the like by use of imaging devices used to guide an injecting needle directly to the disease site. The polynucleotides of the present invention may also be administered to disease sites at the time of surgical intervention.

By "cell proliferative disease" is meant any human or animal disease or disorder, affecting any one or any combination of organs, cavities, or body parts, which is characterized by single or multiple local abnormal proliferations of cells, groups of cells, or tissues, whether benign or malignant.

Any amount of the polynucleotides of the present invention may be administered as long as it has a biologically inhibiting effect on the proliferation of the treated cells. Moreover, it is possible to administer more than one of the polynucleotide of the present invention simultaneously to the same site. By "biologically inhibiting" is meant partial or total growth inhibition as well as decreases in the rate of proliferation or growth of the cells. The biologically inhibitory dose may be determined by assessing the effects of the polynucleotides of the present invention on target malignant or abnormally proliferating cell growth in tissue culture, tumor growth in animals and cell cultures, or any other method known to one of ordinary skill in the art.

The present invention is further directed to antibody-based therapies which involve administering of anti-polypeptides and anti-polynucleotide antibodies to a mammalian, preferably human, patient for treating, preventing, and/or diagnosing one or more of the described diseases, disorders, and/or conditions. Methods for producing anti-polypeptides and anti-polynucleotide antibodies polyclonal and monoclonal antibodies are described in detail elsewhere herein. Such antibodies may be provided in pharmaceutically acceptable compositions as known in the art or as described herein.

A summary of the ways in which the antibodies of the present invention may be used therapeutically includes binding polynucleotides or polypeptides of the present invention locally or systemically in the body or by direct cytotoxicity of the antibody, e.g. as mediated by complement (CDC) or by effector cells (ADCC). Some of these approaches are described in more detail below. Armed with the teachings provided herein, one of ordinary skill in the art will know how to use the antibodies of the present invention for diagnostic, monitoring or therapeutic purposes without undue experimentation.

In particular, the antibodies, fragments and derivatives of the present invention are useful for treating, preventing, and/or diagnosing a subject having or developing cell proliferative and/or differentiation diseases, disorders, and/or conditions as described herein. Such treatment comprises administering a single or multiple doses of the antibody, or a fragment, derivative, or a conjugate thereof.

The antibodies of this invention may be advantageously utilized in combination with other monoclonal or chimeric antibodies, or with lymphokines or hematopoietic growth factors, for example, which serve to increase the number or activity of effector cells which interact with the antibodies.

It is preferred to use high affinity and/or potent in vivo inhibiting and/or neutralizing antibodies against polypeptides or polynucleotides of the present invention, fragments or regions thereof, for both immunoassays directed to and therapy of diseases, disorders, and/or conditions related to polynucleotides or polypeptides, including fragments thereof, of the present invention. Such antibodies, fragments, or regions, will preferably have an affinity for polynucleotides or polypeptides, including fragments thereof. Preferred binding affinities include those with a dissociation constant or Kd less than $5 \times 10^{-6}M$, $10^{-6}M$, $5 \times 10^{-7}M$, $10^{-7}M$, $5 \times 10^{-8}M$, $10^{-8}M$, $5 \times 10^{-9}M$, $10^{-9}M$, $5 \times 10^{-10}M$, $10^{-10}M$, $5 \times 10^{-11}M$, $10^{-11}M$, $5 \times 10^{-12}M$, $10^{-12}M$, $5 \times 10^{-13}M$, $10^{-13}M$, $5 \times 10^{-14}M$, $10^{-14}M$, $5 \times 10^{-15}M$, and $10^{-15}M$.

Moreover, polypeptides of the present invention may be useful in inhibiting the angiogenesis of proliferative cells or tissues, either alone, as a protein fusion, or in combination with other polypeptides directly or indirectly, as described elsewhere herein. In a most preferred embodiment, said antiangiogenesis effect may be achieved indirectly, for example, through the inhibition of hematopoietic, tumor-specific cells, such as tumor-associated macrophages (See Joseph I B, et al. J Natl Cancer Inst, 90(21):1648-53 (1998), which is hereby incorporated by reference). Antibodies directed to polypeptides or polynucleotides of the present invention may also result in inhibition of angiogenesis directly, or indirectly (See Witte L, et al., Cancer Metastasis Rev. 17(2):155-61 (1998), which is hereby incorporated by reference)).

Polypeptides, including protein fusions, of the present invention, or fragments thereof may be useful in inhibiting proliferative cells or tissues through the induction of apoptosis. Said polypeptides may act either directly, or indirectly to induce apoptosis of proliferative cells and tissues, for example in the activation of a death-domain receptor, such as tumor necrosis factor (TNF) receptor-1, CD95 (Fas/APO-1), TNF-receptor-related apoptosis-mediated protein (TRAMP) and TNF-related apoptosis-inducing ligand (TRAIL) receptor-1 and -2 (See Schulze-Osthoff K, et al., Eur J Biochem 254(3):439-59 (1998), which is hereby incorporated by reference). Moreover, in another preferred embodiment of the present invention, said polypeptides may induce apoptosis through other mechanisms, such as in the activation of other proteins which will activate apoptosis, or through stimulating the expression of said proteins, either alone or in combination with small molecule drugs or adjuvants, such as apoptonin, galectins, thioredoxins, antiinflammatory proteins (See for example, Mutat. Res. 400(1-2):447-55 (1998), Med. Hypotheses. 50(5):423-33 (1998), Chem. Biol. Interact. April 24;

111-112:23-34 (1998), J Mol Med. 76(6):402-12 (1998), Int. J. Tissue React. 20(1):3-15 (1998), which are all hereby incorporated by reference).

Polypeptides, including protein fusions to, or fragments thereof, of the present invention are useful in inhibiting the metastasis of proliferative cells or tissues. Inhibition may occur as a direct result of administering polypeptides, or antibodies directed to said polypeptides as described elsewhere herein, or indirectly, such as activating the expression of proteins known to inhibit metastasis, for example alpha 4 integrins, (See, e.g., Curr Top Microbiol Immunol 1998; 231: 125-41, which is hereby incorporated by reference). Such therapeutic affects of the present invention may be achieved either alone, or in combination with small molecule drugs or adjuvants.

In another embodiment, the invention provides a method of delivering compositions containing the polypeptides of the invention (e.g., compositions containing polypeptides or polypeptide antibodies associated with heterologous polypeptides, heterologous nucleic acids, toxins, or prodrugs) to targeted cells expressing the polypeptide of the present invention. Polypeptides or polypeptide antibodies of the invention may be associated with heterologous polypeptides, heterologous nucleic acids, toxins, or prodrugs via hydrophobic, hydrophilic, ionic and/or covalent interactions.

Polypeptides, protein fusions to, or fragments thereof, of the present invention are useful in enhancing the immunogenicity and/or antigenicity of proliferating cells or tissues, either directly, such as would occur if the polypeptides of the present invention 'vaccinated' the immune response to respond to proliferative antigens and immunogens, or indirectly, such as in activating the expression of proteins known to enhance the immune response (e.g. chemokines), to said antigens and immunogens.

Diseases at the Cellular Level

Diseases associated with increased cell survival or the inhibition of apoptosis that could be treated, prevented, and/or diagnosed by the polynucleotides or polypeptides and/or antagonists or agonists of the invention, include cancers (such as follicular lymphomas, carcinomas with p53 mutations, and hormone-dependent tumors, including, but not limited to colon cancer, cardiac tumors, pancreatic cancer, melanoma, retinoblastoma, glioblastoma, lung cancer, intestinal cancer, testicular cancer, stomach cancer, neuroblastoma, myxoma, myoma, lymphoma, endothelioma, osteoblastoma, osteoclastoma, osteosarcoma, chondrosarcoma, adenoma, breast cancer, prostate cancer, Kaposi's sarcoma and ovarian cancer); autoimmune diseases, disorders, and/or conditions (such as, multiple sclerosis, Sjogren's syndrome, Hashimoto's thyroiditis, biliary cirrhosis, Behcet's disease, Crohn's disease, polymyositis, systemic lupus erythematosus and immune-related glomerulonephritis and rheumatoid arthritis) and viral infections (such as herpes viruses, pox viruses and adenoviruses), inflammation, graft v. host disease, acute graft rejection, and chronic graft rejection. In preferred embodiments, the polynucleotides or polypeptides, and/or agonists or antagonists of the invention are used to inhibit growth, progression, and/or metastasis of cancers, in particular those listed above.

Additional diseases or conditions associated with increased cell survival that could be treated, prevented or diagnosed by the polynucleotides or polypeptides, or agonists or antagonists of the invention, include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstron's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

Diseases associated with increased apoptosis that could be treated, prevented, and/or diagnosed by the polynucleotides or polypeptides, and/or agonists or antagonists of the invention, include AIDS; neurodegenerative diseases, disorders, and/or conditions (such as Alzheimer's disease, Parkinson's disease, Amyotrophic lateral sclerosis, Retinitis pigmentosa, Cerebellar degeneration and brain tumor or prior associated disease); autoimmune diseases, disorders, and/or conditions (such as, multiple sclerosis, Sjogren's syndrome, Hashimoto's thyroiditis, biliary cirrhosis, Behcet's disease, Crohn's disease, polymyositis, systemic lupus erythematosus and immune-related glomerulonephritis and rheumatoid arthritis) myelodysplastic syndromes (such as aplastic anemia), graft v. host disease, ischemic injury (such as that caused by myocardial infarction, stroke and reperfusion injury), liver injury (e.g., hepatitis related liver injury, ischemia/reperfusion injury, cholestosis (bile duct injury) and liver cancer); toxin-induced liver disease (such as that caused by alcohol), septic shock, cachexia and anorexia.

Wound Healing and Epithelial Cell Proliferation

In accordance with yet a further aspect of the present invention, there is provided a process for utilizing the polynucleotides or polypeptides, and/or agonists or antagonists of the invention, for therapeutic purposes, for example, to stimulate epithelial cell proliferation and basal keratinocytes for the purpose of wound healing, and to stimulate hair follicle production and healing of dermal wounds. Polynucleotides or polypeptides, as well as agonists or antagonists of the invention, may be clinically useful in stimulating wound healing including surgical wounds, excisional wounds, deep wounds involving damage of the dermis and epidermis, eye tissue wounds, dental tissue wounds, oral cavity wounds, diabetic ulcers, dermal ulcers, cubitus ulcers, arterial ulcers, venous stasis ulcers, burns resulting from heat exposure or chemicals, and other abnormal wound healing conditions such as uremia, malnutrition, vitamin deficiencies and complications associated with systemic treatment with steroids, radiation therapy and antineoplastic drugs and antimetabolites. Polynucleotides or polypeptides, and/or agonists or antagonists of the invention, could be used to promote dermal reestablishment subsequent to dermal loss The polynucleotides or polypeptides, and/or agonists or antagonists of the invention, could be used to increase the adherence of skin grafts to a wound bed and to stimulate re-epithelialization from the wound bed. The following are a non-exhaustive list of grafts that polynucleotides or polypeptides, agonists or antagonists of the invention, could be used to increase adherence to a wound bed: autografts, artificial skin, allografts, autodermic graft, autoepidermic grafts, avascular grafts, Blair-Brown grafts, bone graft, brephoplastic grafts, cutis graft, delayed graft, dermic graft, epidermic graft, fascia graft, full thickness graft, heterologous graft, xenograft, homologous graft, hyperplastic graft, lamellar graft, mesh graft, mucosal graft, Ollier-Thiersch graft, omenpal graft, patch graft, pedicle graft, penetrating graft, split skin graft, thick split graft. The polynucleotides or polypeptides, and/or agonists or antagonists of the invention, can be used to promote skin strength and to improve the appearance of aged skin.

It is believed that the polynucleotides or polypeptides, and/or agonists or antagonists of the invention, will also produce changes in hepatocyte proliferation, and epithelial cell proliferation in the lung, breast, pancreas, stomach, small intestine, and large intestine. The polynucleotides or polypeptides, and/or agonists or antagonists of the invention, could promote proliferation of epithelial cells such as sebocytes, hair follicles, hepatocytes, type II pneumocytes, mucin-producing goblet cells, and other epithelial cells and their progenitors contained within the skin, lung, liver, and gastrointestinal tract. The polynucleotides or polypeptides, and/or agonists or antagonists of the invention, may promote proliferation of endothelial cells, keratinocytes, and basal keratinocytes.

The polynucleotides or polypeptides, and/or agonists or antagonists of the invention, could also be used to reduce the side effects of gut toxicity that result from radiation, chemotherapy treatments or viral infections. The polynucleotides or polypeptides, and/or agonists or antagonists of the invention, may have a cytoprotective effect on the small intestine mucosa. The polynucleotides or polypeptides, and/or agonists or antagonists of the invention, may also stimulate healing of mucositis (mouth ulcers) that result from chemotherapy and viral infections.

The polynucleotides or polypeptides, and/or agonists or antagonists of the invention, could further be used in full regeneration of skin in full and partial thickness skin defects, including burns, (i.e., repopulation of hair follicles, sweat glands, and sebaceous glands), treatment of other skin defects such as psoriasis. The polynucleotides or polypeptides, and/ or agonists or antagonists of the invention, could be used to treat epidermolysis bullosa, a defect in adherence of the epidermis to the underlying dermis which results in frequent, open and painful blisters by accelerating reepithelialization of these lesions. The polynucleotides or polypeptides, and/or agonists or antagonists of the invention, could also be used to treat gastric and duodenal ulcers and help heal by scar formation of the mucosal lining and regeneration of glandular mucosa and duodenal mucosal lining more rapidly. Inflammatory bowel diseases, such as Crohn's disease and ulcerative colitis, are diseases which result in destruction of the mucosal surface of the small or large intestine, respectively. Thus, the polynucleotides or polypeptides, and/or agonists or antagonists of the invention, could be used to promote the resurfacing of the mucosal surface to aid more rapid healing and to prevent progression of inflammatory bowel disease.

Treatment with the polynucleotides or polypeptides, and/or agonists or antagonists of the invention, is expected to have a significant effect on the production of mucus throughout the gastrointestinal tract and could be used to protect the intestinal mucosa from injurious substances that are ingested or following surgery. The polynucleotides or polypeptides, and/ or agonists or antagonists of the invention, could be used to treat diseases associate with the under expression of the polynucleotides of the invention.

Moreover, the polynucleotides or polypeptides, and/or agonists or antagonists of the invention, could be used to prevent and heal damage to the lungs due to various pathological states. A growth factor such as the polynucleotides or polypeptides, and/or agonists or antagonists of the invention, which could stimulate proliferation and differentiation and promote the repair of alveoli and bronchiolar epithelium to prevent or treat acute or chronic lung damage. For example, emphysema, which results in the progressive loss of alveoli, and inhalation injuries, i.e., resulting from smoke inhalation and burns, that cause necrosis of the bronchiolar epithelium and alveoli could be effectively treated, prevented, and/or diagnosed using the polynucleotides or polypeptides, and/or agonists or antagonists of the invention. Also, the polynucleotides or polypeptides, and/or agonists or antagonists of the invention, could be used to stimulate the proliferation of and differentiation of type II pneumocytes, which may help treat or prevent disease such as hyaline membrane diseases, such as infant respiratory distress syndrome and bronchopulmonary displasia, in premature infants.

The polynucleotides or polypeptides, and/or agonists or antagonists of the invention, could stimulate the proliferation and differentiation of hepatocytes and, thus, could be used to alleviate or treat liver diseases and pathologies such as fulminant liver failure caused by cirrhosis, liver damage caused by viral hepatitis and toxic substances (i.e., acetaminophen, carbon tetrachloride and other hepatotoxins known in the art).

In addition, the polynucleotides or polypeptides, and/or agonists or antagonists of the invention, could be used treat or prevent the onset of diabetes mellitus. In patients with newly diagnosed Types I and II diabetes, where some islet cell function remains, the polynucleotides or polypeptides, and/or agonists or antagonists of the invention, could be used to maintain the islet function so as to alleviate, delay or prevent permanent manifestation of the disease. Also, the polynucleotides or polypeptides, and/or agonists or antagonists of the invention, could be used as an auxiliary in islet cell transplantation to improve or promote islet cell function.

Infectious Disease

A polypeptide or polynucleotide and/or agonist or antagonist of the present invention can be used to treat, prevent, and/or diagnose infectious agents. For example, by increasing the immune response, particularly increasing the proliferation and differentiation of B and/or T cells, infectious diseases may be treated, prevented, and/or diagnosed. The immune response may be increased by either enhancing an existing immune response, or by initiating a new immune response. Alternatively, polypeptide or polynucleotide and/or agonist or antagonist of the present invention may also directly inhibit the infectious agent, without necessarily eliciting an immune response.

Viruses are one example of an infectious agent that can cause disease or symptoms that can be treated, prevented, and/or diagnosed by a polynucleotide or polypeptide and/or agonist or antagonist of the present invention. Examples of viruses, include, but are not limited to Examples of viruses, include, but are not limited to the following DNA and RNA viruses and viral families: Arbovirus, Adenoviridae, Arenaviridae, Arterivirus, Birnaviridae, Bunyaviridae, Caliciviridae, Circoviridae, Coronaviridae, Dengue, EBV, HIV, Flaviviridae, Hepadnaviridae (Hepatitis), Herpesviridae (such as, Cytomegalovirus, Herpes Simplex, Herpes Zoster), Mononegavirus (e.g., Paramyxoviridae, Morbillivirus, Rhabdoviridae), Orthomyxoviridae (e.g., Influenza A, Influenza B, and parainfluenza), Papiloma virus, Papovaviridae, Parvoviridae, Picornaviridae, Poxyiridae (such as Smallpox or Vaccinia), Reoviridae (e.g., Rotavirus), Retroviridae (HTLV-I, HTLV-II, Lentivirus), and Togaviridae (e.g., Rubivirus). Viruses falling within these families can cause a variety of diseases or symptoms, including, but not limited to: arthritis, bronchiolitis, respiratory syncytial virus, encephalitis, eye infections (e.g., conjunctivitis, keratitis), chronic fatigue syndrome, hepatitis (A, B, C, E, Chronic Active, Delta), Japanese B encephalitis, Junin, Chikungunya, Rift Valley fever, yellow fever, meningitis, opportunistic infections (e.g., AIDS), pneumonia, Burkitt's Lymphoma, chickenpox, hemorrhagic fever, Measles, Mumps, Parainfluenza, Rabies, the common cold, Polio, leukemia, Rubella, sexually transmitted diseases, skin diseases (e.g., Kaposi's, warts), and viremia. polynucleotides or polypeptides, or agonists or antagonists of the invention, can be used to treat, prevent, and/or diagnose any of these symptoms or diseases. In specific embodiments, polynucleotides, polypeptides, or agonists or antagonists of the invention are used to treat, prevent, and/or diagnose: meningitis, Dengue, EBV, and/or hepatitis (e.g., hepatitis B). In an additional specific embodiment polynucleotides, polypeptides, or agonists or antagonists of the invention are used to treat patients nonresponsive to one or more other commercially available hepatitis vaccines. In a further specific embodiment polynucleotides, polypeptides, or agonists or antagonists of the invention are used to treat, prevent, and/or diagnose AIDS.

Similarly, bacterial or fungal agents that can cause disease or symptoms and that can be treated, prevented, and/or diagnosed by a polynucleotide or polypeptide and/or agonist or antagonist of the present invention include, but not limited to, include, but not limited to, the following Gram-Negative and Gram-positive bacteria and bacterial families and fungi: Actinomycetales (e.g., *Corynebacterium, Mycobacterium, Norcardia*), *Cryptococcus neoformans, Aspergillosis*, Bacillaceae (e.g., *Anthrax, Clostridium*), Bacteroidaceae, *Blastomycosis*, Bordetella, Borrelia (e.g., *Borrelia burgdorferi*), *Brucellosis, Candidiasis, Campylobacter, Coccidioidomycosis, Cryptococcosis, Dermatocycoses, E. coli* (e.g., *Enterotoxigenic E. coli* and *Enterohemorrhagic E. coli*), Enterobacteriaceae (*Klebsiella, Salmonella* (e.g., *Salmonella typhi*, and *Salmonella paratyphi*), *Serratia, Yersinia*), *Erysipelothrix, Helicobacter, Legionellosis, Leptospirosis, Listeria*, Mycoplasmatales, *Mycobacterium leprae, Vibrio cholerae*, Neisseriaceae (e.g., *Acinetobacter Gonorrhea, Menigococcal*), *Meisseria meningitidis*, Pasteurellacea Infections (e.g., *Actinobacillus, Heamophilus* (e.g., *Heamophilus influenza* type B), *Pasteurella*), *Pseudomonas*, Rickettsiaceae, Chlamydiaceae, *Syphilis, Shigella* spp., Staphylococcal, Meningiococcal, Pneumococcal and Streptococcal (e.g., *Streptococcus pneumoniae* and Group B *Streptococcus*). These bacterial or fungal families can cause the following diseases or symptoms, including, but not limited to: bacteremia, endocarditis, eye infections (conjunctivitis, tuberculosis, uveitis), gingivitis, opportunistic infections (e.g., AIDS related infections), paronychia, prosthesis-related infections, Reiter's Disease, respiratory tract infections, such as Whooping Cough or Empyema, sepsis, Lyme Disease, Cat-Scratch Disease, Dysentery, Paratyphoid Fever, food poisoning, Typhoid, pneumonia, Gonorrhea, meningitis (e.g., mengitis types A and B), *Chlamydia, Syphilis, Diphtheria, Leprosy, Paratuberculosis, Tuberculosis, Lupus, Botulism*, gangrene, tetanus, impetigo, Rheumatic Fever, Scarlet Fever, sexually transmitted diseases, skin diseases (e.g., cellulitis, *dermatocycoses*), toxemia, urinary tract infections, wound infections. Polynucleotides or polypeptides, agonists or antagonists of the invention, can be used to treat, prevent, and/or diagnose any of these symptoms or diseases. In specific embodiments, polynucleotides, polypeptides, agonists or antagonists of the invention are used to treat, prevent, and/or diagnose: tetanus, Diphtheria, botulism, and/or meningitis type B.

Moreover, parasitic agents causing disease or symptoms that can be treated, prevented, and/or diagnosed by a polynucleotide or polypeptide and/or agonist or antagonist of the present invention include, but not limited to, the following families or class: Amebiasis, Babesiosis, Coccidiosis, Cryptosporidiosis, Dientamoebiasis, Dourine, Ectoparasitic, Giardiasis, Helminthiasis, Leishmaniasis, Theileriasis, Toxoplasmosis, Trypanosomiasis, and Trichomonas and Sporozoans (e.g., *Plasmodium virax, Plasmodium falciparium, Plasmodium malariae* and *Plasmodium ovale*). These parasites can cause a variety of diseases or symptoms, including, but not limited to: Scabies, Trombiculiasis, eye infections, intestinal disease (e.g., dysentery, giardiasis), liver disease, lung disease, opportunistic infections (e.g., AIDS related), malaria, pregnancy complications, and toxoplasmosis. polynucleotides or polypeptides, or agonists or antagonists of the invention, can be used to treat, prevent, and/or diagnose any of these symptoms or diseases. In specific embodiments, polynucleotides, polypeptides, or agonists or antagonists of the invention are used to treat, prevent, and/or diagnose malaria.

Preferably, treatment or prevention using a polypeptide or polynucleotide and/or agonist or antagonist of the present invention could either be by administering an effective amount of a polypeptide to the patient, or by removing cells from the patient, supplying the cells with a polynucleotide of the present invention, and returning the engineered cells to the patient (ex vivo therapy). Moreover, the polypeptide or polynucleotide of the present invention can be used as an antigen in a vaccine to raise an immune response against infectious disease.

Regeneration

A polynucleotide or polypeptide and/or agonist or antagonist of the present invention can be used to differentiate, proliferate, and attract cells, leading to the regeneration of tissues. (See, Science 276:59-87 (1997).) The regeneration of tissues could be used to repair, replace, or protect tissue damaged by congenital defects, trauma (wounds, burns, incisions, or ulcers), age, disease (e.g. osteoporosis, osteocarthritis, periodontal disease, liver failure), surgery, including cosmetic plastic surgery, fibrosis, reperfusion injury, or systemic cytokine damage.

Tissues that could be regenerated using the present invention include organs (e.g., pancreas, liver, intestine, kidney, skin, endothelium), muscle (smooth, skeletal or cardiac), vasculature (including vascular and lymphatics), nervous, hematopoietic, and skeletal (bone, cartilage, tendon, and ligament) tissue. Preferably, regeneration occurs without or decreased scarring. Regeneration also may include angiogenesis.

Moreover, a polynucleotide or polypeptide and/or agonist or antagonist of the present invention may increase regeneration of tissues difficult to heal. For example, increased tendon/ligament regeneration would quicken recovery time after damage. A polynucleotide or polypeptide and/or agonist or antagonist of the present invention could also be used prophylactically in an effort to avoid damage. Specific diseases that could be treated, prevented, and/or diagnosed include of tendinitis, carpal tunnel syndrome, and other tendon or ligament defects. A further example of tissue regeneration of non-healing wounds includes pressure ulcers, ulcers associated with vascular insufficiency, surgical, and traumatic wounds.

Similarly, nerve and brain tissue could also be regenerated by using a polynucleotide or polypeptide and/or agonist or antagonist of the present invention to proliferate and differentiate nerve cells. Diseases that could be treated, prevented, and/or diagnosed using this method include central and peripheral nervous system diseases, neuropathies, or mechanical and traumatic diseases, disorders, and/or conditions (e.g., spinal cord disorders, head trauma, cerebrovascular disease, and stoke). Specifically, diseases associated with peripheral nerve injuries, peripheral neuropathy (e.g., resulting from chemotherapy or other medical therapies), localized neuropathies, and central nervous system diseases (e.g., Alzheimer's disease, Parkinson's disease, Huntington's disease, amyotrophic lateral sclerosis, and Shy-Drager syndrome), could all be treated, prevented, and/or diagnosed using the polynucleotide or polypeptide and/or agonist or antagonist of the present invention.

Chemotaxis

A polynucleotide or polypeptide and/or agonist or antagonist of the present invention may have chemotaxis activity. A chemotaxic molecule attracts or mobilizes cells (e.g., monocytes, fibroblasts, neutrophils, T-cells, mast cells, eosinophils, epithelial and/or endothelial cells) to a particular site in the body, such as inflammation, infection, or site of hyperproliferation. The mobilized cells can then fight off and/or heal the particular trauma or abnormality.

A polynucleotide or polypeptide and/or agonist or antagonist of the present invention may increase chemotaxic activity of particular cells. These chemotactic molecules can then be used to treat, prevent, and/or diagnose inflammation, infection, hyperproliferative diseases, disorders, and/or conditions, or any immune system disorder by increasing the number of cells targeted to a particular location in the body. For example, chemotaxic molecules can be used to treat, prevent, and/or diagnose wounds and other trauma to tissues by attracting immune cells to the injured location. Chemotactic molecules of the present invention can also attract fibroblasts, which can be used to treat, prevent, and/or diagnose wounds.

It is also contemplated that a polynucleotide or polypeptide and/or agonist or antagonist of the present invention may inhibit chemotactic activity. These molecules could also be used to treat, prevent, and/or diagnose diseases, disorders, and/or conditions. Thus, a polynucleotide or polypeptide and/or agonist or antagonist of the present invention could be used as an inhibitor of chemotaxis.

Binding Activity

A polypeptide of the present invention may be used to screen for molecules that bind to the polypeptide or for molecules to which the polypeptide binds. The binding of the polypeptide and the molecule may activate (agonist), increase, inhibit (antagonist), or decrease activity of the polypeptide or the molecule bound. Examples of such molecules include antibodies, oligonucleotides, proteins (e.g., receptors), or small molecules.

Preferably, the molecule is closely related to the natural ligand of the polypeptide, e.g., a fragment of the ligand, or a natural substrate, a ligand, a structural or functional mimetic. (See, Coligan et al., Current Protocols in Immunology 1(2): Chapter 5 (1991).) Similarly, the molecule can be closely related to the natural receptor to which the polypeptide binds, or at least, a fragment of the receptor capable of being bound by the polypeptide (e.g., active site). In either case, the molecule can be rationally designed using known techniques.

Preferably, the screening for these molecules involves producing appropriate cells which express the polypeptide, either as a secreted protein or on the cell membrane. Preferred cells include cells from mammals, yeast, Drosophila, or E. coli. Cells expressing the polypeptide (or cell membrane containing the expressed polypeptide) are then preferably contacted with a test compound potentially containing the molecule to observe binding, stimulation, or inhibition of activity of either the polypeptide or the molecule.

The assay may simply test binding of a candidate compound to the polypeptide, wherein binding is detected by a label, or in an assay involving competition with a labeled competitor. Further, the assay may test whether the candidate compound results in a signal generated by binding to the polypeptide.

Alternatively, the assay can be carried out using cell-free preparations, polypeptide/molecule affixed to a solid support, chemical libraries, or natural product mixtures. The assay may also simply comprise the steps of mixing a candidate compound with a solution containing a polypeptide, measuring polypeptide/molecule activity or binding, and comparing the polypeptide/molecule activity or binding to a standard.

Preferably, an ELISA assay can measure polypeptide level or activity in a sample (e.g., biological sample) using a monoclonal or polyclonal antibody. The antibody can measure polypeptide level or activity by either binding, directly or indirectly, to the polypeptide or by competing with the polypeptide for a substrate.

Additionally, the receptor to which a polypeptide of the invention binds can be identified by numerous methods known to those of skill in the art, for example, ligand panning and FACS sorting (Coligan, et al., Current Protocols in Immun., 1(2), Chapter 5, (1991)). For example, expression cloning is employed wherein polyadenylated RNA is prepared from a cell responsive to the polypeptides, for example, NIH3T3 cells which are known to contain multiple receptors for the FGF family proteins, and SC-3 cells, and a cDNA library created from this RNA is divided into pools and used to transfect COS cells or other cells that are not responsive to the polypeptides. Transfected cells which are grown on glass slides are exposed to the polypeptide of the present invention, after they have been labeled. The polypeptides can be labeled by a variety of means including iodination or inclusion of a recognition site for a site-specific protein kinase.

Following fixation and incubation, the slides are subjected to auto-radiographic analysis. Positive pools are identified and sub-pools are prepared and re-transfected using an iterative sub-pooling and re-screening process, eventually yielding a single clones that encodes the putative receptor.

As an alternative approach for receptor identification, the labeled polypeptides can be photoaffinity linked with cell membrane or extract preparations that express the receptor molecule. Cross-linked material is resolved by PAGE analysis and exposed to X-ray film. The labeled complex containing the receptors of the polypeptides can be excised, resolved into peptide fragments, and subjected to protein microsequencing. The amino acid sequence obtained from microsequencing would be used to design a set of degenerate oligonucleotide probes to screen a cDNA library to identify the genes encoding the putative receptors.

Moreover, the techniques of gene-shuffling, motif-shuffling, exon-shuffling, and/or codon-shuffling (collectively referred to as "DNA shuffling") may be employed to modulate the activities of polypeptides of the invention thereby effectively generating agonists and antagonists of polypeptides of the invention. See generally, U.S. Pat. Nos. 5,605,793, 5,811,238, 5,830,721, 5,834,252, and 5,837,458, and Patten, P. A., et al., Curr. Opinion Biotechnol. 8:724-33 (1997); Harayama, S. Trends Biotechnol. 16(2):76-82 (1998); Hansson, L. O., et al., J. Mol. Biol. 287:265-76 (1999); and Lorenzo, M. M. and Blasco, R. Biotechniques 24(2):308-13 (1998) (each of these patents and publications are hereby incorporated by reference). In one embodiment, alteration of polynucleotides and corresponding polypeptides of the invention may be achieved by DNA shuffling. DNA shuffling involves the assembly of two or more DNA segments into a desired polynucleotide sequence of the invention molecule by homologous, or site-specific, recombination. In another embodiment, polynucleotides and corresponding polypeptides of the invention may be altered by being subjected to random mutagenesis by error-prone PCR, random nucleotide insertion or other methods prior to recombination. In another embodiment, one or more components, motifs, sections, parts, domains, fragments, etc., of the polypeptides of the invention may be recombined with one or more components, motifs, sections, parts, domains, fragments, etc. of one or more heterologous molecules. In preferred embodiments, the heterologous molecules are family members. In further preferred embodiments, the heterologous molecule is a growth factor such as, for example, platelet-derived growth factor (PDGF), insulin-like growth factor (IGF-I), transforming growth factor (TGF)-alpha, epidermal growth factor (EGF), fibroblast growth factor (FGF), TGF-beta, bone morphogenetic protein (BMP)-2, BMP-4, BMP-5, BMP-6, BMP-7, activins A and B, decapentaplegic (dpp), 60A, OP-2, dorsalin, growth differentiation factors (GDFs), nodal, MIS, inhibin-alpha, TGF-beta1, TGF-beta2, TGF-beta3, TGF-beta5, and glial-derived neurotrophic factor (GDNF).

Other preferred fragments are biologically active fragments of the polypeptides of the invention. Biologically active fragments are those exhibiting activity similar, but not necessarily identical, to an activity of the polypeptide. The biological activity of the fragments may include an improved desired activity, or a decreased undesirable activity.

Additionally, this invention provides a method of screening compounds to identify those which modulate the action of the polypeptide of the present invention. An example of such an assay comprises combining a mammalian fibroblast cell, a the polypeptide of the present invention, the compound to be screened and 3[H] thymidine under cell culture conditions where the fibroblast cell would normally proliferate. A control assay may be performed in the absence of the compound to be screened and compared to the amount of fibroblast proliferation in the presence of the compound to determine if the compound stimulates proliferation by determining the uptake of 3[H] thymidine in each case. The amount of fibroblast cell proliferation is measured by liquid scintillation chromatography which measures the incorporation of 3[H] thymidine. Both agonist and antagonist compounds may be identified by this procedure.

In another method, a mammalian cell or membrane preparation expressing a receptor for a polypeptide of the present invention is incubated with a labeled polypeptide of the present invention in the presence of the compound. The ability of the compound to enhance or block this interaction could then be measured. Alternatively, the response of a known second messenger system following interaction of a compound to be screened and the receptor is measured and the ability of the compound to bind to the receptor and elicit a second messenger response is measured to determine if the compound is a potential agonist or antagonist. Such second messenger systems include but are not limited to, cAMP guanylate cyclase, ion channels or phosphoinositide hydrolysis.

All of these above assays can be used as diagnostic or prognostic markers. The molecules discovered using these assays can be used to treat, prevent, and/or diagnose disease or to bring about a particular result in a patient (e.g., blood vessel growth) by activating or inhibiting the polypeptide/molecule. Moreover, the assays can discover agents which may inhibit or enhance the production of the polypeptides of the invention from suitably manipulated cells or tissues. Therefore, the invention includes a method of identifying compounds which bind to the polypeptides of the invention comprising the steps of: (a) incubating a candidate binding compound with the polypeptide; and (b) determining if binding has occurred. Moreover, the invention includes a method of identifying agonists/antagonists comprising the steps of: (a) incubating a candidate compound with the polypeptide, (b) assaying a biological activity, and (b) determining if a biological activity of the polypeptide has been altered.

Also, one could identify molecules bind a polypeptide of the invention experimentally by using the beta-pleated sheet regions contained in the polypeptide sequence of the protein. Accordingly, specific embodiments of the invention are directed to polynucleotides encoding polypeptides which comprise, or alternatively consist of, the amino acid sequence of each beta pleated sheet regions in a disclosed polypeptide sequence. Additional embodiments of the invention are directed to polynucleotides encoding polypeptides which comprise, or alternatively consist of, any combination or all of contained in the polypeptide sequences of the invention. Additional preferred embodiments of the invention are directed to polypeptides which comprise, or alternatively consist of, the amino acid sequence of each of the beta pleated sheet regions in one of the polypeptide sequences of the invention. Additional embodiments of the invention are directed to polypeptides which comprise, or alternatively consist of, any combination or all of the beta pleated sheet regions in one of the polypeptide sequences of the invention.

Targeted Delivery

In another embodiment, the invention provides a method of delivering compositions to targeted cells expressing a receptor for a polypeptide of the invention, or cells expressing a cell bound form of a polypeptide of the invention.

As discussed herein, polypeptides or antibodies of the invention may be associated with heterologous polypeptides, heterologous nucleic acids, toxins, or prodrugs via hydrophobic, hydrophilic, ionic and/or covalent interactions. In one embodiment, the invention provides a method for the specific delivery of compositions of the invention to cells by administering polypeptides of the invention (including antibodies) that are associated with heterologous polypeptides or nucleic acids. In one example, the invention provides a method for delivering a therapeutic protein into the targeted cell. In another example, the invention provides a method for delivering a single stranded nucleic acid (e.g., antisense or ribozymes) or double stranded nucleic acid (e.g., DNA that can integrate into the cell's genome or replicate episomally and that can be transcribed) into the targeted cell.

In another embodiment, the invention provides a method for the specific destruction of cells (e.g., the destruction of tumor cells) by administering polypeptides of the invention (e.g., polypeptides of the invention or antibodies of the invention) in association with toxins or cytotoxic prodrugs.

By "toxin" is meant compounds that bind and activate endogenous cytotoxic effector systems, radioisotopes, holotoxins, modified toxins, catalytic subunits of toxins, or any molecules or enzymes not normally present in or on the surface of a cell that under defined conditions cause the cell's death. Toxins that may be used according to the methods of the invention include, but are not limited to, radioisotopes known in the art, compounds such as, for example, antibodies (or complement fixing containing portions thereof) that bind an inherent or induced endogenous cytotoxic effector system, thymidine kinase, endonuclease, RNAse, alpha toxin, ricin, abrin, *Pseudomonas* exotoxin A, diphtheria toxin, saporin, momordin, gelonin, pokeweed antiviral protein, alpha-sarcin and cholera toxin. By "cytotoxic prodrug" is meant a non-toxic compound that is converted by an enzyme, normally present in the cell, into a cytotoxic compound. Cytotoxic prodrugs that may be used according to the methods of the invention include, but are not limited to, glutamyl derivatives of benzoic acid mustard alkylating agent, phosphate derivatives of etoposide or mitomycin C, cytosine arabinoside, daunorubisin, and phenoxyacetamide derivatives of doxorubicin.

Drug Screening

Further contemplated is the use of the polypeptides of the present invention, or the polynucleotides encoding these polypeptides, to screen for molecules which modify the activities of the polypeptides of the present invention. Such a method would include contacting the polypeptide of the present invention with a selected compound(s) suspected of having antagonist or agonist activity, and assaying the activity of these polypeptides following binding.

This invention is particularly useful for screening therapeutic compounds by using the polypeptides of the present invention, or binding fragments thereof, in any of a variety of drug screening techniques. The polypeptide or fragment employed in such a test may be affixed to a solid support, expressed on a cell surface, free in solution, or located intracellularly. One method of drug screening utilizes eukaryotic or prokaryotic host cells which are stably transformed with recombinant nucleic acids expressing the polypeptide or fragment. Drugs are screened against such transformed cells in competitive binding assays. One may measure, for example, the formulation of complexes between the agent being tested and a polypeptide of the present invention.

Thus, the present invention provides methods of screening for drugs or any other agents which affect activities mediated by the polypeptides of the present invention. These methods comprise contacting such an agent with a polypeptide of the present invention or a fragment thereof and assaying for the presence of a complex between the agent and the polypeptide or a fragment thereof, by methods well known in the art. In such a competitive binding assay, the agents to screen are typically labeled. Following incubation, free agent is separated from that present in bound form, and the amount of free or uncomplexed label is a measure of the ability of a particular agent to bind to the polypeptides of the present invention.

Another technique for drug screening provides high throughput screening for compounds having suitable binding affinity to the polypeptides of the present invention, and is described in great detail in European Patent Application 84/03564, published on Sep. 13, 1984, which is incorporated herein by reference herein. Briefly stated, large numbers of different small peptide test compounds are synthesized on a solid substrate, such as plastic pins or some other surface. The peptide test compounds are reacted with polypeptides of the present invention and washed. Bound polypeptides are then detected by methods well known in the art. Purified polypeptides are coated directly onto plates for use in the aforementioned drug screening techniques. In addition, non-neutralizing antibodies may be used to capture the peptide and immobilize it on the solid support.

This invention also contemplates the use of competitive drug screening assays in which neutralizing antibodies capable of binding polypeptides of the present invention specifically compete with a test compound for binding to the polypeptides or fragments thereof. In this manner, the antibodies are used to detect the presence of any peptide which shares one or more antigenic epitopes with a polypeptide of the invention.

The human TRP-PLIK2 polypeptides and/or peptides of the present invention, or immunogenic fragments or oligopeptides thereof, can be used for screening therapeutic drugs or compounds in a variety of drug screening techniques. The fragment employed in such a screening assay may be free in solution, affixed to a solid support, borne on a cell surface, or located intracellularly. The reduction or abolition of activity of the formation of binding complexes between the ion channel protein and the agent being tested can be measured. Thus, the present invention provides a method for screening or assessing a plurality of compounds for their specific binding affinity with a TRP-PLIK2 polypeptide, or a bindable peptide fragment, of this invention, comprising providing a plurality of compounds, combining the TRP-PLIK2 polypeptide, or a bindable peptide fragment, with each of a plurality of compounds for a time sufficient to allow binding under suitable conditions and detecting binding of the TRP-PLIK2 polypeptide or peptide to each of the plurality of test compounds, thereby identifying the compounds that specifically bind to the TRP-PLIK2 polypeptide or peptide.

Methods of identifying compounds that modulate the activity of the novel human TRP-PLIK2 polypeptides and/or peptides are provided by the present invention and comprise combining a potential or candidate compound or drug modulator of immunoglobulin biological activity with an TRP-PLIK2 polypeptide or peptide, for example, the TRP-PLIK2 amino acid sequence as set forth in SEQ ID NOS:2, 4, 6, or 8, and measuring an effect of the candidate compound or drug modulator on the biological activity of the TRP-PLIK2 polypeptide or peptide. Such measurable effects include, for example, physical binding interaction; the ability to cleave a suitable immunoglobulin substrate; effects on native and cloned TRP-PLIK2-expressing cell line; and effects of modulators or other immunoglobulin-mediated physiological measures.

Another method of identifying compounds that modulate the biological activity of the novel TRP-PLIK2 polypeptides of the present invention comprises combining a potential or candidate compound or drug modulator of a immunoglobulin biological activity with a host cell that expresses the TRP-PLIK2 polypeptide and measuring an effect of the candidate compound or drug modulator on the biological activity of the TRP-PLIK2 polypeptide. The host cell can also be capable of being induced to express the TRP-PLIK2 polypeptide, e.g., via inducible expression. Physiological effects of a given modulator candidate on the TRP-PLIK2 polypeptide can also be measured. Thus, cellular assays for particular immunoglobulin modulators may be either direct measurement or quantification of the physical biological activity of the TRP-PLIK2 polypeptide, or they may be measurement or quantification of a physiological effect. Such methods preferably employ a TRP-PLIK2 polypeptide as described herein, or an overexpressed recombinant TRP-PLIK2 polypeptide in suitable host cells containing an expression vector as described herein, wherein the TRP-PLIK2 polypeptide is expressed, overexpressed, or undergoes upregulated expression.

Another aspect of the present invention embraces a method of screening for a compound that is capable of modulating the biological activity of a TRP-PLIK2 polypeptide, comprising providing a host cell containing an expression vector harboring a nucleic acid sequence encoding a TRP-PLIK2 polypeptide, or a functional peptide or portion thereof (e.g., SEQ ID NOS:2, 4, 6, or 8); determining the biological activity of the expressed TRP-PLIK2 polypeptide in the absence of a modulator compound; contacting the cell with the modulator compound and determining the biological activity of the expressed TRP-PLIK2 polypeptide in the presence of the modulator compound. In such a method, a difference between the activity of the TRP-PLIK2 polypeptide in the presence of the modulator compound and in the absence of the modulator compound indicates a modulating effect of the compound.

Essentially any chemical compound can be employed as a potential modulator or ligand in the assays according to the present invention. Compounds tested as immunoglobulin modulators can be any small chemical compound, or biological entity (e.g., protein, sugar, nucleic acid, lipid). Test compounds will typically be small chemical molecules and peptides. Generally, the compounds used as potential modulators can be dissolved in aqueous or organic (e.g., DMSO-based) solutions. The assays are designed to screen large chemical libraries by automating the assay steps and providing compounds from any convenient source. Assays are typically run in parallel, for example, in microtiter formats on microtiter plates in robotic assays. There are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs, Switzerland), for example. Also, compounds may be synthesized by methods known in the art.

High throughput screening methodologies are particularly envisioned for the detection of modulators of the novel TRP-PLIK2 polynucleotides and polypeptides described herein. Such high throughput screening methods typically involve providing a combinatorial chemical or peptide library containing a large number of potential therapeutic compounds (e.g., ligand or modulator compounds). Such combinatorial chemical libraries or ligand libraries are then screened in one or more assays to identify those library members (e.g., particular chemical species or subclasses) that display a desired characteristic activity. The compounds so identified can serve as conventional lead compounds, or can themselves be used as potential or actual therapeutics.

A combinatorial chemical library is a collection of diverse chemical compounds generated either by chemical synthesis or biological synthesis, by combining a number of chemical building blocks (i.e., reagents such as amino acids). As an example, a linear combinatorial library, e.g., a polypeptide or peptide library, is formed by combining a set of chemical building blocks in every possible way for a given compound length (i.e., the number of amino acids in a polypeptide or peptide compound). Millions of chemical compounds can be synthesized through such combinatorial mixing of chemical building blocks.

The preparation and screening of combinatorial chemical libraries is well known to those having skill in the pertinent art. Combinatorial libraries include, without limitation, peptide libraries (e.g. U.S. Pat. No. 5,010,175; Furka, 1991, Int. J. Pept. Prot. Res., 37:487-493; and Houghton et al., 1991, Nature, 354:84-88). Other chemistries for generating chemical diversity libraries can also be used. Nonlimiting examples of chemical diversity library chemistries include, peptides (PCT Publication No. WO 91/019735), encoded peptides (PCT Publication No. WO 93/20242), random bio-oligomers (PCT Publication No. WO 92/00091), benzodiazepines (U.S. Pat. No. 5,288,514), diversomers such as hydantoins, benzodiazepines and dipeptides (Hobbs et al., 1993, Proc. Natl. Acad. Sci. USA, 90:6909-6913), vinylogous polypeptides (Hagihara et al., 1992, J. Amer. Chem. Soc., 114:6568), non-peptidal peptidomimetics with glucose scaffolding (Hirschmann et al., 1992, J. Amer. Chem. Soc., 114:9217-9218), analogous organic synthesis of small compound libraries (Chen et al., 1994, J. Amer. Chem. Soc., 116:2661), oligocarbamates (Cho et al., 1993, Science, 261:1303), and/or peptidyl phosphonates (Campbell et al., 1994, J. Org. Chem., 59:658), nucleic acid libraries (see Ausubel, Berger and Sambrook, all supra), peptide nucleic acid libraries (U.S. Pat. No. 5,539,083), antibody libraries (e.g., Vaughn et al., 1996, Nature Biotechnology, 14(3):309-314) and PCT/US96/10287, now U.S. Pat. Nos. 5,977,322; 6,512,097; and 7,388,088), carbohydrate libraries (e.g., Liang et al., 1996, Science, 274-1520-1522) and U.S. Pat. No. 5,593,853), small organic molecule libraries (e.g., benzodiazepines, Baum C&EN, Jan. 18, 1993, page 33; and U.S. Pat. No. 5,288,514; isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; and the like).

Devices for the preparation of combinatorial libraries are commercially available (e.g., 357 MPS, 390 MPS, Advanced Chem Tech, Louisville Ky.; Symphony, Rainin, Woburn, Mass.; 433A Applied Biosystems, Foster City, Calif.; 9050 Plus, Millipore, Bedford, Mass.). In addition, a large number of combinatorial libraries are commercially available (e.g., ComGenex, Princeton, N.J.; Asinex, Moscow, Russia; Tripos, Inc., St. Louis, Mo.; ChemStar, Ltd., Moscow, Russia; 3D Pharmaceuticals, Exton, Pa.; Martek Biosciences, Columbia, Md., and the like).

In one embodiment, the invention provides solid phase based in vitro assays in a high throughput format, where the cell or tissue expressing an ion channel is attached to a solid phase substrate. In such high throughput assays, it is possible to screen up to several thousand different modulators or ligands in a single day. In particular, each well of a microtiter plate can be used to perform a separate assay against a selected potential modulator, or, if concentration or incubation time effects are to be observed, every 5-10 wells can test a single modulator. Thus, a single standard microtiter plate can assay about 96 modulators. If 1536 well plates are used, then a single plate can easily assay from about 100 to about 1500 different compounds. It is possible to assay several different plates per day; thus, for example, assay screens for up to about 6,000-20,000 different compounds are possible using the described integrated systems.

In another of its aspects, the present invention encompasses screening and small molecule (e.g., drug) detection assays which involve the detection or identification of small molecules that can bind to a given protein, i.e., a TRP-PLIK2 polypeptide or peptide. Particularly preferred are assays suitable for high throughput screening methodologies.

In such binding-based detection, identification, or screening assays, a functional assay is not typically required. All that is needed is a target protein, preferably substantially purified, and a library or panel of compounds (e.g., ligands, drugs, small molecules) or biological entities to be screened or assayed for binding to the protein target. Preferably, most small molecules that bind to the target protein will modulate activity in some manner, due to preferential, higher affinity binding to functional areas or sites on the protein.

An example of such an assay is the fluorescence based thermal shift assay (3-Dimensional Pharmaceuticals, Inc., 3DP, Exton, Pa.) as described in U.S. Pat. Nos. 6,020,141 and 6,036,920 to Pantoliano et al.; see also, J. Zimmerman, 2000, Gen. Eng. News, 20(8)). The assay allows the detection of small molecules (e.g., drugs, ligands) that bind to expressed, and preferably purified, ion channel polypeptide based on affinity of binding determinations by analyzing thermal unfolding curves of protein-drug or ligand complexes. The drugs or binding molecules determined by this technique can be further assayed, if desired, by methods, such as those described herein, to determine if the molecules affect or modulate function or activity of the target protein.

To purify a TRP-PLIK2 polypeptide or peptide to measure a biological binding or ligand binding activity, the source may be a whole cell lysate that can be prepared by successive freeze-thaw cycles (e.g., one to three) in the presence of standard protease inhibitors. The TRP-PLIK2 polypeptide may be partially or completely purified by standard protein purification methods, e.g., affinity chromatography using specific antibody described infra, or by ligands specific for an epitope tag engineered into the recombinant TRP-PLIK2 polypeptide molecule, also as described herein. Binding activity can then be measured as described.

Compounds which are identified according to the methods provided herein, and which modulate or regulate the biological activity or physiology of the TRP-PLIK2 polypeptides according to the present invention are a preferred embodiment of this invention. It is contemplated that such modulatory compounds may be employed in treatment and therapeutic methods for treating a condition that is mediated by the novel TRP-PLIK2 polypeptides by administering to an individual in need of such treatment a therapeutically effective amount of the compound identified by the methods described herein.

In addition, the present invention provides methods for treating an individual in need of such treatment for a disease, disorder, or condition that is mediated by the TRP-PLIK2 polypeptides of the invention, comprising administering to the individual a therapeutically effective amount of the TRP-PLIK2-modulating compound identified by a method provided herein.

Antisense And Ribozyme (Antagonists)

In specific embodiments, antagonists according to the present invention are nucleic acids corresponding to the sequences contained in SEQ ID NO: 1, 3, 5, 7, and/or 97, or the complementary strand thereof, and/or to nucleotide sequences contained a deposited clone. In one embodiment, antisense sequence is generated internally by the organism, in another embodiment, the antisense sequence is separately administered (see, for example, O'Connor, Neurochem., 56:560 (1991). Oligodeoxynucleotides as Antisense Inhibitors of Gene Expression, CRC Press, Boca Raton, Fla. (1988). Antisense technology can be used to control gene expression through antisense DNA or RNA, or through triple-helix formation. Antisense techniques are discussed for example, in Okano, Neurochem., 56:560 (1991); Oligodeoxynucleotides as Antisense Inhibitors of Gene Expression, CRC Press, Boca Raton, Fla. (1988). Triple helix formation is discussed in, for instance, Lee et al., Nucleic Acids Research, 6:3073 (1979); Cooney et al., Science, 241:456 (1988); and Dervan et al., Science, 251:1300 (1991). The methods are based on binding of a polynucleotide to a complementary DNA or RNA.

For example, the use of c-myc and c-myb antisense RNA constructs to inhibit the growth of the non-lymphocytic leukemia cell line HL-60 and other cell lines was previously described. (Wickstrom et al. (1988); Anfossi et al. (1989)). These experiments were performed in vitro by incubating cells with the oligoribonucleotide. A similar procedure for in vivo use is described in WO 91/15580. Briefly, a pair of oligonucleotides for a given antisense RNA is produced as follows: A sequence complimentary to the first 15 bases of the open reading frame is flanked by an EcoR1 site on the 5 end and a HindIII site on the 3 end. Next, the pair of oligonucleotides is heated at 90° C. for one minute and then annealed in 2× ligation buffer (20 mM TRIS HCl pH 7.5, 10 mM MgCl2, 10mM dithiothreitol (DTT) and 0.2 mM ATP) and then ligated to the EcoR1/Hind III site of the retroviral vector PMV7 (WO 91/15580).

For example, the 5' coding portion of a polynucleotide that encodes the mature polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of the receptor. The antisense RNA oligonucleotide hybridizes to the mRNA in vivo and blocks translation of the mRNA molecule into receptor polypeptide.

In one embodiment, the antisense nucleic acid of the invention is produced intracellularly by transcription from an exogenous sequence. For example, a vector or a portion thereof, is transcribed, producing an antisense nucleic acid (RNA) of the invention. Such a vector would contain a sequence encoding the antisense nucleic acid of the invention. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in vertebrate cells. Expression of the sequence encoding a polypeptide of the invention, or fragments thereof, can be by any promoter known in the art to act in vertebrate, preferably human cells. Such promoters can be inducible or constitutive. Such promoters include, but are not limited to, the SV40 early promoter region (Bemoist and Chambon, Nature, 29:304-310 (1981), the promoter contained in the 3' long terminal repeat of Rous sarcoma virus (Yamamoto et al., Cell, 22:787-797 (1980), the herpes thymidine promoter (Wagner et al., Proc. Natl. Acad. Sci. U.S.A., 78:1441-1445 (1981), the regulatory sequences of the metallothionein gene (Brinster et al., Nature, 296:39-42 (1982)), etc.

The antisense nucleic acids of the invention comprise a sequence complementary to at least a portion of an RNA transcript of a gene of interest. However, absolute complementarity, although preferred, is not required. A sequence "complementary to at least a portion of an RNA," referred to herein, means a sequence having sufficient complementarity to be able to hybridize with the RNA, forming a stable duplex; in the case of double stranded antisense nucleic acids of the invention, a single strand of the duplex DNA may thus be tested, or triplex formation may be assayed. The ability to hybridize will depend on both the degree of complementarity and the length of the antisense nucleic acid Generally, the larger the hybridizing nucleic acid, the more base mismatches with a RNA sequence of the invention it may contain and still form a stable duplex (or triplex as the case may be). One skilled in the art can ascertain a tolerable degree of mismatch by use of standard procedures to determine the melting point of the hybridized complex.

Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have been shown to be effective at inhibiting translation of mRNAs as well. See generally, Wagner, R., Nature, 372:333-335 (1994). Thus, oligonucleotides complementary to either the 5'- or 3'-non-translated, non-coding regions of a polynucleotide sequence of the invention could be used in an antisense approach to inhibit translation of endogenous mRNA. Oligonucleotides complementary to the 5' untranslated region of the mRNA should include the complement of the AUG start codon. Antisense oligonucleotides complementary to mRNA coding regions are less efficient inhibitors of translation but could be used in accordance with the invention. Whether designed to hybridize to the 5'-, 3'- or coding region of mRNA, antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

The polynucleotides of the invention can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger et al., Proc. Natl. Acad. Sci. U.S.A. 86:6553-6556 (1989); Lemaitre et al., Proc. Natl. Acad. Sci., 84:648-652 (1987); PCT Publication NO: WO88/09810, published Dec. 15, 1988) or the blood-brain barrier (see, e.g., PCT Publication NO: WO89/10134, published Apr. 25, 1988), hybridization-triggered cleavage agents. (See, e.g., Krol et al., BioTechniques, 6:958-976 (1988)) or intercalating agents. (See, e.g., Zon, Pharm. Res., 5:539-549 (1988)). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including, but not limited to, 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine.

The antisense oligonucleotide may also comprise at least one modified sugar moiety selected from the group including, but not limited to, arabinose, 2-fluoroarabinose, xylulose, and hexose.

In yet another embodiment, the antisense oligonucleotide comprises at least one modified phosphate backbone selected from the group including, but not limited to, a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an a-anomeric oligonucleotide. An a-anomeric oligonucleotide forms specific double-stranded hybrids with complementary RNA in which, contrary to the usual b-units, the strands run parallel to each other (Gautier et al., Nucl. Acids Res., 15:6625-6641 (1987)). The oligonucleotide is a 2-O-methylribonucleotide (Inoue et al., Nucl. Acids Res., 15:6131-6148 (1987)), or a chimeric RNA-DNA analogue (Inoue et al., FEBS Lett. 215:327-330 (1987)).

Polynucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (Nucl. Acids Res., 16:3209 (1988)), methylphosphonate oligonucleotides can be prepared by use of controlled pore glass polymer supports (Sarin et al., Proc. Natl. Acad. Sci. U.S.A., 85:7448-7451 (1988)), etc.

While antisense nucleotides complementary to the coding region sequence of the invention could be used, those complementary to the transcribed untranslated region are most preferred.

Potential antagonists according to the invention also include catalytic RNA, or a ribozyme (See, e.g., PCT International Publication WO 90/11364, published Oct. 4, 1990; Sarver et al, Science, 247:1222-1225 (1990). While ribozymes that cleave mRNA at site specific recognition sequences can be used to destroy mRNAs corresponding to the polynucleotides of the invention, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, Nature, 334:585-591 (1988). There are numerous potential hammerhead ribozyme cleavage sites within each nucleotide sequence disclosed in the sequence listing. Preferably, the ribozyme is engineered so that the cleavage recognition site is located near the 5' end of the mRNA corresponding to the polynucleotides of the invention; i.e., to increase efficiency and minimize the intracellular accumulation of non-functional mRNA transcripts.

As in the antisense approach, the ribozymes of the invention can be composed of modified oligonucleotides (e.g. for improved stability, targeting, etc.) and should be delivered to cells which express the polynucleotides of the invention in vivo. DNA constructs encoding the ribozyme may be introduced into the cell in the same manner as described above for the introduction of antisense encoding DNA. A preferred method of delivery involves using a DNA construct "encoding" the ribozyme under the control of a strong constitutive promoter, such as, for example, pol III or pol II promoter, so that transfected cells will produce sufficient quantities of the ribozyme to destroy endogenous messages and inhibit translation. Since ribozymes unlike antisense molecules, are catalytic, a lower intracellular concentration is required for efficiency.

Antagonist/agonist compounds may be employed to inhibit the cell growth and proliferation effects of the polypeptides of the present invention on neoplastic cells and tissues, i.e. stimulation of angiogenesis of tumors, and, therefore, retard or prevent abnormal cellular growth and proliferation, for example, in tumor formation or growth.

The antagonist/agonist may also be employed to prevent hyper-vascular diseases, and prevent the proliferation of epithelial lens cells after extracapsular cataract surgery. Prevention of the mitogenic activity of the polypeptides of the present invention may also be desirous in cases such as restenosis after balloon angioplasty.

The antagonist/agonist may also be employed to prevent the growth of scar tissue during wound healing.

The antagonist/agonist may also be employed to treat, prevent, and/or diagnose the diseases described herein.

Thus, the invention provides a method of treating or preventing diseases, disorders, and/or conditions, including but not limited to the diseases, disorders, and/or conditions listed throughout this application, associated with overexpression of a polynucleotide of the present invention by administering to a patient (a) an antisense molecule directed to the polynucleotide of the present invention, and/or (b) a ribozyme directed to the polynucleotide of the present invention.

invention, and/or (b) a ribozyme directed to the polynucleotide of the present invention.

Biotic Associations

A polynucleotide or polypeptide and/or agonist or antagonist of the present invention may increase the organisms ability, either directly or indirectly, to initiate and/or maintain biotic associations with other organisms. Such associations may be symbiotic, nonsymbiotic, endosymbiotic, macrosymbiotic, and/or microsymbiotic in nature. In general, a polynucleotide or polypeptide and/or agonist or antagonist of the present invention may increase the organisms ability to form biotic associations with any member of the fungal, bacterial, lichen, mycorrhizal, cyanobacterial, dinoflaggellate, and/or algal, kingdom, phylums, families, classes, genuses, and/or species.

The mechanism by which a polynucleotide or polypeptide and/or agonist or antagonist of the present invention may increase the host organisms ability, either directly or indirectly, to initiate and/or maintain biotic associations is variable, though may include, modulating osmolarity to desirable levels for the symbiont, modulating pH to desirable levels for the symbiont, modulating secretions of organic acids, modulating the secretion of specific proteins, phenolic compounds, nutrients, or the increased expression of a protein required for host-biotic organisms interactions (e.g., a receptor, ligand, etc.). Additional mechanisms are known in the art and are encompassed by the invention (see, for example, "Microbial Signalling and Communication", eds., R. England, G. Hobbs, N. Bainton, and D. McL. Roberts, Cambridge University Press, Cambridge, (1999); which is hereby incorporated herein by reference).

In an alternative embodiment, a polynucleotide or polypeptide and/or agonist or antagonist of the present invention may decrease the host organisms ability to form biotic associations with another organism, either directly or indirectly. The mechanism by which a polynucleotide or polypeptide and/or agonist or antagonist of the present invention may decrease the host organisms ability, either directly or indirectly, to initiate and/or maintain biotic associations with another organism is variable, though may include, modulating osmolarity to undesirable levels, modulating pH to undesirable levels, modulating secretions of organic acids, modulating the secretion of specific proteins, phenolic compounds, nutrients, or the decreased expression of a protein required for host-biotic organisms interactions (e.g., a receptor, ligand, etc.). Additional mechanisms are known in the art and are encompassed by the invention (see, for example, "Microbial Signalling and Communication", eds., R. England, G. Hobbs, N. Bainton, and D. McL. Roberts, Cambridge University Press, Cambridge, (1999); which is hereby incorporated herein by reference).

The hosts ability to maintain biotic associations with a particular pathogen has significant implications for the overall health and fitness of the host. For example, human hosts have symbiosis with enteric bacteria in their gastrointestinal tracts, particularly in the small and large intestine. In fact, bacteria counts in feces of the distal colon often approach $10^{12}$ per milliliter of feces. Examples of bowel flora in the gastrointestinal tract are members of the Enterobacteriaceae, *Bacteriodes*, in addition to a-hemolytic *streptococci, E. coli, Bifobacteria, Anaerobic cocci, Eubacteria, Costridia, lactobacilli*, and yeasts. Such bacteria, among other things, assist the host in the assimilation of nutrients by breaking down food stuffs not typically broken down by the hosts digestive system, particularly in the hosts bowel. Therefore, increasing the hosts ability to maintain such a biotic association would help assure proper nutrition for the host.

Aberrations in the enteric bacterial population of mammals, particularly humans, has been associated with the following disorders: diarrhea, ileus, chronic inflammatory disease, bowel obstruction, duodenal diverticula, biliary calculous disease, and malnutrition. A polynucleotide or polypeptide and/or agonist or antagonist of the present invention are useful for treating, detecting, diagnosing, prognosing, and/or ameliorating, either directly or indirectly, and of the above mentioned diseases and/or disorders associated with aberrant enteric flora population.

The composition of the intestinal flora, for example, is based upon a variety of factors, which include, but are not limited to, the age, race, diet, malnutrition, gastric acidity, bile salt excretion, gut motility, and immune mechanisms. As a result, the polynucleotides and polypeptides, including agonists, antagonists, and fragments thereof, may modulate the ability of a host to form biotic associations by affecting, directly or indirectly, at least one or more of these factors.

Although the predominate intestinal flora comprises anaerobic organisms, an underlying percentage represents aerobes (e.g., *E. coli*). This is significant as such aerobes rapidly become the predominate organisms in intraabdominal infections—effectively becoming opportunistic early in infection pathogenesis. As a result, there is an intrinsic need to control aerobe populations, particularly for immune compromised individuals.

In a preferred embodiment, a polynucleotides and polypeptides, including agonists, antagonists, and fragments thereof, are useful for inhibiting biotic associations with specific enteric symbiont organisms in an effort to control the population of such organisms.

Biotic associations occur not only in the gastrointestinal tract, but also on an in the integument. As opposed to the gastrointestinal flora, the cutaneous flora is comprised almost equally with aerobic and anaerobic organisms. Examples of cutaneous flora are members of the gram-positive cocci (e.g., *S. aureus*, coagulase-negative *staphylococci, micrococcus, M. sedentarius*), gram-positive bacilli (e.g., *Corynebacterium* species, *C. minutissimum, Brevibacterium* species, *Pro-*

*poionibacterium* species, *P. acnes*), gram-negative bacilli (e.g., *Acinebacter* species), and fungi (*Pityrosporum orbiculare*). The relatively low number of flora associated with the integument is based upon the inability of many organisms to adhere to the skin. The organisms referenced above have acquired this unique ability. Therefore, the polynucleotides and polypeptides of the present invention may have uses which include modulating the population of the cutaneous flora, either directly or indirectly.

Aberrations in the cutaneous flora are associated with a number of significant diseases and/or disorders, which include, but are not limited to the following: impetigo, eethyma, blistering distal dactulitis, pustules, folliculitis, cutaneous abscesses, pitted keratolysis, trichomycosis axcillaris, dermatophytosis complex, axillary odor, erthyrasma, cheesy foot odor, acne, tinea versicolor, seborrheic dermititis, and *Pityrosporum* folliculitis, to name a few. A polynucleotide or polypeptide and/or agonist or antagonist of the present invention are useful for treating, detecting, diagnosing, prognosing, and/or ameliorating, either directly or indirectly, and of the above mentioned diseases and/or disorders associated with aberrant cutaneous flora population.

Additional biotic associations, including diseases and disorders associated with the aberrant growth of such associations, are known in the art and are encompassed by the invention. See, for example, "Infectious Disease", Second Edition, Eds., S. L., Gorbach, J. G., Bartlett, and N. R., Blacklow, W.B. Saunders Company, Philadelphia, (1998); which is hereby incorporated herein by reference).

Pheromones

In another embodiment, a polynucleotide or polypeptide and/or agonist or antagonist of the present invention may increase the organisms ability to synthesize, release, and/or respond to a pheromone, either directly or indirectly. Such a pheromone may, for example, alter the organisms behavior and/or metabolism.

A polynucleotide or polypeptide and/or agonist or antagonist of the present invention may modulate the biosynthesis and/or release of pheromones, the organisms ability to respond to pheromones (e.g., behaviorally, and/or metabolically), and/or the organisms ability to detect pheromones, either directly or indirectly. Preferably, any of the pheromones, and/or volatiles released from the organism, or induced, by a polynucleotide or polypeptide and/or agonist or antagonist of the invention have behavioral effects on the organism.

For example, recent studies have shown that administration of picogram quantities of androstadienone, the most prominent androstene present on male human axillary hair and on the male axillary skin, to the female vomeronasal organ resulted in a significant reduction of nervousness, tension and other negative feelings in the female recipients (Grosser-B I, et al., Psychoneuroendocrinology, 25(3): 289-99 (2000)).

Other Activities

The polypeptide of the present invention, as a result of the ability to stimulate vascular endothelial cell growth, may be employed in treatment for stimulating re-vascularization of ischemic tissues due to various disease conditions such as thrombosis, arteriosclerosis, and other cardiovascular conditions. These polypeptide may also be employed to stimulate angiogenesis and limb regeneration, as discussed above.

The polypeptide may also be employed for treating wounds due to injuries, burns, post-operative tissue repair, and ulcers since they are mitogenic to various cells of different origins, such as fibroblast cells and skeletal muscle cells, and therefore, facilitate the repair or replacement of damaged or diseased tissue.

The polypeptide of the present invention may also be employed stimulate neuronal growth and to treat, prevent, and/or diagnose neuronal damage which occurs in certain neuronal disorders or neuro-degenerative conditions such as Alzheimer's disease, Parkinson's disease, and AIDS-related complex. The polypeptide of the invention may have the ability to stimulate chondrocyte growth, therefore, they may be employed to enhance bone and periodontal regeneration and aid in tissue transplants or bone grafts.

The polypeptide of the invention may also be employed to maintain organs before transplantation or for supporting cell culture of primary tissues.

The polypeptide of the present invention may also be employed for inducing tissue of mesodermal origin to differentiate in early embryos.

The polypeptide or polynucleotides and/or agonist or antagonists of the present invention may also increase or decrease the differentiation or proliferation of embryonic stem cells, besides, as discussed above, hematopoietic lineage.

The polypeptide or polynucleotides and/or agonist or antagonists of the present invention may also be used to modulate mammalian characteristics, such as body height, weight, hair color, eye color, skin, percentage of adipose tissue, pigmentation, size, and shape (e.g., cosmetic surgery). Similarly, polypeptides or polynucleotides and/or agonist or antagonists of the present invention may be used to modulate mammalian metabolism affecting catabolism, anabolism, processing, utilization, and storage of energy.

Polypeptide or polynucleotides and/or agonist or antagonists of the present invention may be used to change a mammal's mental state or physical state by influencing biorhythms, caricadic rhythms, depression (including depressive diseases, disorders, and/or conditions), tendency for violence, tolerance for pain, reproductive capabilities (preferably by Activin or Inhibin-like activity), hormonal or endocrine levels, appetite, libido, memory, stress, or other cognitive qualities.

Polypeptide or polynucleotides and/or agonist or antagonists of the present invention may also be used to prepare individuals for extraterrestrial travel, low gravity environments, prolonged exposure to extraterrestrial radiation levels, low oxygen levels, reduction of metabolic activity, exposure to extraterrestrial pathogens, etc. Such a use may be administered either prior to an extraterrestrial event, during an extraterrestrial event, or both. Moreover, such a use may result in a number of beneficial changes in the recipient, such as, for example, any one of the following, non-limiting, effects: an increased level of hematopoietic cells, particularly red blood cells which would aid the recipient in coping with low oxygen levels; an increased level of B-cells, T-cells, antigen presenting cells, and/or macrophages, which would aid the recipient in coping with exposure to extraterrestrial pathogens, for example; a temporary (i.e., reversible) inhibition of hematopoietic cell production which would aid the recipient in coping with exposure to extraterrestrial radiation levels; increase and/or stability of bone mass which would aid the recipient in coping with low gravity environments; and/or decreased metabolism which would effectively facilitate the recipients ability to prolong their extraterrestrial travel by any one of the following, non-limiting means: (i) aid the recipient by decreasing their basal daily energy requirements; (ii) effectively lower the level of oxidative and/or metabolic stress in recipient (i.e., to enable recipient to cope with increased extraterrestrial radiation levels by decreasing the level of internal oxidative/metabolic damage acquired during normal basal energy requirements; and/or (iii) enabling recipient to subsist at a lower metabolic temperature (i.e., cryogenic, and/or sub-cryogenic environment).

Polypeptide or polynucleotides and/or agonist or antagonists of the present invention may also be used to increase the efficacy of a pharmaceutical composition, either directly or indirectly. Such a use may be administered in simultaneous conjunction with said pharmaceutical, or separately through either the same or different route of administration (e.g., intravenous for the polynucleotide or polypeptide of the present invention, and orally for the pharmaceutical, among others described herein.).

Polypeptide or polynucleotides and/or agonist or antagonists of the present invention may also be used as a food additive or preservative, such as to increase or decrease storage capabilities, fat content, lipid, protein, carbohydrate, vitamins, minerals, cofactors or other nutritional components.

Polypeptide or polynucleotides and/or agonist or antagonists of the present invention may also be used to prepare individuals for extraterrestrial travel, low gravity environments, prolonged exposure to extraterrestrial radiation levels, low oxygen levels, reduction of metabolic activity, exposure to extraterrestrial pathogens, etc. Such a use may be administered either prior to an extraterrestrial event, during an extraterrestrial event, or both. Moreover, such a use may result in a number of beneficial changes in the recipient, such as, for example, any one of the following, non-limiting, effects: an increased level of hematopoietic cells, particularly red blood cells which would aid the recipient in coping with low oxygen levels; an increased level of B-cells, T-cells, antigen presenting cells, and/or macrophages, which would aid the recipient in coping with exposure to extraterrestrial pathogens, for example; a temporary (i.e., reversible) inhibition of hematopoietic cell production which would aid the recipient in coping with exposure to extraterrestrial radiation levels; increase and/or stability of bone mass which would aid the recipient in coping with low gravity environments; and/or decreased metabolism which would effectively facilitate the recipients ability to prolong their extraterrestrial travel by any one of the following, non-limiting means: (i) aid the recipient by decreasing their basal daily energy requirements; (ii) effectively lower the level of oxidative and/or metabolic stress in recipient (i.e., to enable recipient to cope with increased extraterrestrial radiation levels by decreasing the level of internal oxidative/metabolic damage acquired during normal basal energy requirements; and/or (iii) enabling recipient to subsist at a lower metabolic temperature (i.e., cryogenic, and/or sub-cryogenic environment).

Polypeptide or polynucleotides and/or agonist or antagonists of the present invention may also be used to increase the efficacy of a pharmaceutical composition, either directly or indirectly. Such a use may be administered in simultaneous conjunction with said pharmaceutical, or separately through either the same or different route of administration (e.g., intravenous for the polynucleotide or polypeptide of the present invention, and orally for the pharmaceutical, among others described herein.).

Also preferred is a method of treatment of an individual in need of an increased level of a protein activity, which method comprises administering to such an individual a pharmaceutical composition comprising an amount of an isolated polypeptide, polynucleotide, or antibody of the claimed invention effective to increase the level of said protein activity in said individual.

Having generally described the invention, the same will be more readily understood by reference to the following examples, which are provided by way of illustration and are not intended as limiting.

REFERENCES

Caterina, M. J., Leffler, A, Malmberg, A. B., Martin, W. J., Trafton, J, Petersen-Zeitz, K. R., Koltzenburg, M, Basbaum, A. I. & Julius, D. Impaired nociception and pain sensation in mice lacking the capsaicin receptor. *Science.* 288, 306-313 (2000).

Caterina, M. J., Rosen, T. A., Tominaga, M., Brake, A. J. & Julius, D. A capsaicin-receptor homologue with a high threshold for noxious heat. *Nature.* 398, 436-41 (1999).

Duncan, L. M., Deeds, J., Hunter, J., Shao, J., Holmgren, L. M., Woolf, E. A., Tepper, R. I. & Shyjan, A. W. Downregulation of the novel gene melastatin correlates with potential for melanoma metastasis. *Cancer Res.* 58, 1115-1520 (1998).

Freichel, M., Suh, S. H., Pfeifer, A., Schweig, U., Trost, C., Weissgerber, P., Biel, M., Philipp, S., Freise, D., Droogmans, G., Hofmann, F., Flockerzi, V. & Nilius, B. Lack of an endothelial store-operated Ca2+ current impairs agonist-dependent vasorelaxation in TRP4−/− mice. *Nat. Cell Biol.* 3, 121-127 (2001).

Harteneck, C., Plant T. D. & Schultz, G. From worm to man: three subfamilies of TRP channels. *Trends Neurosci.* 23, 159-166 (2000).

Inoue, R., Okada, T., Onoue, H., Hara, Y., Shimizu, S., Naitoh, S., Ito, Y. & Mori, Y. The transient receptor potential protein homologue TRP6 is the essential component of vascular alpha(1)-adrenoceptor-activated Ca(2+)-permeable cation channel. *Circ Res.* 88, 325-332 (2001).

Liman, E. R., Corey, D. P. & Dulac, C. TRP2: a candidate transduction channel for mammalian pheromone sensory signaling. *Proc Natl Acad Sci USA.* 96, 5791-5796 (1999).

Missiaen, L., Robberecht, W., van den Bosch, L., Callewaert, G., Parys, J. B., Wuytack, F., Raeymaekers, L., Nilius, B., Eggermont, J. & De Smedt, H. Abnormal intracellular $Ca^{2+}$ homeostasis and disease. *Cell Calcium.* 28, 1-21 (2000).

Nagamine, K., Kudoh, J., Minoshima, S., Kawasaki, K., Asakawa, S., Ito F. & Shimizu, N. Molecular cloning of a novel putative Ca2+ channel protein (TRPC7) highly expressed in brain. *Genomics* 54, 124-131 (1998)

Peng, J. B., Chen, X. Z., Berger, U. V., Vassilev, P. M., Tsukaguchi, H., Brown, E. M. & Hediger, M. A. Molecular cloning and characterization of a channel-like transporter mediating intestinal calcium absorption. *J. Biol. Chem.* 274, 22739-22746 (1999).

Prawitt, D., Enklaar, T., Klemm, G., Gartner, B., Spangenberg, C., Winterpacht, A., Higgins, M., Pelletier, J. & Zabel, B. Identification and characterization of MTR1, a novel gene with homology to melastatin (MLSN1) and the trp family located in the BWS-WT2 critical region on chromosome 11p15.5 and showing allele-specific expression. *Hum Mol Genet.* 9, 203-16 (2000).

Runnels, L. W., Yue, L. & Clapham, D. E. TRP-PLIK, a bifunctional protein kinase and ion channel activities. *Science* 291, 1043-1047 (2001).

Ryazanov, A. G., Ward, M. D., Mendola, C. E., Pavur, K. S., Dorovkov, M. V., Wiedmann, M., Erdjument-Bromage, H., Tempst, P., Parmer, T. G., Prostko, C. R., Germino, F. J. & Hait, W. N. Identification of a new class of protein kinases represented by eukaryotic elongation factor-2 kinase. *Proc. Natl. Acad. Sci. USA* 94, 4884-4889 (1997).

Strotmann, R., Harteneck, C., Nunnenmacher, K., Schultz, G. & Plant, T. D. OTRPC4, a nonselective cation channel that confers sensitivity to extracellular osmolarity. *Nat. Cell Biol.* 2, 695-702 (2000).

Tsavaler, L., Shapero, M. H., Morkowski, S. & Laus R. TRP-P8, a novel prostate-specific gene, is up-regulated in prostate cancer and other malignancies and shares high homology with transient receptor potential calcium channel proteins. *Cancer Res.* 61, 3760-3769 (2001).

Walker, R. G., Willingham, A. T. & Zuker, C. S. A *Drosophila* mechanosensory transduction channel. *Science.* 287, 2229-34 (2000).

Xu, S. Z. & Beech, D. J. TrpC1 is a membrane-spanning subunit of store-operated $Ca^{2+}$ channels in native vascular smooth muscle. *Circ Res.* 88, 84-7 (2001).

Yue, L., Peng, J. B., Hediger, M. A., Clapham, D. E. CaT1 manifests the pore properties of the calcium-release-activated calcium channel. *Nature.* 410, 705-709 (2001).

Zygmunt, P. M., Petersson, J., Andersson, D. A., Chuang, H., Sorgard, M., Di Marzo V., Julius, D. & Hogestatt, E. D. Vanilloid receptors on sensory nerves mediate the vasodilator action of anandamide. *Nature.* 400, 452-457 (1999).

EXAMPLES

Description of the Preferred Embodiments

Example 1

Method Used to Identify the Novel TRP-PLIK2 Polynucleotide of the Present Invention—Bioinformatics Analysis Ion channel sequences (mouse TRP1a, gi|1911245, SEQ ID NO:108; mouse TRP2, gi|4324938, SEQ ID NO:107; mouse TRP4, gi|4200415, SEQ ID NO:106; mouse TRP5, gi|6048344, SEQ ID NO:105; human TRP7, gi|13928756, SEQ ID NO:104; mouse TRP3, gi|6014703, SEQ ID NO:103; mouse TRP6, gi|2979524, SEQ ID NO:102; mouse TRP8, gi|5326854, SEQ ID NO:101; *Drosophila* NOMPC, gi|7328583, SEQ ID NO:100; *C. elegans* Y71A12B.4, gi|11065673, SEQ ID NO:99) in the TRP/NOMPC family were used as probes to search the human genomic sequence database. The search program used was the gapped BLAST program TBLASTN (Altschul et al., 1997). A multiple sequence alignment of TRP/NOMPC family members was generated using the Align program in software VECTOR NTI® 5.5, using the ClustalW algorithm. A Hidden Markov Model (HMM) specific for NOMPC family was constructed using the HMMERBUILD program in the Genewise/Wise2 package from the above multiple sequence alignment (Bateman et al., 2000). This HMM model was then used to search the human genomic sequence database using the software program GENEWISEDB in the Genewise/Wise2 package. Results from the TBLASTN and GENEWISEDB searches were pooled and a potential TRP family member was identified in human BAC AL354795 (GENBANK® Accession No. gi|AL354795). The high scoring hit segments from the genomic sequence hits from BAC AL354795 were extracted and searched back against non-redundant protein and patent sequence databases. The most similar protein sequence for each genomic sequence hit was used as a template to predict putative exons from the BAC AL354795 genomic sequence using the GENEWISEDB program in the Genewise/Wise2 package (FIGS. 10A-B; SEQ ID NO:10 to 24). From this analysis, exons encoding the potential novel ion channel was identified based upon sequence homology. To extend the 5' and 3' sequences of putative novel ion channel molecules, the genomic regions surrounding the matching exons were analyzed using GENSCAN and FGENESH programs to generate de novo exons. Based on this analysis, the partial sequence of a novel human ion channel related gene was identified directly from the genomic sequences provided in FIGS. 10A-B (SEQ ID NO:10 to 24) and is shown in FIGS. 11A-C (SEQ ID NO:97 and 98). The full-length clone was obtained using a combination of N- and C-terminal cloning protocols as described below.

Example 2

Cloning the Novel Transient Receptor Potential Channel Member, TRP-PLIK2

Probe Design

Using the predicted exon genomic sequence from BAC AL354795 (FIGS. 10A-B; SEQ ID NO:10 to 24), an anti-sense 80 bp oligo with biotin on the 5' end was designed with the following sequence;

BAC57.80 bTTCTCAATGACACCCCAAGGAGGGAT (SEQ ID NO:25)

TCCAACTGTCCAGATTTTCTCAAGGA

ATGAGAGGAATGGGATTTCAAGGC

Solution Hybridization and DNA Capture

One microliter of the anti-sense biotinylated oligo containing one hundred and fifty nanograms was added to six microliters (six micrograms) of a mixture of commercially available brain, fetal brain, heart, fetal heart, kidney and fetal kidney cDNA libraries that had been converted into single-stranded covalently closed circular form (generated by the in vivo f1 phage super-infection method) and seven microliters of 100% formamide in a 0.5 ml PCR tube. The mixture was heated in a thermal cycler to 95° C. for 2 min. Fourteen microliters of 2× hybridization buffer (50% formamide, 1.5 M NaCl, 0.04 M $NaPO_4$, pH 7.2, 5 mM EDTA, 0.2% SDS) was added to the heated probe/cDNA library mixture and incubated at 42° C. for 26 hours. Hybrids between the biotinylated oligo and the circular cDNA were isolated by diluting the hybridization mixture to 220 microliters in a solution containing 1 M NaCl, 10 mM Tris-HCl pH 7.5, 1 mM EDTA, pH 8.0 and adding 125 microliters of streptavidin magnetic beads. This solution was incubated at 42° C. for 60 min, and mixed every 5-min to re-suspend the beads. The beads are separated from the solution with a magnet and washed three times in 200 microliters of 0.1×SSPE, 0.1% SDS at 45° C.

The single stranded cDNAs were release from the biotinylated oligo/streptavidin magnetic bead complex by adding 50 microliters of 0.1 N NaOH and incubating at room temperature for 10 min. Six microliters of 3 M sodium acetate was added along with 15 micrograms of glycogen and the solution ethanol precipitated with 120 microliters of 100% ethanol. The precipitated DNA was re-suspended in 12 microliters of TE (10 mM Tris-HCl, pH 8.0), 1 mM EDTA, pH 8.0). The single stranded cDNA was converted into double strands in a thermal cycler by mixing 5 microliters of the captured DNA with 1.5 microliters of 10 micromolar standard T7 primer and 1.5 microliters of 10×PCR buffer.

Sequence of the primer used to the repair single-stranded circular DNA isolated from the primary selection.

T7Sport 5'-TAATACGACTCACTATAGGG-3'   (SEQ ID NO:26)

The mixture was heated to 95° C. for 20 seconds then ramped down to 59° C. At this time 15 microliters of a repair mix, that was preheated to 70° C. was added to the DNA (Repair mix contains 4 microliters of 5 mM dNTPs (1.25 mM each), 1.5 microliters of 10×PCR buffer, 9.25 microliters of water, and 0.25 microliters of Taq polymerase). The solution was ramped back to 73° C. and incubated for 23 min. The repaired DNA was ethanol precipitate and re-suspended in 10 microliters of TE. Two microliters were electroporated per tube of 40 microliters of *E. coli* DH12S cells. Three hundred and thirty three microliters are plated onto one 150-mm plate of LB agar plus 100 micrograms/milliliter of ampicillin. After overnight incubation at 37° C., the colonies from all plates are harvested by scraping into 10 mls of LB+50 micrograms/milliliter of ampicillin and 2 mls of sterile glycerol.

The second round of selection was initiated by making single-strand circular DNA from the primary selected library using the method listed above. The single stranded circular cDNA was assayed for the presence of BAC57/AL 354795 transcripts by PCR using the following primers BAC57.1s GTCCAAGCATGTTGGGGAT   (SEQ ID NO:27)

BAC57.1a TCTTTTCCAATAAGGTCTCTCTGG   (SEQ ID NO:28)

The secondary selection was set up using the method described above. The resulting single-stranded circular DNA that was captured was converted into double strands using the BAC57.1a primer (SEQ ID NO:28).

The resulting double stranded DNA was electroporated into DH10B and the resulting colonies inoculated into 96 deep well blocks. After overnight growth, DNA was prepared and screened for BAC 57/AL 354795 sequences using the BAC57 primer pair (SEQ ID NO:27 and 28). The DNA was cut with Sal I and Not I and the inserts sized by agarose gel electrophoresis. Those cDNA clones that were positive by PCR and mapped back to the original BAC from which the probe was designed, had their inserts sized and two clones were chosen for DNA sequencing. The sequence for one of the clones is presented in FIGS. 11A-C. The sequence was determined to represent a partial sequence.

C-Terminal Cloning

Using the predicted exon genomic sequence from BAC AL354795 described as above, oligonucletides with the following sequences was used to amplify fragments from the human kidney library (Clontech). The reaction mixture in 50 ul containing 5 ul cDNA library, 0.5 mM each primer, 5 mM dNTPs (1.25 mM each), 5 ul of 10×PCR and 0.5 unit of TAQPLUS® Precision polymerase (Stratagene). The reaction was repeated for 30 cycles (94° C. for 45 seconds, 55° C. for 45 seconds, and 72° C. for 4 minutes). The amplified fragments were cloned into the sequencing vector pCR4 Blunt-TOPO (Invitrogen) for sequence analysis.

95-NJF-C   ATGATTATCCTATCTAAGTCCCAGAA (SEQ ID NO:29)
           ATC 95-3-NC    CAAGGAATGAGAGGAATGGGATTT   (SEQ ID NO:30)

-continued

| | | |
|---|---|---|
| 95-3-C | AAATCCCATTCCTCTCATTCCTTG | (SEQ ID NO:31) |
| 95-9-NC | GTAGCCTGAAAGAAGGGTATGCTG | (SEQ ID NO:32) |
| 95-9-C | CAGCATACCCTTCTTTCAGGCTAC | (SEQ ID NO:33) |
| 95-10-NC | GAACATGTGACATCTCAGCTTTGC | (SEQ ID NO:34) |
| 95-10C | GCAAAGCTGAGATGTCACATGTTC | (SEQ ID NO:35) |
| 95-10S-NC | AGGGCAGGATGGCTGGCTTGA | (SEQ ID NO:36) |
| 95-10S-C | TCAAGCCAGCCATCCTGCCCT | (SEQ ID NO:37) |
| 95-12-NC | GCAAGTAGAATGCTTTCTCTTGGC | (SEQ ID NO:38) |
| 95-12-C | GCCAAGAGAAAGCATTCTACTTGC | (SEQ ID NO:39) |
| 95-13-NC | AGGGGAGCTCATTGTCATGGG | (SEQ ID NO:40) |
| 95-13-C | CCCATGACAATGAGCTCCCCTC | (SEQ ID NO:41) |
| 95-14-NC | CCAACCTGTAGACAGTTATTTCTTCT CC | (SEQ ID NO:42) |
| 95-14-C | GGAGAAGAAATAACTGTCTACAGGTT GG | (SEQ ID NO:43) |
| 95-15-NC | TTATAGTTGCATATCATCTTCTGGGG A | (SEQ ID NO:44) |

The resulting full-length encoding polynucleotide sequence for TRP-PLIK2 is shown in FIGS. 1A-G (SEQ ID NO:1).

Additional clones corresponding to the TRP-PLIK2 splice variants of the present invention were isolated according to the above methods. The full-length polynucleotide sequence of each of the TRP-PLIK2 splice variants are provided in FIGS. 2A-G (SEQ ID NO:4), FIGS. 3A-G (SEQ ID NO:6), and FIGS. 4A-G (SEQ ID NO:8) for TRP-PLIK2b, TRP-PLIK2c, and TRP-PLIK2d, respectively.

Example 3

Expression Profiling of Novel Human Immunoglobulin Protein, TRP-PLIK2

RT-PCR

A PCR primer pair was designed to measure the steady state levels of the TRP-PLIK2 mRNA by quantitative RT-PCR.

BAC57.1s GTCCAAGCATGTTGGGGAT   (SEQ ID NO:27)

BAC57.1a TCTTTTCCAATAAGGTCTCTCTGG   (SEQ ID NO:28)

Briefly, first strand cDNA was made from commercially available mRNA. The relative amount of cDNA used in each assay was determined by performing a parallel experiment using a primer pair for a gene expressed in equal amounts in all tissues, cyclophilin. The cyclophilin primer pair detected small variations in the amount of cDNA in each sample and these data were used for normalization of the data obtained with the primer pair for the TRP-PLIK2 transcript. The PCR data was converted into a relative assessment of the difference in transcript abundance amongst the tissues tested and the data is presented in FIG. 7. Transcripts corresponding to the TRP-PLIK2 transcript were found to be highly expressed in the bone marrow, kidney and testis; significantly in liver, and to a lesser extent in small intestine, spinal cord, prostate, uterus, lung, lymph node, stomach, heart, brain, thymus, and pancreas.

Northern Blot Analysis

Human tissue Northern blots (Clontech) were probed with an RNA probe derived from a 507-bp fragment of TRP-PLIK2 (SEQ ID NO:1) amplified from the primer pair 95-3-C and 95-5-NC. Hybridization of the blot was performed at 68° C. in ExpressHyb (Clontech) for 6 hours, with $1 \times 10^6$ cpm/ml of $P^{32}$ labeled probe. Autoradiography was performed for 1 week at −70° C.

The results of the Northern hybridization are shown in FIG. 8. As shown, Transcripts corresponding to the TRP-PLIK2 transcript were found to be highly expressed in kidney, and to a lesser extent in brain and skeletal muscle.

Example 4

Method of Assessing the Expression Profile of the Novel TRP-PLIK2 Polypeptides of the Present Invention Using Expanded mRNA Tissue and Cell Sources Total RNA from tissues was isolated using the TRIZOL® protocol (Invitrogen) and quantified by determining its absorbance at 260 nM. An assessment of the 18s and 28s ribosomal RNA bands was made by denaturing gel electrophoresis to determine RNA integrity.

The specific sequence to be measured was aligned with related genes found in GENBANK® to identity regions of significant sequence divergence to maximize primer and probe specificity. Gene-specific primers and probes were designed using the ABI primer express software to amplify small amplicons (150 base pairs or less) to maximize the likelihood that the primers function at 100% efficiency. All primer/probe sequences were searched against Public GEN-BANK® databases to ensure target specificity. Primers and probes were obtained from ABI.

For TRP-PLIK2, the primer probe sequences were as follows

```
Forward Primer
5'-AGAAAATACACTGCCGCTCAAGA-3'    (SEQ ID NO:267)

Reverse Primer
5'-GTTGGGACCGCCTTCCA-3'           (SEQ ID NO:268)

TAQMAN ® Probe
5'-CCCACGACCGGCACGCCTT-3'         (SEQ ID NO:269)
```

DNA Contamination

To access the level of contaminating genomic DNA in the RNA, the RNA was divided into 2 aliquots and one half was treated with Rnase-free Dnase (Invitrogen). Samples from both the Dnase-treated and non-treated were then subjected to reverse transcription reactions with (RT+) and without (RT−) the presence of reverse transcriptase. TAQMAN® assays were carried out with gene-specific primers (see above) and the contribution of genomic DNA to the signal detected was evaluated by comparing the threshold cycles obtained with the RT+/RT− non-Dnase treated RNA to that on the RT+/RT− Dnase treated RNA. The amount of signal contributed by genomic DNA in the Dnased RT− RNA must be less that 10% of that obtained with Dnased RT+ RNA. If not the RNA was not used in actual experiments.

Reverse Transcription Reaction and Sequence Detection 100 ng of Dnase-treated total RNA was annealed to 2.5 µM of the respective gene-specific reverse primer in the presence of 5.5 mM Magnesium Chloride by heating the sample to 72° C. for 2 min and then cooling to 55° C. for 30 min. 1.25 U/µl of MuLv reverse transcriptase and 500 µM of each dNTP was added to the reaction and the tube was incubated at 37° C. for 30 min. The sample was then heated to 90° C. for 5 min to denature enzyme.

Quantitative sequence detection was carried out on an ABI PRISM® 7700 by adding to the reverse transcribed reaction 2.5 µM forward and reverse primers, 500 µM of each dNTP, buffer and 5U AMPLITAQ GOLD®. The PCR reaction was then held at 94° C. for 12 min, followed by 40 cycles of 94° C. for 15 sec and 60° C. for 30 sec.

Data Handling

The threshold cycle (Ct) of the lowest expressing tissue (the highest Ct value) was used as the baseline of expression and all other tissues were expressed as the relative abundance to that tissue by calculating the difference in Ct value between the baseline and the other tissues and using it as the exponent in $2^{(\Delta Ct)}$ The expanded expression profile of the TRP-PLIK2 polypeptide, is provided in FIG. 5 and are described elsewhere herein.

Example 5

Method of Assessing the Putative Kinase Activity of the TRP-PLIK2 Polypeptide

A number of methods may be employed to assess the potential kinase activity of the TRP-PLIK2 polypeptides. One preferred method is described below. A fusion construct is made whereby the TRP-PLIK2 encoding polynucleotide is operably linked to the coding region of the HA protein. CHO-K1 or HEK-293 cells grown on 100-mm dishes are transiently transfected with 8 µg of novel TRP-PLIK2-HA cDNA construct in the pTracer-CMV2 (Invitrogen) vector with LipofectAMINE 2000 (Gibco). Cells are harvested after 48 hours with 3 ml of RIPA buffer [50 mM Tris (pH 7.4), 150 mM NaCl, 1 mM EDTA, 1% IGEPAL CA-630, 0.5% (w/v) deoxycholate, 0.1% (w/v) SDS, and 10 mM iodoacetamide]. TRP-PLIK2-HA is immunoprecipitated with mouse monoclonal immunoglobulin G2a (IgG2a) HA probe (F-7) coupled to agarose (Santa Cruz Biotechnology). The agarose is sedimented and washed three times with RIPA buffer, and 2×SDS sample buffer is added. The samples may be resolved by SDS-PAGE and Western blotting following standard methods. HA probe Y-11 antibody could be the primary antibody (Santa Cruz Biotechnology), and horseradish peroxidase-linked antibody to rabbit Ig (Amersham Pharmacia Biotech) could be the secondary antibody. The SUPERSIGNAL® West Dura substrate may be used for chemiluminescent detection (Pierce)

For phosphorylation experiment, purified GST-kinase fusion proteins and mutants are incubated at 37° C. for 30 min in the presence or absence of MBP as a test substrate in a 50-µl reaction. These reactions are performed in KIN buffer {50 mM Mops (pH 7.2), 100 mM NaCl, 20 mM MgCl2, 0.5 mM ATP, and 2 µCi of [−32P]ATP}. Immunokinase reactions containing immunopurified TRP-PLIK2-HA are incubated at 37° C. for 30 min in a 50-µl reaction containing KIN buffer with 75 mM n-octyl-D-glucopyranoside. The reactions are terminated by the addition of 2×SDS sample buffer, and the proteins were resolved by SDS-PAGE and Coomassie staining for the GST-kinase experiment or by SDS-PAGE and Western blotting for the immunokinase assay. The gels are dried, and 32P incorporation is visualized by autoradiography for the GST-kinase experiment. For the immunokinase experiment, 32P incorporation may be visualized by autoradiography of the transferred proteins on polyvinylidene difluoride membrane (Bio-Rad) before Western blotting.

In the case of the TRP-PLIK2 polypeptide of the present invention, the kinase activity was demonstrated as described below. Briefly:

Bacterial Expression and Protein Purification

The TRP-PLIK2 kinase domain (amino acids 1428 to 2018 of SEQ ID NO:2) was subcloned into the bacterial expression vector pGEX-6p-2 (Amersham) to generate a TRP-PLIK2-GST fusion protein. The primers used were as follows:

```
                                       (SEQ ID NO:270)
95-20-BamHI-C  CGGGATCCACGATGGGAGTTGACAAGATCTCAGCCT
               CC (SEQ ID NO:271)
95-15HA-Not-NC ATAGTTAGCGGCCGCTTAAGCGTAATCTGGAACATC
               GTATGGGTATAGTTGCATATCATCTTCTGGG
```

The resulting TRP-PLIK2-GST fusion protein construct was transformed into *E. Coli* B121-CodonPlus-RIL (Stratagene) and single colonies were picked and grown overnight. The overnight culture was diluted 1:50 and induced with 1 mM IPTG as the O.D. reached 0.7-1. The culture was harvested after 3.5 hr and stored frozen.

The bacteria pellets were solubilized in urea buffer (20 mM Tris pH 7, 150 mM NaCl, 8M urea, 7 mM β-mercaptoethanol) for 1.5 hr and centrifuged at 10000×g for 30 min. The supernatant was dialyzed against renaturing buffer (10% glycerol, 20 mM Tris pH 7, 100 mM NaCl, 2.5 mM DTT, 0.1% Triton X-100, and protease inhibitor cocktail). The solubilized lysates were than purified using Glutathione Sepharose 4B beads (Amersham). The purified TRP-PLIK2 kinase domain was then cleaved from the GST fusion protein using proteolytic cleavage and the purified TRP-PLIK2 kinase domain was subjected to further analysis.

Kinase Assay

For phosphorylation experiments, the purified TRP-PLIK2-GST fusion protein was incubated at 30° C. for 30 min in the presence or absence of MBP or Histon as a test substrate in a 50-µl reaction. These reactions were performed in KIN buffer {50 mM Mops (pH 7.2), 100 mM NaCl, 20 mM MgCl2, 0.5 mM ATP, and 2 µCi of [γ32P]ATP}. The reactions were terminated by the addition of 2×SDS sample buffer, and the proteins were resolved by SDS-PAGE and Coomassie staining for the GST-kinase experiment or by SDS-PAGE. The gels were dried, and 32P incorporation was visualized by autoradiography for the GST-kinase experiment.

The results show that the TRP-PLIK2 kinase domain does contain kinase activity as predicted (see FIG. 13). Moreover, the TRP-PLIK2 kinase domain can be autophosphorylated and phosphorylate substrate polypeptides. MBP was determined to be a preferred substrate over Histon. These results are consistent with the TRP-PLIK2 polypeptide representing a novel transient potential receptor protein.

Example 6

Complementary Polynucleotides

Antisense molecules or nucleic acid sequences complementary to the TRP-PLIK2 protein-encoding sequence, or any part thereof, was used to decrease or to inhibit the expression of naturally occurring TRP-PLIK2. Although the use of antisense or complementary oligonucleotides comprising about 15 to 35 base-pairs is described, essentially the same procedure is used with smaller or larger nucleic acid sequence fragments. An oligonucleotide based on the coding sequence of TRP-PLIK2 protein, as shown in FIGS. 1A-G, or as depicted in SEQ ID NO:1, for example, is used to inhibit expression of naturally occurring TRP-PLIK2. The complementary oligonucleotide is typically designed from the most unique 5' sequence and is used either to inhibit transcription by preventing promoter binding to the coding sequence, or to inhibit translation by preventing the ribosome from binding to the TRP-PLIK2 protein-encoding transcript, among others. However, other regions may also be targeted.

Using an appropriate portion of a 5' sequence of SEQ ID NO:1, an effective antisense oligonucleotide includes any of about 15-35 nucleotides spanning the region which translates into the signal or 5' coding sequence, among other regions, of the polypeptide as shown in FIGS. 1A-G (SEQ ID NO:2). Appropriate oligonucleotides were designed using OLIGO 4.06 software and the TRP-PLIK2 protein coding sequence (SEQ ID NO:1). The preferred oligonucleotide is deoxynucleotide, or chimeric deoxynucleotide/ribonucleotide based and is provided below. The oligonucleotide was synthesized using chemistry essentially as described in U.S. Pat. No. 5,849,902; which is hereby incorporated herein by reference in its entirety.

| ID # | Sequence | |
|------|----------|---|
| 16520 | CCUUGACAGUCUCCCACACUGACAG | (SEQ ID NO:310) |

The TRP-PLIK2 polypeptide has been shown to be involved in the regulation of mammalian NF-KB and apoptosis pathways. Subjecting cells with an effective amount of the above antisense oligonucleotide resulted in a significant increase in IkBa expression/activity providing convincing evidence that TRP-PLIK2 at least regulates the activity and/or expression of IkBa either directly, or indirectly. Moreover, the results suggest that TRP-PLIK2 is involved in the negative regulation of NF-κB/IkBa activity and/or expression, either directly or indirectly. The IkBa assay used is described below and was based upon the analysis of IkBa activity as a downstream marker for proliferative signal transduction events.

Transfection of Post-Quiescent A549 Cells with AntiSense Oligonucleotides.

Materials needed:
A549 cells maintained in DMEM with high glucose (Gibco-BRL) supplemented with 10% Fetal Bovine Serum, 2 mM L-Glutamine, and 1× penicillin/streptomycin.
Opti-MEM (Gibco-BRL)
Lipofectamine 2000 (Invitrogen)
Antisense oligomers (Sequitur)
Polystyrene tubes.
Tissue culture treated plates.

Quiescent cells were prepared as follows:

Day 0: 300,000 A549 cells were seeded in a T75 tissue culture flask in 10 ml of A549 media, and incubated in at 37° C., 5% $CO_2$ in a humidified incubator for 48 hours.

Day 2: The T75 flasks were rocked to remove any loosely adherent cells, and the A549 growth media removed and replenished with 10 ml of fresh A549 media. The cells were cultured for six days without changing the media to create a quiescent cell population.

Day 8: Quiescent cells were plated in multi-well format and transfected with antisense oligonucleotides.

A549 cells were transfected according to the following:
1. Trypsinize T75 flask containing quiescent population of A549 cells.
2. Count the cells and seed 24-well plates with 60K quiescent A549 cells per well.
3. Allow the cells to adhere to the tissue culture plate (approximately 4 hours).
4. Transfect the cells with antisense and control oligonucleotides according to the following:
   a. A 10× stock of lipofectamine 2000 (10 ug/ml is 10×) was prepared, and diluted lipid was allowed to stand at RT for 15 minutes.
      Stock solution of lipofectamine 2000 was 1 mg/ml.
      10× solution for transfection was 10 ug/ml.
      To prepare 10× solution, dilute 10 ul of lipofectamine 2000 stock per 1 ml of Opti-MEM (serum free media).
   b. A 10× stock of each oligomer was prepared to be used in the transfection.
      Stock solutions of oligomers were at 100 uM in 20 mM HEPES, pH 7.5.
      10× concentration of oligomer was 0.25 uM.
      To prepare the 10× solutions, dilute 2.5 ul of oligomer per 1 ml of Opti-MEM.
   c. Equal volumes of the 10× lipofectamine 2000 stock and the 10× oligomer solutions were mixed well, and incubated for 15 minutes at RT to allow complexation of the oligomer and lipid. The resulting mixture was 5×.
   d. After the 15 minute complexation, 4 volumes of full growth media was added to the oligomer/lipid complexes (solution was 1×).
   e. The media was aspirated from the cells, and 0.5 ml of the 1× oligomer/lipid complexes added to each well.
   f. The cells were incubated for 16-24 hours at 37° C. in a humidified $CO_2$ incubator.
   g. Cell pellets were harvested for RNA isolation and TAQMAN® analysis of downstream marker genes.

TAQMAN® Reactions

Quantitative RT-PCR analysis was performed on total RNA preps that had been treated with DNaseI or poly A selected RNA. The Dnase treatment may be performed using methods known in the art, though preferably using a Qiagen RNEASY® kit to purify the RNA samples, wherein DNAse I treatment is performed on the column.

Briefly, a master mix of reagents was prepared according to the following table:

| Dnase I Treatment | |
| --- | --- |
| Reagent | Per r'xn (in uL) |
| 10× Buffer | 2.5 |
| Dnase I (1 unit/ul @ 1 unit per ug sample) | 2 |
| DEPC $H_2O$ | 0.5 |
| RNA sample @ 0.1 ug/ul (2-3 ug total) | 20 |
| Total | 25 |

Next, 5 ul of master mix was aliquoted per well of a 96-well PCR reaction plate (PE part # N801-0560). RNA samples were adjusted to 0.1 ug/ul with DEPC treated $H_2O$ (if necessary), and 20 ul was added to the aliquoted master mix for a final reaction volume of 25 ul.

The wells were capped using strip well caps (PE part # N801-0935), placed in a plate, and briefly spun in a centrifuge to collect all volume in the bottom of the tubes. Generally, a short spin up to 500 rpm in a SORVALL® RT is sufficient The plates were incubated at 37° C. for 30 mins. Then, an equal volume of 0.1 mM EDTA in 10 mM Tris was added to each well, and heat inactivated at 70° C. for 5 min. The plates were stored at −80° C. upon completion.

RT Reaction

A master mix of reagents was prepared according to the following table:

| | RT reaction | |
| --- | --- | --- |
| Reagent | RT Per Rx'n (in ul) | No RT Per Rx'n (in ul) |
| 10× RT buffer | 5 | 2.5 |
| $MgCl_2$ | 11 | 5.5 |
| DNTP mixture | 10 | 5 |
| Random Hexamers | 2.5 | 1.25 |
| Rnase inhibitors | 1.25 | 0.625 |
| RT enzyme | 1.25 | — |
| Total RNA 500 ng (100 ng no RT) | 19.0 max | 10.125 max |
| DEPC $H_2O$ | — | — |
| Total | 50 uL | 25 uL |

Samples were adjusted to a concentration so that 500 ng of RNA was added to each RT rx'n (10 ng for the no RT). A maximum of 19 ul can be added to the RT rx'n mixture (10.125 ul for the no RT.) Any remaining volume up to the maximum values was filled with DEPC treated $H_2O$, so that the total reaction volume was 50 ul (RT) or 25 ul (no RT).

On a 96-well PCR reaction plate (PE part # N801-0560), 37.5 ul of master mix was aliquoted (22.5 ul of no RT master mix), and the RNA sample added for a total reaction volume of 50 ul (25 ul, no RT). Control samples were loaded into two or even three different wells in order to have enough template for generation of a standard curve.

The wells were capped using strip well caps (PE part # N801-0935), placed in a plate, and spin briefly in a centrifuge to collect all volume in the bottom of the tubes. Generally, a short spin up to 500 rpm in a SORVALL® RT is sufficient.

For the RT-PCR reaction, the following thermal profile was used:
25° C. for 10 min
48° C. for 30 min
95° C. for 5 min
4° C. hold (for 1 hour)
Store plate @−20° C. or lower upon completion.

TAQMAN® Reaction (Template Comes from RT Plate.)

A master mix was prepared according to the following table:

| TAQMAN ® reaction (per well) | |
| --- | --- |
| Reagent | Per Rx'n (in ul) |
| TaqMan Master Mix | 4.17 |
| 100 uM Probe (SEQ ID NO: 309) | .025 |
| 100 uM Forward primer (SEQ ID NO: 307) | .05 |

-continued

| TAQMAN ® reaction (per well) | |
| --- | --- |
| Reagent | Per Rx'n (in ul) |
| 100 uM Reverse primer (SEQ ID NO: 308) | .05 |
| Template | — |
| DEPC H$_2$O | 18.21 |
| Total | 22.5 |

The primers used for the RT-PCR reaction is as follows:

IkBa primer and probes:

```
Forward Primer:
GAGGATGAGGAGAGCTATGACACA        (SEQ ID NO:307)

Reverse Primer:
CCCTTTGCACTCATAACGTCAG          (SEQ ID NO:308)

TAQMAN ® Probe:
AAACACACAGTCATCATAGGGCAGCTCGT   (SEQ ID NO:309)
```

Using a GILSON® P-10 repeat pipetter, 22.5 ul of master mix was aliquoted per well of a 96-well optical plate. Then, using P-10 pipetter, 2.5 ul of sample was added to individual wells. Generally, RT samples are run in triplicate with each primer/probe set used, and no RT samples are run once and only with one primer/probe set, often gapdh (or other internal control).

A standard curve is then constructed and loaded onto the plate. The curve has five points plus one no template control (NTC, =DEPC treated H$_2$O). The curve was made with a high point of 50 ng of sample (twice the amount of RNA in unknowns), and successive samples of 25, 10, 5, and 1 ng. The curve was made from a control sample(s) (see above).

The wells were capped using optical strip well caps (PE part # N801-0935), placed in a plate, and spun in a centrifuge to collect all volume in the bottom of the tubes. Generally, a short spin up to 500 rpm in a SORVALL® RT is sufficient.

Plates were loaded onto a PE 5700 sequence detector making sure the plate is aligned properly with the notch in the upper right hand corner. The lid was tightened down and run using the 5700 and 5700 quantitation program and the SYBR® probe using the following thermal profile:

50° C. for 2 min
95° C. for 10 min
and the following for 40 cycles:
  95° C. for 15 sec
  60° C. for 1 min
Change the reaction volume to 25 ul.

Once the reaction was complete, a manual threshold of around 0.1 was set to minimize the background signal. Additional information relative to operation of the GENEAMP® 5700 machine may be found in reference to the following manuals: "GENEAMP® 5700 Sequence Detection System Operator Training CD"; and the "User's Manual for 5700 Sequence Detection System"; available from Perkin-Elmer and hereby incorporated by reference herein in their entirety.

Example 7

Method of Assessing the Putative Ion Channel Activity of the TRP-PLIK2 Polypeptide A number of methods may be employed to assess the potential ion channel activity of the TRP-PLIK2 polypeptides. One preferred method is described below CHO-K1 cells transfected with a suitable mammalian expression vector comprising the TRP-PLIK2 encoding polynucleotide sequence is prepared using methods known in the art. The transfected cells are transferred to cover slips 12 hours after transfection, and electrophysiological measurements are made 24 hours after transfection (22±2° C.). The TRP-PLIK2-expressing CHO-K1 cells are detected by GFP fluorescence. Membrane currents are digitized at 10 or 20 kHz and digitally filtered off line at 1 kHz. Voltage stimuli lasting 500 ms are delivered at 5-s intervals, with either voltage ramps or voltage steps from 100 to +100 mV. The internal pipette solution for macroscopic and single-channel currents may contain 145 mM Cs-methanesulfonate, 8 mM NaCl, 5 mM ATP, 1 mM MgCl2, 10 mM EGTA, 4.1 mM CaCl2, and 10 mM Hepes, with pH adjusted to 7.2 with CsOH after addition of ATP. The standard extracellular solution may contain 140 mM NaCl, 5 mM CsCl, 2.8 mM KCl, 2 mM CaCl2, 1 mM MgCl2, 10 mM Hepes, and 10 mM glucose, with pH adjusted to 7.4 with NaOH. Relative ion permeabilities may be measured with the pipette solution containing 145 mM Cs-methanesulfonate, 10 mM CsCl, 5 mM ATP, 10 mM EGTA, and 10 mM Hepes (pH 7.2) and the external solution containing 110 mM NMDG+, 30 mM X+ (Na+, Ca2+, K+, or Cs+), 10 mM Hepes, and 10 mM glucose (pH 7.4). The relative permeability for monovalent ions may be calculated according to the equation PX/PCs=([Cs+]o/[X+]o)exp[F(EX ECs)/RT]. The PCa/PCs permeability ratio is calculated according to the equation PCa/PCs={[Cs+]o exp(FECs/RT) exp(FECa/RT)[exp(FECa/RT)+1]})/(4[Ca2+]o), where R, T, and F are the gas constant, absolute temperature, and Faraday's constant, respectively. Statistical comparisons are made with the two-way analysis of ariance (ANOVA) and two-tailed t test with Bonferroni correction; P<0.05 indicated statistical significance.

Example 8

Method of Assessing Ability of TRP-PLIK2 Polypeptides to Associate with Other Proteins Using the Yeast Two-Hybrid System In an effort to determine whether the TRP-PLIK2 polypeptides of the present invention are capable of functioning as an ion channel or kinase protein, it would be important to effectively test the interaction between TRP-PLIK2 and various portions of other proteins, particularly known ion channel proteins, for example, in a yeast two-hybrid system. Such a system could be created using methods known in the art (see, for example, S. Fields and O, Song, Nature, 340:245-246 (1989); and Gaston-S M and Loughlin-K R, Urology, 53(4): 835-42 (1999); which are hereby incorporated herein by reference in their entirety, including the articles referenced therein).

Cytoplasmic NH and COOH terminal domains of different proteins, preferably ion channel proteins (such as those referenced herein), could be subcloned and expressed as fusion proteins of the GAL4 DNA binding (DB) domain using molecular biology techniques within the skill of the artisan.

Exemplary subunits which could be used in the two-hybrid system to assess TRP-PLIK2s ability to associate with other ion channel proteins include, but are not limited to, the NH and/or C-terminal domain TRP1, TRP2, TRP3, TRP4, TRP5, TRP6, TRP7, signalling proteins, etc.

Example 9

Method of Assessing Ability of TRP-PLIK2 Polypeptides to Form Oligomeric Complexes With Itself or Other Ion Channel Proteins in Solution Aside from determining whether the TRP-PLIK2 polypeptides are capable of interacting with other proteins, preferably ion channel proteins, in a yeast two-hybrid assay, it would be an important next step to assess its ability to form oligomeric complexes with itself, in addition to other proteins, preferably ion channel proteins, in solution. Such a finding would be significant as it would provide convincing evidence that TRP-PLIK2 could serve as an ion channel protein.

A number of methods could be used to that are known in the art, for example, the method described by Sanguinetti, M. C., et al., Nature, 384:80-83 (1996) could be adapted using methods within the skill of the artisan.

Example 10

Method of Identifying the Cognate Ligand of the TRP-PLIK2 Polypeptide

A number of methods are known in the art for identifying the cognate binding partner of a particular polypeptide. For example, the encoding TRP-PLIK2 polynucleotide could be engineered to comprise an epitope tag. The epitope could be any epitope known in the art or disclosed elsewhere herein. Once created, the epitope tagged TRP-PLIK2 encoding polynucleotide could be cloned into an expression vector and used to transfect a variety of cell lines representing different tissue origins (e.g., brain, testis, kidney, testis, liver, etc.). The transfected cell lines could then be induced to overexpress the TRP-PLIK2 polypeptide. The presence of the TRP-PLIK2 polypeptide on the cell surface could be determined by fractionating whole cell lysates into cellular and membrane protein fractions and performing immunoprecipitation using the antibody directed against the epitope engineered into the TRP-PLIK2 polypeptide. Monoclonal or polyclonal antibodies directed against the TRP-PLIK2 polypeptide could be created and used in place of the antibodies directed against the epitope.

Alternatively, the cell surface proteins could be distinguished from cellular proteins by biotinylating the surface proteins and then performing immunoprecipitations with antibody specific to the TRP-PLIK2 protein. After electrophoretic separation, the biotinylated protein could be detected with streptavidin-HRP (using standard methods known to those skilled in the art). Identification of the proteins bound to TRP-PLIK2 could be made in those cells by immunoprecipation, followed by one-dimensional electrophoresis, followed by various versions of mass spectrometry. Such massspectrometry methods are known in the art, such as for example the methods taught by Ciphergen Biosystems Inc. (see U.S. Pat. No. 5,792,664; which is hereby incorporated herein by reference).

Example 11

Isolation of a Specific Clone from the Deposited Sample

The deposited material in the sample assigned the ATCC® Deposit Number cited in Table 1 for any given cDNA clone also may contain one or more additional plasmids, each comprising a cDNA clone different from that given clone. Thus, deposits sharing the same ATCC® Deposit Number contain at least a plasmid for each cDNA clone identified in Table 1. Typically, each ATCC® deposit sample cited in Table 1 comprises a mixture of approximately equal amounts (by weight) of about 1-10 plasmid DNAs, each containing a different cDNA clone and/or partial cDNA clone; but such a deposit sample may include plasmids for more or less than 2 cDNA clones.

Two approaches can be used to isolate a particular clone from the deposited sample of plasmid DNA(s) cited for that clone in Table 1. First, a plasmid is directly isolated by screening the clones using a polynucleotide probe corresponding to SEQ ID NO:1, 3, 5, 7, and/or 97.

Particularly, a specific polynucleotide with 30-40 nucleotides is synthesized using an Applied Biosystems DNA synthesizer according to the sequence reported. The oligonucleotide is labeled, for instance, with 32P-(-ATP using T4 polynucleotide kinase and purified according to routine methods. (E.g., Maniatis et al., Molecular Cloning: A Laboratory Manual, Cold Spring Harbor Press, Cold Spring, N.Y. (1982).) The plasmid mixture is transformed into a suitable host, as indicated above (such as XL-1 Blue (Stratagene)) using techniques known to those of skill in the art, such as those provided by the vector supplier or in related publications or patents cited above. The transformants are plated on 1.5% agar plates (containing the appropriate selection agent, e.g., ampicillin) to a density of about 150 transformants (colonies) per plate. These plates are screened using Nylon membranes according to routine methods for bacterial colony screening (e.g., Sambrook et al., Molecular Cloning: A Laboratory Manual, 2nd Edit., (1989), Cold Spring Harbor Laboratory Press, pages 1.93 to 1.104), or other techniques known to those of skill in the art.

Alternatively, two primers of 17-20 nucleotides derived from both ends of the SEQ ID NO:1, 3, 5, 7, and/or 97 (i.e., within the region of SEQ ID NO:1, 3, 5, 7, and/or 97 bounded by the 5' NT and the 3' NT of the clone defined in Table 1) are synthesized and used to amplify the desired cDNA using the deposited cDNA plasmid as a template. The polymerase chain reaction is carried out under routine conditions, for instance, in 25 ul of reaction mixture with 0.5 ug of the above cDNA template. A convenient reaction mixture is 1.5-5 mM MgC12, 0.01% (w/v) gelatin, 20 uM each of dATP, dCTP, dGTP, dTTP, 25 pmol of each primer and 0.25 Unit of Taq polymerase. Thirty five cycles of PCR (denaturation at 94 degree C. for 1 min; annealing at 55 degree C. for 1 min; elongation at 72 degree C. for 1 min) are performed with a Perkin-Elmer Cetus automated thermal cycler. The amplified product is analyzed by agarose gel electrophoresis and the DNA band with expected molecular weight is excised and purified. The PCR product is verified to be the selected sequence by subcloning and sequencing the DNA product.

The polynucleotide(s) of the present invention, the polynucleotide encoding the polypeptide of the present invention, or the polypeptide encoded by the deposited clone may represent partial, or incomplete versions of the complete coding region (i.e., full-length gene). Several methods are known in the art for the identification of the 5' or 3' non-coding and/or coding portions of a gene which may not be present in the deposited clone. The methods that follow are exemplary and should not be construed as limiting the scope of the invention. These methods include but are not limited to, filter probing, clone enrichment using specific probes, and protocols similar or identical to 5' and 3' "RACE" protocols that are well known in the art. For instance, a method similar to 5' RACE is available for generating the missing 5' end of a desired full-length transcript. (Fromont-Racine et al., Nucleic Acids Res. 21(7):1683-1684 (1993)).

Briefly, a specific RNA oligonucleotide is ligated to the 5' ends of a population of RNA presumably containing full-length gene RNA transcripts. A primer set containing a primer specific to the ligated RNA oligonucleotide and a primer specific to a known sequence of the gene of interest is used to PCR amplify the 5' portion of the desired full-length gene. This amplified product may then be sequenced and used to generate the full-length gene.

This above method starts with total RNA isolated from the desired source, although poly-A+ RNA can be used. The RNA preparation can then be treated with phosphatase if necessary to eliminate 5' phosphate groups on degraded or damaged RNA that may interfere with the later RNA ligase step. The phosphatase should then be inactivated and the RNA treated with tobacco acid pyrophosphatase in order to remove the cap structure present at the 5' ends of messenger RNAs. This reaction leaves a 5' phosphate group at the 5' end of the cap cleaved RNA which can then be ligated to an RNA oligonucleotide using T4 RNA ligase.

This modified RNA preparation is used as a template for first strand cDNA synthesis using a gene specific oligonucleotide. The first strand synthesis reaction is used as a template for PCR amplification of the desired 5' end using a primer specific to the ligated RNA oligonucleotide and a primer specific to the known sequence of the gene of interest. The resultant product is then sequenced and analyzed to confirm that the 5' end sequence belongs to the desired gene. Moreover, it may be advantageous to optimize the RACE protocol to increase the probability of isolating additional 5' or 3' coding or non-coding sequences. Various methods of optimizing a RACE protocol are known in the art, though a detailed description summarizing these methods can be found in B. C. Schaefer, Anal. Biochem., 227:255-273, (1995).

An alternative method for carrying out 5' or 3' RACE for the identification of coding or non-coding sequences is provided by Frohman, M. A., et al., Proc. Nat'l. Acad. Sci. USA, 85:8998-9002 (1988). Briefly, a cDNA clone missing either the 5' or 3' end can be reconstructed to include the absent base pairs extending to the translational start or stop codon, respectively. In some cases, cDNAs are missing the start of translation, therefor. The following briefly describes a modification of this original 5' RACE procedure. Poly A+ or total RNAs reverse transcribed with SUPERSCRIPT® II (Gibco/BRL) and an antisense or I complementary primer specific to the cDNA sequence. The primer is removed from the reaction with a MICROCON® Concentrator (Amicon). The first-strand cDNA is then tailed with dATP and terminal deoxynucleotide transferase (Gibco/BRL). Thus, an anchor sequence is produced which is needed for PCR amplification. The second strand is synthesized from the dA-tail in PCR buffer, Taq DNA polymerase (Perkin-Elmer Cetus), an oligo-dT primer containing three adjacent restriction sites (XhoIJ SalI and ClaI) at the 5' end and a primer containing just these restriction sites. This double-stranded cDNA is PCR amplified for 40 cycles with the same primers as well as a nested cDNA-specific antisense primer. The PCR products are size-separated on an ethidium bromide-agarose gel and the region of gel containing cDNA products the predicted size of missing protein-coding DNA is removed. cDNA is purified from the agarose with the Magic PCR Prep kit (Promega), restriction digested with XhoI or SalI, and ligated to a plasmid such as PBLUESCRIPT® SKII (Stratagene) at XhoI and EcoRV sites. This DNA is transformed into bacteria and the plasmid clones sequenced to identify the correct protein-coding inserts. Correct 5' ends are confirmed by comparing this sequence with the putatively identified homologue and overlap with the partial cDNA clone. Similar methods known in the art and/or commercial kits are used to amplify and recover 3' ends.

Several quality-controlled kits are commercially available for purchase. Similar reagents and methods to those above are supplied in kit form from Gibco/BRL for both 5' and 3' RACE for recovery of full length genes. A second kit is available from Clontech which is a modification of a related technique, SLIC (single-stranded ligation to single-stranded cDNA), developed by Dumas et al., Nucleic Acids Res., 19:5227-32 (1991). The major differences in procedure are that the RNA is alkaline hydrolyzed after reverse transcription and RNA ligase is used to join a restriction site-containing anchor primer to the first-strand cDNA. This obviates the necessity for the dA-tailing reaction which results in a polyT stretch that is difficult to sequence past.

An alternative to generating 5' or 3' cDNA from RNA is to use cDNA library double-stranded DNA. An asymmetric PCR-amplified antisense cDNA strand is synthesized with an antisense cDNA-specific primer and a plasmid-anchored primer. These primers are removed and a symmetric PCR reaction is performed with a nested cDNA-specific antisense primer and the plasmid-anchored primer.

RNA Ligase Protocol for Generating the 5' or 3' End Sequences to Obtain Full Length Genes Once a gene of interest is identified, several methods are available for the identification of the 5' or 3' portions of the gene which may not be present in the original cDNA plasmid. These methods include, but are not limited to, filter probing, clone enrichment using specific probes and protocols similar and identical to 5' and 3'RACE. While the full-length gene may be present in the library and can be identified by probing, a useful method for generating the 5' or 3' end is to use the existing sequence information from the original cDNA to generate the missing information. A method similar to 5'RACE is available for generating the missing 5' end of a desired full-length gene. (This method was published by Fromont-Racine et al., Nucleic Acids Res., 21(7): 1683-1684 (1993)). Briefly, a specific RNA oligonucleotide is ligated to the 5' ends of a population of RNA presumably 30 containing full-length gene RNA transcript and a primer set containing a primer specific to the ligated RNA oligonucleotide and a primer specific to a known sequence of the gene of interest, is used to PCR amplify the 5' portion of the desired full length gene which may then be sequenced and used to generate the full length gene. This method starts with total RNA isolated from the desired source, poly A RNA may be used but is not a prerequisite for this procedure. The RNA preparation may then be treated with phosphatase if necessary to eliminate 5' phosphate groups on degraded or damaged RNA which may interfere with the later RNA ligase step. The phosphatase if used is then inactivated and the RNA is treated with tobacco acid pyrophosphatase in order to remove the cap structure present at the 5' ends of messenger RNAs. This reaction leaves a 5' phosphate group at the 5' end of the cap cleaved RNA which can then be ligated to an RNA oligonucleotide using T4 RNA ligase. This modified RNA preparation can then be used as a template for first strand cDNA synthesis using a gene specific oligonucleotide. The first strand synthesis reaction can then be used as a template for PCR amplification of the desired 5' end using a primer specific to the ligated RNA oligonucleotide and a primer specific to the known sequence of the apoptosis related of interest. The resultant product is then sequenced and analyzed to confirm that the 5' end sequence belongs to the relevant apoptosis related.

Example 12

Chromosomal Mapping of the Polynucleotides

An oligonucleotide primer set is designed according to the sequence at the 5' end of SEQ ID NO:1. This primer preferably spans about 100 nucleotides. This primer set is then used in a polymerase chain reaction under the following set of conditions: 30 seconds, 95 degree C.; 1 minute, 56 degree C.; 1 minute, 70 degree C. This cycle is repeated 32 times followed by one 5 minute cycle at 70 degree C. Mammalian DNA, preferably human DNA, is used as template in addition to a somatic cell hybrid panel containing individual chromosomes or chromosome fragments (Bios, Inc). The reactions are analyzed on either 8% polyacrylamide gels or 3.5% agarose gels. Chromosome mapping is determined by the presence of an approximately 100 bp PCR fragment in the particular somatic cell hybrid.

Example 13

Bacterial Expression of a Polypeptide

A polynucleotide encoding a polypeptide of the present invention is amplified using PCR oligonucleotide primers corresponding to the 5' and 3' ends of the DNA sequence, as outlined in Example 11, to synthesize insertion fragments. The primers used to amplify the cDNA insert should preferably contain restriction sites, such as BamHI and XbaI, at the 5' end of the primers in order to clone the amplified product into the expression vector. For example, BamHI and XbaI correspond to the restriction enzyme sites on the bacterial expression vector pQE-9. (Qiagen, Inc., Chatsworth, Calif.). This plasmid vector encodes antibiotic resistance (Ampr), a bacterial origin of replication (ori), an IPTG-regulatable promoter/operator (P/O), a ribosome binding site (RBS), a 6-histidine tag (6-His), and restriction enzyme cloning sites.

The pQE-9 vector is digested with BamHI and XbaI and the amplified fragment is ligated into the pQE-9 vector maintaining the reading frame initiated at the bacterial RBS. The ligation mixture is then used to transform the E. coli strain M15/rep4 (Qiagen, Inc.) which contains multiple copies of the plasmid pREP4, that expresses the lacI repressor and also confers kanamycin resistance (Kanr). Transformants are identified by their ability to grow on LB plates and ampicillin/kanamycin resistant colonies are selected. Plasmid DNA is isolated and confirmed by restriction analysis.

Clones containing the desired constructs are grown overnight (O/N) in liquid culture in LB media supplemented with both Amp (100 ug/ml) and Kan (25 ug/ml). The O/N culture is used to inoculate a large culture at a ratio of 1:100 to 1:250. The cells are grown to an optical density 600 (O.D.600) of between 0.4 and 0.6. IPTG (Isopropyl-B-D-thiogalactopyranoside) is then added to a final concentration of 1 mM. IPTG induces by inactivating the lacI repressor, clearing the P/O leading to increased gene expression.

Cells are grown for an extra 3 to 4 hours. Cells are then harvested by centrifugation (20 mins at 6000×g). The cell pellet is solubilized in the chaotropic agent 6 Molar Guanidine HCl by stirring for 3-4 hours at 4 degree C. The cell debris is removed by centrifugation, and the supernatant containing the polypeptide is loaded onto a nickel-nitrilo-triacetic acid ("Ni-NTA") affinity resin column (available from QIAGEN, Inc., supra). Proteins with a 6×His tag bind to the Ni-NTA resin with high affinity and can be purified in a simple one-step procedure (for details see: The QIAexpressionist (1995) QIAGEN, Inc., supra).

Briefly, the supernatant is loaded onto the column in 6 M guanidine-HCl, pH 8, the column is first washed with 10 volumes of 6 M guanidine-HCl, pH 8, then washed with 10 volumes of 6 M guanidine-HCl pH 6, and finally the polypeptide is eluted with 6 M guanidine-HCl, pH 5.

The purified protein is then renatured by dialyzing it against phosphate-buffered saline (PBS) or 50 mM Na-acetate, pH 6 buffer plus 200 mM NaCl. Alternatively, the protein can be successfully refolded while immobilized on the Ni-NTA column. The recommended conditions are as follows: renature using a linear 6M-1M urea gradient in 500 mM NaCl, 20% glycerol, 20 mM Tris/HCl pH 7.4, containing protease inhibitors. The renaturation should be performed over a period of 1.5 hours or more. After renaturation the proteins are eluted by the addition of 250 mM imidazole. Imidazole is removed by a final dialyzing step against PBS or 50 mM sodium acetate pH 6 buffer plus 200 mM NaCl. The purified protein is stored at 4 degree C. or frozen at −80 degree C.

Example 14

Purification of a Polypeptide from an Inclusion Body

The following alternative method can be used to purify a polypeptide expressed in E coli when it is present in the form of inclusion bodies. Unless otherwise specified, all of the following steps are conducted at 4-10 degree C.

Upon completion of the production phase of the E. coli fermentation, the cell culture is cooled to 4-10 degree C. and the cells harvested by continuous centrifugation at 15,000 rpm (Heraeus Sepatech). On the basis of the expected yield of protein per unit weight of cell paste and the amount of purified protein required, an appropriate amount of cell paste, by weight, is suspended in a buffer solution containing 100 mM Tris, 50 mM EDTA, pH 7.4. The cells are dispersed to a homogeneous suspension using a high shear mixer.

The cells are then lysed by passing the solution through a MICROFLUIDIZER® (Microfluidics, Corp. or APV Gaulin, Inc.) twice at 4000-6000 psi. The homogenate is then mixed with NaCl solution to a final concentration of 0.5 M NaCl, followed by centrifugation at 7000×g for 15 min. The resultant pellet is washed again using 0.5M NaCl, 100 mM Tris, 50 mM EDTA, pH 7.4.

The resulting washed inclusion bodies are solubilized with 1.5 M guanidine hydrochloride (GuHCl) for 2-4 hours. After 7000×g centrifugation for 15 min., the pellet is discarded and the polypeptide containing supernatant is incubated at 4 degree C. overnight to allow further GuHCl extraction.

Following high speed centrifugation (30,000×g) to remove insoluble particles, the GuHCl solubilized protein is refolded by quickly mixing the GuHCl extract with 20 volumes of buffer containing 50 mM sodium, pH 4.5, 150 mM NaCl, 2 mM EDTA by vigorous stirring. The refolded diluted protein solution is kept at 4 degree C. without mixing for 12 hours prior to further purification steps.

To clarify the refolded polypeptide solution, a previously prepared tangential filtration unit equipped with 0.16 um membrane filter with appropriate surface area (e.g., Filtron), equilibrated with 40 mM sodium acetate, pH 6.0 is employed. The filtered sample is loaded onto a cation exchange resin (e.g., POROS® HS-50, Perceptive Biosystems). The column is washed with 40 mM sodium acetate, pH 6.0 and eluted with 250 mM, 500 mM, 1000 mM, and 1500 mM NaCl in the same buffer, in a stepwise manner. The absorbance at 280 nm of the effluent is continuously monitored. Fractions are collected and further analyzed by SDS-PAGE.

Fractions containing the polypeptide are then pooled and mixed with 4 volumes of water. The diluted sample is then loaded onto a previously prepared set of tandem columns of strong anion (POROS® HQ-50, Perceptive Biosystems) and weak anion (POROS® CM-20, Perceptive Biosystems) exchange resins. The columns are equilibrated with 40 mM sodium acetate, pH 6.0. Both columns are washed with 40 mM sodium acetate, pH 6.0, 200 mM NaCl. The CM-20 column is then eluted using a 10 column volume linear gradient ranging from 0.2 M NaCl, 50 mM sodium acetate, pH 6.0 to 1.0 M NaCl, 50 mM sodium acetate, pH 6.5. Fractions are collected under constant A280 monitoring of the effluent. Fractions containing the polypeptide (determined, for instance, by 16% SDS-PAGE) are then pooled.

The resultant polypeptide should exhibit greater than 95% purity after the above refolding and purification steps. No major contaminant bands should be observed from Coomassie blue stained 16% SDS-PAGE gel when 5 ug of purified protein is loaded. The purified protein can also be tested for endotoxin/LPS contamination, and typically the LPS content is less than 0.1 ng/ml according to LAL assays.

Example 15

Cloning and Expression of a Polypeptide in a Baculovirus Expression System

In this example, the plasmid shuttle vector pAc373 is used to insert a polynucleotide into a baculovirus to express a polypeptide. A typical baculovirus expression vector contains the strong polyhedrin promoter of the *Autographa californica* nuclear polyhedrosis virus (AcMNPV) followed by convenient restriction sites, which may include, for example BamHI, Xba I and Asp718. The polyadenylation site of the simian virus 40 ("SV40") is often used for efficient polyadenylation. For easy selection of recombinant virus, the plasmid contains the beta-galactosidase gene from *E. coli* under control of a weak *Drosophila* promoter in the same orientation, followed by the polyadenylation signal of the polyhedrin gene. The inserted genes are flanked on both sides by viral sequences for cell-mediated homologous recombination with wild-type viral DNA to generate a viable virus that express the cloned polynucleotide.

Many other baculovirus vectors can be used in place of the vector above, such as pVL941 and pAcIM1, as one skilled in the art would readily appreciate, as long as the construct provides appropriately located signals for transcription, translation, secretion and the like, including a signal peptide and an in-frame AUG as required. Such vectors are described, for instance, in Luckow et al., Virology 170:31-39 (1989).

A polynucleotide encoding a polypeptide of the present invention is amplified using PCR oligonucleotide primers corresponding to the 5' and 3' ends of the DNA sequence, as outlined in Example 11, to synthesize insertion fragments. The primers used to amplify the cDNA insert should preferably contain restriction sites at the 5' end of the primers in order to clone the amplified product into the expression vector. Specifically, the cDNA sequence contained in the deposited clone, including the AUG initiation codon and the naturally associated leader sequence identified elsewhere herein (if applicable), is amplified using the PCR protocol described in Example 11. If the naturally occurring signal sequence is used to produce the protein, the vector used does not need a second signal peptide. Alternatively, the vector can be modified to include a baculovirus leader sequence, using the standard methods described in Summers et al., "A Manual of Methods for Baculovirus Vectors and Insect Cell Culture Procedures," Texas Agricultural Experimental Station Bulletin No. 1555 (1987).

The amplified fragment is isolated from a 1% agarose gel using a commercially available kit ("GENECLEAN®," BIO 101 Inc., La Jolla, Calif.). The fragment then is digested with appropriate restriction enzymes and again purified on a 1% agarose gel.

The plasmid is digested with the corresponding restriction enzymes and optionally, can be dephosphorylated using calf intestinal phosphatase, using routine procedures known in the art. The DNA is then isolated from a 1% agarose gel using a commercially available kit ("GENECLEAN®" BIO 101 Inc., La Jolla, Calif.).

The fragment and the dephosphorylated plasmid are ligated together with T4 DNA ligase. *E. coli* HB101 or other suitable *E. coli* hosts such as XL-1 Blue (Stratagene Cloning Systems, La Jolla, Calif.) cells are transformed with the ligation mixture and spread on culture plates. Bacteria containing the plasmid are identified by digesting DNA from individual colonies and analyzing the digestion product by gel electrophoresis. The sequence of the cloned fragment is confirmed by DNA sequencing.

Five ug of a plasmid containing the polynucleotide is co-transformed with 1.0 ug of a commercially available linearized baculovirus DNA ("BACULOGOLD® baculovirus DNA", Pharmingen, San Diego, Calif.), using the lipofection method described by Felgner et al., Proc. Natl. Acad. Sci. USA 84:7413-7417 (1987). One ug of BACULOGOLD® virus DNA and 5 ug of the plasmid are mixed in a sterile well of a microtiter plate containing 50 ul of serum-free Grace's medium (Life Technologies Inc., Gaithersburg, Md.). Afterwards, 10 ul Lipofectin plus 90 ul Grace's medium are added, mixed and incubated for 15 minutes at room temperature. Then the transfection mixture is added drop-wise to Sf9 insect cells (ATCC® CRL 1711) seeded in a 35 mm tissue culture plate with 1 ml Grace's medium without serum. The plate is then incubated for 5 hours at 27 degrees C. The transfection solution is then removed from the plate and 1 ml of Grace's insect medium supplemented with 10% fetal calf serum is added. Cultivation is then continued at 27 degrees C. for four days.

After four days the supernatant is collected and a plaque assay is performed, as described by Summers and Smith, supra. An agarose gel with "Blue Gal" (Life Technologies Inc., Gaithersburg) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gaithersburg, page 9-10.) After appropriate incubation, blue stained plaques are picked with the tip of a micropipettor (e.g., Eppendorf). The agar containing the recombinant viruses is then resuspended in a microcentrifuge tube containing 200 ul of Grace's medium and the suspension containing the recombinant baculovirus is used to infect Sf9 cells seeded in 35 mm dishes. Four days later the supernatants of these culture dishes are harvested and then they are stored at 4 degree C.

To verify the expression of the polypeptide, Sf9 cells are grown in Grace's medium supplemented with 10% heat-inactivated FBS. The cells are infected with the recombinant baculovirus containing the polynucleotide at a multiplicity of infection ("MOI") of about 2. If radiolabeled proteins are desired, 6 hours later the medium is removed and is replaced with SF900 II medium minus methionine and cysteine (available from Life Technologies Inc., Rockville, Md.). After 42 hours, 5 uCi of 35S-methionine and 5 uCi 35S-cysteine (available from Amersham) are added. The cells are further incubated for 16 hours and then are harvested by centrifugation. The proteins in the supernatant as well as the intracellular proteins are analyzed by SDS-PAGE followed by autoradiography (if radiolabeled).

Microsequencing of the amino acid sequence of the amino terminus of purified protein may be used to determine the amino terminal sequence of the produced protein.

Example 16

Expression of a Polypeptide in Mammalian Cells

The polypeptide of the present invention can be expressed in a mammalian cell. A typical mammalian expression vector contains a promoter element, which mediates the initiation of transcription of mRNA, a protein coding sequence, and signals required for the termination of transcription and polyadenylation of the transcript. Additional elements include enhancers, Kozak sequences and intervening sequences flanked by donor and acceptor sites for RNA splicing. Highly efficient transcription is achieved with the early and late promoters from SV40, the long terminal repeats (LTRs) from Retroviruses, e.g., RSV, HTLVI, HIVI and the early promoter of the cytomegalovirus (CMV). However, cellular elements can also be used (e.g., the human actin promoter).

Suitable expression vectors for use in practicing the present invention include, for example, vectors such as pSVL and pMSG (Pharmacia, Uppsala, Sweden), pRSVcat (ATCC® 37152), pSV2dhfr (ATCC® 37146), pBC12MI (ATCC® 67109), pCMVSport 2.0, and pCMVSport 3.0. Mammalian host cells that could be used include, human Hela, 293, H9 and Jurkat cells, mouse NIH3T3 and C127 cells, Cos 1, Cos 7 and CV1, quail QC1-3 cells, mouse L cells and Chinese hamster ovary (CHO) cells.

Alternatively, the polypeptide can be expressed in stable cell lines containing the polynucleotide integrated into a chromosome. The co-transfection with a selectable marker such as dhfr, gpt, neomycin, hygromycin allows the identification and isolation of the transformed cells.

The transformed gene can also be amplified to express large amounts of the encoded protein. The DHFR (dihydrofolate reductase) marker is useful in developing cell lines that carry several hundred or even several thousand copies of the gene of interest. (See, e.g., Alt, F. W., et al., J. Biol. Chem. . . . 253:1357-1370 (1978); Hamlin, J. L. and Ma, C., Biochem. et Biophys. Acta, 1097:107-143 (1990); Page, M. J. and Sydenham, M. A., Biotechnology 9:64-68 (1991).) Another useful selection marker is the enzyme glutamine synthase (GS) (Murphy et al., Biochem J. 227:277-279 (1991); Bebbington et al., Bio/Technology 10:169-175 (1992). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of proteins.

A polynucleotide of the present invention is amplified according to the protocol outlined in herein. If the naturally occurring signal sequence is used to produce the protein, the vector does not need a second signal peptide. Alternatively, if the naturally occurring signal sequence is not used, the vector can be modified to include a heterologous signal sequence. (See, e.g., WO 96/34891.) The amplified fragment is isolated from a 1% agarose gel using a commercially available kit ("GENECLEAN®," BIO 101 Inc., La Jolla, Calif.). The fragment then is digested with appropriate restriction enzymes and again purified on a 1% agarose gel.

The amplified fragment is then digested with the same restriction enzyme and purified on a 1% agarose gel. The isolated fragment and the dephosphorylated vector are then ligated with T4 DNA ligase. E. coli HB101 or XL-1 Blue cells are then transformed and bacteria are identified that contain the fragment inserted into plasmid pC6 using, for instance, restriction enzyme analysis.

Chinese hamster ovary cells lacking an active DHFR gene is used for transformation. Five µg of an expression plasmid is cotransformed with 0.5 ug of the plasmid pSVneo using lipofectin (Felgner et al., supra). The plasmid pSV2-neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of methotrexate plus 1 mg/ml G418. After about 10-14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 uM, 2 uM, 5 uM, 10 mM, 20 mM). The same procedure is repeated until clones are obtained which grow at a concentration of 100-200 uM. Expression of the desired gene product is analyzed, for instance, by SDS-PAGE and Western blot or by reversed phase HPLC analysis.

Example 17

Protein Fusions

The polypeptides of the present invention are preferably fused to other proteins. These fusion proteins can be used for a variety of applications. For example, fusion of the present polypeptides to His-tag, HA-tag, protein A, IgG domains, and maltose binding protein facilitates purification. (See Example described herein; see also EP A 394,827; Traunecker, et al., Nature 331:84-86 (1988).) Similarly, fusion to IgG-1, IgG-3, and albumin increases the half-life time in vivo. Nuclear localization signals fused to the polypeptides of the present invention can target the protein to a specific subcellular localization, while covalent heterodimer or homodimers can increase or decrease the activity of a fusion protein. Fusion proteins can also create chimeric molecules having more than one function. Finally, fusion proteins can increase solubility and/or stability of the fused protein compared to the non-fused protein. All of the types of fusion proteins described above can be made by modifying the following protocol, which outlines the fusion of a polypeptide to an IgG molecule.

Briefly, the human Fc portion of the IgG molecule can be PCR amplified, using primers that span the 5' and 3' ends of the sequence described below. These primers also should have convenient restriction enzyme sites that will facilitate cloning into an expression vector, preferably a mammalian expression vector. Note that the polynucleotide is cloned without a stop codon, otherwise a fusion protein will not be produced.

The naturally occurring signal sequence may be used to produce the protein (if applicable). Alternatively, if the naturally occurring signal sequence is not used, the vector can be modified to include a heterologous signal sequence. (See, e.g., WO 96/34891 and/or U.S. Pat. No. 6,066,781, supra.)

Human IgG Fc region:

(SEQ ID NO:262)
GGGATCCGGAGCCCAAATCTTCTGACAAAACTCACACATGCCCACC

GTGCCCAGCACCTGAATTCGAGGGTGCACCGTCAGTCTTCCTCTTCCCCC

CAAAACCCAAGGACACCCTCATGATCTCCCGGACTCCTGAGGTCACATGC

GTGGTGGTGGACGTAAGCCACGAAGACCCTGAGGTCAAGTTCAACTGGTA

CGTGGACGGCGTGGAGGTGCATAATGCCAAGACAAAGCCGCGGGAGGAGC

AGTACAACAGCACGTACCGTGTGGTCAGCGTCCTCACCGTCCTGCACCAG

GACTGGCTGAATGGCAAGGAGTACAAGTGCAAGGTCTCCAACAAAGCCCT

CCCAACCCCCATCGAGAAAACCATCTCCAAAGCCAAAGGGCAGCCCCGAG

AACCACAGGTGTACACCCTGCCCCCATCCCGGGATGAGCTGACCAAGAAC

CAGGTCAGCCTGACCTGCCTGGTCAAAGGCTTCTATCCAAGCGACATCGC

CGTGGAGTGGGAGAGCAATGGGCAGCCGGAGAACAACTACAAGACCACGC

CTCCCGTGCTGGACTCCGACGGCTCCTTCTTCCTCTACAGCAAGCTCACC

GTGGACAAGAGCAGGTGGCAGCAGGGGAACGTCTTCTCATGCTCCGTGAT

GCATGAGGCTCTGCACAACCACTACACGCAGAAGAGCCTCTCCCTGTCTC

CGGGTAAATGAGTGCGACGGCCGCGACTCTAGAGGAT

Example 18

Method of Creating N- and C-Terminal Deletion Mutants Corresponding to the TRP-PLIK2 Polypeptide of the Present Invention As described elsewhere herein, the present invention encompasses the creation of N- and C-terminal deletion mutants, in addition to any combination of N- and C-terminal deletions thereof, corresponding to the TRP-PLIK2 polypeptide of the present invention. A number of methods are available to one skilled in the art for creating such mutants. Such methods may include a combination of PCR amplification and gene cloning methodology. Although one of skill in the art of molecular biology, through the use of the teachings provided or referenced herein, and/or otherwise known in the art as standard methods, could readily create each deletion mutant of the present invention, exemplary methods are described below.

Briefly, using the isolated cDNA clone encoding the full-length TRP-PLIK2 polypeptide sequence (as described in Example 11, for example), appropriate primers of about 15-25 nucleotides derived from the desired 5' and 3' positions of SEQ ID NO:1, SEQ ID NO:3, SEQ ID NO:5, or SEQ ID NO:7 may be designed to PCR amplify, and subsequently clone, the intended N- and/or C-terminal deletion mutant. Such primers could comprise, for example, an initiation and stop codon for the 5' and 3' primer, respectively. Such primers may also comprise restriction sites to facilitate cloning of the deletion mutant post amplification. Moreover, the primers may comprise additional sequences, such as, for example, flag-tag sequences, kozac sequences, or other sequences discussed and/or referenced herein.

For example, in the case of the W739 to L2017 TRP-PLIK2 N-terminal deletion mutant, the following primers could be used to amplify a cDNA fragment corresponding to this deletion mutant:

(SEQ ID NO:263)
5' Primer
5'-GCAGCA GCGGCCGC TGGTTAAAGATTATTATAAGC-3'
    NotI (SEQ ID NO:264)
3' Primer
5'-GCAGCA GTCGAC TAGTTGCATATCATCTTCTGGGG-3'
    SalI For example, in the case of the M1 to P1287 TRP-PLIK2 C-terminal deletion mutant, the following primers could be used to amplify a cDNA fragment corresponding to this deletion mutant:

(SEQ ID NO:265)
5' Primer
5'-GCAGCA GCGGCCGC ATGATTATCCTATCTAAGTCCCAG-3'
    NotI (SEQ ID NO:266)
3' Primer
5'-GCAGCA GTCGAC GGGATGCCGGCCTCCAGCCAGGCTC-3'
    SalI The resulting C-terminal deletion mutant could be used as a potential, membrane bound, TRP-PLIK2 decoy receptor. Any C-terminal deletion between amino acid 1200 to 1600 of SEQ ID NO:2 would be preferred.

Representative PCR amplification conditions are provided below, although the skilled artisan would appreciate that other conditions may be required for efficient amplification. A 100 ul PCR reaction mixture may be prepared using 10 ng of the template DNA (cDNA clone of TRP-PLIK2, TRP-PLIK2b, TRP-PLIK2c, or TRP-PLIK2d), 200 uM 4dNTPs, 1 uM primers, 0.25U Taq DNA polymerase (PE), and standard Taq DNA polymerase buffer. Typical PCR cycling condition are as follows:

20-25 cycles: 45 sec, 93 degrees
2 min, 50 degrees
2 min, 72 degrees
1 cycle: 10 min, 72 degrees After the final extension step of PCR, 5U Klenow Fragment may be added and incubated for 15 min at 30 degrees.

Upon digestion of the fragment with the NotI and SalI restriction enzymes, the fragment could be cloned into an appropriate expression and/or cloning vector which has been similarly digested (e.g., pSport1, among others). The skilled artisan would appreciate that other plasmids could be equally substituted, and may be desirable in certain circumstances. The digested fragment and vector are then ligated using a DNA ligase, and then used to transform competent *E. coli* cells using methods provided herein and/or otherwise known in the art.

The 5' primer sequence for amplifying any additional N-terminal deletion mutants may be determined by reference to the following formula:

(S+(X*3)) to ((S+(X*3))+25), wherein 'S' is equal to the nucleotide position of the initiating start codon of the TRP-PLIK2 gene (SEQ ID NO:1), TRP-PLIK2b gene (SEQ ID NO:3), TRP-PLIK2c gene (SEQ ID NO:5), or TRP-PLIK2d gene (SEQ ID NO:7) and 'X' is equal to the most N-terminal amino acid of the intended N-terminal deletion mutant. The first term will provide the start 5' nucleotide position of the 5' primer, while the second term will provide the end 3' nucleotide position of the 5' primer corresponding to sense strand of SEQ ID NO:1, SEQ ID NO:3, SEQ ID NO:5, or SEQ ID NO:7. Once the corresponding nucleotide positions of the primer are determined, the final nucleotide sequence may be created by the addition of applicable restriction site sequences to the 5' end of the sequence, for example. As referenced herein, the addition of other sequences to the 5' primer may be desired in certain circumstances (e.g., kozac sequences, etc.).

The 3' primer sequence for amplifying any additional N-terminal deletion mutants may be determined by reference to the following formula:

(S+(X*3)) to ((S+(X*3))–25), wherein 'S' is equal to the nucleotide position of the initiating start codon of the TRP-PLIK2 gene (SEQ ID NO:1), TRP-PLIK2b gene (SEQ ID NO:3), TRP-PLIK2c gene (SEQ ID NO:5), or TRP-PLIK2b gene (SEQ ID NO:7) and 'X' is equal to the most C-terminal amino acid of the intended N-terminal deletion mutant. The first term will provide the start 5' nucleotide position of the 3' primer, while the second term will provide the end 3' nucleotide position of the 3' primer corresponding to the anti-sense strand of SEQ ID NO: 1, SEQ ID NO:3, SEQ ID NO:5, or SEQ ID NO:7. Once the corresponding nucleotide positions of the primer are determined, the final nucleotide sequence may be created by the addition of applicable restriction site sequences to the 5' end of the sequence, for example. As referenced herein, the addition of other sequences to the 3' primer may be desired in certain circumstances (e.g., stop codon sequences, etc.). The skilled artisan would appreciate that modifications of the above nucleotide positions may be necessary for optimizing PCR amplification.

The same general formulas provided above may be used in identifying the 5' and 3' primer sequences for amplifying any C-terminal deletion mutant of the present invention. Moreover, the same general formulas provided above may be used in identifying the 5' and 3' primer sequences for amplifying any combination of N-terminal and C-terminal deletion mutant of the present invention. The skilled artisan would appreciate that modifications of the above nucleotide positions may be necessary for optimizing PCR amplification.

Example 19

Regulation of Protein Expression Via Controlled Aggregation in the Endoplasmic Reticulum As described more particularly herein, proteins regulate diverse cellular processes in higher organisms, ranging from rapid metabolic changes to growth and differentiation. Increased production of specific proteins could be used to prevent certain diseases and/or disease states. Thus, the ability to modulate the expression of specific proteins in an organism would provide significant benefits.

Numerous methods have been developed to date for introducing foreign genes, either under the control of an inducible, constitutively active, or endogenous promoter, into organisms. Of particular interest are the inducible promoters (see, M. Gossen, et al., Proc. Natl. Acad. Sci. USA., 89:5547 (1992); Y. Wang, et al., Proc. Natl. Acad. Sci. USA, 91:8180 (1994), D. No., et al., Proc. Natl. Acad. Sci. USA, 93:3346 (1996); and V. M. Rivera, et al., Nature Med, 2:1028 (1996); in addition to additional examples disclosed elsewhere herein). In one example, the gene for erythropoietin (Epo) was transferred into mice and primates under the control of a small molecule inducer for expression (e.g., tetracycline or rapamycin) (see, D. Bohl, et al., Blood, 92:1512, (1998); K. G. Rendahl, et al., Nat. Biotech, 16:757, (1998); V. M. Rivera, et al., Proc. Natl. Acad. Sci. USA, 96:8657 (1999); and X. Ye et al., Science, 283:88 (1999). Although such systems enable efficient induction of the gene of interest in the organism upon addition of the inducing agent (i.e., tetracycline, rapamycin, etc.), the levels of expression tend to peak at 24 hours and trail off to background levels after 4 to 14 days. Thus, controlled transient expression is virtually impossible using these systems, though such control would be desirable.

A new alternative method of controlling gene expression levels of a protein from a transgene (i.e., includes stable and transient transformants) has recently been elucidated (V. M. Rivera., et al., Science, 287:826-830, (2000)). This method does not control gene expression at the level of the mRNA like the aforementioned systems. Rather, the system controls the level of protein in an active secreted form. In the absence of the inducing agent, the protein aggregates in the ER and is not secreted. However, addition of the inducing agent results in dis-aggregation of the protein and the subsequent secretion from the ER. Such a system affords low basal secretion, rapid, high level secretion in the presence of the inducing agent, and rapid cessation of secretion upon removal of the inducing agent. In fact, protein secretion reached a maximum level within 30 minutes of induction, and a rapid cessation of secretion within 1 hour of removing the inducing agent. The method is also applicable for controlling the level of production for membrane proteins.

Detailed methods are presented in V. M. Rivera., et al., Science, 287:826-830, (2000)), briefly:

Fusion protein constructs are created using polynucleotide sequences of the present invention with one or more copies (preferably at least 2, 3, 4, or more) of a conditional aggregation domain (CAD) a domain that interacts with itself in a ligand-reversible manner (i.e., in the presence of an inducing agent) using molecular biology methods known in the art and discussed elsewhere herein. The CAD domain may be the mutant domain isolated from the human FKBP12 (Phe$^{36}$ to Met) protein (as disclosed in V. M. Rivera., et al., Science, 287:826-830, (2000), or alternatively other proteins having domains with similar ligand-reversible, self-aggregation properties. As a principle of design the fusion protein vector would contain a furin cleavage sequence operably linked between the polynucleotides of the present invention and the CAD domains. Such a cleavage site would enable the proteolytic cleavage of the CAD domains from the polypeptide of the present invention subsequent to secretion from the ER and upon entry into the trans-Golgi (J. B. Denault, et al., FEBS Lett., 379:113, (1996)). Alternatively, the skilled artisan would recognize that any proteolytic cleavage sequence could be substituted for the furin sequence provided the substituted sequence is cleavable either endogenously (e.g., the furin sequence) or exogenously (e.g., post secretion, post purification, post production, etc.). The preferred sequence of each feature of the fusion protein construct, from the 5' to 3' direction with each feature being operably linked to the other, would be a promoter, signal sequence, "X" number of (CAD)$_x$ domains, the furin sequence (or other proteolytic sequence), and the coding sequence of the polypeptide of the present invention. The artisan would appreciate that the promotor and signal sequence, independent from the other, could be either the endogenous promotor or signal sequence of a polypeptide of the present invention, or alternatively, could be a heterologous signal sequence and promotor.

The specific methods described herein for controlling protein secretion levels through controlled ER aggregation are not meant to be limiting are would be generally applicable to any of the polynucleotides and polypeptides of the present invention, including variants, homologues, orthologs, and fragments therein.

Example 20

Alteration of Protein Glycosylation Sites to Enhance Characteristics of Polypeptides of the Invention Many eukaryotic cell surface and proteins are post-translationally processed to incorporate N-linked and O-linked carbohydrates (Kornfeld and Kornfeld (1985) Annu. Rev. Biochem. 54:631-64; Rademacher et al., (1988) Annu. Rev. Biochem. 57:785-838). Protein glycosylation is thought to serve a variety of functions including: augmentation of protein folding, inhibition of protein aggregation, regulation of intracellular trafficking to organelles, increasing resistance to proteolysis, modulation of protein antigenicity, and mediation of intercellular adhesion (Fieldler and Simons (1995) Cell, 81:309-312; Helenius (1994) Mol. Biol. Of the Cell 5:253-265; Olden et al., (1978) Cell, 13:461-473; Caton et al., (1982) Cell, 37:417-427; Alexamnder and Elder (1984), Science, 226:1328-1330; and Flack et al., (1994), J. Biol. Chem., 269:14015-14020). In higher organisms, the nature and extent of glycosylation can markedly affect the circulating half-life and bio-availability of proteins by mechanisms involving receptor mediated uptake and clearance (Ashwell and Morrell, (1974), Adv. Enzymol., 41:99-128; Ashwell and Harford (1982), Ann. Rev. Biochem., 51:531-54). Receptor systems have been identified that are thought to play a major role in the clearance of serum proteins through recognition of various carbohydrate structures on the glycoproteins (Stockert (1995), Physiol. Rev., 75:591-609; Kery et al., (1992), Arch. Biochem. Biophys., 298:49-55). Thus, production strategies resulting in incomplete attachment of terminal sialic acid residues might provide a means of shortening the bioavailability and half-life of glycoproteins. Conversely, expression strategies resulting in saturation of terminal sialic acid attachment sites might lengthen protein bioavailability and half-life.

In the development of recombinant glycoproteins for use as pharmaceutical products, for example, it has been speculated that the pharmacodynamics of recombinant proteins can be modulated by the addition or deletion of glycosylation sites from a glycoproteins primary structure (Berman and Lasky (1985a) Trends in Biotechnol., 3:51-53). However, studies have reported that the deletion of N-linked glycosylation sites often impairs intracellular transport and results in the intracellular accumulation of glycosylation site variants (Machamer and Rose (1988), J. Biol Chem., 263:5955-5960; Gallagher et al., (1992), J. Virology., 66:7136-7145; Collier et al., (1993), Biochem., 32:7818-7823; Claffey et al., (1995) Biochemica et Biophysica Acta, 1246:1-9; Dube et al., (1988), J. Biol. Chem. 263:17516-17521). While glycosylation site variants of proteins can be expressed intracellularly, it has proved difficult to recover useful quantities from growth conditioned cell culture medium.

Moreover, it is unclear to what extent a glycosylation site in one species will be recognized by another species glycosylation machinery. Due to the importance of glycosylation in protein metabolism, particularly the secretion and/or expression of the protein, whether a glycosylation signal is recognized may profoundly determine a proteins ability to be expressed, either endogenously or recombinantly, in another organism (i.e., expressing a human protein in E. coli, yeast, or viral organisms; or an E. coli, yeast, or viral protein in human, etc.). Thus, it may be desirable to add, delete, or modify a glycosylation site, and possibly add a glycosylation site of one species to a protein of another species to improve the proteins functional, bioprocess purification, and/or structural characteristics (e.g., a polypeptide of the present invention).

A number of methods may be employed to identify the location of glycosylation sites within a protein. One preferred method is to run the translated protein sequence through the PROSITE computer program (Swiss Institute of Bioinformatics). Once identified, the sites could be systematically deleted, or impaired, at the level of the DNA using mutagenesis methodology known in the art and available to the skilled artisan, Preferably using PCR-directed mutagenesis (See Maniatis, Molecular Cloning: A Laboratory Manual, Cold Spring Harbor Press, Cold Spring, N.Y. (1982)). Similarly, glycosylation sites could be added, or modified at the level of the DNA using similar methods, preferably PCR methods (See, Maniatis, supra). The results of modifying the glycosylation sites for a particular protein (e.g., solubility, secretion potential, activity, aggregation, proteolytic resistance, etc.) could then be analyzed using methods know in the art.

Example 21

Method of Enhancing the Biological Activity/Functional Characteristics of Invention Through Molecular Evolution Although many of the most biologically active proteins known are highly effective for their specified function in an organism, they often possess characteristics that make them undesirable for transgenic, therapeutic, and/or industrial applications. Among these traits, a short physiological half-life is the most prominent problem, and is present either at the level of the protein, or the level of the proteins mRNA. The ability to extend the half-life, for example, would be particularly important for a proteins use in gene therapy, transgenic animal production, the bioprocess production and purification of the protein, and use of the protein as a chemical modulator among others. Therefore, there is a need to identify novel variants of isolated proteins possessing characteristics which enhance their application as a therapeutic for treating diseases of animal origin, in addition to the proteins applicability to common industrial and pharmaceutical applications.

Thus, one aspect of the present invention relates to the ability to enhance specific characteristics of invention through directed molecular evolution. Such an enhancement may, in a non-limiting example, benefit the inventions utility as an essential component in a kit, the inventions physical attributes such as its solubility, structure, or codon optimization, the inventions specific biological activity, including any associated enzymatic activity, the proteins enzyme kinetics, the proteins Ki, Kcat, Km, Vmax, Kd, protein-protein activity, protein-DNA binding activity, antagonist/inhibitory activity (including direct or indirect interaction), agonist activity (including direct or indirect interaction), the proteins antigenicity (e.g., where it would be desirable to either increase or decrease the antigenic potential of the protein), the immunogenicity of the protein, the ability of the protein to form dimers, trimers, or multimers with either itself or other proteins, the antigenic efficacy of the invention, including its subsequent use a preventative treatment for disease or disease states, or as an effector for targeting diseased genes. Moreover, the ability to enhance specific characteristics of a protein may also be applicable to changing the characterized activity of an enzyme to an activity completely unrelated to its initially characterized activity. Other desirable enhancements of the invention would be specific to each individual protein, and would thus be well known in the art and contemplated by the present invention.

For example, an engineered transient potential receptor may be constitutively active upon binding of its cognate ligand. Alternatively, an engineered transient potential receptor may be constitutively active in the absence of ligand binding. In yet another example, an engineered transient potential receptor may be capable of being activated with less than all of the regulatory factors and/or conditions typically required for transient potential receptor activation (e.g., ligand binding, phosphorylation, conformational changes, etc.). Such transient potential receptors would be useful in screens to identify transient potential receptor modulators, among other uses described herein.

Directed evolution is comprised of several steps. The first step is to establish a library of variants for the gene or protein of interest. The most important step is to then select for those variants that entail the activity you wish to identify. The design of the screen is essential since your screen should be selective enough to eliminate non-useful variants, but not so stringent as to eliminate all variants. The last step is then to repeat the above steps using the best variant from the previous screen. Each successive cycle, can then be tailored as necessary, such as increasing the stringency of the screen, for example.

Over the years, there have been a number of methods developed to introduce mutations into macromolecules. Some of these methods include, random mutagenesis, "error-prone" PCR, chemical mutagenesis, site-directed mutagenesis, and other methods well known in the art (for a comprehensive listing of current mutagenesis methods, see Maniatis, Molecular Cloning: A Laboratory Manual, Cold Spring Harbor Press, Cold Spring, N.Y. (1982)). Typically, such methods have been used, for example, as tools for identifying the core functional region(s) of a protein or the function of specific domains of a protein (if a multi-domain protein). However, such methods have more recently been applied to the identification of macromolecule variants with specific or enhanced characteristics.

Random mutagenesis has been the most widely recognized method to date. Typically, this has been carried out either through the use of "error-prone" PCR (as described in Moore, J., et al, Nature Biotechnology 14:458, (1996), or through the application of randomized synthetic oligonucleotides corresponding to specific regions of interest (as described by Derbyshire, K. M. et al, Gene, 46:145-152, (1986), and Hill, D E, et al, Methods Enzymol., 55:559-568, (1987). Both approaches have limits to the level of mutagenesis that can be obtained. However, either approach enables the investigator to effectively control the rate of mutagenesis. This is particularly important considering the fact that mutations beneficial to the activity of the enzyme are fairly rare. In fact, using too high a level of mutagenesis may counter or inhibit the desired benefit of a useful mutation.

While both of the aforementioned methods are effective for creating randomized pools of macromolecule variants, a third method, termed "DNA Shuffling", or "sexual PCR" (WPC, Stemmer, PNAS, 91:10747, (1994)) has recently been elucidated. DNA shuffling has also been referred to as "directed molecular evolution", "exon-shuffling", "directed enzyme evolution", "in vitro evolution", and "artificial evolution". Such reference terms are known in the art and are encompassed by the invention. This new, preferred, method apparently overcomes the limitations of the previous methods in that it not only propagates positive traits, but simultaneously eliminates negative traits in the resulting progeny.

DNA shuffling accomplishes this task by combining the principal of in vitro recombination, along with the method of "error-prone" PCR. In effect, you begin with a randomly digested pool of small fragments of your gene, created by Dnase I digestion, and then introduce said random fragments into an "error-prone" PCR assembly reaction. During the PCR reaction, the randomly sized DNA fragments not only hybridize to their cognate strand, but also may hybridize to other DNA fragments corresponding to different regions of the polynucleotide of interest—regions not typically accessible via hybridization of the entire polynucleotide. Moreover, since the PCR assembly reaction utilizes "error-prone" PCR reaction conditions, random mutations are introduced during the DNA synthesis step of the PCR reaction for all of the fragments—further diversifying the potential hybridization sites during the annealing step of the reaction.

A variety of reaction conditions could be utilized to carry-out the DNA shuffling reaction. However, specific reaction conditions for DNA shuffling are provided, for example, in PNAS, 91:10747, (1994). Briefly:

Prepare the DNA substrate to be subjected to the DNA shuffling reaction. Preparation may be in the form of simply purifying the DNA from contaminating cellular material, chemicals, buffers, oligonucleotide primers, deoxynucleotides, RNAs, etc., and may entail the use of DNA purification kits as those provided by Qiagen, Inc., or by the Promega, Corp., for example.

Once the DNA substrate has been purified, it would be subjected to Dnase I digestion. About 2-4 ug of the DNA substrate(s) would be digested with 0.0015 units of Dnase I (Sigma) per ul in 100 ul of 50 mM Tris-HCL, pH 7.4/1 mM $MgCl2$ for 10-20 min. at room temperature. The resulting fragments of 10-50 bp could then be purified by running them through a 2% low-melting point agarose gel by electrophoresis onto DE81 ion-exchange paper (Whatmann) or could be purified using MICROCON® concentrators (Amicon) of the appropriate molecular weight cutoff, or could use oligonucleotide purification columns (Qiagen), in addition to other methods known in the art. If using DE81 ion-exchange paper, the 10-50 bp fragments could be eluted from said paper using 1 M NaCl, followed by ethanol precipitation.

The resulting purified fragments would then be subjected to a PCR assembly reaction by re-suspension in a PCR mixture containing: 2 mM of each dNTP, 2.2 mM $MgCl2$, 50 mM KCl, 10 mM Tris.HCL, pH 9.0, and 0.1% Triton X-100, at a final fragment concentration of 10-30 ng/ul. No primers are added at this point. Taq DNA polymerase (Promega) would be used at 2.5 units per 100 ul of reaction mixture. A PCR program of 94 C for 60 s; 94 C for 30 s, 50-55 C for 30 s, and 72 C for 30 s using 30-45 cycles, followed by 72 C for 5 min using an MJ RESEARCH® (Cambridge, Mass.) PTC-150 thermocycler. After the assembly reaction is completed, a 1:40 dilution of the resulting primerless product would then be introduced into a PCR mixture (using the same buffer mixture used for the assembly reaction) containing 0.8 um of each primer and subjecting this mixture to 15 cycles of PCR (using 94 C for 30 s, 50 C for 30 s, and 72 C for 30 s). The referred primers would be primers corresponding to the nucleic acid sequences of the polynucleotide(s) utilized in the shuffling reaction. Said primers could consist of modified nucleic acid base pairs using methods known in the art and referred to else where herein, or could contain additional sequences (i.e., for adding restriction sites, mutating specific base-pairs, etc.).

The resulting shuffled, assembled, and amplified product can be purified using methods well known in the art (e.g., Qiagen PCR purification kits) and then subsequently cloned using appropriate restriction enzymes.

Although a number of variations of DNA shuffling have been published to date, such variations would be obvious to the skilled artisan and are encompassed by the invention. The DNA shuffling method can also be tailored to the desired level of mutagenesis using the methods described by Zhao, et al. (Nucl Acid Res., 25(6):1307-1308, (1997).

As described above, once the randomized pool has been created, it can then be subjected to a specific screen to identify the variant possessing the desired characteristic(s). Once the variant has been identified, DNA corresponding to the variant could then be used as the DNA substrate for initiating another round of DNA shuffling. This cycle of shuffling, selecting the optimized variant of interest, and then re-shuffling, can be repeated until the ultimate variant is obtained. Examples of model screens applied to identify variants created using DNA shuffling technology may be found in the following publications: J. C., Moore, et al., J. Mol. Biol., 272:336-347, (1997), F. R., Cross, et al., Mol. Cell. Biol., 18:2923-2931, (1998), and A. Crameri., et al., Nat. Biotech., 15:436-438, (1997).

DNA shuffling has several advantages. First, it makes use of beneficial mutations. When combined with screening, DNA shuffling allows the discovery of the best mutational combinations and does not assume that the best combination contains all the mutations in a population. Secondly, recombination occurs simultaneously with point mutagenesis. An effect of forcing DNA polymerase to synthesize full-length genes from the small fragment DNA pool is a background mutagenesis rate. In combination with a stringent selection method, enzymatic activity has been evolved up to 16000 fold increase over the wild-type form of the enzyme. In essence, the background mutagenesis yielded the genetic variability on which recombination acted to enhance the activity.

A third feature of recombination is that it can be used to remove deleterious mutations. As discussed above, during the process of the randomization, for every one beneficial mutation, there may be at least one or more neutral or inhibitory mutations. Such mutations can be removed by including in the assembly reaction an excess of the wild-type random-size fragments, in addition to the random-size fragments of the selected mutant from the previous selection. During the next selection, some of the most active variants of the polynucleotide/polypeptide/enzyme, should have lost the inhibitory mutations.

Finally, recombination enables parallel processing. This represents a significant advantage since there are likely multiple characteristics that would make a protein more desirable (e.g. solubility, activity, etc.). Since it is increasingly difficult to screen for more than one desirable trait at a time, other methods of molecular evolution tend to be inhibitory. However, using recombination, it would be possible to combine the randomized fragments of the best representative variants for the various traits, and then select for multiple properties at once.

DNA shuffling can also be applied to the polynucleotides and polypeptides of the present invention to decrease their immunogenicity in a specified host. For example, a particular variant of the present invention may be created and isolated using DNA shuffling technology. Such a variant may have all of the desired characteristics, though may be highly immunogenic in a host due to its novel intrinsic structure. Specifically, the desired characteristic may cause the polypeptide to have a non-native structure which could no longer be recognized as a "self" molecule, but rather as a "foreign", and thus activate a host immune response directed against the novel variant. Such a limitation can be overcome, for example, by including a copy of the gene sequence for a xenobiotic ortholog of the native protein in with the gene sequence of the novel variant gene in one or more cycles of DNA shuffling. The molar ratio of the ortholog and novel variant DNAs could be varied accordingly. Ideally, the resulting hybrid variant identified would contain at least some of the coding sequence which enabled the xenobiotic protein to evade the host immune system, and additionally, the coding sequence of the original novel variant that provided the desired characteristics.

Likewise, the invention encompasses the application of DNA shuffling technology to the evolution of polynucleotides and polypeptides of the invention, wherein one or more cycles of DNA shuffling include, in addition to the gene template DNA, oligonucleotides coding for known allelic sequences, optimized codon sequences, known variant sequences, known polynucleotide polymorphism sequences, known ortholog sequences, known homologue sequences, additional homologous sequences, additional non-homologous sequences, sequences from another species, and any number and combination of the above.

In addition to the described methods above, there are a number of related methods that may also be applicable, or desirable in certain cases. Representative among these are the methods discussed in PCT applications WO 98/31700, and WO 98/32845, which are hereby incorporated by reference. Furthermore, related methods can also be applied to the polynucleotide sequences of the present invention in order to evolve invention for creating ideal variants for use in gene therapy, protein engineering, evolution of whole cells containing the variant, or in the evolution of entire enzyme pathways containing polynucleotides of the invention as described in PCT applications WO 98/13485, WO 98/13487, WO 98/27230, WO 98/31837, and Crameri, A., et al., Nat. Biotech., 15:436-438, (1997), respectively.

Additional methods of applying "DNA Shuffling" technology to the polynucleotides and polypeptides of the present invention, including their proposed applications, may be found in U.S. Pat. No. 5,605,793; PCT Application No. WO 95/22625; PCT Application No. WO 97/20078; PCT Application No. WO 97/35966; and PCT Application No. WO 98/42832; PCT Application No. WO 00/09727 specifically provides methods for applying DNA shuffling to the identification of herbicide selective crops which could be applied to the polynucleotides and polypeptides of the present invention; additionally, PCT Application No. WO 00/12680 provides methods and compositions for generating, modifying, adapting, and optimizing polynucleotide sequences that confer detectable phenotypic properties on plant species; each of the above are hereby incorporated in their entirety herein for all purposes.

Example 22

Method of Determining Alterations in a Gene Corresponding to a Polynucleotide

RNA isolated from entire families or individual patients presenting with a phenotype of interest (such as a disease) is be isolated. cDNA is then generated from these RNA samples using protocols known in the art. (See, Sambrook.) The cDNA is then used as a template for PCR, employing primers surrounding regions of interest in SEQ ID NO:1. Suggested PCR conditions consist of 35 cycles at 95 degrees C. for 30 seconds; 60-120 seconds at 52-58 degrees C.; and 60-120 seconds at 70 degrees C., using buffer solutions described in Sidransky et al., Science 252:706 (1991).

PCR products are then sequenced using primers labeled at their 5' end with T4 polynucleotide kinase, employing SequiTherm Polymerase. (Epicentre Technologies). The intron-exon borders of selected exons is also determined and genomic PCR products analyzed to confirm the results. PCR products harboring suspected mutations is then cloned and sequenced to validate the results of the direct sequencing.

PCR products are cloned into T-tailed vectors as described in Holton et al., Nucleic Acids Research, 19:1156 (1991) and sequenced with T7 polymerase (United States Biochemical). Affected individuals are identified by mutations not present in unaffected individuals.

Genomic rearrangements are also observed as a method of determining alterations in a gene corresponding to a polynucleotide. Genomic clones isolated according to Example 11 are nick-translated with digoxigenindeoxy-uridine 5'-triphosphate (Boehringer Manheim), and FISH performed as described in Johnson et al., Methods Cell Biol. 35:73-99 (1991). Hybridization with the labeled probe is carried out using a vast excess of human cot-1 DNA for specific hybridization to the corresponding genomic locus.

Chromosomes are counterstained with 4,6-diamino-2-phenylindole and propidium iodide, producing a combination of C- and R-bands. Aligned images for precise mapping are obtained using a triple-band filter set (Chroma Technology, Brattleboro, Vt.) in combination with a cooled charge-coupled device camera (Photometrics, Tucson, Ariz.) and variable excitation wavelength filters. (Johnson et al., Genet. Anal. Tech. Appl., 8:75 (1991).) Image collection, analysis and chromosomal fractional length measurements are performed using the ISEE® Graphical Program System. (Inovision Corporation, Durham, N.C.) Chromosome alterations of the genomic region hybridized by the probe are identified as insertions, deletions, and translocations. These alterations are used as a diagnostic marker for an associated disease.

Example 23

Method of Detecting Abnormal Levels of a Polypeptide in a Biological Sample

A polypeptide of the present invention can be detected in a biological sample, and if an increased or decreased level of the polypeptide is detected, this polypeptide is a marker for a particular phenotype. Methods of detection are numerous, and thus, it is understood that one skilled in the art can modify the following assay to fit their particular needs.

For example, antibody-sandwich ELISAs are used to detect polypeptides in a sample, preferably a biological sample. Wells of a microtiter plate are coated with specific antibodies, at a final concentration of 0.2 to 10 ug/ml. The antibodies are either monoclonal or polyclonal and are produced by the method described elsewhere herein. The wells are blocked so that non-specific binding of the polypeptide to the well is reduced.

The coated wells are then incubated for >2 hours at RT with a sample containing the polypeptide. Preferably, serial dilutions of the sample should be used to validate results. The plates are then washed three times with deionized or distilled water to remove unbounded polypeptide.

Next, 50 ul of specific antibody-alkaline phosphatase conjugate, at a concentration of 25-400 ng, is added and incubated for 2 hours at room temperature. The plates are again washed three times with deionized or distilled water to remove unbounded conjugate.

Add 75 ul of 4-methylumbelliferyl phosphate (MUP) or p-nitrophenyl phosphate (NPP) substrate solution to each well and incubate 1 hour at room temperature. Measure the reaction by a microtiter plate reader. Prepare a standard curve, using serial dilutions of a control sample, and plot polypeptide concentration on the X-axis (log scale) and fluorescence or absorbance of the Y-axis (linear scale). Interpolate the concentration of the polypeptide in the sample using the standard curve.

Example 24

Formulation

The invention also provides methods of treatment and/or prevention diseases, disorders, and/or conditions (such as, for example, any one or more of the diseases or disorders disclosed herein) by administration to a subject of an effective amount of a Therapeutic. By therapeutic is meant a polynucleotides or polypeptides of the invention (including fragments and variants), agonists or antagonists thereof, and/or antibodies thereto, in combination with a pharmaceutically acceptable carrier type (e.g., a sterile carrier).

The Therapeutic will be formulated and dosed in a fashion consistent with good medical practice, taking into account the clinical condition of the individual patient (especially the side effects of treatment with the Therapeutic alone), the site of delivery, the method of administration, the scheduling of administration, and other factors known to practitioners. The "effective amount" for purposes herein is thus determined by such considerations.

As a general proposition, the total pharmaceutically effective amount of the Therapeutic administered parenterally per dose will be in the range of about 1 ug/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, the Therapeutic is typically administered at a dose rate of about 1 ug/kg/hour to about 50 ug/kg/hour, either by 1-4 injections per day or by continuous subcutaneous infusions, for example, using a mini-pump. An intravenous bag solution may also be employed. The length of treatment needed to observe changes and the interval following treatment for responses to occur appears to vary depending on the desired effect.

Therapeutics can be administered orally, rectally, parenterally, intracistemally, intravaginally, intraperitoneally, topically (as by powders, ointments, gels, drops or transdermal patch), bucally, or as an oral or nasal spray. "Pharmaceutically acceptable carrier" refers to a non-toxic solid, semisolid or liquid filler, diluent, encapsulating material or formulation auxiliary of any. The term "parenteral" as used herein refers to modes of administration which include intravenous, intramuscular, intraperitoneal, intrasternal, subcutaneous and intraarticular injection and infusion.

In yet an additional embodiment, the Therapeutics of the invention are delivered orally using the drug delivery technology described in U.S. Pat. No. 6,258,789, which is hereby incorporated by reference herein.

In yet an additional embodiment, the Therapeutics of the invention are delivered orally using the drug delivery technology described in U.S. Pat. No. 6,258,789, which is hereby incorporated by reference herein.

Therapeutics of the invention are also suitably administered by sustained-release systems. Suitable examples of sustained-release Therapeutics are administered orally, rectally, parenterally, intracisternally, intravaginally, intraperitoneally, topically (as by powders, ointments, gels, drops or transdermal patch), bucally, or as an oral or nasal spray. "Pharmaceutically acceptable carrier" refers to a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

Therapeutics of the invention may also be suitably administered by sustained-release systems. Suitable examples of sustained-release Therapeutics include suitable polymeric materials (such as, for example, semi-permeable polymer matrices in the form of shaped articles, e.g., films, or microcapsules), suitable hydrophobic materials (for example as an emulsion in an acceptable oil) or ion exchange resins, and sparingly soluble derivatives (such as, for example, a sparingly soluble salt).

Sustained-release matrices include polylactides (U.S. Pat. No. 3,773,919, EP 58,481B1), copolymers of L-glutamic acid and gamma-ethyl-L-glutamate (Sidman et al., Biopolymers 22:547-556 (1983)), poly (2-hydroxyethyl methacrylate) (Langer et al., J. Biomed. Mater. Res. 15:167-277 (1981), and Langer, Chem. Tech. 12:98-105 (1982)), ethylene vinyl acetate (Langer et al., Id.) or poly-D-(−)-3-hydroxybutyric acid (EP 133,988).

Sustained-release Therapeutics also include liposomally entrapped Therapeutics of the invention (see, generally, Langer, Science 249:1527-1533 (1990); Treat et al., in Liposomes in the Therapy of Infectious Disease and Cancer, Lopez-Berestein and Fidler (eds.), Liss, New York, pp. 317-327 and 353-365 (1989)). Liposomes containing the Therapeutic are prepared by methods known per se: DE 3,218,121; Epstein et al., Proc. Natl. Acad. Sci. (USA) 82:3688-3692 (1985); Hwang et al., Proc. Natl. Acad. Sci. (USA) 77:4030-4034 (1980); EP 52,322B1; EP 36,676B1; EP 88,046B1; EP 143,949B1; EP 142,641B1; Japanese Pat. Appl. 83-118008; U.S. Pat. Nos. 4,485,045 and 4,544,545; and EP 102,324. Ordinarily, the liposomes are of the small (about 200-800 Angstroms) unilamellar type in which the lipid content is greater than about 30 mol. percent cholesterol, the selected proportion being adjusted for the optimal Therapeutic.

In yet an additional embodiment, the Therapeutics of the invention are delivered by way of a pump (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)).

Other controlled release systems are discussed in the review by Langer (Science 249:1527-1533 (1990)).

For parenteral administration, in one embodiment, the Therapeutic is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to the Therapeutic.

Generally, the formulations are prepared by contacting the Therapeutic uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium; and/or nonionic surfactants such as polysorbates, poloxamers, or PEG.

The Therapeutic will typically be formulated in such vehicles at a concentration of about 0.1 mg/ml to 100 mg/ml, preferably 1-10 mg/ml, at a pH of about 3 to 8. It will be understood that the use of certain of the foregoing excipients, carriers, or stabilizers will result in the formation of polypeptide salts.

Any pharmaceutical used for therapeutic administration can be sterile. Sterility is readily accomplished by filtration through sterile filtration membranes (e.g., 0.2 micron membranes). Therapeutics generally are placed into a container having a sterile access port, for example, an intravenous solution bag or vial having a stopper pierceable by a hypodermic injection needle.

Therapeutics ordinarily will be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous Therapeutic solution, and the resulting mixture is lyophilized. The infusion solution is prepared by reconstituting the lyophilized Therapeutic using bacteriostatic Water-for-Injection.

The invention also provides a pharmaceutical pack or kit comprising one or more containers filled with one or more of the ingredients of the Therapeutics of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the Therapeutics may be employed in conjunction with other therapeutic compounds.

The Therapeutics of the invention may be administered alone or in combination with adjuvants. Adjuvants that may be administered with the Therapeutics of the invention include, but are not limited to, alum, alum plus deoxycholate (ImmunoAg), MTP-PE (Biocine Corp.), QS21 (Genentech, Inc.), BCG, and MPL. In a specific embodiment, Therapeutics of the invention are administered in combination with alum. In another specific embodiment, Therapeutics of the invention are administered in combination with QS-21. Further adjuvants that may be administered with the Therapeutics of the invention include, but are not limited to, Monophosphoryl lipid immunomodulator, AdjuVax 100a, QS-21, QS-18, CRL1005, Aluminum salts, MF-59, and Virosomal adjuvant technology. Vaccines that may be administered with the Therapeutics of the invention include, but are not limited to, vaccines directed toward protection against MMR (measles, mumps, rubella), polio, varicella, tetanus/diphtheria, hepatitis A, hepatitis B, *haemophilus influenzae* B, whooping cough, pneumonia, influenza, Lyme's Disease, rotavirus, cholera, yellow fever, Japanese encephalitis, poliomyelitis, rabies, typhoid fever, and pertussis. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

The Therapeutics of the invention may be administered alone or in combination with other therapeutic agents. Therapeutic agents that may be administered in combination with the Therapeutics of the invention, include but not limited to, other members of the TNF family, chemotherapeutic agents, antibiotics, steroidal and non-steroidal anti-inflammatories, conventional immunotherapeutic agents, cytokines and/or growth factors. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

In one embodiment, the Therapeutics of the invention are administered in combination with members of the TNF family. TNF, TNF-related or TNF-like molecules that may be administered with the Therapeutics of the invention include, but are not limited to, soluble forms of TNF-alpha, lymphotoxin-alpha (LT-alpha, also known as TNF-beta), LT-beta (found in complex heterotrimer LT-alpha2-beta), OPGL, FasL, CD27L, CD30L, CD40L, 4-1BBL, DcR3, OX40L, TNF-gamma (International Publication No. WO 96/14328), AIM-I (International Publication No. WO 97/33899), endokine-alpha (International Publication No. WO 98/07880), TR6 (International Publication No. WO 98/30694), OPG, and neutrokine-alpha (International Publication No. WO 98/18921, OX40, and nerve growth factor (NGF), and soluble forms of Fas, CD30, CD27, CD40 and 4-IBB, TR2 (International Publication No. WO 96/34095), DR3 (International Publication No. WO 97/33904), DR4 (International Publication No. WO 98/32856), TR5 (International Publication No. WO 98/30693), TR6 (International Publication No. WO 98/30694), TR7 (International Publication No. WO 98/41629), TRANK, TR9 (International Publication No. WO 98/56892), TR10 (International Publication No. WO 98/54202), 312C2 (International Publication No. WO 98/06842), and TR12, and soluble forms CD154, CD70, and CD153.

In certain embodiments, Therapeutics of the invention are administered in combination with antiretroviral agents, nucleoside reverse transcriptase inhibitors, non-nucleoside reverse transcriptase inhibitors, and/or protease inhibitors. Nucleoside reverse transcriptase inhibitors that may be administered in combination with the Therapeutics of the invention, include, but are not limited to, RETROVIR® (zidovudine/AZT), VIDEX® (didanosine/ddI), HIVID® (zalcitabine/ddC), ZERIT® (stavudine/d4T), EPIVIR® (lamivudine/3TC), and COMBIVIR® (zidovudine/lamivudine). Non-nucleoside reverse transcriptase inhibitors that may be administered in combination with the Therapeutics of the invention, include, but are not limited to, VIRAMUNE® (nevirapine), RESCRIPTOR® (delavirdine), and SUSTIVA® (efavirenz). Protease inhibitors that may be administered in combination with the Therapeutics of the invention, include, but are not limited to, CRIXIVAN® (indinavir), NORVIR® (ritonavir), INVIRASE® (saquinavir), and VIRACEPT® (nelfinavir). In a specific embodiment, antiretroviral agents, nucleoside reverse transcriptase inhibitors, non-nucleoside reverse transcriptase inhibitors, and/or protease inhibitors may be used in any combination with Therapeutics of the invention to treat AIDS and/or to prevent or treat HIV infection.

In other embodiments, Therapeutics of the invention may be administered in combination with anti-opportunistic infection agents. Anti-opportunistic agents that may be administered in combination with the Therapeutics of the invention, include, but are not limited to, TRIMETHOPRIM-SULFAMETHOXAZOLE, DAPSONE, PENTAMIDINE, ATOVAQUONE, ISONIAZID, RIFAMPIN, PYRAZINAMIDE, ETHAMBUTOL, RIFABUTIN, CLARITHROMYCIN, AZITHROMYCIN, GANCICLOVIR, FOSCARNET, CIDOFOVIR, FLUCONAZOLE, ITRACONAZOLE, KETOCONAZOLE, ACYCLOVIR, FAMCICOLVIR, PYRIMETHAMINE, LEUCOVORIN, NEUPOGEN® (filgrastim/G-CSF), and LEUKINE® (sargramostim/GM-CSF). In a specific embodiment, Therapeutics of the invention are used in any combination with TRIMETHOPRIM-SULFAMETHOXAZOLE, DAPSONE, PENTAMIDINE, and/or ATOVAQUONE to prophylactically treat or prevent an opportunistic *Pneumocystis carinii* pneumonia infection. In another specific embodiment, Therapeutics of the invention are used in any combination with ISONIAZID, RIFAMPIN, PYRAZINAMIDE, and/or ETHAMBUTOL to prophylactically treat or prevent an opportunistic *Mycobacterium avium* complex infection. In another specific embodiment, Therapeutics of the invention are used in any combination with RIFABUTIN, CLARITHROMYCIN, and/or AZITHROMYCIN to prophylactically treat or prevent an opportunistic *Mycobacterium tuberculosis* infection. In another specific embodiment, Therapeutics of the invention are used in any combination with GANCICLOVIR, FOSCARNET, and/or CIDOFOVIR to prophylactically treat or prevent an opportunistic cytomegalovirus infection. In another specific embodiment, Therapeutics of the invention are used in any combination with FLUCONAZOLE, ITRACONAZOLE, and/or KETOCONAZOLE to prophylactically treat or prevent an opportunistic fungal infection. In another specific embodiment, Therapeutics of the invention are used in any combination with ACYCLOVIR and/or FAMCICOLVIR to prophylactically treat or prevent an opportunistic herpes simplex virus type I and/or type II infection. In another specific embodiment, Therapeutics of the invention are used in any combination with PYRIMETHAMINE and/or LEUCOVORIN to prophylactically treat or prevent an opportunistic *Toxoplasma gondii* infection. In another specific embodiment, Therapeutics of the invention are used in any combination with LEUCOVORIN and/or NEUPOGEN® to prophylactically treat or prevent an opportunistic bacterial infection.

In a further embodiment, the Therapeutics of the invention are administered in combination with an antiviral agent. Antiviral agents that may be administered with the Therapeutics of the invention include, but are not limited to, acyclovir, ribavirin, amantadine, and remantidine.

In a further embodiment, the Therapeutics of the invention are administered in combination with an antibiotic agent. Antibiotic agents that may be administered with the Therapeutics of the invention include, but are not limited to, amoxicillin, beta-lactamases, aminoglycosides, beta-lactam (glycopeptide), beta-lactamases, Clindamycin, chloramphenicol, cephalosporins, ciprofloxacin, ciprofloxacin, erythromycin, fluoroquinolones, macrolides, metronidazole, penicillins, quinolones, rifampin, streptomycin, sulfonamide, tetracyclines, trimethoprim, trimethoprim-sulfamthoxazole, and vancomycin.

Conventional nonspecific immunosuppressive agents, that may be administered in combination with the Therapeutics of the invention include, but are not limited to, steroids, cyclosporine, cyclosporine analogs, cyclophosphamide methylprednisone, prednisone, azathioprine, FK-506, 15-deoxyspergualin, and other immunosuppressive agents that act by suppressing the function of responding T cells.

In specific embodiments, Therapeutics of the invention are administered in combination with immunosuppressants. Immunosuppressants preparations that may be administered with the Therapeutics of the invention include, but are not limited to, ORTHOCLONE® (OKT3), SANDIMMUNE®/NEORAL®/SANGDYA (cyclosporin), PROGRAF® (tacrolimus), CELLCEPT® (mycophenolate), Azathioprine, glucorticosteroids, and RAPAMUNE® (sirolimus). In a specific embodiment, immunosuppressants may be used to prevent rejection of organ or bone marrow transplantation.

In an additional embodiment, Therapeutics of the invention are administered alone or in combination with one or more intravenous immune globulin preparations. Intravenous immune globulin preparations that may be administered with the Therapeutics of the invention include, but not limited to, GAMMAR®, IVEEGAM®, SANDOGLOBULIN, GAMMAGARD® S/D, and GAMIMUNE®. In a specific embodiment, Therapeutics of the invention are administered in combination with intravenous immune globulin preparations in transplantation therapy (e.g., bone marrow transplant).

In an additional embodiment, the Therapeutics of the invention are administered alone or in combination with an anti-inflammatory agent. Anti-inflammatory agents that may be administered with the Therapeutics of the invention include, but are not limited to, glucocorticoids and the non-steroidal anti-inflammatories, aminoarylcarboxylic acid derivatives, arylacetic acid derivatives, arylbutyric acid derivatives, arylcarboxylic acids, arylpropionic acid derivatives, pyrazoles, pyrazolones, salicylic acid derivatives, thiazinecarboxamides, e-acetamidocaproic acid, S-adenosylmethionine, 3-amino-4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole, and tenidap.

In another embodiment, compositions of the invention are administered in combination with a chemotherapeutic agent. Chemotherapeutic agents that may be administered with the Therapeutics of the invention include, but are not limited to, antibiotic derivatives (e.g., doxorubicin, bleomycin, daunorubicin, and dactinomycin); antiestrogens (e.g., tamoxifen); antimetabolites (e.g., fluorouracil, 5-FU, methotrexate, floxuridine, interferon alpha-2b, glutamic acid, plicamycin, mercaptopurine, and 6-thioguanine); cytotoxic agents (e.g., carmustine, BCNU, lomustine, CCNU, cytosine arabinoside, cyclophosphamide, estramustine, hydroxyurea, procarbazine, mitomycin, busulfan, cis-platin, and vincristine sulfate); hormones (e.g., medroxyprogesterone, estramustine phosphate sodium, ethinyl estradiol, estradiol, megestrol acetate, methyltestosterone, diethylstilbestrol diphosphate, chlorotrianisene, and testolactone); nitrogen mustard derivatives (e.g., mephalen, chorambucil, mechlorethamine (nitrogen mustard) and thiotepa); steroids and combinations (e.g., bethamethasone sodium phosphate); and others (e.g., dicarbazine, asparaginase, mitotane, vincristine sulfate, vinblastine sulfate, and etoposide).

In a specific embodiment, Therapeutics of the invention are administered in combination with CHOP (cyclophosphamide, doxorubicin, vincristine, and prednisone) or any combination of the components of CHOP. In another embodiment, Therapeutics of the invention are administered in combination with Rituximab. In a further embodiment, Therapeutics of the invention are administered with Rituxmab and CHOP, or Rituxmab and any combination of the components of CHOP.

In an additional embodiment, the Therapeutics of the invention are administered in combination with cytokines. Cytokines that may be administered with the Therapeutics of the invention include, but are not limited to, IL2, IL3, IL4, IL5, IL6, IL7, IL10, IL12, IL13, IL15, anti-CD40, CD40L, IFN-gamma and TNF-alpha. In another embodiment, Therapeutics of the invention may be administered with any interleukin, including, but not limited to, IL-1alpha, IL-1beta, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, and IL-21.

In an additional embodiment, the Therapeutics of the invention are administered in combination with angiogenic proteins. Angiogenic proteins that may be administered with the Therapeutics of the invention include, but are not limited to, Glioma Derived Growth Factor (GDGF), as disclosed in European Patent Number EP-399816B1; Platelet Derived Growth Factor-A (PDGF-A), as disclosed in European Patent Number EP-682110; Platelet Derived Growth Factor-B (PDGF-B), as disclosed in European Patent Number EP-282317; Placental Growth Factor (P1GF), as disclosed in International Publication Number WO 92/06194; Placental Growth Factor-2 (P1GF-2), as disclosed in Hauser et al., Growth Factors, 4:259-268 (1993); Vascular Endothelial Growth Factor (VEGF), as disclosed in International Publication Number WO 90/13649; Vascular Endothelial Growth Factor-A (VEGF-A), as disclosed in European Patent Number EP-506477B1; Vascular Endothelial Growth Factor-2 (VEGF-2), as disclosed in International Publication Number WO 96/39515; Vascular Endothelial Growth Factor B (VEGF-3); Vascular Endothelial Growth Factor B-186 (VEGF-B186), as disclosed in International Publication Number WO 96/26736; Vascular Endothelial Growth Factor-D (VEGF-D), as disclosed in International Publication Number WO 98/02543; Vascular Endothelial Growth Factor-D (VEGF-D), as disclosed in International Publication Number WO 98/07832; and Vascular Endothelial Growth Factor-E (VEGF-E), as disclosed in German Patent Number DE19639601. The above mentioned references are incorporated herein by reference herein.

In an additional embodiment, the Therapeutics of the invention are administered in combination with hematopoietic growth factors. Hematopoietic growth factors that may be administered with the Therapeutics of the invention include, but are not limited to, LEUKINE® (SARGRAMOSTIM) and NEUPOGEN® (FILGRASTIM).

In an additional embodiment, the Therapeutics of the invention are administered in combination with Fibroblast Growth Factors. Fibroblast Growth Factors that may be administered with the Therapeutics of the invention include, but are not limited to, FGF-1, FGF-2, FGF-3, FGF-4, FGF-5, FGF-6, FGF-7, FGF-8, FGF-9, FGF-10, FGF-11, FGF-12, FGF-13, FGF-14, and FGF-15.

In an additional embodiment, the Therapeutics of the invention are administered in combination with other immune factors. Immune factors that may be administered with the Therapeutics of the invention include, but are not limited to, Ly9, CD2, CD48, CD58, 2B4, CD84, CDw15O, CTLA4, CTLA4Ig, Bsl1, Bsl2, Bsl3, BLYS, TRAIL, APRIL, B7, B7 antagonists, B7 agonists, and Ret16.

In a specific embodiment, formulations of the present invention may further comprise antagonists of P-glycoprotein (also referred to as the multiresistance protein, or PGP), including antagonists of its encoding polynucleotides (e.g., antisense oligonucleotides, ribozymes, zinc-finger proteins, etc.). P-glycoprotein is well known for decreasing the efficacy of various drug administrations due to its ability to export intracellular levels of absorbed drug to the cell exterior. While this activity has been particularly pronounced in cancer cells in response to the administration of chemotherapy regimens, a variety of other cell types and the administration of other drug classes have been noted (e.g., T-cells and anti-HIV drugs). In fact, certain mutations in the PGP gene significantly reduces PGP function, making it less able to force drugs out of cells. People who have two versions of the mutated gene—one inherited from each parent—have more than four times less PGP than those with two normal versions of the gene. People may also have one normal gene and one mutated one. Certain ethnic populations have increased incidence of such PGP mutations. Among individuals from Ghana, Kenya, the Sudan, as well as African Americans, frequency of the normal gene ranged from 73% to 84%. In contrast, the frequency was 34% to 59% among British whites, Portuguese, Southwest Asian, Chinese, Filipino and Saudi populations. As a result, certain ethnic populations may require increased administration of PGP antagonist in the formulation of the present invention to arrive at the an efficacious dose of the therapeutic (e.g., those from African descent). Conversely, certain ethnic populations, particularly those having increased frequency of the mutated PGP (e.g., of Caucasian descent, or non-African descent) may require less pharmaceutical compositions in the formulation due to an effective increase in efficacy of such compositions as a result of the increased effective absorption (e.g., less PGP activity) of said composition.

Moreover, in another specific embodiment, formulations of the present invention may further comprise antagonists of OATP2 (also referred to as the multiresistance protein, or MRP2), including antagonists of its encoding polynucleotides (e.g., antisense oligonucleotides, ribozymes, zinc-finger proteins, etc.). The invention also further comprises any additional antagonists known to inhibit proteins thought to be attributable to a multidrug resistant phenotype in proliferating cells.

Preferred antagonists that formulations of the present may comprise include the potent P-glycoprotein inhibitor elacridar, and/or LY-335979. Other P-glycoprotein inhibitors known in the art are also encompassed by the present invention.

In additional embodiments, the Therapeutics of the invention are administered in combination with other therapeutic or prophylactic regimens, such as, for example, radiation therapy.

Example 25

Method of Treating Decreased Levels of the Polypeptide

The present invention relates to a method for treating an individual in need of an increased level of a polypeptide of the invention in the body comprising administering to such an individual a composition comprising a therapeutically effective amount of an agonist of the invention (including polypeptides of the invention). Moreover, it will be appreciated that conditions caused by a decrease in the standard or normal expression level of a secreted protein in an individual can be treated by administering the polypeptide of the present invention, preferably in the secreted form. Thus, the invention also provides a method of treatment of an individual in need of an increased level of the polypeptide comprising administering to such an individual a Therapeutic comprising an amount of the polypeptide to increase the activity level of the polypeptide in such an individual.

For example, a patient with decreased levels of a polypeptide receives a daily dose 0.1-100 ug/kg of the polypeptide for six consecutive days. Preferably, the polypeptide is in the secreted form. The exact details of the dosing scheme, based on administration and formulation, are provided herein.

Example 26

Method of Treating Increased Levels of the Polypeptide

The present invention also relates to a method of treating an individual in need of a decreased level of a polypeptide of the invention in the body comprising administering to such an individual a composition comprising a therapeutically effective amount of an antagonist of the invention (including polypeptides and antibodies of the invention).

In one example, antisense technology is used to inhibit production of a polypeptide of the present invention. This technology is one example of a method of decreasing levels of a polypeptide, preferably a secreted form, due to a variety of etiologies, such as cancer. For example, a patient diagnosed with abnormally increased levels of a polypeptide is administered intravenously antisense polynucleotides at 0.5, 1.0, 1.5, 2.0 and 3.0 mg/kg day for 21 days. This treatment is repeated after a 7-day rest period if the treatment was well tolerated. The formulation of the antisense polynucleotide is provided herein.

Example 27

Method of Treatment Using Gene Therapy-Ex Vivo

One method of gene therapy transplants fibroblasts, which are capable of expressing a polypeptide, onto a patient. Generally, fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin) is added. The flasks are then incubated at 37 degree C. for approximately one week.

At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al., DNA, 7:219-25 (1988)), flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention can be amplified using PCR primers which correspond to the 5' and 3' end sequences respectively as set forth in Example 11 using primers and having appropriate restriction sites and initiation/stop codons, if necessary. Preferably, the 5' primer contains an EcoRI site and the 3' primer includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is then used to transform bacteria HB101, which are then plated onto agar containing kanamycin for the purpose of confirming that the vector has the gene of interest properly inserted.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his. Once the fibroblasts have been efficiently infected, the fibroblasts are analyzed to determine whether protein is produced.

The engineered fibroblasts are then transplanted onto the host, either alone or after having been grown to confluence on cytodex 3 microcarrier beads.

Example 28

Gene Therapy Using Endogenous Genes Corresponding to Polynucleotides of the Invention Another method of gene therapy according to the present invention involves operably associating the endogenous polynucleotide sequence of the invention with a promoter via homologous recombination as described, for example, in U.S. Pat. No. 5,641,670, issued Jun. 24, 1997; International Publication NO: WO 96/29411, published Sep. 26, 1996; International Publication NO: WO 94/12650, published Aug. 4, 1994; Koller et al., Proc. Natl. Acad. Sci. USA, 86:8932-8935 (1989); and Zijlstra et al., Nature, 342:435-438 (1989). This method involves the activation of a gene which is present in the target cells, but which is not expressed in the cells, or is expressed at a lower level than desired.

Polynucleotide constructs are made which contain a promoter and targeting sequences, which are homologous to the 5' non-coding sequence of endogenous polynucleotide sequence, flanking the promoter. The targeting sequence will be sufficiently near the 5' end of the polynucleotide sequence so the promoter will be operably linked to the endogenous sequence upon homologous recombination. The promoter and the targeting sequences can be amplified using PCR. Preferably, the amplified promoter contains distinct restriction enzyme sites on the 5' and 3' ends. Preferably, the 3' end of the first targeting sequence contains the same restriction enzyme site as the 5' end of the amplified promoter and the 5' end of the second targeting sequence contains the same restriction site as the 3' end of the amplified promoter.

The amplified promoter and the amplified targeting sequences are digested with the appropriate restriction enzymes and subsequently treated with calf intestinal phosphatase. The digested promoter and digested targeting sequences are added together in the presence of T4 DNA ligase. The resulting mixture is maintained under conditions appropriate for ligation of the two fragments. The construct is size fractionated on an agarose gel then purified by phenol extraction and ethanol precipitation.

In this Example, the polynucleotide constructs are administered as naked polynucleotides via electroporation. However, the polynucleotide constructs may also be administered with transfection-facilitating agents, such as liposomes, viral sequences, viral particles, precipitating agents, etc. Such methods of delivery are known in the art.

Once the cells are transfected, homologous recombination will take place which results in the promoter being operably linked to the endogenous polynucleotide sequence. This results in the expression of polynucleotide corresponding to the polynucleotide in the cell. Expression may be detected by immunological staining, or any other method known in the art.

Fibroblasts are obtained from a subject by skin biopsy. The resulting tissue is placed in DMEM+10% fetal calf serum. Exponentially growing or early stationary phase fibroblasts are trypsinized and rinsed from the plastic surface with nutrient medium. An aliquot of the cell suspension is removed for counting, and the remaining cells are subjected to centrifugation. The supernatant is aspirated and the pellet is resuspended in 5 ml of electroporation buffer (20 mM HEPES pH 7.3, 137 mM NaCl, 5 mM KCl, 0.7 mM Na2 HPO4, 6 mM dextrose). The cells are recentrifuged, the supernatant aspirated, and the cells resuspended in electroporation buffer containing 1 mg/ml acetylated bovine serum albumin. The final cell suspension contains approximately $3 \times 10^6$ cells/ml. Electroporation should be performed immediately following resuspension.

Plasmid DNA is prepared according to standard techniques. For example, to construct a plasmid for targeting to the locus corresponding to the polynucleotide of the invention, plasmid pUC18 (MBI Fermentas, Amherst, N.Y.) is digested with HindIII. The CMV promoter is amplified by PCR with an XbaI site on the 5' end and a BamHI site on the 3' end. Two non-coding sequences are amplified via PCR: one non-coding sequence (fragment 1) is amplified with a HindIII site at the 5' end and an Xba site at the 3' end; the other non-coding sequence (fragment 2) is amplified with a BamHI site at the 5' end and a HindIII site at the 3' end. The CMV promoter and the fragments (1 and 2) are digested with the appropriate enzymes (CMV promoter—XbaI and BamHI; fragment 1—XbaI; fragment 2—BamHI) and ligated together. The resulting ligation product is digested with HindIII, and ligated with the HindIII-digested pUC18 plasmid.

Plasmid DNA is added to a sterile cuvette with a 0.4 cm electrode gap (Bio-Rad). The final DNA concentration is generally at least 120 μg/ml. 0.5 ml of the cell suspension (containing approximately $1.5 \times 10^6$ cells) is then added to the cuvette, and the cell suspension and DNA solutions are gently mixed. Electroporation is performed with a Gene-Pulser apparatus (Bio-Rad). Capacitance and voltage are set at 960 μF and 250-300 V, respectively. As voltage increases, cell survival decreases, but the percentage of surviving cells that stably incorporate the introduced DNA into their genome increases dramatically. Given these parameters, a pulse time of approximately 14-20 mSec should be observed.

Electroporated cells are maintained at room temperature for approximately 5 min, and the contents of the cuvette are then gently removed with a sterile transfer pipette. The cells are added directly to 10 ml of prewarmed nutrient media (DMEM with 15% calf serum) in a 10 cm dish and incubated at 37 degree C. The following day, the media is aspirated and replaced with 10 ml of fresh media and incubated for a further 16-24 hours.

The engineered fibroblasts are then injected into the host, either alone or after having been grown to confluence on cytodex 3 microcarrier beads. The fibroblasts now produce the protein product. The fibroblasts can then be introduced into a patient as described above.

Example 29

Method of Treatment Using Gene Therapy—In Vivo

Another aspect of the present invention is using in vivo gene therapy methods to treat disorders, diseases and conditions. The gene therapy method relates to the introduction of naked nucleic acid (DNA, RNA, and antisense DNA or RNA) sequences into an animal to increase or decrease the expression of the polypeptide. The polynucleotide of the present invention may be operatively linked to a promoter or any other genetic elements necessary for the expression of the polypeptide by the target tissue. Such gene therapy and delivery techniques and methods are known in the art, see, for example, WO90/11092, WO98/11779; U.S. Pat. Nos. 5,693,622, 5,705,151, 5,580,859; Tabata et al., Cardiovasc. Res. 35(3):470-479 (1997); Chao et al., Pharmacol. Res. 35(6):517-522 (1997); Wolff, Neuromuscul. Disord. 7(5):314-318 (1997); Schwartz et al., Gene Ther. 3(5):405-411 (1996); Tsurumi et al., Circulation 94(12):3281-3290 (1996) (incorporated herein by reference).

The polynucleotide constructs may be delivered by any method that delivers injectable materials to the cells of an animal, such as, injection into the interstitial space of tissues (heart, muscle, skin, lung, liver, intestine and the like). The polynucleotide constructs can be delivered in a pharmaceutically acceptable liquid or aqueous carrier.

The term "naked" polynucleotide, DNA or RNA, refers to sequences that are free from any delivery vehicle that acts to assist, promote, or facilitate entry into the cell, including viral sequences, viral particles, liposome formulations, lipofectin or precipitating agents and the like. However, the polynucleotides of the present invention may also be delivered in liposome formulations (such as those taught in Felgner P. L. et al. (1995) Ann. NY Acad. Sci. 772:126-139 and Abdallah B. et al. (1995) Biol. Cell 85(1):1-7) which can be prepared by methods well known to those skilled in the art.

The polynucleotide vector constructs used in the gene therapy method are preferably constructs that will not integrate into the host genome nor will they contain sequences that allow for replication. Any strong promoter known to those skilled in the art can be used for driving the expression of DNA. Unlike other gene therapies techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for periods of up to six months.

The polynucleotide construct can be delivered to the interstitial space of tissues within the an animal, including of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. Delivery to the interstitial space of muscle tissue is preferred for the reasons discussed below. They may be conveniently delivered by injection into the tissues comprising these cells. They are preferably delivered to and expressed in persistent, non-dividing cells which are differentiated, although delivery and expression may be achieved in non-differentiated or less completely differentiated cells, such as, for example, stem cells of blood or skin fibroblasts. In vivo muscle cells are particularly competent in their ability to take up and express polynucleotides.

For the naked polynucleotide injection, an effective dosage amount of DNA or RNA will be in the range of from about 0.05 g/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and may depend on the condition being treated and the route of administration. The preferred route of administration is by the parenteral route of injection into the interstitial space of tissues. However, other parenteral routes may also be used, such as, inhalation of an aerosol formulation particularly for delivery to lungs or bronchial tissues, throat or mucous membranes of the nose. In addition, naked polynucleotide constructs can be delivered to arteries during angioplasty by the catheter used in the procedure.

The dose response effects of injected polynucleotide in muscle in vivo is determined as follows. Suitable template DNA for production of mRNA coding for polypeptide of the present invention is prepared in accordance with a standard recombinant DNA methodology. The template DNA, which may be either circular or linear, is either used as naked DNA or complexed with liposomes. The quadriceps muscles of mice are then injected with various amounts of the template DNA.

Five to six week old female and male Balb/C mice are anesthetized by intraperitoneal injection with 0.3 ml of 2.5% Avertin. A 1.5 cm incision is made on the anterior thigh, and the quadriceps muscle is directly visualized. The template DNA is injected in 0.1 ml of carrier in a 1 cc syringe through a 27 gauge needle over one minute, approximately 0.5 cm from the distal insertion site of the muscle into the knee and about 0.2 cm deep. A suture is placed over the injection site for future localization, and the skin is closed with stainless steel clips.

After an appropriate incubation time (e.g., 7 days) muscle extracts are prepared by excising the entire quadriceps. Every fifth 15 um cross-section of the individual quadriceps muscles is histochemically stained for protein expression. A time course for protein expression may be done in a similar fashion except that quadriceps from different mice are harvested at different times. Persistence of DNA in muscle following injection may be determined by Southern blot analysis after preparing total cellular DNA and HIRT supernatants from injected and control mice. The results of the above experimentation in mice can be use to extrapolate proper dosages and other treatment parameters in humans and other animals using naked DNA.

Example 30

Transgenic Animals

The polypeptides of the invention can also be expressed in transgenic animals. Animals of any species, including, but not limited to, mice, rats, rabbits, hamsters, guinea pigs, pigs, micro-pigs, goats, sheep, cows and non-human primates, e.g., baboons, monkeys, and chimpanzees may be used to generate transgenic animals. In a specific embodiment, techniques described herein or otherwise known in the art, are used to express polypeptides of the invention in humans, as part of a gene therapy protocol.

Any technique known in the art may be used to introduce the transgene (i.e., polynucleotides of the invention) into animals to produce the founder lines of transgenic animals. Such techniques include, but are not limited to, pronuclear microinjection (Paterson et al., Appl. Microbiol. Biotechnol. 40:691-698 (1994); Carver et al., Biotechnology (NY) 11:1263-1270 (1993); Wright et al., Biotechnology (NY) 9:830-834 (1991); and Hoppe et al., U.S. Pat. No. 4,873,191 (1989)); retrovirus mediated gene transfer into germ lines (Van der Putten et al., Proc. Natl. Acad. Sci., USA 82:6148-6152 (1985)), blastocysts or embryos; gene targeting in embryonic stem cells (Thompson et al., Cell 56:313-321 (1989)); electroporation of cells or embryos (Lo, 1983, Mol Cell. Biol. 3:1803-1814 (1983)); introduction of the polynucleotides of the invention using a gene gun (see, e.g., Ulmer et al., Science 259:1745 (1993); introducing nucleic acid constructs into embryonic pleuripotent stem cells and transferring the stem cells back into the blastocyst; and sperm-mediated gene transfer (Lavitrano et al., Cell 57:717-723 (1989); etc. For a review of such techniques, see Gordon, "Transgenic Animals," Intl. Rev. Cytol. 115:171-229 (1989), which is incorporated by reference herein in its entirety.

Any technique known in the art may be used to produce transgenic clones containing polynucleotides of the invention, for example, nuclear transfer into enucleated oocytes of nuclei from cultured embryonic, fetal, or adult cells induced to quiescence (Campell et al., Nature 380:64-66 (1996); Wilmut et al., Nature 385:810-813 (1997)).

The present invention provides for transgenic animals that carry the transgene in all their cells, as well as animals which carry the transgene in some, but not all their cells, i.e., mosaic animals or chimeric. The transgene may be integrated as a single transgene or as multiple copies such as in concatamers, e.g., head-to-head tandems or head-to-tail tandems. The transgene may also be selectively introduced into and activated in a particular cell type by following, for example, the teaching of Lasko et al. (Lasko et al., Proc. Natl. Acad. Sci. USA 89:6232-6236 (1992)). The regulatory sequences required for such a cell-type specific activation will depend upon the particular cell type of interest, and will be apparent to those of skill in the art. When it is desired that the polynucleotide transgene be integrated into the chromosomal site of the endogenous gene, gene targeting is preferred. Briefly, when such a technique is to be utilized, vectors containing some nucleotide sequences homologous to the endogenous gene are designed for the purpose of integrating, via homologous recombination with chromosomal sequences, into and disrupting the function of the nucleotide sequence of the endogenous gene. The transgene may also be selectively introduced into a particular cell type, thus inactivating the endogenous gene in only that cell type, by following, for example, the teaching of Gu et al. (Gu et al., Science 265: 103-106 (1994)). The regulatory sequences required for such a cell-type specific inactivation will depend upon the particular cell type of interest, and will be apparent to those of skill in the art.

Once transgenic animals have been generated, the expression of the recombinant gene may be assayed utilizing standard techniques. Initial screening may be accomplished by Southern blot analysis or PCR techniques to analyze animal tissues to verify that integration of the transgene has taken place. The level of mRNA expression of the transgene in the tissues of the transgenic animals may also be assessed using techniques which include, but are not limited to, Northern blot analysis of tissue samples obtained from the animal, in situ hybridization analysis, and reverse transcriptase-PCR (RT-PCR). Samples of transgenic gene-expressing tissue may also be evaluated immunocytochemically or immunohistochemically using antibodies specific for the transgene product.

Once the founder animals are produced, they may be bred, inbred, outbred, or crossbred to produce colonies of the particular animal. Examples of such breeding strategies include, but are not limited to: outbreeding of founder animals with more than one integration site in order to establish separate lines; inbreeding of separate lines in order to produce compound transgenics that express the transgene at higher levels because of the effects of additive expression of each transgene; crossing of heterozygous transgenic animals to produce animals homozygous for a given integration site in order to both augment expression and eliminate the need for screening of animals by DNA analysis; crossing of separate homozygous lines to produce compound heterozygous or homozygous lines; and breeding to place the transgene on a distinct background that is appropriate for an experimental model of interest.

Transgenic animals of the invention have uses which include, but are not limited to, animal model systems useful in elaborating the biological function of polypeptides of the present invention, studying diseases, disorders, and/or conditions associated with aberrant expression, and in screening for compounds effective in ameliorating such diseases, disorders, and/or conditions.

Example 31

Knock-Out Animals

Endogenous gene expression can also be reduced by inactivating or "knocking out" the gene and/or its promoter using targeted homologous recombination. (E.g., see Smithies et al., Nature 317:230-234 (1985); Thomas & Capecchi, Cell 51:503-512 (1987); Thompson et al., Cell 5:313-321 (1989); each of which is incorporated by reference herein in its entirety). For example, a mutant, non-functional polynucleotide of the invention (or a completely unrelated DNA sequence) flanked by DNA homologous to the endogenous polynucleotide sequence (either the coding regions or regulatory regions of the gene) can be used, with or without a selectable marker and/or a negative selectable marker, to transfect cells that express polypeptides of the invention in vivo. In another embodiment, techniques known in the art are used to generate knockouts in cells that contain, but do not express the gene of interest. Insertion of the DNA construct, via targeted homologous recombination, results in inactivation of the targeted gene. Such approaches are particularly suited in research and agricultural fields where modifications to embryonic stem cells can be used to generate animal offspring with an inactive targeted gene (e.g., see Thomas & Capecchi 1987 and Thompson 1989, supra). However this approach can be routinely adapted for use in humans provided the recombinant DNA constructs are directly administered or targeted to the required site in vivo using appropriate viral vectors that will be apparent to those of skill in the art.

In further embodiments of the invention, cells that are genetically engineered to express the polypeptides of the invention, or alternatively, that are genetically engineered not to express the polypeptides of the invention (e.g., knockouts) are administered to a patient in vivo. Such cells may be obtained from the patient (i.e., animal, including human) or an MHC compatible donor and can include, but are not limited to fibroblasts, bone marrow cells, blood cells (e.g., lymphocytes), adipocytes, muscle cells, endothelial cells etc. The cells are genetically engineered in vitro using recombinant DNA techniques to introduce the coding sequence of polypeptides of the invention into the cells, or alternatively, to disrupt the coding sequence and/or endogenous regulatory sequence associated with the polypeptides of the invention, e.g., by transduction (using viral vectors, and preferably vectors that integrate the transgene into the cell genome) or transfection procedures, including, but not limited to, the use of plasmids, cosmids, YACs, naked DNA, electroporation, liposomes, etc. The coding sequence of the polypeptides of the invention can be placed under the control of a strong constitutive or inducible promoter or promoter/enhancer to achieve expression, and preferably secretion, of the polypeptides of the invention. The engineered cells which express and preferably secrete the polypeptides of the invention can be introduced into the patient systemically, e.g., in the circulation, or intraperitoneally.

Alternatively, the cells can be incorporated into a matrix and implanted in the body, e.g., genetically engineered fibroblasts can be implanted as part of a skin graft; genetically engineered endothelial cells can be implanted as part of a lymphatic or vascular graft. (See, for example, Anderson et al. U.S. Pat. No. 5,399,349; and Mulligan & Wilson, U.S. Pat. No. 5,460,959 each of which is incorporated by reference herein in its entirety).

When the cells to be administered are non-autologous or non-MHC compatible cells, they can be administered using well known techniques which prevent the development of a host immune response against the introduced cells. For example, the cells may be introduced in an encapsulated form which, while allowing for an exchange of components with the immediate extracellular environment, does not allow the introduced cells to be recognized by the host immune system.

Transgenic and "knock-out" animals of the invention have uses which include, but are not limited to, animal model systems useful in elaborating the biological function of polypeptides of the present invention, studying diseases, disorders, and/or conditions associated with aberrant expression, and in screening for compounds effective in ameliorating such diseases, disorders, and/or conditions.

Example 32

Method of Isolating Antibody Fragments Directed Against TRP-PLIK2 Polypeptides, TRP-PLIK2b, TRP-PLIK2c, and/or TRP-PLIK2d from a Library of scFvs Naturally occurring V-genes isolated from human PBLs are constructed into a library of antibody fragments which contain reactivities against TRP-PLIK2 polypeptides, TRP-PLIK2b, TRP-PLIK2c, and/or TRP-PLIK2d to which the donor may or may not have been exposed (see e.g., U.S. Pat. No. 5,885,793 incorporated herein by reference in its entirety).

Rescue of the Library. A library of scFvs is constructed from the RNA of human PBLs as described in PCT publication WO 92/01047. To rescue phage displaying antibody fragments, approximately 109 $E. coli$ harboring the phagemid are used to inoculate 50 ml of 2×TY containing 1% glucose and 100 µg/ml of ampicillin (2×TY-AMP-GLU) and grown to an O.D. of 0.8 with shaking. Five ml of this culture is used to inoculate 50 ml of 2×TY-AMP-GLU, 2×108 TU of delta gene 3 helper (M13 delta gene III, see PCT publication WO 92/01047) are added and the culture incubated at 37° C. for 45 minutes without shaking and then at 37° C. for 45 minutes with shaking. The culture is centrifuged at 4000 r.p.m. for 10 min. and the pellet resuspended in 2 liters of 2×TY containing 100 µg/ml ampicillin and 50 ug/ml kanamycin and grown overnight. Phage are prepared as described in PCT publication WO 92/01047.

M13 delta gene III is prepared as follows: M13 delta gene III helper phage does not encode gene III protein, hence the phage (mid) displaying antibody fragments have a greater avidity of binding to antigen. Infectious M13 delta gene III particles are made by growing the helper phage in cells harboring a pUC19 derivative supplying the wild type gene III protein during phage morphogenesis. The culture is incubated for 1 hour at 37° C. without shaking and then for a further hour at 37° C. with shaking. Cells are spun down (IEC-Centra 8,400 r.p.m. for 10 min), resuspended in 300 ml 2×TY broth containing 100 µg ampicillin/ml and 25 µg kanamycin/ml (2×TY-AMP-KAN) and grown overnight, shaking at 37° C. Phage particles are purified and concentrated from the culture medium by two PEG-precipitations (Sambrook et al., 1990), resuspended in 2 ml PBS and passed through a 0.45 µm filter (Minisart NML; Sartorius) to give a final concentration of approximately 1013 transducing units/ml (ampicillin-resistant clones).

Panning of the Library. Immunotubes (Nunc) are coated overnight in PBS with 4 ml of either 100 µg/ml or 10 µg/ml of a polypeptide of the present invention. Tubes are blocked with 2% Marvel-PBS for 2 hours at 37° C. and then washed 3 times in PBS. Approximately 1013 TU of phage is applied to the tube and incubated for 30 minutes at room temperature tumbling on an over and under turntable and then left to stand for another 1.5 hours. Tubes are washed 10 times with PBS 0.1% Tween-20 and 10 times with PBS. Phage are eluted by adding 1 ml of 100 mM triethylamine and rotating 15 minutes on an under and over turntable after which the solution is immediately neutralized with 0.5 ml of 1.0M Tris-HCl, pH 7.4. Phage are then used to infect 10 ml of mid-log $E. coli$ TG1 by incubating eluted phage with bacteria for 30 minutes at 37° C. The $E. coli$ are then plated on TYE plates containing 1% glucose and 100 µg/ml ampicillin. The resulting bacterial library is then rescued with delta gene 3 helper phage as described above to prepare phage for a subsequent round of selection. This process is then repeated for a total of 4 rounds of affinity purification with tube-washing increased to 20 times with PBS, 0.1% Tween-20 and 20 times with PBS for rounds 3 and 4.

Characterization of Binders. Eluted phage from the 3rd and 4th rounds of selection are used to infect $E. coli$ HB 2151 and soluble scFv is produced (Marks, et al., 1991) from single colonies for assay. ELISAs are performed with microtitre plates coated with either 10 pg/ml of the polypeptide of the present invention in 50 mM bicarbonate pH 9.6. Clones positive in ELISA are further characterized by PCR fingerprinting (see, e.g., PCT publication WO 92/01047) and then by sequencing. These ELISA positive clones may also be further characterized by techniques known in the art, such as, for example, epitope mapping, binding affinity, receptor signal transduction, ability to block or competitively inhibit antibody/antigen binding, and competitive agonistic or antagonistic activity.

Moreover, in another preferred method, the antibodies directed against the polypeptides of the present invention may be produced in plants. Specific methods are disclosed in U.S. Pat. Nos. 5,959,177, and 6,080,560, which are hereby incorporated in their entirety herein. The methods not only describe methods of expressing antibodies, but also the means of assembling foreign multimeric proteins in plants (i.e., antibodies, etc,), and the subsequent secretion of such antibodies from the plant.

Example 33

Identification and Cloning of VH and VL Domains of Antibodies Directed Against the TRP-PLIK2, TRP-PLIK2b, TRP-PLIK2c, and/or TRP-PLIK2d Polypeptide VH and VL domains may be identified and cloned from cell lines expressing an antibody directed against a TRP-PLIK2, TRP-PLIK2b, TRP-PLIK2c, and/or TRP-PLIK2d epitope by performing PCR with VH and VL specific primers on cDNA made from the antibody expressing cell lines. Briefly, RNA is isolated from the cell lines and used, as a template for RT-PCR designed to amplify the VH and VL domains of the antibodies expressed by the EBV cell lines. Cells may be lysed using the TRIZOL® reagent (Life Technologies, Rockville, Md.) and extracted with one fifth volume of chloroform. After addition of chloroform, the solution is allowed to incubate at room temperature for 10 minutes, and then centrifuged at 14,000 rpm for 15 minutes at 4 C in a tabletop centrifuge. The supernatant is collected and RNA is precipitated using an equal volume of isopropanol. Precipitated RNA is pelleted by centrifuging at 14,000 rpm for 15 minutes at 4 C in a tabletop centrifuge.

Following centrifugation, the supernatant is discarded and washed with 75% ethanol. Following the wash step, the RNA is centrifuged again at 800 rpm for 5 minutes at 4 C. The supernatant is discarded and the pellet allowed to air dry. RNA is the dissolved in DEPC water and heated to 60 C for 10 minutes. Quantities of RNA can be determined using optical density measurements. cDNA may be synthesized, according to methods well-known in the art and/or described herein, from 1.5-2.5 micrograms of RNA using reverse transciptase and random hexamer primers. cDNA is then used as a template for PCR amplification of VH and VL domains.

Primers used to amplify VH and VL genes are shown below. Typically a PCR reaction makes use of a single 5'primer and a single 3'primer. Sometimes, when the amount of available RNA template is limiting, or for greater efficiency, groups of 5' and/or 3'primers may be used. For example, sometimes all five VH-5'primers and all JH3'primers are used in a single PCR reaction. The PCR reaction is carried out in a 50 microliter volume containing 1×PCR buffer, 2 mM of each dNTP, 0.7 units of High Fidelity Taq polymerse, 5'primer mix, 3'primer mix and 7.5 microliters of cDNA. The 5' and 3'primer mix of both VH and VL can be made by pooling together 22 pmole and 28 pmole, respectively, of each of the individual primers. PCR conditions are: 96 C for 5 minutes; followed by 25 cycles of 94 C for 1 minute, 50 C for 1 minute, and 72 C for 1 minute; followed by an extension cycle of 72 C for 10 minutes. After the reaction has been completed, sample tubes may be stored at 4 C.

Primer Sequences Used to Amplify VH Domains.

| Primer name | Primer Sequence | SEQ ID NO: |
| --- | --- | --- |
| Hu VH1-5' | CAGGTGCAGCTGGTGCAGTCTGG | 272 |
| Hu VH2-5' | CAGGTCAACTTAAGGGAGTCTGG | 273 |
| Hu VH3-5' | GAGGTGCAGCTGGTGGAGTCTGG | 274 |
| Hu VH4-5' | CAGGTGCAGCTGCAGGAGTCGGG | 275 |
| Hu VH5-5' | GAGGTGCAGCTGTTGCAGTCTGC | 276 |
| Hu VH6-5' | CAGGTACAGCTGCAGCAGTCAGG | 277 |
| Hu JH1-5' | TGAGGAGACGGTGACCAGGGTGCC | 278 |
| Hu JH3-5' | TGAAGAGACGGTGACCATTGTCCC | 279 |
| Hu JH4-5' | TGAGGAGACGGTGACCAGGGTTCC | 280 |
| Hu JH6-5' | TGAGGAGACGGTGACCGTGGTCCC | 281 |

Primer Sequences Used to Amplify VL Domains

| Primer name | Primer Sequence | SEQ ID NO: |
| --- | --- | --- |
| Hu Vkappa1-5' | GACATCCAGATGACCCAGTCTCC | 282 |
| Hu Vkappa2a-5' | GATGTTGTGATGACTCAGTCTCC | 283 |
| Hu Vkappa2b-5' | GATATTGTGATGACTCAGTCTCC | 284 |
| Hu Vkappa3-5' | GAAATTGTGTTGACGCAGTCTCC | 285 |
| Hu Vkappa4-5' | GACATCGTGATGACCCAGTCTCC | 286 |
| Hu Vkappa5-5' | GAAACGACACTCACGCAGTCTCC | 287 |
| Hu Vkappa6-5' | GAAATTGTGCTGACTCAGTCTCC | 288 |
| Hu Vlambda1-5' | CAGTCTGTGTTGACGCAGCCGCC | 289 |
| Hu Vlambda2-5' | CAGTCTGCCCTGACTCAGCCTGC | 290 |
| Hu Vlambda3-5' | TCCTATGTGCTGACTCAGCCACC | 291 |
| Hu Vlambda3b-5' | TCTTCTGAGCTGACTCAGGACCC | 292 |
| Hu Vlambda4-5' | CACGTTATACTGACTCAACCGCC | 293 |
| Hu Vlambda5-5' | CAGGCTGTGCTCACTCAGCCGTC | 294 |
| Hu Vlambda6-5' | AATTTTATGCTGACTCAGCCCCA | 295 |
| Hu Jkappa1-3' | ACGTTTGATTTCCACCTTGGTCCC | 296 |
| Hu Jkappa2-3' | ACGTTTGATCTCCAGCTTGGTCCC | 297 |
| Hu Jkappa3-3' | ACGTTTGATATCCACTTTGGTCCC | 298 |
| Hu Jkappa4-3' | ACGTTTGATCTCCACCTTGGTCCC | 299 |
| Hu Jkappa5-3' | ACGTTTAATCTCCAGTCGTGTCCC | 300 |
| Hu Vlambda1-3' | CAGTCTGTGTTGACGCAGCCGCC | 301 |
| Hu Vlambda2-3' | CAGTCTGCCCTGACTCAGCCTGC | 302 |
| Hu Vlambda3-3' | TCCTATGTGCTGACTCAGCCACC | 303 |

-continued

| Primer name | Primer Sequence | SEQ ID NO: |
|---|---|---|
| Hu Vlambda3b-3' | TCTTCTGAGCTGACTCAGGACCC | 304 |
| Hu Vlambda4-3' | CACGTTATACTGACTCAACCGCC | 305 |
| Hu Vlambda5-3' | CAGGCTGTGCTCACTCAGCCGTC | 306 |
| Hu Vlambda6-3' | AATTTTATGCTGACTCAGCCCCA | 307 |

PCR samples are then electrophoresed on a 1.3% agarose gel. DNA bands of the expected sizes (~506 base pairs for VH domains, and 344 base pairs for VL domains) can be cut out of the gel and purified using methods well known in the art and/or described herein.

Purified PCR products can be ligated into a PCR cloning vector (TA vector from Invitrogen Inc., Carlsbad, Calif.). Individual cloned PCR products can be isolated after transfection of E. coli and blue/white color selection. Cloned PCR products may then be sequenced using methods commonly known in the art and/or described herein.

The PCR bands containing the VH domain and the VL domains can also be used to create full-length Ig expression vectors. VH and VL domains can be cloned into vectors containing the nucleotide sequences of a heavy (e.g., human IgG1 or human IgG4) or light chain (human kappa or human ambda) constant regions such that a complete heavy or light chain molecule could be expressed from these vectors when transfected into an appropriate host cell. Further, when cloned heavy and light chains are both expressed in one cell line (from either one or two vectors), they can assemble into a complete functional antibody molecule that is secreted into the cell culture medium. Methods using polynucleotides encoding VH and VL antibody domain to generate expression vectors that encode complete antibody molecules are well known within the art.

Example 34

Assays Detecting Stimulation or Inhibition of B Cell Proliferation and Differentiation Generation of functional humoral immune responses requires both soluble and cognate signaling between B-lineage cells and their microenvironment. Signals may impart a positive stimulus that allows a B-lineage cell to continue its programmed development, or a negative stimulus that instructs the cell to arrest its current developmental pathway. To date, numerous stimulatory and inhibitory signals have been found to influence B cell responsiveness including IL-2, IL-4, IL-5, IL-6, IL-7, IL10, IL-13, IL-14 and IL-15. Interestingly, these signals are by themselves weak effectors but can, in combination with various co-stimulatory proteins, induce activation, proliferation, differentiation, homing, tolerance and death among B cell populations.

One of the best studied classes of B-cell co-stimulatory proteins is the TNF-superfamily. Within this family CD40, CD27, and CD30 along with their respective ligands CD154, CD70, and CD153 have been found to regulate a variety of immune responses. Assays which allow for the detection and/or observation of the proliferation and differentiation of these B-cell populations and their precursors are valuable tools in determining the effects various proteins may have on these B-cell populations in terms of proliferation and differentiation. Listed below are two assays designed to allow for the detection of the differentiation, proliferation, or inhibition of B-cell populations and their precursors.

In Vitro Assay—Purified polypeptides of the invention, or truncated forms thereof, is assessed for its ability to induce activation, proliferation, differentiation or inhibition and/or death in B-cell populations and their precursors. The activity of the polypeptides of the invention on purified human tonsillar B cells, measured qualitatively over the dose range from 0.1 to 10,000 ng/mL, is assessed in a standard B-lymphocyte co-stimulation assay in which purified tonsillar B cells are cultured in the presence of either formalin-fixed *Staphylococcus aureus* Cowan I (SAC) or immobilized anti-human IgM antibody as the priming agent. Second signals such as IL-2 and IL-15 synergize with SAC and IgM crosslinking to elicit B cell proliferation as measured by tritiated-thymidine incorporation. Novel synergizing agents can be readily identified using this assay. The assay involves isolating human tonsillar B cells by magnetic bead (MACS) depletion of CD3-positive cells. The resulting cell population is greater than 95% B cells as assessed by expression of CD45R (B220).

Various dilutions of each sample are placed into individual wells of a 96-well plate to which are added 105 B-cells suspended in culture medium (RPMI 1640 containing 10% FBS, 5×10−5M 2ME, 100 U/ml penicillin, 10 ug/ml streptomycin, and 10-5 dilution of SAC) in a total volume of 150 ul. Proliferation or inhibition is quantitated by a 20 h pulse (1 uCi/well) with 3H-thymidine (6.7 Ci/mM) beginning 72 h post factor addition. The positive and negative controls are IL2 and medium respectively.

In Vivo Assay—BALB/c mice are injected (i.p.) twice per day with buffer only, or 2 mg/Kg of a polypeptide of the invention, or truncated forms thereof. Mice receive this treatment for 4 consecutive days, at which time they are sacrificed and various tissues and serum collected for analyses. Comparison of H&E sections from normal spleens and spleens treated with polypeptides of the invention identify the results of the activity of the polypeptides on spleen cells, such as the diffusion of peri-arterial lymphatic sheaths, and/or significant increases in the nucleated cellularity of the red pulp regions, which may indicate the activation of the differentiation and proliferation of B-cell populations. Immunohistochemical studies using a B cell marker, anti-CD45R (B220), are used to determine whether any physiological changes to splenic cells, such as splenic disorganization, are due to increased B-cell representation within loosely defined B-cell zones that infiltrate established T-cell regions.

Flow cytometric analyses of the spleens from mice treated with polypeptide is used to indicate whether the polypeptide specifically increases the proportion of ThB+, CD45R (B220) dull B cells over that which is observed in control mice.

Likewise, a predicted consequence of increased mature B-cell representation in vivo is a relative increase in serum Ig titers. Accordingly, serum IgM and IgA levels are compared between buffer and polypeptide-treated mice.

One skilled in the art could easily modify the exemplified studies to test the activity of polynucleotides of the invention (e.g., gene therapy), agonists, and/or antagonists of polynucleotides or polypeptides of the invention.

Example 35

T Cell Proliferation Assay

A CD3-induced proliferation assay is performed on PBMCs and is measured by the uptake of 3H-thymidine. The assay is performed as follows. Ninety-six well plates are coated with 100 (l/well of mAb to CD3 (HIT3a, Pharmingen) or isotype-matched control mAb (B33.1) overnight at 4 degrees C. (1 (g/ml in 0.05M bicarbonate buffer, pH 9.5), then washed three times with PBS. PBMC are isolated by F/H gradient centrifugation from human peripheral blood and added to quadruplicate wells (5×104/well) of mAb coated plates in RPMI containing 10% FCS and P/S in the presence of varying concentrations of polypeptides of the invention (total volume 200 ul). Relevant protein buffer and medium alone are controls. After 48 hr. culture at 37 degrees C., plates are spun for 2 min. at 1000 rpm and 100 (l of supernatant is removed and stored −20 degrees C. for measurement of IL-2 (or other cytokines) if effect on proliferation is observed. Wells are supplemented with 100 ul of medium containing 0.5 uCi of 3H-thymidine and cultured at 37 degrees C. for 18-24 hr. Wells are harvested and incorporation of 3H-thymidine used as a measure of proliferation. Anti-CD3 alone is the positive control for proliferation. IL-2 (100 U/ml) is also used as a control which enhances proliferation. Control antibody which does not induce proliferation of T cells is used as the negative controls for the effects of polypeptides of the invention.

One skilled in the art could easily modify the exemplified studies to test the activity of polynucleotides of the invention (e.g., gene therapy), agonists, and/or antagonists of polynucleotides or polypeptides of the invention.

Example 36

Effect of Polypeptides of the Invention on the Expression of MHC Class II, Costimulatory and Adhesion Molecules and Cell Differentiation of Monocytes and Monocyte-Derived Human Dendritic Cells Dendritic cells are generated by the expansion of proliferating precursors found in the peripheral blood: adherent PBMC or elutriated monocytic fractions are cultured for 7-10 days with GM-CSF (50 ng/ml) and IL-4 (20 ng/ml). These dendritic cells have the characteristic phenotype of immature cells (expression of CD1, CD80, CD86, CD40 and MHC class II antigens). Treatment with activating factors, such as TNF−, causes a rapid change in surface phenotype (increased expression of MHC class I and II, costimulatory and adhesion molecules, downregulation of FC(R11, upregulation of CD83). These changes correlate with increased antigen-presenting capacity and with functional maturation of the dendritic cells.

FACS analysis of surface antigens is performed as follows. Cells are treated 1-3 days with increasing concentrations of polypeptides of the invention or LPS (positive control), washed with PBS containing 1% BSA and 0.02 mM sodium azide, and then incubated with 1:20 dilution of appropriate FITC- or PE-labeled monoclonal antibodies for 30 minutes at 4 degrees C. After an additional wash, the labeled cells are analyzed by flow cytometry on a FACScan (Becton Dickinson).

Effect on the production of cytokines. Cytokines generated by dendritic cells, in particular IL-12, are important in the initiation of T-cell dependent immune responses. IL-12 strongly influences the development of Th1 helper T-cell immune response, and induces cytotoxic T and NK cell function. An ELISA is used to measure the IL-12 release as follows. Dendritic cells (106/ml) are treated with increasing concentrations of polypeptides of the invention for 24 hours. LPS (100 ng/ml) is added to the cell culture as positive control. Supernatants from the cell cultures are then collected and analyzed for IL-12 content using commercial ELISA kit (e.g., R & D Systems (Minneapolis, Minn.)). The standard protocols provided with the kits are used.

Effect on the expression of MHC Class II, costimulatory and adhesion molecules. Three major families of cell surface antigens can be identified on monocytes: adhesion molecules, molecules involved in antigen presentation, and Fc receptor. Modulation of the expression of MHC class II antigens and other costimulatory molecules, such as B7 and ICAM-1, may result in changes in the antigen presenting capacity of monocytes and ability to induce T cell activation. Increase expression of Fc receptors may correlate with improved monocyte cytotoxic activity, cytokine release and phagocytosis.

FACS analysis is used to examine the surface antigens as follows. Monocytes are treated 1-5 days with increasing concentrations of polypeptides of the invention or LPS (positive control), washed with PBS containing 1% BSA and 0.02 mM sodium azide, and then incubated with 1:20 dilution of appropriate FITC- or PE-labeled monoclonal antibodies for 30 minutes at 4 degrees C. After an additional wash, the labeled cells are analyzed by flow cytometry on a FACScan (Becton Dickinson).

Monocyte activation and/or increased survival. Assays for molecules that activate (or alternatively, inactivate) monocytes and/or increase monocyte survival (or alternatively, decrease monocyte survival) are known in the art and may routinely be applied to determine whether a molecule of the invention functions as an inhibitor or activator of monocytes. Polypeptides, agonists, or antagonists of the invention can be screened using the three assays described below. For each of these assays, Peripheral blood mononuclear cells (PBMC) are purified from single donor leukopacks (American Red Cross, Baltimore, Md.) by centrifugation through a HISTO-PAQUE® gradient (Sigma). Monocytes are isolated from PBMC by counterflow centrifugal elutriation.

Monocyte Survival Assay. Human peripheral blood monocytes progressively lose viability when cultured in absence of serum or other stimuli. Their death results from internally regulated process (apoptosis). Addition to the culture of activating factors, such as TNF-alpha dramatically improves cell survival and prevents DNA fragmentation. Propidium iodide (PI) staining is used to measure apoptosis as follows. Monocytes are cultured for 48 hours in polypropylene tubes in serum-free medium (positive control), in the presence of 100 ng/ml TNF-alpha (negative control), and in the presence of varying concentrations of the compound to be tested. Cells are suspended at a concentration of 2×106/ml in PBS containing PI at a final concentration of 5 (g/ml, and then incubated at room temperature for 5 minutes before FACScan analysis. PI uptake has been demonstrated to correlate with DNA fragmentation in this experimental paradigm.

Effect on cytokine release. An important function of monocytes/macrophages is their regulatory activity on other cellular populations of the immune system through the release of cytokines after stimulation. An ELISA to measure cytokine release is performed as follows. Human monocytes are incubated at a density of 5×105 cells/ml with increasing concentrations of the a polypeptide of the invention and under the same conditions, but in the absence of the polypeptide. For IL-12 production, the cells are primed overnight with IFN (100 U/ml) in presence of a polypeptide of the invention. LPS (10 ng/ml) is then added. Conditioned media are collected after 24 h and kept frozen until use. Measurement of TNF-alpha, IL-10, MCP-1 and IL-8 is then performed using a commercially available ELISA kit (e.g., R & D Systems (Minneapolis, Minn.)) and applying the standard protocols provided with the kit.

Oxidative burst. Purified monocytes are plated in 96-w plate at 2-1×105 cell/well. Increasing concentrations of polypeptides of the invention are added to the wells in a total volume of 0.2 ml culture medium (RPMI 1640+10% FCS, glutamine and antibiotics). After 3 days incubation, the plates are centrifuged and the medium is removed from the wells. To the macrophage monolayers, 0.2 ml per well of phenol red solution (140 mM NaCl, 10 mM potassium phosphate buffer pH 7.0, 5.5 mM dextrose, 0.56 mM phenol red and 19 U/ml of HRPO) is added, together with the stimulant (200 nM PMA). The plates are incubated at 37 (C for 2 hours and the reaction is stopped by adding 20 µl 1N NaOH per well. The absorbance is read at 610 nm. To calculate the amount of H2O2 produced by the macrophages, a standard curve of a H2O2 solution of known molarity is performed for each experiment.

One skilled in the art could easily modify the exemplified studies to test the activity of polynucleotides of the invention (e.g., gene therapy), agonists, and/or antagonists of polynucleotides or polypeptides of the invention.

Example 37

Suppression of TNF Alpha-Induced Adhesion Molecule Expression by a Polypeptide of the Invention The recruitment of lymphocytes to areas of inflammation and angiogenesis involves specific receptor-ligand interactions between cell surface adhesion molecules (CAMs) on lymphocytes and the vascular endothelium. The adhesion process, in both normal and pathological settings, follows a multi-step cascade that involves intercellular adhesion molecule-1 (ICAM-1), vascular cell adhesion molecule-1 (VCAM-1), and endothelial leukocyte adhesion molecule-1 (E-selectin) expression on endothelial cells (EC). The expression of these molecules and others on the vascular endothelium determines the efficiency with which leukocytes may adhere to the local vasculature and extravasate into the local tissue during the development of an inflammatory response. The local concentration of cytokines and growth factor participate in the modulation of the expression of these CAMs.

Tumor necrosis factor alpha (TNF-a), a potent proinflammatory cytokine, is a stimulator of all three CAMs on endothelial cells and may be involved in a wide variety of inflammatory responses, often resulting in a pathological outcome.

The potential of a polypeptide of the invention to mediate a suppression of TNF-a induced CAM expression can be examined. A modified ELISA assay which uses ECs as a solid phase absorbent is employed to measure the amount of CAM expression on TNF-a treated ECs when co-stimulated with a member of the FGF family of proteins.

To perform the experiment, human umbilical vein endothelial cell (HUVEC) cultures are obtained from pooled cord harvests and maintained in growth medium (EGM-2; Clonetics, San Diego, Calif.) supplemented with 10% FCS and 1% penicillin/streptomycin in a 37 degree C. humidified incubator containing 5% CO2. HUVECs are seeded in 96-well plates at concentrations of 1×104 cells/well in EGM medium at 37 degree C. for 18-24 hrs or until confluent. The monolayers are subsequently washed 3 times with a serum-free solution of RPMI-1640 supplemented with 100 U/ml penicillin and 100 mg/ml streptomycin, and treated with a given cytokine and/or growth factor(s) for 24 h at 37 degree C. Following incubation, the cells are then evaluated for CAM expression.

Human Umbilical Vein Endothelial cells (HUVECs) are grown in a standard 96 well plate to confluence. Growth medium is removed from the cells and replaced with 90 ul of 199 Medium (10% FBS). Samples for testing and positive or negative controls are added to the plate in triplicate (in 10 ul volumes). Plates are incubated at 37 degree C. for either 5 h (selectin and integrin expression) or 24 h (integrin expression only). Plates are aspirated to remove medium and 100 µl of 0.1% paraformaldehyde-PBS (with Ca++ and Mg++) is added to each well. Plates are held at 4° C. for 30 min.

Fixative is then removed from the wells and wells are washed 1× with PBS(+Ca,Mg)+0.5% BSA and drained. Do not allow the wells to dry. Add 10 µl of diluted primary antibody to the test and control wells. Anti-ICAM-1-Biotin, Anti-VCAM-1-Biotin and Anti-E-selectin-Biotin are used at a concentration of 10 µg/ml (1:10 dilution of 0.1 mg/ml stock antibody). Cells are incubated at 37° C. for 30 min. in a humidified environment. Wells are washed ×3 with PBS(+Ca,Mg)+0.5% BSA.

Then add 20 µl of diluted EXTRAVIDIN®-Alkaline Phosphatase (1:5,000 dilution) to each well and incubated at 37° C. for 30 min. Wells are washed ×3 with PBS(+Ca,Mg)+0.5% BSA. 1 tablet of p-Nitrophenol Phosphate pNPP is dissolved in 5 ml of glycine buffer (pH 10.4). 100 µl of pNPP substrate in glycine buffer is added to each test well. Standard wells in triplicate are prepared from the working dilution of the EXTRAVIDIN®-Alkaline Phosphatase in glycine buffer: 1:5,000 (100)>10-0.5>10-1>10-1.5. 5 µl of each dilution is added to triplicate wells and the resulting AP content in each well is 5.50 ng, 1.74 ng, 0.55 ng, 0.18-ng. 100 µl of pNNP reagent must then be added to each of the standard wells. The plate must be incubated at 37° C. for 4 h. A volume of 50 µl of 3M NaOH is added to all wells. The results are quantified on a plate reader at 405 nm. The background subtraction option is used on blank wells filled with glycine buffer only. The template is set up to indicate the concentration of AP-conjugate in each standard well [5.50 ng; 1.74 ng; 0.55 ng; 0.18 ng]. Results are indicated as amount of bound AP-conjugate in each sample.

One skilled in the art could easily modify the exemplified studies to test the activity of polynucleotides of the invention (e.g., gene therapy), agonists, and/or antagonists of polynucleotides or polypeptides of the invention.

It will be clear that the invention may be practiced otherwise than as particularly described in the foregoing description and examples. Numerous modifications and variations of the present invention are possible in light of the above teachings and, therefore, are within the scope of the appended claims.

The entire disclosure of each document cited (including patents, patent applications, journal articles, abstracts, laboratory manuals, books, or other disclosures) in the Background of the Invention, Detailed Description, and Examples is hereby incorporated herein by reference. Further, the hard copy of the sequence listing submitted herewith and the corresponding computer readable form are both incorporated herein by reference in their entireties.

What is claimed is:

1. An isolated polypeptide comprising a sequence selected from the group consisting of:
   (a) an isolated polypeptide comprising amino acids 1 to 2017 of SEQ ID NO:2;
   (b) an isolated polypeptide comprising amino acids 2 to 2017 of SEQ ID NO:2;
   (c) an isolated polypeptide comprising the sequence encoded by nucleotides 1 to 6051 of SEQ ID NO:1; and
   (d) an isolated polypeptide comprising the sequence encoded by nucleotides 4 to 6051 of SEQ ID NO:1.

2. The isolated polypeptide of claim 1, wherein said polypeptide is (a).

3. The isolated polypeptide of claim 1, wherein said polypeptide is (b).

4. The isolated polypeptide of claim 1, wherein said polypeptide is (c).

5. The isolated polypeptide of claim 1, wherein said polypeptide is (d).

6. An isolated polypeptide produced by a method comprising:
   (a) culturing an isolated recombinant host cell comprising a vector that comprises the coding region encoding the polypeptide of claim 1 under conditions in which said polypeptide is expressed; and
   (b) recovering said polypeptide.

7. The isolated polypeptide of claim 1 further comprising a heterologous polypeptide sequence.

8. The isolated polypeptide of claim 7 wherein said heterologous polypeptide is the Fc domain of an immunoglobulin.

9. An isolated polypeptide comprising the polypeptide encoded by the cDNA clone contained in plasmid TRP-PLIK2 in ATCC Deposit No. PTA-4175.

10. An isolated polypeptide comprising at least 2012 contiguous amino acids of SEQ ID NO:2.

11. An isolated polypeptide comprising amino acids 6 to 2017 of SEQ ID NO:2.

12. An isolated polypeptide comprising amino acids 1 to 2012 of SEQ ID NO:2.

13. An isolated polypeptide comprising the sequence of SEQ ID NO:2, in which said sequence contains at least one, but no more than seven, total amino acid substitutions, wherein said polypeptide has protein kinase activity.

* * * * *